US008999929B2

(12) United States Patent
Mohammadi et al.

(10) Patent No.: US 8,999,929 B2
(45) Date of Patent: Apr. 7, 2015

(54) FIBROBLAST GROWTH FACTOR 1 PROTEIN FRAGMENTS AND METHODS OF USE

(71) Applicants: Salk Institute for Biological Studies, La Jolla, CA (US); New York University, New York, NY (US)

(72) Inventors: Moosa Mohammadi, Scarsdale, NY (US); Regina M. Goetz, New York, NY (US); Ronald M. Evans, La Jolla, CA (US); Michael Downes, San Diego, CA (US); Jae Myoung Suh, San Diego, CA (US)

(73) Assignees: Salk Institute for Biological Studies, La Jolla, CA (US); New York University, New York, NY (US)

( * ) Notice: Subject to any disclaimer, the term of this patent is extended or adjusted under 35 U.S.C. 154(b) by 0 days.

(21) Appl. No.: 14/176,992

(22) Filed: Feb. 10, 2014

(65) Prior Publication Data
US 2014/0155316 A1 Jun. 5, 2014

Related U.S. Application Data

(63) Continuation-in-part of application No. 13/838,350, filed on Mar. 15, 2013.

(60) Provisional application No. 61/656,871, filed on Jun. 7, 2012, provisional application No. 61/664,085, filed on Jun. 25, 2012.

(51) Int. Cl.
*A61K 38/18* (2006.01)
*C07K 14/50* (2006.01)
*A61K 45/06* (2006.01)

(52) U.S. Cl.
CPC ............. *A61K 38/1825* (2013.01); *C07K 14/50* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,132,408 | A | 7/1992 | Baird et al. |
| 5,478,804 | A | 12/1995 | Calabresi et al. |
| 6,326,484 | B1 | 12/2001 | Gage et al. |
| 6,982,170 | B1 | 1/2006 | Maciag et al. |
| 7,491,697 | B2 | 2/2009 | Beals et al. |
| 7,582,607 | B2 | 9/2009 | Frye et al. |
| 7,622,445 | B2 | 11/2009 | Frye et al. |
| 7,655,627 | B2 | 2/2010 | Frye et al. |
| 7,956,033 | B2 | 6/2011 | Cheng et al. |
| 8,168,591 | B2 * | 5/2012 | Takada et al. ............ 514/9.1 |
| 2004/0259780 | A1 | 12/2004 | Glasebrook et al. |
| 2007/0142278 | A1 | 6/2007 | Beals et al. |
| 2007/0237768 | A1 | 10/2007 | Glaesner et al. |
| 2007/0265200 | A1 | 11/2007 | Glaesner et al. |
| 2007/0293430 | A1 | 12/2007 | Frye et al. |
| 2007/0299007 | A1 | 12/2007 | Frye et al. |
| 2008/0103096 | A1 | 5/2008 | Frye et al. |
| 2008/0255045 | A1 | 10/2008 | Cujec et al. |
| 2008/0261875 | A1 | 10/2008 | Etgen et al. |
| 2009/0111742 | A1 | 4/2009 | Kharitonenkov et al. |
| 2009/0118190 | A1 | 5/2009 | Beals et al. |
| 2009/0305986 | A1 | 12/2009 | Belouski et al. |
| 2010/0062984 | A1 | 3/2010 | Kumar et al. |
| 2010/0158914 | A1 | 6/2010 | Desnoyers |
| 2010/0184665 | A1 | 7/2010 | Suzuki et al. |
| 2010/0216715 | A1 | 8/2010 | Tagmose et al. |
| 2010/0285131 | A1 | 11/2010 | Belouski et al. |
| 2010/0286042 | A1 | 11/2010 | Imamura et al. |
| 2010/0323954 | A1 | 12/2010 | Li et al. |
| 2011/0053841 | A1 | 3/2011 | Yayon et al. |
| 2011/0104152 | A1 | 5/2011 | Sonoda |
| 2011/0150901 | A1 | 6/2011 | Smith et al. |
| 2011/0172401 | A1 | 7/2011 | Cujec et al. |
| 2011/0190207 | A1 | 8/2011 | Mohammadi et al. |
| 2011/0195077 | A1 | 8/2011 | Glass et al. |
| 2012/0288886 | A1 | 11/2012 | Mohammadi et al. |
| 2013/0023474 | A1 | 1/2013 | Ling et al. |

(Continued)

FOREIGN PATENT DOCUMENTS

EP          0 645 451 B1      8/2001
WO      WO 2011/047267 A1    4/2011

(Continued)

OTHER PUBLICATIONS

Andrukhova et al., "FGF23 Acts Directly on Renal Proximal Tubules to Induce Phosphaturia Through Activation of the ERK1/2-SGK1 Signaling Pathway," *Bone* 51:621-628, 2012.

Beenken et al., "Plasticity in Interactions of Fibroblast Growth Factor 1 (FGF1) N Terminus With FGF Receptors Underlies Promiscuity of FGF1," *J. Biol. Chem.* 287:3067-3078, 2012.

Beenken & Mohammadi, "The Structural Biology of the FGF19 Subfamily," *Adv. Exp. Med. Biol.* 728:1-24, 2012.

Goetz et al., "Klotho Coreceptors Inhibit Signaling by Paracrine Fibroblast Growth Factor 8 Subfamily Ligands," *Mol. Cell. Biol.* 32:1944-1954, 2012.

Goetz et al., "Conversion of a Paracrine Fibroblast Growth Factor Into an Endocrine Fibroblast Growth Factor," *J. Biol. Chem.* 287:29134-29146, 2012.

(Continued)

*Primary Examiner* — Marianne P Allen
(74) *Attorney, Agent, or Firm* — Klarquist Sparkman, LLP

(57) ABSTRACT

The present invention relates to a chimeric protein that includes an N-terminus coupled to a C-terminus, where the N-terminus includes a portion of a paracrine fibroblast growth factor ("FGF") and the C-terminus includes a C-terminal portion of an FGF19 molecule. The portion of the paracrine FGF is modified to decrease binding affinity for heparin and/or heparan sulfate compared to the portion without the modification. The present invention also relates to pharmaceutical compositions including chimeric proteins according to the present invention, methods for treating a subject suffering from diabetes, obesity, or metabolic syndrome, and methods of screening for compounds with enhanced binding affinity for the βKlotho-FGF receptor complex involving the use of chimeric proteins of the present invention.

26 Claims, 13 Drawing Sheets

(56) References Cited

U.S. PATENT DOCUMENTS

| | | |
|---|---|---|
| 2013/0058896 A1* | 3/2013 | Takada et al. .............. 424/85.7 |
| 2013/0116171 A1 | 5/2013 | Jonker et al. |
| 2013/0231277 A1 | 9/2013 | Mohammadi et al. |
| 2013/0331317 A1 | 12/2013 | Mohammadi et al. |
| 2013/0331325 A1 | 12/2013 | Mohammadi et al. |
| 2014/0094406 A1 | 4/2014 | Mohammadi et al. |
| 2014/0107022 A1 | 4/2014 | Mohammadi et al. |
| 2014/0171361 A1 | 6/2014 | Jonker et al. |

FOREIGN PATENT DOCUMENTS

| | | |
|---|---|---|
| WO | WO 2011/130729 A2 | 10/2011 |
| WO | WO 2013/184958 A1 | 12/2013 |
| WO | WO 2013/184960 A2 | 12/2013 |
| WO | WO 2013/184962 A1 | 12/2013 |

OTHER PUBLICATIONS

Imamura et al., "Recovery of Mitogenic Activity of a Growth Factor Mutant with a Nuclear Translocation Sequence," *Science* 249:1567-1570, 1990.

Jonker et al., "A PPARgamma-FGF1 Axis is Required for Adaptive Adipose Remodelling and Metabolic Homeostasis," *Nature* 485:391-394, 2012.

Olsen et al., "Insights Into the Molecular Basis for Fibroblast Growth Factor Receptor Autoinhibition and Ligand-Binding Promiscuity," *Proc. Natl. Acad. Sci. USA* 101:935-940, 2004.

Wei et al., "Fibroblast Growth Factor 21 Promotes Bone Loss by Potentiating the Effects of Peroxisome Proliferator-Activated Receptor γ," *Proc. Natl. Acad. Sci. USA* 109:3143-3148, 2012.

Wu et al., "C-Terminal Tail of FGF19 Determines Its Specificity Toward Klotho Co-Receptors," *J. Biol. Chem.* 283:33304-33309, 2008.

Wu et al., "FGF19-Induced Hepatocyte Proliferation is Mediated Through FGFR4 Activation," *J. Biol. Chem.* 285:5165-5170, 2010.

Wu et al., "Separating Mitogenic and Metabolic Activities of Fibroblast Growth Factor 19 (FGF19)," *Proc. Natl. Acad. Sci. USA* 107:14158-14163, 2010.

Wu et al., "A Unique FGF23 With the Ability of Activate FGFR Signaling Through Both αKlotho and βKlotho," *J. Mol. Biol.* 418:82-89, 2012.

Yie et al., "FGF21 N- and C-Termini Play Different Roles in Receptor Interaction and Activation," *FEBS Lett.* 583:19-24, 2009.

Zhang et al., Receptor Specificity of the Fibroblast Growth Factor Family: The Complete Mammalian FGF Family, *J. Biol. Chem.* 281:15694-15700, 2006.

Ge et al., "Characterization of a FGF19 Variant with Altered Receptor Specificity Revealed a Central Role for FGFR1c in the Regulation of Glucose Metabolism," *PloS One* 7:e33603, 2012.

Goetz et al., "Molecular Insights Into the Klotho-Dependent, Endocrine Mode of Action of Fibroblast Growth Factor 19 Subfamily Members," *Mol Cell Biol.* 27:3417-3428, 2007.

Goetz et al., "Isolated C-Terminal Tail of FGF23 Alleviates Hypophosphatemia by Inhibiting FGF23-FGFR-Klotho Complex Formation," *Proc Natl Acad Sci USA* 107:407-412, 2010.

Hutley et al., "Fibroblast Growth Factor 1: A Key Regulator of Human Adipogenesis," *Diabetes* 53:3097-3106, 2004.

Igarashi et al., "Characterization of Recombinant Human Fibroblast Growth Factor (FGF)-10 Reveals Functional Similarities with Keratinocyte Growth Factor (FGF-7)," *J Biol Chem.* 273: 13230-13235, 1998.

Kharitonenkov et al., "The Metabolic State of Diabetic Monkeys is Regulated by Fibroblast Growth Factor-21," *Endocrinology* 148:774-781, 2007.

Mohammadi et al., "Structural Basis for Fibroblast Growth Factor Receptor Activation," *Cytokine Growth Factor Rev.* 16:107-137, 2005.

Motomura et al., "An FGF1:FGF2 Chimeric Growth Factor Exhibits Universal FGF Receptor Specificity, Enhanced Stability and Augmented Activity Useful for Epithelial Proliferation and Radioprotection," *Biochim Biophys Acta.* 1780:1432-1440, 2008.

Nakayama et al., "Post Treatment with an FGF Chimeric Growth Factor Enhances Epithelial Cell Proliferation to Improve Recovery from Radiation-Induced Intestinal Damage," *Int J Radiat Oncol Biol Phys.* 78:860-867, 2010.

Presta et al., "Structure-Function Relationship of Basic Fibroblast Growth Factor: Site-Directed Mutagenesis of a Putative Heparin-Binding and Receptor-Binding Region," *Biochem Biophys Res Commun.* 185:1098-1107, 1992.

Razzaque, "The FGF23-Klotho Axis: Endocrine Regulation of Phosphate Homeostasis," *Nat Rev Endocrinol* 5:611-619, 2009.

Wu et al., "FGF19 Regulates Cell Proliferation, Glucose and Bile Acid Metabolism via FGFR4-Dependent and Independent Pathways," *PLoS One* 6:e17868, 2011.

Wu et al., "Selective Activation of FGFR4 by an FGF19 Variant Does Not Improve Glucose Metabolism in *ob/ob* Mice," *Proc Natl Acad Sci USA* 106:14379-14384, 2009.

Zakrzewska et al., "Increased Protein Stability of FGF1 Can Compensate for its Reduced Affinity for Heparin," *J Biol Chem.* 284:25388-25403, 2009.

\* cited by examiner

FIG. 2

```
FGF19 (169)  LPMV  EEPE DLRGH  LESDMFSSPL  ETDSMDPFGL  VTGLEAVRSP  WFEK - - - - - - - P
FGF21 (168)  PGLP  PALPE - - -  PPGILAPQPP  DVGSSDPLSM  V - GPSQGRSP  SYAS - - - - - - ELP
FGF23 (163)  - - EI  PLI - - HFNTP  IPRRHTRSAE  DDSERDPLN -  VLKPRARMTP  APASCSQELP

FGF19                                                               
FGF21                                                               
FGF23 (212)  SAEDNSPMAS  DPLGVVRGGR  VNTHAGGTGP  EGCRPFAKFI
```

| | | | | | | |
|---|---|---|---|---|---|---|
| FGF19C-tail (169) | L P M V P E E | P E D L R G H L E S | D M F S S P L E T D | S M D P F G L V T G | L E A V R S P S F E | K | (SEQ ID NO:346)
| FGF19C-tail/21-1 | L P M V P E E | P E D L R G H L E S | D M F S S P L E T D | S M D P F G L V T G | L E A V R S P S F A | K | (SEQ ID NO:347)
| FGF19C-tail/21-2 | L P M V P E E | P E D L R G H L E S | D M F S S P L E T D | S M D P F G L V T G | L S A V R S P S F E | K | (SEQ ID NO:348)
| FGF19C-tail/21-3 | L P M V P E E | P E D L R G H L E S | D L F S S P L E T D | S M D P F G L V T G | L E A V R S P S F E | K | (SEQ ID NO:349)
| FGF19C-tail/21-4 | L P M V P E E | P E D L R G H L E S | D M F S S P L E T D | S M D P F G M L V T G | L E A V R S P S F E | K | (SEQ ID NO:350)
| FGF19C-tail/21-5 | L P M V P E E | P E D L R G H P E S | D M F S S P L E T D | S M D P F G L V T G | L E A V R S P S F E | K | (SEQ ID NO:351)
| FGF19C-tail/21-6 | L P M V P E E | P E D L R H L E S | D M F S S P L E T D | S M D P F G L V T G | L E A V R S P S F E | K | (SEQ ID NO:352)
| FGF19C-tail/21-7 | L P M V P E E | P E D L R L G H L E S | D M F S S P L E T D | S M D P F G L V T G | L E A V R S P S F E | K | (SEQ ID NO:353)
| FGF19C-tail/21-8 | L P M V P A E | P E D L R G H L E S | D M F S S P L E T D | S M D P F G L V T G | L E A V R S P S F E | K | (SEQ ID NO:354)
| FGF19C-tail/21-9 | L P M P P E E | P E D L R G H L E S | D M F S S P L E T D | S M D P F G L V T G | L E A V R S P S F E | K | (SEQ ID NO:355)
| FGF19C-tail/21-10 | L P L V P E E | P E D L R G H L E S | D M F S S P L E T D | S M D P F G L V T G | L E A V R S P S F E | K | (SEQ ID NO:355)
| FGF19C-tail/21-11 | L G M V P E E | P E D L R G H L E S | D M F S S P L E T D | S M D P F G L V T G | L E A V R S P S F E | K | (SEQ ID NO:356)
| FGF21C-tail (168) | P G L P P A L | P E - - - - - | I L A P P D V G | S S D P L S M V - G | P S Q G R S P S Y A | S | |

FIG. 13

SEQUENCE LISTING

<160> NUMBER OF SEQ ID NOS: 356

<210> SEQ ID NO 1
<211> LENGTH: 155
<212> TYPE: PRT
<213> ORGANISM: Homo sapiens

<400> SEQUENCE: 1

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly

```
                    35                  40                  45
Thr Arg Asp Arg Ser Asp Gln His Ile Gln Leu Gln Leu Ser Ala Glu
 50                  55                  60
Ser Val Gly Glu Val Tyr Ile Lys Ser Thr Glu Thr Gly Gln Tyr Leu
 65                  70                  75                  80
Ala Met Asp Thr Asp Gly Leu Leu Tyr Gly Ser Gln Thr Pro Asn Glu
                     85                  90                  95
Glu Cys Leu Phe Leu Glu Arg Leu Glu Glu Asn His Tyr Asn Thr Tyr
                    100                 105                 110
Ile Ser Lys Lys His Ala Glu Lys Asn Trp Phe Val Gly Leu Lys Lys
                    115                 120                 125
Asn Gly Ser Cys Lys Arg Gly Pro Arg Thr His Tyr Gly Gln Lys Ala
                    130                 135                 140
Ile Leu Phe Leu Pro Leu Pro Val Ser Ser Asp
145                 150                 155

<210> SEQ ID NO 2
<211> LENGTH: 155
<212> TYPE: PRT
<213> ORGANISM: Papio anubis

<400> SEQUENCE: 2

Met Ala Glu Gly Glu Ile Thr Thr Phe Thr Ala Leu Thr Glu Lys Phe
  1                   5                  10                  15
Asn Leu Pro Pro Ala Asn Tyr Lys Lys Pro Lys Leu Leu Tyr Cys Ser
                     20                  25                  30
Asn Gly Gly His Phe Leu Arg Ile Leu Pro Asp Gly Thr Val Asp Gly
                     35                  40                  45
Thr Arg Asp Arg Ser Asp Gln His Ile Gln Leu Gln Leu Ser Ala Glu
 50                  55                  60
Ser Val Gly Glu Val Tyr Ile Lys Ser Thr Glu Thr Gly Gln Tyr Leu
 65                  70                  75                  80
Ala Met Asp Thr Asp Gly Leu Leu Tyr Gly Ser Gln Thr Pro Asn Glu
                     85                  90                  95
Glu Cys Leu Phe Leu Glu Arg Leu Glu Glu Asn His Tyr Asn Thr Tyr
                    100                 105                 110
Ile Ser Lys Lys His Ala Glu Lys Asn Trp Phe Val Gly Leu Lys Lys
                    115                 120                 125
Asn Gly Ser Cys Lys Arg Gly Pro Arg Thr His Tyr Gly Gln Lys Ala
                    130                 135                 140
Ile Leu Phe Leu Pro Leu Pro Val Ser Ser Asp
145                 150                 155

<210> SEQ ID NO 3
<211> LENGTH: 155
<212> TYPE: PRT
<213> ORGANISM: Pongo abelii

<400> SEQUENCE: 3

Met Ala Glu Gly Glu Ile Thr Thr Phe Thr Ala Leu Thr Glu Lys Phe
  1                   5                  10                  15
Asn Leu Pro Pro Gly Asn Tyr Lys Lys Pro Lys Leu Leu Tyr Cys Ser
                     20                  25                  30
Asn Gly Gly His Phe Leu Arg Ile Leu Pro Asp Gly Thr Val Asp Gly
                     35                  40                  45
Thr Arg Asp Arg Ser Asp Gln His Ile Gln Leu Gln Leu Ser Ala Glu
```

```
                    50                  55                  60
Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 4
<211> LENGTH: 155
<212> TYPE: PRT
<213> ORGANISM: Callithrix jacchus

<400> SEQUENCE: 4

Met Ala Glu Gly Glu Ile Thr Thr Phe Thr Ala Leu Thr Glu Lys Phe
  1               5                  10                  15

Asp Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
         50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 5
<211> LENGTH: 155
<212> TYPE: PRT
<213> ORGANISM: Equus caballus

<400> SEQUENCE: 5

Met Ala Glu Gly Glu Ile Thr Thr Phe Thr Ala Leu Thr Glu Lys Phe
  1               5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
         50                  55                  60

Ser Val Gly Glu Val Tyr Ile Lys Ser Thr Glu Thr Gly Gln Tyr Leu
```

65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 6
<211> LENGTH: 155
<212> TYPE: PRT
<213> ORGANISM: Pan troglodytes

<400> SEQUENCE: 6

Met Ala Glu Gly Glu Ile Thr Thr Phe Thr Ala Leu Thr Glu Lys Phe
1               5                   10                  15

Asn Leu Pro Ser Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 7
<211> LENGTH: 155
<212> TYPE: PRT
<213> ORGANISM: Loxodonta africana

<400> SEQUENCE: 7

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Gly Thr Glu Thr Gly Gln Tyr Leu
65                  70                  75                  80

Ala Met Asp Thr Asp Gly Leu Leu Tyr Gly Ser Gln Thr Pro Asn Glu

```
                    85                  90                  95

Glu Cys Leu Phe Leu Glu Arg Leu Glu Glu Asn His Tyr Asn Thr Tyr
                   100                 105                 110

Thr Ser Lys Lys His Ala Glu Lys Asn Trp Phe Val Gly Leu Lys Lys
                   115                 120                 125

Asn Gly Ser Cys Lys Arg Gly Pro Arg Thr His Tyr Gly Gln Lys Ala
                   130                 135                 140

Ile Leu Phe Leu Pro Leu Pro Val Ser Ser Asp
145                 150                 155

<210> SEQ ID NO 8
<211> LENGTH: 155
<212> TYPE: PRT
<213> ORGANISM: Canis lupus familiaris

<400> SEQUENCE: 8

Met Ala Glu Gly Glu Ile Thr Thr Phe Thr Ala Leu Thr Glu Lys Phe
1               5                   10                  15

Asn Leu Pro Pro Gly Asn Tyr Met Lys Pro Lys Leu Leu Tyr Cys Ser
                    20                  25                  30

Asn Gly Gly His Phe Leu Arg Ile Leu Pro Asp Gly Thr Val Asp Gly
                    35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                    85                  90                  95

Glu Cys Leu Phe Leu Glu Arg Leu Glu Glu Asn His Tyr Asn Thr Tyr
                   100                 105                 110

Thr Ser Lys Lys His Ala Glu Lys Asn Trp Phe Val Gly Leu Lys Lys
                   115                 120                 125

Asn Gly Ser Cys Lys Arg Gly Pro Arg Thr His Tyr Gly Gln Lys Ala
                   130                 135                 140

Ile Leu Phe Leu Pro Leu Pro Val Ser Ser Asp
145                 150                 155

<210> SEQ ID NO 9
<211> LENGTH: 155
<212> TYPE: PRT
<213> ORGANISM: Ailuropoda melanoleuca

<400> SEQUENCE: 9

Met Ala Glu Gly Glu Ile Thr Thr Phe Thr Ala Leu Thr Glu Lys Phe
1               5                   10                  15

Asn Leu Pro Ala Gly Asn Tyr Lys Lys Pro Lys Leu Leu Tyr Cys Ser
                    20                  25                  30

Asn Gly Gly His Phe Leu Arg Ile Leu Pro Asp Gly Thr Val Asp Gly
                    35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                    85                  90                  95

Glu Cys Leu Phe Leu Glu Arg Leu Glu Glu Asn His Tyr Asn Thr Tyr
```

```
                    100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 10
<211> LENGTH: 155
<212> TYPE: PRT
<213> ORGANISM: Saimiri boliviensis boliviensis

<400> SEQUENCE: 10

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 11
<211> LENGTH: 155
<212> TYPE: PRT
<213> ORGANISM: Sus scrofa

<400> SEQUENCE: 11

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Ser Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
```

```
              115                 120                 125
Asn Gly Ser Cys Lys Arg Gly Pro Arg Thr His Tyr Gly Gln Lys Ala
            130                 135                 140
Ile Leu Phe Leu Pro Leu Pro Val Ser Ser Asp
145                 150                 155

<210> SEQ ID NO 12
<211> LENGTH: 155
<212> TYPE: PRT
<213> ORGANISM: Otolemur garnettii

<400> SEQUENCE: 12

Met Ala Glu Gly Glu Ile Thr Thr Phe Thr Ala Leu Thr Glu Lys Phe
1               5                   10                  15
Asn Leu Pro Leu Gly Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Gln Asp Arg Ser Asp Gln His Ile Gln Leu Gln Leu Ser Ala Glu
    50                  55                  60
Ser Val Gly Glu Val Tyr Ile Lys Ser Thr Gln Thr Gly Gln Tyr Leu
65                  70                  75                  80
Ala Met Asp Ser Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
            100                 105                 110
Val Ser Lys Lys His Ala Glu Lys Asn Trp Phe Val Gly Leu Lys Lys
        115                 120                 125
Asn Gly Ser Cys Lys Arg Gly Pro Arg Thr His Tyr Gly Gln Lys Ala
    130                 135                 140
Ile Leu Phe Leu Pro Leu Pro Val Ser Ser Asp
145                 150                 155

<210> SEQ ID NO 13
<211> LENGTH: 155
<212> TYPE: PRT
<213> ORGANISM: Rhinolophus ferrumequinum

<400> SEQUENCE: 13

Met Ala Glu Gly Glu Val Thr Thr Phe Thr Ala Leu Thr Glu Lys Phe
1               5                   10                  15
Asn Leu Pro Thr Gly Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Arg Asp Lys Ser Asp Gln His Ile Gln Leu Gln Leu Ser Ala Glu
    50                  55                  60
Ser Val Gly Glu Val Tyr Ile Lys Ser Thr Glu Ser Gly Gln Tyr Leu
65                  70                  75                  80
Ala Met Asp Ser Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
            100                 105                 110
Thr Ser Lys Lys His Ala Glu Lys Asn Trp Phe Val Gly Leu Lys Lys
        115                 120                 125
Asn Gly Ser Cys Lys Arg Gly Pro Arg Thr His Tyr Gly Gln Lys Ala
```

```
        130                 135                 140
Ile Leu Phe Leu Pro Leu Pro Val Ser Ser Asp
145                 150                 155

<210> SEQ ID NO 14
<211> LENGTH: 155
<212> TYPE: PRT
<213> ORGANISM: Sorex araneus

<400> SEQUENCE: 14

Met Ala Glu Gly Glu Ile Thr Thr Phe Gly Ala Leu Met Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly His Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 15
<211> LENGTH: 155
<212> TYPE: PRT
<213> ORGANISM: Oryctolagus cuniculus

<400> SEQUENCE: 15

Met Ala Glu Gly Glu Val Thr Thr Phe Thr Ala Leu Thr Glu Lys Phe
1               5                   10                  15

Asn Leu Pro Ala Gly Asn Tyr Lys Leu Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
```

<210> SEQ ID NO 16
<211> LENGTH: 155
<212> TYPE: PRT
<213> ORGANISM: Cricetulus griseus

<400> SEQUENCE: 16

Met Ala Glu Gly Glu Ile Thr Thr Phe Ser Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Arg
65                  70                  75                  80

Asn Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 17
<211> LENGTH: 155
<212> TYPE: PRT
<213> ORGANISM: Sarcophilus harrisii

<400> SEQUENCE: 17

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Thr Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155

```
<210> SEQ ID NO 18
<211> LENGTH: 155
<212> TYPE: PRT
<213> ORGANISM: Mus musculus

<400> SEQUENCE: 18
```

| | | | | | | | | | | | | | | |
|---|---|---|---|---|---|---|---|---|---|---|---|---|---|---|
|Met|Ala|Glu|Gly|Glu|Ile|Thr|Thr|Phe|Ala|Ala|Leu|Thr|Glu|Arg|Phe|
|1| | | |5| | | | |10| | | | |15| |

| | | | | | | | | | | | | | | |
|---|---|---|---|---|---|---|---|---|---|---|---|---|---|---|
|Asn|Leu|Pro|Leu|Gly|Asn|Tyr|Lys|Lys|Pro|Lys|Leu|Leu|Tyr|Cys|Ser|
| | | |20| | | | |25| | | | |30| | |

| | | | | | | | | | | | | | | |
|---|---|---|---|---|---|---|---|---|---|---|---|---|---|---|
|Asn|Gly|Gly|His|Phe|Leu|Arg|Ile|Leu|Pro|Asp|Gly|Thr|Val|Asp|Gly|
| | | |35| | | | |40| | | | |45| | |

| | | | | | | | | | | | | | | |
|---|---|---|---|---|---|---|---|---|---|---|---|---|---|---|
|Thr|Arg|Asp|Arg|Ser|Asp|Gln|His|Ile|Gln|Leu|Gln|Leu|Ser|Ala|Glu|
| |50| | | | |55| | | | |60| | | | |

| | | | | | | | | | | | | | | |
|---|---|---|---|---|---|---|---|---|---|---|---|---|---|---|
|Ser|Ala|Gly|Glu|Val|Tyr|Ile|Lys|Gly|Thr|Glu|Thr|Gly|Gln|Tyr|Leu|
|65| | | | |70| | | | |75| | | | |80|

| | | | | | | | | | | | | | | |
|---|---|---|---|---|---|---|---|---|---|---|---|---|---|---|
|Ala|Met|Asp|Thr|Glu|Gly|Leu|Leu|Tyr|Gly|Ser|Gln|Thr|Pro|Asn|Glu|
| | | | |85| | | | |90| | | | |95| |

| | | | | | | | | | | | | | | |
|---|---|---|---|---|---|---|---|---|---|---|---|---|---|---|
|Glu|Cys|Leu|Phe|Leu|Glu|Arg|Leu|Glu|Glu|Asn|His|Tyr|Asn|Thr|Tyr|
| | | |100| | | | |105| | | | |110| | |

| | | | | | | | | | | | | | | |
|---|---|---|---|---|---|---|---|---|---|---|---|---|---|---|
|Thr|Ser|Lys|Lys|His|Ala|Glu|Lys|Asn|Trp|Phe|Val|Gly|Leu|Lys|Lys|
| | | |115| | | | |120| | | | |125| | |

| | | | | | | | | | | | | | | |
|---|---|---|---|---|---|---|---|---|---|---|---|---|---|---|
|Asn|Gly|Ser|Cys|Lys|Arg|Gly|Pro|Arg|Thr|His|Tyr|Gly|Gln|Lys|Ala|
| | | |130| | | | |135| | | | |140| | |

| | | | | | | | | |
|---|---|---|---|---|---|---|---|---|
|Ile|Leu|Phe|Leu|Pro|Leu|Pro|Val|Ser|Ser|Asp|
|145| | | | |150| | | | |155|

```
<210> SEQ ID NO 19
<211> LENGTH: 154
<212> TYPE: PRT
<213> ORGANISM: Cavia porcellus

<400> SEQUENCE: 19
```

| | | | | | | | | | | | | | | |
|---|---|---|---|---|---|---|---|---|---|---|---|---|---|---|
|Met|Ala|Glu|Gly|Glu|Ile|Thr|Thr|Phe|Ala|Ala|Leu|Thr|Glu|Lys|Phe|
|1| | | |5| | | | |10| | | | |15| |

| | | | | | | | | | | | | | | |
|---|---|---|---|---|---|---|---|---|---|---|---|---|---|---|
|Asn|Leu|Pro|Pro|Gly|Asn|Tyr|Lys|Lys|Pro|Lys|Leu|Leu|Tyr|Cys|Ser|
| | | |20| | | | |25| | | | |30| | |

| | | | | | | | | | | | | | | |
|---|---|---|---|---|---|---|---|---|---|---|---|---|---|---|
|Asn|Gly|Gly|His|Phe|Leu|Arg|Ile|Leu|Pro|Asp|Gly|Thr|Val|Asp|Gly|
| | | |35| | | | |40| | | | |45| | |

| | | | | | | | | | | | | | | |
|---|---|---|---|---|---|---|---|---|---|---|---|---|---|---|
|Thr|Arg|Asp|Arg|Ser|Asp|Gln|His|Ile|Gln|Leu|Gln|Leu|Ser|Ala|Glu|
| |50| | | | |55| | | | |60| | | | |

| | | | | | | | | | | | | | | |
|---|---|---|---|---|---|---|---|---|---|---|---|---|---|---|
|Gly|Val|Gly|Glu|Val|Tyr|Ile|Gln|Ser|Thr|Glu|Thr|Gly|Gln|Tyr|Leu|
|65| | | | |70| | | | |75| | | | |80|

| | | | | | | | | | | | | | | |
|---|---|---|---|---|---|---|---|---|---|---|---|---|---|---|
|Ala|Met|Asp|Thr|Asp|Gly|Leu|Leu|Tyr|Gly|Ser|Gln|Thr|Pro|Ser|Glu|
| | | | |85| | | | |90| | | | |95| |

| | | | | | | | | | | | | | | |
|---|---|---|---|---|---|---|---|---|---|---|---|---|---|---|
|Glu|Cys|Leu|Phe|Leu|Glu|Arg|Leu|Glu|Glu|Asn|His|Tyr|Asn|Thr|Tyr|
| | | |100| | | | |105| | | | |110| | |

| | | | | | | | | | | | | | | |
|---|---|---|---|---|---|---|---|---|---|---|---|---|---|---|
|Thr|Ser|Lys|Lys|His|Val|Glu|Lys|Asn|Trp|Phe|Val|Gly|Leu|Lys|Lys|
| | | |115| | | | |120| | | | |125| | |

| | | | | | | | | | | | | | | |
|---|---|---|---|---|---|---|---|---|---|---|---|---|---|---|
|Asn|Gly|Ser|Cys|Lys|Arg|Gly|Pro|Arg|Thr|His|Tyr|Gly|Gln|Lys|Ala|
| | | |130| | | | |135| | | | |140| | |

| | | | | | | | |
|---|---|---|---|---|---|---|---|
|Ile|Leu|Phe|Leu|Pro|Leu|Pro|Val|Ser|Asp|
|145| | | | |150| | | | |

```
<210> SEQ ID NO 20
<211> LENGTH: 155
<212> TYPE: PRT
```

-continued

<213> ORGANISM: Monodelphis domestica

<400> SEQUENCE: 20

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Thr Glu
    50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Lys Gly Pro Arg Thr His Tyr Gly Gln Lys Ala
    130                 135                 140

Ile Leu Phe Leu Pro Leu Pro Val Ser Ser Glu
145                 150                 155

<210> SEQ ID NO 21
<211> LENGTH: 155
<212> TYPE: PRT
<213> ORGANISM: Desmodus rotundus

<400> SEQUENCE: 21

Met Ala Glu Gly Glu Val Thr Thr Phe Thr Ala Leu Thr Glu Lys Phe
1               5                   10                  15

Asn Leu Pro Leu Glu Ser Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Gly Ser Gly Gln Tyr Leu
65                  70                  75                  80

Ala Met Asp Ser Ala Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Asn Ser Asp
145                 150                 155

<210> SEQ ID NO 22
<211> LENGTH: 155
<212> TYPE: PRT
<213> ORGANISM: Bos taurus

<400> SEQUENCE: 22

```
Met Ala Glu Gly Glu Thr Thr Phe Thr Ala Leu Thr Glu Lys Phe
1               5                  10                  15

Asn Leu Pro Leu Gly Asn Tyr Lys Pro Lys Leu Leu Tyr Cys Ser
            20                  25                  30

Asn Gly Gly Tyr Phe Leu Arg Ile Leu Pro Asp Gly Thr Val Asp Gly
        35                  40                  45

Thr Lys Asp Arg Ser Asp Gln His Ile Gln Leu Gln Leu Cys Ala Glu
    50                  55                  60

Ser Ile Gly Glu Val Tyr Ile Lys Ser Thr Glu Thr Gly Gln Phe Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys His Trp Phe Val Gly Leu Lys Lys
                115                 120                 125

Asn Gly Arg Ser Lys Leu Gly Pro Arg Thr His Phe Gly Gln Lys Ala
    130                 135                 140

Ile Leu Phe Leu Pro Leu Pro Val Ser Ser Asp
145                 150                 155
```

<210> SEQ ID NO 23
<211> LENGTH: 155
<212> TYPE: PRT
<213> ORGANISM: Ornithorhynchus anatinus

<400> SEQUENCE: 23

```
Met Ala Glu Gly Glu Ile Thr Thr Phe Thr Ala Leu Met Glu Lys Phe
1               5                  10                  15

Asp Leu Pro Leu Gly Asn Tyr Lys Lys Pro Arg Leu Leu Tyr Cys Ser
            20                  25                  30

Asn Gly Gly Tyr Phe Leu Arg Ile Gln Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly His Tyr Leu
65                  70                  75                  80

Ala Met Asp Thr Glu Gly Leu Leu Tyr Gly Ser Gln Ala Pro Ser Glu
                85                  90                  95

Asp Cys Leu Phe Leu Glu Arg Leu Glu Glu Asn His Tyr Asn Thr Tyr
                100                 105                 110

Val Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ala Ser Asp
145                 150                 155
```

<210> SEQ ID NO 24
<211> LENGTH: 155
<212> TYPE: PRT
<213> ORGANISM: Taeniopygia guttata

<400> SEQUENCE: 24

```
Met Ala Glu Gly Glu Ile Thr Thr Phe Ser Ala Leu Thr Glu Lys Phe
1               5                  10                  15
```

```
Asn Leu Pro Pro Gly Asn Tyr Lys Pro Lys Leu Leu Tyr Cys Ser
             20                  25                  30

Asn Gly Gly His Phe Leu Arg Ile Leu Pro Asp Gly Thr Val Asp Gly
         35                  40                  45

Thr Arg Asp Arg Ser Asp Gln His Ile Gln Leu Gln Leu Ser Ala Glu
     50                  55                  60

Ser Val Gly Val Val His Ile Gln Ser Thr Gln Ser Gly Gln Tyr Leu
 65                  70                  75                  80

Ala Met Asp Thr Asn Gly Leu Leu Tyr Gly Ser Gln Leu Pro Pro Gly
                 85                  90                  95

Glu Cys Leu Phe Leu Glu Arg Leu Glu Glu Asn His Tyr Asn Thr Tyr
            100                 105                 110

Val Ser Lys Met His Ala Asp Lys Asn Trp Phe Val Gly Leu Lys Lys
            115                 120                 125

Asn Gly Thr Ser Lys Leu Gly Pro Arg Thr His Tyr Gly Gln Lys Ala
    130                 135                 140

Ile Leu Phe Leu Pro Leu Pro Val Ala Ala Asp
145                 150                 155

<210> SEQ ID NO 25
<211> LENGTH: 155
<212> TYPE: PRT
<213> ORGANISM: Dasypus novemcinctus

<400> SEQUENCE: 25

Met Ala Glu Gly Glu Ile Thr Thr Phe Met Ala Leu Met Glu Lys Phe
1               5                   10                  15

Asn Leu Pro Leu Glu Asn Tyr Lys His Pro Arg Leu Leu Tyr Cys Arg
             20                  25                  30

Asn Gly Gly His Phe Leu Arg Ile Leu Pro Asp Gly Thr Val Asp Gly
         35                  40                  45

Thr Arg Asp Arg Ser Asp Gln His Ile Gln Leu Gln Leu Ser Ala Glu
     50                  55                  60

Ser Val Gly Glu Val Tyr Ile Lys Ser Ala Glu Thr Gly Gln Tyr Leu
 65                  70                  75                  80

Ala Met Asp Thr Asp Gly Leu Leu Tyr Gly Ser Glu Thr Pro Ser Glu
                 85                  90                  95

Glu Cys Leu Phe Met Glu Lys Leu Glu Glu Asn Asn Tyr Asn Thr Tyr
            100                 105                 110

Ile Ser Lys Lys His Ala Glu Lys Lys Trp Phe Val Gly Leu Lys Lys
            115                 120                 125

Asp Gly Ser Ser Lys Arg Gly Pro Gln Thr His Tyr Gly Gln Lys Ala
    130                 135                 140

Ile Leu Phe Leu Pro Leu Pro Val Ser Ser Asp
145                 150                 155

<210> SEQ ID NO 26
<211> LENGTH: 155
<212> TYPE: PRT
<213> ORGANISM: Xenopus Silurana tropicalis

<400> SEQUENCE: 26

Met Ala Glu Gly Asp Ile Thr Thr Phe Asn Pro Ile Ala Glu Ser Phe
1               5                   10                  15

Ser Leu Pro Ile Gly Asn Tyr Lys Lys Pro Lys Leu Leu Tyr Cys Asn
             20                  25                  30
```

```
Asn Gly Gly Tyr Phe Leu Arg Ile Leu Pro Asp Gly Val Val Asp Gly
            35                  40                  45

Thr Arg Asp Arg Asp Asp Leu Tyr Ile Thr Leu Lys Leu Ser Ala Gln
    50                  55                  60

Ser Gln Gly Glu Val His Ile Lys Ser Thr Glu Thr Gly Ser Tyr Leu
65                  70                  75                  80

Ala Met Asp Ser Ser Gly Gln Leu Tyr Gly Thr Leu Thr Pro Asn Glu
                85                  90                  95

Glu Ser Leu Phe Leu Glu Thr Leu Glu Glu Asn His Tyr Asn Thr Tyr
                100                 105                 110

Lys Ser Lys Lys Tyr Ala Glu Asn Asn Trp Phe Val Gly Ile Lys Lys
            115                 120                 125

Asn Gly Ala Ser Lys Lys Gly Ser Arg Thr His Tyr Gly Gln Lys Ala
        130                 135                 140

Ile Leu Phe Leu Pro Leu Pro Ala Ser Pro Asp
145                 150                 155

<210> SEQ ID NO 27
<211> LENGTH: 155
<212> TYPE: PRT
<213> ORGANISM: Heterocephalus glaber

<400> SEQUENCE: 27

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
    50                  55                  60

Gly Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Ala Ser Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 28
<211> LENGTH: 155
<212> TYPE: PRT
<213> ORGANISM: Pteropus alecto

<400> SEQUENCE: 28

Met Ala Glu Gly Glu Val Thr Thr Phe Thr Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45
```

```
Thr Arg Asp Lys Ser Asp Gln His Ile Gln Leu Gln Leu Ser Ala Glu
            50                  55                  60

Ser Val Gly Glu Val Tyr Ile Lys Ser Thr Glu Ser Gly Gln Tyr Leu
 65                  70                  75                  80

Ala Met Asp Ser Asp Gly Leu Leu Tyr Gly Ser Gln Thr Pro Asp Glu
                85                  90                  95

Asp Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 29
<211> LENGTH: 155
<212> TYPE: PRT
<213> ORGANISM: Tupaia chinensis

<400> SEQUENCE: 29

Met Ala Glu Gly Glu Ile Thr Thr Phe Ala Ala Leu Thr Glu Lys Phe
 1                5                  10                  15

Asp Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Thr Ala Glu
            50                  55                  60

Asn Val Gly Glu Val Tyr Ile Lys Ser Thr Glu Thr Gly Gln Tyr Leu
 65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Ala Leu Lys Lys
            115                 120                 125

Asn Gly Ser Cys Lys Leu Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 30
<211> LENGTH: 155
<212> TYPE: PRT
<213> ORGANISM: Columba livia

<400> SEQUENCE: 30

Met Ala Glu Gly Glu Ile Thr Thr Phe Thr Ala Leu Thr Glu Lys Phe
 1                5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Lys Val Asp Gly
            35                  40                  45

Thr Arg Asp Arg Ser Asp Gln His Ile Gln Leu Gln Leu Ser Ala Glu
            50                  55                  60
```

```
Ser Val Gly Glu Val Tyr Ile Lys Ser Thr Gln Ser Gly Gln Tyr Leu
 65                  70                  75                  80

Ala Met Asp Pro Thr Gly Leu Leu Tyr Gly Ser Gln Leu Leu Gly Glu
                 85                  90                  95

Glu Cys Leu Phe Leu Glu Arg Ile Glu Glu Asn His Tyr Asn Thr Tyr
            100                 105                 110

Val Ser Lys Lys His Ala Asp Lys Asn Trp Phe Val Gly Leu Lys Lys
        115                 120                 125

Asn Gly Asn Ser Lys Leu Gly Pro Arg Thr His Tyr Gly Gln Lys Ala
    130                 135                 140

Ile Leu Phe Leu Pro Leu Pro Val Ser Ala Asp
145                 150                 155
```

<210> SEQ ID NO 31
<211> LENGTH: 155
<212> TYPE: PRT
<213> ORGANISM: Ovis aries

<400> SEQUENCE: 31

```
Met Ala Glu Gly Glu Thr Thr Thr Phe Arg Ala Leu Thr Glu Lys Phe
  1               5                  10                  15

Asn Leu Pro Leu Gly Asn Tyr Lys Lys Pro Lys Leu Leu Tyr Cys Ser
                 20                  25                  30

Asn Gly Gly Tyr Phe Leu Arg Ile Leu Pro Asp Gly Arg Val Asp Gly
             35                  40                  45

Thr Lys Asp Arg Ser Asp Gln His Ile Gln Leu Gln Leu Tyr Ala Glu
 50                  55                  60

Ser Ile Gly Glu Val Tyr Ile Lys Ser Thr Glu Thr Gly Gln Phe Leu
 65                  70                  75                  80

Ala Met Asp Thr Asn Gly Leu Leu Tyr Gly Ser Gln Thr Pro Ser Glu
                 85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Ile Gly Leu Lys Lys
        115                 120                 125

Asn Gly Ser Ser Lys Leu Gly Pro Arg Thr His Phe Gly Gln Lys Ala
    130                 135                 140

Ile Leu Phe Leu Pro Leu Pro Val Ser Ser Asp
145                 150                 155
```

<210> SEQ ID NO 32
<211> LENGTH: 155
<212> TYPE: PRT
<213> ORGANISM: Gallus gallus

<400> SEQUENCE: 32

```
Met Ala Glu Gly Glu Ile Thr Thr Phe Thr Ala Leu Thr Glu Arg Phe
  1               5                  10                  15

Gly Leu Pro Leu Gly Asn Tyr Lys Lys Pro Lys Leu Leu Tyr Cys Ser
                 20                  25                  30

Asn Gly Gly His Phe Leu Arg Ile Leu Pro Asp Gly Lys Val Asp Gly
             35                  40                  45

Thr Arg Asp Arg Ser Asp Gln His Ile Gln Leu Gln Leu Ser Ala Glu
 50                  55                  60

Asp Val Gly Glu Val Tyr Ile Lys Ser Thr Ala Ser Gly Gln Tyr Leu
 65                  70                  75                  80
```

Ala Met Asp Thr Asn Gly Leu Leu Tyr Gly Ser Gln Leu Pro Gly Glu
                85                  90                  95

Glu Cys Leu Phe Leu Glu Arg Leu Glu Asn His Tyr Asn Thr Tyr
            100                 105                 110

Ile Ser Lys Lys His Ala Asp Lys Asn Trp Phe Val Gly Leu Lys Lys
        115                 120                 125

Asn Gly Asn Ser Lys Leu Gly Pro Arg Thr His Tyr Gly Gln Lys Ala
130                 135                 140

Ile Leu Phe Leu Pro Leu Pro Val Ser Ala Asp
145                 150                 155

<210> SEQ ID NO 33
<211> LENGTH: 98
<212> TYPE: PRT
<213> ORGANISM: Vicugna pacos

<400> SEQUENCE: 33

Gln Leu Gln Leu Ser Ala Glu Ser Val Gly Glu Val Tyr Ile Lys Ser
1               5                   10                  15

Thr Glu Thr Gly Gln Tyr Leu Ala Met Asp Thr Asp Gly Leu Leu His
            20                  25                  30

Gly Ser Gln Thr Pro Asn Glu Glu Cys Leu Phe Leu Glu Arg Leu Glu
        35                  40                  45

Glu Asn His Tyr Asn Thr Tyr Thr Ser Lys Lys His Ala Glu Lys Asn
    50                  55                  60

Trp Phe Val Gly Leu Lys Lys Asn Gly Ser Cys Lys Arg Gly Pro Arg
65                  70                  75                  80

Thr His Tyr Gly Gln Lys Ala Ile Leu Phe Leu Pro Leu Pro Val Ser
                85                  90                  95

Ser Asp

<210> SEQ ID NO 34
<211> LENGTH: 155
<212> TYPE: PRT
<213> ORGANISM: Anolis carolinensis

<400> SEQUENCE: 34

Met Ala Glu Gly Glu Ile Thr Thr Phe Thr Ala Leu Thr Glu Arg Phe
1               5                   10                  15

Ala Leu Pro Met Glu Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Met Asp Arg Asn Asp Ser Tyr Ile Gln Leu Leu Leu Thr Ala Glu
    50                  55                  60

Asp Val Gly Val Val Tyr Ile Lys Gly Thr Glu Thr Gly Gln Tyr Leu
65                  70                  75                  80

Ala Met Asp Ala Asn Gly His Leu Tyr Gly Ser Gln Leu Pro Thr Glu
                85                  90                  95

Glu Cys Leu Phe Val Glu Thr Leu Glu Glu Asn His Tyr Asn Thr Tyr
            100                 105                 110

Thr Ser Lys Met His Gly Asp Lys Lys Trp Tyr Val Gly Leu Lys Lys
        115                 120                 125

Asn Gly Lys Gly Lys Leu Gly Pro Arg Thr His Arg Gly Gln Lys Ala
130                 135                 140

```
Ile Leu Phe Leu Pro Leu Pro Val Ser Pro Asp
145                 150                 155
```

<210> SEQ ID NO 35
<211> LENGTH: 155
<212> TYPE: PRT
<213> ORGANISM: Otolemur garnettii

<400> SEQUENCE: 35

```
Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Gln Asp Arg Ser Asp Gln His Ile Gln Leu Gln Leu Ser Ala Glu
        50                  55                  60

Ser Val Gly Glu Val Tyr Ile Lys Ser Thr Gln Thr Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Val Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155
```

<210> SEQ ID NO 36
<211> LENGTH: 155
<212> TYPE: PRT
<213> ORGANISM: Felis catus

<400> SEQUENCE: 36

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155
```

<210> SEQ ID NO 37
<211> LENGTH: 155
<212> TYPE: PRT
<213> ORGANISM: Pelodiscus sinensis

<400> SEQUENCE: 37

Met Ala Glu Gly Glu Ile Thr Thr Phe Thr Ala Leu Thr Glu Lys Phe
1               5                   10                  15

Asn Leu Pro Leu Gly Asn Tyr Lys Asn Pro Lys Leu Leu Tyr Cys Ser
            20                  25                  30

Asn Gly Gly Tyr Phe Leu Arg Ile His Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly Gln Phe Leu
65                  70                  75                  80

Ala Met Asp Ala Asn Gly Leu Leu Tyr Gly Ser Leu Ser Pro Ser Glu
                85                  90                  95

Glu Cys Leu Phe Leu Glu Arg Met Glu Glu Asn His Tyr Asn Thr Tyr
            100                 105                 110

Ile Ser Lys Lys His Ala Asp Lys Asn Trp Phe Val Gly Leu Lys Lys
        115                 120                 125

Asn Gly Ser Cys Lys Leu Gly Pro Arg Thr His Tyr Gly Gln Lys Ala
    130                 135                 140

Val Leu Phe Leu Pro Leu Pro Val Ser Ala Asp
145                 150                 155

<210> SEQ ID NO 38
<211> LENGTH: 155
<212> TYPE: PRT
<213> ORGANISM: Latimeria chalumnae

<400> SEQUENCE: 38

Met Ala Glu Asp Lys Ile Thr Thr Leu Lys Ala Leu Ala Glu Lys Phe
1               5                   10                  15

Asn Leu Pro Met Gly Asn Tyr Lys Lys Ala Lys Leu Leu Tyr Cys Ser
            20                  25                  30

Asn Gly Gly Tyr Phe Leu Arg Ile Pro Pro Asp Gly Lys Val Glu Gly
        35                  40                  45

Ile Arg Glu Arg Ser Asp Lys Tyr Ile Gln Leu Gln Met Asn Ala Glu
    50                  55                  60

Ser Leu Gly Met Val Ser Ile Lys Gly Val Glu Ala Gly Gln Tyr Leu
65                  70                  75                  80

Ala Met Asn Thr Asn Gly Leu Leu Tyr Gly Ser Gln Ser Leu Thr Glu
                85                  90                  95

Glu Cys Leu Phe Met Glu Lys Met Glu Glu Asn His Tyr Asn Thr Tyr
            100                 105                 110

Arg Ser Lys Thr His Ala Asp Lys Asn Trp Tyr Val Gly Ile Arg Lys
        115                 120                 125

Asn Gly Ser Ile Lys Pro Gly Pro Arg Thr His Ile Gly Gln Lys Ala
    130                 135                 140

Val Leu Phe Leu Pro Leu Pro Ala Ser Ser Asp
145                 150                 155

<210> SEQ ID NO 39
<211> LENGTH: 155

```
<212> TYPE: PRT
<213> ORGANISM: Tursiops truncatus

<400> SEQUENCE: 39

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ala Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 40
<211> LENGTH: 155
<212> TYPE: PRT
<213> ORGANISM: Mustela putorius furo

<400> SEQUENCE: 40

Met Ala Glu Gly Glu Ile Thr Thr Phe Thr Ala Leu Met Glu Lys Phe
1               5                   10                  15

Asn Leu Pro Ala Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 41
<211> LENGTH: 155
<212> TYPE: PRT
<213> ORGANISM: Nomascus leucogenys
```

-continued

```
<400> SEQUENCE: 41

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 42
<211> LENGTH: 155
<212> TYPE: PRT
<213> ORGANISM: Gorilla gorilla

<400> SEQUENCE: 42

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 43
<211> LENGTH: 155
<212> TYPE: PRT
<213> ORGANISM: Erinaceus europaeus

<400> SEQUENCE: 43

Met Ala Glu Gly Glu Ile Thr Thr Phe Thr Ala Leu Thr Glu Lys Phe
```

```
1               5                   10                  15
Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 44
<211> LENGTH: 91
<212> TYPE: PRT
<213> ORGANISM: Procavia capensis

<400> SEQUENCE: 44

Met Ala Glu Gly Glu Ile Thr Thr Phe Thr Ala Leu Thr Glu Lys Phe
1               5                   10                  15

Asn Leu Pro Leu Glu Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Gly Thr Glu Thr Gly Gln Tyr Leu
65                  70                  75                  80

Ala Met Asp Thr Asp Gly Leu Leu Tyr Gly Ser
                85                  90

<210> SEQ ID NO 45
<211> LENGTH: 114
<212> TYPE: PRT
<213> ORGANISM: Dipodomys ordii

<400> SEQUENCE: 45

Met Ala Glu Gly Glu Ile Thr Thr Phe Thr Ala Leu Thr Glu Arg Phe
1               5                   10                  15

Gln Leu Gln Leu Ser Ala Glu Ser Val Gly Glu Val Tyr Ile Lys Ser
                20                  25                  30

Thr Glu Thr Gly Gln Tyr Leu Ala Met Asp Ala Asp Gly Leu Leu Tyr
            35                  40                  45

Gly Ser Gln Thr Pro Asp Glu Glu Cys Leu Phe Leu Glu Arg Leu Glu
        50                  55                  60

Glu Asn His Tyr Asn Thr Tyr Ile Ala Lys Lys His Ala Glu Lys Asn
65                  70                  75                  80

Trp Phe Val Gly Leu Lys Lys Asn Gly Ser Cys Lys Arg Gly Pro Arg
```

```
                    85                  90                  95

Thr His Tyr Gly Gln Lys Ala Ile Leu Phe Leu Pro Leu Pro Val Ser
            100                 105                 110

Ser Asp

<210> SEQ ID NO 46
<211> LENGTH: 92
<212> TYPE: PRT
<213> ORGANISM: Petromyzon marinus

<400> SEQUENCE: 46

Met Glu Val Gly His Ile Gly Thr Leu Pro Val Val Pro Ala Gly Pro
1               5                   10                  15

Val Phe Pro Gly Ser Phe Lys Glu Pro Arg Arg Leu Tyr Cys Arg Ser
                20                  25                  30

Ala Gly His His Leu Gln Ile Leu Gly Asp Gly Thr Val Ser Gly Thr
            35                  40                  45

Gln Asp Glu Asn Glu Pro His Ala Val Leu Gln Leu Gln Ala Val Arg
    50                  55                  60

Arg Gly Val Val Thr Ile Arg Gly Leu Cys Ala Glu Arg Phe Leu Ala
65                  70                  75                  80

Met Ser Thr Glu Gly His Leu Tyr Gly Ala Val Arg
                85                  90

<210> SEQ ID NO 47
<211> LENGTH: 98
<212> TYPE: PRT
<213> ORGANISM: Echinops telfairi

<400> SEQUENCE: 47

Gln Leu Lys Leu Val Ala Glu Ser Val Gly Val Val Tyr Ile Lys Ser
1               5                   10                  15

Ile Lys Thr Gly Gln Tyr Leu Ala Met Asn Pro Asp Gly Leu Leu Tyr
                20                  25                  30

Gly Ser Glu Thr Pro Glu Glu Cys Leu Phe Leu Glu Thr Leu Glu
            35                  40                  45

Glu Asn His Tyr Thr Thr Phe Lys Ser Lys Lys His Val Glu Lys Asn
    50                  55                  60

Trp Phe Val Gly Leu Arg Lys Asn Gly Arg Val Lys Ile Gly Pro Arg
65                  70                  75                  80

Thr His Gln Gly Gln Lys Ala Ile Leu Phe Leu Pro Leu Pro Val Ser
                85                  90                  95

Ser Asp

<210> SEQ ID NO 48
<211> LENGTH: 155
<212> TYPE: PRT
<213> ORGANISM: Macaca mulatta

<400> SEQUENCE: 48

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
```

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 49
<211> LENGTH: 155
<212> TYPE: PRT
<213> ORGANISM: Pteropus vampyrus

<400> SEQUENCE: 49

Met Ala Glu Gly Glu Val Thr Thr Phe Thr Ala Leu Thr Glu Arg Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Lys Ser Asp Gln His Ile Gln Leu Gln Leu Ser Ala Glu
        50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asp Glu
                85                  90                  95

Asp Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 50
<211> LENGTH: 155
<212> TYPE: PRT
<213> ORGANISM: Myotis lucifugus

<400> SEQUENCE: 50

Met Ala Glu Gly Glu Val Thr Thr Phe Thr Ala Leu Thr Glu Arg Phe
1               5                   10                  15

Asn Leu Pro Leu Glu Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Ser Gly Gln Tyr Leu

```
                65                  70                  75                  80
Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
               100                 105                 110

Thr Ser Lys Lys His Ala Glu Lys Asn Trp Phe Val Gly Leu Lys Lys
               115                 120                 125

Asn Gly Ser Cys Lys Arg Gly Pro Arg Thr His Tyr Gly Gln Lys Ala
           130                 135                 140

Ile Leu Phe Leu Pro Leu Pro Val Ser Ser Asp
145                 150                 155

<210> SEQ ID NO 51
<211> LENGTH: 155
<212> TYPE: PRT
<213> ORGANISM: Microcebus murinus

<400> SEQUENCE: 51

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Ala Gly Glu Val Tyr Ile Lys Ser Thr Gln Thr Gly Arg Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
               100                 105                 110

Val Ser Lys Lys His Ala Glu Lys Asn Trp Phe Val Gly Leu Lys Lys
               115                 120                 125

Asn Gly Ser Cys Lys Arg Gly Pro Arg Thr His Tyr Gly Gln Lys Ala
           130                 135                 140

Ile Leu Phe Leu Pro Leu Pro Val Ser Ser Asp
145                 150                 155

<210> SEQ ID NO 52
<211> LENGTH: 144
<212> TYPE: PRT
<213> ORGANISM: Ochotona princeps

<400> SEQUENCE: 52

Met Ala Glu Gly Glu Val Thr Thr Phe Ser Ala Leu Thr Glu Lys Phe
1               5                   10                  15

Asn Leu Pro Gly Gly Asn Tyr Lys Leu Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Leu His Glu Val Phe Ile Lys Ser Thr Glu
        50                  55                  60

Thr Gly Gln Tyr Leu Ala Met Asp Thr Asp Gly Leu Leu Tyr Gly Ser
65                  70                  75                  80

Gln Thr Pro Ser Glu Glu Cys Leu Phe Leu Glu Arg Leu Glu Glu Asn
```

```
                    85                  90                  95
His Tyr Asn Thr Tyr Thr Ser Lys Lys His Ala Glu Lys Asn Trp Phe
                100                 105                 110
Val Gly Ile Lys Lys Asn Gly Ser Cys Lys Arg Gly Pro Arg Thr His
                115                 120                 125
Tyr Gly Gln Lys Ala Ile Leu Phe Leu Pro Leu Pro Val Ser Ser Asp
            130                 135                 140
```

<210> SEQ ID NO 53
<211> LENGTH: 155
<212> TYPE: PRT
<213> ORGANISM: Rattus norvegicus

<400> SEQUENCE: 53

```
Met Ala Glu Gly Glu Ile Thr Thr Phe Ala Ala Leu Thr Glu Arg Phe
1               5                   10                  15
Asn Leu Pro Leu Gly Asn Tyr Lys Lys Pro Lys Leu Leu Tyr Cys Ser
                20                  25                  30
Asn Gly Gly His Phe Leu Arg Ile Leu Pro Asp Gly Thr Val Asp Gly
            35                  40                  45
Thr Arg Asp Arg Ser Asp Gln His Ile Gln Leu Gln Leu Ser Ala Glu
        50                  55                  60
Ser Ala Gly Glu Val Tyr Ile Lys Gly Thr Glu Thr Gly Gln Tyr Leu
65                  70                  75                  80
Ala Met Asp Thr Glu Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
                100                 105                 110
Thr Ser Lys Lys His Ala Glu Lys Asn Trp Phe Val Gly Leu Lys Lys
            115                 120                 125
Asn Gly Ser Cys Lys Arg Gly Pro Arg Thr His Tyr Gly Gln Lys Ala
        130                 135                 140
Ile Leu Phe Leu Pro Leu Pro Val Ser Ser Asp
145                 150                 155
```

<210> SEQ ID NO 54
<211> LENGTH: 155
<212> TYPE: PRT
<213> ORGANISM: Choloepus hoffmanni

<400> SEQUENCE: 54

```
Met Ala Glu Gly Glu Ile Thr Thr Phe Thr Ala Leu Met Glu Lys Phe
1               5                   10                  15
Asn Leu Pro Pro Gly Asn Tyr Met Lys Pro Lys Leu Leu Tyr Cys Ser
                20                  25                  30
Asn Gly Gly His Phe Leu Arg Ile Leu Pro Asp Gly Thr Val Asp Gly
            35                  40                  45
Thr Arg Asp Arg Ser Asp Leu His Ile Gln Leu Gln Leu Ser Ala Glu
        50                  55                  60
Ser Val Gly Glu Val Tyr Ile Lys Ser Ala Glu Thr Gly Gln Tyr Leu
65                  70                  75                  80
Ala Met Asp Thr Gly Gly Leu Leu Tyr Gly Ser Gln Thr Pro Ser Glu
                85                  90                  95
Glu Cys Leu Phe Leu Glu Arg Leu Glu Glu Asn His Tyr Asn Thr Tyr
                100                 105                 110
Val Ser Lys Lys His Ala Glu Lys Asn Trp Phe Val Gly Leu Lys Lys
```

```
            115                 120                 125

Asn Gly Ser Ser Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 55
<211> LENGTH: 155
<212> TYPE: PRT
<213> ORGANISM: Ictidomys tridecemlineatus

<400> SEQUENCE: 55

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 56
<211> LENGTH: 155
<212> TYPE: PRT
<213> ORGANISM: Tarsius syrichta

<400> SEQUENCE: 56

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
```

```
        130             135                 140

Ile Leu Phe Leu Pro Leu Pro Val Ser Ser Asp
145                 150                 155

<210> SEQ ID NO 57
<211> LENGTH: 155
<212> TYPE: PRT
<213> ORGANISM: Tupaia belangeri

<400> SEQUENCE: 57

Met Ala Glu Gly Glu Ile Thr Thr Phe Ala Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Thr Ala Glu
    50                  55                  60

Asn Val Gly Glu Val Tyr Ile Lys Ser Thr Glu Thr Gly Gln Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Ala Leu Lys Lys
        115                 120                 125

Asn Gly Ser Cys Lys Leu Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 58
<211> LENGTH: 56
<212> TYPE: PRT
<213> ORGANISM: Meleagris gallopavo

<400> SEQUENCE: 58

Met Ala Glu Gly Glu Ile Thr Thr Phe Thr Ala Leu Thr Glu Arg Phe
1               5                   10                  15

Gly Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His
    50                  55

<210> SEQ ID NO 59
<211> LENGTH: 155
<212> TYPE: PRT
<213> ORGANISM: Macropus eugenii

<400> SEQUENCE: 59

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45
```

```
Thr Arg Asp Arg Asn Asp Gln His Ile Gln Leu Gln Leu Ser Ala Glu
        50                  55                  60

Ser Val Gly Glu Val Tyr Ile Lys Ser Thr Glu Ser Gly Gln Tyr Leu
65                  70                  75                  80

Ala Met Asp Thr Asn Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155

<210> SEQ ID NO 60
<211> LENGTH: 147
<212> TYPE: PRT
<213> ORGANISM: Danio rerio

<400> SEQUENCE: 60

Met Thr Glu Ala Asp Ile Ala Val Lys Ser Ser Pro Arg Asp Tyr Lys
1               5                   10                  15

Lys Leu Thr Arg Leu Tyr Cys Met Asn Gly Gly Phe His Leu Gln Ile
            20                  25                  30

Leu Ala Asp Gly Thr Val Ala Gly Ala Ala Asp Glu Asn Thr Tyr Ser
        35                  40                  45

Ile Leu Arg Ile Lys Ala Thr Ser Pro Gly Val Val Ile Glu Gly
    50                  55                  60

Ser Glu Thr Gly Leu Tyr Leu Ser Met Asn Glu His Gly Lys Leu Tyr
65                  70                  75                  80

Ala Ser Ser Leu Val Thr Asp Glu Ser Tyr Phe Leu Glu Lys Met Glu
                85                  90                  95

Glu Asn His Tyr Asn Thr Tyr Gln Ser Gln Lys His Gly Glu Asn Trp
            100                 105                 110

Tyr Val Gly Ile Lys Lys Asn Gly Lys Met Lys Arg Gly Pro Arg Thr
        115                 120                 125

His Ile Gly Gln Lys Ala Ile Phe Phe Leu Pro Arg Gln Val Glu Gln
    130                 135                 140

Glu Glu Asp
145

<210> SEQ ID NO 61
<211> LENGTH: 468
<212> TYPE: DNA
<213> ORGANISM: Homo sapiens

<400> SEQUENCE: 61
atggctgaag ggaaatcac caccttcaca gccctgaccg agaagtttaa tctgcctcca      60
gggaattaca gaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac caatgaggaa tgtttgttc     300 ctggaaaggc tggaggagaa ccattacaac acctatatat ccaagaagca tgcagagaag     360
```

```
aattggtttg ttggcctcaa gaagaatggg agctgcaaac gcggtcctcg gactcactat    420
ggccagaaag caatcttgtt tctcccctg ccagtctctt ctgattaa                  468

<210> SEQ ID NO 62
<211> LENGTH: 468
<212> TYPE: DNA
<213> ORGANISM: Olive Baboon

<400> SEQUENCE: 62
atggctgaag gggaaatcac cacgttcaca gccctgaccg agaagtttaa tctgcctcca     60
gcgaattaca agaagcccaa actgctctac tgtagcaacg ggggacactt cttgaggatc    120
cttccggatg gcacagtgga tgggacaagg acaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctacatat ccaagaagca cgcagagaag    360
aattggtttg ttggcctcaa gaagaatgga agctgcaaac gtggtcctcg gactcactat    420
ggccagaaag caatcttgtt tcttcccctg ccagtctctt ctgattaa                 468

<210> SEQ ID NO 63
<211> LENGTH: 468
<212> TYPE: DNA
<213> ORGANISM: Sumatran orangutan

<400> SEQUENCE: 63
atggctgaag gggaaatcac caccttcaca gccctgaccg agaagtttaa tctgcctcca     60
gggaattaca agaagcccaa actcctctac tgtagcaacg ggggccactt cttgaggatc    120
cttccggatg gcacagtgga tgggacaagg acaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctcccctg ccagtctctt ccgattaa                 468

<210> SEQ ID NO 64
<211> LENGTH: 468
<212> TYPE: DNA
<213> ORGANISM: White-tufted-ear marmoset

<400> SEQUENCE: 64
atggctgaag gggaaatcac caccttcaca gccctgaccg agaagtttga tctgcctcca     60
gggaattaca agaagcccaa actcctctac tgtagcaatg ggggccactt cttgaggatc    120
cttccggatg gcacagtgga tgggacaagg acaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggagaggc tggaggagaa ccattacaac acctatatat ccaagaaaca tgcagagaag    360
aattggtttg tcggcctcaa gaagaatgga agctgtaaac gtggtcctcg gactcactat    420
ggtcagaaag cgatcttgtt tctcccctg ccagtttctt ctgattaa                 468

<210> SEQ ID NO 65
```

-continued

```
<211> LENGTH: 468
<212> TYPE: DNA
<213> ORGANISM: Horse

<400> SEQUENCE: 65
atggctgaag gagaaatcac aaccttcacg gccctgaccg agaagtttaa tctgcctcca      60
gggaattaca agaagcccaa actcctctac tgtagcaatg ggggccactt cctgaggatc     120
cttccagatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct gttgtacggc tcacagacac aaacgagga atgtttgttc      300 ctggaaaggc tggaggaaaa ccattacaac acctacacat ccaagaagca tgcagagaag     360
aactggttcg ttggtctcaa gaagaatggg agctgcaaac gcggtcctcg gactcactat     420
gggcagaaag caatcttgtt tcttcccctg cccgtctcct ctgactaa                   468

<210> SEQ ID NO 66
<211> LENGTH: 468
<212> TYPE: DNA
<213> ORGANISM: Chimpanzee

<400> SEQUENCE: 66
atggctgaag gggaaatcac caccttcaca gccctgaccg agaagtttaa tctgccttca      60
gggaattaca agaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac aaatgagga atgtttgttc      300 ctggaacggc tggaggagaa ccattacaac acctatatat ccaagaagca tgcagagaag     360
aattggtttg ttggcctcaa gaagaatgga agctgcaaac gcggtcctcg gactcactat     420
ggccagaaag caatcttgtt tctccccctg ccagtctctt ccgattaa                   468

<210> SEQ ID NO 67
<211> LENGTH: 408
<212> TYPE: DNA
<213> ORGANISM: Elephant

<400> SEQUENCE: 67
atggccgaag gggaaatcac aactttcaca gccctgacag agaagttcaa cctgcctcca      60
gggaattaca agaagcccaa actcctctac tgtagcaatg gaggtcactt cttaaggatc     120
cttccagatg gcacagtgga tggcaccagg gacaggagtg accagcacat tcagctgcag     180
ctcagtgcgg aaagcgtggg ggaggtgtat ataaagggca ccgagactgg ccagtacttg     240
gccatggaca ccgacgggct tttatacggc tcacagacac aaatgagga atgtttgttc      300 ctggaaaggc tggaggaaaa ccattacaac acctacacat ccaagaagca cgcagagaag     360
ggccagaaag caatcttgtt tctccccctg ccagtctcct ctgattaa                   408

<210> SEQ ID NO 68
<211> LENGTH: 468
<212> TYPE: DNA
<213> ORGANISM: Dog

<400> SEQUENCE: 68
atggctgaag gggaaatcac aaccttcact gccctgacgg agaagtttaa tctgcctccg      60
gggaattaca tgaagcccaa actcctctac tgtagcaacg ggggccactt cctgaggatc     120
```

```
cttccagatg gcacagtgga tgggacaagg gacaggagcg accagcacat tcagctgcag    180
ctcagcgcgg aaagcgtggg ggaggtgtat ataaagagca ccgagactgg ccagtacttg    240
gccatggaca ccgatgggct tctgtacggc tcacagacac cgaatgagga atgtttgttc    300
ctggaaaggc tggaggaaaa ccattacaac acctacacat ccaagaagca tgcagaaaaa    360
aattggtttg ttggtctcaa gaagaatgga agctgcaaac gcggtcctcg gactcactat    420
ggtcaaaaag caattttgtt tctcccccctg ccagtgtcct ctgattaa              468

<210> SEQ ID NO 69
<211> LENGTH: 468
<212> TYPE: DNA
<213> ORGANISM: Giant panda

<400> SEQUENCE: 69
atggctgaag gggagatcac aaccttcacc gccctgacgg agaagtttaa tctgcctgcg     60
gggaattaca agaagcccaa actcctctac tgtagcaacg ggggccactt cctgaggatc    120
cttccagatg gcacagtgga cgggacgagg gacaggagcg accagcacat tcaactgcag    180
ctcagcgcgg aaagcgtagg ggaggtgtac ataaagagca ccgagaccgg ccagtacttg    240
gccatggaca ccgatgggct tctgtacggc tcacagacac caaatgagga atgtttgttc    300
ctggaaaggc tggaggaaaa ccattacaac acctacacat ccaagaagca cgcggagaag    360
aattggtttg ttggtctcaa gaagaatgga agctgcaaac gtggtcctcg gactcactat    420
ggccagaaag caattctgtt tctcccccctg ccagtctcct ctgattaa              468

<210> SEQ ID NO 70
<211> LENGTH: 468
<212> TYPE: DNA
<213> ORGANISM: Bolivian squirrel monkey

<400> SEQUENCE: 70
atggctgaag gggaaatcac caccttcaca gccctgaccg agaagtttga tctgcctcca     60
gggaattaca agaagcccaa actcctctac tgtagcaacg ggggccactt ccttgaggatc   120 cttccggatg gcacagtgga tgggaccagg gacaggagca tcttcacat tcagctgcag    180 ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaaaca cgcagagaag    360
aattggtttg ttggcctcaa gaagaatgga agctgcaagc gcggtcctcg gactcactat    420
ggccagaaag caatcttgtt tctcccccctg ccagtctctt ctgattaa              468

<210> SEQ ID NO 71
<211> LENGTH: 468
<212> TYPE: DNA
<213> ORGANISM: Pig

<400> SEQUENCE: 71
atggctgaag gcgaaatcac aaccttcacg gccctgaccg agaagtttaa tctgcctcca     60
ggaaattaca agaagcccaa gctcctctac tgcagcaacg ggggccattt cctcaggatc    120
cttccagatg gcacagtgga tgggaccagg gacaggagcg accagcacat tcagctgcag    180
ctcagtgcgg aaagcgtggg ggaggtgtat ataaagagta cggagactgg ccagtacttg    240
gccatggaca ccagcgggct tttgtacggc tcacagacac ccagtgagga gtgtttgttc    300
```

```
ctggagaggc tggaggaaaa ccattacaat acctacacat ccaagaagca cgcagagaag    360
aactggttcg ttggcctcaa gaagaatgga agctgcaaac gcggtcctcg gactcactat    420
ggccagaaag ccatcctgtt tctcccctg ccagtatcct cggattaa                  468

<210> SEQ ID NO 72
<211> LENGTH: 468
<212> TYPE: DNA
<213> ORGANISM: Small-eared galago

<400> SEQUENCE: 72
atggctgaag gggaaatcac aaccttcaca gccctcacag agaagtttaa tctgcctcta     60
ggaaattaca agaagcccaa gctcctctac tgtagcaacg ggggtcactt tctgaggatc    120
ctgccggatg gcaccgtgga tgggacacaa gacaggagcg accagcacat tcagctgcag    180
ctcagtgcgg aaagcgtggg ggaggtgtat ataaagagta cccagactgg ccagtacttg    240
gccatggact ccgacgggct tttatacggc tcacaaacac caaatgagga atgcctgttc    300
ctggaacggc tggaggaaaa ccattacaac acctatgtgt ccaagaagca cgccgagaag    360
aattggtttg tcggtctcaa gaagaacgga agttgcaaac gtggtcctcg gactcactac    420
ggccagaaag caatcttgtt tctcccctg ccagtctcct ctgattaa                  468

<210> SEQ ID NO 73
<211> LENGTH: 468
<212> TYPE: DNA
<213> ORGANISM: Greater horseshoe bat

<400> SEQUENCE: 73
ttaatcagag gagactggca gggggagaaa caggattgct ttctggccat agtgagtccg     60
aggaccgcgc ttgcagcttc cattcttctt gagcccaacg aaccaattct tttctgcgtg    120
cttcttggac gtgtaggtgt tgtaatggtt ttcctccagc cttcccagga acagacattc    180
ctcatttggt gtctgtgagc cgtacaaaag cccgtcggag tccatggcca agtactggcc    240
actctcggtg ctctttatat acacctcccc cacgctttcc gcactgagct gcagctgaat    300
gtgctggtca ctcttgtccc ttgtcccatc cactgtgcca tctggaagga tcctcaggaa    360 gtggccccg ttgctgcagt agagaagttt gggtttcttg taattccctg taggcagatt    420
aaacttctca gtaagggctg tgaacgtggt gacttcccct tcggccat                 468

<210> SEQ ID NO 74
<211> LENGTH: 468
<212> TYPE: DNA
<213> ORGANISM: European shrew

<400> SEQUENCE: 74
ctagtcggag gagacgggca gggggagaaa caagatcgct ttctggccgt agtgagtccg     60
gggaccacgc ttgcagcttc cgttcttctt cagaccaaca aaccaattct tctcggcatg    120
cttcttggag gtataggtgt tgtaatggtt ttcctccagc ctttccagaa acagacattc    180
ctcattcggt gtttgtgagc cgtataaaag cccgtcggtg tccatggcca agtaatggcc    240
agtctccgtg ctctttatat acacctcccc cacgctttcc gcactgagct gcagctgaat    300
gtgctggtcg ctgcggtccc tggtcccatc cactgtgccg tccgggagga tgcgcaggaa    360 gtggccccg ttgctgcagt acaggagttt gggcttcttg tagttccctg gtggcaggtt    420
aaacttctcc gtgagggccc caaggtggt gatctccccc tcggccat                  468
```

<210> SEQ ID NO 75
<211> LENGTH: 468
<212> TYPE: DNA
<213> ORGANISM: Rabbit

<400> SEQUENCE: 75

| | | | | | | |
|---|---|---|---|---|---|---|
| atggctgagg | gggaggtcac | caccttcaca | gccctgaccg | agaagttcaa | cctgcctgca | 60 |
| gggaactaca | agttgcccaa | actcctctac | tgcagcaacg | ggggccactt | cctgaggatc | 120 |
| ctgccggacg | gcactgtgga | cggcacaagg | gacaggagcg | accagcacat | tcagctgcag | 180 |
| ctgagtgcgg | aaagcgtggg | ggaggtgtat | ataaagagta | cggagaccgg | ccagtacttg | 240 |
| gccatggaca | ccgacggcct | tttatacggc | tcgcaaacgc | ccagtgagga | gtgtttgttc | 300 |
| ctggaacggc | tggaggagaa | ccactacaac | acctacacgt | ccaagaagca | cgccgagaag | 360 |
| aactggttcg | tggggctgaa | gaaaaacggg | agctgcaagc | gcgtcctcg | gactcactac | 420 |
| ggccagaaag | ccatcttgtt | cctcccctg | ccggtctcct | ccgactaa | | 468 |

<210> SEQ ID NO 76
<211> LENGTH: 468
<212> TYPE: DNA
<213> ORGANISM: Chinese hamster

<400> SEQUENCE: 76

| | | | | | | |
|---|---|---|---|---|---|---|
| atggctgaag | gagaaatcac | caccttctca | gccctgacag | agagatttaa | tctgcctcca | 60 |
| ggaaactaca | agaagcccaa | actgctctac | tgcagcaacg | ggggccactt | cttgaggatc | 120 |
| cttccagatg | gcacagtgga | tgggacaagg | gacaggagtg | accagcacat | tcagctgcag | 180 |
| ctgagtgcgg | aaagcgcggg | cgaagtgtat | ataaagggta | cagagacagg | ccagtacagg | 240 |
| aacatggaca | cggatggcct | tttatacggc | tcacagacac | caaatgaaga | atgcctgttc | 300 |
| ctggaaggc | tggaagaaaa | ccattacaac | acttatacat | ccaagaagca | cgcagagaag | 360 |
| aactggtttg | tgggcctcaa | gaaaaacggg | agctgcaagc | gtggtcctcg | gactcactat | 420 |
| ggccagaaag | caatcttgtt | tctccccctg | cctgtatctt | ctgactag | | 468 |

<210> SEQ ID NO 77
<211> LENGTH: 468
<212> TYPE: DNA
<213> ORGANISM: Tasmanian devil

<400> SEQUENCE: 77

| | | | | | | |
|---|---|---|---|---|---|---|
| atggccgaag | gggagatcac | aaccttcaca | gccctgaccg | aaagatttaa | tctgccactg | 60 |
| gggaattaca | agaagcccaa | gcttctctac | tgtagcaatg | ggggccactt | tttgaggatt | 120 |
| cttcctgatg | gtaaagtgga | tgggacaagg | gacagaaatg | atcaacacat | tcaactgcaa | 180 |
| ctaagcgcgg | aaagcgtggg | tgaggtgtat | ataaagagca | ctgagtctgg | ccagtatttg | 240 |
| gctatggaca | ccgatggact | tttatacggc | tcacagacac | ccactgaaga | atgcttgttc | 300 |
| ctggagagat | tggaggagaa | tcattacaac | acctacatat | caaagaagca | tgcggagaaa | 360 |
| aattggtttg | tgggcctcaa | gaaaaatgga | agctgcaaaa | gaggtcccag | gactcactat | 420 |
| ggccagaaag | ccatcctctt | ccttcccctc | cctgtgtcct | ctgagtaa | | 468 |

<210> SEQ ID NO 78
<211> LENGTH: 468
<212> TYPE: DNA
<213> ORGANISM: House mouse

<400> SEQUENCE: 78

```
atggctgaag gggagatcac aaccttcgca gccctgaccg agaggttcaa cctgcctcta      60
ggaaactaca aaaagcccaa actgctctac tgcagcaacg ggggccactt cttgaggatc     120
cttcctgatg gcaccgtgga tgggacaagg gacaggagcg accagcacat tcagctgcag     180
ctcagtgcgg aaagtgcggg cgaagtgtat ataaagggta cggagaccgg ccagtacttg     240
gccatggaca ccgaagggct tttatacggc tcgcagacac caaatgagga atgtctgttc     300
ctggaaaggc tggaagaaaa ccattataac acttacacct ccaagaagca tgcggagaag     360
aactggtttg tgggcctcaa gaagaacggg agctgtaagc gcggtcctcg gactcactat     420
ggccagaaag ccatcttgtt tctgcccctc ccggtgtctt ctgactag               468
```

<210> SEQ ID NO 79
<211> LENGTH: 465
<212> TYPE: DNA
<213> ORGANISM: Domestic guinea pig

<400> SEQUENCE: 79

```
atggctgaag gagaaatcac aacttttgca gccctgactg agaagtttaa tctgcctcca      60
gggaattata agaagcccaa actgctctac tgcagcaatg ggggccactt cctgaggatc     120
cttccagacg gcacagtgga cggcacaaga gacaggagcg accagcacat tcagctgcag     180
ctcagtgcgg aaggcgtggg ggaggtgtat atacagagca ccgagaccgg ccagtacttg     240
gccatggaca ccgacgggct tttatacggc tcacagacac caagtgagga atgcttgttc     300
ctggaaaggc tggaggaaaa ccattacaac acctacacat ccaagaagca tgtggagaag     360
aattggtttg ttggcctcaa gaagaacgga agctgcaagc gtggtcctcg gactcactat     420
ggccagaaag caatcttgtt cctcccctttg ccagtctctg attag                    465
```

<210> SEQ ID NO 80
<211> LENGTH: 468
<212> TYPE: DNA
<213> ORGANISM: Gray short-tailed opossum

<400> SEQUENCE: 80

```
atggccgaag gggagatcac aaccttcaca gccctgactg aaagatttaa cctgccactg      60
gggaattaca agaaacccaa gcttctctac tgtagcaatg ggggccattt cttgaggatc     120
cttcctgatg gcaaagtgga tgggacacgg gacagaaatg atcaacacat tcaactgcag     180
ctgagcacgg aaagtgtggg tgaggtgtat ataaagagca ctgagtctgg ccagtatttg     240
gctatggaca ccgatggact tttatatggc tcacagacac ccagtgaaga atgcttgttt     300
ctggagaggt tggaggagaa tcattacaac acctacacat cgaagaagca tgcagagaaa     360
aattggtttg ttggtctcaa gaagaatgga agctgcaaaa aggtcccag gactcactac      420 ggccagaaag ccatcctgtt ccttcccctc cctgtgtcct ctgagtaa                468
```

<210> SEQ ID NO 81
<211> LENGTH: 468
<212> TYPE: DNA
<213> ORGANISM: Common vampire bat

<400> SEQUENCE: 81

```
atggctgaag gggaagtcac cacgttcaca gctctgactg agaagtttaa tctgcctctg      60
gagagttaca agaagcccaa acttctctac tgcagcaacg gtggccactt cctgaggatc     120
cttccagatg gtacagtgga tgggacaagg gacaagagcg accagcacat tcagctgcag     180
ctcagtgcgg aaagcgtggg ggaggtgtac ataaagagca ccgggagtgg ccagtacttg     240
```

| | | |
|---|---|---|
| gccatggact ccgccgggct tttgtatggc tcacagacac caaatgagga atgtttgttc | 300 | |
| ctggaaaggc tggaggaaaa ccattacaac acctacacat ccaagaagca tgcagaaaag | 360 | |
| aattggttcg tggggctcaa gaagaatgga agctgcaagc gtggcccccg gactcattat | 420 | |
| ggccagaaag caatcttgtt tctccccctg ccagtcaact ctgattaa | 468 | |

<210> SEQ ID NO 82
<211> LENGTH: 468
<212> TYPE: DNA
<213> ORGANISM: Cattle

<400> SEQUENCE: 82

| | | |
|---|---|---|
| atggctgaag agaaaccac gaccttcacg gccctgactg agaagtttaa cctgcctcta | 60 | |
| ggcaattaca agaagcccaa gctcctctac tgcagcaacg ggggctactt cctgagaatc | 120 | |
| ctcccagatg gcacagtgga tgggacgaag acaggagcg accagcacat tcagctgcag | 180 | |
| ctctgtgcgg aaagcatagg ggaggtgtat attaagagta cggagactgg ccagttcttg | 240 | |
| gccatggaca ccgacgggct tttgtacggc tcacagacac ccaatgagga atgtttgttc | 300 | |
| ctggaaaggt tggaggaaaa ccattacaac acctacatat ccaagaagca tgcagagaag | 360 | |
| cattggttcg ttggtctcaa gaagaacgga aggtctaaac tcggtcctcg gactcacttc | 420 | |
| ggccagaaag ccatcttgtt tctccccctg ccagtctcct ctgattaa | 468 | |

<210> SEQ ID NO 83
<211> LENGTH: 468
<212> TYPE: DNA
<213> ORGANISM: Platypus

<400> SEQUENCE: 83

| | | |
|---|---|---|
| atggcggagg gtgaaatcac cacgttcaca gccctgatgg agaagttcga cctaccccctg | 60 | |
| ggcaactaca aaaagcctag gctgctctac tgcagcaatg gcggctactt cctgcgcatc | 120 | |
| cagccagacg gtaaagtgga cgggaccagg gatcggagcg atcagcacat tcaactgcag | 180 | |
| ctaagcgcgg aaagcgtggg cgaggtgtat ataagagca ccgagtctgg ccactatttg | 240 | |
| gctatggaca ccgaaggact tttatatggc tcacaggcac ccagtgaaga ctgcttgttc | 300 | |
| ctggagcggc tggaggagaa ccactataac acgtacgtgt ccaagaagca cgctgagaag | 360 | |
| aattggtttg tcggtctcaa gaagaacggg agctgcaaac gaggtccccg gactcactac | 420 | |
| ggccagaaag ccatcctctt cctcccgctc cccgtggcat ccgactag | 468 | |

<210> SEQ ID NO 84
<211> LENGTH: 468
<212> TYPE: DNA
<213> ORGANISM: Zebra finch

<400> SEQUENCE: 84

| | | |
|---|---|---|
| atggccgagg gggagatcac caccttcagc gccctgacgg agaagttcaa cctgccccccg | 60 | |
| gggaactaca agaagcccaa actgctgtac tgcagcaacg gggggcattt cctgcgcatc | 120 | |
| ctcccggacg gcaccgtgga tgcaccagg accgcagcg accagcacat tcagctccag | 180 | |
| ctgagtgcag agagcgtggg ggtggtgcac atccagagca cccagtcggg gcagtacctg | 240 | |
| gccatggaca ccaacgggct gctctacggc tcgcagctgc cacccggtga gtgtctgttc | 300 | |
| ctggaaaggc tggaggagaa ccattacaac acctacgtct ccaaaatgca cgcggacaag | 360 | |
| aactggtttg tggggctgaa gaagaacggg acaagcaagc tgggcccgcg gactcactac | 420 | |

```
ggccagaagg cgatcctgtt cctgccgctg cccgtggcgg ccgactga          468
```

<210> SEQ ID NO 85
<211> LENGTH: 468
<212> TYPE: DNA
<213> ORGANISM: Nine-banded armadillo

<400> SEQUENCE: 85

```
ttaatcagag gagactggca ggggaagaaa caagatagct ttctggccat agtgagtctg   60
aggaccacgt ttgctgcttc cgtccttctt gagaccaaca aaccatttct tctctgcatg  120
cttcttggat atgtaggtgt tgtaattgtt ttcttccagc ttttccatga acaagcattc  180
ctcacttggt gtctctgagc catataaaag cccgtcggtg tccatggcta agtactggcc  240
ggtctctgca ctctttatat acacctcccc cacgctttcc gcactgagct gcagctgaat  300
gtgttggtcg ctcctgtccc ttgtcccatc caccgtgcca tctggaagga tcctcaagaa  360
gtggcccccg tttctgcagt agaggagtct ggggtgcttg taattttcta ggggcaggtt  420
gaacttctcc atcagggcca tgaaggttgt gatctcccct tcagccat              468
```

<210> SEQ ID NO 86
<211> LENGTH: 468
<212> TYPE: DNA
<213> ORGANISM: Xenopus Silurana tropicalis

<400> SEQUENCE: 86

```
atggcagagg gagacatcac aacattcaac cccattgcag agtccttcag tcttccaatt   60
ggcaactaca agaaaccaaa acttctgtac tgtaataatg gagggtattt tttgcgcatc  120
ctcccagatg gggttgtgga tggaacaaga gacagagatg acctttacat tacactgaag  180
ttaagcgcac aaagccaagg ggaggtgcat atcaaaagca cagagacagg gagttactta  240
gccatggact ccagtggaca gttgtatgga actctcacac caaatgaaga aagcctgttt  300
ctggagacat tagaagagaa tcactataac acatacaagt caaagaagta tgcagaaaat  360
aactggtttg tggggataaa gaagaacggg gcaagcaaaa agggatcaag gactcactat  420
ggacaaaaag ccatccttt tctgccgctg ccagcatcac ctgactag               468
```

<210> SEQ ID NO 87
<211> LENGTH: 465
<212> TYPE: DNA
<213> ORGANISM: Heterocephalus glaber

<400> SEQUENCE: 87

```
atggcggaag gcgaaattac cacctttacc gcgctgaccg aaaaatttaa cctgccgccg   60
ggcaactata aaaaaccgaa actgctgtat tgcagcaacg gcggccattt tctgcgcatt  120
ctgccggatg gcaaagtgga tggcacccgc gatcgcagcg atcagcatat tcagctgcag  180
ctgagcgcgg aaggcgtggg cgaagtgtat attaaaagca ccgaaaccgg ccagtatctg  240
gcgatggata ccgatggcct gctgtatggc agccagaccg cgagcgaaga tgcctgtttt  300
ctggaacgcc tggaagaaaa ccattataac acctatatta gcaaaaaaca tgcggaaaaa  360
aactggtttg tgggcctgaa aaaaaacggc agctgcaaac gcggcccgcg cacccattat  420
ggccagaaag cgattctgtt tctgccgctg ccggtgagca gcgat                 465
```

<210> SEQ ID NO 88
<211> LENGTH: 465
<212> TYPE: DNA
<213> ORGANISM: Black flying fox

```
<400> SEQUENCE: 88
atggcggaag gcgaagtgac caccttacc gcgctgaccg aacgctttaa cctgccgccg      60
ggcaactata aaaaaccgaa actgctgtat tgcagcaacg gcggccatt tctgcgcatt      120 ctgccggatg gcaccgtgga tggcacccgc gataaaagcg atcagcatat tcagctgcag    180
ctgagcgcgg aaagcgtggg cgaagtgtat attaaaagca ccgaaagcgg ccagtatctg    240
gcgatggata gcgatggcct gctgtatggc agccagaccc cggatgaaga ttgcctgttt    300
ctggaacgcc tggaagaaaa ccattataac acctatacca gcaaaaaaca tgcggaaaaa    360
aactggtttg tgggcctgaa aaaaaacggc agctgcaaac gcggcccgcg cacccattat    420
ggccagaaag cgattctgtt tctgccgctg ccggtgagca gcgat                    465

<210> SEQ ID NO 89
<211> LENGTH: 465
<212> TYPE: DNA
<213> ORGANISM: Chinese tree shrew

<400> SEQUENCE: 89
atggcggaag gcgaaattac cacctttgcg gcgctgaccg aaaaatttga tctgccgccg    60
ggcaactata aaaaaccgaa actgctgtat tgcagcaacg gcggccatt tctgcgcatt     120 ctgccggatg gcaccgtgga tggcacccgc gatcgcagcg atcagcatat tcagctgcag   180
ctgaccgcgg aaaacgtggg cgaagtgtat attaaaagca ccgaaaccgg ccagtatctg   240
gcgatggatg cggatggcct gctgtatggc agccagaccc cgaacgaaga atgcctgttt   300
ctggaacgcc tggaagaaaa ccattataac acctatatta gcaaaaaaca tgcggaaaaa   360
aactggtttg tggcgctgaa aaaaaacggc agctgcaaac tgggcccgcg cacccattat   420
ggccagaaag cgattctgtt tctgccgctg ccggtgagca gcgat                   465

<210> SEQ ID NO 90
<211> LENGTH: 465
<212> TYPE: DNA
<213> ORGANISM: Rock pigeon

<400> SEQUENCE: 90
atggcggaag gcgaaattac cacctttacc gcgctgaccg aaaaatttaa cctgccgccg    60
ggcaactata aaaaaccgaa actgctgtat tgcagcaacg gcggccatt tctgcgcatt    120 ctgccggatg gcaaagtgga tggcacccgc gatcgcagcg atcagcatat tcagctgcag   180
ctgagcgcgg aaagcgtggg cgaagtgtat attaaaagca cccagagcgg ccagtatctg   240
gcgatggatc cgaccggcct gctgtatggc agccagctgc tgggcgaaga atgcctgttt   300
ctggaacgca ttgaagaaaa ccattataac acctatgtga gcaaaaaaca tgcggataaa   360
aactggtttg tgggcctgaa aaaaaacggc aacagcaaac tgggcccgcg cacccattat   420
ggccagaaag cgattctgtt tctgccgctg ccggtgagcg cggat                   465

<210> SEQ ID NO 91
<211> LENGTH: 468
<212> TYPE: DNA
<213> ORGANISM: Sheep

<400> SEQUENCE: 91
atggctgaag gagaaaccac aaccttcagg gccctgactg agaagtttaa cctgcctcta    60
ggcaattaca agaagcccaa gctcctctat tgcagcaacg ggggctactt cctgagaatc   120
```

```
ctcccagatg gcagagtgga tgggacgaag gacaggagcg accagcacat tcagctgcag      180
ctctatgcgg aaagcatagg ggaggtgtat attaagagta cggagactgg ccagttcttg      240
gccatggaca ccaacgggct tttgtacggc tcacaaacac ccagtgagga atgtttgttc      300
ctggaaaggc tggaggaaaa ccattataac acctacatat ccaagaagca tgcagagaag      360
aattggttca ttggtctcaa gaagaacgga agctccaaac tcggtcctcg gactcacttc      420
ggccagaaag ccatcttgtt tctcccctg ccagtttcct ctgattaa               468
```

```
<210> SEQ ID NO 92
<211> LENGTH: 468
<212> TYPE: DNA
<213> ORGANISM: Chicken

<400> SEQUENCE: 92
atggccgagg gggagataac caccttcacc gccctgaccg agcgcttcgg cctgccgctg       60
ggcaactaca agaagcccaa actcctgtac tgcagcaacg ggggccactt cctacggatc      120
ctgccggacg caaggtgga cgggacgcgg gaccggagtg accagcacat tcagctgcag      180
ctcagcgcgg aagatgtggg cgaggtctat ataaagagca cagcgtcggg gcagtacctg      240
gcaatggaca ccaacgggct cctgtatggc tcgcagctac caggcgagga gtgcttgttc      300
cttgagaggc tcgaggagaa ccattacaac acatacatct ccaaaaagca cgcagacaag      360
aactggttcg tcgggctgaa gaaaaacggg aacagcaagc tggggccgcg gactcactat      420
gggcaaaagg cgatcctctt cctcccattg ccggtgtcgg ctgactga               468
```

```
<210> SEQ ID NO 93
<211> LENGTH: 297
<212> TYPE: DNA
<213> ORGANISM: Alpaca

<400> SEQUENCE: 93
cagctgcagc tcagtgcgga aagcgtgggg gaggtgtata taaagagtac cgagactggc       60
cagtacttgg ccatggacac cgacgggctt ttgcacggct cacagacacc aaatgaggaa      120
tgtttgttcc tggaaaggct ggaggagaac cattacaaca cctacacgtc caagaagcac      180
gccgaaaaga attggtttgt tggtctcaag aagaatggaa gctgcaaacg cggtcctcgg      240
actcactacg gccagaaggc gatcttgttt ctcccttgc cagtctcctc tgattaa         297
```

```
<210> SEQ ID NO 94
<211> LENGTH: 408
<212> TYPE: DNA
<213> ORGANISM: Anole lizard

<400> SEQUENCE: 94
atggctgaag gtgaaataac aacattcaca gccttgaccg agaggtttgc tctcccaatg       60
gagaattaca agaagcccaa actcctgtat tgcagcaatg gaggccactt cctgaggatc      120
cttccagatg gaaaagtgga tggcaccatg gaccggaatg acagctatat tcagttgctg      180
ttaacagcag aagatgtggg tgtggtatat ataaaggca ctgagaccgg cagtacttg       240 gccatggatg ccaatggaca tttatatggc tcgcagttgc caacagaaga gtgtttattt      300
gtggaaacgc tggaagaaaa ccattacaat acatatacct caaagatgca tggcgataag      360
ggccaaaagg caatactttt ccttccactg ccagtatcac ctgattag                 408
```

```
<210> SEQ ID NO 95
<211> LENGTH: 468
```

<212> TYPE: DNA
<213> ORGANISM: Bushbaby

<400> SEQUENCE: 95

```
atggctgaag ggaaatcac aaccttcaca gccctcacag agaagtttaa tctgcctcta      60
ggaaattaca agaagcccaa gctcctctac tgtagcaacg ggggtcactt tctgaggatc     120
ctgccggatg gcaccgtgga tgggacacaa gacaggagcg accagcacat tcagctgcag    180
ctcagtgcgg aaagcgtggg ggaggtgtat ataaagagta cccagactgg ccagtacttg    240
gccatggact ccgacgggct tttatacggc tcacaaacac caaatgagga atgcctgttc    300
ctggaacggc tggaggaaaa ccattacaac acctatgtgt ccaagaagca cgccgagaag    360
aattggtttg tcggtctcaa gaagaacgga agttgcaaac gtggtcctcg gactcactac    420
ggccagaaag caatcttgtt ctcccccctg ccagtctcct ctgattaa                 468
```

<210> SEQ ID NO 96
<211> LENGTH: 468
<212> TYPE: DNA
<213> ORGANISM: Cat

<400> SEQUENCE: 96

```
atggctgaag ggaaatcac aaccttcacg gccctgacgg agaagttcaa tctgcctcca      60
gggaattaca agaaacccaa actcctctac tgtagcaacg ggggccactt cctgaggatc    120
cttccagatg gcacagtgga tgggacgagg acaggagcg accagcacat tcagctgcag     180
ctcagtgcgg aaagcgtggg ggaggtgtat ataaagagta ccgagactgg ccagtacttg    240
gccatggaca ccgacgggct tttgtacggc tcacagacac caaatgagga atgcttgttc    300
ctggaaaggc tggaagaaaa ccattacaac acctacacat ccaagaagca cgcagaaaag    360
aattggtttg tgggtctcaa gaagaatgga agctgcaaac gcggtccccg gactcactat    420
ggccagaagg caattttgtt ctcccccctg ccagtctcct ctgattaa                 468
```

<210> SEQ ID NO 97
<211> LENGTH: 468
<212> TYPE: DNA
<213> ORGANISM: Chinese softshell

<400> SEQUENCE: 97

```
atggctgaag ggaaataac aacgttcacc gccctgaccg aaaaattcaa ccttcccctg      60
gggaattaca agaatcccaa actcttatat tgcagcaatg gaggctactt cttgaggata    120
catccagatg gcaaagtaga tgggacaagg gaccgaagtg accaacacat tcagctgcag    180
ctaagtgcgg aaagcgtggg tgaggtatat ataagagca ctgagtctgg acagttttg      240
gctatggacg ccaatggact tttatatgga tcactgtcac cgagtgagga atgcttattc    300
ttggaaagaa tggaagaaaa tcattataac acctacatct ccaagaagca tgcagacaag    360
aactggttcg ttggcttaaa gaagaatgga agctgcaaac tggaccgcg gacgcactac     420
ggccaaaagg ccgtccttttt ccttccactg ccagtgtcag ctgattaa                468
```

<210> SEQ ID NO 98
<211> LENGTH: 468
<212> TYPE: DNA
<213> ORGANISM: Coelacanth

<400> SEQUENCE: 98

```
atggctgaag acaaaataac aacactgaag gccttggctg aaaaatttaa ccttcctatg      60
```

```
ggaaattaca agaaagcaaa actcctctac tgcagcaacg agggtatttt cctgcgaata      120
cccccagacg ggaaagtgga aggaattaga gaacgaagcg acaagtacat tcagctgcaa      180
atgaatgcag aaagtttagg catggtgtct ataaagggtg tggaggcagg gcaataccta      240
gctatgaata caaatggact cctgtatgga tctcagtctc taactgaaga atgccttttc      300
atggaaaaga tggaagaaaa ccactacaac acatacaggt ctaagacaca tgcagataaa      360
aactggtatg ttggcattag aaagaacggt agcatcaaac caggaccaag gactcacatt      420
ggccaaaagg ctgttctttt tctccctctg cctgcctcga gtgattag                  468
```

<210> SEQ ID NO 99
<211> LENGTH: 468
<212> TYPE: DNA
<213> ORGANISM: Dolphin

<400> SEQUENCE: 99

```
atggctgaag gggaaatcac aaccttcaca gccctgaccg agaagtttaa tctgcctcca       60
gggaattaca agaagcccaa actcctctac tgtagcaacg ggggccactt cctgaggatc      120
cttccagatg gcacagtgga tgggacaagg acaggagtg accagcacat tcagctgcag       180
ctcagtgcgg aaagcgtggg ggaggtgtat ataaagagta cggagactgg ccagtacttg      240
gccatggaca ccgacgggct tttgtacggc tcacagacac ccaatgagga atgtttgttc      300
ctggaaaggt tggaggaaaa ccattacaac acctacgcat ccaagaagca tgcagaaaag      360
aattggttcg ttggtctcaa gaagaacgga agctgcaaac gcggtcctcg gactcactac      420
ggccagaaag caatcttgtt tctcccctg ccagtctcct ccgattaa                    468
```

<210> SEQ ID NO 100
<211> LENGTH: 468
<212> TYPE: DNA
<213> ORGANISM: Ferret

<400> SEQUENCE: 100

```
atggctgaag gggaaatcac aaccttcaca gccctgatgg agaagtttaa tctgcctgcg       60
gggaattaca agaagcccaa actcctctac tgtagcaatg ggggccactt cctgaggatc      120
cttccagatg gcacagtgga cggcacaagg acaggagcg accagcacat tcagctgcag       180
ctcagtgcgg aaagcgtggg ggaggtgtac ataaagagta ccgagactgg ccagtacttg      240
gccatggaca ccgatgggct tttgtacggc tcacaaacac caaatgagga atgtctgttc      300
ctggaaaggc tggaggaaaa ccattacaac acctacacat ccaagaagca cgctgagaag      360
aattggtttg taggtctcaa gaagaacgga agctgcaaac gcggtcctcg gactcactat      420
ggccagaaag caattctgtt tctcccctg ccagtctcct ctgattaa                    468
```

<210> SEQ ID NO 101
<211> LENGTH: 468
<212> TYPE: DNA
<213> ORGANISM: Gibbon

<400> SEQUENCE: 101

```
atggccgaag gggaaatcac caccttcaca gccctgaccg agaagtttaa tctgcctcca       60
gggaattaca agaagcccaa actcctctac tgtagcaacg ggggccactt cttgaggatc      120
cttccggatg gcacagtgga tgggacaagg acaggagcg accagcacat tcagctgcag       180
ctcagtgcgg aaagcgtggg ggaggtgtat ataaagagta ccgagactgg ccagtacttg      240
gccatggaca ccgacgggct tttatacggc tcacagacac caaatgagga atgtttgttc      300
```

```
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ctgattaa                 468
```

<210> SEQ ID NO 102
<211> LENGTH: 468
<212> TYPE: DNA
<213> ORGANISM: Gorilla

<400> SEQUENCE: 102

```
atggctgaag gggaaatcac caccttcaca gccctgaccg agaagtttaa tctgcctcca     60
gggaattaca agaagcccaa actcctctac tgtagcaatg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ccgattaa                 468
```

<210> SEQ ID NO 103
<211> LENGTH: 468
<212> TYPE: DNA
<213> ORGANISM: Hedgehog

<400> SEQUENCE: 103

```
atggctgaag gagaaatcac caccttcacg gccctgactg agaagtttaa tctgccacta     60
gggaattaca agaagcccaa gctcctctac tgtagcaacg ggggccactt cctgaggatc    120
cttccagatg gcaccgtgga tgggacaagg gacaggagcg accagcatat tcagctgcag    180
ctcagtgcgg aaagcgtggg ggaggtgtat ataaagagta cggagactgg ccagtacttg    240
gccatggaca ccgacgggct tttatacggc tcacaaacac caaatgagga atgtctgttc    300
cttgaaaggc tggaagagaa ccattacaat acctacacat ccaagaagca tgccgagaag    360
aactggtttg ttggcctcaa gaagaatgga agctgcaagc gtggtcctcg gactcattat    420
ggccagaaag ctattttgtt tctccccctg ccagtttcct ctgattaa                 468
```

<210> SEQ ID NO 104
<211> LENGTH: 273
<212> TYPE: DNA
<213> ORGANISM: Hyrax

<400> SEQUENCE: 104

```
atggctgaag gcgaaatcac aaccttcaca gccctgactg agaagtttaa cctgccacta     60
gagaattaca agaagcccaa actcctctac tgtagcaacg gaggccactt cctgaggatc    120
cttccggacg gcacagtgga tgcaccaggg acaggagtg accagcacat tcagctgcag    180
ctcagtgcgg aaagcgtggg ggaggtgtat ataaagggca ccgagactgg ccagtacttg    240
gccatggaca ccgacgggct tttatatggc tca                                 273
```

<210> SEQ ID NO 105
<211> LENGTH: 349
<212> TYPE: DNA
<213> ORGANISM: Kangaroo rat
```

<400> SEQUENCE: 105

```
atggctgaag gggaaatcac aaccttcaca gccctgacgg aaaggtttaa ttcagctgca        60
actgagtgcg gaaagcgtgg gggaggtcta tataaagagc accgagactg ccaatactt       120
ggccatggat gccgacgggc ttttatacgg ctcacagaca cctgatgaag aatgcttgtt       180
cctggagagg ctggaagaaa atcattataa cacctacata gccaagaaac atgctgaaaa       240
gaattggttt gtcggcctca aaaagaatgg aagctgcaag cgtggtcctc ggactcacta       300
tggccagaaa gcaatcctgt tcctcccctt gcctgtctcc tctgattag                   349
```

<210> SEQ ID NO 106
<211> LENGTH: 276
<212> TYPE: DNA
<213> ORGANISM: Lamprey

<400> SEQUENCE: 106

```
atggaggtgg ccacatcgg cacgctgccc gtggtccccg cggggcccgt gttccccggc         60
agtttcaagg agccacggcg cctctactgc cgcagcgcgg ccaccacct ccagatcctg        120
ggggacggca ccgtgagtgg cacccaggac gagaacgagc ccacgccgt tctgcagctg       180
caggcggtgc gccgcggggt ggtgacgatc cgtgggctct gcgccgagag gttcctcgcc       240
atgagcacgg agggacacct gtacggggcg gtgagg                                 276
```

<210> SEQ ID NO 107
<211> LENGTH: 297
<212> TYPE: DNA
<213> ORGANISM: Lesser hedgehog tenrec

<400> SEQUENCE: 107

```
cagctgaagc tcgttgccga aagcgtgggg gtggtgtata taaagagcat caagaccggc        60
cagtacttgg ccatgaaccc cgacgggctt ttatacggct ccgagacccc agaggaagaa       120
tgcttgttcc tggaaacgct ggaggaaaac cactacacca ccttcaaatc taagaagcac       180
gtagagaaga attggttcgt tggtctccgg aagaatggaa gggtcaagat cgggcctcgg       240
actcaccaag gccagaaagc aatcttgttc ctgcccctcc ggtgtcctc tgattaa           297
```

<210> SEQ ID NO 108
<211> LENGTH: 468
<212> TYPE: DNA
<213> ORGANISM: Rhesus monkey

<400> SEQUENCE: 108

```
atggctgaag gggaaatcac cacgttcaca gccctgaccg agaagtttaa tctgcctcca        60
gggaattaca gaagcccaa actgctctac tgtagcaatg ggggccactt cttgaggatc       120
cttccggatg gcacagtgga tgggacaagg acaggagcg accagcacat tcagctgcag       180
ctcagtgcgg aaagcgtggg ggaggtgtat ataaagagta ccgagactgg ccagtacttg       240
gccatggaca ccgacgggct tttatacggc tcacagacac caaatgagga atgtttgttc       300
ctggaaaggc tggaggagaa ccattacaac acctatacat ccaagaagca cgcagagaag       360
aattggtttg ttggcctcaa gaagaatgga agctgcaaac gtggtcctcg gactcactat       420
ggccagaaag caatcttgtt cttcccctg ccagtctctt ctgattaa                     468
```

<210> SEQ ID NO 109
<211> LENGTH: 468
<212> TYPE: DNA
<213> ORGANISM: Megabat

<400> SEQUENCE: 109

```
atggccgagg gggaagtcac gacgttcacg gccctgaccg agaggtttaa cctgcctcca    60
gggaattaca agaagcccaa acttctctac tgcagcaacg ggggccactt cctgaggatc   120
ctcccagatg gcacagtgga tgggacaagg acaagagcg accagcacat tcagctgcag   180
ctcagtgcgg aaagtgtggg ggaggtgtat ataaagagca ccgagagtgg ccagtacttg   240
gccatggact ccgacgggct tttgtacggc tcacagacac cagatgagga ctgtttgttc   300
ctggaaaggc tggaggaaaa ccattacaac acctacacat ccaagaagca cgcagagaag   360
aattggtttg ttgggctcaa gaagaatgga agctgcaagc gcggtccccg gactcactac   420
ggccagaaag cgatcctgtt tctccccctg ccagtctcct ctgattag               468
```

<210> SEQ ID NO 110
<211> LENGTH: 468
<212> TYPE: DNA
<213> ORGANISM: Microbat

<400> SEQUENCE: 110

```
atggctgagg gggaagtcac cacattcacg gccctgaccg agaggttcaa tctgcctctg    60
gagaactaca agaagcccaa gcttctctac tgcagcaacg ggggccactt cctgcggatc   120
ctcccagacg gcaccgtgga cgggacgagg acaggagcg accagcacat tcagctgcag   180
ctcagtgcgg aaagcgtggg ggaggtgtat ataaagagca ccgagagtgg ccagtacttg   240
gccatggact ccgacgggct tttgtacggc tcacaaacac ccaatgagga atgtttgttc   300
ctggaaaggc tggaggagaa ccactacaac acctacacgt ccaagaagca cgcagaaaag   360
aattggttcg ttgggctcaa gaagaacgga agctgcaagc gtggtcctcg gacgcattat   420
ggccagaaag caatcttgtt tctccccctg ccagtctcct ccgattaa                468
```

<210> SEQ ID NO 111
<211> LENGTH: 468
<212> TYPE: DNA
<213> ORGANISM: Mouse lemur

<400> SEQUENCE: 111

```
atggccgaag gggagatcac aaccttcacg gccctcaccg agaagtttaa cctgcctccg    60
gggaactaca agaagcccaa gctcctctac tgcagcaacg gcggccactt cctgcgcatc   120
cttcccgacg gcaccgtgga tggcacgaga gacaggagcg accagcacat tcagctgcag   180
ctcagtgcgg aaagcgcggg ggaggtgtat ataaagagca cccagactgg ccggtacttg   240
gccatggacg ccgacgggct tttatacggc tcacaaacac caaatgagga atgtttgttc   300
ctggaaaggc tggaggaaaa ccattacaac acctacgtat ccaagaagca cgcagagaag   360
aattggtttg ttggcctcaa gaagaatgga agttgcaaac gcggccccg gactcactat   420
ggccagaaag caatcttgtt tctgcccctg ccagtctcct ctgattaa                468
```

<210> SEQ ID NO 112
<211> LENGTH: 436
<212> TYPE: DNA
<213> ORGANISM: Pika

<400> SEQUENCE: 112

```
atggccgagg gagaagtcac caccttctca gccctgacgg agaagttcaa tctgcctgga    60
ggaaactaca agttgcccaa gctcctttac tgtagcaacg gaggccactt cctgaggatc   120
```

| | |
|---|---|
| cttccagatg gcacagtgga tgggaccagg acaggagcg acctgcacag aggtgtttat | 180 |
| aaagagtacg gagactggcc agtacttggc tatggacacc gatggccttt tatatggctc | 240 |
| gcagacaccc agtgaggagt gtttgttcct ggagcggctg gaggagaacc actacaacac | 300 |
| ctacacatcc aagaagcatg ccgagaagaa ctggtttgtg ggcatcaaga gaatggaag | 360 |
| ctgcaagcgt ggtcctcgga ctcactacgg ccagaaagcc atcttgtttc tccctctgcc | 420 |
| agtctcttct gactaa | 436 |

<210> SEQ ID NO 113
<211> LENGTH: 468
<212> TYPE: DNA
<213> ORGANISM: Rat

<400> SEQUENCE: 113

| | |
|---|---|
| atggccgaag gggagatcac aacctttgca gccctgaccg agaggttcaa tctgcctcta | 60 |
| gggaactaca aaaacccaa actgctctac tgcagcaacg ggggccactt cttgaggatt | 120 |
| cttcccgatg gcaccgtgga tgggaccagg acaggagcg accagcacat tcagctgcag | 180 |
| ctcagtgcgg aaagcgcggg cgaagtgtat ataaagggta cagagactgg ccagtacttg | 240 |
| gccatggaca ccgaagggct tttatacggc tcgcagacac caaatgaaga atgcctattc | 300 |
| ctggaaaggc tagaagaaaa ccattataac acttacacat ccaagaagca cgcggagaag | 360 |
| aactggtttg tgggcctcaa gaagaacggg agttgtaagc gcggtcctcg gactcactac | 420 |
| ggccagaaag ccatcttgtt tctccccctc ccggtatctt ctgactaa | 468 |

<210> SEQ ID NO 114
<211> LENGTH: 468
<212> TYPE: DNA
<213> ORGANISM: Sloth

<400> SEQUENCE: 114

| | |
|---|---|
| atggctgaag gggaaatcac aaccttcaca gctctgatgg agaagtttaa cctgccacca | 60 |
| gggaattaca tgaagcccaa actcctctac tgtagcaacg ggggccactt cttgaggatc | 120 |
| cttccagacg gcacagtgga tgggacaagg acaggagcg acctgcacat tcagctgcag | 180 |
| ctcagtgcgg aaagcgtggg ggaggtgtat ataaagagtg cggagaccgg ccagtactta | 240 |
| gccatggaca ccgcgcgggct tttatacggc tcacagacac caagtgagga atgcctgttc | 300 |
| ctagaaaggc tggaggaaaa ccattacaac acctacgtat ccaagaagca tgcggagaag | 360 |
| aactggttcg ttggcctaaa gaagaatgga agcagcaaac gcggccccg gactcactat | 420 |
| ggccagaaag ccatcttgtt tcttcccctg ccagtctcct ctgattaa | 468 |

<210> SEQ ID NO 115
<211> LENGTH: 468
<212> TYPE: DNA
<213> ORGANISM: Squirrel

<400> SEQUENCE: 115

| | |
|---|---|
| atggctgaag gggaaatcac aaccttcaca gccctgaccg agaagttcaa tctgcctcca | 60 |
| gggaactaca agaagcccaa actgctctac tgtagcaacg gaggccactt cttgaggatc | 120 |
| cttcctgatg gcacagtgga tgggacaaga gacaggagcg accaacacat tcagctgcag | 180 |
| ctcagtgcgg aaagcgtggg ggaggtgtat ataaagagta ccgagaccgg ccagtacttg | 240 |
| gccatggaca ccgacgggct tttatatggc tcacagaccc caaatgagga atgcttattc | 300 |
| ctggaaaggc tggaggaaaa ccattacaac acgtacacat ccaagaagca tgcagagaag | 360 |

```
aattggtttg ttggcctcaa gaagaacgga agctgcaagc gcggtccccg gactcactat      420
ggccagaaag cgatcttgtt tctcccactg cctgtctcct ctgattag                    468

<210> SEQ ID NO 116
<211> LENGTH: 468
<212> TYPE: DNA
<213> ORGANISM: Tarsier

<400> SEQUENCE: 116
atggccgaag ggaaatcac aaccttcaca gccctgaccg agaagttcaa cctgccccccg       60 gggaattaca agaagcccaa actcctctac tgcagcaacg ggggccactt cttgaggatc      120
cttccggatg gcactgtgga tggaacgagg acaggagcg accagcacat tcagctgcag       180
ctcagcgcgg aaagcgtggg ggaggtgtat ataaagagta ccgagaccgg ccagtacttg      240
gccatggaca ccgacgggct tttgtacggc tcacagacac caaatgagga gtgtctgttc      300
ctggaaaggc tggaagagaa tcattacaat acctacgtgt ccaagaagca tgcggagaag      360
aattggtttg tcggcctcaa gaagaatgga agctgcaaac gcggtcctcg gactcactat      420
ggccagaaag caatcttgtt tctcccccctg ccagtttcct ctgattaa                   468

<210> SEQ ID NO 117
<211> LENGTH: 468
<212> TYPE: DNA
<213> ORGANISM: Tree shrew

<400> SEQUENCE: 117
atggctgaag ggaaatcac gaccttcgca gccctgaccg agaagtttga tctgcctcca       60
gggaattaca agaagcccaa acttctctac tgtagcaacg ggggccattt cttgaggatt      120
cttccagatg gcaccgtgga tgggacaaga gacaggagcg accagcacat tcagctgcag      180
ctcactgcgg aaaacgtggg ggaggtgtac ataaagagta cggagactgg ccagtacttg      240
gccatggacg ccgacgggct tttatatggc tcacagacac caaacgagga tgtttgttc       300 ctggaaaggc tggaggagaa ccattacaac acctacatat ccaagaagca cgcagagaag      360
aattggtttg ttgccctcaa gaagaacgga agctgcaaac tcggtcctcg gactcactat      420
ggccagaaag caatcttgtt tctcccccctg ccagtctcct ctgattaa                   468

<210> SEQ ID NO 118
<211> LENGTH: 168
<212> TYPE: DNA
<213> ORGANISM: Turkey

<400> SEQUENCE: 118
atggccgagg ggagataac caccttcaca gccctgaccg agcgcttcgg cctgccgctg       60
ggcaactaca agaagcccaa actcctgtac tgcagcaacg ggggccactt cctacggatc      120
ctgccggacg gcaaggtgga cgggacgcgg gaccggagcg accagcac                   168

<210> SEQ ID NO 119
<211> LENGTH: 468
<212> TYPE: DNA
<213> ORGANISM: Wallaby

<400> SEQUENCE: 119
atggccgaag ggagatcac aaccttcaca gccctgaccg aaagatttaa cctgccactg       60
gggaattaca agaagcccaa gcttctctac tgtagcaatg ggggccactt tttgaggatc      120
```

-continued

```
cttcctgatg gcaaagtgga tgggacaagg gacagaaatg atcaacacat tcaactgcaa      180
ctaagcgcgg aaagcgtggg tgaggtgtat ataaagagca ctgagtctgg gcagtatttg      240
gccatggaca ccaatggact tttatatggc tcacagaccc ccagcgaaga atgcttattc      300
ctggagaggt tggaggagaa tcattacaac acctacatat caaagaagca tgcggagaaa      360
aattggtttg ttggcctcaa gaagaacgga agttgcaaaa gaggtcccag gactcactat      420
ggccagaaag ccatcctatt ccttcccctc cctgtgtcct ctgagtaa                  468
```

<210> SEQ ID NO 120
<211> LENGTH: 444
<212> TYPE: DNA
<213> ORGANISM: Zebrafish

<400> SEQUENCE: 120

```
atgaccgagg ccgatattgc ggtaaagtcc agcccgcgcg actataaaaa actgacgcgg      60
ctgtactgta tgaatggagg atttcacctt cagatcctgg cggacgggac agtggctgga     120
gcagcagacg aaaacacata cagcatactg cgcataaaag caacaagtcc aggagtggtg     180
gtgatcgaag gatcagaaac aggtctttac ctctcgatga atgaacatgg caagctgtac     240
gcttcatcat tagtgacgga tgaaagttat ttcctggaga gatgtgagga aaaccactac     300
aacacatatc agtctcaaaa gcacggtgaa aactggtacg tcggaataaa aaagaacggg     360
aaaatgaaac ggggcccaag aactcacatc ggacaaaagg ccattttctt tcttccacga     420
caggtggagc aggaagagga ctga                                              444
```

<210> SEQ ID NO 121
<211> LENGTH: 155
<212> TYPE: PRT
<213> ORGANISM: Homo sapiens

<400> SEQUENCE: 121

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 122
<211> LENGTH: 155
<212> TYPE: PRT
<213> ORGANISM: Gorilla gorilla

<400> SEQUENCE: 122

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 123
<211> LENGTH: 155
<212> TYPE: PRT
<213> ORGANISM: Pongo abelii

<400> SEQUENCE: 123

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 124
<211> LENGTH: 155
<212> TYPE: PRT
<213> ORGANISM: Macaca mulatta

<400> SEQUENCE: 124

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 125
<211> LENGTH: 155
<212> TYPE: PRT
<213> ORGANISM: Pan troglodytes

<400> SEQUENCE: 125

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 126
<211> LENGTH: 155
<212> TYPE: PRT
<213> ORGANISM: Pan paniscus

<400> SEQUENCE: 126

Met Ala Ala Gly Ser Ile Thr Thr Leu Pro Ala Leu Pro Glu Asp Gly
1               5                   10                  15
```

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 127
<211> LENGTH: 155
<212> TYPE: PRT
<213> ORGANISM: Saimiri boliviensis boliviensis

<400> SEQUENCE: 127

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 128
<211> LENGTH: 155
<212> TYPE: PRT
<213> ORGANISM: Nomascus leucogenys

<400> SEQUENCE: 128

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
                115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 129
<211> LENGTH: 155
<212> TYPE: PRT
<213> ORGANISM: Equus caballus

<400> SEQUENCE: 129

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Ser Ser Trp Tyr Val Ala Leu Lys
                115                 120                 125

Arg Thr Gly Gln Tyr Lys Leu Gly Pro Lys Thr Gly Pro Gly Gln Lys
        130                 135                 140

Ala Ile Leu Phe Leu Pro Met Ser Ala Lys Ser
145                 150                 155

<210> SEQ ID NO 130
<211> LENGTH: 155
<212> TYPE: PRT
<213> ORGANISM: Bos taurus

<400> SEQUENCE: 130

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

```
Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Ser Ser Trp Tyr Val Ala Leu Lys
                115                 120                 125

Arg Thr Gly Gln Tyr Lys Leu Gly Pro Lys Thr Gly Pro Gly Gln Lys
                130                 135                 140

Ala Ile Leu Phe Leu Pro Met Ala Ser Lys Ser
145                 150                 155

<210> SEQ ID NO 131
<211> LENGTH: 155
<212> TYPE: PRT
<213> ORGANISM: Papio anubis

<400> SEQUENCE: 131

Met Ala Ala Gly Ser Ile Thr Thr Leu Pro Ala Leu Pro Glu Asp Gly
 1                5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
                 35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
                115                 120                 125

Arg Thr Gly Gln Tyr Lys Leu Gly Ser Lys Thr Gly Pro Gly Gln Lys
                130                 135                 140

Ala Ile Leu Phe Leu Pro Met Ala Ser Lys Ser
145                 150                 155

<210> SEQ ID NO 132
<211> LENGTH: 155
<212> TYPE: PRT
<213> ORGANISM: Vicugna pacos

<400> SEQUENCE: 132

Met Ala Ala Gly Ser Ile Thr Thr Leu Pro Ala Leu Pro Glu Asp Gly
 1                5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
                 35                  40                  45

Val Asp Gly Val Arg Glu Lys Ser Asp Pro His Ile Lys Leu Gln Leu
 50                  55                  60
```

```
Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 133
<211> LENGTH: 155
<212> TYPE: PRT
<213> ORGANISM: Ovis aries

<400> SEQUENCE: 133

Met Ala Ala Gly Ser Ile Thr Thr Leu Pro Ala Leu Pro Glu Asp Gly
  1               5                  10                  15

Gly Ser Ser Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 134
<211> LENGTH: 108
<212> TYPE: PRT
<213> ORGANISM: Capreolus capreolus

<400> SEQUENCE: 134

Arg Ile His Pro Asp Gly Arg Val Asp Gly Val Arg Glu Lys Ser Asp
  1               5                  10                  15

Pro His Ile Lys Leu Gln Leu Gln Ala Glu Glu Arg Gly Val Val Ser
                 20                  25                  30

Ile Lys Gly Val Cys Ala Asn Arg Tyr Leu Ala Met Lys Glu Asp Gly
            35                  40                  45

Arg Leu Leu Ala Ser Lys Cys Val Thr Asp Glu Cys Phe Phe Phe Glu
        50                  55                  60

Arg Leu Glu Ser Asn Asn Tyr Asn Thr Tyr Arg Ser Arg Lys Tyr Ser
 65                  70                  75                  80
```

```
Ser Trp Tyr Val Ala Leu Lys Arg Thr Gly Gln Tyr Lys Leu Gly Pro
            85                  90                  95

Lys Thr Gly Pro Gly Gln Lys Ala Ile Leu Phe Leu
            100                 105

<210> SEQ ID NO 135
<211> LENGTH: 96
<212> TYPE: PRT
<213> ORGANISM: Loxodonta africana

<400> SEQUENCE: 135

Val Lys Leu Gln Leu Gln Ala Glu Glu Arg Gly Val Val Ser Ile Lys
  1               5                  10                  15

Gly Val Cys Ala Asn Arg Tyr Leu Ala Met Lys Glu Asp Gly Arg Leu
             20                  25                  30

Leu Ala Ser Arg Cys Val Thr Asp Glu Cys Phe Phe Phe Glu Arg Leu
         35                  40                  45

Glu Ser Asn Asn Tyr Asn Thr Tyr Arg Ser Arg Lys Tyr Thr Ser Trp
     50                  55                  60

Tyr Val Ala Leu Lys Arg Thr Gly Gln Tyr Lys Leu Gly Ser Lys Thr
 65                  70                  75                  80

Gly Pro Gly Gln Lys Ala Ile Leu Phe Leu Pro Met Ser Ala Lys Ser
                 85                  90                  95

<210> SEQ ID NO 136
<211> LENGTH: 120
<212> TYPE: PRT
<213> ORGANISM: Sus scrofa

<400> SEQUENCE: 136

Asn Gly Gly Phe Phe Leu Arg Ile His Pro Asp Gly Arg Val Asp Gly
  1               5                  10                  15

Val Arg Glu Lys Ser Asp Pro His Ile Lys Leu Gln Leu Gln Ala Glu
             20                  25                  30

Glu Arg Gly Val Val Ser Ile Lys Gly Val Cys Ala Asn Arg Tyr Leu
         35                  40                  45

Ala Met Lys Glu Asp Gly Arg Leu Leu Ala Ser Lys Cys Val Thr Asp
     50                  55                  60

Glu Cys Phe Phe Phe Glu Arg Leu Glu Ser Asn Asn Tyr Asn Thr Tyr
 65                  70                  75                  80

Arg Ser Arg Lys Tyr Ser Ser Trp Tyr Val Ala Leu Lys Arg Thr Gly
                 85                  90                  95

Gln Tyr Lys Leu Gly Pro Lys Thr Gly Pro Gly Gln Lys Ala Ile Leu
             100                 105                 110

Phe Leu Pro Met Ser Ala Lys Ser
         115                 120

<210> SEQ ID NO 137
<211> LENGTH: 96
<212> TYPE: PRT
<213> ORGANISM: Ailuropoda melanoleuca

<400> SEQUENCE: 137

Val Lys Leu Gln Leu Gln Ala Glu Glu Arg Gly Val Val Ser Ile Lys
  1               5                  10                  15

Gly Val Cys Ala Asn Arg Tyr Leu Ala Met Lys Glu Asp Gly Arg Leu
             20                  25                  30

Leu Ala Ser Lys Cys Val Thr Asp Glu Cys Phe Phe Phe Glu Arg Leu
```

```
                    35                  40                  45
Glu Ser Asn Asn Tyr Asn Thr Tyr Arg Ser Arg Lys Tyr Ser Ser Trp
 50                  55                  60

Tyr Val Ala Leu Lys Arg Thr Gly Gln Tyr Lys Leu Gly Pro Lys Thr
 65                  70                  75                  80

Gly Pro Gly Gln Lys Ala Ile Leu Phe Leu Pro Met Ser Ala Lys Ser
                 85                  90                  95
```

<210> SEQ ID NO 138
<211> LENGTH: 155
<212> TYPE: PRT
<213> ORGANISM: Choloepus hoffmanni

<400> SEQUENCE: 138

```
Met Ala Ala Gly Ser Ile Thr Thr Leu Pro Ala Leu Pro Glu Asp Gly
  1               5                  10                  15

Gly Ser Gly Ala Leu Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Gln Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Ser Ser Trp Tyr Val Ala Leu Lys
             115                 120                 125

Arg Thr Gly Gln Tyr Lys Leu Gly Pro Lys Thr Gly Pro Gly Gln Lys
         130                 135                 140

Ala Ile Leu Phe Leu Pro Met Ser Ala Lys Ser
145                 150                 155
```

<210> SEQ ID NO 139
<211> LENGTH: 155
<212> TYPE: PRT
<213> ORGANISM: Bubalus bubalis

<400> SEQUENCE: 139

```
Met Ala Ala Gly Ser Ile Thr Thr Leu Pro Leu Pro Glu Asp Gly
  1               5                  10                  15

Gly Ser Gly Ala Phe Pro Pro Gly His Phe Lys Asp Pro Lys Arg Leu
                 20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Ser Asn Tyr
                100                 105                 110

Asn Thr Tyr Arg Ser Arg Lys Tyr Ser Ser Trp Tyr Val Ala Leu Lys
```

```
                    115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 140
<211> LENGTH: 155
<212> TYPE: PRT
<213> ORGANISM: Canis lupus familiaris

<400> SEQUENCE: 140

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Lys Gly Gly Phe Phe Leu Arg Ile His Pro Asp Gly Arg
        35                  40                  45

Val Asp Gly Val Arg Glu Lys Ser Asp Pro His Val Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 141
<211> LENGTH: 154
<212> TYPE: PRT
<213> ORGANISM: Rattus norvegicus

<400> SEQUENCE: 141

Met Ala Ala Gly Ser Ile Thr Ser Leu Pro Ala Leu Pro Glu Asp Gly
1               5                   10                  15

Gly Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
```

```
            130                 135                 140
Ile Leu Phe Leu Pro Met Ser Ala Lys Ser
145                 150
```

<210> SEQ ID NO 142
<211> LENGTH: 134
<212> TYPE: PRT
<213> ORGANISM: Heterocephalus glaber

<400> SEQUENCE: 142

```
Pro Pro Gly His Phe Lys Asp Pro Lys Arg Leu Tyr Cys Lys Asn Gly
1               5                   10                  15

Gly Phe Phe Leu Arg Ile His Pro Asp Gly Arg Val Asp Gly Val Arg
            20                  25                  30

Glu Lys Ser Asp Pro His Val Lys Leu Gln Leu Gln Ala Glu Glu Arg
        35                  40                  45

Gly Val Val Ser Ile Lys Gly Val Cys Ala Asn Arg Tyr Leu Ala Met
    50                  55                  60

Lys Glu Asp Gly Arg Leu Leu Ala Ser Lys Cys Val Thr Asp Glu Cys
65                  70                  75                  80

Phe Phe Phe Glu Arg Leu Glu Ser Asn Asn Tyr Asn Thr Tyr Arg Ser
                85                  90                  95

Arg Lys Tyr Ser Ser Trp Tyr Val Ala Leu Lys Arg Thr Gly Gln Tyr
            100                 105                 110

Lys Leu Gly Ser Lys Thr Gly Pro Gly Gln Lys Ala Ile Leu Phe Leu
        115                 120                 125

Pro Met Ser Ala Lys Ser
    130
```

<210> SEQ ID NO 143
<211> LENGTH: 155
<212> TYPE: PRT
<213> ORGANISM: Otolemur garnettii

<400> SEQUENCE: 143

```
Met Ala Ala Gly Ser Ile Thr Thr Leu Pro Ser Leu Pro Glu Asp Gly
1               5                   10                  15

Gly Ser Asp Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Leu
                85                  90                  95

Ile Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 144
<211> LENGTH: 154
<212> TYPE: PRT
<213> ORGANISM: Mus musculus

<400> SEQUENCE: 144

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 145
<211> LENGTH: 144
<212> TYPE: PRT
<213> ORGANISM: Ictidomys tridecemlineatus

<400> SEQUENCE: 145

Leu Pro Glu Asp Gly Gly Gly Ala Phe Pro Pro Gly His Phe Lys
1               5                   10                  15

Asp Pro Lys Arg Leu Tyr Cys Lys Asn Gly Gly Phe Phe Leu Arg Ile
            20                  25                  30

His Pro Asp Gly Arg Val Asp Gly Val Arg Glu Lys Ser Asp Pro His
        35                  40                  45

Ile Lys Leu Gln Leu Gln Ala Glu Asp Arg Gly Val Val Ser Ile Lys
    50                  55                  60

Gly Val Cys Ala Asn Arg Tyr Leu Ala Met Lys Glu Asp Gly Arg Leu
65                  70                  75                  80

Leu Ala Ser Lys Cys Val Thr Asp Glu Cys Phe Phe Phe Glu Arg Leu
                85                  90                  95

Glu Ser Asn Asn Tyr Asn Thr Tyr Arg Ser Arg Lys Tyr Ser Ser Trp
            100                 105                 110

Tyr Val Ala Leu Lys Arg Thr Gly Gln Tyr Lys Leu Gly Ser Lys Thr
        115                 120                 125

Gly Pro Gly Gln Lys Ala Ile Leu Phe Leu Pro Met Ser Ala Lys Ser
    130                 135                 140

<210> SEQ ID NO 146
<211> LENGTH: 106
<212> TYPE: PRT
<213> ORGANISM: Felis catus

<400> SEQUENCE: 146

His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
50                  55                  60

Gly Arg Leu Leu Ala Ser Lys Cys Val Thr Asp Glu Cys Phe Phe Phe
65              70                  75                  80

Glu Arg Leu Glu Ser Asn Asn Tyr Asn Thr Tyr Arg Ser Arg Lys Tyr
                85                  90                  95

Ser Ser Trp Tyr Val Ala Leu Lys Arg Thr
            100                 105

<210> SEQ ID NO 147
<211> LENGTH: 96
<212> TYPE: PRT
<213> ORGANISM: Cavia porcellus

<400> SEQUENCE: 147

Val Lys Leu Gln Leu Gln Ala Glu Asp Arg Gly Val Val Ser Ile Lys
1               5                   10                  15

Gly Val Cys Ala Asn Arg Tyr Leu Ala Met Lys Glu Asp Gly Arg Leu
            20                  25                  30

Leu Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
50                  55                  60

Tyr Val Ala Leu Lys Arg Thr Gly Gln Tyr Lys Leu Gly Ser Lys Thr
65              70                  75                  80

Gly Pro Gly Gln Lys Ala Ile Leu Phe Leu Pro Met Ser Ala Lys Ser
                85                  90                  95

<210> SEQ ID NO 148
<211> LENGTH: 156
<212> TYPE: PRT
<213> ORGANISM: Sarcophilus harrisii

<400> SEQUENCE: 148

Met Ala Ala Gly Ser Ile Thr Thr Leu Pro Ala Leu Ala Gly Asp Gly
1               5                   10                  15

Ala Ser Gly Gly Ala Phe Pro Pro Gly His Phe Gln Asp Pro Lys Arg
            20                  25                  30

Leu Tyr Cys Lys Asn Gly Gly Phe Phe Leu Arg Ile His Pro Asp Gly
        35                  40                  45

His Val Asp Gly Ile Arg Glu Lys Ser Asp Pro His Ile Lys Leu Gln
50                  55                  60

Leu Gln Ala Glu Glu Arg Gly Val Val Ser Ile Lys Gly Val Cys Ala
65              70                  75                  80

Asn Arg Tyr Leu Ala Met Lys Glu Asp Gly Arg Leu Leu Ala Leu Lys
                85                  90                  95

Cys Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
        130                 135                 140

Lys Ala Ile Leu Phe Leu Pro Met Ser Ala Lys Ser
145                 150                 155

<210> SEQ ID NO 149
<211> LENGTH: 156
<212> TYPE: PRT
<213> ORGANISM: Monodelphis domestica

<400> SEQUENCE: 149

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Phe Leu Arg Ile His Pro Asp Gly
        35                  40                  45

Arg Val Asp Gly Ile Arg Glu Lys Ser Asp Pro Asn Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Leu Pro Met Ser Ala Lys Ser
145                 150                 155

<210> SEQ ID NO 150
<211> LENGTH: 155
<212> TYPE: PRT
<213> ORGANISM: Oryctolagus cuniculus

<400> SEQUENCE: 150

Met Ala Ala Glu Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

```
Ala Ile Leu Phe Leu Pro Met Ser Ala Lys Ser
145                 150                 155

<210> SEQ ID NO 151
<211> LENGTH: 125
<212> TYPE: PRT
<213> ORGANISM: Meleagris gallopavo

<400> SEQUENCE: 151

Arg Leu Tyr Cys Lys Asn Gly Gly Phe Phe Leu Arg Ile Asn Pro Asp
1               5                   10                  15

Gly Arg Val Asp Gly Val Arg Glu Lys Ser Asp Pro His Ile Lys Leu
            20                  25                  30

Gln Leu Gln Ala Glu Glu Arg Gly Val Val Ser Ile Lys Gly Val Ser
        35                  40                  45

Ala Asn Arg Phe Leu Ala Met Lys Glu Asp Gly Arg Leu Leu Ala Leu
    50                  55                  60

Lys Cys Ala Thr Glu Glu Cys Phe Phe Phe Glu Arg Leu Glu Ser Asn
65                  70                  75                  80

Asn Tyr Asn Thr Tyr Arg Ser Arg Lys Tyr Ser Asp Trp Tyr Val Ala
                85                  90                  95

Leu Lys Arg Thr Gly Gln Tyr Lys Pro Gly Pro Lys Thr Gly Pro Gly
            100                 105                 110

Gln Lys Ala Ile Leu Phe Leu Pro Met Ser Ala Lys Ser
        115                 120                 125

<210> SEQ ID NO 152
<211> LENGTH: 158
<212> TYPE: PRT
<213> ORGANISM: Gallus gallus

<400> SEQUENCE: 152

Met Ala Ala Gly Ala Ala Gly Ser Ile Thr Thr Leu Pro Ala Leu Pro
1               5                   10                  15

Asp Asp Gly Gly Gly Gly Ala Phe Pro Pro Gly His Phe Lys Asp Pro
            20                  25                  30

Lys Arg Leu Tyr Cys Lys Asn Gly Gly Phe Phe Leu Arg Ile Asn Pro
        35                  40                  45

Asp Gly Arg Val Asp Gly Val Arg Glu Lys Ser Asp Pro His Ile Lys
    50                  55                  60

Leu Gln Leu Gln Ala Glu Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
            100                 105                 110

Asn Asn Tyr Asn Thr Tyr Arg Ser Arg Lys Tyr Ser Asp Trp Tyr Val
        115                 120                 125

Ala Leu Lys Arg Thr Gly Gln Tyr Lys Pro Gly Pro Lys Thr Gly Pro
    130                 135                 140

Gly Gln Lys Ala Ile Leu Phe Leu Pro Met Ser Ala Lys Ser
145                 150                 155

<210> SEQ ID NO 153
<211> LENGTH: 153
<212> TYPE: PRT
<213> ORGANISM: Taeniopygia guttata
```

<400> SEQUENCE: 153

| Met | Ala | Ala | Ala | Gly | Gly | Ile | Ala | Thr | Leu | Pro | Asp | Asp | Gly | Gly | Ser |
| 1 | | | | 5 | | | | | 10 | | | | | 15 | |

| Gly | Ala | Phe | Pro | Pro | Gly | His | Phe | Lys | Asp | Pro | Lys | Arg | Leu | Tyr | Cys |
| | | | 20 | | | | | 25 | | | | | 30 | | |

| Lys | Asn | Gly | Gly | Phe | Phe | Leu | Arg | Ile | Asn | Pro | Asp | Gly | Lys | Val | Asp |
| | | | 35 | | | | 40 | | | | | 45 | | | |

| Gly | Val | Arg | Glu | Lys | Ser | Asp | Pro | His | Ile | Lys | Leu | Gln | Leu | Gln | Ala |
| | 50 | | | | | 55 | | | | | 60 | | | | |

| Glu | Glu | Arg | Gly | Val | Val | Ser | Ile | Lys | Gly | Val | Ser | Ala | Asn | Arg | Phe |
| 65 | | | | | 70 | | | | | 75 | | | | | 80 |

| Leu | Ala | Met | Lys | Glu | Asp | Gly | Arg | Leu | Leu | Ala | Leu | Lys | Tyr | Ala | Thr |
| | | | | 85 | | | | | 90 | | | | | 95 | |

| Glu | Glu | Cys | Phe | Phe | Phe | Glu | Arg | Leu | Glu | Ser | Asn | Asn | Tyr | Asn | Thr |
| | | | 100 | | | | | 105 | | | | | 110 | | |

| Tyr | Arg | Ser | Arg | Lys | Tyr | Ser | Asp | Trp | Tyr | Val | Ala | Leu | Lys | Arg | Thr |
| | | | 115 | | | | | 120 | | | | | 125 | | |

| Gly | Gln | Tyr | Lys | Pro | Gly | Pro | Lys | Thr | Gly | Pro | Gly | Gln | Lys | Ala | Ile |
| | 130 | | | | | 135 | | | | | 140 | | | | |

| Leu | Phe | Leu | Pro | Met | Ser | Ala | Lys | Ser | | | | | | | |
| 145 | | | | | 150 | | | | | | | | | | |

<210> SEQ ID NO 154
<211> LENGTH: 155
<212> TYPE: PRT
<213> ORGANISM: Cynops pyrrhogaster

<400> SEQUENCE: 154

| Met | Ala | Ala | Gly | Ser | Ile | Thr | Ser | Leu | Pro | Ala | Leu | Pro | Glu | Asp | Gly |
| 1 | | | | 5 | | | | | 10 | | | | | 15 | |

| Asn | Gly | Gly | Thr | Phe | Thr | Pro | Gly | Gly | Phe | Lys | Glu | Pro | Lys | Arg | Leu |
| | | | 20 | | | | | 25 | | | | | 30 | | |

| Tyr | Cys | Lys | Asn | Gly | Gly | Phe | Phe | Leu | Arg | Ile | Asn | Ser | Asp | Gly | Lys |
| | | | 35 | | | | | 40 | | | | | 45 | | |

| Val | Asp | Gly | Ala | Arg | Glu | Lys | Ser | Asp | Ser | Tyr | Ile | Lys | Leu | Gln | Leu |
| | 50 | | | | | 55 | | | | | 60 | | | | |

| Gln | Ala | Glu | Glu | Arg | Gly | Val | Val | Ser | Ile | Lys | Gly | Val | Cys | Ala | Asn |
| 65 | | | | | 70 | | | | | 75 | | | | | 80 |

| Arg | Tyr | Leu | Ala | Met | Lys | Asp | Asp | Gly | Arg | Leu | Met | Ala | Leu | Lys | Trp |
| | | | | 85 | | | | | 90 | | | | | 95 | |

| Ile | Thr | Asp | Glu | Cys | Phe | Phe | Phe | Glu | Arg | Leu | Glu | Ser | Asn | Asn | Tyr |
| | | | 100 | | | | | 105 | | | | | 110 | | |

| Asn | Thr | Tyr | Arg | Ser | Arg | Lys | Tyr | Ser | Asp | Trp | Tyr | Val | Ala | Leu | Lys |
| | | | 115 | | | | | 120 | | | | | 125 | | |

| Arg | Thr | Gly | Gln | Tyr | Lys | Asn | Gly | Ser | Lys | Thr | Gly | Ala | Gly | Gln | Lys |
| | 130 | | | | | 135 | | | | | 140 | | | | |

| Ala | Ile | Leu | Phe | Leu | Pro | Met | Ser | Ala | Lys | Ser | | | | | |
| 145 | | | | | 150 | | | | | 155 | | | | | |

<210> SEQ ID NO 155
<211> LENGTH: 155
<212> TYPE: PRT
<213> ORGANISM: Xenopus laevis

<400> SEQUENCE: 155

Met Ala Ala Gly Ser Ile Thr Thr Leu Pro Thr Glu Ser Glu Asp Gly
1               5                   10                  15

Gly Asn Thr Pro Phe Ser Pro Gly Ser Phe Lys Asp Pro Lys Arg Leu
            20                  25                  30

Tyr Cys Lys Asn Gly Gly Phe Phe Leu Arg Ile Asn Ser Asp Gly Arg
        35                  40                  45

Val Asp Gly Ser Arg Asp Lys Ser Asp Ser His Ile Lys Leu Gln Leu
    50                  55                  60

Gln Ala Val Glu Arg Gly Val Val Ser Ile Gly Ile Thr Ala Asn
65                  70                  75                  80

Arg Tyr Leu Ala Met Lys Glu Asp Gly Arg Leu Thr Ser Leu Arg Cys
                85                  90                  95

Ile Thr Asp Glu Cys Phe Phe Phe Glu Arg Leu Glu Ala Asn Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Asn Gly Ser Ser Thr Gly Pro Gly Gln Lys
        130                 135                 140

Ala Ile Leu Phe Leu Pro Met Ser Ala Lys Ser
145                 150                 155

<210> SEQ ID NO 156
<211> LENGTH: 156
<212> TYPE: PRT
<213> ORGANISM: Didelphis albiventris

<400> SEQUENCE: 156

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Phe Leu Arg Ile His Pro Asp Gly
        35                  40                  45

Arg Val Asp Gly Ile Arg Glu Lys Ser Asp Pro Asn Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
            115                 120                 125

Lys Arg Thr Gly Gln Tyr Lys Leu Gly Ser Lys Thr Gly Pro Gly Gln
        130                 135                 140

Lys Ala Ile Leu Phe Ser Pro Cys Leu Leu Arg Cys
145                 150                 155

<210> SEQ ID NO 157
<211> LENGTH: 96
<212> TYPE: PRT
<213> ORGANISM: Myotis lucifugus

<400> SEQUENCE: 157

Val Lys Leu Gln Leu Gln Ala Glu Glu Arg Gly Val Val Ser Ile Lys
1               5                   10                  15

```
Gly Val Cys Ala Asn Arg Tyr Leu Ala Met Lys Glu Asp Gly Arg Leu
            20                  25                  30

Gln Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
 50                  55                  60

Tyr Val Ala Leu Lys Arg Asn Gly Gln Tyr Lys Leu Gly Pro Lys Thr
 65                  70                  75                  80

Gly Pro Gly Gln Lys Ala Ile Leu Phe Leu Pro Met Ser Ala Lys Ser
                85                  90                  95
```

<210> SEQ ID NO 158
<211> LENGTH: 140
<212> TYPE: PRT
<213> ORGANISM: Anolis carolinensis

<400> SEQUENCE: 158

```
Ala Ala Ala Ala Ser Phe Pro Pro Gly Pro Phe Lys Asp Pro Lys Arg
1               5                  10                  15

Leu Tyr Cys Lys Asn Gly Gly Phe Phe Leu Arg Ile Asn Pro Asp Gly
            20                  25                  30

Gly Val Asp Gly Val Arg Glu Lys Ser Asp Pro Asn Ile Lys Leu Leu
        35                  40                  45

Leu Gln Ala Glu Glu Arg Gly Val Val Ser Ile Lys Gly Val Cys Ala
 50                  55                  60

Asn Arg Phe Leu Ala Met Asn Glu Asp Gly Arg Leu Leu Ala Leu Lys
65                  70                  75                  80

Tyr Val Thr Asp Glu Cys Phe Phe Phe Glu Arg Leu Glu Ser Asn Asn
                85                  90                  95

Tyr Asn Thr Tyr Arg Ser Arg Lys Tyr Arg Asp Trp Tyr Ile Ala Leu
                100                 105                 110

Lys Arg Thr Gly Gln Tyr Lys Leu Gly Pro Lys Thr Gly Arg Gly Gln
            115                 120                 125

Lys Ala Ile Leu Phe Leu Pro Met Ser Ala Lys Ser
        130                 135                 140
```

<210> SEQ ID NO 159
<211> LENGTH: 94
<212> TYPE: PRT
<213> ORGANISM: Dasypus novemcinctus

<400> SEQUENCE: 159

```
Met Ala Ala Gly Ser Ile Thr Thr Leu Pro Ala Leu Pro Glu Asp Gly
1               5                  10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Asn Ile Lys Leu Gln Leu
 50                  55                  60

Gln Ala Glu Glu Arg Gly Val Val Ser Ile Lys Gly Val Cys Ala Asn
65                  70                  75                  80

Arg Tyr Leu Ala Met Arg Glu Asp Gly Arg Leu Gln Ala Ser
                85                  90
```

<210> SEQ ID NO 160
<211> LENGTH: 189

<212> TYPE: PRT
<213> ORGANISM: Tupaia belangeri

<400> SEQUENCE: 160

Ala Gly Val Arg Ala Glu Arg Glu Ala Pro Gly Ser Gly Asp Ser
1               5                   10                  15

Arg Gly Thr Asp Pro Ala Ala Arg Ser Leu Ile Arg Arg Pro Asp Ala
            20                  25                  30

Ala Ala Arg Glu Ala Leu Leu Gly Ala Arg Ser Arg Val Gln Gly Ser
        35                  40                  45

Ser Thr Ser Trp Pro Ala Ser Ser Arg Thr Gly Ile Lys Leu Pro Asp
50                  55                  60

Asp Ser Gly Gln Gly Met Gly Gly Tyr Pro Leu Asp Arg Pro Ser Arg
65                  70                  75                  80

Ser Thr Gly Arg Gly Leu Gly Gly Ala Pro Asp Pro Ala Val Lys Leu
                85                  90                  95

Gln Leu Gln Ala Glu Glu Arg Gly Val Val Ser Ile Lys Gly Val Cys
            100                 105                 110

Ala Asn Arg Tyr Leu Ala Met Lys Glu Asp Gly Arg Leu Leu Ala Ser
        115                 120                 125

Lys Cys Val Thr Asp Glu Cys Phe Phe Phe Glu Arg Leu Glu Ser Asn
130                 135                 140

Asn Tyr Asn Thr Tyr Arg Ser Arg Lys Tyr Ser Ser Trp Tyr Val Ala
145                 150                 155                 160

Leu Lys Arg Thr Gly Gln Tyr Lys Leu Gly Ser Lys Thr Gly Pro Gly
                165                 170                 175

Gln Lys Ala Ile Leu Phe Leu Pro Met Ser Ala Lys Ser
            180                 185

<210> SEQ ID NO 161
<211> LENGTH: 154
<212> TYPE: PRT
<213> ORGANISM: Xenopus silurana tropicalis

<400> SEQUENCE: 161

Met Ala Ala Gly Ser Ile Thr Thr Leu Pro Thr Glu Ser Glu Asp Gly
1               5                   10                  15

Asn Thr Pro Phe Pro Pro Gly Asn Phe Lys Asp Pro Lys Arg Leu Tyr
            20                  25                  30

Cys Lys Asn Gly Gly Tyr Phe Leu Arg Ile Asn Ser Asp Gly Arg Val
        35                  40                  45

Asp Gly Ser Arg Asp Lys Ser Asp Leu His Ile Lys Leu Gln Leu Gln
50                  55                  60

Ala Val Glu Arg Gly Val Val Ser Ile Lys Gly Ile Thr Ala Asn Arg
65                  70                  75                  80

Tyr Leu Ala Met Lys Glu Asp Gly Arg Leu Thr Ser Leu Lys Cys Ile
                85                  90                  95

Thr Asp Glu Cys Phe Phe Tyr Glu Arg Leu Glu Ala Asn Asn Tyr Asn
            100                 105                 110

Thr Tyr Arg Ser Arg Lys Asn Asn Ser Trp Tyr Val Ala Leu Lys Arg
        115                 120                 125

Thr Gly Gln Tyr Lys Asn Gly Ser Thr Thr Gly Pro Gly Gln Lys Ala
130                 135                 140

Ile Leu Phe Leu Pro Met Ser Ala Lys Ser
145                 150

<210> SEQ ID NO 162
<211> LENGTH: 155
<212> TYPE: PRT
<213> ORGANISM: Latimeria chalumnae

<400> SEQUENCE: 162

```
Met Ala Ala Gly Gly Ile Thr Thr Leu Pro Ala Val Pro Glu Asp Gly
1               5                   10                  15

Gly Ser Ser Thr Phe Pro Pro Gly Asn Phe Lys Glu Pro Lys Arg Leu
                20                  25                  30

Tyr Cys Lys Asn Gly Gly Tyr Phe Leu Arg Ile Asn Pro Asp Gly Arg
            35                  40                  45

Val Asp Gly Thr Arg Glu Lys Asn Asp Pro Tyr Ile Lys Leu Gln Leu
    50                  55                  60

Gln Ala Glu Ser Ile Gly Val Val Ser Ile Lys Gly Val Cys Ser Asn
65                  70                  75                  80

Arg Tyr Leu Ala Met Asn Glu Asp Cys Arg Leu Phe Gly Leu Lys Tyr
                85                  90                  95

Pro Thr Asp Glu Cys Phe Phe His Glu Arg Leu Glu Ser Asn Asn Tyr
            100                 105                 110

Asn Thr Tyr Arg Ser Lys Lys Tyr Ser Asp Trp Tyr Val Ala Leu Lys
        115                 120                 125

Arg Thr Gly Gln Tyr Lys Pro Gly Pro Lys Thr Gly Leu Gly Gln Lys
    130                 135                 140

Ala Ile Leu Phe Leu Pro Met Ser Ala Lys Ser
145                 150                 155
```

<210> SEQ ID NO 163
<211> LENGTH: 155
<212> TYPE: PRT
<213> ORGANISM: Tetraodon nigroviridis

<400> SEQUENCE: 163

```
Met Ala Thr Gly Gly Ile Thr Thr Leu Pro Ser Thr Pro Glu Asp Gly
1               5                   10                  15

Gly Ser Ser Gly Phe Pro Pro Gly Ser Phe Lys Asp Pro Lys Arg Leu
                20                  25                  30

Tyr Cys Lys Asn Gly Gly Phe Phe Leu Arg Ile Lys Ser Asp Gly Val
            35                  40                  45

Val Asp Gly Ile Arg Glu Lys Ser Asp Pro His Ile Lys Leu Gln Leu
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Thr Lys Arg
                85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Thr Met Phe Val Gly Leu Thr
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155
```

<210> SEQ ID NO 164
<211> LENGTH: 155

```
<212> TYPE: PRT
<213> ORGANISM: Gasterosteus aculeatus

<400> SEQUENCE: 164

Met Ala Thr Ala Gly Phe Ala Thr Leu Pro Ser Thr Pro Glu Asp Gly
1               5                   10                  15

Gly Ser Gly Gly Phe Thr Pro Gly Gly Phe Lys Asp Pro Lys Arg Leu
            20                  25                  30

Tyr Cys Lys Asn Gly Gly Phe Phe Leu Arg Ile Arg Ser Asp Gly Gly
        35                  40                  45

Val Asp Gly Ile Arg Glu Lys Ser Asp Ala His Ile Lys Leu Gln Ile
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Val Arg Arg
                85                  90                  95

Ala Thr Asp Glu Cys Tyr Phe Leu Glu Arg Leu Glu Ser Asn Asn Tyr
            100                 105                 110

Asn Thr Tyr Arg Ser Arg Lys Tyr Pro Gly Met Tyr Val Ala Leu Lys
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155

<210> SEQ ID NO 165
<211> LENGTH: 155
<212> TYPE: PRT
<213> ORGANISM: Takifugu rubripes

<400> SEQUENCE: 165

Met Ala Thr Gly Gly Ile Thr Thr Leu Pro Ser Thr Pro Glu Asp Gly
1               5                   10                  15

Gly Ser Gly Gly Phe Pro Pro Gly Ser Phe Lys Asp Pro Lys Arg Leu
            20                  25                  30

Tyr Cys Lys Asn Gly Gly Phe Phe Leu Arg Ile Arg Ser Asp Gly Ala
        35                  40                  45

Val Asp Gly Thr Arg Glu Lys Thr Asp Pro His Ile Lys Leu Gln Leu
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Met Lys Arg
                85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Asn Met Phe Val Gly Leu Thr
        115                 120                 125

Arg Thr Gly Asn Tyr Lys Ser Gly Thr Lys Thr Gly Pro Cys Gln Lys
    130                 135                 140

Ala Ile Leu Phe Leu Pro Met Ser Ala Lys Tyr
145                 150                 155

<210> SEQ ID NO 166
<211> LENGTH: 155
<212> TYPE: PRT
<213> ORGANISM: Oncorhynchus mykiss
```

<400> SEQUENCE: 166

Met Ala Thr Gly Glu Ile Thr Thr Leu Pro Ala Thr Pro Glu Asp Gly
1               5                   10                  15

Gly Ser Gly Gly Phe Leu Pro Gly Asn Phe Lys Glu Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Asp Lys Asn Asp Pro His Asn Lys Leu Gln Leu
    50                  55                  60

Gln Ala Thr Ser Val Gly Glu Val Ile Lys Gly Val Ser Ala Asn
65                  70                  75                  80

Arg Tyr Leu Ala Met Asn Ala Asp Gly Arg Leu Phe Gly Pro Arg Arg
                85                  90                  95

Thr Thr Asp Glu Cys Tyr Phe Met Glu Arg Leu Glu Ser Asn Asn Tyr
            100                 105                 110

Asn Thr Tyr Arg Ser Arg Lys Tyr Pro Glu Met Tyr Val Ala Leu Lys
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Arg Arg
145                 150                 155

<210> SEQ ID NO 167
<211> LENGTH: 150
<212> TYPE: PRT
<213> ORGANISM: Salmo salar

<400> SEQUENCE: 167

Met Ala Thr Gly Glu Ile Thr Thr Leu Pro Ala Thr Pro Glu Asp Gly
1               5                   10                  15

Gly Ser Gly Gly Phe Pro Pro Gly Asn Phe Lys Asp Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Glu Lys Asn Asp Pro His Lys Gln Pro Gln Phe
    50                  55                  60

Val Arg Ala Trp Thr Leu Gln Gly Val Lys Arg Ser Thr Gly Met Leu
65                  70                  75                  80

Ala His Val Asp Ser Asn Ala Ser His Asn Cys Val Lys Val Ala Gly
                85                  90                  95

Cys Ser Leu Gly Glu Phe Gly Ser Met Ser Asn Arg Pro His Asn Arg
            100                 105                 110

Arg Pro Arg Val Ala Thr Pro Ala Gln Asp Leu His Ile Arg Leu Leu
        115                 120                 125

His Leu Arg Asp Arg Leu Lys Pro Ala Thr Arg Thr Ala Asp Lys Thr
    130                 135                 140

Glu Glu Tyr Phe Cys Leu
145                 150

<210> SEQ ID NO 168
<211> LENGTH: 154
<212> TYPE: PRT
<213> ORGANISM: Danio rerio

<400> SEQUENCE: 168

Met Ala Thr Gly Gly Ile Thr Thr Leu Pro Ala Ala Pro Asp Ala Glu

```
  1               5                  10                 15
Asn Ser Ser Phe Pro Ala Gly Ser Phe Arg Asp Pro Lys Arg Leu Tyr
            20                  25                 30

Cys Lys Asn Gly Gly Phe Phe Leu Arg Ile Asn Ala Asp Gly Arg Val
            35                  40                 45

Asp Gly Ala Arg Asp Lys Ser Asp Pro His Ile Arg Leu Gln Leu Gln
    50                  55                 60

Ala Thr Ala Val Gly Glu Val Leu Ile Lys Gly Ile Cys Thr Asn Arg
65                  70                  75                 80

Phe Leu Ala Met Asn Ala Asp Gly Arg Leu Phe Gly Thr Lys Arg Thr
                85                  90                 95

Thr Asp Glu Cys Tyr Phe Leu Glu Arg Leu Glu Ser Asn Asn Tyr Asn
            100                 105                110

Thr Tyr Arg Ser Arg Lys Tyr Pro Asp Trp Tyr Val Ala Leu Lys Arg
            115                 120                125

Thr Gly Gln Tyr Lys Ser Gly Ser Lys Thr Ser Pro Gly Gln Lys Ala
            130                 135                140

Ile Leu Phe Leu Pro Met Ser Ala Lys Cys
145                 150

<210> SEQ ID NO 169
<211> LENGTH: 155
<212> TYPE: PRT
<213> ORGANISM: Oreochromis niloticus

<400> SEQUENCE: 169

Met Ala Thr Gly Gly Ile Thr Thr Leu Pro Ala Thr Pro Glu Asp Gly
1               5                  10                 15

Gly Ser Ser Gly Phe Pro Pro Gly Asn Phe Lys Asp Pro Lys Arg Leu
            20                  25                 30

Tyr Cys Lys Asn Gly Gly Phe Phe Leu Arg Ile Lys Ser Asp Gly Gly
            35                  40                 45

Val Asp Gly Ile Arg Glu Lys Asn Asp Pro His Ile Lys Leu Gln Leu
    50                  55                 60

Gln Ala Thr Ser Val Gly Glu Val Val Ile Lys Gly Ile Cys Ala Asn
65                  70                  75                 80

Arg Tyr Leu Ala Met Asn Arg Asp Gly Arg Leu Phe Gly Ala Arg Arg
                85                  90                 95

Ala Thr Asp Glu Cys Tyr Phe Leu Glu Arg Leu Glu Ser Asn Asn Tyr
            100                 105                110

Asn Thr Tyr Arg Ser Arg Lys Tyr Pro Asn Met Tyr Val Ala Leu Lys
            115                 120                125

Arg Thr Gly Gln Tyr Lys Ser Gly Ser Lys Thr Gly Pro Gly Gln Lys
            130                 135                140

Ala Ile Leu Phe Leu Pro Met Ser Ala Lys Cys
145                 150                 155

<210> SEQ ID NO 170
<211> LENGTH: 155
<212> TYPE: PRT
<213> ORGANISM: Oryzias latipes

<400> SEQUENCE: 170

Met Ala Thr Gly Glu Ile Thr Thr Leu Pro Ser Pro Ala Glu Asn Ser
1               5                  10                 15

Arg Ser Asp Gly Phe Pro Pro Gly Asn Tyr Lys Asp Pro Lys Arg Leu
```

```
                  20                  25                  30
Tyr Cys Lys Asn Gly Gly Leu Phe Leu Arg Ile Lys Pro Asp Gly Gly
              35                  40                  45
Val Asp Gly Ile Arg Glu Lys Lys Asp Pro His Val Lys Leu Arg Leu
 50                  55                  60
Gln Ala Thr Ser Ala Gly Glu Val Val Ile Lys Gly Val Cys Ser Asn
 65                  70                  75                  80
Arg Tyr Leu Ala Met His Gly Asp Gly Arg Leu Phe Gly Val Arg Gln
              85                  90                  95
Ala Thr Glu Glu Cys Tyr Phe Leu Glu Arg Leu Glu Ser Asn Asn Tyr
             100                 105                 110
Asn Thr Tyr Arg Ser Lys Lys Tyr Pro Asn Met Tyr Val Ala Leu Lys
             115                 120                 125
Arg Thr Gly Gln Tyr Lys Pro Gly Asn Lys Thr Gly Pro Gly Gln Lys
             130                 135                 140
Ala Ile Leu Phe Leu Pro Met Ser Ala Lys Tyr
145                 150                 155

<210> SEQ ID NO 171
<211> LENGTH: 468
<212> TYPE: DNA
<213> ORGANISM: Homo sapiens

<400> SEQUENCE: 171
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468

<210> SEQ ID NO 172
<211> LENGTH: 468
<212> TYPE: DNA
<213> ORGANISM: Gorilla

<400> SEQUENCE: 172
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468

<210> SEQ ID NO 173
<211> LENGTH: 468
<212> TYPE: DNA
<213> ORGANISM: Sumatran orangutan
```

<400> SEQUENCE: 173

```
atggcagccg ggagcatcac cacgctgccc gccttgcccg aggatggcgg cagcggcgcc    60
ttcccgccgg gccacttcaa ggaccccaag cggctgtact gcaaaaacgg gggcttcttc   120
ctgcgcatcc accccgacgg ccgagttgac ggggtccgag agaagagcga ccctcacatc   180
aaactacaac ttcaagcaga agaaagagga gttgtgtcta tcaaaggagt gtgtgctaac   240
cgctaccttg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctga               468
```

<210> SEQ ID NO 174
<211> LENGTH: 468
<212> TYPE: DNA
<213> ORGANISM: Rhesus monkey

<400> SEQUENCE: 174

```
atggcagccg ggagcatcac cacgctgccc gccttgcccg aggatggcgg cagcggcgcc    60
ttcccgcctg gccacttcaa ggaccccaag cggctgtact gcaaaaacgg gggcttcttc   120
ctgcgcattc accccgacgg ccgagttgac ggggtccggg agaagagcga ccctcacatc   180
aaattacaac ttcaagcaga agagagagga gttgtgtcta tcaaaggagt gtgtgctaac   240
cgttaccttg ctatgaagga agatggaaga ttactggctt ctaaatgtgt tacagatgag   300
tgtttctttt ttgaacgatt ggaatctaat aactacaata cttaccggtc aaggaaatac   360
accagttggt atgtggcact gaaacgaact gggcaatata aacttggatc caaaacagga   420
cctgggcaga aagctatact ttttcttcca atgtctgcta agagctga               468
```

<210> SEQ ID NO 175
<211> LENGTH: 468
<212> TYPE: DNA
<213> ORGANISM: Chimpanzee

<400> SEQUENCE: 175

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
cgttaccttg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctga               468
```

<210> SEQ ID NO 176
<211> LENGTH: 468
<212> TYPE: DNA
<213> ORGANISM: Pygmy chimpanzee

<400> SEQUENCE: 176

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
```

```
ctgcgcatcc accccgacgg ccgagttgac ggggtccggg agaagagcga ccctcacatc    180
aagctacaac ttcaagcaga agagagagga gttgtgtcta tcaaaggagt gtgtgctaac    240
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                 468
```

<210> SEQ ID NO 177
<211> LENGTH: 468
<212> TYPE: DNA
<213> ORGANISM: Bolivian squirrel monkey
<400> SEQUENCE: 177

```
atggcagccg ggagcatcac cacgctgccc gccctgcccg aagacggcgg cagcggcgcc     60
ttcccgcccg gccacttcaa agaccccaag cggctgtact gcaaaaacgg gggcttcttc    120
ctgcgaatcc accccgacgg ccgagtggac ggggtccggg agaagagcga ccctcacatc    180
aaactacaac ttcaagcaga agagagagga gttgtatcta tcaaaggagt gtgtgctaac    240
cgttaccttg ctatgaagga agatggaaga ttactggctt ctaaatgtgt tacggacgag    300
tgtttctttt ttgaacgatt ggaatctaat aactacaata cttaccgatc aaggaaatac    360
accagttggt atgtggcact gaaacgaact gggcagtata aacttggatc caaaacagga    420
cctgggcaga aagctatact ttttcttcca atgtctgcta agagctga                 468
```

<210> SEQ ID NO 178
<211> LENGTH: 468
<212> TYPE: DNA
<213> ORGANISM: Northern white-cheeked gibbon
<400> SEQUENCE: 178

```
atggcagccg ggagcatcac cacgctgccc gccttgccgg aggatggcgg cagcggcgcc     60
ttcccgcccg gccacttcaa ggaccccaag cggctgtact gcaaaaacgg gggtttcttc    120
ctgcgcatcc accccgacgg tcgagttgac ggggtccggg agaagagcga ccctcacatc    180
aaactacaac ttcaagcaga agagagagga gttgtgtcta tcaaaggagt gtgtgctaac    240
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                 468
```

<210> SEQ ID NO 179
<211> LENGTH: 468
<212> TYPE: DNA
<213> ORGANISM: Horse
<400> SEQUENCE: 179

```
atggcagccg ggagcatcac cacgctgccc gccctgcccg aggacggcgg cagcggcgcc     60
ttcccgcccg gccacttcaa ggaccccaag cggctctact gcaaaaacgg gggcttcttc    120
ctgcgcatcc accccgacgg ccgagtggac ggggtccggg agaagagcga ccctcacatc    180
aaactacaac ttcaagcaga agagagaggg gttgtgtcta tcaaaggagt gtgtgcgaac    240
cgttatcttg ctatgaagga agatggaagg ttactggctt ctaaatgtgt tacggacgag    300
tgtttctttt ttgaacgatt ggaatctaat aactacaata cttaccggtc aaggaaatac    360
```

```
tccagttggt atgtggccct gaaacgaacg gggcagtata aacttggacc caaaacagga    420
cctggacaga aagctatact ttttcttcca atgtctgcta agagctga                468
```

<210> SEQ ID NO 180
<211> LENGTH: 468
<212> TYPE: DNA
<213> ORGANISM: Cattle

<400> SEQUENCE: 180

```
atggccgccg ggagcatcac cacgctgcca gccctgccgg aggacggcgg cagcggcgct    60
ttcccgccgg gccacttcaa ggaccccaag cggctgtact gcaagaacgg gggcttcttc   120
ctgcgcatcc accccgacgg ccgagtggac ggggtccgcg agaagagcga cccacacatc   180
aaactacaac ttcaagcaga agagagaggg gttgtgtcta tcaaaggagt gtgtgcaaac   240
cgttaccttg ctatgaaaga agatggaaga ttactagctt ctaaatgtgt tacagacgag   300
tgtttctttt ttgaacgatt ggagtctaat aactacaata cttaccggtc aaggaaatac   360
tccagttggt atgtggcact gaaacgaact gggcagtata aacttggacc caaaacagga   420
cctgggcaga aagctatact ttttcttcca atgtctgcta agagctga                468
```

<210> SEQ ID NO 181
<211> LENGTH: 468
<212> TYPE: DNA
<213> ORGANISM: Olive baboon

<400> SEQUENCE: 181

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcattc accccgacgg ccgagttgac ggggtccggg agaagagcga ccctcacatc   180
aaattacaac ttcaagcaga agagagagga gttgtgtcta tcaaaggagt gtgtgctaac   240
cgttaccttg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctga                468
```

<210> SEQ ID NO 182
<211> LENGTH: 468
<212> TYPE: DNA
<213> ORGANISM: Alpaca

<400> SEQUENCE: 182

```
atggcagctg ggagcatcac cacgctgccc gccctgccgg aggacggcgg cagcggcgcc    60
ttcccgcccg gccacttcaa ggaccccaag cggttgtact gcaaaaacgg gggcttcttc   120
ctgcgcatcc accccgacgg ccgagtggac ggggtccggg agaagagcga ccctcacatc   180
aaactacaac ttcaagcaga agagagaggg gtcgtgtcta tcaaaggagt gtgtgcaaac   240
cgttaccttg ctatgaagga agatggaaga ttactggctt ctaaatgtgt cacagacgag   300
tgtttctttt ttgaacgatt ggaatctaat aactacaata cttaccggtc aaggaaatac   360
tccagttggt atgtggcact gaaacgaact gggcagtaca aacttggacc caaaacagga   420
cctgggcaga aagctatact tttccttcca atgtctgcta agagctga                468
```

<210> SEQ ID NO 183

```
<211> LENGTH: 468
<212> TYPE: DNA
<213> ORGANISM: Sheep

<400> SEQUENCE: 183
atggccgccg ggagcatcac cacgctgcca gccctgccgg aggacggcgg cagcagcgct      60
ttcccgcccg gccactttaa ggaccccaag cggctgtact gcaagaacgg gggcttcttc     120
ctgcgcatcc accccgacgg ccgagtggac ggggtccgcg agaagagcga ccctcacatc     180
aaactacaac ttcaagcaga agagagggg gttgtgtcta tcaaaggagt gtgtgcaaac     240
cgttaccttg ctatgaaaga agatggaaga ttactagctt ctaaatgtgt tacagacgag     300
tgtttctttt ttgaacgatt ggagtctaat aactacaata cttaccggtc aaggaaatac     360
tccagttggt atgtggcact gaaacgaact gggcagtata acttggacc caaaacagga     420 cctgggcaga aagctatact ttttcttcca atgtctgcta agagctga                468

<210> SEQ ID NO 184
<211> LENGTH: 325
<212> TYPE: DNA
<213> ORGANISM: Western roe deer

<400> SEQUENCE: 184
gcgcatccac cccgacggcc gagtggacgg ggtccgcgag aagagtgacc ctcacatcaa      60
actacaactt caagcagaag agagggggt tgtgtctatc aaaggagtgt gtgcgaaccg     120
ttatcttgct atgaaagaag acggaagatt attggcttca aatgtgttac agacgaatg     180 tttcttttt gaacgattgg agtctaataa ctacaatact taccggtcaa ggaaatactc     240
cagttggtat gtggcactga acgaactgg gcagtataaa cttggaccca aaacaggacc     300
tgggcagaaa gctatacttt ttctt                                        325

<210> SEQ ID NO 185
<211> LENGTH: 288
<212> TYPE: DNA
<213> ORGANISM: Elephant

<400> SEQUENCE: 185
gttaaactac agcttcaagc agaagagaga ggtgttgtgt ctatcaaagg agtgtgtgcc      60
aaccgttatc tggctatgaa ggaagatgga agattgctgg cttctagatg tgtgacagat     120
gaatgtttct ctttgaacg actggaatct aataactaca atacttaccg gtcaaggaaa     180
tacaccagtt ggtatgtggc actgaaacga acggggcagt ataaacttgg atccaaaaca     240
ggacctggac agaaagctat actttttctt cccatgtctg ctaagagc                288

<210> SEQ ID NO 186
<211> LENGTH: 361
<212> TYPE: DNA
<213> ORGANISM: Pig

<400> SEQUENCE: 186
gaacgggggc ttcttcctgc gcatccaccc cgacggccga gtggatgggg tccgggagaa      60
gagcgaccct cacatcaaac tacaacttca gcagaagag agaggggttg tgtctatcaa     120
aggagtgtgt gcaaaccgtt atcttgctat gaaggaagat ggaagattac tggcttctaa     180
atgtgttaca gacgagtgtt ctttttttga cgactggaa tctaataact acaatactta     240
ccggtcgagg aaatactcca gttggtatgt ggcactgaaa cgaactgggc agtataaact     300
tggacccaaa acaggacctg gcagaaagc tatactttt cttccaatgt ctgctaagag     360
```

<210> SEQ ID NO 187
<211> LENGTH: 288
<212> TYPE: DNA
<213> ORGANISM: Panda

<400> SEQUENCE: 187

```
gtcaaactgc aacttcaagc ggaagagaga ggggttgtat ccatcaaagg agtatgtgca      60
aatcgctatc ttgccatgaa ggaagatgga agattactgg cttctaaatg tgttaccgat     120
gagtgtttct tttttgagcg actggaatct aataactaca atacttaccg gtcaaggaaa     180
tactccagtt ggtatgtggc actgaaacga actgggcagt ataaacttgg acccaaaaca     240
ggacctgggc agaaagctat acttttctt ccaatgtctg ctaagagc                    288
```

<210> SEQ ID NO 188
<211> LENGTH: 468
<212> TYPE: DNA
<213> ORGANISM: Sloth

<400> SEQUENCE: 188

```
atggcagccg ggagcatcac cacgctgccc gccctgcccg aggacggagg cagcggcgcc      60
ttaccgcccg gccacttcaa agatcccaag cggctctact gcaaaaacgg ggcttcttc     120
ctgcgtatcc atcccgacgg cagagtggac ggggtccggg agaagagcga cccccacatc     180
aaactacaac ttcaagcaga agagagaggg gttgtgtcta tcaaaggtgt gtgtgcaaac     240
cgatatcttg ctatgaagga agatggaaga ttacaggctt ctaaatgtgt aacggacgag     300
tgtttctttt ttgaacgatt ggaatctaat aactacaata cgtaccgatc aaggaaatac     360
tccagttggt atgtggcact gaaacgaact gggcaatata aacttggacc caaaacagga     420
cctgggcaga aagccatact tttcttcca atgtctgcta agagctga                   468
```

<210> SEQ ID NO 189
<211> LENGTH: 468
<212> TYPE: DNA
<213> ORGANISM: Water buffalo

<400> SEQUENCE: 189

```
atggccgccg ggagcatcac cacgctgcca cccctgccgg aggacggcgg cagcggcgct      60
ttcccgcccg gccacttcaa ggaccccaag cggctgtact gcaagaacgg gggcttcttc     120
ctgcgcatcc accccgacgg ccgagtggac ggggtccgcg agaagagcga cccacacatc     180
aaactacaac ttcaagcaga agagagaggg gttgtgtcta tcaaaggagt gtgtgcaaac     240
cgttaccttg ctatgaaaga agatggaaga ttactagctt ccaaatgtgt tacagacgag     300
tgtttctttt ttgaacgatt ggagtctagt aactacaata cttaccggtc aaggaaatac     360
tccagttggt atgtggcact gaaacgaact gggcagtata aacttggacc caaaacagga     420
cctgggcaga aagctatact ttttcttcca atgtctgcta agagctga                  468
```

<210> SEQ ID NO 190
<211> LENGTH: 468
<212> TYPE: DNA
<213> ORGANISM: Dog

<400> SEQUENCE: 190

```
atggcagccg ggagcatcac cacgctgccc gccctgccgg aggacggcgg cagcggcgcc      60
```

```
ttcccgcccg gccacttcaa ggaccccaag aggctgtact gcaaaaaagg gggcttcttc    120
ctgcggatcc accccgacgg ccgggtggac ggggtccggg agaagagcga tccccacgtc    180
aaattgcaac ttcaagcaga agagagaggc gttgtgtcca tcaaggagt  atgtgcaaat    240 cgctatcttg ctatgaagga agatggaaga ttactggctt ctaaatgtgt tactgacgag    300
tgcttctttt ttgaacgatt ggaatctaat aactacaata cttaccggtc aaggaaatac    360
tccagttggt atgtggcact gaaacgaact gggcagtata aacttggacc aaaaacagga    420
cctgggcaga aagctatact ttttcttcca atgtctgcta agagctga                 468
```

<210> SEQ ID NO 191
<211> LENGTH: 465
<212> TYPE: DNA
<213> ORGANISM: Norway rat

<400> SEQUENCE: 191

```
atggctgccg gcagcatcac ttcgcttccc gcactgccgg aggacggcgg cggcgccttc    60 ccaccccggcc acttcaagga tcccaagcgg ctctactgca gaacggcgg cttcttcctg    120 cgcatccatc cagacggccg cgtggacggc gtccgggaga gagcgaccc acacgtcaaa    180 ctacagctcc aagcagaaga gagaggagtt gtgtccatca agggagtgtg tgcgaaccgg    240
tacctggcta tgaaggaaga tggacggctg ctggcttcta agtgtgttac agaagagtgt    300
ttcttctttg aacgcctgga gtccaataac tacaacactt accggtcacg gaaatactcc    360
agttggtatg tggcactgaa acgaactggg cagtataaac tcggatccaa acggggcct    420 ggacagaagg ccatactgtt tcttccaatg tctgctaaga gctga                    465
```

<210> SEQ ID NO 192
<211> LENGTH: 405
<212> TYPE: DNA
<213> ORGANISM: Naked mole-rat

<400> SEQUENCE: 192

```
ccacccggcc acttcaagga cccaaagcgg ctgtactgca aaaacggggg cttcttcctg    60
cgcatccacc ccgacggccg cgtggacggg gtccggagaga agcgaccc tcacgtcaaa    120 ctacaacttc aagcagaaga gagaggagtt gtgtctatta agggagtgtg tgcgaaccgt    180
taccttgcta tgaaggaaga tggaagatta ctggcttcta aatgtgttac agatgagtgt    240 ttctttttg aacgattgga atctaataac tacaatactt atcggtcaag gaaatactcc    300
agttggtatg tggcactgaa acgaactgga caatataaac ttggatccaa acaggaccg    360 gggcagaaag ctatacttttt tcttccaatg tctgctaaga gctga                    405
```

<210> SEQ ID NO 193
<211> LENGTH: 468
<212> TYPE: DNA
<213> ORGANISM: Bushbaby

<400> SEQUENCE: 193

```
atggcagccg ggagcatcac cacgctgccc tccctgcccg aggacggcgg cagcgacgcc    60
tttccgcccg gccacttcaa ggaccccaag cgactgtact gcaaaaacgg gggcttcttc    120
ctgcgcatcc accccgacgg ccgagtggac ggggtccggg agaagagcga cccttacatc    180
aaactacaac ttcaagcaga agagagagga gttgtgtcta tcaaaggagt gtgtgcgaac    240
cgttaccttg ctatgaagga agacggaaga ttgctggctt ctaaattgat tacagacgag    300
tgcttctttt ttgaacgact ggaatctaat aactacaata cttaccggtc aagaaaatac    360
```

```
tccagttggt atgtggcact gaaacgaact ggacagtata aacttggatc caaaacagga      420
cctgggcaga aagctatact ttttcttcca atgtctgcta agagctga                  468
```

<210> SEQ ID NO 194
<211> LENGTH: 465
<212> TYPE: DNA
<213> ORGANISM: House mouse

<400> SEQUENCE: 194

```
atggctgcca gcggcatcac ctcgcttccc gcactgccgg aggacggcgg cgccgccttc      60
ccaccaggcc acttcaagga ccccaagcgg ctctactgca gaacggcgg cttcttcctg      120 cgcatccatc ccgacggccg cgtggatggc gtccgcgaga gagcgaccc acacgtcaaa      180 ctacaactcc aagcagaaga gagaggagtt gtgtctatca agggagtgtg tgccaaccgg      240
taccttgcta tgaaggaaga tggacggctg ctggcttcta agtgtgttac agaagagtgt      300
ttcttctttg aacgactgga atctaataac tacaatactt accggtcacg gaaatactcc      360
agttggtatg tggcactgaa acgaactggg cagtataaac tcggatccaa aacgggacct      420
ggacagaagg ccatactgtt tcttccaatg tctgctaaga gctga                     465
```

<210> SEQ ID NO 195
<211> LENGTH: 432
<212> TYPE: DNA
<213> ORGANISM: Squirrel

<400> SEQUENCE: 195

```
ctgcccgagg acggcggcgg cggcgccttc ccgcccggcc actttaagga ccccaagcgg      60
ctctactgca aaacggagg cttcttcctg cgcatccacc ccgacggccg agtggacggg      120
gtccgggaga gagcgaccc ccacatcaag ctccagcttc aagccgaaga ccgaggggtt      180
gtgtccatca agggagtgtg tgcaaaccga tacctggcca tgaaggagga cgggaggctc      240
ctggcttcta aatgtgttac ggacgagtgt ttcttttttg aacgactgga atcaaataac      300
tacaatactt accggtcaag gaaatactcc agttggtatg tggccctgaa acgaacaggg      360
cagtataaac ttggatccaa aacaggacct gggcagaaag ctatacttttt tcttccaatg      420 tctgctaaga gc                                                         432
```

<210> SEQ ID NO 196
<211> LENGTH: 318
<212> TYPE: DNA
<213> ORGANISM: Domestic cat

<400> SEQUENCE: 196

```
ccacttcaag gacccccaagc gtctgtactg caaaaacggg ggcttcttcc tgcgcatcca      60
ccccgacggc cgagtggatg gggtccggga gaagagcgac cctcacatca aactgcaact      120
tcaggcagaa gagagagggg ttgtgtccat caaaggagtc tgtgcaaacc gctatcttgc      180
catgaaggaa gatggaagat tactggcttc taaatgtgtt acggacgagt gtttctttttt      240 tgaacgattg gaatctaata actacaatac ttatcggtca aggaaatact ccagctggta      300
tgtggcactg aaacgaac                                                   318
```

<210> SEQ ID NO 197
<211> LENGTH: 288
<212> TYPE: DNA
<213> ORGANISM: Guinea pig -continued

<400> SEQUENCE: 197

```
gttaaactac aacttcaagc cgaagacaga ggagttgtgt ctatcaaggg agtctgtgcg      60
aaccgttacc ttgctatgaa ggaagacgga agattattgg cttccaaatg tgttacagat     120
gaatgtttct tttttgaacg actggaatct aataactaca acacttaccg gtcaaggaaa     180
tactccagtt ggtatgtggc actgaaacga actggacaat ataaacttgg gtccaaaaca     240
ggaccagggc agaaagccat acttttttctt ccaatgtctg cgaagagc                 288
```

<210> SEQ ID NO 198
<211> LENGTH: 471
<212> TYPE: DNA
<213> ORGANISM: Tasmanian devil

<400> SEQUENCE: 198

```
atggccgcgg gcagcatcac cacgttgccg ccctggccg gggatggagc cagcggggc       60 gcctttcccc cgggccactt ccaggacccc aagcggctgt actgcaagaa cggaggcttc    120
ttcttgcgca tccatcccga cggtcacgtg acggcatcc gcgagaagag cgatccgcac     180
attaaacttc agcttcaggc agaagagaga ggagtagtgt ctattaaagg agtttgtgcc    240
aaccgctatc ttgccatgaa agaggatggc agattactgg ctctgaaatg tgtgactgaa    300
gagtgtttct tctttgaacg tctagagtcc aacaattaca acacttatcg ctcaaggaaa    360
tactccaatt ggtatgtggc attgaaacgc acaggccagt ataagcttgg atccaagact    420
ggaccagggc agaaagccat cctttttcctt cccatgtctg ctaagagctg a            471
```

<210> SEQ ID NO 199
<211> LENGTH: 471
<212> TYPE: DNA
<213> ORGANISM: Gray short-tailed opossum

<400> SEQUENCE: 199

```
atggccgcag gcagcatcac cacgctgcca gccctgtccg gggacggagg cggcggggc      60 gcctttcccc cgggccactt caaggacccc aagcggctgt actgcaagaa cggaggcttc    120
ttcctgcgca tccaccccga cggccgtgtg acggcatcc gcgagaagag cgacccgaac     180
attaaactac aacttcaggc agaagagaga ggagtggtgt ctattaaagg agtatgtgcc    240
aatcgctatc ttgccatgaa ggaagatgga agattattgg ctttgaaata tgtgaccgaa    300
gagtgtttct ttttcgaacg cttggagtcc aacaactaca acacttatcg ctcgaggaaa    360
tattccaatt ggtacgtggc actgaaacga acggggcagt acaagcttgg atccaagact    420
ggcccggggc agaaagccat cctttttcctc cccatgtctg ctaagagctg a            471
```

<210> SEQ ID NO 200
<211> LENGTH: 468
<212> TYPE: DNA
<213> ORGANISM: Rabbit

<400> SEQUENCE: 200

```
atggcagccg agagcatcac cacgctgccc gccctgccgg aggatggagg cagcggcgcc     60
ttcccgcccg ccacttcaa ggaccccaag cggctgtact gcaaaaacgg ggtttcttc     120 ctgcgtatcc accccgacgg ccgcgtggac ggggtccggg agaagagcga cccacacatc    180
aaattacaac ttcaagcaga agagagagga gttgtatcca tcaaaggtgt gtgtgcaaac    240
cgttaccttg ctatgaagga agatggaaga ctgctggctt ctaaatgtgt tacagacgag    300
tgcttctttt ttgaacgact ggagtctaat aactacaata cttaccggtc aaggaaatat    360
```

```
tccagctggt atgtggcact gaaacgaact gggcagtata aacttggatc caaaacagga    420
cctgggcaga aggctatact ttttcttcca atgtctgcta agagctga                468

<210> SEQ ID NO 201
<211> LENGTH: 375
<212> TYPE: DNA
<213> ORGANISM: Turkey

<400> SEQUENCE: 201
cggctctact gtaagaacgg cggcttcttc ctgcgcatca atcccgacgg cagagtggac     60
ggcgtccgcg agaagagcga tccgcacatc aaactgcagc ttcaggcaga agaaagagga    120
gtggtatcaa tcaaaggtgt aagtgcaaac cgctttctgg ctatgaagga ggatggcaga    180
ttgctggcac tgaaatgtgc aacagaagaa tgtttctttt ttgagcgttt ggaatctaat    240
aattataaca cttaccggtc acggaagtac tctgattggt atgtggcact gaaaagaact    300
ggacagtaca agcccggacc aaaaactgga cctggacaga agctatcct ttttcttcca    360 atgtctgcta aaagc                                                    375

<210> SEQ ID NO 202
<211> LENGTH: 477
<212> TYPE: DNA
<213> ORGANISM: Gallus gallus

<400> SEQUENCE: 202
atggcggcgg gggcggcggg gagcatcacc acgctgccgg cgctgcccga cgacgggggc     60
ggcggcgctt ttccccccgg gcacttcaag gaccccaagc ggctctactg caagaacggc    120
ggcttcttcc tgcgcatcaa ccccgacggc agggtggacg gcgtccgcga agagcgat     180 ccgcacatca aactgcagct tcaagcagaa gaaagaggag tagtatcaat caaaggcgta    240
agtgcaaacc gctttctggc tatgaaggag gatggcagat gctggcact gaaatgtgca    300 acagaggaat gtttctttt cgagcgcttg gaatctaata actataacac ttaccggtca    360
cggaagtact ctgattggta tgtggcactg aaaaggactg gacagtacaa gcccggacca    420
aaaactggac ctggacagaa agctatcctt tttcttccaa tgtctgctaa aagctga      477

<210> SEQ ID NO 203
<211> LENGTH: 462
<212> TYPE: DNA
<213> ORGANISM: Zebra finch

<400> SEQUENCE: 203
atggcggcgg cgggggggcat cgctacgctg cccgacgacg gcggcagcgg cgcctttccc     60
ccggggcact caaggaccc caagcgcctg tactgcaaga acggcggctt cttcctgcgc    120
atcaaccccg acgggaaggt ggacggcgtc cgcgagaaga gcgacccgca catcaagctg    180
cagcttcagg cggaggaacg aggagtggtg tccatcaaag tgtcagtgc caatcgcttc    240 ctggccatga agaggatggg cagattgctg gccttgaaat atgcaacaga gaatgtttc    300 ttttttgaac gtttggaatc caataactat aacacttacc ggtcacggaa atactcggat    360
tggtatgtgg cactgaaaag aactggacag tacaaacctg gaccaaaaac tggacctgga    420
cagaaagcta tccttttcct tcctatgtct gctaaaagct ga                      462

<210> SEQ ID NO 204
<211> LENGTH: 468
<212> TYPE: DNA
```

<213> ORGANISM: Japanese firebelly newt

<400> SEQUENCE: 204

| | | |
|---|---|---|
| atggctgctg ggagcatcac cagtctccct gccctacccg aggacgggaa tggcggcacc | 60 |
| ttcacacccg gcggattcaa agagccgaag aggctgtact gcaagaacgg gggcttcttt | 120 |
| ctccggatca actccgacgg caaggtggac ggagcccggg agaagagcga ctcctacatt | 180 |
| aaactgcagc ttcaagcaga agagcgcggt gtggtgtcca tcagggagt atgtgcaaac | 240 |
| cgctatctcg ctatgaagga tgatggcagg ctgatggcgc tgaaatggat aaccgatgaa | 300 |
| tgcttctttt tcgagcgact ggagtccaac aactataaca cgtatcgatc acggaaatat | 360 |
| tccgattggt atgtggcgct gaaaagaact gggcaataca aaaatggatc aaaaaccgga | 420 |
| gcaggacaga aagcaatcct ttttctaccc atgtcggcca agagttga | 468 |

<210> SEQ ID NO 205
<211> LENGTH: 468
<212> TYPE: DNA
<213> ORGANISM: African clawed frog

<400> SEQUENCE: 205

| | | |
|---|---|---|
| atggcggcag ggagcatcac aactctgcca actgaatccg aggatggggg aaacactcct | 60 |
| ttttcaccag ggagttttaa agaccccaag aggctctact gcaagaacgg gggcttcttc | 120 |
| ctcaggataa actcagacgg gagagtggac gggtcaaggg acaaaagtga ctcgcacata | 180 |
| aaattacagc tacaagctgt agagcgggga gtggtatcaa taagggaat cactgcaaat | 240 |
| cgctaccttg ccatgaagga gatgggaga ttaacatcgc tgaggtgtat aacagatgaa | 300 |
| tgcttctttt ttgaacgact ggaagctaat aactacaaca cttaccggtc tcggaaatac | 360 |
| agcagctggt atgtggcact aaagcgaacc gggcagtaca aaaatggatc gagcactgga | 420 |
| ccgggacaaa aagctatttt atttctccca atgtccgcaa agagctga | 468 |

<210> SEQ ID NO 206
<211> LENGTH: 471
<212> TYPE: DNA
<213> ORGANISM: White-eared opossum

<400> SEQUENCE: 206

| | | |
|---|---|---|
| atggcagcag gcagcatcac cacattgccg gccctgtccg gggacggagg cggcggggga | 60 |
| gcctttcctc caggccactt caaggacccc aagcggctgt actgcaagaa cggaggcttc | 120 |
| ttcctgcgca tccaccccga cggccgcgtg gacggcatcc gcgagaagag cgacccgaac | 180 |
| attaaactac aacttcaggc agaagagaga ggagtagtgt ctattaaagg agtatgtgcc | 240 |
| aaccgatatc ttgccatgaa ggaggatggc agattattgg ctttgaaata tgtgaccgaa | 300 |
| gagtgtttct tttttgaacg tttggagtcc aacaactaca cacttatcg ctcaagaaaa | 360 |
| tattccaatt ggtatgtggc actgaaacga acggggcagt ataagcttgg atccaagact | 420 |
| ggcccggggc agaaagccat cctttttctcc ccatgtctgc taagatgctg a | 471 |

<210> SEQ ID NO 207
<211> LENGTH: 288
<212> TYPE: DNA
<213> ORGANISM: Microbat

<400> SEQUENCE: 207

| | | |
|---|---|---|
| gtcaaactcc aacttcaagc agaagagaga ggggtcgtgt ctatcaaagg agtgtgtgcc | 60 |
| aaccgctatc tcgctatgaa ggaggacggc cggttacagg cttctaaatg tgttacggat | 120 |

```
gagtgtttct tttttgaacg gttggaatcc aataactaca acacttaccg gtcaagaaag      180
tactccagtt ggtatgtggc attgaagcgg aatgggcagt ataaacttgg acccaaaaca      240
ggacctggcc agaaagccat acttttcctt cccatgtctg ctaagagc                   288
```

<210> SEQ ID NO 208
<211> LENGTH: 420
<212> TYPE: DNA
<213> ORGANISM: Anole lizard

<400> SEQUENCE: 208

```
gcggcggcgg cctcttccc  cccgggcccc ttcaaggacc ccaagcgcct ctactgcaag      60
aacgggggct tcttcctgcg gatcaacccc gacggcggcg tggacggcgt ccgagagaag     120
agcgacccca acatcaaatt gctgctccag gcagaggaga gaggtgtagt gtccatcaaa     180
ggtgtatgcg caaaccgttt cctggctatg aatgaagacg gtcgattgtt agcactgaaa     240
tacgtaacag atgaatgctt ctttttttgaa cgcttggaat ctaataatta caatacttat    300
cggtctcgta ataccgtga ttggtacatt gcactgaaac gaactggtca gtacaaactt      360
ggaccaaaaa ctggacgagg ccagaaagct atccttttcc ttccaatgtc tgccaaaagt     420
```

<210> SEQ ID NO 209
<211> LENGTH: 282
<212> TYPE: DNA
<213> ORGANISM: Armadillo

<400> SEQUENCE: 209

```
atggcagccg ggagcatcac cacgctgccc gctctgcccg aggacggcgg cagcggcgcc      60
ttcccgccgg gccacttcaa ggaccccaag cggctgtact gcaaaaacgg gggcttcttc     120
ctgcgcatcc atcccgacgg ccgagtggac ggggtccggg agaagagcga ccctaacatc     180
aaactacaac ttcaagcaga agagagaggg gtcgtgtcta tcaaaggcgt gtgtgcgaac     240
cgttaccttg ctatgcggga agacggaaga ctccaggcgt ct                        282
```

<210> SEQ ID NO 210
<211> LENGTH: 567
<212> TYPE: DNA
<213> ORGANISM: Tree shrew

<400> SEQUENCE: 210

```
gcggggggtta gagctgagag ggaggaggca ccggggagcg gtgacagccg ggggaccgat      60
cccgccgcgc gttcgctcat caggaggccg gatgctgcag cgcgagaggc gcttcttgga     120
gccaggagcc gggttcaggg cagctccacc tcctggccag cctcgtcacg aaccgggatc     180
aagttgccgg acgactcagg tcaaggaatg gcggctatc ctctggaccg cccgagccgg      240
agcacagggc gagggctggg cggtgccccg gaccctgccg taaaactaca gcttcaagcg     300
gaagagagag gggtcgtgtc tatcaaagga gtgtgtgcaa accgttacct ggccatgaag     360
gaggatgggc gactgctggc ttctaaatgt gttacagatg agtgtttctt ttttgaacga     420
ctggaatcta ataactacaa tacttaccgg tcccgaaagt actccagctg gtatgtggca     480
ctgaaacgaa ctgggcagta taaacttgga tccaaaacag gacctgggca gaaagctata     540
ctttttcttc caatgtctgc taaaagc                                         567
```

<210> SEQ ID NO 211
<211> LENGTH: 465
<212> TYPE: DNA

<213> ORGANISM: Western clawed frog

<400> SEQUENCE: 211

| | |
|---|---|
| atggcagcag gaagcatcac aaccctacca accgaatctg aggatggaaa cactcctttc | 60 |
| ccaccgggga actttaagga ccccaagagg ctctactgca agaatggggg ctacttcctc | 120 |
| aggattaact cagacgggag agtggacgga tcaagggata aaagtgactt acacataaaa | 180 |
| ttacagctac aagcagtaga gcggggagtg gtatcaataa agggaatcac tgcaaatcgc | 240 |
| taccttgcca tgaaggaaga tgggagatta acatcgctga agtgtataac agatgaatgc | 300 |
| ttcttttatg aacgattgga agctaataac tacaacactt accggtctcg gaaaaacaac | 360 |
| agctggtatg tggcactaaa gcgaactggg cagtataaaa atggatcgac cactggacca | 420 |
| ggacaaaaag ctattttgtt tctcccaatg tcagcaaaaa gctga | 465 |

<210> SEQ ID NO 212
<211> LENGTH: 468
<212> TYPE: DNA
<213> ORGANISM: Coelacanth

<400> SEQUENCE: 212

| | |
|---|---|
| atggctgcgg gaggaatcac taccctgccg gcggtacctg aggatggagg cagcagcacc | 60 |
| ttccctccag gaaacttcaa ggagcccaag agactttact gtaagaatgg aggctatttc | 120 |
| ttaaggataa accccgatgg aagagtggat ggaacaaggg agaaaatga tccttatata | 180 |
| aaattacaac tgcaagctga atctatagga gtggtgtcga taagggagt ttgttcaaac | 240 |
| cgttacctag cgatgaatga agactgtaga cttttttggat tgaaatatcc aacggatgaa | 300 |
| tgtttcttcc atgagaggct ggagtccaac aactacaata cttatcgttc aaagaagtat | 360 |
| tcggattggt atgtggcgct gaaacggact ggtcagtaca aacctgggcc aaaaactgga | 420 |
| ctgggacaaa aagcaatcct tttccttccg atgtctgcca agagttga | 468 |

<210> SEQ ID NO 213
<211> LENGTH: 468
<212> TYPE: DNA
<213> ORGANISM: Spotted green pufferfish

<400> SEQUENCE: 213

| | |
|---|---|
| atggccacgg gagggatcac gacgcttcca tccacacctg aagacggcgg cagcagcggc | 60 |
| tttcctcccg gcagcttcaa ggatcccaaa aggctctact gtaaaaacgg aggtttcttc | 120 |
| ctgaggatca gtccgacgg ggtcgtggac ggaatccggg agaagagtga ccccacata | 180 |
| aagcttcagc tccaggcgac ctctgtgggg gaggtggtca tcaaggggt gtgcgctaac | 240 |
| cgctatctgg ccatgaacag atggacgg ctgttcggaa cgaaacgagc cacggacgaa | 300 |
| tgccatttct tagagcggct tgagagcaac aactacaaca cttaccgctc caggaagtac | 360 |
| ccaaccatgt ttgtgggact gacgcggacg ggccagtaca agtctgggag caaaactgga | 420 |
| ccgggccaaa aggccatcct ttttcttccg atgtccgcca aatgctaa | 468 |

<210> SEQ ID NO 214
<211> LENGTH: 468
<212> TYPE: DNA
<213> ORGANISM: Stickleback

<400> SEQUENCE: 214

| | |
|---|---|
| atggccacgg caggcttcgc gacgcttccc tccacgcccg aagacggcgg cagcggcggc | 60 |
| ttcaccccg ggggattcaa ggatcccaag aggctgtact gcaaaaacgg gggcttcttc | 120 |

```
ttgaggatca ggtccgacgg aggtgtagat ggaatcaggg agaagagcga cgcccacata    180
aagctccaaa tccaggcgac gtcggtgggg gaggtggtca tcaaaggagt ctgtgccaac    240
cgctatctgg ccatgaacag agacggccgg ctgttcggag tgagacgggc gacggacgaa    300
tgctacttcc tggagcggct ggagagtaac aactacaaca cctaccgctc caggaagtac    360
cccggcatgt acgtggctct gaagcggacc ggccagtaca agtccgggag caaaaccgga    420
cccggtcaaa aggccattct gttcctcccc atgtcggcta agtgctaa                 468

<210> SEQ ID NO 215
<211> LENGTH: 468
<212> TYPE: DNA
<213> ORGANISM: Fugu rubripes

<400> SEQUENCE: 215
atggccacgg gagggatcac aacacttcca tccacacctg aagacggcgg cagcggcggt    60
tttcctcccg ggagcttcaa ggatcccaaa aggctgtact gtaaaaacgg cggcttcttc    120
ctgaggatca ggtccgacgg ggccgtggac ggaacccggg agaagactga cccccacata    180
aagcttcagc tccaggcgac ctctgtgggg gaggtggtca tcaaggggt ttgtgctaat    240 cgttatctgg ccatgaacag agatggacga ctgtttggaa tgaaacgagc gacggatgaa    300
tgccacttct tagagcggct cgagagcaac aactacaaca cctaccgctc caggaagtac    360
cccaacatgt ttgtgggact gacgcgaact ggcaactaca agtctgggac taaaactgga    420
ccgggccaaa aggccatcct ctttcttccg atgtcggcca aatactaa                 468

<210> SEQ ID NO 216
<211> LENGTH: 468
<212> TYPE: DNA
<213> ORGANISM: Rainbow trout

<400> SEQUENCE: 216
atggccacag gagaaatcac cactctaccc gccacacctg aagatggagg cagtggcggc    60
ttccttccag gaaactttaa ggagcccaag aggttgtact gtaaaaatgg aggctacttc    120
ttgaggataa actctaacgg aagcgtggac gggatcagag ataagaacga ccccacaat    180 aagcttcaac tccaggcgac ctcagtgggg gaagtagtaa tcaagggggt ctcagccaac    240
cgctatctgg ccatgaatgc agatggaaga ctgtttggac cgagacggac aacagatgaa    300
tgctacttca tggagaggct ggagagtaac aactacaaca cctaccgctc tcgaaagtac    360
cctgaaatgt atgtggcact gaaaaggact ggccagtaca agtcaggatc caaaactgga    420
cccggccaaa aagccatcct cttcctcccc atgtcagcca gacgctga                 468

<210> SEQ ID NO 217
<211> LENGTH: 453
<212> TYPE: DNA
<213> ORGANISM: Salmon

<400> SEQUENCE: 217
atggccacag gagaaatcac cactctaccc gccacacctg aagatggagg cagtggcggc    60
ttccctccag gaaactttaa ggatcccaag aggctgtact gtaaaaacgg gggctacttc    120
ttgagaataa actctaatgg aagcgtggac gggatccgag agaagaacga ccccacaaa    180 cagcctcaat tgtcagggc atggactctt caaggtgtca acgttccac agggatgctg    240 gcccatgttg actccaacgc ttcccacaat tgtgtcaagg tggctggatg ttctttggga    300
```

| | |
|---|---|
| gaatttggca gtatgtccaa ccggcctcat aaccgcagac cacgtgtagc tacaccagcc | 360 |
| caggacctcc acatccggct tcttcatcta cgggatcgtc tgaaaccagc cacccgaaca | 420 |
| gctgataaaa ctgaggagta tttctgtctg taa | 453 |

<210> SEQ ID NO 218
<211> LENGTH: 465
<212> TYPE: DNA
<213> ORGANISM: Zebrafish

<400> SEQUENCE: 218

| | |
|---|---|
| atggccaccg agggatcac cacactcccg gccgctccgg acgccgaaaa cagcagcttt | 60 |
| cccgcgggca gcttcaggga tcccaagcgc ctgtactgca aaaacggagg attcttcctg | 120 |
| cggatcaacg cggacggccg agtggacgga gcccgagaca gagcgaccc gcacattcgt | 180 |
| ctgcagctgc aggcgacggc agtgggtgaa gtactcatta aaggcatctg taccaaccgt | 240 |
| ttccttgcca tgaacgcaga cggacgactg ttcgggacga aaaggaccac agatgaatgt | 300 |
| tatttcctgg agcgcctgga gtccaacaac tacaacacat acagatcccg caagtatccc | 360 |
| gactggtacg tggctctgaa gagaaccggc cagtataaaa gcggctctaa aaccagcccg | 420 |
| ggacagaagg ccatcctgtt tctgcccatg tcggccaaat gctga | 465 |

<210> SEQ ID NO 219
<211> LENGTH: 468
<212> TYPE: DNA
<213> ORGANISM: Nile tilapia

<400> SEQUENCE: 219

| | |
|---|---|
| atggccacgg gaggaatcac aacacttccc gctacacctg aagacggcgg cagcagcggc | 60 |
| tttcctcctg ggaacttcaa ggaccctaaa aggctgtact gtaaaaatgg tggcttcttc | 120 |
| ttgaggataa aatctgatgg aggagtggat ggaatacgag agaaaaacga ccccacata | 180 |
| aagcttcaac tccaggcgac ctcagtggga gaagtggtca tcaaagggat ttgtgcaaac | 240 |
| cgatatctgg caatgaacag agatggacga ctgtttggag cgagaagagc aacagatgag | 300 |
| tgctacttct tagagcggct cgagagcaac aactacaaca cctaccgctc caggaagtac | 360 |
| ccaaacatgt acgtggcgct gaagcggact ggccagtaca agtctggaag caaaactgga | 420 |
| ccgggtcaaa aggcaattct ctttctccca atgtctgcta atgctaa | 468 |

<210> SEQ ID NO 220
<211> LENGTH: 468
<212> TYPE: DNA
<213> ORGANISM: Medaka

<400> SEQUENCE: 220

| | |
|---|---|
| atggctacgg gagaaatcac aacacttccc tccccagctg aaaacagcag aagcgatggc | 60 |
| tttcctccag ggaactacaa ggatcctaag aggctctact gtaaaaatgg aggtttgttt | 120 |
| ttgaggatta aacctgatgg aggagtggat ggaatccggg aaaaaaaga tccccacgtt | 180 |
| aagcttcgcc ttcaggctac ctcagcggga gaggtggtga tcaaaggagt tgttcaaac | 240 |
| agatatctgg cgatgcatgg agatggacgt ctatttggag tgacaagc aacagaggaa | 300 |
| tgctacttct tggagcgact agagagcaac aactataaca cctatcgctc taaaaagtac | 360 |
| ccaaacatgt acgtggcact gaagcggaca ggccagtaca acctggaaa caaaactgga | 420 |
| ccaggtcaaa aggccattct ctttctgcct atgtctgcca agtactaa | 468 |

-continued

```
<210> SEQ ID NO 221
<211> LENGTH: 206
<212> TYPE: PRT
<213> ORGANISM: Homo sapiens

<400> SEQUENCE: 221

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205

<210> SEQ ID NO 222
<211> LENGTH: 268
<212> TYPE: PRT
<213> ORGANISM: Homo sapiens

<400> SEQUENCE: 222

Met Ser Leu Ser Phe Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ala Ser Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
```

```
                130                 135                 140
Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
                180                 185                 190

Asn Lys Arg Gly Lys Ala Lys Arg Gly Cys Ser Pro Arg Val Lys Pro
                195                 200                 205

Gln His Ile Ser Thr His Phe Leu Pro Arg Phe Lys Gln Ser Glu Gln
                210                 215                 220

Pro Glu Leu Ser Phe Thr Val Thr Val Pro Glu Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
                260                 265

<210> SEQ ID NO 223
<211> LENGTH: 208
<212> TYPE: PRT
<213> ORGANISM: Homo sapiens

<400> SEQUENCE: 223

Met Ala Leu Gly Gln Lys Leu Phe Ile Thr Met Ser Arg Gly Ala Gly
1                   5                   10                  15

Arg Leu Gln Gly Thr Leu Trp Ala Leu Val Phe Leu Gly Ile Leu Val
                20                  25                  30

Gly Met Val Val Pro Ser Pro Ala Gly Thr Arg Ala Asn Asn Thr Leu
                35                  40                  45

Leu Asp Ser Arg Gly Trp Gly Thr Leu Leu Ser Arg Ser Arg Ala Gly
                50                  55                  60

Leu Ala Gly Glu Ile Ala Gly Val Asn Trp Glu Ser Gly Tyr Leu Val
65                  70                  75                  80

Gly Ile Lys Arg Gln Arg Leu Tyr Cys Asn Val Gly Ile Gly Phe
                85                  90                  95

His Leu Gln Val Leu Pro Asp Gly Arg Ile Ser Gly Thr His Glu Glu
                100                 105                 110

Asn Pro Tyr Ser Leu Leu Glu Ile Ser Thr Val Glu Arg Gly Val Val
                115                 120                 125

Ser Leu Phe Gly Val Arg Ser Ala Leu Phe Val Ala Met Asn Ser Lys
                130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
                180                 185                 190

Ser Lys Val Ser Pro Ile Met Thr Val Thr His Phe Leu Pro Arg Ile
                195                 200                 205

<210> SEQ ID NO 224
<211> LENGTH: 208
<212> TYPE: PRT
<213> ORGANISM: Homo sapiens
```

<400> SEQUENCE: 224

```
Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205
```

<210> SEQ ID NO 225
<211> LENGTH: 207
<212> TYPE: PRT
<213> ORGANISM: Homo sapiens

<400> SEQUENCE: 225

```
Met Ala Glu Val Gly Gly Val Phe Ala Ser Leu Asp Trp Asp Leu His
1               5                   10                  15

Gly Phe Ser Ser Ser Leu Gly Asn Val Pro Leu Ala Asp Ser Pro Gly
            20                  25                  30

Phe Leu Asn Glu Arg Leu Gly Gln Ile Glu Gly Lys Leu Gln Arg Gly
        35                  40                  45

Ser Pro Thr Asp Phe Ala His Leu Lys Gly Ile Leu Arg Arg Arg Gln
    50                  55                  60

Leu Tyr Cys Arg Thr Gly Phe His Leu Glu Ile Phe Pro Asn Gly Thr
65                  70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Tyr Gly Ser Lys Lys
        115                 120                 125

Leu Thr Arg Glu Cys Val Phe Arg Glu Gln Phe Glu Glu Asn Trp Tyr
    130                 135                 140

Asn Thr Tyr Ala Ser Thr Leu Tyr Lys His Ser Asp Ser Glu Arg Gln
145                 150                 155                 160
```

```
Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
            180                 185                 190

Pro Ser Lys Leu Pro Ser Met Ser Arg Asp Leu Phe His Tyr Arg
        195                 200                 205

<210> SEQ ID NO 226
<211> LENGTH: 211
<212> TYPE: PRT
<213> ORGANISM: Homo sapiens

<400> SEQUENCE: 226

Met Ala Pro Leu Ala Glu Val Gly Gly Phe Leu Gly Gly Leu Glu Gly
1               5                   10                  15

Leu Gly Gln Gln Val Gly Ser His Phe Leu Leu Pro Pro Ala Gly Glu
            20                  25                  30

Arg Pro Pro Leu Leu Gly Glu Arg Arg Ser Ala Ala Glu Arg Ser Ala
        35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210

<210> SEQ ID NO 227
<211> LENGTH: 621
<212> TYPE: DNA
<213> ORGANISM: Homo sapiens

<400> SEQUENCE: 227
atgtcggggc cgggacggc cgcggtagcg ctgctcccgg cggtcctgct ggccttgctg      60
gcgccctggg cgggccgagg gggcgccgcc gcacccactg cacccaacgg cacgctggag     120
gccgagctag agcgccgctg ggagagcctg gtggcgctct cgttggcgcg cctgccggtg     180
gcagcgcagc ccaaggaggc ggccgtccag agcggcgccg gcgactacct gctgggcatc     240
aagcggctgc ggcggctcta ctgcaacgtg gcatcggct tccacctcca ggcgctcccc      300
gacggccgca tcggcggcgc gcacgcggac acccgcgaca gcctgctgga gctctcgccc     360
```

```
gtggagcggg gcgtggtgag catcttcggc gtggccagcc ggttcttcgt ggccatgagc    420
agcaagggca agctctatgg ctcgcccttc ttcaccgatg agtgcacgtt caaggagatt    480
ctccttccca acaactacaa cgcctacgag tcctacaagt accccggcat gttcatcgcc    540
ctgagcaaga atgggaagac caagaagggg aaccgagtgt cgcccaccat gaaggtcacc    600
cacttcctcc ccaggctgtg a                                              621

<210> SEQ ID NO 228
<211> LENGTH: 807
<212> TYPE: DNA
<213> ORGANISM: Homo sapiens

<400> SEQUENCE: 228
atgagcttgt ccttcctcct cctcctcttc ttcagccacc tgatcctcag cgcctgggct     60
cacggggaga agcgtctcgc ccccaaaggg caacccggac ccgctgccac tgataggaac    120
cctagaggct ccagcagcag acagagcagc agtagcgcta tgtcttcctc ttctgcctcc    180
tcctcccccg cagcttctct gggcagccaa ggaagtggct ggagcagag cagtttccag    240 tggagcccct cggggcgccg gaccggcagc ctctactgca gagtgggcat cggtttccat    300
ctgcagatct acccggatgg caaagtcaat ggatcccacg aagccaatat gttaagtgtt    360
ttggaaatat ttgctgtgtc tcaggggatt gtaggaatac gaggagtttt cagcaacaaa    420 ttttagcga tgtcaaaaaa aggaaaactc catgcaagtg ccaagttcac agatgactgc    480
aagttcaggg agcgttttca agaaaatagc tataatacct atgcctcagc aatacataga    540
actgaaaaaa cagggcggga gtggtatgtg gccctgaata aaagaggaaa agccaaacga    600
gggtgcagcc ccgggttaa accccagcat atctctaccc attttctgcc aagattcaag    660
cagtcggagc agccagaact ttctttcacg gttactgttc ctgaaaagaa aaagccacct    720
agccctatca agccaaagat tcccctttct gcacctcgga aaaataccaa ctcagtgaaa    780
tacagactca gtttcgctt tggataa                                        807

<210> SEQ ID NO 229
<211> LENGTH: 627
<212> TYPE: DNA
<213> ORGANISM: Homo sapiens

<400> SEQUENCE: 229
atggccctgg acagaaaact gttcatcact atgtcccggg gagcaggacg tctgcagggc     60
acgctgtggg ctctcgtctt cctaggcatc tagtgggca tggtggtgcc ctcgcctgca    120
ggcacccgtg ccaacaacac gctgctggac tcgagggct ggggcaccct gctgtccagg    180
tctcgcgcgg ggctagctgg agagattgcc ggggtgaact gggaaagtgg ctatttggtg    240
gggatcaagc ggcagcggag gctctactgc aacgtgggca tcggctttca cctccaggtg    300
ctccccgacg gccggatcag cgggacccac gaggagaacc cctacagcct gctggaaatt    360
tccactgtgg agcgaggcgt ggtgagtctc tttggagtga gaagtgccct cttcgttgcc    420
atgaacagta aaggaagatt gtacgcaacg cccagcttcc aagaagaatg caagttcaga    480
gaaaccctcc tgcccaacaa ttacaatgcc tacgagtcag acttgtacca agggacctac    540
attgccctga gcaaatacgg acgggtaaag cggggcagca aggtgtcccc gatcatgact    600
gtcactcatt tccttcccag gatctaa                                       627

<210> SEQ ID NO 230
<211> LENGTH: 627
```

<212> TYPE: DNA
<213> ORGANISM: Homo sapiens

<400> SEQUENCE: 230

```
atggctccct taggtgaagt tgggaactat ttcggtgtgc aggatgcggt accgtttggg      60
aatgtgcccg tgttgccggt ggacagcccg gttttgttaa gtgaccacct gggtcagtcc     120
gaagcagggg ggctccccag gggacccgca gtcacggact tggatcattt aaagggatt     180
ctcaggcgga ggcagctata ctgcaggact ggatttcact tagaaatctt ccccaatggt     240
actatccagg gaaccaggaa agaccacagc cgatttggca ttctggaatt tatcagtata     300
gcagtgggcc tggtcagcat tcgaggcgtg acagtggac tctacctcgg gatgaatgag      360
aagggggagc tgtatggatc agaaaaacta acccaagagt gtgtattcag agaacagttc     420
gaagaaaact ggtataatac gtactcatca aacctatata agcacgtgga cactggaagg     480
cgatactatg ttgcattaaa taaagatggg accccgagag aagggactag gactaaacgg     540
caccagaaat tcacacattt tttacctaga ccagtggacc ccgacaaagt acctgaactg     600
tataaggata ttctaagcca aagttga                                         627
```

<210> SEQ ID NO 231
<211> LENGTH: 624
<212> TYPE: DNA
<213> ORGANISM: Homo sapiens

<400> SEQUENCE: 231

```
atggcagagg tggggggcgt cttcgcctcc ttggactggg atctacacgg cttctcctcg      60
tctctgggga acgtgccctt agctgactcc ccaggtttcc tgaacgagcg cctgggccaa     120
atcgagggga agctgcagcg tggctcaccc acagacttcg cccacctgaa ggggatcctg     180
cggcgccgcc agctctactg ccgcaccggc ttccacctgg atcttccc caacggcacg       240
gtgcacggga cccgccacga ccacagccgc ttcggaatcc tggagtttat cagcctggct     300
gtggggctga tcagcatccg gggagtggac tctggcctgt acctaggaat gaatgagcga     360
ggagaactct atgggtcgaa gaaactcaca cgtgaatgtg ttttccggga acagtttgaa     420
gaaaactggt acaacaccta tgcctcaacc ttgtacaaac attcggactc agagagacag     480
tattacgtgg ccctgaacaa agatggctca ccccgggagg gatacaggac taaacgacac     540
cagaaattca ctcactttt acccaggcct gtagatcctt ctaagttgcc ctccatgtcc     600
agagacctct ttcactatag gtaa                                            624
```

<210> SEQ ID NO 232
<211> LENGTH: 636
<212> TYPE: DNA
<213> ORGANISM: Homo sapiens

<400> SEQUENCE: 232

```
atggctccct tagccgaagt cggggggcttt ctgggcggcc tggagggctt gggccagcag      60
gtgggttcgc atttcctgtt gcctcctgcc ggggagcggc cgccgctgct gggcgagcgc     120
aggagcgcgg cggagcggag cgcgcgcggc gggccggggg ctgcgcagct ggcgcacctg     180
cacggcatcc tgcgccgccg gcagctctat tgccgcaccg gcttccacct gcagatcctg     240
cccgacggca gcgtgcaggg caccccggcag gaccacagcc tcttcggtat cttggaattc     300
atcagtgtgg cagtgggact ggtcagtatt agaggtgtgg acagtggtct ctatcttgga     360
atgaatgaca aaggagaact ctatggatca gagaaactta cttccgaatg catctttagg     420
```

```
gagcagtttg aagagaactg gtataacacc tattcatcta acatatataa acatggagac    480
actggccgca ggtattttgt ggcacttaac aaagacggaa ctccaagaga tggcgccagg    540
tccaagaggc atcagaaatt tacacatttc ttacctagac cagtggatcc agaaagagtt    600
ccagaattgt acaaggacct actgatgtac acttga                              636
```

<210> SEQ ID NO 233
<211> LENGTH: 216
<212> TYPE: PRT
<213> ORGANISM: Homo sapiens

<400> SEQUENCE: 233

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
        210                 215
```

<210> SEQ ID NO 234
<211> LENGTH: 216
<212> TYPE: PRT
<213> ORGANISM: Gorilla gorilla

<400> SEQUENCE: 234

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
```

```
            65                  70                  75                  80
Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 235
<211> LENGTH: 216
<212> TYPE: PRT
<213> ORGANISM: Pan troglodytes

<400> SEQUENCE: 235

Met Arg Asn Gly Cys Val Val His Val Trp Ile Leu Ala Gly Leu
1               5                   10                  15

Trp Leu Ala Val Ala Gly Arg Pro Leu Ala Phe Ser Asp Ala Gly Arg
                20                  25                  30

His Val His Tyr Cys Trp Gly Asp Pro Ile Pro Leu Arg His Leu Tyr
            35                  40                  45

Thr Ser Gly Pro His Gly Leu Ser Ser Cys Phe Leu Arg Ile Pro Ala
    50                  55                  60

Asn Cys Val Met Asn Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 236
<211> LENGTH: 216
<212> TYPE: PRT
<213> ORGANISM: Macaca mulatta

<400> SEQUENCE: 236

```
Met Arg Ser Gly Cys Val Val His Ala Trp Ile Leu Ala Ser Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Thr
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Ala Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 237
<211> LENGTH: 216
<212> TYPE: PRT
<213> ORGANISM: Pongo abelii

<400> SEQUENCE: 237

```
Met Arg Ser Gly Cys Val Val His Ala Trp Ile Leu Ala Gly Leu
1               5                   10                  15

Trp Leu Ala Val Ala Gly Arg Pro Leu Ala Phe Ser Asp Ser Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110
```

```
Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Arg His Leu Glu Ser Asp Met Phe Ser Ser Pro Leu
                180                 185                 190

Glu Thr Asp Ser Met Asp Pro Phe Gly Leu Val Thr Gly Leu Glu Ala
                195                 200                 205

Val Arg Ser Pro Ser Phe Glu Lys
    210                 215

<210> SEQ ID NO 238
<211> LENGTH: 216
<212> TYPE: PRT
<213> ORGANISM: Nomascus leucogenys

<400> SEQUENCE: 238

Met Arg Ser Glu Cys Val Val His Ala Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
                35                  40                  45

Thr Ser Gly Pro His Gly Leu Ser Ser Cys Phe Leu Arg Ile Arg Ala
50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
                195                 200                 205

Val Arg Ser Pro Ser Phe Glu Lys
    210                 215

<210> SEQ ID NO 239
<211> LENGTH: 142
<212> TYPE: PRT
<213> ORGANISM: Callithrix jacchus

<400> SEQUENCE: 239
```

Met Trp Lys Ala Thr Ala Gly Gly Gln Gln Gly Gln Ser Glu Ala Gln
1               5                   10                  15

Met Ser Thr Cys Pro His Val Pro Arg Pro Leu Trp Ile Ala Gln Ser
            20                  25                  30

Cys Leu Phe Ser Leu Gln Leu Gln Tyr Ser Glu Glu Asp Cys Ala Phe
        35                  40                  45

Glu Glu Glu Ile Arg Pro Asp Gly Tyr Asn Val Tyr Trp Ser Glu Lys
50                  55                  60

His Arg Leu Pro Val Ser Leu Ser Ser Ala Lys Gln Arg Gln Leu Tyr
65                  70                  75                  80

Lys Lys Arg Gly Phe Leu Pro Leu Ser His Phe Leu Pro Met Leu Pro
                85                  90                  95

Ile Ala Pro Glu Glu Pro Glu Asp Leu Arg Gly His Leu Glu Ser Asp
                100                 105                 110

Val Phe Ser Ser Pro Leu Glu Thr Asp Ser Met Asp Pro Phe Gly Leu
            115                 120                 125

Val Thr Gly Leu Glu Ala Val Asn Ser Pro Ser Phe Glu Lys
            130                 135                 140

<210> SEQ ID NO 240
<211> LENGTH: 219
<212> TYPE: PRT
<213> ORGANISM: Microcebus murinus

<400> SEQUENCE: 240

Met Pro Ser Gly Gln Ser Gly Cys Val Ala Ala Arg Ala Leu Ile Leu
1               5                   10                  15

Ala Gly Leu Trp Leu Thr Ala Ala Gly Arg Pro Leu Ala Phe Ser Asp
                20                  25                  30

Ala Gly Pro His Val His Tyr Gly Trp Gly Pro Ile Arg Leu Arg
            35                  40                  45

His Leu Tyr Thr Ala Gly Pro His Gly Leu Ser Ser Cys Phe Leu Arg
50                  55                  60

Ile Arg Ala Asp Gly Ser Val Asp Cys Ala Arg Gly Gln Ser Ala His
65                  70                  75                  80

Ser Leu Leu Glu Ile Arg Ala Val Ala Leu Arg Thr Val Ala Ile Lys
                85                  90                  95

Gly Val His Ser Val Arg Tyr Leu Cys Met Gly Ala Asp Gly Arg Met
                100                 105                 110

Gln Gly Leu Leu Arg Tyr Ser Glu Glu Asp Cys Ala Phe Glu Glu Glu
            115                 120                 125

Ile Arg Pro Asp Gly Tyr Asn Val Tyr Arg Ser Glu Lys His Arg Leu
            130                 135                 140

Pro Val Ser Leu Ser Ser Ala Arg Gln Arg Gln Leu Tyr Lys Gly Arg
145                 150                 155                 160

Gly Phe Leu Pro Leu Ser His Phe Leu Pro Met Leu Pro Val Thr Pro
                165                 170                 175

Ala Glu Thr Gly Asp Leu Arg Asp His Leu Glu Ser Asp Met Phe Ala
            180                 185                 190

Ser Pro Leu Glu Thr Asp Ser Met Asp Pro Phe Gly Ile Ala Thr Arg
            195                 200                 205

Leu Gly Val Val Lys Ser Pro Ser Phe Gln Lys
210                 215

<210> SEQ ID NO 241

<211> LENGTH: 138
<212> TYPE: PRT
<213> ORGANISM: Choloepus hoffmanni

<400> SEQUENCE: 241

Leu Leu Glu Met Lys Ala Val Ala Leu Arg Ala Val Ala Ile Lys Gly
1               5                   10                  15

Val His Ser Ala Leu Tyr Leu Cys Met Asn Ala Asp Gly Ser Leu His
                20                  25                  30

Gly Leu Pro Arg Tyr Ser Ala Glu Asp Cys Ala Phe Glu Glu Ile
            35                  40                  45

Arg Pro Asp Gly Tyr Asn Val Tyr Trp Ser Arg Lys His Gly Leu Pro
50                  55                  60

Val Ser Leu Ser Ser Ala Lys Gln Arg Gln Leu Tyr Lys Gly Arg Gly
65                  70                  75                  80

Phe Leu Pro Leu Ser His Phe Leu Pro Met Leu Pro Met Thr Pro Ala
                85                  90                  95

Glu Pro Ala Asp Pro Gly Asp Val Glu Ser Asp Met Phe Ser Ser
            100                 105                 110

Pro Leu Glu Thr Asp Ser Met Asp Pro Phe Gly Ile Ala Ser Arg Leu
            115                 120                 125

Glu Leu Val Asn Ser Pro Ser Phe Gln Thr
        130                 135

<210> SEQ ID NO 242
<211> LENGTH: 205
<212> TYPE: PRT
<213> ORGANISM: Ailuropoda melanoleuca

<400> SEQUENCE: 242

Val Leu Ala Gly Leu Cys Leu Ala Val Ala Gly Arg Pro Leu Ala Phe
1               5                   10                  15

Ser Asp Ala Gly Pro His Val His Tyr Gly Trp Gly Glu Pro Ile Arg
                20                  25                  30

Leu Arg His Leu Tyr Thr Ala Gly Pro His Gly Leu Ser Ser Cys Phe
            35                  40                  45

Leu Arg Ile Arg Ala Asp Gly Gly Val Asp Cys Ala Arg Gly Gln Ser
50                  55                  60

Ala His Ser Leu Val Glu Ile Arg Ala Val Ala Leu Arg Thr Val Ala
65                  70                  75                  80

Ile Lys Gly Val His Ser Val Arg Tyr Leu Cys Met Gly Ala Asp Gly
                85                  90                  95

Arg Met Gln Gly Leu Pro Gln Tyr Ser Ala Gly Asp Cys Ala Phe Glu
            100                 105                 110

Glu Glu Ile Arg Pro Asp Gly Tyr Asn Val Tyr Arg Ser Lys Lys His
            115                 120                 125

Arg Leu Pro Val Ser Leu Ser Gly Ala Lys Gln Arg Gln Leu Tyr Lys
130                 135                 140

Asp Arg Gly Phe Leu Pro Leu Ser His Phe Leu Pro Met Leu Pro Gly
145                 150                 155                 160

Ser Pro Ala Glu Pro Arg Asp Leu Gln Asp His Ala Gly Ser Asp Gly
            165                 170                 175

Phe Ser Ala Pro Leu Glu Thr Asp Ser Met Asp Pro Phe Gly Ile Ala
            180                 185                 190

Thr Lys Met Gly Leu Val Lys Ser Pro Ser Phe Gln Lys
            195                 200                 205

<210> SEQ ID NO 243
<211> LENGTH: 218
<212> TYPE: PRT
<213> ORGANISM: Sus scrofa

<400> SEQUENCE: 243

```
Met Arg Ser Ala Pro Ser Arg Cys Ala Val Arg Ala Leu Val Leu
1               5                   10                  15

Ala Gly Leu Trp Leu Ala Ala Gly Arg Pro Leu Ala Phe Ser Asp
                20                  25                  30

Ala Gly Pro His Val His Tyr Gly Trp Gly Glu Ser Val Arg Leu Arg
            35                  40                  45

His Leu Tyr Thr Ala Ser Pro His Gly Val Ser Cys Phe Leu Arg
    50                  55                  60

Ile His Ser Asp Gly Pro Val Asp Cys Ala Pro Gly Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Arg Tyr Leu Cys Met Gly Ala Asp Gly Lys Met Gln
                100                 105                 110

Gly Gln Thr Gln Tyr Ser Asp Glu Asp Cys Ala Phe Glu Glu Glu Ile
            115                 120                 125

Arg Pro Asp Gly Tyr Asn Val Tyr Trp Ser Lys Lys His His Leu Pro
            130                 135                 140

Val Ser Leu Ser Ser Ala Arg Gln Arg Gln Leu Tyr Lys Gly Arg Gly
145                 150                 155                 160

Phe Leu Pro Leu Ser His Phe Leu Pro Met Leu Ser Thr Leu Pro Ala
                165                 170                 175

Glu Pro Glu Asp Leu Gln Asp Pro Phe Lys Ser Asp Leu Phe Ser Leu
                180                 185                 190

Pro Leu Glu Thr Asp Ser Met Asp Pro Phe Arg Ile Ala Ala Lys Leu
                195                 200                 205

Gly Ala Val Lys Ser Pro Ser Phe Tyr Lys
        210                 215
```

<210> SEQ ID NO 244
<211> LENGTH: 218
<212> TYPE: PRT
<213> ORGANISM: Bos taurus

<400> SEQUENCE: 244

```
Met Arg Ser Ala Pro Ser Arg Cys Ala Val Arg Ala Leu Val Leu
1               5                   10                  15

Ala Gly Leu Trp Leu Ala Ala Gly Arg Pro Leu Ala Phe Ser Asp
                20                  25                  30

Ala Gly Pro His Val His Tyr Gly Trp Gly Glu Ser Val Arg Leu Arg
            35                  40                  45

His Leu Tyr Thr Ala Gly Pro Gln Gly Leu Tyr Ser Cys Phe Leu Arg
    50                  55                  60

Ile His Ser Asp Gly Ala Val Asp Cys Ala Gln Val Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Val Leu Tyr Leu Cys Met Asp Ala Asp Gly Lys Met
                100                 105                 110
```

-continued

```
Gln Gly Leu Thr Gln Tyr Ser Ala Glu Asp Cys Ala Phe Glu Glu Glu
            115                 120                 125

Ile Arg Pro Asp Gly Tyr Asn Val Tyr Trp Ser Arg Lys His His Leu
130                 135                 140

Pro Val Ser Leu Ser Ser Arg Gln Arg Gln Leu Phe Lys Ser Arg
145                 150                 155                 160

Gly Phe Leu Pro Leu Ser His Phe Leu Pro Met Leu Ser Thr Ile Pro
                165                 170                 175

Ala Glu Pro Glu Asp Leu Gln Glu Pro Leu Lys Pro Asp Phe Phe Leu
                180                 185                 190

Pro Leu Lys Thr Asp Ser Met Asp Pro Phe Gly Leu Ala Thr Lys Leu
            195                 200                 205

Gly Ser Val Lys Ser Pro Ser Phe Tyr Asn
            210                 215

<210> SEQ ID NO 245
<211> LENGTH: 192
<212> TYPE: PRT
<213> ORGANISM: Canis lupus familiaris

<400> SEQUENCE: 245

Leu Ala Phe Ser Asp Ala Gly Pro His Val His Ser Phe Trp Gly Glu
1               5                   10                  15

Pro Ile Arg Leu Arg His Leu Tyr Thr Ala Gly Pro His Gly Leu Ser
            20                  25                  30

Ser Cys Phe Leu Arg Ile Arg Ala Asp Gly Gly Val Asp Cys Ala Arg
        35                  40                  45

Gly Gln Ser Ala His Ser Leu Met Glu Met Arg Ala Val Ala Leu Arg
    50                  55                  60

Thr Val Ala Ile Lys Gly Val His Ser Gly Arg Tyr Leu Cys Met Gly
65                  70                  75                  80

Ala Asp Gly Arg Met Gln Gly Leu Pro Gln Tyr Ser Ala Gly Asp Cys
                85                  90                  95

Thr Phe Glu Glu Glu Ile Arg Pro Asp Gly Tyr Asn Val Tyr Trp Ser
            100                 105                 110

Lys Lys His His Leu Pro Ile Ser Leu Ser Ser Ala Lys Gln Arg Gln
        115                 120                 125

Leu Tyr Lys Gly Arg Gly Phe Leu Pro Leu Ser His Phe Leu Pro Ile
    130                 135                 140

Leu Pro Gly Ser Pro Thr Glu Pro Arg Asp Leu Glu Asp His Val Glu
145                 150                 155                 160

Ser Asp Gly Phe Ser Ala Ser Leu Glu Thr Asp Ser Met Asp Pro Phe
                165                 170                 175

Gly Ile Ala Thr Lys Ile Gly Leu Val Lys Ser Pro Ser Phe Gln Lys
                180                 185                 190

<210> SEQ ID NO 246
<211> LENGTH: 218
<212> TYPE: PRT
<213> ORGANISM: Oryctolagus cuniculus

<400> SEQUENCE: 246

Met Arg Arg Ala Pro Ser Gly Gly Ala Ala Arg Ala Leu Val Leu
1               5                   10                  15

Ala Gly Leu Trp Leu Ala Ala Ala Ala Arg Pro Leu Ala Leu Ser Asp
            20                  25                  30
```

-continued

```
Ala Gly Pro His Leu His Tyr Gly Trp Gly Glu Pro Val Arg Leu Arg
            35                  40                  45

His Leu Tyr Ala Thr Ser Ala His Gly Val Ser His Cys Phe Leu Arg
 50                  55                  60

Ile Arg Ala Asp Gly Ala Val Asp Cys Glu Arg Ser Gln Ser Ala His
 65                  70                  75                  80

Ser Leu Leu Glu Ile Arg Ala Val Ala Leu Arg Thr Val Ala Phe Lys
                85                  90                  95

Gly Val His Ser Ser Arg Tyr Leu Cys Met Gly Ala Asp Gly Arg Met
            100                 105                 110

Arg Gly Gln Leu Gln Tyr Ser Glu Glu Asp Cys Ala Phe Gln Glu Glu
        115                 120                 125

Ile Ser Ser Gly Tyr Asn Val Tyr Arg Ser Thr Thr His His Leu Pro
130                 135                 140

Val Ser Leu Ser Ser Ala Lys Gln Arg His Leu Tyr Lys Thr Arg Gly
145                 150                 155                 160

Phe Leu Pro Leu Ser His Phe Leu Pro Val Leu Pro Leu Ala Ser Glu
                165                 170                 175

Glu Thr Ala Ala Leu Gly Asp His Pro Glu Ala Asp Leu Phe Ser Pro
            180                 185                 190

Pro Leu Glu Thr Asp Ser Met Asp Pro Phe Gly Met Ala Thr Lys Leu
        195                 200                 205

Gly Pro Val Lys Ser Pro Ser Phe Gln Lys
    210                 215
```

<210> SEQ ID NO 247
<211> LENGTH: 215
<212> TYPE: PRT
<213> ORGANISM: Pteropus vampyrus

<400> SEQUENCE: 247

```
Met Arg Ser Pro Cys Ala Val Ala Arg Ala Leu Val Leu Ala Gly Leu
 1               5                  10                  15

Trp Leu Ala Ser Ala Ala Gly Pro Leu Ala Leu Ser Asp Ala Gly Pro
            20                  25                  30

His Val His Tyr Gly Trp Gly Glu Ala Ile Arg Leu Arg His Leu Tyr
        35                  40                  45

Thr Ala Gly Pro His Gly Pro Ser Ser Cys Phe Leu Arg Ile Arg Ala
 50                  55                  60

Asp Gly Ala Val Asp Cys Ala Arg Gly Gln Ser Ala His Ser Leu Val
 65                  70                  75                  80

Glu Ile Arg Ala Val Ala Leu Arg Asn Val Ala Ile Lys Gly Val His
                85                  90                  95

Ser Val Arg Tyr Leu Cys Met Gly Ala Asp Gly Arg Met Leu Gly Leu
            100                 105                 110

Leu Gln Tyr Ser Ala Asp Asp Cys Ala Phe Glu Glu Glu Ile Arg Pro
        115                 120                 125

Asp Gly Tyr Asn Val Tyr His Ser Lys Lys His His Leu Pro Val Ser
130                 135                 140

Leu Ser Ser Ala Lys Gln Arg Gln Leu Tyr Lys Asp Arg Gly Phe Leu
145                 150                 155                 160

Pro Leu Ser His Phe Leu Pro Met Leu Pro Arg Ser Pro Thr Glu Pro
                165                 170                 175

Glu Asn Phe Glu Asp His Leu Glu Ala Asp Thr Phe Ser Ser Leu Glu
```

```
                180             185             190
Thr Asp Asp Met Asp Pro Phe Gly Ile Ala Ser Lys Leu Gly Leu Glu
            195                 200                 205
Glu Ser Pro Ser Phe Gln Lys
        210                 215

<210> SEQ ID NO 248
<211> LENGTH: 219
<212> TYPE: PRT
<213> ORGANISM: Tursiops truncates

<400> SEQUENCE: 248

Met Arg Ser Ala Pro Ser Arg Cys Ala Val Ala Arg Ala Leu Val Leu
1               5                   10                  15
Ala Gly Leu Trp Leu Ala Ala Ala Gly Arg Pro Leu Ala Phe Ser Asp
            20                  25                  30
Ala Gly Pro His Val His Tyr Gly Trp Gly Glu Ser Val Arg Leu Arg
        35                  40                  45
His Leu Tyr Thr Ala Gly Pro Gln Gly Leu Ser Ser Cys Phe Leu Arg
    50                  55                  60
Ile His Ser Asp Gly Ala Val Asp Cys Ala Pro Val Gln Ser Ala His
65                  70                  75                  80
Ser Leu Met Glu Ile Arg Ala Val Ala Leu Ser Thr Val Ala Ile Lys
                85                  90                  95
Gly Glu Arg Ser Val Leu Tyr Leu Cys Met Gly Ala Asp Gly Lys Met
            100                 105                 110
Gln Gly Leu Ser Gln Tyr Ser Ala Glu Asp Cys Ala Phe Glu Glu Glu
        115                 120                 125
Ile Arg Pro Asp Gly Tyr Asn Val Tyr Trp Ser Lys Lys His His Leu
    130                 135                 140
Pro Val Ser Leu Ser Ser Ala Arg Gln Arg Gln Leu Phe Lys Gly Arg
145                 150                 155                 160
Gly Phe Leu Pro Leu Ser His Phe Leu Pro Met Leu Ser Thr Ile Pro
                165                 170                 175
Thr Glu Pro Asp Glu Ile Gln Asp His Leu Lys Pro Asp Leu Phe Ala
            180                 185                 190
Leu Pro Leu Lys Thr Asp Ser Met Asp Pro Phe Gly Leu Ala Thr Lys
        195                 200                 205
Leu Gly Val Val Lys Ser Pro Ser Phe Tyr Lys
    210                 215

<210> SEQ ID NO 249
<211> LENGTH: 219
<212> TYPE: PRT
<213> ORGANISM: Myotis lucifugus

<400> SEQUENCE: 249

Met Gln Ser Ala Trp Ser Arg Arg Val Val Ala Arg Ala Leu Val Leu
1               5                   10                  15
Ala Ser Leu Gly Leu Ala Ser Ala Gly Gly Pro Leu Gly Leu Ser Asp
            20                  25                  30
Ala Gly Pro His Val His Tyr Gly Trp Gly Glu Ser Ile Arg Leu Arg
        35                  40                  45
His Leu Tyr Thr Ser Gly Pro His Gly Pro Ser Ser Cys Phe Leu Arg
    50                  55                  60
Ile Arg Ala Asp Gly Ala Val Asp Cys Ala Arg Gly Gln Ser Ala His
```

```
                65                  70                  75                  80
Ser Leu Val Glu Ile Arg Ala Val Ala Leu Arg Lys Val Ala Ile Lys
                    85                  90                  95

Gly Val His Ser Ala Leu Tyr Leu Cys Met Gly Gly Asp Gly Arg Met
                100                 105                 110

Leu Gly Leu Pro Gln Phe Ser Pro Glu Asp Cys Ala Phe Glu Glu Glu
                115                 120                 125

Ile Arg Pro Asp Gly Tyr Asn Val Tyr Arg Ser Gln Lys His Gln Leu
            130                 135                 140

Pro Val Ser Leu Ser Ser Ala Arg Gln Arg Gln Leu Phe Lys Ala Arg
145                 150                 155                 160

Gly Phe Leu Pro Leu Ser His Phe Leu Pro Met Leu Pro Ser Ser Pro
                    165                 170                 175

Ala Gly Pro Val Pro Arg Glu Arg Pro Ser Glu Pro Asp Glu Phe Ser
                180                 185                 190

Ser Pro Leu Glu Thr Asp Ser Met Asp Pro Phe Gly Ile Ala Asn Asn
                195                 200                 205

Leu Arg Leu Val Arg Ser Pro Ser Phe Gln Glu
            210                 215

<210> SEQ ID NO 250
<211> LENGTH: 185
<212> TYPE: PRT
<213> ORGANISM: Ornithorhynchus anatinus

<400> SEQUENCE: 250

Met Leu Ser Cys Val Val Leu Pro Ser Leu Leu Glu Ile Lys Ala Val
1               5                   10                  15

Ala Val Arg Thr Val Ala Ile Lys Gly Val His Ile Ser Arg Tyr Leu
                20                  25                  30

Cys Met Glu Glu Asp Gly Lys Thr Pro Trp Ala Arg Leu Leu Glu Ile
            35                  40                  45

Lys Ala Val Ala Val Arg Thr Val Ala Ile Lys Gly Val His Ser Ser
        50                  55                  60

Arg Tyr Leu Cys Met Glu Glu Asp Gly Lys Leu His Gly Gln Ile Trp
65                  70                  75                  80

Tyr Ser Ala Glu Asp Cys Ala Phe Glu Glu Glu Ile Arg Pro Asp Gly
                    85                  90                  95

Tyr Asn Val Tyr Lys Ser Lys Lys Tyr Gly Val Pro Val Ser Leu Ser
                100                 105                 110

Ser Ala Lys Gln Arg Gln Gln Phe Lys Gly Arg Asp Phe Leu Pro Leu
            115                 120                 125

Ser Arg Phe Leu Pro Met Ile Asn Thr Val Pro Val Glu Pro Ala Glu
        130                 135                 140

Phe Gly Asp Tyr Ala Asp Tyr Phe Glu Ser Asp Ile Phe Ser Ser Pro
145                 150                 155                 160

Leu Glu Thr Asp Ser Met Asp Pro Phe Arg Ile Ala Pro Lys Leu Ser
                    165                 170                 175

Pro Val Lys Ser Pro Ser Phe Gln Lys
                180                 185

<210> SEQ ID NO 251
<211> LENGTH: 212
<212> TYPE: PRT
<213> ORGANISM: Monodelphis domestica
```

-continued

<400> SEQUENCE: 251

Met Ala Gln Leu Leu Ala Pro Leu Leu Thr Leu Ala Ala Leu Trp Leu
1               5                   10                  15

Ala Pro Thr Ala Arg Ala Arg Pro Leu Val Asp Ala Gly Pro His Val
            20                  25                  30

Tyr Tyr Gly Trp Gly Glu Pro Ile Arg Leu Arg His Leu Tyr Thr Ala
        35                  40                  45

Asn Arg His Gly Leu Ala Ser Phe Ser Phe Leu Arg Ile His Arg Asp
    50                  55                  60

Gly Arg Val Asp Gly Ser Arg Ser Gln Ser Ala Leu Ser Leu Leu Glu
65                  70                  75                  80

Ile Lys Ala Val Ala Leu Arg Met Val Ala Ile Lys Gly Val His Ser
                85                  90                  95

Ser Arg Tyr Leu Cys Met Gly Asp Ala Gly Lys Leu Gln Gly Ser Val
            100                 105                 110

Arg Phe Ser Ala Glu Asp Cys Thr Phe Glu Glu Gln Ile Arg Pro Asp
        115                 120                 125

Gly Tyr Asn Val Tyr Gln Ser Pro Lys Tyr Asn Leu Pro Val Ser Leu
    130                 135                 140

Cys Thr Asp Lys Gln Arg Gln Gln Ala His Gly Lys Glu His Leu Pro
145                 150                 155                 160

Leu Ser His Phe Leu Pro Met Ile Asn Ala Ile Pro Leu Glu Ala Glu
                165                 170                 175

Glu Pro Glu Gly Pro Arg Met Leu Ala Ala Pro Leu Gly Thr Asp Ser
            180                 185                 190

Met Asp Pro Phe Gly Leu Thr Ser Lys Leu Leu Pro Val Lys Ser Pro
        195                 200                 205

Ser Phe Gln Lys
    210

<210> SEQ ID NO 252
<211> LENGTH: 220
<212> TYPE: PRT
<213> ORGANISM: Anolis carolinensis

<400> SEQUENCE: 252

Met Cys Arg Arg Ala Leu Pro Leu Leu Gly Ala Leu Leu Gly Leu Ala
1               5                   10                  15

Ala Val Ala Ser Arg Ala Leu Pro Leu Thr Asp Ala Gly Pro His Val
            20                  25                  30

Ser Tyr Gly Trp Gly Glu Pro Val Arg Leu Arg His Leu Tyr Thr Ala
        35                  40                  45

Gly Arg Gln Gly Leu Phe Ser Gln Phe Leu Arg Ile His Ala Asp Gly
    50                  55                  60

Arg Val Asp Gly Ala Gly Ser Gln Asn Arg Gln Ser Leu Leu Glu Ile
65                  70                  75                  80

Arg Ala Val Ser Leu Arg Ala Val Ala Leu Lys Gly Val His Ser Ser
                85                  90                  95

Arg Tyr Leu Cys Met Glu Glu Asp Gly Arg Leu Arg Gly Met Leu Arg
            100                 105                 110

Tyr Ser Ala Glu Asp Cys Ser Phe Glu Glu Met Arg Pro Asp Gly
        115                 120                 125

Tyr Asn Ile Tyr Lys Ser Lys Lys Tyr Gly Val Leu Val Ser Leu Ser
    130                 135                 140

```
Asn Ala Arg Gln Arg Gln Gln Phe Lys Gly Lys Asp Phe Leu Pro Leu
145                 150                 155                 160

Ser His Phe Leu Pro Met Ile Asn Thr Val Pro Val Glu Ser Ala Asp
                165                 170                 175

Phe Gly Glu Tyr Gly Asp Thr Arg Gln His Tyr Glu Ser Asp Ile Phe
            180                 185                 190

Ser Ser Arg Leu Glu Thr Asp Ser Met Asp Pro Phe Gly Leu Thr Ser
        195                 200                 205

Glu Val Ser Ser Val Gln Ser Pro Ser Phe Gly Lys
    210                 215                 220
```

<210> SEQ ID NO 253
<211> LENGTH: 179
<212> TYPE: PRT
<213> ORGANISM: Ochotona princeps

<400> SEQUENCE: 253

```
Val Arg Ser Arg Gly Ala Met Ala Arg Ala Leu Val Leu Ala Thr Leu
1               5                   10                  15

Trp Leu Ala Ala Thr Gly Arg Pro Leu Ala Leu Ser Asp Ala Gly Pro
            20                  25                  30

His Leu His Tyr Gly Trp Gly Glu Pro Ile Arg Leu Arg His Leu Tyr
        35                  40                  45

Ala Thr Ser Ala His Gly Leu Ser His Cys Phe Leu Arg Ile Arg Thr
    50                  55                  60

Asp Gly Thr Val Asp Cys Glu Arg Ser Gln Ser Ala His Leu Gln Tyr
65                  70                  75                  80

Ser Glu Glu Asp Cys Ala Phe Glu Glu Glu Ile Ser Ser Gly Tyr Asn
                85                  90                  95

Val Tyr Arg Ser Arg Arg Tyr Gln Leu Pro Val Ser Leu Gly Ser Ala
            100                 105                 110

Arg Gln Arg Gln Leu Gln Arg Ser Arg Gly Phe Leu Pro Leu Ser His
        115                 120                 125

Phe Leu Pro Val Leu Pro Ala Ala Ser Glu Glu Val Ala Ala Pro Ala
    130                 135                 140

Asp His Pro Gln Ala Asp Pro Phe Ser Pro Leu Glu Thr Asp Ser Met
145                 150                 155                 160

Asp Pro Phe Gly Met Ala Thr Lys Arg Gly Leu Val Lys Ser Pro Ser
                165                 170                 175

Phe Gln Lys
```

<210> SEQ ID NO 254
<211> LENGTH: 221
<212> TYPE: PRT
<213> ORGANISM: Cavia porcellus

<400> SEQUENCE: 254

```
Met Trp Ser Ala Pro Ser Gly Cys Val Val Ile Arg Ala Leu Val Leu
1               5                   10                  15

Ala Gly Leu Trp Leu Ala Val Ala Gly Arg Pro Leu Ala Arg Arg Ser
            20                  25                  30

Leu Ala Leu Ser Asp Gln Gly Pro His Leu Tyr Tyr Gly Trp Asp Gln
        35                  40                  45

Pro Ile Arg Leu Arg His Leu Tyr Ala Ala Gly Pro Tyr Gly Arg Ser
    50                  55                  60

Arg Cys Phe Leu Arg Ile His Thr Asp Gly Ala Val Asp Cys Val Glu
```

```
                65                  70                  75                  80
Glu Gln Ser Glu His Cys Leu Leu Glu Ile Arg Ala Val Ala Leu Glu
                    85                  90                  95

Thr Val Ala Ile Lys Asp Ile Asn Ser Val Arg Tyr Leu Cys Met Gly
                100                 105                 110

Pro Asp Gly Arg Met Arg Gly Leu Pro Trp Tyr Ser Glu Asp Cys
            115                 120                 125

Ala Phe Lys Glu Glu Ile Ser Tyr Pro Gly Tyr Ser Val Tyr Arg Ser
        130                 135                 140

Gln Lys His His Leu Pro Ile Val Leu Ser Val Lys Gln Arg Gln
145                 150                 155                 160

Gln Tyr Gln Ser Lys Gly Val Val Pro Leu Ser Tyr Phe Leu Pro Met
                165                 170                 175

Leu Pro Lys Ala Ser Val Glu Pro Ser Asp Glu Glu Ser Ser Val
            180                 185                 190

Phe Ser Leu Pro Leu Lys Thr Asp Ser Met Asp Pro Phe Gly Met Ala
        195                 200                 205

Ser Glu Ile Gly Leu Val Lys Ser Pro Ser Phe Gln Lys
    210                 215                 220
```

<210> SEQ ID NO 255
<211> LENGTH: 196
<212> TYPE: PRT
<213> ORGANISM: Tupaia belangeri

<400> SEQUENCE: 255

```
Met Arg Arg Thr Pro Ser Gly Phe Ala Val Ala Arg Val Leu Phe Leu
1               5                   10                  15

Gly Ser Leu Trp Leu Ala Ala Ala Gly Ser Pro Leu Ala Leu Ser Asp
                20                  25                  30

Ala Gly Pro His Val Asn Tyr Gly Trp Asp Glu Ser Ile Arg Leu Arg
            35                  40                  45

His Leu Tyr Thr Ala Ser Pro His Gly Ser Thr Ser Cys Phe Leu Arg
        50                  55                  60

Ile Arg Asp Asp Gly Ser Val Asp Cys Ala Arg Gly Gln Ser Leu His
65                  70                  75                  80

Ser Leu Leu Glu Ile Lys Ala Val Ala Leu Gln Thr Val Ala Ile Lys
                85                  90                  95

Gly Val Tyr Ser Val Arg Tyr Leu Cys Met Asp Ala Asp Gly Arg Met
                100                 105                 110

Gln Gly Leu Ser Thr Lys His Gly Leu Pro Val Ser Leu Ser Ser Ala
            115                 120                 125

Lys Gln Arg Gln Leu Leu Thr Val Arg Gly Phe Pro Ser Leu Pro His
        130                 135                 140

Phe Leu Leu Met Met Ala Lys Thr Ser Ala Gly Pro Gly Asn Pro Arg
145                 150                 155                 160

Asp His Pro Gly Ser Asn Thr Phe Ser Leu Pro Leu Glu Thr Asp Ser
                165                 170                 175

Met Asp Pro Phe Gly Met Thr Thr Arg His Gly Leu Val Lys Ser Pro
            180                 185                 190

Ser Phe Gln Asn
        195
```

<210> SEQ ID NO 256
<211> LENGTH: 218

<212> TYPE: PRT
<213> ORGANISM: Rattus norvegicus

<400> SEQUENCE: 256

```
Met Ala Arg Lys Trp Ser Gly Arg Ile Val Arg Ala Leu Val Leu
1               5                   10                  15

Ala Thr Leu Trp Leu Ala Val Ser Gly Arg Pro Leu Val Gln Ser
                20                  25                  30

Gln Ser Val Ser Asp Glu Gly Pro Leu Phe Leu Tyr Gly Trp Gly Lys
        35                  40                  45

Ile Thr Arg Leu Gln Tyr Leu Tyr Ser Ala Gly Pro Tyr Val Ser Asn
    50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
                85                  90                  95

Ile Ala Ile Lys Asp Val Ser Ser Val Arg Tyr Leu Cys Met Ser Ala
                100                 105                 110

Asp Gly Lys Ile Tyr Gly Leu Ile Arg Tyr Ser Glu Glu Asp Cys Thr
            115                 120                 125

Phe Arg Glu Glu Met Asp Cys Leu Gly Tyr Asn Gln Tyr Arg Ser Met
    130                 135                 140

Lys His His Leu His Ile Ile Phe Ile Lys Ala Lys Pro Arg Glu Gln
145                 150                 155                 160

Leu Gln Gly Gln Lys Pro Ser Asn Phe Ile Pro Ile Phe His Arg Ser
                165                 170                 175

Phe Phe Glu Ser Thr Asp Gln Leu Arg Ser Lys Met Phe Ser Leu Pro
                180                 185                 190

Leu Glu Ser Asp Ser Met Asp Pro Phe Arg Met Val Glu Asp Val Asp
            195                 200                 205

His Leu Val Lys Ser Pro Ser Phe Gln Lys
        210                 215
```

<210> SEQ ID NO 257
<211> LENGTH: 218
<212> TYPE: PRT
<213> ORGANISM: Mus musculus

<400> SEQUENCE: 257

```
Met Ala Arg Lys Trp Asn Gly Arg Ala Val Ala Arg Ala Leu Val Leu
1               5                   10                  15

Ala Thr Leu Trp Leu Ala Val Ser Gly Arg Pro Leu Ala Gln Ser
                20                  25                  30

Gln Ser Val Ser Asp Glu Asp Pro Leu Phe Leu Tyr Gly Trp Gly Lys
        35                  40                  45

Ile Thr Arg Leu Gln Tyr Leu Tyr Ser Ala Gly Pro Tyr Val Ser Asn
    50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
                85                  90                  95

Ile Ala Ile Lys Asp Val Ser Ser Val Arg Tyr Leu Cys Met Ser Ala
                100                 105                 110

Asp Gly Lys Ile Tyr Gly Leu Ile Arg Tyr Ser Glu Glu Asp Cys Thr
            115                 120                 125
```

```
Phe Arg Glu Glu Met Asp Cys Leu Gly Tyr Asn Gln Tyr Arg Ser Met
    130                 135                 140

Lys His His Leu His Ile Ile Phe Ile Gln Ala Lys Pro Arg Glu Gln
145                 150                 155                 160

Leu Gln Asp Gln Lys Pro Ser Asn Phe Ile Pro Val Phe His Arg Ser
                165                 170                 175

Phe Phe Glu Thr Gly Asp Gln Leu Arg Ser Lys Met Phe Ser Leu Pro
            180                 185                 190

Leu Glu Ser Asp Ser Met Asp Pro Phe Arg Met Val Glu Asp Val Asp
        195                 200                 205

His Leu Val Lys Ser Pro Ser Phe Gln Lys
    210                 215
```

<210> SEQ ID NO 258
<211> LENGTH: 227
<212> TYPE: PRT
<213> ORGANISM: Gallus gallus

<400> SEQUENCE: 258

```
Met Gly Pro Ala Arg Pro Ala Ala Pro Gly Ala Ala Leu Ala Leu Leu
1               5                   10                  15

Gly Ile Ala Ala Ala Ala Ala Ala Arg Ser Leu Pro Leu Pro Asp
                20                  25                  30

Val Gly Gly Pro His Val Asn Tyr Gly Trp Gly Glu Pro Ile Arg Leu
            35                  40                  45

Arg His Leu Leu His Arg Pro Gly Lys His Gly Leu Phe Ser Cys Phe
        50                  55                  60

Leu Arg Ile Gly Gly Asp Gly Arg Val Asp Ala Val Gly Ser Gln Ser
65                  70                  75                  80

Pro Gln Ser Leu Leu Glu Ile Arg Ala Val Ala Val Arg Thr Val Ala
                85                  90                  95

Ile Lys Gly Val Gln Ser Ser Arg Tyr Leu Cys Met Asp Glu Ala Gly
                100                 105                 110

Arg Leu His Gly Gln Leu Ser Tyr Ser Ile Glu Asp Cys Ser Phe Glu
            115                 120                 125

Glu Glu Ile Arg Pro Asp Gly Tyr Asn Val Tyr Lys Ser Lys Lys Tyr
    130                 135                 140

Gly Ile Ser Val Ser Leu Ser Ser Ala Lys Gln Arg Gln Gln Phe Lys
145                 150                 155                 160

Gly Lys Asp Phe Leu Pro Leu Ser His Phe Leu Pro Met Ile Asn Thr
                165                 170                 175

Val Pro Val Glu Val Thr Asp Phe Gly Glu Tyr Gly Asp Tyr Ser Gln
            180                 185                 190

Ala Phe Glu Pro Glu Val Tyr Ser Ser Pro Leu Glu Thr Asp Ser Met
        195                 200                 205

Asp Pro Phe Gly Ile Thr Ser Lys Leu Ser Pro Val Lys Ser Pro Ser
    210                 215                 220

Phe Gln Lys
225
```

<210> SEQ ID NO 259
<211> LENGTH: 237
<212> TYPE: PRT
<213> ORGANISM: Taeniopygia guttata

<400> SEQUENCE: 259

```
Met Val Ile Ile Ser Asn Leu Tyr Leu Met Gln Asn Asp Val Met Met
1               5                   10                  15

Asn Met Arg Arg Ala Pro Leu Arg Val His Ala Ala Arg Ser Ser Ala
            20                  25                  30

Thr Pro Ala Ser Ala Leu Pro Leu Pro Pro Asp Ala Gly Pro His
        35                  40                  45

Leu Lys Tyr Gly Trp Gly Glu Pro Ile Arg Leu Arg His Leu Tyr Thr
    50                  55                  60

Ala Ser Lys His Gly Leu Phe Ser Cys Phe Leu Arg Ile Gly Ala Asp
65                  70                  75                  80

Gly Arg Val Asp Ala Ala Gly Ser Gln Ser Pro Gln Ser Leu Leu Glu
                85                  90                  95

Ile Arg Ala Val Ala Val Arg Thr Val Ala Ile Lys Gly Val Gln Ser
            100                 105                 110

Ser Arg Tyr Leu Cys Met Asp Glu Ala Gly Arg Leu His Gly Gln Leu
        115                 120                 125

Arg Asn Ser Thr Glu Asp Cys Ser Phe Glu Glu Ile Arg Pro Asp
130                 135                 140

Gly Tyr Asn Val Tyr Arg Ser Lys Lys His Gly Ile Ser Val Ser Leu
145                 150                 155                 160

Ser Ser Ala Lys Gln Arg Gln Gln Phe Lys Gly Lys Asp Phe Leu Pro
                165                 170                 175

Leu Ser His Phe Leu Pro Met Ile Asn Thr Val Pro Met Glu Ser Ala
            180                 185                 190

Asp Phe Gly Glu Tyr Gly Asp Tyr Ser Gln Ala Phe Glu Ala Glu Ala
        195                 200                 205

Phe Ser Ser Pro Leu Glu Thr Asp Ser Met Asp Pro Phe Gly Ile Ala
210                 215                 220

Ser Lys Leu Ser Leu Val Lys Ser Pro Ser Phe Gln Asn
225                 230                 235

<210> SEQ ID NO 260
<211> LENGTH: 210
<212> TYPE: PRT
<213> ORGANISM: Danio rerio

<400> SEQUENCE: 260

Met Leu Leu Leu Leu Phe Val Thr Val Cys Gly Ser Ile Gly Val Glu
1               5                   10                  15

Ser Leu Pro Leu Pro Asp Ser Gly Pro His Leu Ala Asn Asp Trp Ser
            20                  25                  30

Glu Ala Val Arg Leu Arg His Leu Tyr Ala Ala Arg His Gly Leu His
        35                  40                  45

Leu Gln Ile Asn Thr Asp Gly Glu Ile Ile Gly Ser Thr Cys Lys Ala
    50                  55                  60

Arg Thr Val Ser Leu Met Glu Ile Trp Pro Val Asp Thr Gly Cys Val
65                  70                  75                  80

Ala Ile Lys Gly Val Ala Ser Ser Arg Phe Leu Cys Met Glu Arg Leu
                85                  90                  95

Gly Asn Leu Tyr Gly Ser His Ile Tyr Thr Lys Glu Asp Cys Ser Phe
            100                 105                 110

Leu Glu Arg Ile Leu Pro Asp Gly Tyr Asn Val Tyr Phe Ser Ser Lys
        115                 120                 125

His Gly Ala Leu Val Thr Leu Ser Gly Ala Lys Asn Lys Leu His Ser
130                 135                 140
```

```
Asn Asp Gly Thr Ser Ala Ser Gln Phe Leu Pro Met Ile Asn Thr Leu
145                 150                 155                 160

Ser Glu Glu His Thr Lys Gln His Ser Gly Glu Gln His Ser Ser Val
                165                 170                 175

Asn His Gly Gln Asp His Gln Leu Gly Leu Glu Ile Asp Ser Met Asp
            180                 185                 190

Pro Phe Gly Lys Ile Ser Gln Ile Val Ile Gln Ser Pro Ser Phe Asn
        195                 200                 205

Lys Arg
    210

<210> SEQ ID NO 261
<211> LENGTH: 215
<212> TYPE: PRT
<213> ORGANISM: Xenopus (Silurana) tropicalis

<400> SEQUENCE: 261

Met Trp Lys Thr Leu Pro Trp Ile Leu Val Pro Met Met Val Ala Val
1               5                   10                  15

Leu Tyr Phe Leu Gly Gly Ala Glu Ser Leu Pro Leu Phe Asp Ala Gly
            20                  25                  30

Pro His Met Gln Asn Gly Trp Gly Glu Ser Ile Arg Ile Arg His Leu
        35                  40                  45

Tyr Thr Ala Arg Arg Phe Gly His Asp Ser Tyr Tyr Leu Arg Ile His
    50                  55                  60

Glu Asp Gly Arg Val Asp Gly Asp Arg Gln Gln Ser Met His Ser Leu
65                  70                  75                  80

Leu Glu Ile Arg Ala Ile Ala Val Gly Ile Val Ala Ile Lys Gly Tyr
                85                  90                  95

Arg Ser Ser Leu Tyr Leu Cys Met Gly Ser Glu Gly Lys Leu Tyr Gly
            100                 105                 110

Met His Ser Tyr Ser Gln Asp Asp Cys Ser Phe Glu Glu Leu Leu
        115                 120                 125

Pro Asp Gly Tyr Asn Met Tyr Lys Ser Arg Lys His Gly Val Ala Val
    130                 135                 140

Ser Leu Ser Lys Glu Lys Gln Lys Gln Gln Tyr Lys Gly Lys Gly Tyr
145                 150                 155                 160

Leu Pro Leu Ser His Phe Leu Pro Val Ile Ser Trp Val Pro Met Glu
                165                 170                 175

Pro Thr Gly Asp Val Glu Asp Asp Ile Tyr Arg Phe Pro Phe Asn Thr
            180                 185                 190

Asp Thr Lys Ser Val Ile Asp Ser Leu Asp Thr Leu Gly Leu Met Asp
        195                 200                 205

Phe Ser Ser Tyr His Lys Lys
    210                 215

<210> SEQ ID NO 262
<211> LENGTH: 219
<212> TYPE: PRT
<213> ORGANISM: Otolemur garnettii

<400> SEQUENCE: 262

Met Pro Ser Gly Leu Arg Gly Arg Val Val Ala Gly Ala Leu Ala Leu
1               5                   10                  15

Ala Ser Phe Trp Leu Ala Val Ala Gly Arg Pro Leu Ala Phe Ser Asp
            20                  25                  30
```

Ala Gly Pro His Val His Tyr Gly Trp Gly Glu Pro Ile Arg Leu Arg
            35                  40                  45

His Leu Tyr Thr Ala Gly Pro His Gly Leu Ser Ser Cys Phe Leu Arg
 50                  55                  60

Val Arg Thr Asp Gly Ala Val Asp Cys Ala Arg Gly Gln Ser Ala His
 65                  70                  75                  80

Ser Leu Leu Glu Ile Arg Ala Val Ala Leu Arg Thr Val Ala Ile Lys
                85                  90                  95

Gly Val His Ser Ala Arg Tyr Leu Cys Met Gly Ala Asp Gly Arg Met
                100                 105                 110

Gln Gly Leu Pro Gln Tyr Ser Glu Glu Asp Cys Ala Phe Glu Glu Glu
            115                 120                 125

Ile Arg Pro Asp Gly Tyr Asn Val Tyr Trp Ser Glu Lys His Arg Leu
130                 135                 140

Pro Val Ser Leu Ser Ser Ala Arg Gln Arg Gln Leu Tyr Lys Gly Arg
145                 150                 155                 160

Gly Phe Leu Pro Leu Ser His Phe Leu Pro Met Leu Pro Val Thr Pro
                165                 170                 175

Ala Glu Pro Gly Asp Leu Arg Asp His Leu Glu Ser Asp Met Phe Ser
            180                 185                 190

Leu Pro Leu Glu Thr Asp Ser Met Asp Pro Phe Gly Ile Ala Thr Arg
        195                 200                 205

Leu Gly Val Val Lys Ser Pro Ser Phe Gln Lys
210                 215

<210> SEQ ID NO 263
<211> LENGTH: 219
<212> TYPE: PRT
<213> ORGANISM: Felis catus

<400> SEQUENCE: 263

Met Arg Ser Ala Pro Ser Gln Cys Ala Val Thr Arg Ala Leu Val Leu
1               5                   10                  15

Ala Gly Leu Trp Leu Ala Ala Ala Gly Arg Pro Leu Ala Phe Ser Asp
            20                  25                  30

Ala Gly Pro His Val His Tyr Gly Trp Gly Glu Pro Ile Arg Leu Arg
            35                  40                  45

His Leu Tyr Thr Ala Gly Pro His Gly Leu Ser Ser Cys Phe Leu Arg
 50                  55                  60

Ile Arg Ala Asp Gly Gly Val Asp Cys Ala Arg Ser Gln Ser Ala His
 65                  70                  75                  80

Ser Leu Val Glu Ile Arg Ala Val Ala Leu Arg Thr Val Ala Ile Lys
                85                  90                  95

Gly Val His Ser Val Arg Tyr Leu Cys Met Gly Ala Asp Gly Arg Met
                100                 105                 110

Gln Gly Leu Leu Gln Tyr Ser Ala Gly Asp Cys Ala Phe Gln Glu Glu
            115                 120                 125

Ile Arg Pro Asp Gly Tyr Asn Val Tyr Arg Ser Glu Lys His Arg Leu
130                 135                 140

Pro Val Ser Leu Ser Ser Ala Ile Gln Arg Gln Leu Tyr Lys Gly Arg
145                 150                 155                 160

Gly Phe Leu Pro Leu Ser His Phe Leu Pro Met Leu Pro Gly Ser Pro
                165                 170                 175

Ala Glu Pro Arg Asp Leu Gln Asp His Val Glu Ser Glu Arg Phe Ser

```
                        180                 185                 190
Ser Pro Leu Glu Thr Asp Ser Met Asp Pro Phe Gly Ile Ala Thr Lys
            195                 200                 205

Met Gly Leu Val Lys Ser Pro Ser Phe Gln Lys
    210                 215

<210> SEQ ID NO 264
<211> LENGTH: 223
<212> TYPE: PRT
<213> ORGANISM: Pelodiscus sinensis

<400> SEQUENCE: 264

Met Trp Arg Ser Leu Cys Lys Ser His Thr Ser Leu Ala Leu Leu Gly
1               5                   10                  15

Leu Cys Phe Ala Val Val Val Arg Ser Leu Pro Phe Ser Asp Ala Gly
            20                  25                  30

Pro His Val Asn Tyr Gly Trp Gly Glu Pro Ile Arg Leu Arg His Leu
        35                  40                  45

Tyr Thr Ala Ser Arg His Gly Leu Phe Asn Tyr Phe Leu Arg Ile Ser
    50                  55                  60

Ser Asp Gly Lys Val Asp Gly Thr Ser Ile Gln Ser Pro His Ser Leu
65                  70                  75                  80

Leu Glu Ile Arg Ala Val Ala Val Arg Thr Val Ala Ile Lys Gly Val
                85                  90                  95

His Ser Ser Arg Tyr Leu Cys Met Glu Glu Asp Gly Lys Leu His Gly
            100                 105                 110

Leu Leu Arg Tyr Ser Thr Glu Asp Cys Ser Phe Glu Glu Glu Ile Arg
        115                 120                 125

Pro Asp Gly Tyr Asn Val Tyr Lys Ser Lys Tyr Gly Ile Ser Val
    130                 135                 140

Ser Leu Ser Ser Ala Lys Gln Arg Gln Gln Phe Lys Gly Lys Asp Phe
145                 150                 155                 160

Leu Pro Leu Ser His Phe Leu Pro Met Ile Asn Thr Val Pro Val Glu
                165                 170                 175

Ser Met Asp Phe Gly Glu Tyr Gly Asp Tyr Ser His Thr Phe Glu Ser
            180                 185                 190

Asp Leu Phe Ser Ser Pro Leu Glu Thr Asp Ser Met Asp Pro Phe Gly
        195                 200                 205

Ile Thr Ser Lys Ile Ser Pro Val Lys Ser Pro Ser Phe Gln Lys
    210                 215                 220

<210> SEQ ID NO 265
<211> LENGTH: 217
<212> TYPE: PRT
<213> ORGANISM: Latimeria chalumnae

<400> SEQUENCE: 265

Met Leu Gln Ala Leu Tyr Asn Leu Cys Thr Ala Leu Val Leu Phe Lys
1               5                   10                  15

Leu Pro Phe Ala Met Val Gly Tyr Thr Leu Pro Ser Ala Asn Glu Gly
            20                  25                  30

Pro His Leu Asn Tyr Asp Trp Gly Glu Ser Val Arg Leu Lys His Leu
        35                  40                  45

Tyr Thr Ser Ser Lys His Gly Leu Ile Ser Tyr Phe Leu Gln Ile Asn
    50                  55                  60

Asp Asp Gly Lys Val Asp Gly Thr Thr Thr Arg Ser Cys Tyr Ser Leu
```

```
            65                  70                  75                  80

Leu Glu Ile Lys Ser Val Gly Pro Gly Val Leu Ala Ile Lys Gly Ile
                85                  90                  95

Gln Ser Ser Arg Tyr Leu Cys Val Glu Lys Asp Gly Lys Leu His Gly
                100                 105                 110

Ser Arg Thr Tyr Ser Ala Asp Asp Cys Ser Phe Lys Glu Asp Ile Leu
            115                 120                 125

Pro Asp Gly Tyr Thr Ile Tyr Val Ser Lys Lys His Gly Ser Val Val
        130                 135                 140

Asn Leu Ser Asn His Lys Gln Lys Arg Gln Asn Arg Arg Thr Leu
145                 150                 155                 160

Pro Pro Phe Ser Gln Phe Leu Pro Leu Met Asp Thr Ile Arg Val Glu
                165                 170                 175

Cys Met Asn Cys Gly Glu His Cys Asp Asp Asn Leu His Asp Glu Leu
                180                 185                 190

Glu Thr Gly Leu Ser Met Asp Pro Phe Glu Ser Thr Ser Lys Lys Ser
            195                 200                 205

Phe Gln Ser Pro Ser Phe His Asn Arg
        210                 215

<210> SEQ ID NO 266
<211> LENGTH: 219
<212> TYPE: PRT
<213> ORGANISM: Mustela putorius furo

<400> SEQUENCE: 266

Met Arg Ser Ala Ala Ser Arg Cys Ala Val Ala Arg Ala Leu Val Leu
1               5                   10                  15

Ala Gly Leu Trp Leu Ala Ala Ala Gly Arg Pro Leu Ala Phe Ser Asp
                20                  25                  30

Ala Gly Pro His Val His Tyr Gly Trp Gly Glu Pro Ile Arg Leu Arg
            35                  40                  45

His Leu Tyr Thr Ala Gly Pro His Gly Leu Ser Ser Cys Phe Leu Arg
        50                  55                  60

Ile Arg Ala Asp Gly Gly Val Asp Cys Ala Arg Gly Gln Ser Ala His
65                  70                  75                  80

Ser Leu Val Glu Ile Arg Ala Val Ala Leu Arg Thr Val Ala Ile Lys
                85                  90                  95

Gly Val Tyr Ser Asp Arg Tyr Leu Cys Met Gly Ala Asp Gly Arg Met
                100                 105                 110

Gln Gly Leu Pro Gln Tyr Ser Ala Gly Asp Cys Ala Phe Glu Glu Glu
            115                 120                 125

Ile Arg Pro Asp Gly Tyr Asn Val Tyr Arg Ser Lys Lys His Arg Leu
        130                 135                 140

Pro Val Ser Leu Ser Ser Ala Lys Gln Arg Gln Leu Tyr Lys Asp Arg
145                 150                 155                 160

Gly Phe Leu Pro Leu Ser His Phe Leu Pro Met Leu Pro Gly Ser Leu
                165                 170                 175

Ala Glu Pro Arg Asp Leu Gln Asp His Val Glu Ala Asp Gly Phe Ser
                180                 185                 190

Ala Pro Leu Glu Thr Asp Ser Met Asp Pro Phe Gly Ile Ala Thr Lys
            195                 200                 205

Met Gly Leu Val Lys Ser Pro Ser Phe Gln Lys
        210                 215
```

<210> SEQ ID NO 267
<211> LENGTH: 218
<212> TYPE: PRT
<213> ORGANISM: Takifugu rubripes

<400> SEQUENCE: 267

Ser Ser Thr Arg Ile Ser Gly Asn Met Val Leu Leu Met Leu Pro Ile
1               5                   10                  15

Thr Val Ala Asn Leu Phe Leu Cys Ala Gly Val Leu Ser Leu Pro Leu
            20                  25                  30

Leu Asp Gln Gly Ser His Phe Pro Gln Gly Trp Glu Gln Val Val Arg
        35                  40                  45

Phe Arg His Leu Tyr Ala Ala Ser Ala Gly Leu His Leu Leu Ile Thr
    50                  55                  60

Glu Glu Gly Ser Ile Gln Gly Ser Ala Asp Pro Thr Leu Tyr Ser Leu
65                  70                  75                  80

Met Glu Ile Arg Pro Val Asp Pro Gly Cys Val Val Ile Arg Gly Ala
                85                  90                  95

Ala Thr Thr Arg Phe Leu Cys Ile Glu Gly Ala Gly Arg Leu Tyr Ser
            100                 105                 110

Ser Gln Thr Tyr Ser Lys Asp Asp Cys Thr Phe Arg Glu Gln Ile Leu
        115                 120                 125

Ala Asp Gly Tyr Ser Val Tyr Arg Ser Val Gly His Gly Ala Leu Val
    130                 135                 140

Ser Leu Gly Asn Tyr Arg Gln Gln Leu Arg Gly Glu Asp Trp Ser Val
145                 150                 155                 160

Pro Thr Leu Ala Gln Phe Leu Pro Arg Ile Ser Ser Leu Asp Gln Asp
                165                 170                 175

Phe Lys Ala Ala Leu Asp Glu Thr Glu Lys Pro Glu Gln Thr Ala Pro
            180                 185                 190

Gln Arg Ser Glu Pro Val Asp Met Val Asp Ser Phe Gly Lys Leu Ser
        195                 200                 205

Gln Ile Ile His Ser Pro Ser Phe His Lys
    210                 215

<210> SEQ ID NO 268
<211> LENGTH: 94
<212> TYPE: PRT
<213> ORGANISM: Equus caballus

<400> SEQUENCE: 268

Ala Ala Gly Arg Pro Leu Ala Leu Ser Asp Ala Gly Pro His Val His
1               5                   10                  15

Tyr Gly Trp Gly Glu Pro Ile Arg Leu Arg His Leu Tyr Thr Ala Gly
            20                  25                  30

Pro His Gly Leu Ser Ser Cys Phe Leu Arg Ile Arg Ala Asp Gly Ala
        35                  40                  45

Val Asp Cys Ala Arg Gly Gln Ser Ala His Ser Leu Val Glu Ile Arg
    50                  55                  60

Ala Val Ala Leu Arg Thr Val Ala Ile Lys Gly Val His Ser Val Arg
65                  70                  75                  80

Tyr Leu Cys Met Gly Ala Asp Gly Arg Met Gln Gly Leu Val
                85                  90

<210> SEQ ID NO 269
<211> LENGTH: 209

<212> TYPE: PRT
<213> ORGANISM: Oryzias latipes

<400> SEQUENCE: 269

Thr Met Leu Leu Ile Val Val Thr Ile Ser Thr Met Val Phe Ser Asp
1               5                   10                  15

Ser Gly Val Ser Ser Met Pro Leu Ser Asp His Gly Pro His Ile Thr
            20                  25                  30

His Ser Trp Ser Gln Val Val Arg Leu Arg His Leu Tyr Ala Val Lys
        35                  40                  45

Pro Gly Gln His Val Gln Ile Arg Glu Asp Gly His Ile His Gly Ser
    50                  55                  60

Ala Glu Gln Thr Leu Asn Ser Leu Leu Glu Ile Arg Pro Val Ala Pro
65                  70                  75                  80

Gly Arg Val Val Phe Arg Gly Val Ala Thr Ser Arg Phe Leu Cys Met
                85                  90                  95

Glu Ser Asp Gly Arg Leu Phe Ser Ser His Thr Phe Asp Lys Asp Asn
            100                 105                 110

Cys Val Phe Arg Glu Gln Ile Leu Ala Asp Gly Tyr Asn Ile Tyr Ile
        115                 120                 125

Ser Asp Gln His Gly Thr Leu Leu Ser Leu Gly Asn His Arg Gln Arg
    130                 135                 140

Gln Gln Gly Leu Asp Arg Asp Val Pro Ala Leu Ala Gln Phe Leu Pro
145                 150                 155                 160

Arg Ile Ser Thr Leu Gln Gln Gly Val Tyr Pro Val Pro Asp Pro Pro
                165                 170                 175

His Gln Met Arg Thr Met Gln Thr Glu Lys Thr Leu Asp Ala Thr Asp
            180                 185                 190

Thr Phe Gly Gln Leu Ser Lys Ile Ile His Ser Pro Ser Phe Asn Lys
        195                 200                 205

Arg

<210> SEQ ID NO 270
<211> LENGTH: 207
<212> TYPE: PRT
<213> ORGANISM: Xiphophorus maculates

<400> SEQUENCE: 270

Met Phe Val Phe Ile Leu Cys Ile Ala Gly Glu Leu Phe Thr Leu Gly
1               5                   10                  15

Val Phe Cys Met Pro Met Met Asp Gln Gly Pro Leu Val Thr His Gly
            20                  25                  30

Trp Gly Gln Val Val Arg His Arg His Leu Tyr Ala Ala Lys Pro Gly
        35                  40                  45

Leu His Leu Leu Ile Ser Glu Asp Gly Gln Ile His Gly Ser Ala Asp
    50                  55                  60

Gln Thr Leu Tyr Ser Leu Leu Glu Ile Gln Pro Val Gly Pro Gly Arg
65                  70                  75                  80

Val Val Ile Lys Gly Val Ala Thr Thr Arg Phe Leu Cys Met Glu Ser
                85                  90                  95

Asp Gly Arg Leu Tyr Ser Thr Glu Thr Tyr Ser Arg Ala Asp Cys Thr
            100                 105                 110

Phe Arg Glu Gln Ile Gln Ala Asp Gly Tyr Asn Val Tyr Thr Ser Asp
        115                 120                 125

Ser His Gly Ala Leu Leu Ser Leu Gly Asn Asn Gln Gln Arg His Ser

```
                  130                 135                 140

Gly Ser Asp Arg Gly Val Pro Ala Leu Ala Arg Phe Leu Pro Arg Leu
145                 150                 155                 160

Asn Thr Leu Gln Gln Ala Val Pro Thr Glu Pro Asp Val Pro Asp Gln
                165                 170                 175

Leu Ser Pro Glu Lys Val Gln Gln Thr Val Asp Met Val Ala Ser Phe
                180                 185                 190

Gly Lys Leu Ser His Ile Ile His Ser Pro Ser Phe His Lys Arg
                195                 200                 205

<210> SEQ ID NO 271
<211> LENGTH: 220
<212> TYPE: PRT
<213> ORGANISM: Ictidomys tridecemlineatus

<400> SEQUENCE: 271

Met Arg Ser Ala Pro Ser Gly Arg Ala Leu Ala Arg Ala Leu Val Leu
1               5                   10                  15

Ala Ser Leu Trp Leu Ala Val Ala Gly Arg Pro Leu Ala Arg Arg Ser
                20                  25                  30

Leu Ala Leu Ser Asp Gln Gly Pro His Leu Tyr Tyr Gly Trp Asp Gln
                35                  40                  45

Pro Ile Arg Leu Arg His Leu Tyr Ala Ala Gly Pro Tyr Gly Phe Ser
            50                  55                  60

Asn Cys Phe Leu Arg Ile Arg Thr Asp Gly Ala Val Asp Cys Glu Glu
65                  70                  75                  80

Lys Gln Ser Glu Arg Ser Leu Met Glu Ile Arg Ala Val Ala Leu Glu
                85                  90                  95

Thr Val Ala Ile Lys Asp Ile Asn Ser Val Arg Tyr Leu Cys Met Gly
                100                 105                 110

Ala Asp Gly Arg Ile Gln Gly Leu Pro Arg Tyr Ser Glu Glu Glu Cys
                115                 120                 125

Thr Phe Lys Glu Glu Ile Ser Tyr Asp Gly Tyr Asn Val Tyr Arg Ser
        130                 135                 140

Gln Lys Tyr His Leu Pro Val Val Leu Ser Ser Ala Lys Gln Arg Gln
145                 150                 155                 160

Leu Tyr Gln Ser Lys Gly Val Val Pro Leu Ser Tyr Phe Leu Pro Met
                165                 170                 175

Leu Pro Leu Ala Ser Ala Glu Thr Arg Asp Arg Leu Glu Ser Asp Val
                180                 185                 190

Phe Ser Leu Pro Leu Glu Thr Asp Ser Met Asp Pro Phe Gly Met Ala
                195                 200                 205

Ser Glu Val Gly Leu Lys Ser Pro Ser Phe Gln Lys
        210                 215                 220

<210> SEQ ID NO 272
<211> LENGTH: 203
<212> TYPE: PRT
<213> ORGANISM: Gasterosteus aculeatus

<400> SEQUENCE: 272

Met Leu Leu Leu Leu Val Pro Ala Tyr Val Ala Ser Val Phe Leu Ala
1               5                   10                  15

Leu Gly Val Val Cys Leu Pro Leu Thr Asp Gln Gly Leu His Met Ala
                20                  25                  30

Asp Asp Trp Gly Gln Ser Val Arg Leu Lys His Leu Tyr Ala Ala Ser
```

```
            35                  40                  45
Pro Gly Leu His Leu Leu Ile Gly Glu Asp Gly Arg Ile Gln Gly Ser
 50                  55                  60

Ala Gln Gln Ser Pro Tyr Ser Leu Leu Glu Ile Ser Ala Val Asp Pro
 65                  70                  75                  80

Gly Cys Val Val Ile Arg Gly Val Ala Thr Ala Arg Phe Leu Cys Ile
                 85                  90                  95

Glu Gly Asp Gly Arg Leu Tyr Ser Ser Asp Thr Tyr Ser Arg Asp Asp
                100                 105                 110

Cys Thr Phe Arg Glu Gln Ile Leu Pro Asp Gly Tyr Ser Val Tyr Val
                115                 120                 125

Ser His Gly His Gly Ala Leu Leu Ser Leu Gly Asn His Arg Gln Arg
130                 135                 140

Leu Gln Gly Arg Asp His Gly Val Pro Ala Leu Ala Gln Phe Leu Pro
145                 150                 155                 160

Arg Val Ser Thr Met Asp Gln Ala Ser Ala Pro Asp Ala Pro Gly Gln
                165                 170                 175

Thr Ala Thr Glu Thr Glu Glu Pro Val Asp Ser Phe Gly Lys Leu Ser
                180                 185                 190

Gln Ile Ile His Ser Pro Ser Phe His Glu Arg
                195                 200
```

<210> SEQ ID NO 273
<211> LENGTH: 208
<212> TYPE: PRT
<213> ORGANISM: Oreochromis niloticus

<400> SEQUENCE: 273

```
Met Leu Leu Leu Ile Val Ser Ile Val Asn Met Leu Phe Gly Val
 1               5                  10                  15

Gly Met Val Cys Met Pro Leu Ser Asp Asn Gly Pro His Ile Ala His
                 20                  25                  30

Gly Trp Ala Gln Val Val Arg Leu Arg His Leu Tyr Ala Thr Arg Pro
                 35                  40                  45

Gly Met His Leu Leu Ile Ser Glu Gly Gly Gln Ile Arg Gly Ser Ala
 50                  55                  60

Val Gln Thr Leu His Ser Leu Met Glu Ile Arg Pro Val Gly Pro Gly
 65                  70                  75                  80

Arg Val Val Ile Arg Gly Val Ala Thr Ala Arg Phe Leu Cys Ile Glu
                 85                  90                  95

Asp Asp Gly Thr Leu Tyr Ser Ser His Ala Tyr Ser Arg Glu Asp Cys
                100                 105                 110

Ile Phe Arg Glu Gln Ile Leu Pro Asp Gly Tyr Asn Ile Tyr Ile Ser
                115                 120                 125

Asp Arg His Gly Val Leu Leu Ser Leu Gly Asn His Arg Gln Arg Leu
130                 135                 140

Gln Gly Leu Asp Arg Gly Asp Pro Ala Leu Ala Gln Phe Leu Pro Arg
145                 150                 155                 160

Ile Ser Thr Leu Asn Gln Ile Pro Ser Pro Gly Ala Asn Ile Gly Asp
                165                 170                 175

His Met Lys Val Ala Lys Thr Glu Glu Pro Val Asp Thr Ile Asp Ser
                180                 185                 190

Phe Gly Lys Phe Ser Gln Ile Ile Asp Ser Pro Ser Phe His Lys Arg
                195                 200                 205
```

<210> SEQ ID NO 274
<211> LENGTH: 152
<212> TYPE: PRT
<213> ORGANISM: Meleagris gallopavo

<400> SEQUENCE: 274

Val Gly Asn Gln Ser Pro Gln Ser Ile Leu Glu Ile Thr Ala Val Asp
1               5                   10                  15

Val Gly Ile Val Ala Ile Lys Gly Leu Phe Ser Gly Arg Tyr Leu Ala
            20                  25                  30

Met Asn Lys Arg Gly Arg Leu Tyr Ala Ser Leu Ser Tyr Ser Ile Glu
        35                  40                  45

Asp Cys Ser Phe Glu Glu Ile Arg Pro Asp Gly Tyr Asn Val Tyr
    50                  55                  60

Lys Ser Lys Lys Tyr Gly Ile Ser Val Ser Leu Ser Ala Lys Gln
65                  70                  75                  80

Arg Gln Gln Phe Lys Gly Lys Asp Phe Leu Pro Leu Ser His Phe Leu
                85                  90                  95

Pro Met Ile Asn Thr Val Pro Val Glu Val Thr Asp Phe Gly Glu Tyr
            100                 105                 110

Gly Asp Tyr Ser Gln Ala Phe Glu Pro Glu Val Tyr Ser Ser Pro Leu
        115                 120                 125

Glu Thr Asp Ser Met Asp Pro Phe Gly Ile Thr Ser Lys Leu Ser Pro
    130                 135                 140

Val Lys Ser Pro Ser Phe Gln Lys
145                 150

<210> SEQ ID NO 275
<211> LENGTH: 216
<212> TYPE: PRT
<213> ORGANISM: Papio Anubis

<400> SEQUENCE: 275

Met Arg Ser Gly Cys Val Val His Ala Trp Ile Leu Ala Ser Leu
1               5                   10                  15

Trp Leu Ala Val Ala Gly Arg Pro Leu Ala Phe Ser Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Thr
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Gln Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Ala Pro Glu Glu Pro
                165                 170                 175

```
Glu Asp Leu Arg Gly Pro Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
    210                 215

<210> SEQ ID NO 276
<211> LENGTH: 216
<212> TYPE: PRT
<213> ORGANISM: Saimiri boliviensis boliviensis

<400> SEQUENCE: 276

Met Arg Ser Gly Cys Val Val His Ala Trp Ile Leu Ala Gly Leu
1               5                   10                  15

Trp Leu Ala Val Val Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Pro His Gly Leu Ser Ser Cys Phe Leu Arg Ile Arg Ser
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Ser Arg Tyr Leu Cys Met Gly Ala Asp Gly Arg Leu Gln Gly Leu
            100                 105                 110

Phe Gln Tyr Ser Glu Glu Asp Cys Ala Phe Glu Glu Glu Ile Arg Pro
        115                 120                 125

Asp Gly Tyr Asn Val Tyr Leu Ser Glu Lys His Arg Leu Pro Val Ser
    130                 135                 140

Leu Ser Ser Ala Lys Gln Arg Gln Leu Tyr Lys Lys Arg Gly Phe Leu
145                 150                 155                 160

Pro Leu Ser His Phe Leu Pro Met Leu Pro Arg Ala Pro Glu Glu Pro
                165                 170                 175

Asp Asp Leu Arg Gly His Leu Glu Ser Asp Val Phe Ser Ser Pro Leu
            180                 185                 190

Glu Thr Asp Ser Met Asp Pro Phe Gly Leu Val Thr Gly Leu Glu Ala
            195                 200                 205

Val Asn Ser Pro Ser Phe Glu Lys
    210                 215

<210> SEQ ID NO 277
<211> LENGTH: 216
<212> TYPE: PRT
<213> ORGANISM: Pteropus alecto

<400> SEQUENCE: 277

Met Arg Ser Pro Cys Ala Val Ala Arg Ala Leu Val Leu Ala Gly Leu
1               5                   10                  15

Trp Leu Ala Ser Ala Ala Gly Pro Leu Ala Leu Ser Asp Ala Gly Pro
            20                  25                  30

His Val His Tyr Gly Trp Gly Glu Ala Ile Arg Leu Arg His Leu Tyr
            35                  40                  45

Thr Ala Gly Pro His Gly Pro Ser Ser Cys Phe Leu Arg Ile Arg Ala
    50                  55                  60
```

```
Asp Gly Ala Val Asp Cys Ala Arg Gly Gln Ser Ala His Ser Leu Val
 65                  70                  75                  80

Glu Ile Arg Ala Val Ala Leu Arg Asn Val Ala Ile Lys Gly Val His
                 85                  90                  95

Ser Val Arg Tyr Leu Cys Met Gly Ala Asp Gly Arg Met Leu Gly Leu
            100                 105                 110

Leu Gln Tyr Ser Ala Asp Cys Ala Phe Glu Glu Ile Arg Pro
        115                 120                 125

Asp Gly Tyr Asn Val Tyr His Ser Lys Lys His Leu Pro Val Ser
    130                 135                 140

Leu Ser Ser Ala Lys Gln Arg Gln Leu Tyr Lys Asp Arg Gly Phe Leu
145                 150                 155                 160

Pro Leu Ser His Phe Leu Pro Met Leu Pro Arg Ser Pro Thr Glu Pro
                165                 170                 175

Glu Asn Phe Glu Asp His Leu Glu Ala Asp Thr Phe Ser Ser Pro Leu
            180                 185                 190

Glu Thr Asp Asp Met Asp Pro Phe Gly Ile Ala Ser Lys Leu Gly Leu
            195                 200                 205

Glu Glu Ser Pro Ser Phe Gln Lys
    210                 215

<210> SEQ ID NO 278
<211> LENGTH: 245
<212> TYPE: PRT
<213> ORGANISM: Myotis davidii

<400> SEQUENCE: 278

Met Ser Gly Gln Asn Ser Gly Arg His Gly Ser Arg Pro Gly Leu Asp
 1               5                  10                  15

Glu Glu Pro Glu Pro Gly Pro Leu Glu Leu Arg Ala Leu Gly Ser Thr
                 20                  25                  30

Arg Ala Asp Pro Gln Leu Cys Asp Phe Leu Glu Asn His Phe Leu Gly
             35                  40                  45

Tyr Thr Cys Leu Glu Leu Asp Ile Cys Leu Ala Thr Tyr Leu Gly Val
 50                  55                  60

Ser His Trp Gly Glu Ser Ile Arg Leu Arg His Leu Tyr Thr Ser Gly
 65                  70                  75                  80

Pro His Gly Pro Ser Ser Cys Phe Leu Arg Ile Arg Val Asp Gly Ala
                 85                  90                  95

Val Asp Cys Ala Arg Gly Gln Ser Ala His Ser Leu Val Glu Ile Arg
            100                 105                 110

Ala Val Ala Leu Arg Lys Val Ala Ile Lys Gly Val His Ser Ala Leu
        115                 120                 125

Tyr Leu Cys Met Glu Gly Asp Gly Arg Met Arg Gly Leu Pro Gln Phe
    130                 135                 140

Ser Pro Glu Asp Cys Ala Phe Glu Glu Ile Arg Pro Asp Gly Tyr
145                 150                 155                 160

Asn Val Tyr Arg Ser Gln Lys His Gln Leu Pro Val Ser Leu Ser Ser
                165                 170                 175

Ala Arg Gln Arg Gln Leu Phe Lys Ala Arg Gly Phe Leu Pro Leu Ser
            180                 185                 190

His Phe Leu Pro Met Leu Pro Ser Ser Pro Ala Glu Pro Val His Arg
            195                 200                 205

Glu Arg Pro Leu Glu Pro Asp Ala Phe Ser Ser Pro Leu Glu Thr Asp
    210                 215                 220
```

```
Ser Met Asp Pro Phe Gly Ile Ala Asn Asn Leu Arg Leu Val Lys Ser
225                 230                 235                 240

Pro Ser Phe Gln Lys
            245
```

<210> SEQ ID NO 279
<211> LENGTH: 250
<212> TYPE: PRT
<213> ORGANISM: Tupaia chinensis

<400> SEQUENCE: 279

```
Met Arg Arg Thr Trp Ser Gly Phe Ala Val Ala Thr Arg Ala Gly Ser
1               5                   10                  15

Pro Leu Ala Leu Ala Asp Ala Gly Pro His Val Asn Tyr Gly Trp Asp
            20                  25                  30

Glu Ser Ile Arg Leu Arg His Leu Tyr Thr Ala Ser Leu His Gly Ser
        35                  40                  45

Thr Ser Cys Phe Leu Arg Ile Arg Asp Asp Gly Ser Val Gly Cys Ala
    50                  55                  60

Arg Gly Gln Ser Met His Ser Leu Leu Glu Ile Lys Ala Val Ala Leu
65                  70                  75                  80

Gln Thr Val Ala Ile Lys Gly Val Tyr Ser Val Arg Tyr Leu Cys Met
                85                  90                  95

Asp Thr Asp Gly Arg Met Gln Gly Leu Pro Gln Tyr Ser Glu Glu Asp
            100                 105                 110

Cys Thr Phe Glu Glu Glu Ile Arg Ser Asp Gly His Asn Val Tyr Arg
        115                 120                 125

Ser Lys Lys His Gly Leu Pro Val Ser Leu Ser Ser Ala Lys Gln Arg
    130                 135                 140

Gln Leu Tyr Lys Gly Arg Gly Phe Leu Ser Leu Ser His Phe Leu Leu
145                 150                 155                 160

Met Met Pro Lys Thr Ser Ala Gly Pro Gly Asn Pro Arg Asp Gln Arg
                165                 170                 175

Asn Pro Arg Asp Gln Arg Asp Pro Asn Thr Phe Ser Leu Pro Leu Glu
            180                 185                 190

Thr Asp Ser Met Asp Pro Phe Gly Met Thr Thr Arg His Gly Leu Leu
        195                 200                 205

Leu Asp Ser Cys Cys Ala Ser Leu Val Leu Leu Asn Ile Ser Thr Asp
    210                 215                 220

Gly Glu Phe Ser Pro Tyr Gly Asn Ile Leu Arg Pro Ser Phe Arg Phe
225                 230                 235                 240

Lys Leu Phe Lys Met Lys Lys Val Thr Asn
                245                 250
```

<210> SEQ ID NO 280
<211> LENGTH: 209
<212> TYPE: PRT
<213> ORGANISM: Heterocephalus glaber

<400> SEQUENCE: 280

```
Met Arg Phe Ser Lys Ser Thr Cys Gly Phe Phe Asn His Gln Arg Leu
1               5                   10                  15

Gln Ala Leu Trp Leu Ser Leu Ser Ser Val Lys Trp Val Leu Asp Ala
            20                  25                  30

Ala Val Glu Gly Arg Pro Ile Arg Leu Arg His Leu Tyr Ala Ala Gly
        35                  40                  45
```

```
Pro Tyr Gly Arg Ser Arg Cys Phe Leu Arg Ile His Thr Asp Gly Ala
    50                  55                  60

Val Asp Cys Val Glu Glu Gln Ser Glu His Cys Leu Leu Glu Ile Arg
65                  70                  75                  80

Ala Val Ala Leu Glu Thr Val Ala Ile Lys Asp Ile Asn Ser Val Arg
                85                  90                  95

Tyr Leu Cys Met Gly Pro Asp Gly Arg Met Gln Gly Leu Pro Trp Tyr
            100                 105                 110

Ser Glu Glu Asp Cys Ala Phe Lys Glu Glu Ile Ser Tyr Pro Gly Tyr
                115                 120                 125

Ser Val Tyr Arg Ser Gln Lys His His Leu Pro Ile Val Leu Ser Ser
    130                 135                 140

Val Lys Gln Arg Gln Tyr Gln Ser Lys Gly Val Val Pro Leu Ser
145                 150                 155                 160

Tyr Phe Leu Pro Met Leu Pro Lys Ala Ser Val Glu Pro Gly Asp Glu
                165                 170                 175

Glu Glu Ser Ala Phe Ser Leu Pro Leu Lys Thr Asp Ser Met Asp Pro
                180                 185                 190

Phe Gly Met Ala Ser Glu Ile Gly Leu Ala Lys Ser Pro Ser Phe Gln
            195                 200                 205

Lys

<210> SEQ ID NO 281
<211> LENGTH: 13
<212> TYPE: PRT
<213> ORGANISM: Artificial
<220> FEATURE:
<223> OTHER INFORMATION: C-Terminal portion of FGF19 of the chimeric
      protein
<220> FEATURE:
<221> NAME/KEY: MISC_FEATURE
<222> LOCATION: (7)..(7)
<223> OTHER INFORMATION: Xaa at position 7 is R or N

<400> SEQUENCE: 281

Thr Gly Leu Glu Ala Val Xaa Ser Pro Ser Phe Glu Lys
1               5                   10

<210> SEQ ID NO 282
<211> LENGTH: 20
<212> TYPE: PRT
<213> ORGANISM: Artificial
<220> FEATURE:
<223> OTHER INFORMATION: C-Terminal portion of FGF19 of the chimeric
      protein
<220> FEATURE:
<221> NAME/KEY: MISC_FEATURE
<222> LOCATION: (14)..(14)
<223> OTHER INFORMATION: Xaa at position 14 is R or N

<400> SEQUENCE: 282

Met Asp Pro Phe Gly Leu Val Thr Gly Leu Glu Ala Val Xaa Ser Pro
1               5                   10                  15

Ser Phe Glu Lys
            20

<210> SEQ ID NO 283
<211> LENGTH: 48
<212> TYPE: PRT
<213> ORGANISM: Artificial
<220> FEATURE:
<223> OTHER INFORMATION: C-Terminal portion of FGF19 of the chimeric
```

```
        protein
<220> FEATURE:
<221> NAME/KEY: MISC_FEATURE
<222> LOCATION: (3)..(3)
<223> OTHER INFORMATION: Xaa at position 3 is M or I
<220> FEATURE:
<221> NAME/KEY: MISC_FEATURE
<222> LOCATION: (4)..(4)
<223> OTHER INFORMATION: Xaa at position 4 is V or A
<220> FEATURE:
<221> NAME/KEY: MISC_FEATURE
<222> LOCATION: (13)..(13)
<223> OTHER INFORMATION: Xaa at position 13 is G or R
<220> FEATURE:
<221> NAME/KEY: MISC_FEATURE
<222> LOCATION: (19)..(19)
<223> OTHER INFORMATION: Xaa at position 19 is M or V
<220> FEATURE:
<221> NAME/KEY: MISC_FEATURE
<222> LOCATION: (42)..(42)
<223> OTHER INFORMATION: Xaa at position 42 is R or N

<400> SEQUENCE: 283

Leu Pro Xaa Xaa Pro Glu Glu Pro Glu Asp Leu Arg Xaa His Leu Glu
1               5                   10                  15

Ser Asp Xaa Phe Ser Ser Pro Leu Glu Thr Asp Ser Met Asp Pro Phe
            20                  25                  30

Gly Leu Val Thr Gly Leu Glu Ala Val Xaa Ser Pro Ser Phe Glu Lys
        35                  40                  45

<210> SEQ ID NO 284
<211> LENGTH: 651
<212> TYPE: DNA
<213> ORGANISM: Homo sapiens

<400> SEQUENCE: 284
atgcggagcg ggtgtgtggt ggtccacgta tggatcctgg ccggcctctg gctggccgtg      60
gccgggcgcc ccctcgcctt ctcggacgcg gggccccacg tgcactacgg ctggggcgac     120
cccatccgcc tgcggcacct gtacacctcc ggccccacg ggctctccag ctgcttcctg      180
cgcatccgtg ccgacggcgt cgtggactgc gcgcggggcc agagcgcgca cagtttgctg     240
gagatcaagg cagtcgctct gcggaccgtg gccatcaagg gcgtgcacag cgtgcggtac     300
ctctgcatgg gcgccgacgg caagatgcag gggctgcttc agtactcgga ggaagactgt     360
gctttcgagg aggagatccg cccagatggc tacaatgtgt accgatccga agcaccgc       420 ctcccggtct ccctgagcag tgccaaacag cggcagctgt acaagaacag aggctttctt     480
ccactctctc atttcctgcc catgctgccc atggtcccag aggagcctga ggacctcagg     540
ggccacttgg aatctgacat gttctcttcg ccccctggaga ccgacagcat ggacccattt    600
gggcttgtca ccggactgga ggccgtgagg agtcccagct tgagaagta a                651

<210> SEQ ID NO 285
<211> LENGTH: 651
<212> TYPE: DNA
<213> ORGANISM: Gorilla

<400> SEQUENCE: 285
atgcggagcg ggtgtgtggt ggtccacgtc tggatcctgg ccggcctctg gctggccgtg      60
gccgggcgcc ccctcgcctt ctcggacgcg gggccccacg tgcactacgg ctggggcgac     120
cccatccgcc tgcggcacct gtacacctcc ggccccacg ggctctccag ctgcttcctg      180
cgcatccgtg ccgacggcgt cgtggactgc gcgcggggcc agagcgcgca cagtttgctg     240
```

| | |
|---|---|
| gagatcaagg cagtcgctct gcggaccgtg gccatcaagg gcgtgcacag cgtgcggtac | 300 |
| ctctgcatgg gcgccgacgg caagatgcag gggctgcttc agtactcgga ggaagactgt | 360 |
| gctttcgagg aggagatccg cccagatggc tacaatgtgt accgatctga gaagcaccgc | 420 |
| ctcccggtct ccctgagcag tgccaaacag cggcagctgt acaagaacag aggctttctt | 480 |
| ccgctctctc atttcctgcc catgctgccc atggtcccag aggagcctga ggacctcagg | 540 |
| ggccacttgg aatctgacat gttctcttca cccctggaga ccgacagcat ggacccattt | 600 |
| gggcttgtca ccggactgga ggccgtgagg agtcctagct ttgagaagta a | 651 |

<210> SEQ ID NO 286
<211> LENGTH: 651
<212> TYPE: DNA
<213> ORGANISM: Pan troglodytes

<400> SEQUENCE: 286

| | |
|---|---|
| atgcggaacg ggtgtgtggt ggtccacgtc tggatcctgg ccggcctctg gctggccgtg | 60 |
| gccgggcgcc ccctcgcctt ctcggacgcg gggcgccacg tgcactactg ctggggcgac | 120 |
| cccatccccc tgcggcacct gtacacctcc ggcccccatg gctctccag ctgcttcctg | 180 |
| cgcatccctg cgaactgcgt catgaactgc gcgcggggcc agagcgcgca cagtttgctg | 240 |
| gagatcaagg cagtcgctct gcggaccgtg gccatcaagg gcgtgcacag cgtgcggtac | 300 |
| ctctgcatgg gcgccgacgg caagatgcag gggctgcttc agtactcgga ggaagactgt | 360 |
| gctttcgagg aggagatccg cccagatggc tacaatgtgt accgatccga gaagcaccgc | 420 |
| ctcccggtct ccctgagcag tgccaaacag cggcagctgt acaagaacag aggctttctt | 480 |
| ccactctctc atttcctgcc catgctgccc atggtcccag aggagcctga ggacctcagg | 540 |
| ggccacttgg aatctgacat gttctcttcg cccctggaga ccgacagcat ggacccattt | 600 |
| gggcttgtca ccggactgga ggccgtgagg agtcccagct ttgagaagta a | 651 |

<210> SEQ ID NO 287
<211> LENGTH: 651
<212> TYPE: DNA
<213> ORGANISM: Macaca mulatta

<400> SEQUENCE: 287

| | |
|---|---|
| atgaggagcg ggtgtgtggt ggtccacgcc tggatcctgg ccagcctctg gctggccgtg | 60 |
| gccgggcgtc ccctcgcctt ctcggacgcg gggccccacg tgcactacgg ctggggcgac | 120 |
| cccatccgcc tgcggcacct gtacacctcc ggcccccatg gctctccag ctgcttcctg | 180 |
| cgcatccgca ccgacggcgt cgtggactgc gcgcggggcc aaagcgcgca cagtttgctg | 240 |
| gagatcaagg cagtagctct gcggaccgtg gccatcaagg gcgtgcacag cgtgcggtac | 300 |
| ctctgcatgg gcgccgacgg caagatgcag gggctgcttc agtactcaga ggaagactgt | 360 |
| gctttcgagg aggagatccg ccctgatggc tacaatgtat accgatccga gaagcaccgc | 420 |
| ctcccggtct ctctgagcag tgccaaacag aggcagctgt acaagaacag aggctttctt | 480 |
| ccgctctctc atttcctacc catgctgccc atggcccag aggagcctga ggacctcagg | 540 |
| ggccacttgg aatctgacat gttctcttcg cccctggaga ctgacagcat ggacccattt | 600 |
| gggcttgtca ccggactgga ggcggtgagg agtcccagct ttgagaaata a | 651 |

<210> SEQ ID NO 288
<211> LENGTH: 651
<212> TYPE: DNA
<213> ORGANISM: Pongo abelii

<400> SEQUENCE: 288

```
atgcggagcg ggtgtgtggt ggtccacgcc tggatcctgg ccggcctctg gctggccgtg      60
gccgggcgcc ccctcgcctt ctcggactcg ggccccacg tgcactacgg ctggggcgac     120
cccatccgct gcggcacct gtacacctcc ggccccacg gctctccag ctgcttcctg       180
cgcatccgtg ccgacggcgt cgtggactgc gcgcggggcc agagcgcgca cagtttgctg     240
gagatcaagg cagtcgctct gcggaccgtg gccatcaagg cgtgcacag cgtgcggtac      300
ctctgcatgg gcgccgacgg caagatgcag gggctgcttc agtactcgga ggaagactgt    360
gctttcgagg aggagatccg cccagatggc tacaatgtgt accgatccga aagcaccgc     420
ctcccggtct ccctgagcag tgccaaacag cggcagctgt acaagaacag gggctttctt   480
ccgctctctc atttcctgcc catgctgccc atggtcccag aggagcctga ggacctcagg   540
cgccacttgg aatccgacat gttctcttcg cccctggaga ccgacagcat ggacccattt    600
gggcttgtca ccggactgga ggccgtgagg agtcccagct ttgagaaata a             651
```

<210> SEQ ID NO 289
<211> LENGTH: 651
<212> TYPE: DNA
<213> ORGANISM: Nomascus leucogenys

<400> SEQUENCE: 289

```
atgcggagcg agtgtgtggt ggtccacgcc tggatcctgg ccggcctctg gctggcagtg     60
gccgggcgcc ccctcgcctt ttcggacgcg ggccccacg tgcactacgg ctggggcgac    120
cccatccgtc tgcggcacct gtacacctcc ggccccacg gctctccag ctgcttcctg    180
cgcatccgtg ccgacggcgt cgtggactgc gcgcggggcc agagcgcgca cagtttgctg    240
gagatcaagg cagtcgctct gcggaccgtg gccataaagg cgtgcacag cgtgcggtac     300
ctctgcatgg gcgccgacgg caagatgcag gggctgcttc agtattcgga ggaagactgt   360
gctttcgagg aggagatccg cccagatggc tacaatgtgt accgatccga aagcaccgc    420
ctccccgtct ccctgagcag tgccaaacag cggcagctgt ataagaacag aggctttctt   480
ccactctctc atttcctgcc catgctgccc atggtcccag aggagcctga ggacctcagg   540
ggccacttgg aatctgacat gttctcttcg cccctggaga ccgacagcat ggacccattt    600
gggcttgtca ccggactgga ggccgtgagg agtcccagct ttgagaaata a             651
```

<210> SEQ ID NO 290
<211> LENGTH: 429
<212> TYPE: DNA
<213> ORGANISM: Callithrix jacchus

<400> SEQUENCE: 290

```
atgtggaagg ccaccgctgg tggccagcag ggacagtccg aagcacaaat gtccacatgt     60
ccccatgttc ctcgtcctct gtggattgct cagagctgcc tgtttttctct gcagctccag   120
tactcggagg aagactgtgc tttcgaggag gagatccgcc ctgatggcta caatgtgtac    180
tggtccgaga agcaccgcct cccggtctcc ctgagcagcg ccaaacagcg gcagctgtac    240
aagaaacgag gctttcttcc actgtcccat ttcctgccca tgctgccat agccccagaa    300
gagcctgagg acctcagggg acacctggaa tctgacgtgt tctcttcacc cctggagact   360
gacagcatgg acccatttgg gcttgtcacg ggactggagg cggtgaacag tcccagcttt   420
gagaagtaa                                                           429
```

<210> SEQ ID NO 291
<211> LENGTH: 660
<212> TYPE: DNA
<213> ORGANISM: Microcebus murinus

<400> SEQUENCE: 291

```
atgccgagcg ggcaaagcgg ttgtgtggcg gcccgcgccc tgatcctggc cggcctctgg      60
ctgaccgcgg ccgggcgccc gctggccttc tccgacgcgg cccgcacgt gcactacggc     120
tggggcgagc ccatccgcct gcggcacctg tacaccgccg gcccccacgg cctctccagc    180
tgcttcctgc gcatccgcgc agacggctcc gtggactgcg cgcggggcca gagcgcacac    240
agtttgctgg agatcagggc ggtcgctctt cggactgtgg ccatcaaggg cgtgcacagc    300
gtgcggtacc tctgcatggg cgcagacggc aggatgcagg gctgctccg gtactcggag    360
gaagactgtg ccttcgagga ggagatccgc cccgatggct acaacgtgta ccggtctgag    420
aagcaccgcc tgccggtgtc tctgagcagc gccaggcaga ggcagctgta caagggcagg    480
ggcttcctgc cgctctctca cttcctgccc atgctgcccg tgaccccggc agagaccggg    540
gacctcaggg accacttgga gtccgacatg ttcgcttcgc ccctggagac cgacagcatg    600
gacccgtttg gatcgccac cagacttggg gtggtgaaga gtcccagctt tcagaaatga    660
```

<210> SEQ ID NO 292
<211> LENGTH: 415
<212> TYPE: DNA
<213> ORGANISM: Choloepus hoffmanni

<400> SEQUENCE: 292

```
ttgctcgaaa tgaaggcagt ggcgctgcgg gccgtggcca tcaagggcgt gcacagtgct      60
ctgtacctct gcatgaacgc cgacggcagt ctgcacgggc tgcctcggta ctctgcagaa    120
gactgtgctt ttgaggagga aatccgcccc gacggctaca atgtgtactg gtctaggaag    180
cacggcctcc ctgtctcttt gagcagtgca aaacagaggc agctgtacaa aggcagaggc    240
tttctgcccc tgtcccactt cctgcccatg ctgcccatga cgccggccga gcccgcagac    300
cccggggatg acgtggagtc ggacatgttc tcttcacctc tggaaaccga cagcatggat    360
ccttttggaa ttgcctccag acttgagctt gtgaacagtc cagcttttcag cataa        415
```

<210> SEQ ID NO 293
<211> LENGTH: 619
<212> TYPE: DNA
<213> ORGANISM: Ailuropoda melanoleuca

<400> SEQUENCE: 293

```
ggtcctagcc ggcctctgcc tggcggtagc cgggcgcccc ctagccttct cggacgcggg      60
gccgcacgtg cactacggct ggggtgagcc catccgccta cggcacctgt acaccgccgg    120
cccccacggc ctctccagct gcttcctgcg catccgtgcc gacggcgggg ttgactgcgc    180
gcggggccag agcgcgcaca gtttggtgga gatcagggca gtcgctctgc ggaccgtggc    240
catcaagggt gtgcacagcg tccggtacct ctgcatgggc gcggacggca ggatgcaagg    300
gctgcctcag tactctgcag gggactgtgc tttcgaggag gagatccgcc ccgacggcta    360
caatgtgtac cggtccaaga agcaccgtct ccccgtctct ctgagcggtg ccaaacagag    420
gcagctttac aaagacagag gctttctgcc cctgtcccac ttcttgccca tgctgcccgg    480
gagcccagca gagcccaggg acctccagga ccatgcggga tcgacgggt tttctgcacc    540
cctagaaaca gacagcatgg accctttggg gatcgccacc aaaatgggac tagtgaagag    600
```
tcccagcttc cagaaataa                                              619

<210> SEQ ID NO 294
<211> LENGTH: 660
<212> TYPE: DNA
<213> ORGANISM: Sus scrofa

<400> SEQUENCE: 294
atgcggagcg ctccgagccg gtgcgcggtg gtccgcgccc tggtcctggc cggcctctgg    60
ctggccgcag ccgggcgccc cctagccttc tcggatgctg gccgcacgt gcactacggc    120 tggggcgagt cggtccgcct gcggcacctg tacactgcga gtccccacgg cgtctccagc    180
tgcttcctgc gcatccactc agacggcccc gtggactgcg cgccgggaca gagcgcgcac    240
agtttgatgg agatcagggc agtcgcgctg agtaccgtgg cgatcaaggg cgagcgcagc    300
ggccgttacc tctgcatggg cgccgacggc aagatgcaag gcagactca gtactcggat    360 gaggactgtg ctttcgagga ggagatccgc cctgatggct acaacgtgta ctggtccaag    420
aaacaccatc tgcccgtctc tctgagcagc gccaggcaga ggcagctgta caaaggcagg    480
ggcttcctgc cgctgtccca ctttctgccc atgctgtcca ctctcccagc cgagccggag    540
gacctccagg acccccttcaa gtccgacctg ttttctttgc ccctggaaac ggacagcatg    600 gacccctttcc ggatcgccgc caaactggga gcggtgaaga gtcccagctt ctataaataa    660

<210> SEQ ID NO 295
<211> LENGTH: 657
<212> TYPE: DNA
<213> ORGANISM: Bos Taurus

<400> SEQUENCE: 295
atgcggagcg ctccgagccg gtgcgccgtg gcccgcgccc tggtcctggc tggcctctgg    60
ctggccgcag ccgggcgccc cctggccttc tcggatgcgg ggccgcacgt gcactacggc    120
tggggcgagt cggttcgctt gcggcacctg tataccgcgg gcccgcaggg cctctacagc    180
tgctttctgc gcatccactc cgacggcgcc gtggactgcg cgcaggtcca gagcgcgcac    240
agtttgatgg agatcagggc ggtcgctctg agcaccgtag ccatcaaggg cgagcgcagc    300
gtgctgtacc tctgcatgga cgccgacggc aagatgcaag gactgaccca gtactcagcc    360
gaggactgtg ctttcgagga ggagatccgt cctgacggct acaacgtgta ctggtccagg    420
aagcaccatc tcccggtctc cctgagcagc tccaggcaga ggcagctgtt caaaagcagg    480
ggcttcctgc cgctgtctca cttcctgccc atgctgtcca ccatcccagc cgaacctgaa    540
gacctccagg aaccctgaa gcctgatttc tttctgcccc tgaaaacaga tagcatggac    600
cctttcgggc tcgccaccaa actgggatcg gtgaagagtc ccagcttcta taattaa       657

<210> SEQ ID NO 296
<211> LENGTH: 579
<212> TYPE: DNA
<213> ORGANISM: Canis lupus familiaris

<400> SEQUENCE: 296
ctagccttct ccgacgcggg gccgcacgtg cactccttct gggggagcc catccgcctg    60 cggcacctgt acaccgccgg cccccacggc ctctccagct gcttcctgcg catccgcgcc    120
gacgcggggg tggactgcgc gcggggccag agcgcgcaca gtctgatgga gatgagggcg    180
gtcgctctgc ggaccgtggc catcaagggc gtgcacagcg gccggtacct ctgcatgggc    240

```
gccgacggca ggatgcaagg gctgcctcag tactccgccg agactgtac tttcgaggag      300 gagatccgtc ccgatggcta caatgtgtac tggtccaaga agcaccatct ccccatctct    360
ctgagtagtg ccaaacagag gcagctctac aagggcaggg gcttttttgcc cctgtcccac   420 ttcttaccta tcttgcccgg gagcccaaca gagcccaggg acctggaaga ccatgtggag    480
tctgacgggt tttctgcatc cctggaaaca gacagcatgg acccttttgg gatcgccacc   540
aaaattggac tagtgaagag tcccagtttc caaaaataa                            579
```

<210> SEQ ID NO 297
<211> LENGTH: 657
<212> TYPE: DNA
<213> ORGANISM: Oryctolagus cuniculus

<400> SEQUENCE: 297

```
atgcgccgcg cgccgagcgg aggtgccgcg gcccgcgcct tggtcctggc cggcctctgg     60
ctggccgcgg ccgcgcgccc cttggccttg tccgacgcgg cccgcatct gcactacggc    120 tggggcgagc ccgtccgcct gcggcacctg tacgccacca cgcccacgg cgtctcgcac    180 tgcttcctgc gtatacgcgc cgacggcgcc gtggactgcg agcggagcca gagcgcacac   240
agcttgctga gatccgagc ggtcgccctg cgcaccgtgg ccttcaaggg cgtgcacagc    300
tcccgctacc tctgcatggg cgccgacggc aggatgcggg ggcagctgca gtactcggag   360
gaggactgtg ccttccagga ggagatcagc tccggctaca acgtgtaccg ctccacgacg    420
caccacctgc ccgtgtctct gagcagtgcc aagcagagac acctgtacaa gaccagaggc   480
ttcctgcccc tctcccactt cctgcccgtg ctgcccctgg cctccgagga gaccgcggcc   540
ctcggcgacc accctgaagc cgacctgttc tccccgcccc tggaaaccga cagcatggac   600
cccttcggca tggccaccaa gctcgggccg gtgaagagcc ccagctttca gaagtag      657
```

<210> SEQ ID NO 298
<211> LENGTH: 651
<212> TYPE: DNA
<213> ORGANISM: Pteropus vampyrus

<400> SEQUENCE: 298

```
atgcggagcc cgtgcgctgt ggcccgcgcc ttggtcctgg ccggcctctg gctggcctca     60
gctgcgggcc ccctcgccct ctcggacgcg gggccgcacg tgcactacgg ctggggcgag    120
gccatccgcc tgcggcacct gtacaccgcc ggccccacg gccctccag ctgcttcctg      180 cgcatccgcg cggatggggc ggtggactgc gcgcggggcc agagcgcgca cagtttggtg   240
gaaatccggg ctgtcgccct gcggaacgtg gctatcaagg gcgtgcacag cgtccgatac   300
ctctgcatgg gagccgacgg caggatgcta gggctgcttc agtactccgc tgacgactgc   360
gccttcgagg aggagatccg cccggacggc tacaacgtgt accactccaa gaagcaccac   420
ctcccggtct ctctgagcag tgccaagcag aggcaactgt acaaggacag ggcttcctg   480 cccctgtccc atttcctgcc catgctgccc aggagcccga cagagcccga gaacttcgaa    540
gaccacttgg aggccgacac gttttcctcg cccctggaga cagacgacat ggaccccttt   600
gggattgcca gtaaattggg gctggaggaa agtcccagct tccagaagta a             651
```

<210> SEQ ID NO 299
<211> LENGTH: 660
<212> TYPE: DNA
<213> ORGANISM: Tursiops truncates

<400> SEQUENCE: 299

```
atgcggagcg ctccgagccg gtgcgccgtg gcccgcgccc tggtcctggc cggcctctgg    60
ctggctgcag ccgggcgccc cctagccttc tcggatgccg gccgcacgt gcactacggc    120 tggggcgagt ccgtccgcct gcggcacctg tacaccgcgg gtccccaggg cctctccagc    180
tgcttcctgc gcatccactc agacggcgcc gtggactgcg cgccggttca gagcgcgcac    240
agtttgatgg agatcagggc agtcgctctg agtaccgtgg ccatcaaggg cgaacgcagc    300
gtcctgtacc tctgcatggg cgccgacggc aaaatgcaag gctgagtca gtactcagct    360 gaggactgtg cctttgagga ggaaatccgt ccggacggct acaacgtgta ctggtccaag    420
aaacaccacc tcccggtgtc cctgagcagc gccaggcagc ggcagctgtt caaaggcagg    480
ggtttcctgc cgctgtctca cttccttccc atgctgtcca ccatccccac agagcccgat    540
gaaatccagg accacttgaa gcccgatttg tttgctttgc ccctgaaaac agatagcatg    600
gacccatttg ggctcgccac caaactggga gtggtgaaga gtcccagctt ctataagtaa    660

<210> SEQ ID NO 300
<211> LENGTH: 660
<212> TYPE: DNA
<213> ORGANISM: Myotis lucifugus

<400> SEQUENCE: 300
atgcaaagcg cgtggagccg acgcgttgtg gcccgagccc tggtcttggc cagcctcggg    60
ctggcctcag ccgggggggcc cctcggtctt tcggacgctg gccgcacgt gcactacggc    120 tgggggggagt ccatccgcct gcgccacctg tacacctccg gccccacgg cccatccagc    180 tgcttcctgc gcatccgcgc tgacggcgca gtggactgcg cgcggggcca gagcgcgcac    240
agtttggtgg agatcagggc cgtcgccttg cggaaagtgg ccatcaaggg cgtgcacagc    300
gccctgtacc tctgcatggg aggcgacggc aggatgctgg ggctgcctca gttctcgccc    360
gaggactgtg ctttcgagga ggagatccgc ccggacggct acaacgtgta ccggtcccag    420
aagcaccagc tgcccgtctc gctgagcagt gcccggcaga ggcagctgtt caaggcccgg    480
ggcttcctgc cgctgtccca cttcctgccc atgctgccca gcagcccgc gggacccgtg    540 ccccgagagc gcccctcgga gccggacgag ttctcttcgc ccctggaaac agacagcatg    600
gacccttttg ggattgccaa caacctgagg ctggtgagaa gtcccagctt caggaataa    660

<210> SEQ ID NO 301
<211> LENGTH: 558
<212> TYPE: DNA
<213> ORGANISM: Ornithorhynchus anatinus

<400> SEQUENCE: 301
atgctttcct gtgtggtttt gcctagtctg ctggagatca aggcggtggc cgtgcgcacg    60
gtggccatca aggggtccca catctctcgg tacctctgca tggaagagga tgggaaaact    120
ccatgggcac gtctgctgga gatcaaggcg gtggccgtgc gcacggtggc catcaaaggg    180
gtccacagct ctcggtacct ctgcatggaa gaggatggaa aactccatgg gcagatttgg    240
tattctgcag aagactgtgc ttttgaagag gaaatacgtc cagatggcta caatgtgtat    300
aaatctaaga aatatggtgt tcctgttttct ttaagcagcg ccaaacaaag gcagcaattc    360
aaaggaagag actttctgcc tctttctcgt ttcttgccaa tgatcaacac agtgcctgtg    420
gagccagcag agtttgggga ctatgccgat tactttgaat cagatatatt ttcctcacct    480
ctggaaactg acagcatgga cccatttaga attgcccta aactgtcccc tgtaaagagc    540
```
cccagctttc agaaataa 558

<210> SEQ ID NO 302
<211> LENGTH: 639
<212> TYPE: DNA
<213> ORGANISM: Monodelphis domestica

<400> SEQUENCE: 302

| atggcccagc | tcctggcccc | gctcctcacc | ctggctgctc | tctggctggc | cccgacggcg | 60 |
| cgtgcccgac | cgctggtgga | cgccgggcct | cacgtctact | acggctgggg | ggagcccatt | 120 |
| cgtctgcggc | atctctacac | ggccaatcgg | cacgggctcg | ccagcttctc | cttcctccgg | 180 |
| atccaccgcg | acggccgcgt | ggacggcagc | cggagtcaga | gcgcgctcag | tttgctggag | 240 |
| atcaaggcgg | tagctcttcg | gatggtggcg | atcaaaggtg | tccatagctc | tcggtacctg | 300 |
| tgtatgggag | acgccgggaa | actccaggga | tcggtgaggt | tctcggccga | ggactgcacc | 360 |
| ttcgaggagc | agattcgccc | cgacggctac | aacgtgtacc | agtcccccaa | gtacaacctc | 420 |
| cccgtctcgc | tctgcactga | caagcagagg | cagcaggccc | acggcaagga | gcacctgccc | 480 |
| ctgtcccact | tcctgcccat | gatcaatgct | attcctttgg | aggccgagga | gcccgagggc | 540 |
| cccaggatgt | tggcggcgcc | tctggagacg | gacagcatgg | accccttcgg | cctcacctcc | 600 |
| aagctgttgc | cggtcaagag | ccccagcttt | cagaaataa | | | 639 |

<210> SEQ ID NO 303
<211> LENGTH: 663
<212> TYPE: DNA
<213> ORGANISM: Anolis carolinensis

<400> SEQUENCE: 303

| atgtgtcggc | gggcgttgcc | tctgctgggg | gcccttctgg | gcttggcggc | cgtggcctcc | 60 |
| cgcgccctcc | cgctcaccga | cgccgggccc | cacgtcagct | acggctgggg | ggagcccgtc | 120 |
| cggctcaggc | acctctacac | cgcggggcgg | cagggcctct | tcagccagtt | cctccgcatc | 180 |
| cacgccgacg | ggagagtcga | cggcgccggc | agccagaacc | ggcagagttt | gctggagatc | 240 |
| cgcgcggtct | cgttgcgcgc | cgtggccctc | aaaggcgtgc | acagctcccg | ctacctctgc | 300 |
| atggaggagg | acggccggct | ccgcgggatg | ctcagatatt | ctgcagaaga | ctgttccttt | 360 |
| gaagaggaga | tgcgtccaga | tggctacaat | atctacaagt | caaagaaata | cggagttttg | 420 |
| gtctccctaa | gtaatgccag | acaaagacag | caattcaaag | ggaaagattt | tcttcctttg | 480 |
| tctcatttct | tgccgatgat | caacactgtg | ccagtggagt | ctgcagactt | tggagagtat | 540 |
| ggtgacacca | ggcagcatta | tgaatcggat | attttcagtt | cacgtcttga | aactgacagc | 600 |
| atggacccctt | ttggcctcac | ttcagaagtg | tcatcagtac | aaagtcctag | ctttgggaaa | 660 |
| taa | | | | | | 663 |

<210> SEQ ID NO 304
<211> LENGTH: 541
<212> TYPE: DNA
<213> ORGANISM: Ochotona princeps

<400> SEQUENCE: 304

| gtgcggagca | gggagccat | ggcccgcgct | ctggttctag | ccactctctg | gctggccgcg | 60 |
| acggggcggc | cgctggcctt | gtccgacgcg | gggccgcacc | tgcactacgg | ctggggcgag | 120 |
| cccatccgcc | tgcggcacct | gtacgccacc | agcgcccacg | gcctctcgca | ctgcttttg | 180 |
| cgcatccgta | ccgacggcac | cgtggactgc | gagcgcagcc | agagcgcgca | cactacagta | 240 |

```
ctcggaggag gactgcgcct tcgaagagga gatcagctct ggctataacg tgtaccgctc    300
caggaggtac cagctgcccg tgtccctggg cagcgccagg cagaggcagc tgcagcggag    360
ccgtggcttc ctgcccctgt cccacttcct gccggtgctg cccgcggcct cggaggaggt    420
ggcggccccc gctgaccacc cgcaagcaga cccttcctcg cccctggaga ccgacagcat    480
ggacccattt ggaatggcca ccaagcgggg gctggtgaag agcccagct  tccagaagtg    540 a                                                                   541
```

<210> SEQ ID NO 305
<211> LENGTH: 666
<212> TYPE: DNA
<213> ORGANISM: Cavia porcellus

<400> SEQUENCE: 305

```
atgtggagtg cgccgagcgg atgtgtggtg atccgcgccc tggtcctggc tggcctgtgg    60
ctggcggtgg cggggcgccc cctggcccgg cggtctctcg cgctatctga ccaggggccg    120
cacttgtact acggctggga ccagccgatc cgccttcggc acctgtacgc cgcgggcccc    180 tacgccgct cgcgctgctt cctgcgcatt cacacggacg cgcgcgtgga ctgcgtcgag    240
gaacagagcg agcactgttt gctggagatc agagcagtcg ctctggagac cgtggccatc    300
aaggacataa acagcgtccg gtacctgtgc atgggcccg acggcaggat gcggggcctg    360
ccctggtatt cggaggagga ctgtgccttc aaggaagaga tcagctaccc gggctacagc    420
gtgtaccgct cccagaagca ccacctcccc atcgtgctga gcagtgtcaa gcagaggcag    480
cagtaccaga gcaaggggt ggtgcccctg tcctacttcc tgcccatgct gcccaaggcc    540
tctgtggagc ccagcgacga ggaggaatcc agcgtgttct cgttgcccct gaagacggac    600
agcatggacc cctttgggat ggccagtgag atcgggctgg tgaagagtcc cagctttcag    660
aagtaa                                                              666
```

<210> SEQ ID NO 306
<211> LENGTH: 595
<212> TYPE: DNA
<213> ORGANISM: Tupaia belangeri
<220> FEATURE:
<221> NAME/KEY: misc_feature
<222> LOCATION: (346)..(347)
<223> OTHER INFORMATION: n is a, c, g, or t

<400> SEQUENCE: 306

```
atgaggagaa caccgagcgg gtttgcagtg gcccgtgtcc tcttcctggg cagcctttgg    60
ctggccgcag ccgggagccc cttggccctg tccgacgccg gccgcatgt  gaactacggc    120 tgggatgagt ccatacgcct gcgacacttg tacaccgcca gcccgcacgg ctccaccagc    180
tgcttcttgc gcatccgtga cgacggctca gtggactgcg cgcggggcca gagtttgcac    240
agtttgctgg agatcaaggc agtcgctttg cagaccgtgg ccatcaaagg cgtgtacagt    300
gtccgctacc tctgcatgga cgccgacggc aggatgcagg ggctgnnggt ccacgaagca    360
cggcctccca gtctccctga gcagtgccaa gcagaggcag ctgttaacgg ttagggctt    420 tccttccctt cccacttcc  tgctcatgat ggccaagact tcagcagggc ctggaaaccc    480
cagggaccac ccagggtcta acactttctc gttgcccctg gaaactgata gcatggaccc    540
atttgggatg accaccagac atgggctggt gaagagtccc agctttcaaa actaa         595
```

<210> SEQ ID NO 307

<211> LENGTH: 657
<212> TYPE: DNA
<213> ORGANISM: Rattus norvegicus

<400> SEQUENCE: 307

```
atggcgagaa agtggagtgg gcgtattgtg gcccgagctc tggtcctggc cactctgtgg      60
ctggccgtgt ctgggcgtcc cctggtccag caatcccagt ctgtgtcgga tgaaggtcca     120
ctctttctct atggctgggg caagattacc cgcctgcagt acctgtactc tgctggtccc     180
tacgtctcca actgcttcct gcgtatccgg agtgacggct ctgtggactg cgaggaggac     240
cagaacgaac gaaatctgtt ggagttccgc gcggttgctc tgaagacaat tgccatcaag     300
gacgtcagca gcgtgcggta cctctgcatg agcgccgacg gcaagatata cgggctgatt     360
cgctactcgg aggaagactg taccttcagg gaggaaatgg actgtttggg ctacaaccag     420
tacaggtcca tgaagcacca cctccacatc atcttcatca aggccaagcc cagagagcag     480
ctccagggcc agaaaccttc aaactttatc cccatatttc accggtcttt ctttgaatcc     540
acggaccagc tgaggtctaa aatgttctct ctgcccctgg agagcgacag catggatccg     600
ttcagaatgg tggaggatgt ggaccaccta gtgaagagtc ccagcttcca gaaatga       657
```

<210> SEQ ID NO 308
<211> LENGTH: 657
<212> TYPE: DNA
<213> ORGANISM: Mus musculus

<400> SEQUENCE: 308

```
atggcgagaa agtggaacgg gcgtgcggtg gcccgagccc tggtcctggc cactctgtgg      60
ctggctgtgt ctgggcgtcc cctggctcag caatcccagt ctgtgtcaga tgaagatcca     120
ctctttctct acggctgggg caagattacc cgcctgcagt acctgtactc cgctggtccc     180
tatgtctcca actgcttcct ccgaatccgg agcgacggct ctgtggactg cgaggaggac     240
caaaacgaac gaaatttgtt ggaattccgc gcggtcgctc tgaagacgat tgccatcaag     300
gacgtcagca gcgtgcggta cctctgcatg agcgcggacg gcaagatata cgggctgatt     360
cgctactcgg aggaagactg taccttcagg gaggaaatgg actgtttagg ctacaaccag     420
tacagatcca tgaagcacca tctccatatc atcttcatcc aggccaagcc cagagaacag     480
ctccaggacc agaaacctc aaactttatc ccgtgtttc accgctcctt ctttgaaacc      540
ggggaccagc tgaggtctaa aatgttctcc ctgcccctgg agagtgacag catggatccg     600
ttcaggatgg tggaggatgt agaccaccta gtgaagagtc ccagcttcca gaaatga       657
```

<210> SEQ ID NO 309
<211> LENGTH: 684
<212> TYPE: DNA
<213> ORGANISM: Gallus gallus

<400> SEQUENCE: 309

```
atggggccgg cccgccccgc cgcacccggc gctgccctgg cgctgctggg gatcgccgcc      60
gccgccgccg ccgccaggtc cctgccgctg cccgacgtcg ggggtccgca cgtcaactac     120
ggctgggggg aacccatccg gctgcggcac ctactacacc gcccaggcaa gcacgggctc     180
ttcagctgct tcctgcgcat cggcggcgac ggccgggtgg acgctgtcgg tagccagagc     240
ccgcagagtc tgtttggaga tccgccgtg gcggtgcgca ccgtggccat caagggcgtg     300
cagagctccc gctacctctg catggacgag gcggggcggg tgcacgggca gctcagctat     360
tccattgagg actgttcctt tgaagaggag attcgtccag acggctacaa cgtgtataaa     420
```

-continued

```
tcaaagaaat acgggatatc ggtgtctttg agcagtgcca acaaagaca gcaattcaaa      480
ggaaaagatt ttctcccgct gtctcacttc ttacccatga tcaacactgt gccagtggag      540
gtgacagact ttggtgaata tggtgattac agccaggctt ttgagccaga ggtctactca      600
tcgcctctcg aaacggacag catggatccc tttgggatca cttccaaact gtctccagtg      660
aagagcccca gctttcagaa atga                                            684
```

<210> SEQ ID NO 310
<211> LENGTH: 714
<212> TYPE: DNA
<213> ORGANISM: Taeniopygia guttata

<400> SEQUENCE: 310

```
atggttatca taagcaatct atatctgatg cagaacgatg ttatgatgaa tatgaggcga       60
gcacccttc gcgttcacgc tgctcgctct tcggccaccc ctgcctccgc gctgccgctg      120
ccgccgcccg acgccggccc gcacctcaaa tacggctggg gagagcccat ccggctgcgg      180
cacctctaca ccgccagcaa gcacgggctc ttcagctgct tcctgcgtat cggcgctgac      240
ggccgggtgg acgcggccgg cagccagagc ccgcagagcc tgctagagat ccgcgccgtg      300
gccgtgcgca ccgtggccat caagggcgtg cagagctccc ggtacctgtg catggacgag      360
gcggggcggc tgcacgggca gctcaggaat tccactgaag actgctcctt tgaggaggag      420
attcgcccag acggctacaa tgtgtataga tctaaaaaac atggaatatc ggtgtctttg      480
agcagtgcca acaaagaca gcagttcaag gggaaagatt tccttcccct gtctcacttc      540
ttgcccatga tcaacactgt gcccatggag tcagcagact ttggtgaata tggtgattac      600
agccaggcct ttgaggcaga ggccttctcc tcacctctgg agacggacag catggacccc      660
tttggcatcg cctccaaact gtccctagtg aagagcccta gcttccaaaa ctga           714
```

<210> SEQ ID NO 311
<211> LENGTH: 633
<212> TYPE: DNA
<213> ORGANISM: Danio rerio

<400> SEQUENCE: 311

```
atgctcctct tactctttgt cactgtttgt ggaagtatcg gcgtggagag cctcccgttg       60
cccgactctg gtccacattt ggcaaatgac tggagtgaag ccgtccggct acgacatctg      120
tacgcagcca gacatggctt acatctgcaa ataaacacag acggagaaat cattggatcc      180
acatgcaaag ctcggacagt aagtttgatg gagatatggc cggtggacac aggctgcgta      240
gccattaagg gagttgcaag ctcccgattt ctttgcatgg aaagactggg aaacctgtac      300
ggatcgcaca tttacactaa agaggactgc tcttttttgg aacgcatcct tccagacggc      360
tacaacgtct acttctcgag caaacacgga gctcttgtga ctttaagtgg tgcgaaaaac      420
aagttgcaca gtaacgatgg gacttctgca tcccagttcc tccccatgat caacacactt      480
tcagaggaac acactaaaca gcactcaggg gaacagcact cttctgttaa ccatggacag      540
gaccatcagt tgggccttga aatagacagt atggacccct tcggaaagat ctctcaaata      600
gtgatccaga gtcccagctt caacaaaaga tga                                  633
```

<210> SEQ ID NO 312
<211> LENGTH: 648
<212> TYPE: DNA
<213> ORGANISM: Xenopus

<400> SEQUENCE: 312

```
atgtggaaga ccctgccttg gattttggtt cccatgatgg tggccgtgct gtatttcctc      60
ggagggcgg aaagtctgcc gcttttgat gccgggccgc acatgcagaa cggctggggg      120
gagtcgatca gaattcggca cctgtatacg gccaggaggt tcgggcacga cagctactac    180
ctccggatac acgaggatgg cagagtcgat ggtgacaggc aacaaagcat gcacagttta    240
ttggaaatca gagcaattgc agttggaatt gttgccatta aagggtatcg cagctctctg    300
tacctgtgca tggggtccga gggaaaactc tatggaatgc acagttactc ccaggatgat    360
tgctcttttg aagaggagct tctcccggat ggatacaaca tgtataaatc aaggaaacat    420
ggcgttgctg tctccctaag caaggagaag cagaagcaac aatacaaagg aaagggctac    480
ctcccgttgt cccatttcct acccgtgata agctgggtgc ccatggagcc caccggagat    540
gtagaagatg atatctacag gtttccattc aatacggaca caaaaagtgt cattgacagc    600
cttgataccc tgggactaat ggattttcg agttatcaca agaaatag                  648
```

<210> SEQ ID NO 313
<211> LENGTH: 660
<212> TYPE: DNA
<213> ORGANISM: Otolemur garnettii

<400> SEQUENCE: 313

```
atgcccagcg ggctgagagg gcgtgtggta gccggcgccc tggccctggc cagcttctgg      60
ctggccgtgg ccgggcgccc gctggccttc tcggatgccg ccctcacgt gcactacggc     120
tggggtgagc ccatccgcct gcgacacctg tacaccgccg cccccacgg cctctccagc     180
tgcttcctgc gcgtacgcac cgacggtgcg gtagactgcg gcgggggcca gagcgcacac    240
agtttgctga aaatcaggc cgtcgctctc cggaccgtgg ccatcaaagg cgtgcacagc     300
gcgcggtacc tctgcatggg cgccgacggc aggatgcagg ggctgcctca gtactcggag    360
gaagactgtg cctttgagga ggagatccgg ccagacggct acaacgtcta ctggtctgag    420
aagcaccgcc tgccggtgtc tctgagcagt gcccggcaga ggcagctgta caagggcagg    480
ggctttctgc cgctctctca cttcctgccc atgctgcctg tgaccccagc cgagcccggg    540
gacctcagag accacctgga atccgacatg ttctctttgc ccctggaaac tgacagcatg    600
gatccatttg ggatcgccac cagactgggc gtggtgaaga gtcccagctt tcagaaatga    660
```

<210> SEQ ID NO 314
<211> LENGTH: 660
<212> TYPE: DNA
<213> ORGANISM: Felis catus

<400> SEQUENCE: 314

```
atgcggagcg cgccgagcca gtgcgcggta acccgcgccc tggtcctagc cggtctctgg      60
ctggcagcag ccgggcgccc cctagccttc tcggacgcgg ggcctcacgt gcactacggc     120
tggggtgagc ccatccgcct gcggcacctg tacaccgccg cccccacgg cctctccagc     180
tgcttcctgc gcatccgagc cgacgggggg gttgactgcg cgcggagcca gagcgcgcac    240
agttggtgg agatcaggc agtcgctctg cggaccgtgg ccatcaaggg cgtgcacagc     300
gtccggtacc tctgcatggg cgccgacggc aggatgcaag ggctgcttca gtactctgct    360
ggggactgtg ccttccaaga ggagatccgg cccgacggct acaatgtgta ccggtccgag    420
aagcaccgtc tccccgtctc tttgagtagt gccatacaga ggcagctgta caagggcaga    480
gggttttttgc ccctgtccca tttcttgccc atgctgcccg gcagcccagc agagcccagg    540
```

```
gacctccagg accacgtgga gtcggagagg ttttcttcac ccctggaaac agacagcatg    600 gaccctttg ggattgccac caaaatgggg ttagtgaaga gtcccagctt ccaaaagtaa    660
```

<210> SEQ ID NO 315
<211> LENGTH: 672
<212> TYPE: DNA
<213> ORGANISM: Pelodiscus sinensis

<400> SEQUENCE: 315

```
atgtggagga gcctgtgcaa atctcacacg tctctggctc tgctgggact ctgctttgcg     60
gtggtcgtga gatctctgcc tttctcggat gcagggccac atgtgaacta tggctggggg    120
gagcctattc gattaaggca cctatacacc gccagcagac acgggctgtt caattacttc    180
ctgaggatca gcagtgatgg caaagtggat ggcaccagca ttcagagtcc tcacagtctg    240
ctggaaatca gggctgtggc agttcgcacg gtggcgatca agggcgtcca cagttcccgg    300
tacctctgca tggaagaaga cgggaagctg catggacttc tcaggtattc tacagaagat    360
tgctcctttg aagaggagat acgcccagat ggctacaatg tatataaatc aaagaaatat    420
ggaatctctg tgtccttaag tagtgccaaa caaagacaac aattcaaagg aaaagacttt    480
cttccattgt ctcacttctt gcctatgatc aatacagtac ctgtggagtc aatggatttt    540
ggagaatatg gtgattatag tcatactttt gaatcagatc tattctcttc acctctcgaa    600
actgacagca tggatccctt tggaatcacc tctaaaatat ctccagtgaa gagccccagc    660
tttcagaaat aa                                                        672
```

<210> SEQ ID NO 316
<211> LENGTH: 654
<212> TYPE: DNA
<213> ORGANISM: Latimeria chalumnae

<400> SEQUENCE: 316

```
atgttacagg cactgtacaa tctctgtaca gctctagttt tgtttaagct tccttttgca     60
atggtggggt acaccctgcc ttctgccaat gaagggcccc atctgaacta tgactgggga    120
gaatctgtaa gactcaaaca tctgtacaca tctagcaagc atggattgat cagttacttt    180
ttacagatca atgatgatgg caaagtagat gggaccacta cacgaagctg ttatagtttg    240
ctcgaaataa aatcagtggg gccaggagtt ttggcaatta aaggcataca gagctccaga    300
taccttgtgt cgagaagga tggaaaattg catggatcgc gcacttattc agcagacgat    360 tgctcctttca aagaggatat actcccagat ggttacacta tctacgtgtc aaagaaacat    420
ggatctgttg ttaatctgag caaccacaaa cagaaacgtc agagaaatcg cagaaccctg    480
cctccatttt ctcagttcct accgcttatg acaccattcg tgtgagtg catgaactgc    540 ggggagcact gtgacgacaa cctgcatgac gagctagaaa caggactgtc catggatccc    600
tttgaaagta catccaaaaa atccttcag agtcccagct tcacaatag ataa            654
```

<210> SEQ ID NO 317
<211> LENGTH: 660
<212> TYPE: DNA
<213> ORGANISM: Mustela putorius furo

<400> SEQUENCE: 317

```
atgcggagcg ccgcgagtcg gtgcgcggta gcccgcgcgc tggtcctagc cggcctttgg     60
ctggccgcag ccgggcgccc cctagccttc tcggacgcgg ggccgcacgt gcactatggc    120
```

| | |
|---|---|
| tggggtgagc ccatccgcct acggcacctg tacaccgccg gcccccacgg cctctccagc | 180 |
| tgcttcctgc gcatccgtgc cgacggcggg gttgactgcg cgcggggcca gagcgcgcac | 240 |
| agtttggtgg agatccgggc agtcgctctg cggacggtgg ccatcaaggg cgtgtacagc | 300 |
| gaccgctatc tctgcatggg tgcggacggc aggatgcaag gctgcctca gtactccgcc | 360 |
| ggagactgtg ctttcgagga ggagatccgc cctgatggct acaacgtgta ccggtccaag | 420 |
| aagcaccgtc tccccgtctc cctgagcagt gcgaaacaaa ggcagctgta caaggaccgg | 480 |
| ggcttttgc ctctgtccca tttcttgccc atgctgcccg ggagcctggc ggagcccagg | 540 |
| gacctccagg accacgtgga ggctgatggg ttttctgccc ccctagaaac agacagcatg | 600 |
| gacccttttg ggattgccac caaaatggga ctagtgaaga gtcccagctt ccaaaaatga | 660 |

<210> SEQ ID NO 318
<211> LENGTH: 654
<212> TYPE: DNA
<213> ORGANISM: Takifugu rubripes

<400> SEQUENCE: 318

| | |
|---|---|
| tcatctacaa ggattagtgg aaacatggtt ctcctcatgc tccccatcac cgttgcaaac | 60 |
| ctcttcctct gtgctggagt tctctccttg cctttgttgg atcaagggtc tcattttccc | 120 |
| caaggctggg aacaggtagt ccgcttcagg cacctgtatg ctgccagtgc agggctgcac | 180 |
| ctgctgatca ctgaagaggg ctcgatccaa ggctctgcag atccaacttt atacagcctg | 240 |
| atggagatcc gtccggtgga cccaggctgt gttgtcatta gaggagcagc aaccacacgc | 300 |
| ttcctctgca tagaaggtgc tggaagactg tactcatcac agacctacag caaagacgac | 360 |
| tgtaccttca gagagcaaat cctagcagac ggctacagcg tctacagatc tgtcggacac | 420 |
| ggagctctgg tcagtctggg aaactaccgg cagcagctga ggggggagga ctggagcgtt | 480 |
| ccgacactgg ctcagttcct ccccagaata agttcactgg atcaggactt taaagctgct | 540 |
| cttgacgaga ctgagaagcc agaacaaact gcacctcaaa gatcggaacc tgtcgacatg | 600 |
| gtggactcat ttggaaagct ctctcagatc atccacagtc ccagttttca caag | 654 |

<210> SEQ ID NO 319
<211> LENGTH: 282
<212> TYPE: DNA
<213> ORGANISM: Equus caballus

<400> SEQUENCE: 319

| | |
|---|---|
| gcggccgggc gcccctagc cttgtccgac gctgggccgc acgtgcacta cggctggggc | 60 |
| gagccgatcc gcctgcggca cctgtacacc gccggccccc acggcctctc cagctgcttc | 120 |
| ctgcgcatcc gcgccgatgg cgccgtggac tgcgcgcggg gccagagcgc gcacagtttg | 180 |
| gtggagatca gagcagtcgc tctgcgcacc gtggccatca agggcgtgca cagcgtccgg | 240 |
| tacctctgca tgggcgccga cggcaggatg caagggctgg ta | 282 |

<210> SEQ ID NO 320
<211> LENGTH: 630
<212> TYPE: DNA
<213> ORGANISM: Oryzias latipes

<400> SEQUENCE: 320

| | |
|---|---|
| accatgctgc tcattgtggt caccattccc acaatggtgt tttctgactc tggagtttcc | 60 |
| agcatgccgc tctctgatca tggacccccac atcactcaca gctggagcca agtggtccgc | 120 |
| ctccggcacc tgtacgcggt caagcctgga caacatgtcc agatcagaga ggatggacac | 180 |

```
atccacggct cagcagaaca aactctgaac agcctgctgg agatccgtcc ggttgctccg    240
ggacgggtgg tcttcagagg agtagccacc tcaaggtttc tgtgcatgga gagcgacggc    300
agactcttct cctcacacac atttgacaag acaactgcg tcttcagaga gcagatcttg    360
gcagacggct acaacatcta catttcagat cagcatggaa ccctgcttag tttgggaaac    420
caccggcaaa ggcagcaggg tttagaccgg gatgttccag ccctggctca gttcctcccc    480
aggatcagca ccctgcagca gggcgtgtac ccagtgccag accccccca ccagatgaga    540 acaatgcaaa cagagaagac tctagatgcc acggacacat ttgggcaact ctctaaaatc    600
attcacagtc ccagcttcaa caaaagatga                                    630

<210> SEQ ID NO 321
<211> LENGTH: 624
<212> TYPE: DNA
<213> ORGANISM: Xiphophorus maculates

<400> SEQUENCE: 321
atgtttgtgt tcattctatg cattgctggt gaactttta ctctgggagt attttgcatg     60
ccaatgatgg accagggggcc acttgtcacc catggctggg ccaggtggt ccggcaccgg   120 catctgtatg cagccaagcc aggactgcac ctactgatca gtgaggatgg acaaatccac   180
ggttccgcag atcaaactct ttacagcctg ctggagatcc aacctgttgg ccccggacgt   240
gttgtgatca aggagtggc aaccacacgc ttcctctgca tggagagcga cggcagattg    300
tactcaactg aaacatacag cagagctgac tgcaccttca gagaacagat ccaggcagac    360
ggctacaacg tctacacctc tgatagccat ggagccctcc tcagtttggg aaacaaccag    420
caaagacaca gcggctcaga ccgtggtgtt ccagctctgg cccgcttcct tcccaggtta    480
aacacccttc agcaggccgt ccccacagag ccggatgttc ctgatcagct cagtccagag    540
aaagtacaac agactgtgga catggtggcc tcctttggca agctctctca tataattcac    600
agtcccagct tccataagag atga                                         624

<210> SEQ ID NO 322
<211> LENGTH: 663
<212> TYPE: DNA
<213> ORGANISM: Ictidomys tridecemlineatus

<400> SEQUENCE: 322
atgcggagcg cgccgagcgg acgtgcctta gcccgcgccc tggtgctggc cagcctctgg     60
ttggcagtgg ccggacgacc cctggcccgg cgctctctgg ctctctccga ccaggggcca   120
cacttgtact atggctggga tcagcccatc cgcctccggc acctgtacgc cgcgggcccc    180
tacggcttct ccaactgttt cctgcgcatc cgcaccgacg cgccgtgga ctgcgaggag    240 aagcagagcg agcgtagttt gatggagatc agggcggtcg ctctggagac tgtggccatc    300
aaggacataa acagcgtccg gtacctctgc atgggcgccg acggcaggat acagggactg    360
cctcggtact cggaggaaga gtgcacgttc aaggaggaga tcagctatga cggctacaac    420
gtgtaccggt cccagaagta ccaccttccc gtggtgctca gcagtgccaa gcagcggcag    480
ctgtaccaga gcaagggcgt ggttcccctg tcctacttcc tgcccatgct gcccctggcc    540
tctgcggaga ccagggaccg cttggaatcc gatgtgttct ctttacctct ggaaactgac    600
agcatggacc cgtttgggat ggccagtgaa gtgggcctga agagcccag cttccagaag    660 taa                                                                663
```

<210> SEQ ID NO 323
<211> LENGTH: 612
<212> TYPE: DNA
<213> ORGANISM: Gasterosteus aculeatus

<400> SEQUENCE: 323

| | | |
|---|---|---|
| atgctgctgc tgctggtccc cgcgtacgtt gccagtgtgt ttttagctct cggggttgtt | 60 |
| tgcttgcccc taacagatca gggtctccac atggccgacg actggggcca gtcggtccga | 120 |
| ctcaagcacc tgtacgccgc cagcccggga ctccacctgc tgatcgggga ggatggtcgg | 180 |
| atccaaggct cggcgcagca aagccctac agcctgctgg agatcagtgc agtggatccg | 240 |
| ggctgtgtgg tcatcagagg agtagcaacc gcacggtttc tctgcatcga aggcgatgga | 300 |
| agactgtact catcggacac ctacagcaga acgactgca ccttcaggga gcagatcctc | 360 |
| ccggacggct acagcgtcta cgtctcccat ggacacgggg ccctgctcag cctggggaac | 420 |
| cacaggcaga ggctgcaggg tcgagaccac ggcgtgccgg ctctggccca gttcctcccg | 480 |
| agggtcagca ccatggatca ggcctcggcc cccgacgcgc ccgggcagac cgccaccgag | 540 |
| acggaagagc ccgtggactc gtttggaaag ctctctcaga tcattcacag tcccagcttc | 600 |
| cacgagagat ga | 612 |

<210> SEQ ID NO 324
<211> LENGTH: 627
<212> TYPE: DNA
<213> ORGANISM: Oreochromis niloticus

<400> SEQUENCE: 324

| | | |
|---|---|---|
| atgctgctgc tcctcatcgt atccattgtc aatatgcttt ttggtgttgg aatggtttgc | 60 |
| atgcccctgt cagacaacgg gccccacatc gcccacggct gggcccaggt ggtccggctc | 120 |
| aggcaccttt acgccaccag accgggaatg cacctgctga tcagtgaggg tggacagatc | 180 |
| cgtggttctg ccgtccagac tctgcacagc ctaatggaga ttcgtccagt cggtccaggc | 240 |
| cgtgttgtca tcagagggggt agcaaccgca aggtttctct gcatagaaga cgacggcaca | 300 |
| ctgtactcat cgcacgccta cagcagagag gactgcatct tcagagagca gatcttgcca | 360 |
| gatgggtaca acatctacat ctctgacaga catggagtcc tgctcagtct gggaaaccac | 420 |
| cggcaaagac tgcagggctt agaccgagga gatccagccc tggcccagtt cctccccagg | 480 |
| atcagcactc tgaatcaaat cccttcccct ggggcaaaca tcggtgacca catgaaagta | 540 |
| gcaaaaacag aagaacctgt ggacacaata gattcatttg aaagttctc tcagatcatt | 600 |
| gacagtccca gcttccataa gagatga | 627 |

<210> SEQ ID NO 325
<211> LENGTH: 456
<212> TYPE: DNA
<213> ORGANISM: Meleagris gallopavo

<400> SEQUENCE: 325

| | | |
|---|---|---|
| gtaggcaatc aatcaccaca gagcatcctt gaaataactg ctgttgatgt cgggatcgtc | 60 |
| gctatcaagg gcttgttctc tggcagatac ctggccatga caaaagggg caggcttat | 120 |
| gcatcactca gctattccat tgaggactgt tcctttgaag aggagattcg tccagatggc | 180 |
| tataacgtgt ataaatcaaa gaaatacgga atatcagtgt ctttgagcag tgccaaacaa | 240 |
| agacaacaat tcaaggaaa agattttctc ccactgtctc acttcttacc catgatcaac | 300 |
| actgtgccag tggaggtgac agactttggt gaatacggtg attacagcca ggcttttgag | 360 |

```
ccagaggtct actcatcgcc tctcgaaacg gacagcatgg atccctttgg gatcacttcc    420
aaactgtctc cagtgaagag ccccagcttt cagaaa                              456
```

<210> SEQ ID NO 326
<211> LENGTH: 651
<212> TYPE: DNA
<213> ORGANISM: Papio Anubis

<400> SEQUENCE: 326

```
atgaggagcg ggtgtgtggt ggtccacgcc tggatcctgg ccagcctctg gctggccgtg     60
gccgggcgtc ccctcgcctt ctcggacgcg gggccccacg tgcactacgg ctggggcgac    120
cccatccgcc tgcggcacct gtacacctcc ggcccccacg gctctccag ctgcttcctg     180 cgcatccgca ccgacggcgt cgtggactgc gcgcggggcc aaagcgcgca cagtttgctg    240
gagatcaagg cagtagctct gcggaccgtg gccatcaagg gcgtgcacag cgtgcggtac    300
ctctgcatgg gcgccgacgg caagatgcag gggctgcttc agtactcaga ggaagactgt    360
gctttcgagg aggagatccg ccctgatggc tacaatgtat accgatccca gaagcaccgc    420
ctcccggtct ccctgagcag tgccaaacag cggcagctgt acaagaacag gggctttctt    480
ccgctgtctc atttcctgcc catgctgccc atggcccag aggagcctga ggacctcagg     540 ggcccttgg aatctgacat gttctcttcg ccctggaga ctgacagcat ggacccattt      600
gggcttgtca ccggactgga ggcggtgagg agtcccagct ttgagaaata a              651
```

<210> SEQ ID NO 327
<211> LENGTH: 651
<212> TYPE: DNA
<213> ORGANISM: Saimiri boliviensis boliviensis

<400> SEQUENCE: 327

```
atgcggagcg ggtgtgtggt ggtccacgcc tggatcctgg ctggcctctg gctggctgtg     60
gtcgggcgcc ccctcgcctt ctccgatgcg gggccgcatg tgcattacgg ctggggcgac    120
cccattcgcc tgcggcacct gtacacctcc agccccacg gcctctccag ctgcttcctg     180
cgcatccgca gcgacggcgt cgtggactgc gcgcggggcc agagcgcgca cagtttgctg    240
gagatcaagg cagtcgctct aaggaccgtg gccatcaagg gcgtgcacag ctcgcggtac    300
ctctgcatgg gcgccgacgg caggctgcag gggctgttcc agtactcgga ggaagactgt    360
gctttcgagg aggagatccg ccccgacggc tacaatgtgt acctatccga gaagcaccgc    420
ctcccggtct ccctgagcag cgccaaacag cggcagctgt acaagaaacg aggctttctt    480
ccgctgtccc atttcctgcc catgctgccc agagcccag aggagcctga tgacctcagg     540
ggccacttgg aatctgacgt gttctcttca ccctggaga ctgatagcat ggacccattt     600
gggcttgtca cgggactgga ggcggtgaac agtcccagct ttgagaagta a              651
```

<210> SEQ ID NO 328
<211> LENGTH: 648
<212> TYPE: DNA
<213> ORGANISM: Pteropus alecto

<400> SEQUENCE: 328

```
atgcgcagcc cgtgcgcggt ggcgcgcgcg ctggtgctgg cgggcctgtg gctggcgagc     60
gcggcgggcc cgctggcgct gagcgatgcg ggccgcatg tgcattatgg ctggggcgaa     120
gcgattcgcc tgcgccatct gtataccgcg ggcccgcatg gcccgagcag ctgctttctg    180
```

```
cgcattcgcg cggatggcgc ggtggattgc gcgcgcggcc agagcgcgca tagcctggtg    240
gaaattcgcg cggtggcgct gcgcaacgtg gcgattaaag gcgtgcatag cgtgcgctat    300
ctgtgcatgg gcgcggatgg ccgcatgctg ggcctgctgc agtatagcgc ggatgattgc    360
gcgtttgaag aagaaattcg cccggatggc tataacgtgt atcatagcaa aaaacatcat    420
ctgccggtga gcctgagcag cgcgaaacag cgccagctgt ataaagatcg cggctttctg    480
ccgctgagcc atttctgcc gatgctgccg cgcagcccga ccgaaccgga aaactttgaa    540
gatcatctgg aagcggatac ctttagcagc ccgctggaaa ccgatgatat ggatccgttt    600
ggcattgcga gcaaactggg cctggaagaa agcccgagct ttcagaaa              648
```

<210> SEQ ID NO 329  
<211> LENGTH: 735  
<212> TYPE: DNA  
<213> ORGANISM: Myotis davidii

<400> SEQUENCE: 329

```
atgagcggcc agaacagcgg ccgccatggc agccgcccgg gcctggatga agaaccggaa     60
ccgggcccgc tggaactgcg cgcgctgggc agcacccgcg cggatccgca gctgtgcgat    120
tttctggaaa accattttct gggctatacc tgcctggaac tggatatttg cctggcgacc    180
tatctgggcg tgagccattg gggcgaaagc attcgcctgc ccatctgta taccagcggc    240 ccgcatggcc cgagcagctg ctttctgcgc attcgcgtgg atggcgcggt ggattgcgcg    300
cgcggccaga gcgcgcatag cctggtggaa attcgcgcgg tggcgctgcg caaagtggcg    360
attaaaggcg tgcatagcgc gctgtatctg tgcatggaag gcgatggccg catgcgcggc    420
ctgccgcagt ttagcccgga agattgcgcg tttgaagaag aaattcgccc ggatggctat    480
aacgtgtatc gcagccagaa acatcagctg ccggtgagcc tgagcagcgc gcgccagcgc    540
cagctgttta agcgcgcggc ctttctgccg ctgagccatt ttctgccgat gctgccgagc    600
agcccggcgg aaccggtgca tcgcgaacgc ccgctggaac cggatgcgtt tagcagcccg    660
ctggaaaccg atagcatgga tccgtttggc attgcgaaca acctgcgcct ggtgaaaagc    720
ccgagctttc agaaa                                                     735
```

<210> SEQ ID NO 330  
<211> LENGTH: 750  
<212> TYPE: DNA  
<213> ORGANISM: Tupaia chinensis

<400> SEQUENCE: 330

```
atgcgccgca cctggagcgg ctttgcggtg gcgacccgcg cgggcagccc gctggcgctg     60
gcggatgcgg ggccgcatgt gaactatggc tgggatgaaa gcattcgcct gcgccatctg    120
tataccgcga gcctgcatgg cagcaccagc tgctttctgc gcattcgcga tgatggcagc    180
gtgggctgcg cgcgcggcca gagcatgcat agcctgctgg aaattaaagc ggtggcgctg    240
cagaccgtgg cgattaaagg cgtgtatagc gtgcgctatc tgtgcatgga taccgatggc    300
cgcatgcagg gcctgccgca gtatagcgaa gaagattgca cctttgaaga agaaattcgc    360
agcgatggcc ataacgtgta tcgcagcaaa aaacatggcc tgccggtgag cctgagcagc    420
gcgaaacagc gccagctgta taaggccgc ggctttctga gcctgagcca ttttctgctg    480
atgatgccga aaccagcgc gggcccgggc aacccgcgcg atcagcgcaa cccgcgcgat    540
cagcgcgatc gaacaccctt tagcctgccg ctggaaaccg atagcatgga tccgtttggc    600
atgaccaccc gccatggcct gctgctggat agctgctgcg cgagcctggt gctgctgaac    660
```

```
attagcaccg atggcgaatt tagcccgtat ggcaacattc tgcgcccgag ctttcgcttt        720
aaactgttta aaatgaaaaa agtgaccaac                                         750

<210> SEQ ID NO 331
<211> LENGTH: 627
<212> TYPE: DNA
<213> ORGANISM: Heterocephalus glaber

<400> SEQUENCE: 331
atgcgcttta gcaaaagcac ctgcggcttt tttaaccatc agcgcctgca ggcgctgtgg         60
ctgagcctga gcagcgtgaa atgggtgctg gatgcggcgg tggaaggccg cccgattcgc        120
ctgcgccatc tgtatgcggc gggcccgtat ggccgcagcc gctgctttct gcgcattcat        180
accgatggcg cggtggattg cgtggaagaa cagagcgaac attgcctgct ggaaattcgc        240
gcggtggcgc tggaaaccgt ggcgattaaa gatattaaca gcgtgcgcta tctgtgcatg        300
ggcccggatg ccgcatgca gggcctgccg tggtatagcg aagaagattg cgcgtttaaa        360
gaagaaatta gctatccggg ctatagcgtg tatcgcagcc agaaacatca tctgccgatt        420
gtgctgagca gcgtgaaaca cgccagcag tatcagagca aaggcgtggt gccgctgagc        480
tattttctgc cgatgctgcc gaaagcgagc gtggaaccgg gcgatgaaga agaaagcgcg        540
tttagcctgc cgctgaaaac cgatagcatg gatccgtttg gcatggcgag cgaaattggc        600
ctggcgaaaa gcccgagctt tcagaaa                                            627

<210> SEQ ID NO 332
<211> LENGTH: 209
<212> TYPE: PRT
<213> ORGANISM: Homo sapiens

<400> SEQUENCE: 332

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190
```

```
Pro Leu Ser Met Val Gly Pro Ser Gln Gly Arg Ser Pro Ser Tyr Ala
            195                 200                 205
Ser

<210> SEQ ID NO 333
<211> LENGTH: 198
<212> TYPE: PRT
<213> ORGANISM: Artificial
<220> FEATURE:
<223> OTHER INFORMATION: Chimeric protein

<400> SEQUENCE: 333

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Asp Gln
        115                 120                 125

Asn Gly Ser Cys Val Arg Gly Pro Arg Thr His Tyr Gly Gln Lys Ala
    130                 135                 140

Ile Leu Phe Leu Pro Leu Pro Met Val Pro Glu Glu Pro Glu Asp
145                 150                 155                 160

Leu Arg Gly His Leu Glu Ser Asp Met Phe Ser Ser Pro Leu Glu Thr
                165                 170                 175

Asp Ser Met Asp Pro Phe Gly Leu Val Thr Gly Leu Glu Ala Val Arg
            180                 185                 190

Ser Pro Ser Phe Glu Lys
        195

<210> SEQ ID NO 334
<211> LENGTH: 174
<212> TYPE: PRT
<213> ORGANISM: Artificial
<220> FEATURE:
<223> OTHER INFORMATION: Chimeric protein

<400> SEQUENCE: 334

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80
```

```
Glu Glu Asn His Tyr Asn Thr Tyr Ile Ser Lys Lys His Ala Glu Lys
                85                  90                  95

Asn Trp Phe Val Gly Leu Asp Gln Asn Gly Ser Cys Val Arg Gly Pro
            100                 105                 110

Arg Thr His Tyr Gly Gln Lys Ala Ile Leu Phe Leu Pro Leu Leu Pro
            115                 120                 125

Met Val Pro Glu Glu Pro Glu Asp Leu Arg Gly His Leu Glu Ser Asp
        130                 135                 140

Met Phe Ser Ser Pro Leu Glu Thr Asp Ser Met Asp Pro Phe Gly Leu
145                 150                 155                 160

Val Thr Gly Leu Glu Ala Val Arg Ser Pro Ser Phe Glu Lys
                165                 170
```

<210> SEQ ID NO 335
<211> LENGTH: 199
<212> TYPE: PRT
<213> ORGANISM: Artificial
<220> FEATURE:
<223> OTHER INFORMATION: Chimeric protein

<400> SEQUENCE: 335

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Asp
            115                 120                 125

Gln Thr Gly Gln Tyr Val Leu Gly Ser Lys Thr Gly Pro Gly Gln Lys
        130                 135                 140

Ala Ile Leu Phe Leu Pro Met Leu Pro Met Val Pro Glu Glu Pro Glu
145                 150                 155                 160

Asp Leu Arg Gly His Leu Glu Ser Asp Met Phe Ser Ser Pro Leu Glu
                165                 170                 175

Thr Asp Ser Met Asp Pro Phe Gly Leu Val Thr Gly Leu Glu Ala Val
            180                 185                 190

Arg Ser Pro Ser Phe Glu Lys
        195
```

<210> SEQ ID NO 336
<211> LENGTH: 175
<212> TYPE: PRT
<213> ORGANISM: Artificial
<220> FEATURE:
<223> OTHER INFORMATION: Chimeric protein

<400> SEQUENCE: 336

```
His Phe Lys Asp Pro Lys Arg Leu Tyr Cys Lys Asn Gly Gly Phe Phe
1               5                   10                  15
```

Leu Arg Ile His Pro Asp Gly Arg Val Asp Gly Val Arg Glu Lys Ser
             20                  25                  30

Asp Pro His Ile Lys Leu Gln Leu Gln Ala Glu Arg Gly Val Val
         35                  40                  45

Ser Ile Lys Gly Val Cys Ala Asn Arg Tyr Leu Ala Met Lys Glu Asp
 50                  55                  60

Gly Arg Leu Leu Ala Ser Lys Cys Val Thr Asp Glu Cys Phe Phe Phe
 65                  70                  75                  80

Glu Arg Leu Glu Ser Asn Asn Tyr Asn Thr Tyr Arg Ser Arg Lys Tyr
                 85                  90                  95

Thr Ser Trp Tyr Val Ala Leu Asp Gln Thr Gly Gln Tyr Val Leu Gly
                100                 105                 110

Ser Lys Thr Gly Pro Gly Gln Lys Ala Ile Leu Phe Leu Pro Met Leu
            115                 120                 125

Pro Met Val Pro Glu Glu Pro Glu Asp Leu Arg Gly His Leu Glu Ser
130                 135                 140

Asp Met Phe Ser Ser Pro Leu Glu Thr Asp Ser Met Asp Pro Phe Gly
145                 150                 155                 160

Leu Val Thr Gly Leu Glu Ala Val Arg Ser Pro Ser Phe Glu Lys
                165                 170                 175

<210> SEQ ID NO 337
<211> LENGTH: 594
<212> TYPE: DNA
<213> ORGANISM: Artificial
<220> FEATURE:
<223> OTHER INFORMATION: Nucleic acid sequence encoding chimeric protein

<400> SEQUENCE: 337
atggctgaag gggaaatcac caccttcaca gccctgaccg agaagtttaa tctgcctcca      60
gggaattaca agaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac aaatgaggaa tgtttgttc      300 ctggaaaggc tggaggagaa ccattacaac acctatatat ccaagaagca tgcagagaag     360
aattggtttg ttggcctcga tcagaatggg agctgcgttc gcggtcctcg gactcactat     420
ggccagaaag caatcttgtt tctcccctg ctgcccatgg tcccagagga gcctgaggac      480
ctcagggggc acttggaatc tgacatgttc tcttcgcccc tggagaccga cagcatggac     540
ccatttgggc ttgtcaccgg actggaggcc gtgaggagtc cagctttga gaag            594

<210> SEQ ID NO 338
<211> LENGTH: 522
<212> TYPE: DNA
<213> ORGANISM: Artificial
<220> FEATURE:
<223> OTHER INFORMATION: Nucleic acid sequence encoding chimeric protein

<400> SEQUENCE: 338
aagcccaaac tcctctactg tagcaacggg ggccacttcc tgaggatcct tccggatggc      60
acagtggatg ggacaaggga caggagcgac cagcacattc agctgcagct cagtgcggaa     120
agcgtggggg aggtgtatat aaagagtacc gagactggcc agtacttggc catggacacc     180
gacgggcttt tatacggctc acagacacca atgaggaat gtttgttcct ggaaaggctg      240

```
gaggagaacc attacaacac ctatatatcc aagaagcatg cagagaagaa ttggtttgtt      300
ggcctcgatc agaatgggag ctgcgttcgc ggtcctcgga ctcactatgg ccagaaagca      360
atcttgtttc tcccctgct gcccatggtc ccagaggagc ctgaggacct caggggccac       420
ttggaatctg acatgttctc ttcgcccctg agaccgaca gcatggaccc atttgggctt       480
gtcaccggac tggaggccgt gaggagtccc agctttgaga ag                        522
```

<210> SEQ ID NO 339
<211> LENGTH: 597
<212> TYPE: DNA
<213> ORGANISM: Artificial
<220> FEATURE:
<223> OTHER INFORMATION: Nucleic acid sequence encoding chimeric protein

<400> SEQUENCE: 339

```
atggcagccg ggagcatcac cacgctgccc gccttgcccg aggatggcgg cagcggcgcc      60
ttcccgcccg ccacttcaa ggaccccaag cggctgtact gcaaaaacgg gggcttcttc      120
ctgcgcatcc accccgacgg ccgagttgac ggggtccggg agaagagcga ccctcacatc      180
aagctacaac ttcaagcaga agagaggagga gttgtgtcta tcaaaggagt gtgtgctaac      240
cgttacctgg ctatgaagga agatggaaga ttactggctt ctaaatgtgt tacggatgag      300
tgttttcttt ttgaacgatt ggaatctaat aactacaata cttaccggtc aaggaaatac      360
accagttggt atgtggcact ggatcagact gggcagtatg ttcttggatc caaaacagga      420
cctgggcaga aagctatact tttcttcca atgctgccca tggtcccaga ggagcctgag      480
gacctcaggg ccacttgga atctgacatg ttctcttcgc ccctggagac cgacagcatg      540
gacccatttg gcttgtcac cggactggag gccgtgagga gtcccagctt tgagaag         597
```

<210> SEQ ID NO 340
<211> LENGTH: 525
<212> TYPE: DNA
<213> ORGANISM: Artificial
<220> FEATURE:
<223> OTHER INFORMATION: Nucleic acid sequence encoding chimeric protein

<400> SEQUENCE: 340

```
cacttcaagg accccaagcg gctgtactgc aaaaacgggg gcttcttcct gcgcatccac      60
cccgacggcc gagttgacgg ggtccgggag aagagcgacc tcacatcaa gctacaactt      120 caagcagaag agaggagagt tgtgtctatc aaaggagtgt gtgctaaccg ttacctggct      180 atgaaggaa atggaagatt actggcttct aaatgtgtta cggatgagtg tttctttttt      240
gaacgattgg aatctaataa ctacaatact taccggtcaa ggaaatacac cagttggtat      300
gtggcactgg atcagactgg gcagtatgtt cttggatcca aaacaggacc tgggcagaaa      360
gctatacttt tcttccaat gctgcccatg gtcccagagg agcctgagga cctcaggggc      420
cacttggaat ctgacatgtt ctcttcgccc ctggagaccg acagcatgga cccatttggg      480
cttgtcaccg gactggaggc cgtgaggagt cccagctttg agaag                      525
```

<210> SEQ ID NO 341
<211> LENGTH: 1044
<212> TYPE: PRT
<213> ORGANISM: Homo sapiens

<400> SEQUENCE: 341

```
Met Lys Pro Gly Cys Ala Ala Gly Ser Pro Gly Asn Glu Trp Ile Phe
1               5                   10                  15
```

```
Phe Ser Thr Asp Glu Ile Thr Thr Arg Tyr Arg Asn Thr Met Ser Asn
             20                  25                  30

Gly Gly Leu Gln Arg Ser Val Ile Leu Ser Ala Leu Ile Leu Leu Arg
         35                  40                  45

Ala Val Thr Gly Phe Ser Gly Asp Gly Arg Ala Ile Trp Ser Lys Asn
 50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                 85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
```

```
                435                 440                 445
Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
    850                 855                 860
```

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Gln Ala
            885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Ser Ile Ala Ile Phe Gln Arg Gln Lys Arg Arg
    1010                1015                1020

Lys Phe Trp Lys Ala Lys Asn Leu Gln His Ile Pro Leu Lys Lys
    1025                1030                1035

Gly Lys Arg Val Val Ser
    1040

<210> SEQ ID NO 342
<211> LENGTH: 1043
<212> TYPE: PRT
<213> ORGANISM: Mouse

<400> SEQUENCE: 342

Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Arg
        35                  40                  45

Ala Val Thr Gly Phe Ser Gly Asp Gly Lys Ala Ile Trp Asp Lys Lys
    50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
            85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
    130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
            165                 170                 175

Ala Leu Leu Asp Ser Leu Val Leu Arg Asn Ile Glu Pro Ile Val Thr

```
                180             185             190
Leu Tyr His Trp Asp Leu Pro Leu Thr Leu Gln Glu Glu Tyr Gly Gly
            195                 200                 205
Trp Lys Asn Ala Thr Met Ile Asp Leu Phe Asn Asp Tyr Ala Thr Tyr
        210                 215                 220
Cys Phe Gln Thr Phe Gly Asp Arg Val Lys Tyr Trp Ile Thr Ile His
225                 230                 235                 240
Asn Pro Tyr Leu Val Ala Trp His Gly Phe Gly Thr Gly Met His Ala
                245                 250                 255
Pro Gly Glu Lys Gly Asn Leu Thr Ala Val Tyr Thr Val Gly His Asn
            260                 265                 270
Leu Ile Lys Ala His Ser Lys Val Trp His Asn Tyr Asp Lys Asn Phe
        275                 280                 285
Arg Pro His Gln Lys Gly Trp Leu Ser Ile Thr Leu Gly Ser His Trp
        290                 295                 300
Ile Glu Pro Asn Arg Thr Asp Asn Met Glu Asp Val Ile Asn Cys Gln
305                 310                 315                 320
His Ser Met Ser Ser Val Leu Gly Trp Phe Ala Asn Pro Ile His Gly
                325                 330                 335
Asp Gly Asp Tyr Pro Glu Phe Met Lys Thr Gly Ala Met Ile Pro Glu
                340                 345                 350
Phe Ser Glu Ala Glu Lys Glu Val Arg Gly Thr Ala Asp Phe Phe
            355                 360                 365
Ala Phe Ser Phe Gly Pro Asn Asn Phe Arg Pro Ser Asn Thr Val Val
        370                 375                 380
Lys Met Gly Gln Asn Val Ser Leu Asn Leu Arg Gln Val Leu Asn Trp
385                 390                 395                 400
Ile Lys Leu Glu Tyr Asp Asp Pro Gln Ile Leu Ile Ser Glu Asn Gly
                405                 410                 415
Trp Phe Thr Asp Ser Tyr Ile Lys Thr Glu Asp Thr Thr Ala Ile Tyr
            420                 425                 430
Met Met Lys Asn Phe Leu Asn Gln Val Leu Gln Ala Ile Lys Phe Asp
        435                 440                 445
Glu Ile Arg Val Phe Gly Tyr Thr Ala Trp Thr Leu Leu Asp Gly Phe
    450                 455                 460
Glu Trp Gln Asp Ala Tyr Thr Thr Arg Arg Gly Leu Phe Tyr Val Asp
465                 470                 475                 480
Phe Asn Ser Glu Gln Lys Glu Arg Lys Pro Lys Ser Ser Ala His Tyr
                485                 490                 495
Tyr Lys Gln Ile Ile Gln Asp Asn Gly Phe Pro Leu Lys Glu Ser Thr
            500                 505                 510
Pro Asp Met Lys Gly Arg Phe Pro Cys Asp Phe Ser Trp Gly Val Thr
        515                 520                 525
Glu Ser Val Leu Lys Pro Glu Phe Thr Val Ser Ser Pro Gln Phe Thr
    530                 535                 540
Asp Pro His Leu Tyr Val Trp Asn Val Thr Gly Asn Arg Leu Leu Tyr
545                 550                 555                 560
Arg Val Glu Gly Val Arg Leu Lys Thr Arg Pro Ser Gln Cys Thr Asp
                565                 570                 575
Tyr Val Ser Ile Lys Lys Arg Val Glu Met Leu Ala Lys Met Lys Val
            580                 585                 590
Thr His Tyr Gln Phe Ala Leu Asp Trp Thr Ser Ile Leu Pro Thr Gly
        595                 600                 605
```

-continued

```
Asn Leu Ser Lys Val Asn Arg Gln Val Leu Arg Tyr Tyr Arg Cys Val
    610                 615                 620

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
                645                 650                 655

Gly Gly Trp Leu Asn Met Asn Thr Ala Lys Ala Phe Gln Asp Tyr Ala
                660                 665                 670

Glu Leu Cys Phe Arg Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                725                 730                 735

Ser Leu Ser Leu His Cys Asp Trp Ala Glu Pro Ala Asn Pro Phe Val
                740                 745                 750

Asp Ser His Trp Lys Ala Ala Glu Arg Phe Leu Gln Phe Glu Ile Ala
            755                 760                 765

Trp Phe Ala Asp Pro Leu Phe Lys Thr Gly Asp Tyr Pro Ser Val Met
770                 775                 780

Lys Glu Tyr Ile Ala Ser Lys Asn Gln Arg Gly Leu Ser Ser Ser Val
785                 790                 795                 800

Leu Pro Arg Phe Thr Ala Lys Glu Ser Arg Leu Val Lys Gly Thr Val
                805                 810                 815

Asp Phe Tyr Ala Leu Asn His Phe Thr Thr Arg Phe Val Ile His Lys
                820                 825                 830

Gln Leu Asn Thr Asn Arg Ser Val Ala Asp Arg Asp Val Gln Phe Leu
            835                 840                 845

Gln Asp Ile Thr Arg Leu Ser Ser Pro Ser Arg Leu Ala Val Thr Pro
850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Asp Leu Ala Leu Glu
                885                 890                 895

Asp Asp Gln Ile Arg Lys Tyr Tyr Leu Glu Lys Tyr Val Gln Glu Ala
                900                 905                 910

Leu Lys Ala Tyr Leu Ile Asp Lys Val Lys Ile Lys Gly Tyr Tyr Ala
            915                 920                 925

Phe Lys Leu Thr Glu Glu Lys Ser Lys Pro Arg Phe Gly Phe Phe Thr
930                 935                 940

Ser Asp Phe Arg Ala Lys Ser Ser Val Gln Phe Tyr Ser Lys Leu Ile
945                 950                 955                 960

Ser Ser Ser Gly Leu Pro Ala Glu Asn Arg Ser Pro Ala Cys Gly Gln
                965                 970                 975

Pro Ala Glu Asp Thr Asp Cys Thr Ile Cys Ser Phe Leu Val Glu Lys
            980                 985                 990

Lys Pro Leu Ile Phe Phe Gly Cys Cys Phe Ile Ser Thr Leu Ala Val
            995                 1000                1005

Leu Leu Ser Ile Thr Val Phe  His His Gln Lys Arg  Arg Lys Phe
    1010                1015                1020
```

Gln Lys Ala Arg Asn Leu Gln Asn Ile Pro Leu Lys Lys Gly His
     1025                1030                1035

Ser Arg Val Phe Ser
    1040

<210> SEQ ID NO 343
<211> LENGTH: 3135
<212> TYPE: DNA
<213> ORGANISM: Homo sapiens

<400> SEQUENCE: 343

| | | | | | |
|---|---|---|---|---|---|
| atgaagccag | gctgtgcggc | aggatctcca | gggaatgaat | ggattttctt | cagcactgat | 60 |
| gaaataacca | cacgctatag | aatacaatg | tccaacgggg | gattgcaaag | atctgtcatc | 120 |
| ctgtcagcac | ttattctgct | acgagctgtt | actggattct | ctggagatgg | aagagctata | 180 |
| tggtctaaaa | atcctaattt | tactccggta | aatgaaagtc | agctgttct | ctatgacact | 240 |
| ttccctaaaa | acttttctg | gggtattggg | actggagcat | gcaagtgga | agggagttgg | 300 |
| aagaaggatg | gaaaaggacc | ttctatatgg | gatcatttca | tccacacaca | ccttaaaaat | 360 |
| gtcagcagca | cgaatggttc | cagtgacagt | tatatttttc | tggaaaaaga | cttatcagcc | 420 |
| ctggatttta | taggagtttc | tttttatcaa | ttttcaattt | cctggccaag | gcttttcccc | 480 |
| gatggaatag | taacagttgc | caacgcaaaa | ggtctgcagt | actacagtac | tcttctggac | 540 |
| gctctagtgc | ttagaaacat | tgaacctata | gttactttat | accactggga | tttgccttg | 600 |
| gcactacaag | aaaaatatgg | ggggtggaaa | aatgatacca | aatagatat | cttcaatgac | 660 |
| tatgccacat | actgttcca | gatgttgg | accgtgtca | aatattggat | tacaattcac | 720 |
| aacccatatc | tagtggcttg | gcatgggtat | gggacaggta | tgcatgcccc | tggagagaag | 780 |
| ggaaatttag | cagctgtcta | cactgtggga | cacaacttga | tcaaggctca | ctcgaaagtt | 840 |
| tggcataact | acaacacaca | tttccgccca | catcagaagg | gttggttatc | gatcacgttg | 900 |
| ggatctcatt | ggatcgagcc | aaaccggtcg | gaaaacacga | tggatatatt | caaatgtcaa | 960 |
| caatccatgg | tttctgtgct | tggatggttt | gccaaccta | tccatgggga | tggcgactat | 1020 |
| ccagagggga | tgagaaagaa | gttgttctcc | gttctaccca | ttttctctga | agcagagaag | 1080 |
| catgagatga | gaggcacagc | tgatttcttt | gcctttttctt | ttggacccaa | caacttcaag | 1140 |
| cccctaaaca | ccatggctaa | aatgggacaa | aatgtttcac | ttaatttaag | agaagcgctg | 1200 |
| aactggatta | aactggaata | caacaaccct | cgaatcttga | ttgctgagaa | tggctggttc | 1260 |
| acagacagtc | gtgtgaaaac | agaagacacc | acggccatct | acatgatgaa | gaatttcctc | 1320 |
| agccaggtgc | ttcaagcaat | aaggttagat | gaaatacgag | tgtttggtta | tactgcctgg | 1380 |
| tctctcctgg | atggctttga | atggcaggat | gcttacacca | tccgccgagg | attattttat | 1440 |
| gtggatttta | acagtaaaca | gaaagagcgg | aaacctaagt | cttcagcaca | ctactacaaa | 1500 |
| cagatcatac | gagaaaatgg | tttttctta | aaagagtcca | cgccagatgt | gcagggccag | 1560 |
| tttccctgtg | acttctcctg | gggtgtcact | gaatctgttc | ttaagcccga | gtctgtggct | 1620 |
| tcgtccccac | agttcagcga | tcctcatctg | tacgtgtgga | acgccactgg | caacagactg | 1680 |
| ttgcaccgag | tggaaggggt | gaggctgaaa | acacgacccg | ctcaatgcac | agattttgta | 1740 |
| aacatcaaaa | acaacttga | gatgttggca | agaatgaaag | tcacccacta | ccggtttgct | 1800 |
| ctggattggg | cctcggtcct | tcccactggc | aacctgtccg | cggtgaaccg | acaggccctg | 1860 |
| aggtactaca | ggtgcgtggt | cagtgagggg | ctgaagcttg | gcatctccgc | gatggtcacc | 1920 |
| ctgtattatc | cgacccacgc | ccacctaggc | ctccccgagc | ctctgttgca | tgccgacggg | 1980 |

```
tggctgaacc catcgacggc cgaggccttc caggcctacg ctgggctgtg cttccaggag    2040 ctggggacc tggtgaagct ctggatcacc atcaacgagc taaccggct aagtgacatc    2100 tacaaccgct ctggcaacga cacctacggg gcggcgcaca acctgctggt ggcccacgcc    2160
ctggcctggc gcctctacga ccggcagttc aggccctcac agcgcgggc cgtgtcgctg    2220 tcgctgcacg cggactgggc ggaacccgcc aaccctatg ctgactcgca ctggagggcg    2280
gccgagcgct tcctgcagtt cgagatcgcc tggttcgccg agccgctctt caagaccggg    2340
gactaccccg cggccatgag ggaatacatt gcctccaagc accgacgggg gctttccagc    2400
tcggccctgc cgcgcctcac cgaggccgaa aggaggctgc tcaagggcac ggtcgacttc    2460
tgcgcgctca accacttcac cactaggttc gtgatgcacg agcagctggc cggcagccgc    2520
tacgactcgg acagggacat ccagtttctg caggacatca cccgcctgag ctcccccacg    2580
cgcctggctg tgattccctg ggggtgcgc aagctgctgc ggtgggtccg gaggaactac    2640
ggcgacatgg acatttacat caccgccagt ggcatcgacg accaggctct ggaggatgac    2700
cggctccgga gtactacct agggaagtac cttcaggagg tgctgaaagc atacctgatt    2760
gataaagtca gaatcaaagg ctattatgca ttcaaactgg ctgaagagaa atctaaaccc    2820
agatttggat tcttcacatc tgatttttaaa gctaaatcct caatacaatt ttacaacaaa    2880
gtgatcagca gcaggggctt ccctttttgag aacagtagtt ctagatgcag tcagacccaa    2940
gaaaatacag agtgcactgt ctgcttattc cttgtgcaga agaaaccact gatattcctg    3000
ggttgttgct tcttctccac cctggttcta ctcttatcaa ttgccatttt tcaaaggcag    3060
aagagaagaa agttttggaa agcaaaaaac ttacaacaca taccattaaa gaaaggcaag    3120
agagttgtta gctaa                                                    3135
```

<210> SEQ ID NO 344
<211> LENGTH: 3132
<212> TYPE: DNA
<213> ORGANISM: House mouse

<400> SEQUENCE: 344

```
atgaagacag gctgtgcagc agggtctccg gggaatgaat ggattttctt cagctctgat     60
gaaagaaaca cacgctctag gaaaacaatg tccaacaggg cactgcaaag atctgccgtg    120
ctgtctgcgt ttgttctgct gcgagctgtt accggcttct ccggagacgg gaaagcaata    180
tgggataaaa acagtacgt gagtccggta aacccaagtc agctgttcct ctatgacact    240
ttccctaaaa acttttcctg gggcgttggg accggagcat ttcaagtgga agggagttgg    300
aagacagatg gaagaggacc ctcgatctgg gatcggtacg tctactcaca cctgagaggt    360
gtcaacggca cagacagatc cactgacagt tacatctttc tggaaaaaga cttgttggct    420
ctggattttt taggagtttc ttttttatcag ttctcaatct cctggccacg gttgtttccc    480
aatggaacag tagcagcagt gaatgcgcaa ggtctccggt actaccgtgc acttctggac    540
tcgctggtac ttaggaatat cgagcccatt gttaccttgt accattggga tttgcctctg    600
acgctccagg aagaatatgg gggctggaaa aatgcaacta tgatagatct cttcaacgac    660
tatgccacat actgcttcca gaccttggga gacccgtgtca atattggat tacaattcac    720 aacccttacc ttgttgcttg gcatgggttt ggcacaggta tgcatgcacc aggagagaag    780
ggaaatttaa cagctgtcta cactgtggga cacaacctga tcaaggcaca ttcgaaagtg    840
tggcataact acgacaaaaa cttccgccct catcagaagg gttggctctc catcaccttg    900
```

```
gggtcccatt ggatagagcc aaacagaaca gacaacatgg aggacgtgat caactgccag    960
cactccatgt cctctgtgct tggatggttc gccaacccca tccacgggga cggcgactac   1020
cctgagttca tgaagacggg cgccatgatc cccgagttct ctgaggcaga aaggaggag   1080
gtgaggggca cggctgattt cttttgccttt tccttcgggc caacaacttc aggccctca   1140
aacaccgtgg tgaaaatggg acaaaatgta tcactcaact taaggcaggt gctgaactgg   1200
attaaactgg aatacgatga ccctcaaatc ttgatttcgg agaacggctg gttcacagat   1260
agctatataa agacagagga caccacggcc atctacatga tgaagaattt cctaaaccag   1320
gttcttcaag caataaaatt tgatgaaatc cgcgtgtttg ttatacggc ctggactctc    1380
ctggatggct ttgagtggca ggatgcctat acgacccgac gagggctgtt ttatgtggac   1440
tttaacagtg agcagaaaga gaggaaaccc aagtcctcgg ctcattacta caagcagatc   1500
atacaagaca acggcttccc tttgaaagag tccacgccag acatgaaggg tcggttcccc   1560
tgtgatttct cttggggagt cactgagtct gttcttaagc ccgagtttac ggtctcctcc   1620
ccgcagttta ccgatcctca cctgtatgtg tggaatgtca ctggcaacag attgctctac   1680
cgagtggaag gggtaaggct gaaaacaaga ccatcccagt gcacagatta tgtgagcatc   1740
aaaaaacgag ttgaaatgtt ggcaaaaatg aaagtcaccc actaccagtt tgctctggac   1800
tggacctcta tccttcccac tggcaatctg tccaaagtta acagacaagt gttaaggtac   1860
tataggtgtg tggtgagcga aggactgaag ctgggcgtct tccccatggt gacgttgtac   1920
cacccaaccc actcccatct cggcctcccc ctgccacttc tgagcagtgg ggggtggcta   1980
aacatgaaca cagccaaggc cttccaggac tacgctgagc tgtgcttccg ggagttgggg   2040
gacttggtga agctctggat caccatcaat gagcctaaca ggctgagtga catgtacaac   2100
cgcacgagta atgacaccta ccgtgcagcc acaacctga tgatcgccca tgcccaggtc    2160
tggcacctct atgataggca gtataggccg gtccagcatg gggctgtgtc gctgtcctta   2220
cattgcgact gggcagaacc tgccaacccc tttgtggatt cacactggaa ggcagccgag   2280
cgcttcctcc agtttgagat cgcctggttt gcagatccgc tcttcaagac tggcgactat   2340
ccatcggtta tgaaggaata catcgcctcc aagaaccagc gagggctgtc tagctcagtc   2400
ctgccgcgct tcaccgcgaa ggagagcagg ctggtgaagg gtaccgtcga cttctacgca   2460
ctgaaccact tcactacgag gttcgtgata cacaagcagc tgaacaccaa ccgctcagtt   2520
gcagacaggg acgtccagtt cctgcaggac atcacccgcc taagctcgcc cagccgcctg   2580
gctgtaacac cctggggagt gcgcaagctc cttgcgtgga tccggaggaa ctacagagac   2640
agggatatct acatcacagc caatggcatc gatgacctgg ctctagagga tgatcagatc   2700
cgaaagtact acttggagaa gtatgtccag gaggctctga agcatatct cattgacaag    2760
gtcaaaatca aaggctacta tgcattcaaa ctgactgaag agaaatctaa gcctagattt   2820
ggatttttca cctctgactt cagagctaag tcctctgtcc agttttacag caagctgatc   2880
agcagcagtg gcctccccgc tgagaacaga agtcctgcgt gtggtcagcc tgcggaagac   2940
acagactgca ccatttgctc atttctcgtg gagaagaaac cactcatctt cttcggttgc   3000
tgcttcatct ccactctggc tgtactgcta tccatcaccg tttttcatca tcaaaagaga   3060
agaaaattcc agaaagcaag gaacttacaa aatataccat tgaagaaagg ccacagcaga   3120
gttttcagct aa                                                        3132

<210> SEQ ID NO 345
<211> LENGTH: 251
```

<212> TYPE: PRT
<213> ORGANISM: Homo sapiens

<400> SEQUENCE: 345

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 346
<211> LENGTH: 48
<212> TYPE: PRT
<213> ORGANISM: Artificial
<220> FEATURE:
<223> OTHER INFORMATION: FGF19 variant

<400> SEQUENCE: 346

Leu Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
                20                  25                  30

Gly Leu Val Thr Gly Leu Glu Ala Val Arg Ser Pro Ser Phe Ala Lys
            35                  40                  45

<210> SEQ ID NO 347
<211> LENGTH: 48
<212> TYPE: PRT
<213> ORGANISM: Artificial
<220> FEATURE:
<223> OTHER INFORMATION: FGF19 variant

<400> SEQUENCE: 347

Leu Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Ser Ala Val Arg Ser Pro Ser Phe Glu Lys
        35                  40                  45

<210> SEQ ID NO 348
<211> LENGTH: 48
<212> TYPE: PRT
<213> ORGANISM: Artificial
<220> FEATURE:
<223> OTHER INFORMATION: FGF19 variant

<400> SEQUENCE: 348

Leu Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Met Val Thr Gly Leu Glu Ala Val Arg Ser Pro Ser Phe Glu Lys
        35                  40                  45

<210> SEQ ID NO 349
<211> LENGTH: 48
<212> TYPE: PRT
<213> ORGANISM: Artificial
<220> FEATURE:
<223> OTHER INFORMATION: FGF19 variant

<400> SEQUENCE: 349

Leu Pro Met Val Pro Glu Glu Pro Glu Asp Leu Arg Gly His Leu Glu
1               5                   10                  15

Ser Asp Leu Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 350
<211> LENGTH: 48
<212> TYPE: PRT
<213> ORGANISM: Artificial
<220> FEATURE:
<223> OTHER INFORMATION: FGF19 variant

<400> SEQUENCE: 350

Leu Pro Met Val Pro Glu Glu Pro Glu Asp Leu Arg Gly His Pro Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 351
<211> LENGTH: 47
<212> TYPE: PRT
<213> ORGANISM: Artificial
<220> FEATURE:
<223> OTHER INFORMATION: FGF19 variant

<400> SEQUENCE: 351

```
Leu Pro Met Val Pro Glu Glu Pro Glu Asp Leu Arg His Leu Glu Ser
1               5                   10                  15

Asp Met Phe Ser Ser Pro Leu Glu Thr Asp Ser Met Asp Pro Phe Gly
                20                  25                  30

Leu Val Thr Gly Leu Glu Ala Val Arg Ser Pro Ser Phe Glu Lys
            35                  40                  45
```

<210> SEQ ID NO 352
<211> LENGTH: 47
<212> TYPE: PRT
<213> ORGANISM: Artificial
<220> FEATURE:
<223> OTHER INFORMATION: FGF19 variant

<400> SEQUENCE: 352

```
Leu Pro Met Val Pro Glu Glu Pro Glu Asp Leu Gly His Leu Glu Ser
1               5                   10                  15

Asp Met Phe Ser Ser Pro Leu Glu Thr Asp Ser Met Asp Pro Phe Gly
                20                  25                  30

Leu Val Thr Gly Leu Glu Ala Val Arg Ser Pro Ser Phe Glu Lys
            35                  40                  45
```

<210> SEQ ID NO 353
<211> LENGTH: 48
<212> TYPE: PRT
<213> ORGANISM: Artificial
<220> FEATURE:
<223> OTHER INFORMATION: FGF19 variant

<400> SEQUENCE: 353

```
Leu Pro Met Val Pro Ala Glu Pro Glu Asp Leu Arg Gly His Leu Glu
1               5                   10                  15

Ser Asp Met Phe Ser Ser Pro Leu Glu Thr Asp Ser Met Asp Pro Phe
                20                  25                  30

Gly Leu Val Thr Gly Leu Glu Ala Val Arg Ser Pro Ser Phe Glu Lys
            35                  40                  45
```

<210> SEQ ID NO 354
<211> LENGTH: 48
<212> TYPE: PRT
<213> ORGANISM: Artificial
<220> FEATURE:
<223> OTHER INFORMATION: FGF19 variant

<400> SEQUENCE: 354

```
Leu Pro Met Pro Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
                20                  25                  30

Gly Leu Val Thr Gly Leu Glu Ala Val Arg Ser Pro Ser Phe Glu Lys
            35                  40                  45
```

<210> SEQ ID NO 355
<211> LENGTH: 48
<212> TYPE: PRT
<213> ORGANISM: Artificial
<220> FEATURE:
<223> OTHER INFORMATION: FGF19 variant

<400> SEQUENCE: 355

```
Leu Pro Leu Val Pro Glu Glu Pro Glu Asp Leu Arg Gly His Leu Glu
1               5                   10                  15
```

```
Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 356
<211> LENGTH: 48
<212> TYPE: PRT
<213> ORGANISM: Artificial
<220> FEATURE:
<223> OTHER INFORMATION: FGF19 variant

<400> SEQUENCE: 356

Leu Gly Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45
```

FIBROBLAST GROWTH FACTOR 1 PROTEIN FRAGMENTS AND METHODS OF USE

This is a continuation-in-part of U.S. patent application Ser. No. 13/838,350, filed Mar. 15, 2013, which claims priority benefit of U.S. Provisional Patent Application No. 61/656,871, filed Jun. 7, 2012, and U.S. Provisional Patent Application No. 61/664,085, filed Jun. 25, 2012, each of which is hereby incorporated by reference in its entirety.

ACKNOWLEDGMENT OF GOVERNMENT SUPPORT

This invention was made with government support under grant numbers DE13686, DK077276, AG019712, DK091392, DK067158, DK057978, DK090962, HL088093, HL105278 and ES010337 awarded by the U.S. National Institutes of Health. The government has certain rights in this invention.

FIELD OF THE INVENTION

The present invention relates to chimeric fibroblast growth factor ("FGF") proteins and uses thereof.

BACKGROUND OF THE INVENTION

Type 2 diabetes is a chronic progressive disorder, which results from end-organ resistance to the action of insulin in combination with insufficient insulin secretion from the pancreas. The metabolic abnormalities associated with insulin resistance and secretory defects, in particular the hyperglycemia, lead over the course of years to extensive irreversible damage to multiple organs including heart, blood vessels, kidney, and eye. Currently, nearly 200 million or 2.9% of the world population have type 2 diabetes (World Health Organization, Diabetes Fact Sheet N° 312, January 2011; Wild et al., "Global Prevalence of Diabetes: Estimates for the Year 2000 and Projections for 2030," *Diabetes Care* 27(5):1047-1053 (2004)), and its prevalence is rising at an alarmingly fast pace in parallel with the rise in the prevalence of overweight and obesity (World Health Organization, Obesity and Overweight Fact Sheet N° 311, January 2011). Until the end of the 20$^{th}$ century, type 2 diabetes was observed only in adults but what was once known as "adult-onset diabetes" is now also diagnosed in children and adolescents, and this growing incidence can be related to the increase in overweight and obesity among children and adolescents. The prevalence of pre-diabetes, an intermediate metabolic stage between normal glucose homeostasis and diabetes, is even greater than that of type 2 diabetes. Currently, nearly 80 million or 26% of the population in the United States alone have pre-diabetes (Center for Disease Control and Prevention, National Diabetes Fact Sheet 2011), and as such are at high risk for progressing to type 2 diabetes. Type 2 diabetes ranks among the ten leading causes of death worldwide, and the World Health Organization projects that mortality from diabetes (90% of which is type 2) will more than double within the next decade (World Health Organization, Diabetes Fact Sheet N° 312, January 2011). Type 2 diabetes also is a major cause of disability. As a consequence of diabetic retinopathy, about 10% of all patients with diabetes in the world develop severe visual impairment and 2% become blind 15 years into the disease (World Health Organization, Diabetes Fact Sheet N° 312, January 2011). Diabetic neuropathy, which affects up to half of all patients with diabetes worldwide (World Health Organization, Diabetes Fact Sheet N° 312, January 2011), accounts for the majority of nontraumatic lower-limb amputations. Indeed, in its recently published first worldwide report on non-infectious diseases, the World Health Organization considers diabetes, together with other chronic non-infectious diseases like cancer and heart disease, a global economic and social burden, which exceeds that imposed by infectious diseases such as HIV/AIDS.

The current drug therapy for type 2 diabetes is focused on correcting the hyperglycemia in the patients. Although a number of small molecules and biologics with different mechanisms of anti-hyperglycemic action are available for use as mono-therapy or combination therapy, most, if not all of these have limited efficacy, limited tolerability, and significant adverse effects (Moller, "New Drug Targets for Type 2 Diabetes and the Metabolic Syndrome," *Nature* 414(6865): 821-827 (2001)). For example, treatment with sulfonylureas, glinides, thiazolidinediones, or insulin has been associated with weight gain, which is an undesired effect since overweight is considered a driving force in the pathogenesis of type 2 diabetes. Some of these treatments have also been associated with increased risk of hypoglycemia. A limitation specific to the thiazolidinediones is the potential for adverse cardiovascular effects (DeSouza et al., "Therapeutic Targets to Reduce Cardiovascular Disease in Type 2 Diabetes," *Nat Rev Drug Discov* 8(5):361-367 (2009)). A meta-analysis of clinical data on the thiazolidinedione rosiglitazone (Avandia®), which was widely used for the treatment of type 2 diabetes, found that the drug increased the risk of myocardial infarction in patients with type 2 diabetes (Nissen et al., "Effect of Rosiglitazone on the Risk of Myocardial Infarction and Death from Cardiovascular Causes," *N Engl J Med* 356 (24):2457-2471 (2007)). Of all diabetic complications, cardiovascular disease is the main cause of morbidity and mortality in patients with diabetes (World Health Organization, Diabetes Fact Sheet N° 312, January 2011; Center for Disease Control and Prevention, National Diabetes Fact Sheet 2011), and hence an aggravation of cardiovascular risk by drug treatment is absolutely unacceptable. In the wake of the debate about the cardiovascular safety of thiazolidinediones, the FDA issued a guidance on evaluating cardiovascular risk in new anti-diabetic therapies to treat type 2 diabetes (Opar A, "Diabetes Drugs Pass Cardiovascular Risk Check," *Nat Rev Drug Discov* 8(5):343-344 (2009)). Meanwhile, thiazolidinediones lost their popularity. Even for glucagon-like peptide-1 agonists, one of the latest class of drugs introduced for the treatment of type 2 diabetes, concerns about safety have been raised, namely the potential for carcinogenicity (Opar A, "Diabetes Drugs Pass Cardiovascular Risk Check," *Nat Rev Drug Discov* 8(5):343-344 (2009)). Therefore, novel therapies that are more effective and safer than existing drugs are needed. Since the currently available drugs do not directly target complications of advanced diabetic disease, especially cardiovascular disease, therapies that are not only effective in lowering blood glucose but also reduce cardiovascular risk factors such as dyslipidemia are particularly desired.

A search conducted by Eli Lilly & Co. for potential novel biotherapeutics to treat type 2 diabetes led to the discovery of fibroblast growth factor (FGF) 21 as a protein that stimulates glucose uptake into adipocytes in an insulin-independent fashion (Kharitonenkov et al., "FGF-21 as a Novel Metabolic Regulator," *J Clin Invest* 115(6):1627-1635 (2005)). FGF21 has since emerged as a key endocrine regulator not only of glucose metabolism but also of lipid metabolism, and has become one of the most promising drug candidates for the treatment of type 2 diabetes, obesity, and metabolic syndrome. In mouse models of diabetes and obesity, pharmacologic doses of FGF21 lower plasma glucose and increase insulin sensitivity (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). Concurrently, FGF21 lowers plasma triglyceride and cholesterol, enhances lipolysis and suppresses lipogenesis, and accelerates energy expenditure (Kharitonenkov et al., "FGF-21 as a Novel Metabolic Regulator," *J Clin Invest* 115(6): 1627-1635 (2005); Coskun et al., "Fibroblast growth factor 21 corrects obesity in mice," *Endocrinology* 149(12):6018-6027 (2008)). In obese mice, FGF21 causes weight loss, in lean mice, it is weight neutral (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). Thus, FGF21 has some of the most desired characteristics of a drug for the treatment of type 2 diabetes; not only does it improve glycemic control, but also directly affects cardiovascular risk factors, such as hypertriglyceridemia, and reduces obesity, which is considered the single most important promoter of type 2 diabetes. Importantly, FGF21 does not induce hypoglycemia (Kharitonenkov et al., "FGF-21 as a Novel Metabolic Regulator," *J Clin Invest* 115(6):1627-1635 (2005)), a side effect that can occur with several of the current anti-diabetic therapies, including insulin. Moreover, FGF21 does not exhibit any mitogenic activity in mice (Kharitonenkov et al., "FGF-21 as a Novel Metabolic Regulator," *J Clin Invest* 115(6):1627-1635 (2005)), ruling out the possibility of a carcinogenic risk. The findings on FGF21 therapy in mouse models of diabetes have been reproduced in diabetic rhesus monkeys (Kharitonenkov et al., "The Metabolic State of Diabetic Monkeys is Regulated by Fibroblast Growth Factor-21," *Endocrinology* 148(2):774-781 (2007)), and are currently followed up with clinical trials in humans (Kharitonenkov et al., "FGF21 Reloaded: Challenges of a Rapidly Growing Field," *Trends Endocrinol Metab* 22(3):81-86 (2011)). However, there is a need for more effective FGF21 therapeutics.

The present invention overcomes these and other deficiencies in the art.

SUMMARY OF THE INVENTION

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF19 molecule. The portion of the paracrine FGF is modified to decrease binding affinity for heparin and/or heparan sulfate compared to the portion without the modification.

Another aspect of the present invention relates to a method for treating a subject suffering from a disorder. This method involves selecting a subject suffering from the disorder. The method also involves providing a chimeric FGF protein, where the chimeric FGF protein includes an N-terminus coupled to a C-terminus. The N-terminus includes a portion of a paracrine FGF and the C-terminus includes a C-terminal portion of FGF19. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Another aspect of the present invention relates to a method of making a chimeric FGF protein possessing enhanced endocrine activity. This method involves introducing one or more modifications to a FGF protein, where the modification decreases the affinity of the FGF protein for heparin and/or heparan sulfate and coupling a C-terminal portion of FGF19 that includes a βKlotho co-receptor binding domain to the modified FGF protein's C-terminus, whereby a chimeric FGF protein possessing enhanced endocrine activity is made.

Yet another aspect of the present invention relates to a method of facilitating fibroblast growth factor receptor ("FGFR")-βKlotho co-receptor complex formation. This method involves providing a cell that includes a βKlotho co-receptor and an FGFR and providing a chimeric FGF protein. The chimeric FGF protein includes a C-terminal portion of FGF19 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-βKlotho co-receptor complex formation.

Yet a further aspect of the present invention relates to a method of screening for agents capable of facilitating FGFR-βKlotho complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF19. The portion of the paracrine FGF is modified to decrease binding affinity for heparin and/or heparan sulfate compared to the portion without the modification. This method also involves providing a binary βKlotho-FGFR complex and providing one or more candidate agents. This method further involves combining the chimeric FGF, the binary βKlotho-FGFR complex, and the one or more candidate agents under conditions permitting the formation of a ternary complex between the chimeric FGF and the binary βKlotho-FGFR complex in the absence of the one or more candidate agents. This method also involves identifying the one or more candidate agents that decrease ternary complex formation between the chimeric FGF and the binary βKlotho-FGFR complex compared to the ternary complex formation in the absence of the one or more candidate agents as suitable for treating the disorder.

Fibroblast growth factors (FGFs) 19, 21, and 23 are hormones that regulate in a Klotho co-receptor-dependent fashion major metabolic processes such as glucose and lipid metabolism (FGF21) and phosphate and vitamin D homeostasis (FGF23). The role of heparan sulfate glycosaminoglycan in the formation of the cell surface signaling complex of endocrine FGFs has remained unclear. To decipher the role of HS in endocrine FGF signaling, we generated FGF19 and FGF23 mutant ligands devoid of HS binding and compared their signaling capacity with that of wild-type ligands. The data presented herein show that the mutated ligands retain full metabolic activity demonstrating that HS does not participate in the formation of the endocrine FGF signaling complex. Here it is shown that heparan sulfate is not a component of the signal transduction unit of FGF19 and FGF23. A paracrine FGF is converted into an endocrine ligand by diminishing heparan sulfate binding affinity of the paracrine FGF and substituting its C-terminal tail for that of an endocrine FGF containing the Klotho co-receptor binding site in order to home the ligand into the target tissue. The ligand conversion provides a novel strategy for engineering endocrine FGF-like molecules for the treatment of metabolic disorders, including global epidemics such as type 2 diabetes and obesity.

BRIEF DESCRIPTION OF THE DRAWINGS

FIG. 1A shows interactions of FGF2 (schematic representation) with a heparin hexasaccharide (shown as sticks) as observed in the crystal structure of the 2:2 FGF2-FGFR1c dimer (PDB ID: 1FQ9; (Schlessinger et al., *Mol. Cell* 6:743-750 (2000), which is hereby incorporated by reference in its entirety)). The heparin hexasaccharide consists of three disaccharide units of 1→4 linked N-sulfated-6-O-sulfated D-glucosamine and 2-O-sulfated L-iduronic acid. Note that the heparin hexasaccharide interacts with both side chain and backbone atoms of residues in the HS-binding site of FGF2. Dashed lines denote hydrogen bonds. K128, R129, and K134, which make the majority of hydrogen bonds with the heparin hexasaccharide, are boxed. The β-strand nomenclature follows the original FGF1 and FGF2 crystal structures (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety). Please note that compared to the prototypical β-trefoil fold seen in soybean trypsin inhibitor (PDB ID: 1TIE; (Onesti et al., *J. Mol. Biol.* 217:153-176 (1991), which is hereby incorporated by reference in its entirety) and interleukin 1β (PDB ID: 111B; (Finzel et al., *J. Mol. Biol.* 209:779-791 (1989), which is hereby incorporated by reference in its entirety), the β10-β11 strand pairing in FGF2 and other paracrine FGFs is less well defined. FIGS. 1B and 1C show cartoon representation of the crystal structures of FGF19 (PDB ID: 2P23; (Goetz et al., *Mol. Cell Biol.* 27:3417-3428 (2007), which is hereby incorporated by reference in its entirety)) (FIG. 1B) and FGF23 (PDB ID: 2P39; (Goetz et al., *Mol. Cell Biol.* 27:3417-3428 (2007), which is hereby incorporated by reference in its entirety)) (FIG. 1C) shown in the same orientation as the FGF2 structure in FIG. 1A. Side chains of residues that map to the corresponding HS-binding sites of these ligands are shown as sticks. Residues selected for mutagenesis to knock out residual HS binding in FGF19 and FGF23 are boxed. NT and CT indicate N- and C-termini of the FGFs. FIG. 1D is a schematic of two working models for the endocrine FGF-FGFR-Klotho signal transduction unit. A recent study on the ternary complex formation between FGF21, FGFR1c and βKlotho supports the 1:2:1 model rather than the 2:2:2 model (Ming et al., *J. Biol. Chem.* 287:19997-20006 (2012), which is hereby incorporated by reference in its entirety). For comparison, a schematic of the paracrine FGF-FGFR-HS signaling unit is shown, which was made based on the crystal structure of the 2:2:2 FGF2-FGFR1c-HS complex (PDB ID: 1FQ9; (Schlessinger et al., *Mol. Cell* 6:743-750 (2000), which is hereby incorporated by reference in its entirety)). HS engages both paracrine FGF and receptor to enhance binding of FGF to its primary and secondary receptors thus promoting receptor dimerization. A question mark denotes whether or not HS is also a component of the endocrine FGF signaling complex.

FIG. 2 shows a sequence alignment of the endocrine FGFs, FGF1, and FGF2. The amino acid sequences of the mature human FGF19, FGF21, and FGF23 ligands are aligned. Also included in the alignment are the human sequences of FGF1 and FGF2, prototypical paracrine FGFs, which were used in the experiments described herein, in which FGF1 and FGF2 were converted into endocrine FGF ligands. Residue numbers corresponding to the human sequence of FGF1 (SEQ ID NO:1) (GenBank Accession No. AAH32697, which is hereby incorporated by reference in its entirety), FGF2 (SEQ ID NO:121) (GenBank Accession No. EAX05222, which is hereby incorporated by reference in its entirety), FGF19 (SEQ ID NO: 233) (GenBank Accession No. NP_005108, which is hereby incorporated by reference in its entirety), FGF21 (SEQ ID NO: 332) (GenBank Accession No. NP_061986, which is hereby incorporated by reference in its entirety), and FGF23 (SEQ ID NO:345) (GenBank accession no. AAG09917, which is hereby incorporated by reference in its entirety) are in parenthesis to the left of the alignment. Secondary structure elements are labeled, and residues containing these elements for known secondary structures are boxed. Gaps (dashes) were introduced to optimize the sequence alignment. The β-trefoil core domain for known FGF crystal structures is shaded gray. Blue bars on top of the alignment indicate the location of the HS-binding regions. HS-binding residues selected for mutagenesis are shaded blue.

FIG. 3A shows an overlay of SPR sensorgrams illustrating heparin binding of FGF2, FGF19, FGF21, and FGF23 (left panel) and an exploded view of the binding responses for FGF19-, FGF21-, and FGF23-heparin interactions (right panel). Heparin was immobilized on a biosensor chip, and 400 nM of FGF2, FGF19, FGF21, or FGF23 were passed over the chip. Note that FGF19, FGF21, and FGF23 exhibit measurable, residual heparin binding and that differences in heparin binding exist between these three endocrine FGFs. FIGS. 3B-3D show overlays of SPR sensorgrams illustrating binding of FGF19 to heparin (FIG. 3B) and lack of interaction between the FGF19$^{K149A}$ mutant and heparin (FIG. 3C) and between the FGF19$^{K149A, R157A}$ mutant and heparin (FIG. 3D). Heparin was immobilized on a biosensor chip, and increasing concentrations of FGF19 were passed over the chip. Thereafter, FGF19$^{K149A}$ or FGF19$^{K149A, R157A}$ was injected over the heparin chip at the highest concentration tested for the wild-type ligand. FIGS. 3E-3G show overlays of SPR sensorgrams illustrating binding of FGF23 to heparin (FIG. 3E), poor interaction between the FGF23$^{R48A, N49A}$ mutant and heparin (FIG. 3F), and lack of interaction between the FGF23$^{R140A, R143A}$ mutant and heparin (FIG. 3G). Heparin was immobilized on a biosensor chip, and increasing concentrations of FGF23 were passed over the chip. FGF23$^{R48A, N49A}$ or FGF23$^{R140A, R143A}$ was then injected over the heparin chip at the highest concentration tested for the wild-type ligand.

FIG. 4A shows results of an immunoblot analysis of phosphorylation of FRS2α (pFRS2α) and 44/42 MAP kinase (p44/42 MAPK) in H4IIE hepatoma cells following stimulation with the FGF19$^{K149A}$ mutant, the FGF19$^{K149A, R157A}$ mutant, or wild-type FGF19. Numbers above the lanes give the amounts of protein added in ng ml$^{-1}$. Total 44/42 MAPK protein expression was used as a loading control. FIG. 4B shows results of an immunoblot analysis of phosphorylation of FRS2α (pFRS2α) and 44/42 MAP kinase (p44/42 MAPK) in a HEK293-αKlotho cell line following stimulation with the FGF23$^{R48A, N49A}$ mutant, the FGF23$^{R140A, R143A}$ mutant, or wild-type FGF23. Numbers above the lanes give the amounts of protein added in ng ml$^{-1}$. Total 44/42 MAPK and αKlotho protein expression were used as loading controls. FIG. 4C shows graphical results of a quantitative analysis of CYP7A1 and CYP8B1 mRNA expression in liver tissue from mice treated with FGF19$^{K149A}$, FGF19$^{K149A, R157A}$, FGF19, or vehicle. 1 mg of protein per kg of body weight was given. Data are presented as mean±SEM; ***, $P<0.001$ by Student's t test. FIG. 4D shows graphical results of analysis of serum phosphate concentrations (serum $P_i$) in mice before and 8 h after intraperitoneal injection of FGF23$^{R48A, N49A}$, FGF23$^{R140A, R143A}$, FGF23, or vehicle. Wild-type mice were given a single dose of protein (0.29 mg kg body weight$^{-1}$), whereas Fgf23 knockout mice received two doses of 0.71 mg kg body weight$^{-1}$ each. Data are presented as mean±SEM; *, P<0.05, and **, P<0.01 by ANOVA.

FIG. 5A is a schematic of human FGF2, FGF19, FGF21, FGF23, and engineered FGF2-FGF19, FGF2-FGF21, and FGF2-FGF23 chimeras. Amino acid boundaries of each ligand and of each component of the chimeras are labeled with residue letter and number. The β-trefoil core domain for the known ligand crystal structures is shaded gray. HS-binding residues mutated in the FGF2 portion of chimeras are labeled with residue letter and number. Also labeled are the arginine residues of the proteolytic cleavage site in the C-terminal region of FGF23 that were mutated to glutamine in both FGF23 and the FGF2-FGF23 chimeras. FIGS. 5B and 5C show overlays of SPR sensorgrams illustrating binding of FGF2$^{WTcore}$-FGF21$^{C-tail}$ (FIG. 5B) and FGF2$^{\Delta HBScore}$-FGF21$^{C-tail}$ (FIG. 5C) to heparin, and fitted saturation binding curves. Heparin was immobilized on a biosensor chip, and increasing concentrations of FGF2$^{WTcore}$-FGF21$^{C-tail}$ or FGF2$^{\Delta HBScore}$-FGF21$^{C-tail}$ were passed over the chip. Dissociation constants ($K_D$s) were derived from the saturation binding curves. FIGS. 5D and 5E show overlays of SPR sensorgrams illustrating binding of FGF2$^{WTcore}$-FGF23$^{C-tail}$ (FIG. 5D) and FGF2$^{\Delta HBScore}$-FGF23$^{C-tail}$ (FIG. 5E) to heparin. Increasing concentrations of FGF2$^{WTcore}$-FGF23$^{C-tail}$ or FGF2$^{\Delta HBScore}$-FGF23$^{C-tail}$ were passed over a chip containing immobilized heparin. FIGS. 5F and 5G show results of immunoblot analysis for Egr1 expression in HEK293 cells following stimulation with chimeras or native FGFs as denoted. Numbers above the lanes give the amounts of protein added in nanomolar. GAPDH protein expression was used as a loading control.

FIGS. 7A and 7B show overlays of SPR sensorgrams illustrating inhibition by FGF2$^{\Delta HBScore}$-FGF23$^{C-tail}$ (FIG. 7A) or FGF23 (FIG. 7B) of αKlotho-FGFR1c binding to FGF23 immobilized on a biosensor chip. Increasing concentrations of FGF2$^{\Delta HBScore}$-FGF23$^{C-tail}$ or FGF23 were mixed with a fixed concentration of αKlotho-FGFR1c complex, and the mixtures were passed over a FGF23 chip. FIG. 7C shows an overlay of SPR sensorgrams illustrating failure of FGF2 to inhibit αKlotho-FGFR1c binding to FGF23. FGF2 and αKlotho-FGFR1c complex were mixed at a molar ratio of 15:1, and the mixture was passed over a biosensor chip containing immobilized FGF23. FIGS. 7D and 7E show overlays of SPR sensorgrams illustrating no inhibition by FGF2$^{\Delta HBScore}$-FGF23$^{C-tail}$ (FIG. 7D) or FGF2 (FIG. 7E) of βKlotho-FGFR1c binding to FGF21. FGF2$^{\Delta HBScore}$-FGF23$^{C-Tail}$ or FGF23 were mixed with βKlotho-FGFR1c complex at a molar ratio of 10:1, and the mixtures were passed over a biosensor chip containing immobilized FGF21. FIG. 7F shows analysis of serum phosphate concentrations (serum P$_i$) in mice before and 8 h after intraperitoneal injection of FGF2$^{\Delta HBScore}$-FGF23$^{C-tail}$, FGF2$^{WTcore}$-FGF23$^{C-tail}$, FGF23, or vehicle. Wild-type mice and αKlotho knockout mice were given 0.21 mg and 0.51 mg of protein, respectively, per kg of body weight. Data are presented as mean±SEM; , P<0.01; *, P<0.001 by ANOVA. FIG. 7G shows quantitative analysis of CYP27B1 mRNA expression in renal tissue from mice injected with FGF2$^{\Delta HBScore}$-FGF23$^{C-tail}$, FGF2$^{WTcore}$-FGF23$^{C-tail}$, FGF23, or vehicle. 0.21 mg of protein per kg of body weight were injected. Data are presented as mean±SEM; ***, P<0.001 by ANOVA.

FIGS. 8A-8B show overlays of SPR sensorgrams illustrating inhibition by FGF2$^{\Delta HBScore}$-FGF21$^{C-tail}$ (FIG. 8A) or FGF21 (FIG. 8B) of βKlotho-FGFR1c binding to FGF21 immobilized on a biosensor chip. Increasing concentrations of FGF2$^{\Delta HBScore}$-FGF21$^{C-tail}$ or FGF21 were mixed with a fixed concentration of βKlotho-FGFR1c complex, and the mixtures were passed over a FGF21 chip. FIG. 8C shows an overlay of SPR sensorgrams illustrating failure of FGF2 to inhibit βKlotho-FGFR1c binding to FGF21. FGF2 and βKlotho-FGFR1c complex were mixed at a molar ratio of 15:1, and the mixture was passed over a biosensor chip containing immobilized FGF21. FIGS. 8D-8E show overlays of SPR sensorgrams illustrating no inhibition by FGF2$^{\Delta HBScore}$-FGF21$^{C-tail}$ (FIG. 8D) or FGF21 (FIG. 8E) of αKlotho-FGFR1c binding to FGF23. FGF2$^{\Delta HBScore}$-FGF21$^{C-tail}$ or FGF21 were mixed with αKlotho-FGFR1c complex at a molar ratio of 10:1, and the mixtures were passed over a biosensor chip containing immobilized FGF23. FIG. 8F shows results of immunoblot analysis for Egr1 expression in HEK293-βKlotho cells stimulated with FGF2$^{\Delta HBScore}$-FGF21$^{C-tail}$ or FGF21. Numbers above the lanes give the amounts of protein added in ng ml$^{-1}$. GAPDH protein expression was used as a loading control. Note that the FGF2$^{\Delta HBScore}$-FGF21$^{C-tail}$ chimera is more potent than native FGF21 at inducing Egr1 expression suggesting that the chimera has agonistic property. This is expected since the core domain of FGF2 has inherently greater binding affinity for FGFR than the core domain of FGF21 (see FIGS. 10A and 10C). FIG. 8G shows graphical results of analysis of blood glucose concentrations in mice before and at the indicated time points after intraperitoneal injection of insulin alone, insulin plus FGF2$^{\Delta HBScore}$-FGF21$^{C-tail}$ chimera, insulin plus FGF21, or vehicle alone. 0.5 units of insulin per kg of body weight and 0.3 mg of FGF21 ligand per kg of body weight were injected. Blood glucose concentrations are expressed as percent of pre-injection values. Data are presented as mean±SEM.

FIG. 9A shows graphical results of analysis of blood glucose concentrations in ob/ob mice before and at the indicated time points after subcutaneous injection of FGF1 or FGF21. FIG. 9B shows graphical results of analysis of blood glucose concentrations in ob/ob mice before and at the indicated time points after subcutaneous injection of FGF1, FGF1$^{\Delta NT}$, or FGF1$^{\Delta HBS}$. FIG. 9C shows graphical results of analysis of blood glucose concentrations in ob/ob mice before and at the indicated time points after subcutaneous injection of FGF1 or FGF1$^{\Delta HBScore}$-FGF21$^{C-tail}$ chimera. For the experiments shown in FIGS. 9A-9C, ob/ob mice were injected with a bolus of 0.5 mg of FGF protein per kg of body weight. Data are presented as mean±SD.

FIGS. 10A-10D show overlays of SPR sensorgrams illustrating binding of FGFR1c to FGF2 (FIG. 10A), FGF19 (FIG. 10B), FGF21 (FIG. 10C), and FGF23 (FIG. 10D), and fitted saturation binding curves. Increasing concentrations of FGFR1c ligand-binding domain were passed over a biosensor chip containing immobilized FGF2, FGF19, FGF21, or FGF23. FIG. 10E shows an overlay of SPR sensorgrams illustrating binding of αKlotho-FGFR1c complex to FGF23. Increasing concentrations of αKlotho-FGFR1c complex were passed over a biosensor chip containing immobilized FGF23. FIG. 8F shows an overlay of SPR sensorgrams showing lack of interaction between the C-terminal tail peptide of FGF23 and FGFR1c. FGF23$^{C\text{-}tail}$ was immobilized on a biosensor chip and increasing concentrations of FGFR1c ligand-binding domain were passed over the chip. Dissociation constants ($K_D5$) given in FIGS. 10A-10E were derived from the saturation binding curves.

FIG. 11 shows an alignment of the C-terminal tail sequences of human FGF19 (SEQ ID NO: 233) (GenBank Accession No. NP_005108, which is hereby incorporated by reference in its entirety), FGF21 (SEQ ID NO: 332) (GenBank Accession No. NP_061986, which is hereby incorporated by reference in its entirety), and FGF23 (SEQ ID NO:345) (GenBank accession no. AAG09917, which is hereby incorporated by reference in its entirety). Residue numbers are in parenthesis to the left of the alignment. Gaps (dashes) were introduced to optimize the alignment. Residues that are identical between FGF19 and FGF21 are shaded gray. Note that 40% of these residues map to the most C-terminal sequence.

FIG. 12 shows an alignment of the C-terminal tail sequences of FGF19 orthologs (including human (SEQ ID NO: 233), gorilla (SEQ ID NO: 234), chimpanzee (SEQ ID NO: 235), gibbon (SEQ ID NO: 238), rhesus monkey (SEQ ID NO: 236), orangutan (SEQ ID NO: 237), marmoset (SEQ ID NO: 239), mouse lemur (SEQ ID NO: 240), sloth (SEQ ID NO: 241), panda (SEQ ID NO: 242), pig (SEQ ID NO: 243), bovine (SEQ ID NO: 244), dog (SEQ ID NO: 245), rabbit (SEQ ID NO: 246), megabat (SEQ ID NO: 247), dolphin (SEQ ID NO: 248), microbat (SEQ ID NO: 249), platypus (SEQ ID NO: 250), opossum (SEQ ID NO: 251), anole lizard (SEQ ID NO: 252), pika (SEQ ID NO: 253), guinea pig (SEQ ID NO: 254), tree shrew (SEQ ID NO: 255), rat (SEQ ID NO: 256), mouse (SEQ ID NO: 257), chicken (SEQ ID NO: 258), zebra finch (SEQ ID NO: 259), zebrafish (SEQ ID NO: 260), and frog (SEQ ID NO: 261)). Residue numbers are in parenthesis to the left of the alignment. Gaps (dashes) were introduced to optimize the alignment. Ortholog residues identical to human FGF19 are shaded gray.

FIG. 13 shows an alignment of the C-terminal tail sequences of human FGF19 (SEQ ID NO:233) (GenBank Accession No. NP_005108, which is hereby incorporated by reference in its entirety), FGF21 (SEQ ID NO:332) (GenBank Accession No. NP_061986, which is hereby incorporated by reference in its entirety), and variants of FGF19 harboring a single amino acid deletion or substitution for a residue unique to FGF21. Residue numbers for the sequences of native FGF19 and FGF21 are in parenthesis to the left of the alignment. Gaps (dashes) were introduced to optimize the alignment. In the sequence of native FGF21(SEQ ID NO:332), residues unique to FGF21 are bold and boxed, and in the sequences of the variants of the FGF19 C-terminal tail, introduced FGF21 residues are also bold and boxed and deleted FGF19 residues are indicated by a dash (bold and boxed).

DETAILED DESCRIPTION OF THE INVENTION

Figures 1A, 1B, 1C, 1D:
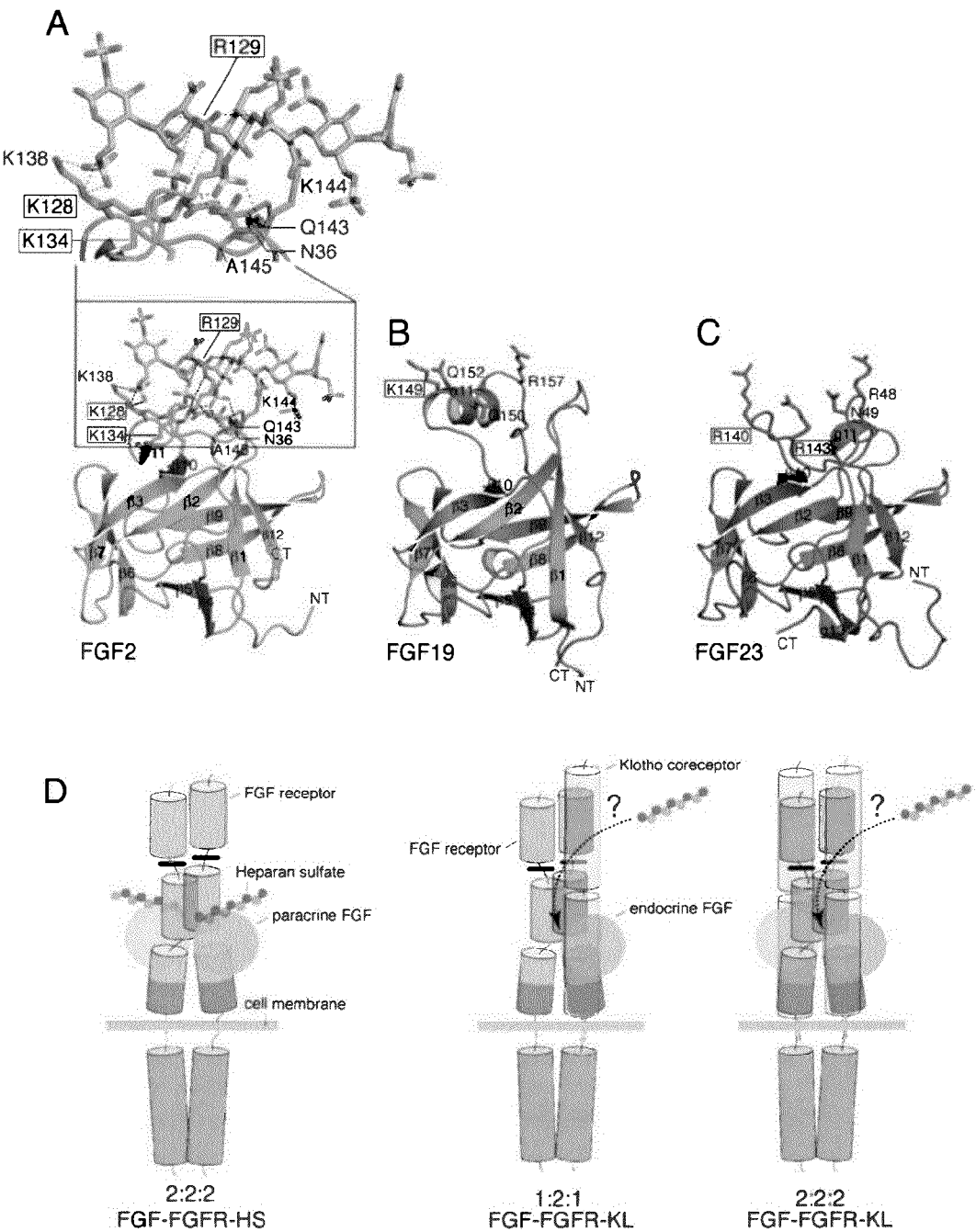
FIGS. 1A-1D are schematic diagrams showing side-by-side comparison of the HS-binding site of FGF2, FGF19, and FGF23, and working model of the endocrine FGF signaling complex.
Figures 3A, 3B, 3C, 3D, 3E, 3F, 3G:
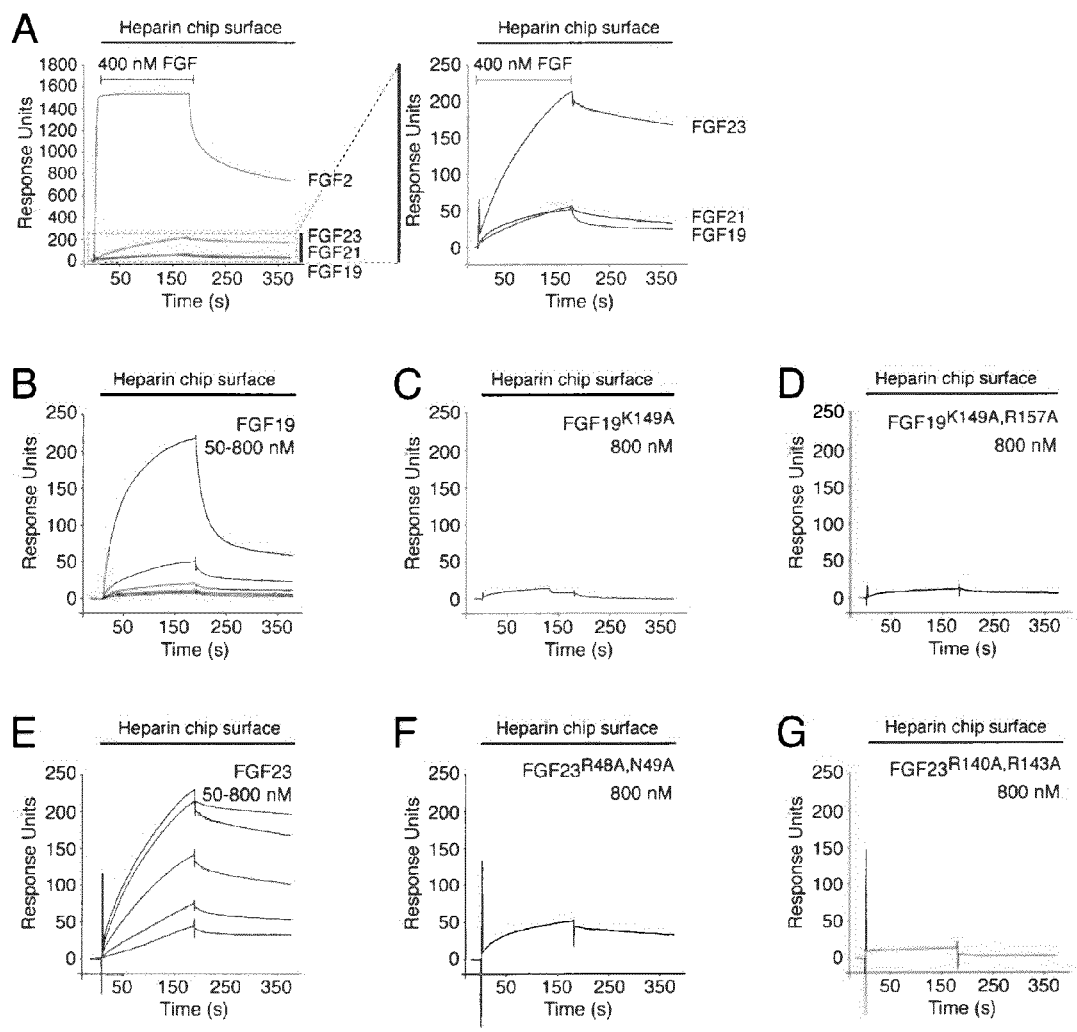
FIGS. 3A-3G show Surface plasmon resonance ("SPR") results relating to knockout of residual heparin binding in FGF19 and FGF23 by site-directed mutagenesis.

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF19. The portion of the paracrine FGF is modified to decrease binding affinity for heparin and/or heparan sulfate compared to the portion without the modification.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryogenesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells and FGFRc-interacting FGFs are produced by mesenchymal cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of specific paracrine FGF signaling loops between the epithelium and the mesenchyme, which is essential for proper organogenesis and patterning during embryonic development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J. Biochem.* 149: 121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149: 121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signaling in Mouse Beta-cells Leads to Diabetes," *Nature* 408:864-868 (2000); Jonker et al., "A PPARγ-FGF1 Axis is Required for Adaptive Adipose Remodeling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331:1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF-21 as a Novel Metabolic Regulator," *J. Clin. Invest.* 115:1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

FGFs share a core homology region of about one hundred and twenty amino acids that fold into a β-trefoil (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety) consisting of twelve β strands in paracrine FGFs (β1-β12) and eleven β strands in endocrine FGFs (β1-β10 and β12) (Mohammadi et al., "Structural Basis for Fibroblast Growth Factor Receptor Activation," *Cytokine Growth Factor Rev.* 16:107-137 (2005); Goetz et al., *Mol. Cell Biol.* 27:3417-3428 (2007), which are hereby incorporated by reference in their entirety). The conserved core region is flanked by divergent N- and C-termini, which play a critical role in conferring distinct biological activity on FGFs (Mohammadi et al., "Structural Basis for Fibroblast Growth Factor Receptor Activation," *Cytokine Growth Factor Rev.* 16:107-137 (2005); Olsen et al., *Genes Dev.* 20:185-198 (2006), which are hereby incorporated by reference in their entirety).

All FGFs interact with pericellular heparan sulfate (HS) glycosaminoglycans albeit with different affinities (Asada et al., *Biochim. Biophys. Acta.* 1790:40-48 (2009), which is hereby incorporated by reference in its entirety). The HS-binding site of FGFs is comprised of the β1-β2 loop and the region between β10 and β12 strands (Mohammadi et al., "Structural Basis for Fibroblast Growth Factor Receptor Activation," *Cytokine Growth Factor Rev.* 16:107-137 (2005), which is hereby incorporated by reference in its entirety). HS interacts with both side chain and main chain atoms of the HS-binding site in paracrine FGFs (Schlessinger et al., *Mol. Cell* 6:743-750 (2000), which is hereby incorporated by reference in its entirety). The HS-binding site of endocrine FGFs deviates from the common conformation adopted by paracrine FGFs such that interaction of HS with backbone atoms of the HS-binding site is precluded (Goetz et al., *Mol. Cell Biol.* 27:3417-3428 (2007), which is hereby incorporated by reference in its entirety). As a result, compared to paracrine FGFs, endocrine FGFs exhibit poor affinity for HS (Beenken and Mohammadi, "The FGF Family: Biology, Pathophysiology and Therapy," *Nat. Rev. Drug Discov.* 8:235-253 (2009); Asada et al., *Biochim. Biophys. Acta.* 1790:40-48 (2009), which are hereby incorporated by reference in their entirety). The poor HS affinity enables these ligands to diffuse freely away from the site of their secretion and enter the blood circulation to reach their distant target organs (Goetz et al., *Mol. Cell Biol.* 27:3417-3428 (2007); Asada et al., *Biochim. Biophys. Acta.* 1790:40-48 (2009), which are hereby incorporated by reference in their entirety).

By contrast, owing to their high HS affinity (Asada et al., *Biochim. Biophys. Acta.* 1790:40-48 (2009), which is hereby incorporated by reference in its entirety), paracrine FGFs are mostly immobilized in the vicinity of the cells secreting these ligands, and hence can only act within the same organ. There is emerging evidence that differences in HS-binding affinity among paracrine FGFs translate into the formation of ligand-specific gradients in the pericellular matrix (Kalinina et al., *Mol. Cell Biol.* 29:4663-4678 (2009); Makarenkova et al., *Sci. Signal* 2:ra55 (2009), which are hereby incorporated by reference in their entirety), which contribute to the distinct functions of these ligands (Beenken and Mohammadi, "The FGF Family: Biology, Pathophysiology and Therapy," *Nat. Rev. Drug Discov.* 8:235-253 (2009); Itoh and Ornitz, "Fibroblast Growth Factors: From Molecular Evolution to Roles in Development, Metabolism and Disease," *J. Biochem.* 149: 121-130 (2011), which are hereby incorporated by reference in their entirety).

Besides controlling ligand diffusion in the extracellular space, HS promotes the formation of the 2:2 paracrine FGF-FGFR signal transduction unit (Schlessinger et al., *Mol. Cell* 6:743-750 (2000); Mohammadi et al., *Curr. Opin. Struct. Biol.* 15:506-516 (2005), which are hereby incorporated by reference in their entirety). HS engages both ligand and receptor to enhance the binding affinity of FGF for receptor and promote dimerization of ligand-bound receptors. Owing to their poor HS-binding affinity, endocrine FGFs rely on Klotho co-receptors to bind their cognate FGFR (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). Klotho co-receptors are single-pass transmembrane proteins with an extracellular domain composed of two type I β-glycosidase domains (Ito et al., *Mech. Dev.* 98:115-119 (2000); Kuro-o et al., *Nature* 390:45-51 (1997), which are hereby incorporated by reference in their entirety). Klotho co-receptors constitutively associate with FGFRs to enhance the binding affinity of endocrine FGFs for their cognate FGFRs in target tissues (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). αKlotho is the co-receptor for FGF23 (Kurosu et al., *J. Biol. Chem.* 281:6120-6123 (2006); Urakawa et al., *Nature* 444:770-774 (2006), which are hereby incorporated by reference in their entirety), and βKlotho is the co-receptor for both FGF19 and FGF21 (Kurosu et al., *J. Biol. Chem.* 282:26687-26695 (2007); Ogawa et al., *Proc. Nat'l. Acad. Sci. U.S.A.* 104:7432-7437 (2007), which are hereby incorporated by reference in their entirety). The C-terminal region of endocrine FGFs mediates binding of these ligands to the FGFR-α/βKlotho co-receptor complex (Goetz et al., *Mol. Cell Biol.* 27:3417-3428 (2007); Goetz et al., *Proc. Nat'l. Acad. Sci. U.S.A.* 107:407-412 (2010); Micanovic et al., *J. Cell Physiol.* 219:227-234 (2009); Wu et al., *J. Biol. Chem.* 283:33304-33309 (2008); Yie et al., *FEBS Lett,* 583: 19-24 (2009); Goetz et al., *Mol. Cell Biol.* 32:1944-1954 (2012), which are hereby incorporated by reference in their entirety).

βKlotho promotes binding of FGF21 to its cognate FGFR by engaging ligand and receptor simultaneously through two distinct binding sites (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). βKlotho plays the same role in promoting binding of FGF19 to its cognate FGFR (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). The binding site for βKlotho was mapped on FGF21 and FGF19 to the C-terminal region of each ligand that follows the β-trefoil core domain (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). In the course of these studies, it was found that the C-terminal tail peptides of FGF21 and FGF19 share a common binding site on βKlotho, and that the C-terminal tail of FGF19 binds tighter than the C-terminal tail of FGF21 to this site (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety).

Endocrine FGFs still possess residual HS-binding affinity, and moreover, there are differences in this residual binding affinity among the endocrine FGFs (Goetz et al., *Mol. Cell Biol.* 27:3417-3428 (2007), which is hereby incorporated by reference in its entirety). These observations raise the possibility that HS may play a role in endocrine FGF signaling. Indeed, there are several reports showing that HS can promote endocrine FGF signaling in the presence as well as in the absence of Klotho co-receptor. It has been shown that HS augments the mitogenic signal elicited by endocrine FGFs in BaF3 cells over-expressing FGFR and Klotho co-receptor by at least two-fold (Suzuki et al., *Mol. Endocrinol.* 22:1006-1014 (2008), which is hereby incorporated by reference in its entirety). In addition, even in the absence of Klotho co-receptor, HS enables endocrine FGFs to induce proliferation of BaF3 cells over-expressing FGFR (Yu et al., *Endocrinology* 146:4647-4656 (2005); Zhang et al., *J. Biol. Chem.* 281: 15694-15700 (2006), which are hereby incorporated by reference in their entirety). Compared to paracrine FGFs, however, significantly higher concentrations of both ligand and HS are needed, and the proliferative response of cells to endocrine FGFs still lags behind that of paracrine FGFs by about one order of magnitude (Zhang et al., *J. Biol. Chem.* 281:15694-15700 (2006), which is hereby incorporated by reference in its entirety).

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, where the first and second polypeptides are different polypeptides. A chimeric polypeptide also encompasses polypeptides that include two or more non-contiguous portions derived from the same polypeptide. A chimeric polypeptide or protein also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

As noted above, a chimeric protein according to the present invention may include an N-terminus coupled to a C-terminus. N-terminus and C-terminus are used herein to refer to the N-terminal region or portion and the C-terminal region or portion, respectively, of the chimeric protein of the present invention. In some embodiments of the present invention, the C-terminal portion and the N-terminal portion of the chimeric protein of the present invention are contiguously joined. In alternative embodiments, the C-terminal portion and the N-terminal portion of the chimeric protein of the present invention are coupled by an intervening spacer. In one embodiment, the spacer may be a polypeptide sequence of 1, 2, 3, 4, 5, 6, 7, 8, 9, 10, or more amino acid residues. In some embodiments, the C-terminal portion and/or the N-terminal portion of the chimeric protein of the present invention may include additional portion(s) coupled to the C-terminal residue and/or the N-terminal residue of the chimeric protein of the present invention, respectively. In some embodiments, the additional portion(s) may be a polypeptide sequence of 1, 2, 3, 4, 5, 6, 7, 8, 9, 10, or more amino acid residues. In some embodiments, the N-terminal portion and/or the C-terminal portion having such additional portion(s) will maintain the activity of the corresponding naturally occurring N-terminal portion and/or C-terminal portion, respectively. In some embodiments, the N-terminal portion and/or the C-terminal portion having such additional portion(s) will have enhanced and/or prolonged activity compared to the corresponding naturally occurring N-terminal portion and/or C-terminal portion, respectively. In other embodiments, the C-terminal portion and/or the N-terminal portion of the chimeric protein of the present invention do not include any additional portion(s) coupled to the C-terminal residue and/or the N-terminal residue of the chimeric protein of the present invention, respectively.

The portion of the paracrine FGF may be derived from any suitable paracrine FGF. Suitable paracrine FGFs in accordance with the present invention include FGF1, FGF2, and ligands of the FGF4 and FGF9 subfamilies. Certain embodiments of the present invention may include a full-length amino acid sequence of a paracrine FGF, rather than a portion of a paracrine FGF.

In one embodiment, the portion of the paracrine FGF is derived from a mammalian FGF. In one embodiment, the portion of the paracrine FGF is derived from a vertebrate FGF. In one embodiment, the portion of the paracrine FGF is derived from a human FGF. In one embodiment, the paracrine FGF is derived from a non-human mammalian FGF. In one embodiment, the portion of the paracrine FGF is derived from a non-human vertebrate FGF. In one embodiment, the paracrine FGF is derived from an ortholog of human FGF, or a polypeptide or protein obtained from one species that is the functional counterpart of a polypeptide or protein from a different species.

In one embodiment according to the present invention, the portion of the paracrine FGF of the chimeric protein includes an N-terminal portion of the paracrine FGF.

In one embodiment, the paracrine FGF is FGF1. In one embodiment, the portion of the FGF1 is from human FGF1 having the following amino acid sequence (GenBank Accession No. AAH32697, which is hereby incorporated by reference in its entirety) (SEQ ID NO: 1):

1 MAEGEITTFT ALTEKFNLPP GNYKKPKLLY CSNG-GHFLRI LPDGTVDGTR DRSDQHIQLQ
61 LSAESVGEVY IKSTETGQYL AMDTDGLLYG SQT-PNEECLF LERLEENHYN TYISKKHAEK
121 NWFVGLKKNG SCKRGPRTHY GQKAILFLPL PVSSD

In one embodiment, the portion of the paracrine FGF includes an amino acid sequence beginning at any one of residues 1 to 25 and ending at any one of residues 150 to 155 of SEQ ID NO: 1 (human FGF1). In one embodiment, the portion of the paracrine FGF includes amino acid residues 1-150, 1-151, 1-152, 1-153, 1-154, 1-155, 2-150, 2-151, 2-152, 2-153, 2-154, 2-155, 3-150, 3-151, 3-152, 3-153, 3-154, 3-155, 4-150, 4-151, 4-152, 4-153, 4-154, 4-155, 5-150, 5-151, 5-152, 5-153, 5-154, 5-155, 6-150, 6-151, 6-152, 6-153, 6-154, 6-155, 7-150, 7-151, 7-152, 7-153, 7-154, 7-155, 8-150, 8-151, 8-152, 8-153, 8-154, 8-155, 9-150, 9-151, 9-152, 9-153, 9-154, 9-155, 10-150, 10-151, 10-152, 10-153, 10-154, 10-155, 11-150, 11-151, 11-152, 11-153, 11-154, 11-155, 12-150, 12-151, 12-152, 12-153, 12-154, 12-155, 13-150, 13-151, 13-152, 13-153, 13-154, 13-155, 14-150, 14-151, 14-152, 14-153, 14-154, 14-155, 15-150, 15-151, 15-152, 15-153, 15-154, 15-155, 16-150, 16-151, 16-152, 16-153, 16-154, 16-155, 17-150, 17-151, 17-152, 17-153, 17-154, 17-155, 18-150, 18-151, 18-152, 18-153, 18-154, 18-155, 19-150, 19-151, 19-152, 19-153, 19-154, 19-155, 20-150, 20-151, 20-152, 20-153, 20-154, 20-155, 21-150, 21-151, 21-152, 21-153, 21-154, 21-155, 22-150, 22-151, 22-152, 22-153, 22-154, 22-155, 23-150, 23-151, 23-152, 23-153, 23-154, 23-155, 24-150, 24-151, 24-152, 24-153, 24-154, 24-155, 25-150, 25-151, 25-152, 25-153, 25-154, or 25-155 of FGF1 (SEQ ID NO: 1). In one embodiment, the portion of the paracrine FGF includes amino acid residues 1-150 or 25-150 of SEQ ID NO: 1.

In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 150 to 155 of SEQ ID NO: 1 (human FGF1). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 150 to 155 of SEQ ID NO: 1 (human FGF1).

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In one embodiment of the present invention, the portion of the paracrine FGF of the chimeric protein is derived from an ortholog of human FGF1. In one embodiment, the portion of FGF1 is derived from *Papio Anubis, Pongo abelii, Callithrix jacchus, Equus caballus, Pan troglodytes, Loxodonta Africana, Canis lupus familiaris, Ailuropoda melanoleuca, Saimiri boliviensis boliviensis, Sus scrofa, Otolemur garnettii, Rhinolophus ferrumequinum, Sorex araneus, Oryctolagus cuniculus, Cricetulus griseus, Sarcophilus harrisii, Mus musculus, Cavia porcellus, Monodelphis domestica, Desmodus rotundus, Bos taurus, Ornithorhynchus anatinus, Taeniopygia guttata, Dasypus novemcinctus, Xenopus Silurana tropicalis, Heterocephalus glaber, Pteropus alecto, Tupaia chinensis, Columba livia, Ovis aries, Gallus gallus, Vicugna pacos, Anolis carolinensis, Otolemur garnettii, Felis catus, Pelodiscus sinensis, Latimeria chalumnae, Tursiops truncates, Mustela putorius furo, Nomascus leucogenys, Gorilla gorilla, Erinaceus europaeus, Procavia capensis, Dipodomys ordii, Petromyzon marinus, Echinops telfairi, Macaca mulatta, Pteropus vampyrus, Myotis lucifugus, Microcebus murinus, Ochotona princeps, Rattus norvegicus, Choloepus hoffmanni, Ictidomys tridecemlineatus, Tarsius syrichta, Tupaia belangeri, Meleagris gallopavo, Macropus eugenii,* or *Danio rerio*. The portions of an ortholog of human paracrine FGF1 include portions corresponding to the above-identified amino acid sequences of human FGF1. Corresponding portions may be determined by, for example, sequence analysis and structural analysis.

In one embodiment, the portion of the FGF1 of the chimeric protein of the present invention is derived from an ortholog of human FGF1 having the amino acid sequence shown in Table 1.

TABLE 1

Amino acid sequence of human FGF1 (SEQ ID NO: 1) (GenBank accession no. AAH32697, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Papio anubis* (olive baboon) FGF1 (SEQ ID NO: 2) (GenBank accession no. NP_001162557, which is hereby incorporated by reference in its entirety):

```
  1 MAEGEITTFT ALTEKFNLPP ANYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Pongo abelii* (Sumatran orangutan) FGF1 (SEQ ID NO: 3) (GenBank accession no. NP_001127073, which is hereby incorporated by reference in its entirety)

```
 60                                                                    M
 61 AEGEITTFTA LTEKFNLPPG NYKKPKLLYC SNGGHFLRIL PDGTVDGTRD RSDQHIQLQL
121 SAESVGEVYI KSTETGQYLA MDTDGLLYGS QTPNEECLFL ERLEENHYNT YISKKHAEKN
181 WFVGLKKNGS CKRGPRTHYG QKAILFLPLP VSSD
```

Amino acid sequence of *Callithrix jacchus* (white-tufted-ear marmoset) FGF1 (SEQ ID NO: 4) (GenBank accession no. XP_002744341, which is hereby incorporated by reference in its entirety):

```
  1 MAEGEITTFT ALTEKFDLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Equus caballus* (horse) FGF1 (SEQ ID NO: 5) (GenBank accession no. NP_001157358, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Pan troglodytes* (chimpanzee) FGF1 (SEQ ID NO: 6) (GenBank accession no. JAA29511, which is hereby incorporated by reference in its entirety):

```
  1 MAEGEITTFT ALTEKFNLPS GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

TABLE 1-continued

Amino acid sequence of *Loxodonta africana* (elephant) FGF1 (SEQ ID NO: 7) (GenBank accession no. XP_003404621, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKGTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Canis lupus familiaris* (dog) FGF1 (SEQ ID NO: 8) (GenBank accession no. XP_849274, which is hereby incorporated by reference in its entirety):

```
  1 MAEGEITTFT ALTEKFNLPP GNYMKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Ailuropoda melanoleuca* (giant panda) FGF1 (SEQ ID NO: 9) (GenBank accession no. XP_002912581, which is hereby incorporated by reference in its entirety):

```
  1 MAEGEITTFT ALTEKFNLPA GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Saimiri boliviensis boliviensis* (Bolivian squirrel monkey) FGF1 (SEQ ID NO: 10) (GenBank accession no. XP_003920596, which is hereby incorporated by reference in its entirety):

```
  1 MAEGEITTFT ALTEKFDLPP GNYKKPKLLY CSNGGHFLRI LPDGTVDGTR DRSDLHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Sus scrofa* (pig) FGF1 (SEQ ID NO: 11) (GenBank accession no. XP_003124058, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTSGLLYG SQTPSEECLF LERLEENHYN TYTSKKHAEK
121 NWFVGLKKNG SCKRGPRTHY GQKAILFLPL PVSSD
```

Amino acid sequence of *Otolemur garnettii* (small-eared galago) FGF1 (SEQ ID NO: 12) (GenBank accession no. XP_003782135, which is hereby incorporated by reference in its entirety):

```
  1 MAEGEITTFT ALTEKFNLPL GNYKKPKLLY CSNGGHFLRI LPDGTVDGTQ DRSDQHIQLQ
 61 LSAESVGEVY IKSTQTGQYL AMDSDGLLYG SQTPNEECLF LERLEENHYN TYVSKKHAEK
121 NWFVGLKKNG SCKRGPRTHY GQKAILFLPL PVSSD
```

Amino acid sequence of *Rhinolophus ferrumequinum* (greater horseshoe bat) FGF1 (SEQ ID NO: 13) (GenBank accession no. ACC62496, which is hereby incorporated by reference in its entirety):

```
  1 MAEGEVTTFT ALTEKFNLPT GNYKKPKLLY CSNGGHFLRI LPDGTVDGTR DKSDQHIQLQ
 61 LSAESVGEVY IKSTESGQYL AMDSDGLLYG SQTPNEECLF LERLEENHYN TYTSKKHAEK
121 NWFVGLKKNG SCKRGPRTHY GQKAILFLPL PVSSD
```

Amino acid sequence of *Sorex araneus* (European shrew) FGF1 (SEQ ID NO: 14) (GenBank accession no. ACE75805, which is hereby incorporated by reference in its entirety):

```
  1 MAEGEITTFG ALMEKFNLPP GNYKKPKLLY CSNGGHFLRI LPDGTVDGTR DRSDQHIQLQ
 61 LSAESVGEVY IKSTETGHYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Oryctolagus cuniculus* (rabbit) FGF1 (SEQ ID NO: 15) (GenBank accession no. NP_001164959, which is hereby incorporated by reference in its entirety):

```
  1 MAEGEVTTFT ALTEKFNLPA GNYKLPKLLY CSNGGHFLRI LPDGTVDGTR DRSDQHIQLQ
 61 LSAESVGEVY IKSTETGQYL AMDTDGLLYG SQTPSEECLF LERLEENHYN TYTSKKHAEK
121 NWFVGLKKNG SCKRGPRTHY GQKAILFLPL PVSSD
```

Amino acid sequence of *Cricetulus griseus* (Chinese hamster) FGF1 (SEQ ID NO: 16) (GenBank accession no. XP_003502469, which is hereby incorporated by reference in its entirety):

```
  1 MAEGEITTFS ALTERFNLPP GNYKKPKLLY CSNGGHFLRI LPDGTVDGTR DRSDQHIQLQ
 61 LSAESAGEVY IKGTETGQYR NMDTDGLLYG SQTPNEECLF LERLEENHYN TYTSKKHAEK
121 NWFVGLKKNG SCKRGPRTHY GQKAILFLPL PVSSD
```

TABLE 1-continued

Amino acid sequence of *Sarcophilus harrisii* (Tasmanian devil) FGF1 (SEQ ID NO: 17) (GenBank accession no. XP_003756738, which is hereby incorporated by reference in its entirety):

```
  1 MAEGEITTFT ALTERFNLPL GNYKKPKLLY CSNGGHFLRI LPDGKVDGTR DRNDQHIQLQ
 61 LSAESVGEVY IKSTESGQYL AMDTDGLLYG SQTPTEECLF LERLEENHYN TYISKKHAEK
121 NWFVGLKKNG SCKRGPRTHY GQKAILFLPL PVSSE
```

Amino acid sequence of *Mus musculus* (house mouse) FGF1 (SEQ ID NO: 18) (GenBank accession no. NP_034327, which is hereby incorporated by reference in its entirety):

```
  1 MAEGEITTFA ALTERFNLPL GNYKKPKLLY CSNGGHFLRI LPDGTVDGTR DRSDQHIQLQ
 61 LSAESAGEVY IKGTETGQYL AMDTEGLLYG SQTPNEECLF LERLEENHYN TYTSKKHAEK
121 NWFVGLKKNG SCKRGPRTHY GQKAILFLPL PVSSD
```

Amino acid sequence of *Cavia porcellus* (domestic guinea pig) FGF1 (SEQ ID NO: 19) (GenBank accession no. XP_003477242, which is hereby incorporated by reference in its entirety):

```
  1 MAEGEITTFA ALTEKFNLPP GNYKKPKLLY CSNGGHFLRI LPDGTVDGTR DRSDQHIQLQ
 61 LSAEGVGEVY IQSTETGQYL AMDTDGLLYG SQTPSEECLF LERLEENHYN TYTSKKHVEK
121 NWFVGLKKNG SCKRGPRTHY GQKAILFLPL PVSD
```

Amino acid sequence of *Monodelphis domestica* (gray short-tailed opossum) FGF1 (SEQ ID NO: 20) (GenBank accession no. XP_001368921, which is hereby incorporated by reference in its entirety):

```
  1 MAEGEITTFT ALTERFNLPL GNYKKPKLLY CSNGGHFLRI LPDGKVDGTR DRNDQHIQLQ
 61 LSTESVGEVY IKSTESGQYL AMDTDGLLYG SQTPSEECLF LERLEENHYN TYTSKKHAEK
121 NWFVGLKKNG SCKKGPRTHY GQKAILFLPL PVSSE
```

Amino acid sequence of *Desmodus rotundus* (common vampire bat) FGF1 (SEQ ID NO: 21) (GenBank accession no. JAA45191, which is hereby incorporated by reference in its entirety):

```
  1 MAEGEVTTFT ALTEKFNLPL ESYKKPKLLY CSNGGHFLRI LPDGTVDGTR DKSDQHIQLQ
 61 LSAESVGEVY IKSTGSGQYL AMDSAGLLYG SQTPNEECLF LERLEENHYN TYTSKKHAEK
121 NWFVGLKKNG SCKRGPRTHY GQKAILFLPL PVNSD
```

Amino acid sequence of *Bos taurus* (cattle) FGF1 (SEQ ID NO: 22) (GenBank accession no. NP_776480, which is hereby incorporated by reference in its entirety):

```
  1 MAEGETTTFT ALTEKFNLPL GNYKKPKLLY CSNGGYFLRI LPDGTVDGTK DRSDQHIQLQ
 61 LCAESIGEVY IKSTETGQFL AMDTDGLLYG SQTPNEECLF LERLEENHYN TYISKKHAEK
121 HWFVGLKKNG RSKLGPRTHF GQKAILFLPL PVSSD
```

Amino acid sequence of *Ornithorhynchus anatinus* (platypus) FGF1 (SEQ ID NO: 23) (GenBank accession no. XP_001514861, which is hereby incorporated by reference in its entirety):

```
  1 MAEGEITTFT ALMEKFDLPL GNYKKPRLLY CSNGGYFLRI QPDGKVDGTR DRSDQHIQLQ
 61 LSAESVGEVY IKSTESGHYL AMDTEGLLYG SQAPSEDCLF LERLEENHYN TYVSKKHAEK
121 NWFVGLKKNG SCKRGPRTHY GQKAILFLPL PVASD
```

Amino acid sequence of *Taeniopygia guttata* (zebra finch) FGF1 (SEQ ID NO: 24) (GenBank accession no. XP_002193287, which is hereby incorporated by reference in its entirety):

```
  1 MAEGEITTFS ALTEKFNLPP GNYKKPKLLY CSNGGHFLRI LPDGTVDGTR DRSDQHIQLQ
 61 LSAESVGVVH IQSTQSGQYL AMDTNGLLYG SQLPPGECLF LERLEENHYN TYVSKMHADK
121 NWFVGLKKNG TSKLGPRTHY GQKAILFLPL PVAAD
```

Amino acid sequence of *Dasypus novemcinctus* (nine-banded armadillo) FGF1 (SEQ ID NO: 25) (GenBank accession no. AC006224, which is hereby incorporated by reference in its entirety):

```
  1 MAEGEITTFM ALMEKFNLPL ENYKHPRLLY CRNGGHFLRI LPDGTVDGTR DRSDQHIQLQ
 61 LSAESVGEVY IKSAETGQYL AMDTDGLLYG SETPSEECLF MEKLEENNYN TYISKKHAEK
121 KWFVGLKKDG SSKRGPQTHY GQKAILFLPL PVSSD
```

Amino acid sequence of *Xenopus Silurana tropicalis* (western clawed frog) FGF1 (SEQ ID NO: 26) (GenBank accession no. ACJ50585, which is hereby incorporated by reference in its entirety):

```
  1 MAEGDITTFN PIAESFSLPI GNYKKPKLLY CNNGGYFLRI LPDGVVDGTR DRDDLYITLK
 61 LSAQSQGEVH IKSTETGSYL AMDSSGQLYG TLTPNEESLF LETLEENHYN TYKSKKYAEN
121 NWFVGIKKNG ASKKGSRTHY GQKAILFLPL PASPD
```

TABLE 1-continued

Amino acid sequence of *Heterocephalus glaber* (naked mole-rat) FGF1
(SEQ ID NO: 27) (GenBank accession no. EHA99379, which is hereby
incorporated by reference in its entirety):

```
  1 MAEGEITTFT ALTEKFNLPP GNYKKPKLLY CSNGGHFLRI LPDGKVDGTR DRSDQHIQLQ
 61 LSAEGVGEVY IKSTETGQYL AMDTDGLLYG SQTASEECLF LERLEENHYN TYISKKHAEK
121 NWFVGLKKNG SCKRGPRTHY GQKAILFLPL PVSSD
```

Amino acid sequence of *Pteropus alecto* (black flying fox) FGF1 (SEQ
ID NO: 28) (GenBank accession no. ELK02961, which is hereby
incorporated by reference in its entirety):

```
  1 MAEGEVTTFT ALTERFNLPP GNYKKPKLLY CSNGGHFLRI LPDGTVDGTR DKSDQHIQLQ
 61 LSAESVGEVY IKSTESGQYL AMDSDGLLYG SQTPDEDCLF LERLEENHYN TYTSKKHAEK
121 NWFVGLKKNG SCKRGPRTHY GQKAILFLPL PVSSD
```

Amino acid sequence of *Tupaia chinensis* (Chinese tree shrew) FGF1
(SEQ ID NO: 29) (GenBank accession no. ELW69091, which is hereby
incorporated by reference in its entirety):

```
  1 MAEGEITTFA ALTEKFDLPP GNYKKPKLLY CSNGGHFLRI LPDGTVDGTR DRSDQHIQLQ
 61 LTAENVGEVY IKSTETGQYL AMDADGLLYG SQTPNEECLF LERLEENHYN TYISKKHAEK
121 NWFVALKKNG SCKLGPRTHY GQKAILFLPL PVSSD
```

Amino acid sequence of *Columba livia* (rock pigeon) FGF1 (SEQ ID NO:
30) (GenBank accession no. EMC79997, which is hereby incorporated by
reference in its entirety):

```
  1 MAEGEITTFT ALTEKFNLPP GNYKKPKLLY CSNGGHFLRI LPDGKVDGTR DRSDQHIQLQ
 61 LSAESVGEVY IKSTQSGQYL AMDPTGLLYG SQLLGEECLF LERIEENHYN TYVSKKHADK
121 NWFVGLKKNG NSKLGPRTHY GQKAILFLPL PVSAD
```

Amino acid sequence of *Ovis aries* (sheep) FGF1 (SEQ ID NO: 31)
(GenBank accession no. XP_004008958, which is hereby
incorporated by reference in its entirety):

```
  1 MAEGETTTFR ALTEKFNLPL GNYKKPKLLY CSNGGYFLRI LPDGRVDGTK DRSDQHIQLQ
 61 LYAESIGEVY IKSTETGQFL AMDTNGLLYG SQTPSEECLF LERLEENHYN TYISKKHAEK
121 NWFIGLKKNG SSKLGPRTHF GQKAILFLPL PVSSD
```

Amino acid sequence of *Gallus gallus* (chicken) FGF1 (SEQ ID NO: 32)
(GenBank accession no. NP_990511, which is hereby incorporated by
reference in its entirety):

```
  1 MAEGEITTFT ALTERFGLPL GNYKKPKLLY CSNGGHFLRI LPDGKVDGTR DRSDQHIQLQ
 61 LSAEDVGEVY IKSTASGQYL AMDTNGLLYG SQLPGEECLF LERLEENHYN TYISKKHADK
121 NWFVGLKKNG NSKLGPRTHY GQKAILFLPL PVSAD
```

Amino acid sequence of *Vicugna pacos* (alpaca) FGF1 (SEQ ID NO: 33)
(Ensembl accession no. ENSVPAP00000007810; partial sequence
corresponding to human FGF1 residues 58 to 155, which is hereby
incorporated by reference in its entirety):

```
  1 QLQLSAESVG EVYIKSTETG QYLAMDTDGL LHGSQTPNEE CLFLERLEEN HYNTYTSKKH
 61 AEKNWFVGLK KNGSCKRGPR THYGQKAILF LPLPVSSD
```

Amino acid sequence of *Anolis carolinensis* (anole lizard) FGF (SEQ
ID NO: 34) (Ensembl accession no. ENSACAP00000013203,
which is hereby incorporated by reference in its entirety):

```
  1 MAEGEITTFT ALTERFALPM ENYKKPKLLY CSNGGHFLRI LPDGKVDGTM DRNDSYIQLL
 61 LTAEDVGVVY IKGTETGQYL AMDANGHLYG SQLPTEECLF VETLEENHYN TYTSKMHGDK
121 KWYVGLKKNG KGKLGPRTHR GQKAILFLPL PVSPD
```

Amino acid sequence of *Otolemur garnettii* (bushbaby) FGF1 (SEQ ID
NO: 35) (Ensembl accession no. ENSOGAP00000004540, which is hereby
incorporated by reference in its entirety):

```
  1 MAEGEITTFT ALTEKFNLPL GNYKKPKLLY CSNGGHFLRI LPDGTVDGTQ DRSDQHIQLQ
 61 LSAESVGEVY IKSTQTGQYL AMDSDGLLYG SQTPNEECLF LERLEENHYN TYVSKKHAEK
121 NWFVGLKKNG SCKRGPRTHY GQKAILFLPL PVSSD
```

Amino acid sequence of *Felis catus* (cat) FGF1 (SEQ ID NO: 36)
(Ensembl accession no. ENSFCAP00000008457, which is hereby
incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

TABLE 1-continued

Amino acid sequence of *Pelodiscus sinensis* (Chinese softshell turtle) FGF1 (SEQ ID NO: 37) (Ensembl accession no. ENSPSIP00000016356, which is hereby incorporated by reference in its entirety):

```
1   MAEGEITTFT ALTEKFNLPL GNYKNPKLLY CSNGGYFLRI HPDGKVDGTR DRSDQHIQLQ
61  LSAESVGEVY IKSTESGQFL AMDANGLLYG SLSPSEECLF LERMEENHYN TYISKKHADK
121 NWFVGLKKNG SCKLGPRTHY GQKAVLFLPL PVSAD
```

Amino acid sequence of *Latimeria chalumnae* (coelacanth) FGF1 (SEQ ID NO: 38) (Ensembl accession no. ENSLACP00000015106, which is hereby incorporated by reference in its entirety):

```
1   MAEDKITTLK ALAEKFNLPM GNYKKAKLLY CSNGGYFLRI PPDGKVEGIR ERSDKYIQLQ
61  MNAESLGMVS IKGVEAGQYL AMNTNGLLYG SQSLTEECLF MEKMEENHYN TYRSKTHADK
121 NWYVGIRKNG SIKPGPRTHI GQKAVLFLPL PASSD
```

Amino acid sequence of *Tursiops truncatus* (dolphin) FGF1 (SEQ ID NO: 39) (Ensembl accession no. ENSTTRP00000004470, which is hereby incorporated by reference in its entirety):

```
1   MAEGEITTFT ALTEKFNLPP GNYKKPKLLY CSNGGHFLRI LPDGTVDGTR DRSDQHIQLQ
61  LSAESVGEVY IKSTETGQYL AMDTDGLLYG SQTPNEECLF LERLEENHYN TYASKKHAEK
121 NWFVGLKKNG SCKRGPRTHY GQKAILFLPL PVSSD
```

Amino acid sequence of *Mustela putorius* furo (ferret) FGF1 (SEQ ID NO: 40) (Ensembl accession no. ENSMPUP00000007888, which is hereby incorporated by reference in its entirety):

```
1   MAEGEITTFT ALMEKFNLPA GNYKKPKLLY CSNGGHFLRI LPDGTVDGTR DRSDQHIQLQ
61  LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Nomascus leucogenys* (gibbon) FGF1 (SEQ ID NO: 41) (Ensembl accession no. ENSNLEP00000011873, which is hereby incorporated by reference in its entirety):

```
1   MAEGEITTFT ALTEKFNLPP GNYKKPKLLY CSNGGHFLRI LPDGTVDGTR DRSDQHIQLQ
61  LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Gorilla gorilla* (gorilla) FGF1 (SEQ ID NO: 42) (Ensembl accession no. ENSGGOP00000017663, which is hereby incorporated by reference in its entirety):

```
1   MAEGEITTFT ALTEKFNLPP GNYKKPKLLY CSNGGHFLRI LPDGTVDGTR DRSDQHIQLQ
61  LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Erinaceus europaeus* (hedgehog) FGF1 (SEQ ID NO: 43) (Ensembl accession no. ENSEEUP00000005318, which is hereby incorporated by reference in its entirety):

```
1   MAEGEITTFT ALTEKFNLPL GNYKKPKLLY CSNGGHFLRI LPDGTVDGTR DRSDQHIQLQ
61  LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Procavia capensis* (hyrax) FGF1 (SEQ ID NO: 44) (Ensembl accession no. ENSPCAP00000010969, which is hereby incorporated by reference in its entirety) (partial sequence corresponding to human FGF1 residues 1 to 91):

```
1   MAEGEITTFT ALTEKFNLPL ENYKKPKLLY CSNGGHFLRI LPDGTVDGTR DRSDQHIQLQ
61  LSAESVGEVY IKGTETGQYL AMDTDGLLYG S
```

Amino acid sequence of *Dipodomys ordii* (kangaroo rat) FGF1 (SEQ ID NO: 45) (Ensembl accession no. ENSDORP00000006889, which is hereby incorporated by reference in its entirety) (partial sequence corresponding to human FGF1 residues 1 to 16 and 58 to 155):

```
1   MAEGEITTFT ALTERF---- ---------- ---------- ---------- -------QLQ
61  LSAESVGEVY IKSTETGQYL AMDADGLLYG SQTPDEECLF LERLEENHYN TYIAKKHAEK
121 NWFVGLKKNG SCKRGPRTHY GQKAILFLPL PVSSD
```

TABLE 1-continued

Amino acid sequence of *Petromyzon marinus* (lamprey) FGF1 (SEQ ID
NO: 46) (Ensembl accession no. ENSPMAP00000010683, which is hereby
incorporated by reference in its entirety) (partial sequence
corresponding to human FGF1 residues 1 to 93):

1 MEVGHIGTLP VVPAGPVFPG SFKEPRRLYC RSAGHHLQIL GDGTVSGTQD ENEPHAVLQL
61 QAVRRGVVTI RGLCAERFLA MSTEGHLYGA VR

Amino acid sequence of *Echinops telfairi* (lesser hedgehog tenrec)
FGF1 (SEQ ID NO: 47) (Ensembl accession no. ENSETEP00000014504,
which is hereby incorporated by reference in its entirety) (partial
sequence corresponding to human FGF1 residues 58 to 155)

1 QLKLVAESVG VVYIKSIKTG QYLAMNPDGL LYGSETPEEE CLFLETLEEN HYTTFKSKKH
61 VEKNWFVGLR KNGRVKIGPR THQGQKAILF LPLPVSSD

Amino acid sequence of *Macaca mulatta* (rhesus monkey) FGF1 (SEQ ID
NO: 48) (Ensembl accession no. ENSMMUP00000030943, which is hereby
incorporated by reference in its entirety):

1 MAEGEITTFT ALTEKFNLPP GNYKKPKLLY CSNGGHFLRI LPDGTVDGTR DRSDQHIQLQ
61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD

Amino acid sequence of *Pteropus vampyrus* (megabat) FGF1 (SEQ ID NO:
49) (Ensembl accession no. ENSPVAP00000004349, which is hereby
incorporated by reference in its entirety):

1 MAEGEVTTFT ALTERFNLPP GNYKKPKLLY CSNGGHFLRI LPDGTVDGTR DKSDQHIQLQ
61 LSAESVGEVY IKSTESGQYL AMDSDGLLYG SQTPDEDCLF LERLEENHYN TYTSKKHAEK
121 NWFVGLKKNG SCKRGPRTHY GQKAILFLPL PVSSD

Amino acid sequence of *Myotis lucifugus* (microbat) FGF1 (SEQ ID NO:
50) (Ensembl accession no. ENSMLUP00000006481, which is hereby
incorporated by reference in its entirety):

1 MAEGEVTTFT ALTERFNLPL ENYKKPKLLY CSNGGHFLRI LPDGTVDGTR DRSDQHIQLQ
61 LSAESVGEVY IKSTESGQYL AMDSDGLLYG SQTPNEECLF LERLEENHYN TYTSKKHAEK
121 NWFVGLKKNG SCKRGPRTHY GQKAILFLPL PVSSD

Amino acid sequence of *Microcebus murinus* (mouse lemur) FGF1 (SEQ ID
NO: 51) (Ensembl accession no. ENSMICP00000008602, which is hereby
incorporated by reference in its entirety):

1 MAEGEITTFT ALTEKFNLPP GNYKKPKLLY CSNGGHFLRI LPDGTVDGTR DRSDQHIQLQ
61 LSAESAGEVY IKSTQTGRYL AMDADGLLYG SQTPNEECLF LERLEENHYN TYVSKKHAEK
121 NWFVGLKKNG SCKRGPRTHY GQKAILFLPL PVSSD

Amino acid sequence of *Ochotona princeps* (pika) FGF1 (SEQ ID NO: 52)
(Ensembl accession no. ENSOPRP00000011739, which is hereby
incorporated by reference in its entirety):

1 MAEGEVTTFS ALTEKFNLPG GNYKLPKLLY CSNGGHFLRI LPDGTVDGTR DRSDLH----
61 -------EVF IKSTETGQYL AMDTDGLLYG SQTPSEECLF LERLEENHYN TYTSKKHAEK
121 NWFVGIKKNG SCKRGPRTHY GQKAILFLPL PVSSD

Amino acid sequence of *Rattus norvegicus* (rat) FGF1 (SEQ ID NO: 53)
(Ensembl accession no. ENSRNOP00000018577, which is hereby
incorporated by reference in its entirety):

1 MAEGEITTFA ALTERFNLPL GNYKKPKLLY CSNGGHFLRI LPDGTVDGTR DRSDQHIQLQ
61 LSAESAGEVY IKGTETGQYL AMDTEGLLYG SQTPNEECLF LERLEENHYN TYTSKKHAEK
121 NWFVGLKKNG SCKRGPRTHY GQKAILFLPL PVSSD

Amino acid sequence of *Choloepus hoffmanni* (sloth) FGF1 (SEQ ID NO:
54) (Ensembl accession no. ENSCHOP00000010964, which is hereby
incorporated by reference in its entirety):

1 MAEGEITTFT ALMEKFNLPP GNYMKPKLLY CSNGGHFLRI LPDGTVDGTR DRSDLHIQLQ
61 LSAESVGEVY IKSAETGQYL AMDTGGLLYG SQTPSEECLF LERLEENHYN TYVSKKHAEK
121 NWFVGLKKNG SSKRGPRTHY GQKAILFLPL PVSSD

Amino acid sequence of *Ictidomys tridecemlineatus* (squirrel) FGF1
(SEQ ID NO: 55) (Ensembl accession no. ENSSTOP00000021782,
which is hereby incorporated by reference in its entirety):

1 MAEGEITTFT ALTEKFNLPP GNYKKPKLLY CSNGGHFLRI LPDGTVDGTR DRSDQHIQLQ
61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD

TABLE 1-continued

Amino acid sequence of *Tarsius syrichta* (tarsier) FGF1 (SEQ ID NO: 56) (Ensembl accession no. ENSTSYP00000006804, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYVSKKHAEK
121 NWFVGLKKNG SCKRGPRTHY GQKAILFLPL PVSSD
```

Amino acid sequence of *Tupaia belangeri* (tree shrew) FGF1 (SEQ ID NO: 57) (Ensembl accession no. ENSTBEP00000010264, which is hereby incorporated by reference in its entirety):

```
  1 MAEGEITTFA ALTEKFDLPP GNYKKPKLLY CSNGGHFLRI LPDGTVDGTR DRSDQHIQLQ
 61 LTAENVGEVY IKSTETGQYL AMDADGLLYG SQTPNEECLF LERLEENHYN TYISKKHAEK
121 NWFVALKKNG SCKLGPRTHY GQKAILFLPL PVSSD
```

Amino acid sequence of *Meleagris gallopavo* (turkey) FGF1 (SEQ ID NO: 58) (Ensembl accession no. ENSMGAP00000016398; partial sequence corresponding to human FGF1 residues 1 to 56, which is hereby incorporated by reference in its entirety):

```
  1 MAEGEITTFT ALTERFGLPL GNYKKPKLLY CSNGGHFLRI LPDGKVDGTR DRSDQH
```

Amino acid sequence of *Macropus eugenii* (wallaby) FGF1 (SEQ ID NO: 59) (Ensembl accession no. ENSMEUP00000015084, which is hereby incorporated by reference in its entirety):

```
  1 MAEGEITTFT ALTERFNLPL GNYKKPKLLY CSNGGHFLRI LPDGKVDGTR DRNDQHIQLQ
 61 LSAESVGEVY IKSTESGQYL AMDTNGLLYG SQTPSEECLF LERLEENHYN TYISKKHAEK
121 NWFVGLKKNG SCKRGPRTHY GQKAILFLPL PVSSE
```

Amino acid sequence of *Danio rerio* (zebrafish) FGF1 (SEQ ID NO: 60) (Ensembl accession no. ENSDARP00000008825, which is hereby incorporated by reference in its entirety):

```
  1 MTEADIAVKS SPRDYKKLTR LYCMNGGFHL QILADGTVAG AADENTYSIL RIKATSPGVV
 61 VIEGSETGLY LSMNEHGKLY ASSLVTDESY FLEKMEENHY NTYQSQKHGE NWYVGIKKNG
121 KMKRGPRTHI GQKAIFFLPR QVEQEED
```

As noted above, the portion of the paracrine FGF may be modified to decrease binding affinity for heparin and/or heparan sulfate compared to the portion without the modification. In one embodiment, the modified portion of the paracrine FGF includes one or more substitutions, additions, or deletions.

In one embodiment, the one or more substitutions are located at one or more amino acid residues of SEQ ID NO: 1 selected from N33, K127, K128, N129, K133, R134, R137, Q142, K143, and combinations thereof. In one embodiment, the one or more substitutions are selected from N33T, K127D, K128Q, N129T, K133V, R134L, R137H, Q142M, K143T/L/I, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. Amino acid residues corresponding to those of SEQ ID NO:1 may be determined by, for example, sequence analysis and structural analysis.

Also encompassed within the present invention are portions of paracrine FGFs other than FGF1 (e.g., FGF2, FGF4, FGF5, FGF6, FGF9, FGF16, and FGF20). The portions derived from paracrine FGFs other than FGF1 include portions corresponding to the above-identified amino acid sequences of FGF1. Corresponding portions may be determined by, for example, sequence analysis and structural analysis.

It will be understood that the portion of the paracrine FGF according to the present invention may be derived from a nucleotide sequence that encodes a paracrine FGF protein. For example, in one embodiment, the nucleotide sequence is the nucleotide sequence that encodes human FGF1 (GenBank Accession No. BC032697, which is hereby incorporated by reference in its entirety) (SEQ ID NO: 61), as follows:

```
                                          ATGGCTGAAG GGAAATCAC CACCTTCACA
121 GCCCTGACCG AGAAGTTTAA TCTGCCTCCA GGGAATTACA AGAAGCCCAA ACTCCTCTAC
181 TGTAGCAACG GGGGCCACTT CCTGAGGATC CTTCCGGATG GCACAGTGGA TGGGACAAGG
241 GACAGGAGCG ACCAGCACAT TCAGCTGCAG CTCAGTGCGG AAAGCGTGGG GGAGGTGTAT
301 ATAAAGAGTA CCGAGACTGG CCAGTACTTG GCCATGGACA CCGACGGGCT TTTATACGGC
361 TCACAGACAC CAAATGAGGA ATGTTTGTTC CTGGAAAGGC TGGAGGAGAA CCATTACAAC
```

```
421 ACCTATATAT CCAAGAAGCA TGCAGAGAAG AATTGGTTTG TTGGCCTCAA GAAGAATGGG

481 AGCTGCAAAC GCGGTCCTCG GACTCACTAT GGCCAGAAAG CAATCTTGTT TCTCCCCCTG

541 CCAGTCTCTT CTGATTAA
```

In another embodiment of the present invention, the portion of the paracrine FGF of the chimeric protein may be derived from a nucleotide sequence that encodes an ortholog of human FGF1. Nucleotide sequences that encode FGF1 orthologs are shown in Table 2.

TABLE 2

Olive Baboon FGF1 gene coding sequence (1-155) (SEQ ID NO: 62)
(GenBank accession no. NM_001169086, which is hereby
incorporated by reference in its entirety):

```
  1     ATGGCTGAAG GGGAAATCAC CACGTTCACA GCCCTGACCG AGAAGTTTAA TCTGCCTCCA
 61     GCGAATTACA AGAAGCCCAA ACTGCTCTAC TGTAGCAACG GGGACACTT  CTTGAGGATC
121     CTTCCGGATG GCACAGTGGA TGGGACAAGG GACAGGAGCG ACCAGCACAT TCAGCTGCAG
181     CTCAGTGCGG AAAGCGTGGG GGAGGTGTAT ATAAAGAGTA CCGAGACTGG CCAGTACTTG
241     GCCATGGACA CCGACGGGCT TTTATACGGC TCACAGACAC CAAATGAGGA ATGTTTGTTC
301     CTGGAAAGGC TGGAGGAGAA CCATTACAAC ACCTACATAT CCAAGAAGCA CGCAGAGAAG
361     AATTGGTTTG TTGGCCTCAA GAAGAATGGA AGCTGCAAAC GTGGTCCTCG GACTCACTAT
421     GGCCAGAAAG CAATCTTGTT TCTTCCCCTG CCAGTCTCTT CTGATTAA
```

Sumatran orangutan FGF1 gene coding sequence (60-214)
(SEQ ID NO: 63) (GenBank accession no. NM_001133601,
which is hereby incorporated by reference in its entirety):

```
211                 ATGGCTGAAG GGGAAATCAC CACCTTCACA
241     GCCCTGACCG AGAAGTTTAA TCTGCCTCCA GGGAATTACA AGAAGCCCAA ACTCCTCTAC
301     TGTAGCAACG GGGCCACTT  CTTGAGGATC CTTCCGGATG GCACAGTGGA TGGGACAAGG
361     GACAGGAGCG ACCAGCACAT TCAGCTGCAG CTCAGTGCGG AAAGCGTGGG GGAGGTGTAT
421     ATAAAGAGTA CCGAGACTGG CCAGTACTTG GCCATGGACA CCGACGGGCT TTTATACGGC
481     TCACAGACAC CAAATGAGGA ATGTTTGTTC CTGGAAAGGC TGGAGGAGAA CCATTACAAC
541     ACCTATATAT CCAAGAAGCA TGCAGAGAAG AATTGGTTTG TTGGCCTCAA GAAGAATGGA
601     AGCTGCAAAC GCGGTCCTCG GACTCACTAT GGCCAGAAAG CAATCTTGTT TCTCCCCCTG
661     CCAGTCTCTT CCGATTAA
```

White-tufted-ear marmoset FGF1 gene coding sequence (1-155)
(SEQ ID NO: 64) (GenBank accession no. XM_002744295,
which is hereby incorporated by reference in its entirety):

```
130              A TGGCTGAAGG GGAAATCACC ACCTTCACAG CCCTGACCGA GAAGTTTGAT
181     CTGCCTCCAG GGAATTACAA GAAGCCCAAA CTCCTCTACT GTAGCAATGG GGGCCACTTC
241     TTGAGGATCC TTCCGGATGG CACAGTGGAT GGGACAAGGG ACAGGAGCGA CCAGCACATT
301     CAGCTGCAGC TCAGTGCGGA AAGCGTGGGG GAGGTGTATA TAAAGAGTAC CGAGACTGGC
361     CAGTACTTGG CCATGGACAC CGACGGGCTT TTATACGGCT CACAGACACC AAATGAGGAA
421     TGTTTGTTCC TGGAGAGGCT GGAGGAGAAC CATTACAACA CCTATATATC CAAGAAACAT
481     GCAGAGAAGA ATTGGTTTGT CGGCCTCAAG AAGAATGGAA GCTGTAAACG TGGTCCTCGG
541     ACTCACTATG GTCAGAAAGC GATCTTGTTT CTCCCCCTGC CAGTTCTTC  TGATTAA
```

Horse FGF1 gene coding sequence (1-155) (SEQ ID NO: 65)
(GenBank accession no. NM_001163886, which is
hereby incorporated by reference in its entirety):

```
 34                          ATGGCTG AAGGAGAAAT CACAACCTTC
 61     ACGGCCCTGA CCGAGAAGTT TAATCTGCCT CCAGGGAATT ACAAGAAGCC CAAACTCCTC
121     TACTGTAGCA ATGGGGGCCA CTTCCTGAGG ATCCTTCCAG ATGGCACAGT GGATGGGACA
181     AGGGACAGGA GCGACCAGCA CATTCAGCTC AGTCGGAAAGCGT GGGGGAGGTG
241     TATATAAAGA GTACCGAGAC TGGCCAGTAC TTGGCCATGG ACACCGACGG GCTGTTGTAC
301     GGCTCACAGA CACCAAACGA GGAATGTTTG TTCCTGGAAA GGCTGGAGGA AAACCATTAC
361     AACACCTACA CATCCAAGAA GCATGCAGAG AAGAACTGGT TCGTTGGTCT CAAGAAGAAT
421     GGGAGCTGCA AACGCGGTCC TCGGACTCAC TATGGGCAGA AAGCAATCTT GTTTCTTCCC
481     CTGCCCGTCT CCTCTGACTA A
```

Chimpanzee FGF1 gene coding sequence (1-155) (SEQ ID NO: 66)
(GenBank accession no. GABD01003589, which is hereby incorporated
by reference in its entirety):

```
 80                  A TGGCTGAAGG GGAAATCACC ACCTTCACAG CCCTGACCGA
121     GAAGTTTAAT CTGCCTTCAG GGAATTACAA GAAGCCCAAA CTCCTCTACT GTAGCAACGG
181     GGGCCACTTC CTGAGGATCC TTCCGGATGG CACAGTGGAT GGGACAAGGG ACAGGAGCGA
241     CCAGCACATT CAGCTGCAGC TCAGTGCGGA AAGCGTGGGG GAGGTGTATA TAAAGAGTAC
301     CGAGACTGGC CAGTACTTGG CCATGGACAC CGACGGGCTT TTATACGGCT CACAGACACC
361     AAATGAGGAA TGTTTGTTCC TGGAACGGCT GGAGGAGAAC CATTACAACA CCTATATATC
421     CAAGAAGCAT GCAGAGAAGA ATTGGTTTGT TGGCCTCAAG AAGAATGAA  GCTGCAAACG
481     CGGTCCTCGG ACTCACTATG GCCAGAAAGC AATCTTGTTT CTCCCCCTGC CAGTCTCTTC
541     CGATTAA
```

TABLE 2-continued

Elephant FGF1 gene coding sequence (1-155) (SEQ ID NO: 67)
(GenBank accession no. XM_003404573, which is
hereby incorporated by reference in its entirety):

```
  1 ATGGCCGAAG GGGAAATCAC AACTTTCACA GCCCTGACAG AGAAGTTCAA CCTGCCTCCA
 61 GGGAATTACA AGAAGCCCAA ACTCCTCTAC TGTAGCAATG GAGGTCACTT CTTAAGGATC
121 CTTCCAGATG GCACAGTGGA TGGCACCAGG GACAGGAGTG ACCAGCACAT TCAGCTGCAG
181 CTCAGTGCGG AAAGCGTGGG GGAGGTGTAT ATAAAGGGCA CCGAGACTGG CCAGTACTTG
241 GCCATGGACA CCGACGGGCT TTTATACGGC TCACAGACAC AAATGAGGA ATGTTTGTTC
301 CTGGAAAGGC TGGAGGAAAA CCATTACAAC ACCTACATAT CCAAGAAGCA CGCAGAGAAG
361 AATTGGTTCG TTGGTCTCAA GAAGAATGGA AGCTGCAAAC GCGGTCCTCG GACTCACTAT
421 GGCCAGAAAG CAATCTTGTT TCTCCCCCTG CCAGTCTCCT CTGATTAA
```

Dog FGF1 gene coding sequence (1-155) (SEQ ID NO: 68)
(GenBank accession no. XM_844181, which is hereby
incorporated by reference in its entirety):

```
164                                           ATGGCTG AAGGGGAAAT
181 CACAACCTTC ACTGCCCTGA CGGAGAAGTT TAATCTGCCT CCGGGGAATT ACATGAAGCC
241 CAAACTCCTC TACTGTAGCA ACGGGGGCCA CTTCCTGAGG ATCCTTCCAG ATGGCACAGT
301 GGATGGGACA AGGGACAGGA GCGACCAGCA CATTCAGCTG CAGCTCAGCG CGGAAAGCGT
361 GGGGGAGGTG TATATAAAGA GCACCGAGAC TGGCCAGTAC TTGGCCATGG ACACCGATGG
421 GCTTCTGTAC GGCTCACAGA CACCGAATGA GGAATGTTTG TTCCTGGAAA GGCTGGAGGA
481 AAACCATTAC AACACCTACA CATCCAAGAA GCATGCAGAA AAAAATTGGT TTGTTGGTCT
541 CAAGAAGAAT GGAAGCTGCA AACGCGGTCC TCGGACTCAC TATGGTCAAA AGCAATTTT
601 GTTTCTCCCC CTGCCAGTGT CCTCTGATTA A
```

Giant panda FGF1 gene coding sequence (1-155) (SEQ ID NO: 69)
(GenBank accession no. XM_002912535, which is hereby
incorporated by reference in its entirety):

```
146                                     ATGGC TGAAGGGGAG ATCACAACCT TCACCGCCCT
181 GACGGAGAAG TTTAATCTGC CTGCGGGGAA TTACAAGAAG CCCAAACTCC TCTACTGTAG
241 CAACGGGGGC CACTTCCTGA GGATCCTTCC AGATGGCACA GTGGACGGGA CGAGGGACAG
301 GAGCGACCAG CACATTCAAC TGCAGCTCAG CGCGGAAAGC GTAGGGGAGG TGTACATAAA
361 GAGCACCGAG ACCGGCCAGT ACTTGGCCAT GGACACCGAT GGGCTTCTGT ACGGCTCACA
421 GACACCAAAT GAGGAATGTT TGTTCCTGGA AAGGCTGGAG GAAAACCATT ACAACACCTA
481 CACATCCAAG AAGCACGCGG AGAAGAATTG GTTTGTTGGT CTCAAGAAGA ATGGAAGCTG
541 CAAACGTGGT CCTCGGACTC ACTATGGCCA GAAAGCAATT CTGTTTCTCC CCCTGCCAGT
601 CTCCTCTGAT TAA
```

Bolivian squirrel monkey FGF1 gene coding sequence (1-155)
(SEQ ID NO: 70) (GenBank accession no. XM_003920547,
which is hereby incorporated by reference in its entirety):

```
130        A TGGCTGAAGG GGAAATCACC ACCTTTACAG CCCTGACCGA AAGTTTGAT
181 CTGCCTCCAG GGAATTACAA GAAGCCCAAA CTCCTCTACT GTAGCAACGG GGGCCACTTC
241 TTGAGGATCC TTCCGGATGG CACAGTGGAT GGGACCAGGG ACAGGAGCGA TCTTCACATT
301 CAGCTGCAGC TCAGTGCGGA AAGCGTGGGG GAGGTGTATA TAAAGAGTAC CGAGACTGGC
361 CAGTACTTGG CCATGGACAC CGACGGGCTT TTATACGGCT CACAGACACC AAATGAGGAA
421 TGTTTGTTCC TGGAAAGGCT GGAGGAGAAC CATTACAACA CCTATATATC CAAGAAACAC
481 GCAGAGAAGA ATTGGTTTGT TGGCCTCAAG AAGAATGAA GCTGCAAGCG CGGTCCTCGG
541 ACTCACTATG CCAGAAAGC AATCTTGTTT CTCCCCCTGC CAGTCTCTTC TGATTAA
```

Pig FGF1 gene coding sequence (1-155) (SEQ ID NO: 71)
(GenBank accession no. XM_003124010, which is
hereby incorporated by reference in its entirety):

```
 35                                    ATGGCT GAAGGCGAAA TCACAACCTT
 61 CACGGCCCTG ACCGAGAAGT TTAATCTGCC TCCAGGAAAT TACAAGAAGC CCAAGCTCCT
121 CTACTGCAGC AACGGGGGCC ATTTCCTCAG GATCCTTCCA GATGGCACAG TGGATGGGAC
181 CAGGGACAGG AGCGACCAGC ACATTCAGCT GCAGCTCAGT GCGGAAAGCG TGGGGGAGGT
241 GTATATAAAG AGTACGGAGA CTGGCCAGTA CTTGGCCATG GACACCAGCG GCTTTTGTA
301 CGGCTCACAG ACACCCAGTG AGGAGTGTTT GTTCCTGGAG AGGCTGGAGG AAAACCATTA
361 CAATACCTAC ACATCCAAGA AGCACGCAGA GAAGAACTGG TTCGTTGGCC TCAAGAAGAA
421 TGGAAGCTGC AAACGCGGTC CTCGGACTCA CTATGGCCAG AAAGCCATCG TGTTTCTCCC
481 CCTGCCAGTA TCCTCGGATT AA
```

Small-eared galago FGF1 gene coding sequence (1-155)
(SEQ ID NO: 72) (GenBank accession no. XM_003782087,
which is hereby incorporated by reference in its entirety):

```
 28                              ATG GCTGAAGGGG AAATCACAAC CTTCACAGCC
 61 CTCACAGAGA AGTTTAATCT GCCTCTAGGA AATTACAAGA AGCCCAAGCT CCTCTACTGT
121 AGCAACGGGG GTCACTTTCT GAGGATCCTG CCGGATGGCA CCGTGGATGG GACACAAGAC
181 AGGAGCGACC AGCACATTCA GCTGCAGCTC AGTGCGGAAA GCGTGGGGGA GGTGTATATA
241 AAGAGTACCC AGACTGGCCA GTACTTGGCC ATGGACTCCG ACGGGCTTTT ATACGGCTCA
301 CAAACACCAA ATGAGGAATG CCTGTTCCTG GAACGGCTGG AGGAAAACCA TTACAACACC
361 TATGTGTCCA AGAAGCACGC CGAGAAGAAT TGGTTTGTCG GTCTCAAGAA GAACGGAAGT
```

TABLE 2-continued

```
421 TGCAAACGTG GTCCTCGGAC TCACTACGGC CAGAAAGCAA TCTTGTTTCT CCCCCTGCCA
481 GTCTCCTCTG ATTAA
```

Greater horseshoe bat FGF1 gene coding sequence (1-155)
(SEQ ID NO: 73) (GenBank accession no. DP000705, which is
hereby incorporated by reference in its entirety):

```
190120                          T TAATCAGAGG AGACTGGCAG
190141 GGGGAGAAAC AGGATTGCTT TCTGGCCATA GTGAGTCCGA GGACCGCGCT TGCAGCTTCC
190201 ATTCTTCTTG AGCCCAACGA ACCAATTCTT TTCTGCGTGC TTCTTGGACG TGTAGGTGTT
190261 GTAATGGTTT TCCTCCAGCC TTTCCAGGAA CAGACATTCC TCATTTGGTG TCTG
194466         TGAGC CGTACAAAAG CCCGTCGGAG TCCATGGCCA AGTACTGGCC ACTCTCGGTG
194521 CTCTTTATAT ACACCTCCCC CACGCTTTCC GCACTGAGCT GCAGCTGAA
208114                                TGTGCTG GTCACTCTTG TCCCTTGTCC
208141 CATCCACTGT GCCATCTGGA AGGATCCTCA GGAAGTGGCC CCCGTTGCTG CAGTAGAGAA
208201 GTTTGGGTTT CTTGTAATTC CCTGTAGGCA GATTAAACTT CTCAGTAAGG GCTGTGAACG
208261 TGGTGACTTC CCCTTCGGCC AT
```

European shrew FGF1 gene coding sequence (1-155)
(SEQ ID NO: 74) (GenBank accession no. DP000767,
which is hereby incorporated by reference in its entirety):

```
138344                              CTAGTCG GAGGAGACGG
138361 GCAGGGGGAG AAACAAGATC GCTTTCTGGC CGTAGTGAGT CCGGGGACCA CGCTTGCAGC
138421 TTCCGTTCTT CTTCAGACCA ACAAACCAAT TCTTCTCGGC ATGCTTCTTG GAGGTATAGG
138481 TGTTGTAATG GTTTTCCTCC AGCCTTTCCA GAAACAGACA TTCCTCATTC GGTGTTTG
143512                                                       TGAGCCGTA
143521 TAAAAGCCCG TCGGTGTCCA TGGCCAAGTA ATGGCCAGTC TCCGTGCTCT TTATATACAC
143581 CTCCCCCACG CTTTCCGCAC TGAGCTGCAG CTGAA
157009                                                       TG TGCTGGTCGC
157021 TGCGGTCCCT GGTCCCATCC ACTGTGCCGT CCGGGAGGAT GCGCAGGAAG TGGCCCCCGT
157081 TGCTGCAGTA CAGGAGTTTG GGCTTCTTGT AGTTCCCTGG TGGCAGGTTA AACTTCTCCA
157141 TGAGGGCCCC AAAGGTGGTG ATCTCCCCCT CGGCCAT
```

Rabbit FGF1 gene coding sequence (1-155) (SEQ ID NO: 75)
(GenBank accession no. NM_001171488, which is
hereby incorporated by reference in its entirety):

```
  1 ATGGCTGAGG GGGAGGTCAC CACCTTCACA GCCCTGACCG AGAAGTTCAA CCTGCCTGCA
 61 GGGAACTACA AGTTGCCCAA ACTCCTCTAC TGCAGCAACG GGGCCACTT CCTGAGGATC
121 CTGCCGGACG GCACTGTGGA CGGCACAAGG GACAGGAGCG ACCAGCACAT TCAGCTGCAG
181 CTGAGTGCGG AAAGCGTGGG GGAGGTGTAT ATAAAGAGTA CGGAGACCGG CCAGTACTTG
241 GCCATGGACA CCGACGGCCT TTTATACGGC TCGCAAACGC CCAGTGAGGA GTGTTTGTTC
301 CTGGAACGGC TGGAGGAGAA CCACTACAAC ACCTACACGT CCAAGAAGCA CGCCGAGAAG
361 AACTGGTTCG TGGGGCTGAA GAAAAACGGG AGCTGCAAGC GCGGTCCTCG GACTCACTAC
421 GGCCAGAAAG CCATCTTGTT CCTCCCCCTG CCGGTCTCCT CCGACTAA
```

Chinese hamster FGF1 gene coding sequence (1-155)
(SEQ ID NO: 76) (GenBank accession no. XM_003502421,
which is hereby incorporated by reference in its entirety):

```
  1 ATGGCTGAAG GAGAAATCAC CACCTTCTCA GCCCTGACAG AGAGATTTAA TCTGCCTCCA
 61 GGAAACTACA AGAAGCCCAA ACTGCTCTAC TGCAGCAACG GGGCCACTT CTTGAGGATC
121 CTTCCAGATG GCACAGTGGA TGGGACAAGG GACAGGAGTG ACCAGCACAT TCAGCTGCAG
181 CTGAGTGCGG AAAGCGCGGG CGAAGTGTAT ATAAAGGGTA CAGAGACAGG CCAGTACAGG
241 AACATGGACA CGGATGGCCT TTTATACGGC TCACAGACAC CAAATGAAGA ATGCCTGTTC
301 CTGGAAAGGC TGGAAGAAAA CCATTACAAC ACTTATACAT CCAAGAAGCA CGCAGAGAAG
361 AACTGGTTTG TGGGCCTCAA GAAAAACGGG AGCTGCAAGC GTGGTCCTCG GACTCACTAT
421 GGCCAGAAAG CAATCTTGTT TCTCCCCCTG CCTGTATCTT CTGACTAG
```

Tasmanian devil FGF1 gene coding sequence (1-155)
(SEQ ID NO: 77) (GenBank accession no. XM_003756690,
which is hereby incorporated by reference in its entirety):

```
 24                    ATGGCCG AAGGGGAGAT CACAACCTTC ACAGCCCTGA
 61 CCGAAAGATT TAATCTGCCA CTGGGGAATT ACAAGAAGCC CAAGCTTCTC TACTGTAGCA
121 ATGGGGGCCA CTTTTTGAGG ATTCTTCCTG ATGGTAAAGT GGATGGGACA AGGGACAGAA
181 ATGATCAACA CATTCAACTG CAACTAAGCG CGGAAAGCGT GGGTGAGGTG TATATAAAGA
241 GCACTGAGTC TGGCCAGTAT TTGGCTATGG ACACCGATGG ACTTTTATAC GGCTCACAGA
301 CACCCACTGA AGAATGCTTG TTCCTGGAGA GATTGGAGGA GAATCATTAC AACACCTACA
361 TATCAAAGAA GCATGCGGAG AAAAATTGGT TTGTGGGCCT CAAGAAAAAT GGAAGCTGCA
421 AAAGAGGTCC CAGGACTCAC TATGGCCAGA AAGCCATCCT CTTCCTTCCC CTCCCTGTGT
481 CCTCTGAGTA A
```

House mouse FGF1 gene coding sequence (1-155)
(SEQ ID NO: 78) (GenBank accession no. NM_010197,
which is hereby incorporated by reference in its entirety):

```
188         ATG GCTGAAGGGG AGATCACAAC CTTCGCAGCC CTGACCGAGA GGTTCAACCT
241 GCCTCTAGGA AACTACAAAA AGCCCAAACT GCTCTACTGC AGCAACGGGG GCCACTTCTT
```

TABLE 2-continued

```
301 GAGGATCCTT CCTGATGGCA CCGTGGATGG GACAAGGGAC AGGAGCGACC AGCACATTCA
361 GCTGCAGCTC AGTGCGGAAA GTGCGGGCGA AGTGTATATA AAGGGTACGG AGACCGGCCA
421 GTACTTGGCC ATGGACACCG AAGGGCTTTT ATACGGCTCG CAGACACCAA ATGAGGAATG
481 TCTGTTCCTG GAAAGGCTGG AAGAAAACCA TTATAACACT TACACCTCCA AGAAGCATGC
541 GGAGAAGAAC TGGTTTGTGG GCCTCAAGAA GAACGGGAGC TGTAAGCGCG GTCCTCGGAC
601 TCACTATGGC CAGAAAGCCA TCTTGTTTCT GCCCCTCCCG GTGTCTTCTG ACTAG
```

Domestic guinea pig FGF1 gene coding sequence (1-154)
(SEQ ID NO: 79) (GenBank accession no. XM_003477194,
which is hereby incorporated by reference in its entirety):

```
  1 ATGGCTGAAG GAGAAATCAC AACTTTTGCA GCCCTGACTG AGAAGTTTAA TCTGCCTCCA
 61 GGGAATTATA AGAAGCCCAA ACTGCTCTAC TGCAGCAATG GGGGCCACTT CCTGAGGATC
121 CTTCCAGACG GCACAGTGGA CGGCACAAGA GACAGGAGCG ACCAGCACAT TCAGCTGCAG
181 CTCAGTGCGG AAGGCGTGGG GGAGGTGTAT ATACAGAGCA CCGAGACCGG CCAGTACTTG
241 GCCATGGACA CCGACGGGCT TTTATACGGC TCACAGACAC CAAGTGAGGA ATGCTTGTTC
301 CTGGAAAGGC TGGAGGAAAA CCATTACAAC ACCTACACAT CCAAGAAGCA TGTGGAGAAG
361 AATTGGTTTG TTGGCCTCAA GAAGAACGGA AGCTGCAAGC GTGGTCCTCG GACTCACTAT
421 GGCCAGAAAG CAATCTTGTT CCTCCCCTTG CCAGTCTCTG ATTAG
```

Gray short-tailed opossum FGF1 gene coding sequence (1-155)
(SEQ ID NO: 80) (GenBank accession no. XM_001368884,
which is hereby incorporated by reference in its entirety):

```
  1 ATGGCCGAAG GGGAGATCAC AACCTTCACA GCCCTGACTG AAAGATTTAA CCTGCCACTG
 61 GGGAATTACA AGAAACCCAA GCTTCTCTAC TGTAGCAATG GGGGCCATTT CTTGAGGATC
121 CTTCCTGATG GCAAAGTGGA TGGGACACGG GACAGAAATG ATCAACACAT TCAACTGCAG
181 CTGAGCACGG AAAGTGTGGG TGAGGTGTAT ATAAAGAGCA CTGAGTCTGG CCAGTATTTG
241 GCTATGGACA CCGATGGACT TTTATATGGC TCACAGACAC CCAGTGAAGA ATGCTTGTTT
301 CTGGAGAGGT TGGAGGAGAA TCATTACAAC ACCTACACAT CGAAGAAGCA TGCAGAGAAA
361 AATTGGTTTG TTGGTCTCAA GAAGAATGGA AGCTGCAAAA AGGGTCCCAG GACTCACTAC
421 GGCCAGAAAG CCATCCTGTT CCTTCCCCTC CCTGTGTCCT CTGAGTAA
```

Common vampire bat FGF1 gene coding sequence (1-155)
(SEQ ID NO: 81) (GenBank accession no. GABZ01008334,
which is hereby incorporated by reference in its entirety):

```
  1 ATGGCTGAAG GGGAAGTCAC CACGTTCACA GCTCTGACTG AGAAGTTTAA TCTGCCTCTG
 61 GAGAGTTACA AGAAGCCCAA ACTTCTCTAC TGCAGCAACG GTGGCCACTT CCTGAGGATC
121 CTTCCAGATG GTACAGTGGA TGGGACAAGG GACAAGAGCG ACCAGCACAT TCAGCTGCAG
181 CTCAGTGCGG AAAGCGTGGG GGAGGTGTAC ATAAAGAGCA CCGGGAGTGG CCAGTACTTG
241 GCCATGGACT CCGCCGGGCT TTTGTATGGC TCACAGACAC CAAATGAGGA ATGTTTGTTC
301 CTGGAAAGGC TGGAGGAAAA CCATTACAAC ACCTACACAT CCAAGAAGCA TGCAGAAAAG
361 AATTGGTTCG TGGGGCTCAA GAAGAATGGA AGCTGCAAGC GTGGCCCCCG GACTCATTAT
421 GGCCAGAAAG CAATCTTGTT TCTCCCCCTG CCAGTCAACT CTGATTAA
```

Cattle FGF1 gene coding sequence (1-155) (SEQ ID NO: 82)
(GenBank accession no. NM_174055, which is hereby
incorporated by reference in its entirety):

```
 918                    ATG GCTGAAGGAG AAACCACGAC CTTCACGGCC CTGACTGAGA
 961 AGTTTAACCT GCCTCTAGGC AATTACAAGA AGCCCAAGCT CCTCTACTGC AGCAACGGGG
1021 GCTACTTCCT GAGAATCCTC CCAGATGGCA CAGTGGATGG GACGAAGGAC AGGAGCGACC
1081 AGCACATTCA GCTGCAGCTC TGTGCGGAAA GCATAGGGGA GGTGTATATT AAGAGTACGG
1141 AGACTGGCCA GTTCTTGGCC ATGGACACCG ACGGGCTTTT GTACGGCTCA CAGACACCCA
1201 ATGAGGAATG TTTGTTCCTG GAAAGGTTGG AGGAAAACCA TTACAACACC TACATATCCA
1261 AGAAGCATGC AGAGAAGCAT TGGTTCGTTG GTCTCAAGAA GAACGGAAGG TCTAAACTCG
1321 GTCCTCGGAC TCACTTCGGC CAGAAAGCCA TCTTGTTTCT CCCCCTGCCA GTCTCCTCTG
1381 ATTAA
```

Platypus FGF1 gene coding sequence (1-155) (SEQ ID NO: 83)
(GenBank accession no. XM_001514811, which is hereby
incorporated by reference in its entirety):

```
  1 ATGGCGGAGG GTGAAATCAC CACGTTCACA GCCCTGATGG AGAAGTTCGA CCTACCCCTG
 61 GGCAACTACA AAAAGCCTAG GCTGCTCTAC TGCAGCAATG GCGGCTACTT CCTGCGCATC
121 CAGCCAGACG GTAAAGTGGA CGGGACCAGG GATCGGAGCG ATCAGCACAT TCAACTGCAG
181 CTAAGCGCGG AAAGCGTGGG CGAGGTGTAT ATAAAGAGCA CCGAGTCTGG CCACTATTTG
241 GCTATGGACA CCGAAGGACT TTTATATGGC TCACAGGCAC CAGTGAAGGA CTGCTTGTTC
301 CTGGAGCGGC TGGAGGAGAA CCACTATAAC ACGTACGTGT CCAAGAAGCA CGCTGAGAAG
361 AATTGGTTTG TCGGTCTCAA GAAGAACGGG AGCTGCAAAC GAGGTCCCCG GACTCACTAC
421 GGCCAGAAAG CCATCCTCTT CCTCCCGCTC CCCGTGGCAT CCGACTAG
```

Zebra finch FGF1 gene coding sequence (1-155) (SEQ ID NO: 84)
(GenBank accession no. XM_002193251, which is hereby
incorporated by reference in its entirety):

```
  1 ATGGCCGAGG GGGAGATCAC CACCTTCAGC GCCCTGACGG AGAAGTTCAA CCTGCCCCCG
 61 GGGAACTACA AGAAGCCCAA ACTGCTGTAC TGCAGCAACG GGGGCATTT CCTGCGCATC
121 CTCCCGGACG GCACCGTGGA TGGCACCAGG GACCGCAGCG ACCAGCACAT TCAGCTCCAG
```

TABLE 2-continued

```
181 CTGAGTGCAG AGAGCGTGGG GGTGGTGCAC ATCCAGAGCA CCCAGTCGGG GCAGTACCTG
241 GCCATGGACA CCAACGGGCT GCTCTACGGC TCGCAGCTGC CACCCGGTGA GTGTCTGTTC
301 CTGGAAAGGC TGGAGGAGAA CCATTACAAC ACCTACGTCT CCAAAATGCA CGCGGACAAG
361 AACTGGTTTG TGGGGCTGAA GAAGAACGGG ACAAGCAAGC TGGGCCCGCG GACTCACTAC
421 GGCCAGAAGG CGATCCTGTT CCTGCCGCTG CCCGTGGCGG CCGACTGA
```

Nine-banded armadillo FGF1 gene coding sequence (1-155)
(SEQ ID NO: 85) (GenBank accession no. DP001080, which is
hereby incorporated by reference in its entirety):

```
178389           TT AATCAGAGGA GACTGGCAGG GGAAGAAACA AGATAGCTTT CTGGCCATAG
178441 TGAGTCTGAG GACCACGTTT GCTGCTTCCG TCCTTCTTGA GACCAACAAA CCATTTCTTC
178501 TCTGCATGCT TCTTGGATAT GTAGGTGTTG TAATTGTTTT CTTCCAGCTT TTCCATGAAC
178561 AAGCATTCCT CACTTGGTGT CTC
182873                                                          TGAGCCAT
182881 ATAAAAGCCC GTCGGTGTCC ATGGCTAAGT ACTGGCCGGT CTCTGCACTC TTTATATACA
182941 CCTCCCCCAC GCTTTCCGCA CTGAGCTGCA GCTGAA
197786                          TGTGT TGGTCGCTCC TGTCCCTTGT CCCATCCACC
197821 GTGCCATCTG GAAGGATCCT CAAGAAGTGG CCCCCGTTTC TGCAGTAGAG GAGTCTGGGG
197881 TGCTTGTAAT TTTCTAGGGG CAGGTTGAAC TTCTCCATCA GGGCCATGAA GGTTGTGATC
197941 TCCCCTTCAG CCAT
```

*Xenopus Silurana tropicalis* FGF1 gene coding sequence (1-155)
(SEQ ID NO: 86) (GenBank accession no. FJ428265, which is hereby
incorporated by reference in its entirety):

```
  1 ATGGCAGAGG GAGACATCAC AACATTCAAC CCCATTGCAG AGTCCTTCAG TCTTCCAATT
 61 GGCAACTACA AGAAACCAAA ACTTCTGTAC TGTAATAATG GAGGGTATTT TTTGCGCATC
121 CTCCCAGATG GGGTTGTGGA TGGAACAAGA GACAGAGATG ACCTTTACAT TACACTGAAG
181 TTAAGCGCAC AAAGCCAAGG GGAGGTGCAT ATCAAAAGCA CAGAGACAGG GAGTTACTTA
241 GCCATGGACT CCAGTGGACA GTTGTATGGA ACTCTCACAC CAAATGAAGA AAGCCTGTTT
301 CTGGAGACAT TAGAAGAGAA TCACTATAAC ACATACAAGT CAAAGAAGTA TGCAGAAAAT
361 AACTGGTTTG TGGGGATAAA GAAGAACGGG GCAAGCAAAA AGGGATCAAG GACTCACTAT
421 GGACAAAAAG CCATCCTTTT TCTGCCGCTG CCAGCATCAC CTGACTAG
```

*Heterocephalus glaber* FGF1 gene coding sequence (1-155)
(SEQ ID NO: 87) (generated using SMS Reverse Translate tool
on the ExPASy Bioinformatics Resource website (www.expasy.org):

```
  1  ATGGCGGAAG GCGAAATTAC CACCTTTACC GCGCTGACCG AAAAATTTAA CCTGCCGCCG
 61  GGCAACTATA AAAAACCGAA ACTGCTGTAT TGCAGCAACG GCGGCCATTT TCTGCGCATT
121  CTGCCGGATG GCAAAGTGGA TGGCACCCGC GATCGCAGCG ATCAGCATAT TCAGCTGCAG
181  CTGAGCGCGG AAGGCGTGGG CGAAGTGTAT ATTAAAAGCA CCGAAACCGG CCAGTATCTG
241  GCGATGGATA CCGATGGCCT GCTGTATGGC AGCCAGACCG GAGCGAAGA ATGCCTGTTT
301  CTGGAACGCC TGGAAGAAAA CCATTATAAC ACCTATATTA GCAAAAAACA TGCGGAAAAA
361  AACTGGTTTG TGGGCCTGAA AAAAAACGGC AGCTGCAAAC GCGGCCCGCG CACCCATTAT
421  GGCCAGAAAG CGATTCTGTT TCTGCCGCTG CCGGTGAGCA GCGAT
```

Black flying fox FGF1 gene coding sequence (1-155)
(SEQ ID NO: 88) (generated using SMS Reverse Translate
tool on the ExPASy Bioinformatics Resource website
(www.expasy.org):

```
  1 ATGGCGGAAG GCGAAGTGAC CACCTTTACC GCGCTGACCG AACGCTTTAA CCTGCCGCCG
 61 GGCAACTATA AAAAACCGAA ACTGCTGTAT TGCAGCAACG GCGGCCATTT TCTGCGCATT
121 CTGCCGGATG GCACCGTGGA TGGCACCCGC GATAAAAGCG ATCAGCATAT TCAGCTGCAG
181 CTGAGCGCGG AAAGCGTGGG CGAAGTGTAT ATTAAAAGCA CCGAAAGCGG CCAGTATCTG
241 GCGATGGATA GCGATGGCCT GCTGTATGGC AGCCAGACCC GGATGAAGA TTGCCTGTTT
301 CTGGAACGCC TGGAAGAAAA CCATTATAAC ACCTATACCA GCAAAAAACA TGCGGAAAAA
361 AACTGGTTTG TGGGCCTGAA AAAAAACGGC AGCTGCAAAC GCGGCCCGCG CACCCATTAT
421 GGCCAGAAAG CGATTCTGTT TCTGCCGCTG CCGGTGAGCA GCGAT
```

Chinese tree shrew FGF1 gene coding sequence (1-155)
(SEQ ID NO: 89) (generated using SMS Reverse Translate
tool on the ExPASy Bioinformatics Resource website
(www.expasy.org):

```
  1 ATGGCGGAAG GCGAAATTAC CACCTTTGCG GCGCTGACCG AAAAATTTGA TCTGCCGCCG
 61 GGCAACTATA AAAAACCGAA ACTGCTGTAT TGCAGCAACG GCGGCCATTT TCTGCGCATT
121 CTGCCGGATG GCACCGTGGA TGGCACCCGC GATCGCAGCG ATCAGCATAT TCAGCTGCAG
181 CTGACCGCGG AAAAACGTGGG CGAAGTGTAT ATTAAAAGCA CCGAAACCGG CCAGTATCTG
241 GCGATGGATG CGGATGGCCT GCTGTATGGC AGCCAGACCC GAACGAAGA ATGCCTGTTT
301 CTGGAACGCC TGGAAGAAAA CCATTATAAC ACCTATATTA GCAAAAAACA TGCGGAAAAA
361 AACTGGTTTG TGGCGCTGAA AAAAAACGGC AGCTGCAAAC TGGGCCCGCG CACCCATTAT
421 GGCCAGAAAG CGATTCTGTT TCTGCCGCTG CCGGTGAGCA GCGAT
```

TABLE 2-continued

Rock pigeon FGF1 gene coding sequence (1-155) (SEQ ID NO: 90)
(generated using SMS Reverse Translate tool on the ExPASy
Bioinformatics Resource website (www.expasy.org):

```
  1 ATGGCGGAAG GCGAAATTAC CACCTTTACC GCGCTGACCG AAAAATTTAA CCTGCCGCCG
 61 GGCAACTATA AAAAACCGAA ACTGCTGTAT TGCAGCAACG GCGGCCATTT TCTGCGCATT
121 CTGCCGGATG CAAAGTGGA TGGCACCCGC GATCGCAGCG ATCAGCATAT TCAGCTGCAG
181 CTGAGCGCGG AAAGCGTGGG CGAAGTGTAT ATTAAAAGCA CCCAGAGCGG CCAGTATCTG
241 GCGATGGATC CGACCGGCCT GCTGTATGGC AGCCAGCTGC TGGGCGAAGA ATGCCTGTTT
301 CTGGAACGCA TTGAAGAAAA CCATTATAAC ACCTATGTGA GCAAAAAACA TGCGGATAAA
361 AACTGGTTTG TGGGCCTGAA AAAAAACGGC AACAGCAAAC TGGGCCCGCG CACCCATTAT
421 GGCCAGAAAG CGATTCTGTT TCTGCCGCTG CCGGTGAGCG CGGAT
```

Sheep FGF1 gene coding sequence (1-155) (SEQ ID NO: 91)
(GenBank accession no. XM_004008909, which is
hereby incorporated by reference in its entirety):

```
361 ATGGCTGAAG GAGAAACCAC AACCTTCAGG GCCCTGACTG AGAAGTTTAA CCTGCCTCTA
421 GGCAATTACA AGAAGCCCAA GCTCCTCTAT TGCAGCAACG GGGCTACTT CCTGAGAATC
481 CTCCCAGATG GCAGAGTGGA TGGGACGAAG GACAGGAGCG ACCAGCACAT TCAGCTGCAG
541 CTCTATGCGG AAAGCATAGG GGAGGTGTAT ATTAAGAGTA CGGAGACTGG CCAGTTCTTG
601 GCCATGGACA CCAACGGGCT TTTGTACGGC TCACAAACAC CCAGTGAGGA ATGTTTGTTC
661 CTGGAAAGGC TGGAGGAAAA CCATTATAAC ACCTACATAT CCAAGAAGCA TGCAGAGAAG
721 AATTGGTTCA TTGGTCTCAA GAAGAACGGA AGCTCCAAAC TCGGTCCTCG GACTCACTTC
781 GGCCAGAAAG CCATCTTGTT TCTCCCCCTG CCAGTTTCCT CTGATTAA
```

Chicken FGF1 gene coding sequence (1-155) (SEQ ID NO: 92)
(GenBank accession no. NM_205180, which is hereby
incorporated by reference in its entirety):

```
 52                                                           ATGGCCGAG
 61 GGGGAGATAA CCACCTTCAC CGCCCTGACC GAGCGCTTCG GCCTGCCGCT GGGCAACTAC
121 AAGAAGCCCA AACTCCTGTA CTGCAGCAAC GGGGGCCACT TCCTACGGAT CCTGCCGGAC
181 GGCAAGGTGG ACGGGACGCG GGACCGGAGT GACCAGCACA TTCAGCTGCA GCTCAGCGCG
241 GAAGATGTGG GCGAGGTCTA TATAAAGAGC ACAGCGTCGG GGCAGTACCT GGCAATGGAC
301 ACCAACGGGC TCCTGTATGG CTCGCAGCTA CCAGGCGAGG AGTGCTTGTT CCTTGAGAGG
361 CTCGAGGAGA ACCATTACAA CACATACATC TCCAAAAAGC ACGCAGACAA GAACTGGTTC
421 GTCGGGCTGA AGAAAAACGG GAACAGCAAG CTGGGGCCGC GGACTCACTA TGGGCAAAAG
481 GCGATCCTCT TCCTCCCATT GCCGGTGTCG GCTGACTGA
```

Alpaca FGF1 gene coding sequence (1-155, excluding 1-57)
(SEQ ID NO: 93) (Ensembl accession no. ENSVPAT00000008395,
which is hereby incorporated by reference in its entirety):

```
  1 CAGCTGCAGC TCAGTGCGGA AAGCGTGGGG GAGGTGTATA TAAAGAGTAC CGAGACTGGC
 61 CAGTACTTGG CCATGGACAC CGACGGGCTT TTGCACGGCT CACAGACACC AAATGAGGAA
121 TGTTTGTTCC TGGAAAGGCT GGAGGAGAAC CATTACAACA CCTACGTC CAAGAAGCAC
181 GCCGAAAAGA ATTGGTTTGT TGGTCTCAAG AAGAATGGAA GCTGCAAACG CGGTCCTCGG
241 ACTCACTACG GCCAGAAGGC GATCTTGTTT CTCCCCTTGC CAGTCTCCTC TGATTAA
```

Anole lizard FGF1 gene coding sequence (1-155) (SEQ ID NO: 94)
(Ensembl accession no. ENSACAT00000013467, which is hereby
incorporated by reference in its entirety):

```
  1 ATGGCTGAAG GTGAAATAAC AACATTCACA GCCTTGACCG AGAGGTTTGC TCTCCCAATG
 61 GAGAATTACA AGAAGCCCAA ACTCCTGTAT TGCAGCAATG GAGGCCACTT CCTGAGGATC
121 CTTCCAGATG GAAAGTGGA TGGCACCATG GACCGGAATG ACAGCTATAT TCAGTTGCTG
181 TTAACAGCAG AAGATGTGGG TGTGGTATAT ATAAAAGGCA CTGAGACCGG GCAGTACTTG
241 GCCATGGATG CCAATGGACA TTTATATGGC TCGCAGTTGC AACAGAAGA GTGTTTATTT
301 GTGGAAACGC TGGAAGAAAA CCATTACAAT ACATATACCT CAAAGATGCA TGGCGATAAG
361 AAGTGGTATG TTGGCTTGAA AAAGAATGGG AAAGGCAAAC TGGGGCCACG GACTCATCGC
421 GGCCAAAAGG CAATACTTTT CCTTCCACTG CCAGTATCAC CTGATTAG
```

Bushbaby FGF1 gene coding sequence (1-155) (SEQ ID NO: 95)
(Ensembl accession no. ENSOGAT00000005081, which is hereby
incorporated by reference in its entirety):

```
  1 ATGGCTGAAG GGGAAATCAC AACCTTCACA GCCCTCACAG AGAAGTTTAA TCTGCCTCTA
 61 GGAAATTACA AGAAGCCCAA GCTCCTCTAC TGTAGCAACG GGGGTCACTT TCTGAGGATC
121 CTGCCGGATG GCACCGTGGA TGGGACACAA GACAGGAGCG ACCAGCACAT TCAGCTGCAG
181 CTCAGTGCGG AAAGCGTGGG GGAGGTGTAT ATAAAGAGTA CCCAGACTGG CCAGTACTTG
241 GCCATGGACT CCGACGGGCT TTTATACGGC TCACAAACAC CAAATGAGGA ATGCCTGTTC
301 CTGGAACGGC TGGAGGAAAA CCATTACAAC ACCTATGTGT CCAAGAAGCA CGCCGAGAAG
361 AATTGGTTTG TCGGTCTCAA GAAGAACGGA AGTTGCAAAC GTGGTCCTCG GACTCACTAC
421 GGCCAGAAAG CAATCTTGTT TCTCCCCCTG CCAGTCTCCT CTGATTAA
```

TABLE 2-continued

Cat FGF1 gene coding sequence (1-155) (SEQ ID NO: 96) (Ensembl accession no. ENSFCAT00000009123, which is hereby incorporated by reference in its entirety):

```
  1 ATGGCTGAAG GGGAAATCAC AACCTTCACG GCCCTGACGG AGAAGTTCAA TCTGCCTCCA
 61 GGGAATTACA AGAAACCCAA ACTCCTCTAC TGTAGCAACG GGGGCCACTT CCTGAGGATC
121 CTTCCAGATG GCACAGTGGA TGGGACGAGG GACAGGAGCG ACCAGCACAT TCAGCTGCAG
181 CTCAGTGCGG AAAGCGTGGG GGAGGTGTAT ATAAAGAGTA CCGAGACTGG CCAGTACTTC
241 GCCATGGACA CCGACGGGCT TTTGTACGGC TCACAGACAC CAAATGAGGA ATGCTTGTTC
301 CTGGAAAGGC TGGAAGAAAA CCATTACAAC ACCTACATAT CAAGAAGCA CGCAGAAAAG
361 AATTGGTTTG TGGGTCTCAA GAAGAATGGA AGCTGCAAAC GCGGTCCCCG GACTCACTAT
421 GGCCAGAAGG CAATTTTGTT TCTCCCCCTG CCAGTCTCCT CTGATTAA
```

Chinese softshell turtle FGF1 gene coding sequence (1-155) (SEQ ID NO: 97) (Ensembl accession no. ENSPSIT00000016432, which is hereby incorporated by reference in its entirety):

```
131            ATGGCTGAAG GGGAAATAAC AACGTTCACC GCCCTGACCG AAAAATTCAA
181 CCTTCCCCTG GGGAATTACA AGAATCCCAA ACTCTTATAT TGCAGCAATG GAGGCTACTT
241 CTTGAGGATA CATCCAGATG GCAAAGTAGA TGGGACAAGG GACCGAAGTG ACCAACACAT
301 TCAGCTGCAG CTAAGTGCGG AAAGCGTGGG TGAGGTATAT ATAAAGAGCA CTGAGTCTGG
361 ACAGTTTTTG GCTATGGACG CCAATGGACT TTTATATGGA TCACTGTCAC CGAGTGAGGA
291 ATGCTTATTC TTGGAAAGAA TGGAAGAAAA TCATTATAAC ACCTACATCT CCAAGAAGCA
351 TGCAGACAAG AACTGGTTCG TTGGCTTAAA GAAGAATGGA AGCTGCAAAC TGGGACCGCG
411 GACGCACTAC GGCCAAAAGG CCGTCCTTTT CCTTCCACTG CCAGTGTCAG CTGATTAA
```

Coelacanth FGF1 gene coding sequence (1-155) (SEQ ID NO: 98) (Ensembl accession no. ENSLACT00000015212, which is hereby incorporated by reference in its entirety):

```
  1 ATGGCTGAAG ACAAAATAAC AACACTGAAG GCCTTGGCTG AAAAATTTAA CCTTCCTATG
 61 GGAAATTACA AGAAAGCAAA ACTCCTCTAC TGCAGCAACG GAGGGTATTT CCTGCGAATA
121 CCCCCAGACG GGAAAGTGGA AGGAATTAGA GAACGAAGCG ACAAGTACAT TCAGCTGCAG
181 ATGAATGCAG AAAGTTTAGG CATGGTGTCT ATAAAGGGTG TGGAGGCAGG GCAATACCTA
241 GCTATGAATA CAAATGGACT CCTGTATGGA TCTCAGTCTC TAACTGAAGA ATGCCTTTTC
301 ATGGAAAAGA TGGAAGAAAA CCACTACAAC ACATACAGGT CTAAGACACA TGCAGATAAA
361 AACTGGTATG TTGGCATTAG AAAGAACGGT AGCATCAAAC CAGGACCAAG GACTCACATT
421 GGCCAAAAGG CTGTTCTTTT TCTCCCTCTG CCTGCCTCGA GTGATTAG
```

Dolphin FGF1 gene coding sequence (1-155) (SEQ ID NO: 99) (Ensembl accession no. ENSTTRT00000004742, which is hereby incorporated by reference in its entirety):

```
  1 ATGGCTGAAG GGGAAATCAC AACCTTCACA GCCCTGACCG AGAAGTTTAA TCTGCCTCCA
 61 GGGAATTACA AGAAGCCCAA ACTCCTCTAC TGTAGCAACG GGGCCACTT CCTGAGGATC
121 CTTCCAGATG GCACAGTGGA TGGGACAAGG GACAGGAGTG ACCAGCACAT TCAGCTGCAG
181 CTCAGTGCGG AAAGCGTGGG GGAGGTGTAT ATAAAGAGTA CGGAGACTGG CCAGTACTTG
241 GCCATGGACA CCGACGGGCT TTTGTACGGC TCACAGACAC CAATGAGGA ATGTTTGTTC
301 CTGGAAAGGT TGGAGGAAAA CCATTACAAC ACCTACGCAT CAAGAAGCA TGCAGAAAAG
361 AATTGGTTCG TTGGTCTCAA GAAGAACGGA AGCTGCAAAC GCGGTCCTCG GACTCACTAC
421 GGCCAGAAAG CAATCTTGTT TCTCCCCCTG CCAGTCTCCT CCGATTAA
```

Ferret FGF1 gene coding sequence (1-155) (SEQ ID NO: 100) (Ensembl accession no. ENSMPUT00000008013, which is hereby incorporated by reference in its entirety):

```
  1                                           ATGGCT GAAGGGGAAA TCACAACCTT
 61 CACAGCCCTG ATGGAGAAGT TTAATCTGCC TGCGGGGAAT TACAAGAAGC CCAAACTCCT
121 CTACTGTAGC AATGGGGGCC ACTTCCTGAG GATCCTTCCA GATGGCACAG TGGACGGCAC
181 AAGGGACAGG AGCGACCAGC ACATTCAGCT GCAGCTCAGT GCGGAAAGCG TGGGGGAGGT
241 GTACATAAAG AGTACCGAGA CTGGCCAGTA CTTGGCCATG GACACCGATG GCTTTTGTA
301 CGGCTCACAA ACACCAAATG AGGAATGTCT GTTCCTGGAA AGGCTGGAGG AAAACCATTA
361 CAACACCTAC ACATCCAAGA AGCACGCTGA GAAGAATTGG TTTGTAGGTC TCAAGAAGAA
421 CGGAAGCTGC AAACGCGGTC CTCGGACTCA CTATGGCCAG AAAGCAATTC TGTTTCTCCC
481 CCTGCCAGTC TCCTCTGATT AA
```

Gibbon FGF1 gene coding sequence (1-155) (SEQ ID NO: 101) (Ensembl accession no. ENSNLET00000012455, which is hereby incorporated by reference in its entirety):

```
241                                                ATGG CCGAAGGGGA
301 AATCACCACC TTCACAGCCC TGACCGAGAA GTTTAATCTG CCTCCAGGGA ATTACAAGAA
361 GCCCAAACTC CTCTACTGTA GCAACGGGGG CCACTTCTTG AGGATCCTTC CGGATGGCAC
421 AGTGGATGGG ACAAGGGACA GGAGCGACCA GCACATTCAG CTGCAGCTCA GTGCGGAAAG
481 CGTGGGGGAG GTGTATATAA AAGTACCGA GACTGGCCAG TACTTGGCCA TGGACACCGA
541 CGGGCTTTTA TACGGCTCAC AGACACCAAA TGAGGAATGT TTGTTCCTGG AAAGGCTGGA
601 GGAGAACCAT TACAACACCT ATATCCAA GAAGCATGCA GAGAAGAATT GGTTTGTTGG
661 CCTCAAGAAG AATGGAAGCT GCAAACGCGG TCCTCGGACT CACTATGGCC AGAAAGCAAT
721 CTTGTTTCTC CCCCTGCCAG TCTCTTCTGA TTAA
```

TABLE 2-continued

Gorilla FGF1 gene coding sequence (1-155) (SEQ ID NO: 102)
(Ensembl accession no. ENSGGOT00000025344, which is hereby
incorporated by reference in its entirety):

```
121                                              ATGG CTGAAGGGGA
181 AATCACCACC TTCACAGCCC TGACCGAGAA GTTTAATCTG CCTCCAGGGA ATTACAAGAA
241 GCCCAAACTC CTCTACTGTA GCAATGGGGG CCACTTCTTG AGGATCCTTC CGGATGGCAC
301 AGTGGATGGG ACAAGGGACA GGAGCGACCA GCACATTCAG CTGCAGCTCA GTGCGGAAAG
361 CGTGGGGGAG GTGTATATAA AGAGTACCGA GACTGGCCAG TACTTGGCCA TGGACACCGA
421 CGGGCTTTTA TACGGCTCAC AGACACCCAA TGAGGAATGT TTGTTCCTGG AAAGGCTGGA
481 GGAGAACCAT TACAACACCT ATATATCCAA GAAGCATGCA GAGAAGAATT GGTTTGTTGG
541 CCTCAAGAAG AATGGAAGCT GCAAACGCGG TCCTCGGACT CACTATGGCC AGAAAGCAAT
601 CTTGTTTCTC CCCCTGCCAG TCTCTTCCGA TTAA
```

Hedgehog FGF1 gene coding sequence (1-155) (SEQ ID NO: 103)
(Ensembl accession no. ENSEEUT00000005832, which is hereby
incorporated by reference in its entirety):

```
  1 ATGGCTGAAG GAGAAATCAC CACCTTCACG GCCCTGACTG AGAAGTTTAA TCTGCCACTA
 61 GGGAATTACA AGAAGCCCAA GCTCCTCTAC TGTAGCAACG GGGCCACTTT CCTGAGGATC
121 CTTCCAGATG GCACCGTGGA TGGGACAAGG GACAGGAGCG ACCAGCATAT TCAGCTGCAG
181 CTCAGTGCGG AAAGCGTGGG GGAGGTGTAT ATAAAGAGTA CGGAGACTGG CCAGTACTTG
241 GCCATGGACA CCGACGGGCT TTTATACGGC TCACAAACAC CAATGAGGA ATGTCTGTTC
301 CTTGAAAGGC TGGAAGAGAA CCATTACAAT ACCTACACAT CCAAGAAGCA TGCCGAGAAG
361 AACTGGTTTG TTGGCCTCAA GAAGAATGGA AGCTGCAAGC GTGGTCCTCG GACTCATTAT
421 GGCCAGAAAG CTATTTTGTT TCTCCCCCTG CCAGTTTCCT CTGATTAA
```

Hyrax FGF1 gene coding sequence (1-155, excluding 1-90)
(SEQ ID NO: 104) (Ensembl accession no. ENSPCAT00000011746,
which is hereby incorporated by reference in its entirety):

```
  1 ATGGCTGAAG GCGAAATCAC AACCTTCACA GCCCTGACTG AGAAGTTTAA CCTGCCACTA
 61 GAGAATTACA AGAAGCCCAA ACTCCTCTAC TGTAGCAACG GAGGCCACTT CCTGAGGATC
121 CTTCCGGACG GCACAGTGGA TGGCACCAGG GACAGGAGTG ACCAGCACAT TCAGCTGCAG
181 CTCAGTGCGG AAAGCGTGGG GGAGGTGTAT ATAAGGGCA CCGAGACTGG CCAGTACTTG
241 GCCATGGACA CCGACGGGCT TTTATATGGC TCA
```

Kangaroo rat FGF1 gene coding sequence (1-155, excluding 1-16
and 58-155) (SEQ ID NO: 105) (Ensembl accession no.
ENSDORT00000007345, which is hereby incorporated by
reference in its entirety):

```
  1 ATGGCTGAAG GGGAAATCAC AACCTTCACA GCCCTGACGG AAAGGTTTAA ----------
    ---------- ---------- ---------- ---------- ---------- ----------
 51 ---------- ---------- ---------- ---------- ---------T TCAGCTGCAA
 62 CTGAGTGCGG AAAGCGTGGG GGAGGTCTAT ATAAAGAGCA CCGAGACTGG CCAATACTTG
122 GCCATGGATG CCGACGGGCT TTTATACGGC TCACAGACAC CTGATGAAGA ATGCTTGTTC
182 CTGGAGAGGC TGGAAGAAAA TCATTATAAC ACCTACATAG CCAAGAAACA TGCTGAAAAG
242 AATTGGTTTG TCGGCCTCAA AAAGAATGGA AGCTGCAAGC GTGGTCCTCG GACTCACTAT
302 GGCCAGAAAG CAATCCTGTT CCTCCCCTTG CCTGTCTCCT CTGATTAG
```

Lamprey FGF1 gene coding sequence (1-155, excluding 94-155)
(SEQ ID NO: 106) (Ensembl accession no. ENSPMAT00000010729,
which is hereby incorporated by reference in its entirety):

```
  1 ATGGAGGTGG GCCACATCGG CACGCTGCCC GTGGTCCCCG CGGGGCCCGT GTTCCCCGGC
 61 AGTTTCAAGG AGCCACGGCG CCTCTACTGC CGCAGCGCGG CCACCACCT CCAGATCCTG
121 GGGGACGGCA CCGTGAGTGG CACCCAGGAC GAGAACGAGC CCCACGCCGT TCTGCAGCTG
181 CAGGCGGTGC GCCGCGGGGT GGTGACGATC CGTGGGCTCT GCGCCGAGAG GTTCCTCGCC
241 ATGAGCACGG AGGGACACCT GTACGGGGCG GTGAGG
```

Lesser hedgehog tenrec FGF1 gene coding sequence (1-155,
excluding 1-57) (SEQ ID NO: 107) (Ensembl accession no.
ENSETET00000017851, which is hereby incorporated by
reference in its entirety):

```
  1 CAGCTGAAGC TCGTTGCCGA AAGCGTGGGG GTGGTGTATA TAAAGAGCAT CAAGACCGGC
 61 CAGTACTTGG CCATGAACCC CGACGGGCTT TTATACGGCT CCGAGACCCC AGAGGAAGAA
121 TGCTTGTTCC TGGAAACGCT GGAGGAAAAC CACTACACCA CCTTCAAATC TAAGAAGCAC
181 GTAGAGAAGA ATTGGTTCGT TGGTCTCCGG AAGAATGAA GGGTCAAGAT CGGGCCTCGG
241 ACTCACCAAG GCCAGAAAGC AATCTTGTTC CTGCCCCTCC GGTGTCCTC TGATTAA
```

Rhesus monkey FGF1 gene coding sequence (1-155)
(SEQ ID NO: 108) (Ensembl accession no. ENSMMUT00000033070,
which is hereby incorporated by reference in its entirety):

```
 36                                        ATGGC TGAAGGGGAA ATCACCACGT
 61 TCACAGCCCT GACCGAGAAG TTTAATCTGC CTCCAGGGAA TTACAAGAAG CCCAAACTGC
121 TCTACTGTAG CAATGGGGGC CACTTCTTGA GGATCCTTCC GGATGGCACA GTGGATGGGA
181 CAAGGGACAG GAGCGACCAG CACATTCAGC TGCAGCTCAG TGCGGAAAGC GTGGGGGAGG
```

TABLE 2-continued

```
241  TGTATATAAA GAGTACCGAG ACTGGCCAGT ACTTGGCCAT GGACACCGAC GGGCTTTTAT
301  ACGGCTCACA GACACCAAAT GAGGAATGTT TGTTCCTGGA AAGGCTGGAG GAGAACCATT
361  ACAACACCTA TACATCCAAG AAGCACGCAG AGAAGAATTG GTTTGTTGGC CTCAAGAAGA
421  ATGGAAGCTG CAAACGTGGT CCTCGGACTC ACTATGGCCA GAAAGCAATT TGTTTCTTC
481  CCCTGCCAGT CTCTTCTGAT TAA
```

Megabat FGF1 gene coding sequence (1-155) (SEQ ID NO: 109)
(Ensembl accession no. ENSPVAT00000004596, which is hereby
incorporated by reference in its entirety):

```
  1  ATGGCCGAGG GGGAAGTCAC GACGTTCACG GCCCTGACCG AGAGGTTTAA CCTGCCTCCA
 61  GGGAATTACA AGAAGCCCAA ACTTCTCTAC TGCAGCAACG GGGGCCACTT CCTGAGGATC
121  CTCCCAGATG GCACAGTGGA TGGGACAAGG GACAAGAGCG ACCAGCACAT TCAGCTGCAG
181  CTCAGTGCGG AAAGTGTGGG GGAGGTGTAT ATAAAGAGCA CCGAGAGTGG CCAGTACTTG
241  GCCATGGACT CCGACGGGCT TTTGTACGGC TCACAGACAC CAGATGAGGA CTGTTTGTTC
301  CTGGAAAGGC TGGAGGAAAA CCATTACAAC ACCTACACAT CCAAGAAGCA CGCAGAGAAG
361  AATTGGTTTG TTGGGCTCAA GAAGAATGGA AGCTGCAAGC GCGGTCCCCG GACTCACTAC
421  GGCCAGAAAG CGATCCTGTT TCTCCCCCTG CCAGTCTCCT CTGATTAG
```

Microbat FGF1 gene coding sequence (1-155) (SEQ ID NO: 110)
(Ensembl accession no. ENSMLUT00000007098, which is hereby
incorporated by reference in its entirety):

```
 66       ATGGC TGAGGGGGAA GTCACCACAT TCACGGCCCT GACCGAGAGG TTCAATCTGC
121  CTCTGGAGAA CTACAAGAAG CCCAAGCTTC TCTACTGCAG CAACGGGGGC CACTTCCTGC
181  GGATCCTCCC AGACGGCACC GTGGACGGGA CGAGGGACAG GAGCGACCAG CACATTCAGC
241  TGCAGCTCAG TGCGGAAAGC GTGGGGGAGG TGTATATAAA GAGCACCGAG AGTGGCCAGT
301  ACTTGGCCAT GGACTCCGAC GGGCTTTTGT ACGGCTCACA AACACCCAAT GAGGAATGTT
361  TGTTCCTGGA AAGGCTGGAG GAGAACCACT ACAACACCTA CACGTCCAAG AAGCACGCAG
421  AAAAGAATTG GTTCGTTGGG CTCAAGAAGA ACGGAAGCTG CAAGCGTGGT CCTCGGACGC
481  ATTATGGCCA GAAAGCAATC TTGTTTCTCC CCCTGCCAGT CTCCTCCGAT TAA
```

Mouse lemur FGF1 gene coding sequence (1-155) (SEQ ID NO: 111)
(Ensembl accession no. ENSMICT00000009454, which is hereby
incorporated by reference in its entirety):

```
  1  ATGGCCGAAG GGGAGATCAC AACCTTCACG GCCCTCACCG AGAAGTTTAA CCTGCCTCCG
 61  GGGAACTACA AGAAGCCCAA GCTCCTCTAC TGCAGCAACG GCGGCCACTT CCTGCGCATC
121  CTTCCCGACG GCACCGTGGA TGGCACGAGA GACAGGAGCG ACCAGCACAT TCAGCTGCAG
181  CTCAGTGCGG AAAGCGCGGG GGAGGTGTAT ATAAAGAGCA CCCAGACTGG CCGGTACTTG
241  GCCATGGACG CCGACGGGCT TTTATACGGC TCACAAACAC CAAATGAGGA ATGTTTGTTC
301  CTGGAAAGGC TGGAGGAAAA CCATTACAAC ACCTACGTAT CCAAGAAGCA CGCAGAGAAG
361  AATTGGTTTG TTGGCCTCAA GAAGAATGGA AGTTGCAAAC GCGGCCCCCG GACTCACTAT
421  GGCCAGAAAG CAATCTTGTT TCTGCCCCTG CCAGTCTCCT CTGATTAA
```

Pika FGF1 gene coding sequence (1-155, excluding 57-67)
(SEQ ID NO: 112) (Ensembl accession no. ENSOPRT00000012854,
which is hereby incorporated by reference in its entirety):

```
  1  ATGGCCGAGG GAGAAGTCAC CACCTTCTCA GCCCTGACGG AGAAGTTCAA TCTGCCTGGA
 61  GGAAACTACA AGTTGCCCAA GCTCCTTTAC TGTAGCAACG GAGGCCACTT CCTGAGGATC
121  CTTCCAGATG GCACAGTGGA TGGGACCAGG ACAGGAGCG ACCTGCACA- ----------
170  ---------- ---------- -GAGGTGTTT ATAAAGAGTA CGGAGACTGG CCAGTACTTG
209  GCTATGGACA CCGATGGCCT TTTATATGGC TCGCAGACAC CCAGTGAGGA GTGTTTGTTC
269  CTGGAGCGGC TGGAGGAGAA CCACTACAAC ACCTACACAT CCAAGAAGCA TGCCGAGAAG
329  AACTGGTTTG TGGGCATCAA GAAGAATGGA AGCTGCAAGC GTGGTCCTCG GACTCACTAC
389  GGCCAGAAAG CCATCTTGTT TCTCCCTCTG CCAGTCTCTT CTGACTAA
```

Rat FGF1 gene coding sequence (1-155) (SEQ ID NO: 113)
(Ensembl accession no. ENSRNOT00000018577, which is
hereby incorporated by reference in its entirety):

```
268                                ATG GCCGAAGGGG AGATCACAAC CTTTGCAGCC
301  CTGACCGAGA GGTTCAATCT GCCTCTAGGG AACTACAAAA AACCCAAACT GCTCTACTGC
361  AGCAACGGGG GCCCACTTCTT GAGGATTCTT CCCGATGGCA CCGTGGATGG GACCAGGGAC
421  AGGAGCGACC AGCACATTCA GCTGCAGCTC AGTGCGGAAA GCGCGGGCGA AGTGTATATA
481  AAGGGTACAG AGACTGGCCA GTACTTGGCC ATGGACACCG AAGGGCTTTT ATACGGCTCA
541  CAGACACCAA ATGAAGAATG CCTATTCCTG GAAAGGCTAG AAGAAAACCA TTATAACACT
601  TACACATCCA AGAAGCACGC GGAGAAGAAC TGGTTTGTGG GCCTCAAGAA GAACGGGAGT
661  TGTAAGCGCG GTCCTCGGAC TCACTACGGC CAGAAAGCCA TCTTGTTTCT CCCCCTCCCG
721  GTATCTTCTG ACTAA
```

Sloth FGF1 gene coding sequence (1-155) (SEQ ID NO: 114)
(Ensembl accession no. ENSCHOT00000012416, which is hereby
incorporated by reference in its entirety):

```
  1  ATGGCTGAAG GGAAATCAC AACCTTCACA GCTCTGATGG AGAAGTTTAA CCTGCCACCA
 61  GGGAATTACA TGAAGCCCAA ACTCCTCTAC TGTAGCAACG GGGCCACTT CTTGAGGATC
121  CTTCCAGACG GCACAGTGGA TGGGACAAGG ACAGGAGCG ACCTGCACAT TCAGCTGCAG
181  CTCAGTGCGG AAAGCGTGGG GGAGGTGTAT ATAAAGAGTG CGGAGACCGG CCAGTACTTA
```

TABLE 2-continued

```
241 GCCATGGACA CCGGCGGGCT TTTATACGGC TCACAGACAC CAAGTGAGGA ATGCCTGTTC
301 CTAGAAAGGC TGGAGGAAAA CCATTACAAC ACCTACGTAT CCAAGAAGCA TGCGGAGAAG
361 AACTGGTTCG TTGGCCTAAA GAAGAATGGA AGCAGCAAAC GCGGCCCCCG GACTCACTAT
421 GGCCAGAAAG CCATCTTGTT TCTTCCCCTG CCAGTCTCCT CTGATTAA
```

Squirrel FGF1 gene coding sequence (1-155) (SEQ ID NO: 115)
(Ensembl accession no. ENSSTOT00000029249, which is hereby
incorporated by reference in its entirety):

```
  1                                                              ATGG
  5 CTGAAGGGGA AATCACAACC TTCACAGCCC TGACCGAGAA GTTCAATCTG CCTCCAGGGA
 65 ACTACAAGAA GCCCAAACTG CTCTACTGTA GCAACGGAGG CCACTTCTTG AGGATCCTTC
125 CTGATGGCAC AGTGGATGGG ACAAGAGACA GGAGCGACCA ACACATTCAG CTGCAGCTCA
185 GTGCGGAAAG CGTGGGGGAG GTGTATATAA AGAGTACCGA GACCGGCCAG TACTTGGCCA
245 TGGACACCGA CGGGCTTTTA TATGGCTCAC AGACCCCAAA TGAGGAATGC TTATTCCTGG
305 AAAGGCTGGA GGAAAACCAT TACAACACGT ACACATCCAA GAAGCATGCA GAGAAGAATT
365 GGTTTGTTGG CCTCAAGAAG AACGGAAGCT GCAAGCGCGG TCCCCGGACT CACTATGGCC
425 AGAAAGCGAT CTTGTTTCTC CCACTGCCTG TCTCCTCTGA TTAG
```

VTarsier FGF1 gene coding sequence (1-155) (SEQ ID NO: 116)
(Ensembl accession no. ENSTSYT00000007425, which is hereby
incorporated by reference in its entirety):

```
  1 ATGGCCGAAG GGAAATCAC AACCTTCACA GCCCTGACCG AGAAGTTCAA CCTGCCCCCG
 61 GGGAATTACA AGAAGCCCAA ACTCCTCTAC TGCAGCAACG GGGGCCACTT CTTGAGGATC
121 CTTCCGGATG GCACTGTGGA TGGAACGAGG GACAGGAGCG ACCAGCACAT TCAGCTGCAG
181 CTCAGCGCGG AAAGCGTGGG GGAGGTGTAT ATAAAGAGTA CCGAGACCGG CCAGTACTTG
241 GCCATGGACA CCGACGGGCT TTTGTACGGC TCACAGACAC CAAATGAGGA GTGTCTGTTC
301 CTGGAAAGGC TGGAAGAGAA TCATTACAAT ACCTACGTGT CCAAGAAGCA TGCGGAGAAG
361 AATTGGTTTG TCGGCCTCAA GAAGAATGGA AGCTGCAAAC GCGGTCCTCG GACTCACTAT
421 GGCCAGAAAG CAATCTTGTT TCTCCCCCTG CCAGTTTCCT CTGATTAA
```

Tree shrew FGF1 gene coding sequence (1-155) (SEQ ID NO: 117)
(Ensembl accession no. ENSTBET00000011861, which is hereby
incorporated by reference in its entirety):

```
  1 ATGGCTGAAG GGAAATCAC GACCTTCGCA GCCCTGACCG AGAAGTTTGA TCTGCCTCCA
 61 GGGAATTACA AGAAGCCCAA ACTTCTCTAC TGTAGCAACG GGGGCCATTT CTTGAGGATT
121 CTTCCAGATG GCACCGTGGA TGGGACAAGA GACAGGAGCG ACCAGCACAT TCAGCTGCAG
181 CTCACTGCGG AAAACGTGGG GGAGGTGTAC ATAAAGAGTA CGGAGACTGG CCAGTACTTG
241 GCCATGGACG CCGACGGGCT TTTATATGGC TCACAGACAC CAAACGAGGA ATGTTTGTTC
301 CTGGAAAGGC TGGAGGAGAA CCATTACAAC ACCTACATAT CCAAGAAGCA CGCAGAGAAG
361 AATTGGTTTG TTGCCCTCAA GAAGAACGGA AGCTGCAAAC TCGGTCCTCG GACTCACTAT
421 GGCCAGAAAG CAATCTTGTT TCTCCCCCTG CCAGTCTCCT CTGATTAA
```

Turkey FGF1 gene coding sequence (1-155, excluding 57-155)
(SEQ ID NO: 118) (Ensembl accession no. ENSMGAT00000017372,
which is hereby incorporated by reference in its entirety):

```
  1 ATGGCCGAGG GGAGATAAC CACCTTCACA GCCCTGACCG AGCGCTTCGG CCTGCCGCTG
 61 GGCAACTACA AGAAGCCCAA ACTCCTGTAC TGCAGCAACG GGGCCACTT CCTACGGATC
121 CTGCCGGACG GCAAGGTGGA CGGGACGCGG GACCGGAGCG ACCAGCAC
```

Wallaby FGF1 gene coding sequence (1-155) (SEQ ID NO: 119)
(Ensembl accession no. ENSMEUT00000016544, which is hereby
incorporated by reference in its entirety):

```
  1 ATGGCCGAAG GGAGATCAC AACCTTCACA GCCCTGACCG AAAGATTTAA CCTGCCACTG
 61 GGGAATTACA AGAAGCCCAA GCTTCTCTAC TGTAGCAATG GGGGCCACTT TTTGAGGATC
121 CTTCCTGATG GCAAAGTGGA TGGGACAAGG GACAGAAATG ATCAACACAT TCAACTGCAA
181 CTAAGCGCGG AAAGCGTGGG TGAGGTGTAT ATAAAGAGCA CTGAGTCTGG GCAGTATTTG
241 GCCATGGACA CCAATGGACT TTTATATGGC TCACAGACCC CCAGCGAAGA ATGCTTATTC
301 CTGGAGAGGT TGGAGGAGAA TCATTACAAC ACCTACATAT CAAAGAAGCA TGCGGAGAAA
361 AATTGGTTTG TTGGCCTCAA GAAGAACGGA AGTTGCAAAA GAGGTCCCAG GACTCACTAT
421 GGCCAGAAAG CCATCCTATT CCTTCCCCTC CCTGTGTCCT CTGAGTAA
```

Zebrafish FGF1 gene coding sequence (1-147) (SEQ ID NO: 120)
(Ensembl accession no. ENSDART00000005842, which is hereby
incorporated by reference in its entirety):

```
178                                                               ATG
181 ACCGAGGCCG ATATTGCGGT AAAGTCCAGC CCGCGCGACT ATAAAAAACT GACGCGGCTG
241 TACTGTATGA ATGGAGGATT TCACCTTCAG ATCCTGGCGG ACGGGACAGT GGCTGGAGCA
124 GCAGACGAAA ACACATACAG CATACTGCGC ATAAAAGCAA CAAGTCCAGG AGTGGTGGTG
184 ATCGAAGGAT CAGAAACAGG TCTTTACCTC TCGATGAATG AACATGGCAA GCTGTACGTC
244 TCATCATTAG TGACGGATGA AAGTTATTTC CTGGAGAAGA TGGAGGAAAA CCACTACAAC
304 ACATATCAGT CTCAAAAGCA CGGTGAAAAC TGGTACGTCG AATAAAAAA GAACGGGAAA
364 ATGAAACGGG GCCCAAGAAC TCACATCGGA CAAAAGGCCA TTTTCTTTCT TCCACGACAG
424 GTGGAGCAGG AAGAGGACTG A
```

As noted above, also encompassed within the present invention are portions of paracrine FGFs other than FGF1 (e.g., FGF2, FGF4, FGF5, FGF6, FGF9, FGF16, and FGF20). The portions derived from paracrine FGF2 include portions corresponding to the above-identified amino acid sequences of FGF1. Corresponding portions may be determined by, for example, sequence analysis and structural analysis.

In one embodiment, the paracrine FGF is FGF2. In one embodiment, the portion of the FGF2 is derived from human FGF2 having the amino acid sequence of SEQ ID NO: 121 (GenBank Accession No. EAX05222, which is hereby incorporated by reference in its entirety), as follows:

```
  1 MAAGSITTLP ALPEDGGSGA FPPGHFKDPK RLYCKNGGFF
    LRIHPDGRVD GVREKSDPHI

61 KLQLQAEERG VVSIKGVCAN RYLAMKEDGR LLASKCVTDE
    CFFFERLESN NYNTYRSRKY

121 TSWYVALKRT GQYKLGSKTG PGQKAILFLP MSAKS
```

In one embodiment, the portion of the paracrine FGF includes an amino acid sequence beginning at any one of residues 1 to 25 and ending at any one of residues 151 to 155 of SEQ ID NO: 121. In one embodiment, the portion of the paracrine FGF includes amino acid residues 1-151, 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155, 15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 21-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-151, 25-152, 25-153, 25-154, or 25-155 of FGF2 (SEQ ID NO: 121). In one embodiment, the portion of the paracrine FGF includes amino acid residues 1-151 or 1-152 of SEQ ID NO: 121.

In one embodiment, the portion of the paracrine FGF of the chimeric protein includes an amino acid sequence that has at least 80%, at least 85%, at least 90%, at least 95%, at least 97% or at least 99% amino acid sequence identity to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 151 to 155 of SEQ ID NO: 121. In one embodiment, the portion of the paracrine FGF includes an amino acid sequence that has at least 80%, at least 85%, at least 90%, at least 95%, at least 97% or at least 99% amino acid sequence homology to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 151 to 155 of SEQ ID NO: 121.

Also encompassed within the present invention are portions of paracrine FGFs other than FGF2 (e.g., FGF1, FGF4, FGF5, FGF6, FGF9, FGF16, and FGF20). The portions derived from paracrine FGFs other than FGF2 include portions corresponding to the above-identified amino acid sequences of FGF2. Corresponding portions may be determined by, for example, sequence analysis and structural analysis.

In one embodiment of the present invention, the portion of the paracrine FGF is derived from an ortholog of a human paracrine FGF. In one embodiment of the present invention, the portion of the paracrine FGF of the chimeric protein is derived from an ortholog of human FGF2. In one embodiment, the portion of the FGF2 is derived from *Gorilla gorilla, Pongo abelii, Macaca mulatta, Pan troglodytes, Pan paniscus, Saimiri boliviensis boliviensis, Nomascus leucogenys, Equus caballus, Bos taurus, Papio Anubis, Vicugna pacos, Ovis aries, Capreolus capreolus, Loxodonta Africana, Sus scrofa, Ailuropoda melanoleuca, Choloepus hoffmanni, Bubalus bubalis, Canis lupus familiaris, Rattus norvegicus, Heterocephalus glaber, Otolemur garnettii, Mus musculus, Ictidomys tridecemlineatus, Felis catus, Cavia porcellus, Sarcophilus harrisii, Monodelphis domestica, Oryctolagus cuniculus, Meleagris gallopavo, Gallus gallus, Taeniopygia guttata, Cynops pyrrhogaster, Xenopus laevis, Didelphis albiventris, Myotis lucifugus, Anolis carolinensis, Dasypus novemcinctus, Tupaia belangeri, Xenopus silurana tropicalis, Latimeria chalumnae, Tetraodon nigroviridis, Gasterosteus aculeatus, Takifugu rubripes, Oncorhynchus mykiss, Salmo salar, Danio rerio, Oreochromis niloticus,* or *Oryzias latipes.* The portions of an ortholog of human paracrine FGF include portions corresponding to the above-identified amino acid sequences of FGF2. Corresponding portions may be determined by, for example, sequence analysis and structural analysis.

In one embodiment, the portion of the FGF2 of the chimeric protein of the present invention is derived from an ortholog of human FGF2 having the amino acid sequence shown in Table 3.

TABLE 3

Amino acid sequence of *Gorilla gorilla* (gorilla) FGF2
(SEQ ID NO: 122) (Ensembl accession no.
ENSGGOP00000004720, which is hereby
incorporated by reference in its entirety):

```
104                                           MAAGSI TTLPALPEDG
120 GSGAFPPGHF KDPKRLYCKN GGFFLRIHPD GRVDGVREKS DPHIKLQLQA EERGVVSIKG
180 VCANRYLAMK EDGRLLASKC VTDECFFFER LESNNYNTYR SRKYTSWYVA LKRTGQYKLG
240 SKTGPGQKAI LFLPMSAKS
```

TABLE 3-continued

Amino acid sequence of *Pongo abelii* (sumatran orangutan)
FGF2 (SEQ ID NO: 123) (GenBank accession no.
XP_002815172, which is hereby incorporated by
reference in its entirety):

```
168                                            MAA GSITTLPALP
181EDGGSGAFPP GHFKDPKRLY CKNGGFFLRI HPDGRVDGVR EKSDPHIKLQ LQAEERGVVS
241IKGVCANRYL AMKEDGRLLA SKCVTDECFF FERLESNNYN TYRSRKYTSW YVALKRTGQY
301KLGSKTGPGQ KAILFLPMSA KS
```

Amino acid sequence of *Macaca mulatta* (rhesus monkey)
FGF2 (SEQ ID NO: 124) (GenBank accession no.
XP_001099284, which is hereby incorporated by
reference in its entirety):

```
83                       MAAGSITT LPALPEDGGS GAFPPGHFKD PKRLYCKNGG
121FFLRIHPDGR VDGVREKSDP HIKLQLQAEE RGVVSIKGVC ANRYLAMKED GRLLASKCVT
181DECFFFERLE SNNYNTYRSR KYTSWYVALK RTGQYKLGSK TGPGQKAILF LPMSAKS
```

Amino acid sequence of *Pan troglodytes* (chimpanzee)
FGF2 (SEQ ID NO: 125) (GenBank accession no.
NP_001103711, which is hereby incorporated by
reference in its entirety):

```
134            MAAGSIT TLPALPEDGG SGAFPPGHFK DPKRLYCKNG GFFLRIHPDG
181RVDGVREKSD PHIKLQLQAE ERGVVSIKGV CANRYLAMKE DGRLLASKCV TDECFFFERL
241ESNNYNTYRS RKYTSWYVAL KRTGQYKLGS KTGPGQKAIL FLPMSAKS
```

Amino acid sequence of *Pan paniscus* (Pygmy chimpanzee)
FGF2 (SEQ ID NO: 126) (GenBank accession no.
XP_003816481, which is hereby incorporated by
reference in its entirety):

```
112                                                    MAAGSITTL
121PALPEDGGSG AFPPGHFKDP KRLYCKNGGF FLRIHPDGRV DGVREKSDPH IKLQLQAEER
181GVVSIKGVCA NRYLAMKEDG RLLASKCVTD ECFFFERLES NNYNTYRSRK YTSWYVALKR
241TGQYKLGSKT GPGQKAILFL PMSAKS
```

Amino acid sequence of *Saimiri boliviensis boliviensis* (Bolivian
squirrel monkey) FGF2 (SEQ ID NO: 127) (GenBank accession no.
XP_003936290, which is hereby incorporated by reference
in its entirety):

```
1MAAGSITTLP ALPEDGGSGA FPPGHFKDPK RLYCKNGGFF LRIHPDGRVD GVREKSDPHI
61KLQLQAEERG VVSIKGVCAN RYLAMKEDGR LLASKCVTDE CFFFERLESN NYNTYRSRKY
121TSWYVALKRT GQYKLGSKTG PGQKAILFLP MSAKS
```

Amino acid sequence of *Nomascus leucogenys* (Northern
white-cheeked gibbon) FGF2 (SEQ ID NO: 128) (GenBank
accession no. XP_003271404, which is hereby
incorporated by reference in its entirety):

```
1MAAGSITTLP ALPEDGGSGA FPPGHFKDPK RLYCKNGGFF LRIHPDGRVD GVREKSDPHI
61KLQLQAEERG VVSIKGVCAN RYLAMKEDGR LLASKCVTDE CFFFERLESN NYNTYRSRKY
121TSWYVALKRT GQYKLGSKTG PGQKAILFLP MSAKS
```

Amino acid sequence of *Equus caballus* (horse) FGF2
(SEQ ID NO: 129) (GenBank accession no. NP_001182150,
which is hereby incorporated by reference in its entirety):

```
1MAAGSITTLP ALPEDGGSGA FPPGHFKDPK RLYCKNGGFF LRIHPDGRVD GVREKSDPHI
61KLQLQAEERG VVSIKGVCAN RYLAMKEDGR LLASKCVTDE CFFFERLESN NYNTYRSRKY
121SSWYVALKRT GQYKLGPKTG PGQKAILFLP MSAKS
```

Amino acid sequence of *Bos taurus* (cattle) FGF2
(SEQ ID NO: 130) (GenBank accession no. NP_776481,
which is hereby incorporated by reference in its entirety):

```
1MAAGSITTLP ALPEDGGSGA FPPGHFKDPK RLYCKNGGFF LRIHPDGRVD GVREKSDPHI
61KLQLQAEERG VVSIKGVCAN RYLAMKEDGR LLASKCVTDE CFFFERLESN NYNTYRSRKY
121SSWYVALKRT GQYKLGPKTG PGQKAILFLP MASKS
```

Amino acid sequence of *Papio anubis* (Olive baboon) FGF2
(SEQ ID NO: 131) (GenBank accession no. XP_003899210,
which is hereby incorporated by reference in its entirety):

```
1MAAGSITTLP ALPEDGGSGA FPPGHFKDPK RLYCKNGGFF LRIHPDGRVD GVREKSDPHI
61KLQLQAEERG VVSIKGVCAN RYLAMKEDGR LLASKCVTDE CFFFERLESN NYNTYRSRKY
121TSWYVALKRT GQYKLGSKTG PGQKAILFLP MSAKS
```

TABLE 3-continued

Amino acid sequence of *Vicugna pacos* (alpaca) FGF2
(SEQ ID NO: 132) (Ensembl accession no. ENSVPAP00000009804,
which is hereby incorporated by reference in its entirety):

```
111                                              MAAGSITTLP
121ALPEDGGSGA FPPGHFKDPK RLYCKNGGFF LRIHPDGRVD GVREKSDPHI KLQLQAEERG
181VVSIKGVCAN RYLAMKEDGR LLASKCVTDE CFFFERLESN NYNTYRSRKY SSWYVALKRT
241GQYKLGPKTG PGQKAILFLP MSAKS
```

Amino acid sequence of *Ovis aries* (sheep) FGF2
(SEQ ID NO: 133) (GenBank accession no. NP_001009769,
which is hereby incorporated by reference in its entirety):

```
  1MAAGSITTLP ALPEDGGSSA FPPGHFKDPK RLYCKNGGFF LRIHPDGRVD GVREKSDPHI
 61KLQLQAEERG VVSIKGVCAN RYLAMKEDGR LLASKCVTDE CFFFERLESN NYNTYRSRKY
121SSWYVALKRT GQYKLGPKTG PGQKAILFLP MSAKS
```

Amino acid sequence of *Capreolus capreolus* (Western roe deer)
FGF2 (partial amino acid sequence corresponding to human FGF2
residues 42 to 149) (SEQ ID NO: 134) (GenBank accession no.
AAF73226, which is hereby incorporated by reference in
its entirety):

```
 1RIHPDGRVDG VREKSDPHIK LQLQAEERGV VSIKGVCANR YLAMKEDGRL LASKCVTDEC
61FFFERLESNN YNTYRSRKYS SWYVALKRTG QYKLGPKTGP GQKAILFL
```

Amino acid sequence of *Loxodonta africana* (elephant) FGF2
(partial amino acid sequence corresponding to human FGF2
residues 60 to 155) (SEQ ID NO: 135) (Ensembl accession no.
ENSLAFP00000008249, which is hereby incorporated by
reference in its entirety):

```
 1VKLQLQAEER GVVSIKGVCA NRYLAMKEDG RLLASRCVTD ECFFFERLES NNYNTYRSRK
61YTSWYVALKR TGQYKLGSKT GPGQKAILFL PMSAKS
```

Amino acid sequence of *Sus scrofa* (pig) FGF2 (partial
amino acid sequence corresponding to human FGF2
residues 36 to 155) (SEQ ID NO: 136) (GenBank accession
no. CAE11791 and Ensembl accession no.
ENSSSCP00000009695, which is hereby incorporated by
reference in its entirety):

```
 1NGGFFLRIHP DGRVDGVREK SDPHIKLQLQ AEERGVVSIK GVCANRYLAM KEDGRLLASK
61CVTDECFFFE RLESNNYNTY RSRKYSSWYV ALKRTGQYKL GPKTGPGQKA ILFLPMSAKS
```

Amino acid sequence of *Ailuropoda melanoleuca* (panda) FGF2
(partial amino acid sequence corresponding to human FGF2
residues 60 to 155)(SEQ ID NO: 137) (Ensembl accession no.
ENSAMEP00000018489, which is hereby incorporated by
reference in its entirety):

```
 1VKLQLQAEER GVVSIKGVCA NRYLAMKEDG RLLASKCVTD ECFFFERLES NNYNTYRSRK
61YSSWYVALKR TGQYKLGPKT GPGQKAILFL PMSAKS
```

Amino acid sequence of *Choloepus hoffmanni* (sloth) FGF2
(SEQ ID NO: 138) (Ensembl accession no.
ENSCHOP00000010051, which is hereby incorporated by
reference in its entirety):

```
 14                                               MAAGSIT
 21TLPALPEDGG SGALPPGHFK DPKRLYCKNG GFFLRIHPDG RVDGVREKSD PHIKLQLQAE
 81ERGVVSIKGV CANRYLAMKE DGRLQASKCV TDECFFFERL ESNNYNTYRS RKYSSWYVAL
141KRTGQYKLGP KTGPGQKAIL FLPMSAKS
```

Amino acid sequence of *Bubalus bubalis* (water buffalo) FGF2
(SEQ ID NO: 139) (GenBank accession no. AFH66795, which is
hereby incorporated by reference in its entirety):

```
  1MAAGSITTLP PLPEDGGSGA FPPGHFKDPK RLYCKNGGFF LRIHPDGRVD GVREKSDPHI
 61KLQLQAEERG VVSIKGVCAN RYLAMKEDGR LLASKCVTDE CFFFERLESS NYNTYRSRKY
121SSWYVALKRT GQYKLGPKTG PGQKAILFLP MSAKS
```

Amino acid sequence of *Canis lupus familiaris* (dog) FGF2
(SEQ ID NO: 140) (GenBank accession no. XP_003432529,
which is hereby incorporated by reference in its entirety):

```
 40                                         M AAGSITTLPA LPEDGGSGAF
 61PPGHFKDPKR LYCKKGGFFL RIHPDGRVDG VREKSDPHVK LQLQAEERGV VSIKGVCANR
121YLAMKEDGRL LASKCVTDEC FFFERLESNN YNTYRSRKYS SWYVALKRTG QYKLGPKTGP
181GQKAILFLPM SAKS
```

TABLE 3-continued

Amino acid sequence of *Rattus norvegicus* (Norway rat) FGF2
(SEQ ID NO: 141) (GenBank accession no. NP_062178,
which is hereby incorporated by reference in its entirety):

```
1   MAAGSITSLP ALPEDGGGAF PPGHFKDPKR LYCKNGGFFL RIHPDGRVDG VREKSDPHVK
61  LQLQAEERGV VSIKGVCANR YLAMKEDGRL LASKCVTEEC FFFERLESNN YNTYRSRKYS
121 SWYVALKRTG QYKLGSKTGP GQKAILFLPM SAKS
```

Amino acid sequence of *Heterocephalus glaber* (naked mole-rat)
FGF2 (partial amino acid sequence corresponding to human FGF2
residues 22 to 155) (SEQ ID NO: 142) (GenBank accession no.
EHB17407, which is hereby incorporated by reference in
its entirety):

```
1   ppghfkdpkr lycknggffl rihpdgrvdg vreksdphvk lqlqaeergv vsikgvcanr
61  ylamkedgrl laskcvtdec ffferlesnn yntyrsrkys swyvalkrtg qyklgsktgp
121 gqkailflpm saks
```

Amino acid sequence of *Otolemur garnettii* (bushbaby) FGF2
(SEQ ID NO: 143) (Ensembl accession no. ENSOGAP00000021960,
which is hereby incorporated by reference in its entirety):

```
52                                                         MAAGSITTL
61  PSLPEDGGSD AFPPGHFKDP KRLYCKNGGF FLRIHPDGRV DGVREKSDPY IKLQLQAEER
121 GVVSIKGVCA NRYLAMKEDG RLLASKLITD ECFFFERLES NNYNTYRSRK YSSWYVALKR
181 TGQYKLGSKT GPGQKAILFL PMSAKS
```

Amino acid sequence of *Mus musculus* (house mouse) FGF2
(SEQ ID NO: 144) (GenBank accession no. NP_032032,
which is hereby incorporated by reference in its entirety):

```
1   MAASGITSLP ALPEDGGAAF PPGHFKDPKR LYCKNGGFFL RIHPDGRVDG VREKSDPHVK
61  LQLQAEERGV VSIKGVCANR YLAMKEDGRL LASKCVTEEC FFFERLESNN YNTYRSRKYS
121 SWYVALKRTG QYKLGSKTGP GQKAILFLPM SAKS
```

Amino acid sequence of *Ictidomys tridecemlineatus* (squirrel)
FGF2 (partial amino acid sequence corresponding to human FGF2
residues 12 to 155) (SEQ ID NO: 145) (Ensembl accession no.
ENSSTOP00000015653, which is hereby incorporated by
reference in its entirety):

```
1   LPEDGGGGAF PPGHFKDPKR LYCKNGGFFL RIHPDGRVDG VREKSDPHIK LQLQAEDRGV
61  VSIKGVCANR YLAMKEDGRL LASKCVTDEC FFFERLESNN YNTYRSRKYS SWYVALKRTG
121 QYKLGSKTGP GQKAILFLPM SAKS
```

Amino acid sequence of *Felis catus* (domestic cat) FGF2
(partial amino acid sequence corresponding to human FGF2
residues 25 to 130) (SEQ ID NO: 146) (GenBank accession no.
ABY47638, which is hereby incorporated by reference in
its entirety):

```
1   HFKDPKRLYC KNGGFFLRIH PDGRVDGVRE KSDPHIKLQL QAEERGVVSI KGVCANRYLA
61  MKEDGRLLAS KCVTDECFFF ERLESNNYNT YRSRKYSSWY VALKRT
```

Amino acid sequence of *Cavia porcellus* (guinea pig) FGF2
(partial amino acid sequence corresponding to human FGF2
residues 60 to 155) (SEQ ID NO: 147) (Ensembl accession no.
ENSCPOP00000004847, which is hereby incorporated by
reference in its entirety):

```
1   VKLQLQAEDR GVVSIKGVCA NRYLAMKEDG RLLASKCVTD ECFFFERLES NNYNTYRSRK
61  YSSWYVALKR TGQYKLGSKT GPGQKAILFL PMSAKS
```

Amino acid sequence of *Sarcophilus harrisii* (Tasmanian devil)
FGF2 (SEQ ID NO: 148) (Ensembl accession no.
ENSSHAP00000012215, which is hereby incorporated by
reference in its entirety):

```
48                                             MAA GSITTLPALA
61  GDGASGGAFP PGHFQDPKRL YCKNGGFFLR IHPDGHVDGI REKSDPHIKL QLQAEERGVV
121 SIKGVCANRY LAMKEDGRLL ALKCVTEECF FFERLESNNY NTYRSRKYSN WYVALKRTGQ
181 YKLGSKTGPG QKAILFLPMS AKS
```

TABLE 3-continued

Amino acid sequence of *Monodelphis domestica* (gray short-tailed opossum) FGF2 (SEQ ID NO: 149) (GenBank accession no. NP_001029148, which is hereby incorporated by reference in its entirety):

```
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFL PMSAKS
```

Amino acid sequence of *Oryctolagus cuniculus* (rabbit) FGF2 (SEQ ID NO: 150) (GenBank accession no. XP_002717284, which is hereby incorporated by reference in its entirety):

```
  1 MAAESITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGSKTG PGQKAILFLP MSAKS
```

Amino acid sequence of *Meleagris gallopavo* (turkey) FGF2 (partial amino acid sequence corresponding to human FGF2 residues 31 to 155) (SEQ ID NO: 151) (Ensembl accession no. ENSMGAP00000010977, which is hereby incorporated by reference in its entirety):

```
  1 RLYCKNGGFF LRINPDGRVD GVREKSDPHI KLQLQAEERG VVSIKGVSAN RFLAMKEDGR
 61 LLALKCATEE CFFFERLESN NYNTYRSRKY SDWYVALKRT GQYKPGPKTG PGQKAILFLP
121 MSAKS
```

Amino acid sequence of *Gallus gallus* (chicken) FGF2 (SEQ ID NO: 152) (GenBank accession no. NP_990764

```
  1 maagaagsit tlpalpddgg ggafppghfk dpkrlyckng gfflrinpdg rvdgvreksd
 61 PHIKLQLQAE ERGVVSIKGV SANRFLAMKE DGRLLALKCA TEECFFFERL ESNNYNTYRS
121 RKYSDWYVAL KRTGQYKPGP KTGPGQKAIL FLPMSAKS
```

Amino acid sequence of *Taeniopygia guttata* (zebra finch) FGF2 (SEQ ID NO: 153) (GenBank accession no. XP_002188397, which is hereby incorporated by reference in its entirety):

```
  1 MAAAGGIATL PDDGGSGAFP PGHFKDPKRL YCKNGGFFLR INPDGKVDGV REKSDPHIKL
 61 QLQAEERGVV SIKGVSANRF LAMKEDGRLL ALKYATEECF FFERLESNNY NTYRSRKYSD
121 WYVALKRTGQ YKPGPKTGPG QKAILFLPMS AKS
```

Amino acid sequence of *Cynops pyrrhogaster* (Japanese firebelly newt) FGF2 (SEQ ID NO: 154) (GenBank accession no. BAB63249, which is hereby incorporated by reference in its entirety):

```
  1 MAAGSITSLP ALPEDGNGGT FTPGGFKEPK RLYCKNGGFF LRINSDGKVD GAREKSDSYI
 61 KLQLQAEERG VVSIKGVCAN RYLAMKDDGR LMALKWITDE CFFFERLESN NYNTYRSRKY
121 SDWYVALKRT GQYKNGSKTG AGQKAILFLP MSAKS
```

Amino acid sequence of *Xenopus laevis* (African clawed frog) FGF2 (SEQ ID NO: 155) (GenBank accession no. NP_001093341, which is hereby incorporated by reference in its entirety):

```
  1 MAAGSITTLP TESEDGGNTP FSPGSFKDPK RLYCKNGGFF LRINSDGRVD GSRDKSDSHI
 61 KLQLQAVERG VVSIKGITAN RYLAMKEDGR LTSLRCITDE CFFFERLEAN NYNTYRSRKY
121 SSWYVALKRT GQYKNGSSTG PGQKAILFLP MSAKS
```

Amino acid sequence of *Didelphis albiventris* (white-eared opossum) FGF2 (SEQ ID NO: 156) (GenBank accession no. ABL77404, which is hereby incorporated by reference in its entirety):

```
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFS PCLLRC
```

Amino acid sequence of *Myotis lucifugus* (microbat) FGF2 (partial amino acid sequence corresponding to human FGF2 residues 60 to 155) (SEQ ID NO: 157) (Ensembl accession no. ENSMLUP00000017859, which is hereby incorporated by reference in its entirety):

```
  1 VKLQLQAEER GVVSIKGVCA NRYLAMKEDG RLQASKCVTD ECFFFERLES NNYNTYRSRK
 61 YSSWYVALKR NGQYKLGPKT GPGQKAILFL PMSAKS
```

TABLE 3-continued

Amino acid sequence of *Anolis carolinensis* (anole lizard) FGF2 (partial amino acid sequence corresponding to human FGF2 residues 16 to 155) (SEQ ID NO: 158) (Ensembl accession no. ENSACAP00000011657, which is hereby incorporated by reference in its entirety):

```
1AAAASFPPGP FKDPKRLYCK NGGFFLRINP DGGVDGVREK SDPNIKLLLQ AEERGVVSIK
61GVCANRFLAM NEDGRLLALK YVTDECFFFE RLESNNYNTY RSRKYRDWYI ALKRTGQYKL
121GPKTGRGQKA ILFLPMSAKS
```

Amino acid sequence of *Dasypus novemcinctus* (armadillo) FGF2 (partial amino acid sequence corresponding to human FGF2 residues 1 to 94) (SEQ ID NO: 159) (Ensembl accession no. ENSDNOP00000011351, which is hereby incorporated by reference in its entirety):

```
124   MAAGSIT TLPALPEDGG SGAFPPGHFK DPKRLYCKNG GFFLRIHPDG RVDGVREKSD
181PNIKLQLQAE ERGVVSIKGV CANRYLAMRE DGRLQAS
```

Amino acid sequence of *Tupaia belangeri* (tree shrew) FGF2 (SEQ ID NO: 160) (Ensembl accession no. ENSTBEP00000000985, which is hereby incorporated by reference in its entirety):

```
1AGVRAEREEA PGSGDSRGTD PAARSLIRRP DAAAREALLG ARSRVQGSST SWPASSRTGI
61KLPDDSGQGM GGYPLDRPSR STGRGLGGAP DPAVKLQLQA EERGVVSIKG VCANRYLAMK
121EDGRLLASKC VTDECFFFER LESNNYNTYR SRKYSSWYVA LKRTGQYKLG SKTGPGQKAI
181LFLPMSAKS
```

Amino acid sequence of *Xenopus silurana* tropicalis (western clawed frog) FGF2 (SEQ ID NO: 161) (GenBank accession no. NP_001017333, which is hereby incorporated by reference in its entirety):

```
1MAAGSITTLP TESEDGNTPF PPGNFKDPKR LYCKNGGYFL RINSDGRVDG SRDKSDLHIK
61LQLQAVERGV VSIKGITANR YLAMKEDGRL TSLKCITDEC FFYERLEANN YNTYRSRKNN
121SWYVALKRTG QYKNGSTTGP GQKAILFLPM SAKS
```

Amino acid sequence of *Latimeria chalumnae* (coelacanth) FGF2 (SEQ ID NO: 162) (Ensembl accession no. ENSLACP00000019200, which is hereby incorporated by reference in its entirety):

```
1MAAGGITTLP AVPEDGGSST FPPGNFKEPK RLYCKNGGYF LRINPDGRVD GTREKNDPYI
61KLQLQAESIG VVSIKGVCSN RYLAMNEDCR LFGLKYPTDE CFFHERLESN NYNTYRSKKY
121SDWYVALKRT GQYKPGPKTG LGQKAILFLP MSAKS
```

Amino acid sequence of *Tetraodon nigroviridis* (spotted green pufferfish) FGF2 (SEQ ID NO: 163) (GenBank accession no. CAG04681, which is hereby incorporated by reference in its entirety):

```
34                              MATGGIT TLPSTPEDGG SSGFPPGSFK
61DPKRLYCKNG GFFLRIKSDG VVDGIREKSD PHIKLQLQAT SVGEVVIKGV CANRYLAMNR
121DGRLFGTKRA TDECHFLERL ESNNYNTYRS RKYPTMFVGL TRTGQYKSGS KTGPGQKAIL
181FLPMSAKC
```

Amino acid sequence of *Gasterosteus aculeatus* (stickleback) FGF2 (SEQ ID NO: 164) (Ensembl accession no. ENSGACP00000022078, which is hereby incorporated by reference in its entirety):

```
1MATAGFATLP STPEDGGSGG FTPGGFKDPK RLYCKNGGFF LRIRSDGGVD GIREKSDAHI
61KLQIQATSVG EVVIKGVCAN RYLAMNRDGR LFGVRRATDE CYFLERLESN NYNTYRSRKY
121PGMYVALKRT GQYKSGSKTG PGQKAILFLP MSAKC
```

Amino acid sequence of *Takifugu rubripes* (fugu rubripes) FGF2 (SEQ ID NO: 165) (GenBank accession no. CAD19830, which is hereby incorporated by reference in its entirety):

```
1MATGGITTLP STPEDGGSGG FPPGSFKDPK RLYCKNGGFF LRIRSDGAVD GTREKTDPHI
61KLQLQATSVG EVVIKGVCAN RYLAMNRDGR LFGMKRATDE CHFLERLESN NYNTYRSRKY
121PNMFVGLTRT GNYKSGTKTG PCQKAILFLP MSAKY
```

Amino acid sequence of *Oncorhynchus mykiss* (rainbow trout) FGF2 (SEQ ID NO: 166) (GenBank accession no. NP_001118008, which is hereby incorporated by reference in its entirety):

```
1MATGEITTLP ATPEDGGSGG FLPGNFKEPK RLYCKNGGYF LRINSNGSVD GIRDKNDPHN
61KLQLQATSVG EVVIKGVSAN RYLAMNADGR LFGPRRTTDE CYFMERLESN NYNTYRSRKY
121PEMYVALKRT GQYKSGSKTG PGQKAILFLP MSARR
```

TABLE 3-continued

Amino acid sequence of *Salmo salar* (salmon) FGF2
(SEQ ID NO: 167) (GenBank accession no. ACJ02099,
which is hereby incorporated by reference in its entirety):

```
  1 MATGEITTLP ATPEDGGSGG FPPGNFKDPK RLYCKNGGYF LRINSNGSVD GIREKNDPHK
 61 QPQFVRAWTL QGVKRSTGML AHVDSNASHN CVKVAGCSLG EFGSMSNRPH NRRPRVATPA
121 QDLHIRLLHL RDRLKPATRT ADKTEEYFCL
```

Amino acid sequence of *Danio rerio* (zebrafish) FGF2
(SEQ ID NO: 168) (GenBank accession no. AAP32155,
which is hereby incorporated by reference in its entirety):

```
  1 MATGGITTLP AAPDAENSSF PAGSFRDPKR LYCKNGGFFL RINADGRVDG ARDKSDPHIR
 61 LQLQATAVGE VLIKGICTNR FLAMNADGRL FGTKRTTDEC YFLERLESNN YNTYRSRKYP
121 DWYVALKRTG QYKSGSKTSP GQKAILFLPM SAKC
```

Amino acid sequence of *Oreochromis niloticus* (Nile tilapia)
FGF2 (SEQ ID NO: 169) (GenBank accession no.
XP_003443412, which is hereby incorporated by
reference in its entirety):

```
  1 MATGGITTLP ATPEDGGSSG FPPGNFKDPK RLYCKNGGFF LRIKSDGGVD GIREKNDPHI
 61 KLQLQATSVG EVVIKGICAN RYLAMNRDGR LFGARRATDE CYFLERLESN NYNTYRSRKY
121 PNMYVALKRT GQYKSGSKTG PGQKAILFLP MSAKC
```

Amino acid sequence of *Oryzias latipes* (medaka) FGF2
(SEQ ID NO: 170) (Ensembl accession no. ENSORLP00000025834,
which is hereby incorporated by reference in its entirety):

```
  1 MATGEITTLP SPAENSRSDG FPPGNYKDPK RLYCKNGGLF LRIKPDGGVD GIREKKDPHV
 61 KLRLQATSAG EVVIKGVCSN RYLAMHGDGR LFGVRQATEE CYFLERLESN NYNTYRSKKY
121 PNMYVALKRT GQYKPGNKTG PGQKAILFLP MSAKY
```

As noted above, the portion of the paracrine FGF may be modified to decrease binding affinity for heparin and/or heparan sulfate compared to the portion without the modification. In one embodiment, the modification of the paracrine FGF includes one or more substitutions, additions, or deletions.

In one embodiment, the modification is one or more substitutions located at one or more amino acid residues of SEQ ID NO: 121 selected from N36, K128, R129, K134, K138, Q143, K144, C78, C96, and combinations thereof. In one embodiment, the one or more substitutions are selected from N36T, K128D, R129Q, K134V, K138H, Q143M, K144T/L/I, C78S, C96S, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. Amino acid residues corresponding to those of SEQ ID NO: 121 may be determined by, for example, sequence analysis and structural analysis.

It will be understood that the portion of the paracrine FGF according to the present invention may be derived from a nucleotide sequence that encodes a paracrine FGF protein. For example, in one embodiment, nucleotide sequence is the nucleotide sequence that encodes human FGF2 (GenBank Accession No. NM_002006, which is hereby incorporated by reference in its entirety)(SEQ ID NO: 171), as follows:

```
468                                    ATG GCAGCCGGGA
481 GCATCACCAC GCTGCCCGCC TTGCCCGAGG ATGGCGGCAG CGGCGCCTTC CCGCCCGGCC
541 ACTTCAAGGA CCCCAAGCGG CTGTACTGCA AAAACGGGGG CTTCTTCCTG CGCATCCACC
601 CCGACGGCCG AGTTGACGGG GTCCGGGAGA GAGCGACCC TCACATCAAG CTACAACTTC
661 AAGCAGAAGA GAGAGGAGTT GTGTCTATCA AAGGAGTGTG TGCTAACCGT TACCTGGCTA
721 TGAAGGAAGA TGGAAGATTA CTGGCTTCTA AATGTGTTAC GGATGAGTGT TTCTTTTTTG
781 AACGATTGGA ATCTAATAAC TACAATACTT ACCGGTCAAG GAAATACACC AGTTGGTATG
841 TGGCACTGAA ACGAACTGGG CAGTATAAAC TTGGATCCAA AACAGGACCT GGGCAGAAAG
901 CTATACTTTT TCTTCCAATG TCTGCTAAGA GCTGA
```

In another embodiment of the present invention, the portion of the paracrine FGF of the chimeric protein may be derived from a nucleotide sequence that encodes an ortholog of human FGF2. Nucleotide sequences that encode FGF2 orthologs are shown in Table 4.

TABLE 4

Gorilla FGF2 gene coding sequence (amino acids
("aa" 104-258) (SEQ ID NO: 172) (Ensembl
accession no. ENSGGOT00000004842, which is
hereby incorporated by reference in its entirety):

```
310           ATGGCAGCC GGGAGCATCA CCACGCTGCC CGCCTTGCCC GAGGATGGCG
359 GCAGCGGCGC CTTCCCGCCC GGCCACTTCA AGGACCCCAA GCGGCTGTAC TGCAAAAACG
419 GGGGCTTCTT CCTGCGCATC CACCCCGACG GCCGAGTTGA CGGGGTCCGG GAGAAGAGCG
479 ACCCTCACAT CAAGCTACAA CTTCAAGCAG AAGAGAGAGG AGTTGTGTCT ATCAAAGGAG
539 TGTGTGCTAA CCGTTACCTT GCTATGAAGG AAGATGGAAG ATTACTGGCT TCTAAATGTG
599 TTACGGATGA GTGTTTCTTT TTTGAACGAT TGGAATCTAA TAACTACAAT ACTTACCGGT
659 CAAGGAAATA CACCCAGTTGG TATGTGCAC TGAAACGAAC TGGGCAGTAT AAACTTGGAT
719 CCAAAACAGG ACCTGGGCAG AAAGCTATAC TTTTTCTTCC AATGTCTGCT AAGAGCTGA
```

Sumatran orangutan FGF2 gene coding sequence (aa 168-322)
(SEQ ID NO: 173) (GenBank accession no.
XM_002815126, which is hereby incorporated by
reference in its entirety):

```
504              ATGGCAG CCGGGAGCAT CACCACGCTG CCCGCCTTGC
541 CGAGGATGG CGGCAGCGGC GCCTTCCCGC CGGGCCACTT CAAGGACCCC AAGCGGCTGT
601 ACTGCAAAAA CGGGGGCTTC TTCCTGCGCA TCCACCCCGA CGGCCGAGTT GACGGGGTCC
661 GAGAGAAGAG CGACCCTCAC ATCAAACTAC AACTTCAAGC AGAAGAAAGA GGAGTTGTGT
721 CTATCAAAGG AGTGTGTGCT AACCGCTACC TTGCTATGAA GGAAGATGGA AGATTACTGG
781 CTTCTAAATG TGTTACGGAT GAGTGTTTCT TTTTTGAACG ATTGGAATCT AATAACTACA
841 ATACTTACCG GTCAAGGAAA TACACCAGTT GGTATGTGGC ACTGAAACGA ACTGGGCAGT
901 ATAAACTTGG ATCCAAAACA GGACCTGGGC AGAAAGCTAT ACTTTTTCTT CCAATGTCTG
961 CTAAGAGCTG A
```

Rhesus monkey FGF2 gene coding sequence (aa 83-237)
(SEQ ID NO: 174) (GenBank accession no.
XM_001099284, which is hereby incorporated by
reference in its entirety):

```
247         ATGG CAGCCGGGAG CATCACCACG CTGCCCGCCT TGCCCGAGGA TGGCGGCAGC
301 GGCGCCTTCC CGCCTGGCCA CTTCAAGGAC CCCAAGCGGC TGTACTGCAA AAACGGGGGC
361 TTCTTCCTGC GCATTCACCC CGACGGCCGA GTTGACGGGG TCCGGGAGAA GAGCGACCCT
421 CACATCAAAT TACAACTTCA AGCAGAAGAG AGAGGAGTTG TGTCTATCAA AGGAGTGTGT
481 GCTAACCGTT ACCTTGCTAT GAAGGAAGAT GGAAGATTAC TGGCTTCTAA ATGTGTTACA
541 GATGAGTGTT TCTTTTTTGA ACGATTGGAA TCTAATAACT ACAATACTTA CCGGTCAAGG
601 AAATACACCA GTTGGTATGT GGCACTGAAA CGAACTGGGC AATATAAACT TGGATCCAAA
661 ACAGGACCTG GCAGAAAGC TATACTTTTT CTTCCAATGT CTGCTAAGAG CTGA
```

Chimpanzee FGF2 gene coding sequence (aa 134-288)
(SEQ ID NO: 175) (GenBank accession no.
NM_001110241, which is hereby incorporated by
reference in its entirety):

```
400                                                       A TGGCAGCCGG GAGCATCACC
421 ACGCTGCCCG CCTTGCCCGA GGATGGCGGC AGCGGCGCCT TCCCGCCCGG CCACTTCAAG
481 GACCCCAAGC GGCTGTACTG CAAAAACGGG GGCTTCTTCC TGCGCATCCA CCCCGACGGC
541 CGAGTTGACG GGGTCCGGGA AGAGCGAC CCTCACATCA AGCTACAACT TCAAGCAGAA
601 GAGAGAGGAG TTGTGTCTAT CAAAGGAGTG TGTGCTAACC GTTACCTTGC TATGAAGGAA
661 GATGGAAGAT TACTGGCTTC TAAATGTGTT ACGGATGAGT GTTTCTTTTT TGAACGATTG
721 GAATCTAATA ACTACAATAC TTACCGGTCA AGGAAATACA CCAGTTGGTA TGTGGCACTG
781 AAACGAACTG GGCAGTATAA ACTTGGATCC AAAACAGGAC TGGGCAGAA AGCTATACTT
841 TTTCTTCCAA TGTCTGCTAA GAGCTGA
```

Pygmy chimpanzee FGF2 gene coding sequence (112-266)
(SEQ ID NO: 176) (GenBank accession no.
XM_003816433, which is hereby incorporated by
reference in its entirety):

```
334                      ATGGCAG CCGGGAGCAT CACCACGCTG
361 CCCGCCTTGC CGAGGATGG CGGCAGCGGC GCCTTCCCGC CGGGCCACTT CAAGGACCCC
421 AAGCGGCTGT ACTGCAAAAA CGGGGGCTTC TTCCTGCGCA TCCACCCCGA CGGCCGAGTT
481 GACGGGGTCC GGGAGAAGAG CGACCCTCAC ATCAAGCTAC AACTTCAAGC AGAAGAGAGA
541 GGAGTTGTGT CTATCAAAGG AGTGTGTGCT AACCGTTACC TTGCTATGAA GGAAGATGGA
601 AGATTACTGG CTTCTAAATG TGTTACGGAT GAGTGTTTCT TTTTTGAACG ATTGGAATCT
661 AATAACTACA ATACTTACCG GTCAAGGAAA TACACCAGTT GGTATGTGGC ACTGAAACGA
721 ACTGGGCAGT ATAAACTTGG ATCCAAAACA GGACCTGGGC AGAAAGCTAT ACTTTTTCTT
781 CCAATGTCTG CTAAGAGCTG A
```

TABLE 4-continued

Bolivian squirrel monkey FGF2 gene coding sequence (1-155)
(SEQ ID NO: 177) (GenBank accession no.
XM_003936241, which is hereby incorporated
by reference in its entirety):

```
 23                                    ATGGCAGC CGGGAGCATC ACCACGCTGC CCGCCCTGCC
 61 CGAAGACGGC GGCAGCGGCG CCTTCCCGCC CGGCCACTTC AAAGACCCCA AGCGGCTGTA
121 CTGCAAAAAC GGGGGCTTCT TCCTGCGAAT CCACCCCGAC GGCCGAGTGG ACGGGGTCCG
181 GGAGAAGAGC GACCCTCACA TCAAACTACA ACTTCAAGCA GAAGAGAGAG GAGTTGTATC
241 TATCAAAGGA GTGTGTGCTA ACCGTTACCT TGCTATGAAG AAGATGGAA GATTACTGGC
301 TTCTAAATGT GTTACGGACG AGTGTTTCTT TTTTGAACGA TTGGAATCTA ATAACTACAA
361 TACTTACCGA TCAAGGAAAT ACACCAGTTG GTATGTGGCA CTGAAACGAA CTGGGCAGTA
421 TAAACTTGGA TCCAAAACAG GACCTGGGCA GAAAGCTATA CTTTTTCTTC AATGTCTGC
481 TAAGAGCTGA
```

Northern white-cheeked gibbon FGF2 gene coding sequence
(aa 1-155) (SEQ ID NO: 178) (GenBank accession no.
XM_003271356, which is hereby incorporated by
reference in its entirety):

```
435                                         ATG GCAGCCGGGA
481 GCATCACCAC GCTGCCCGCC TTGCCGGAGG ATGGCGGCAG CGGCGCCTTC CCGCCCGGCC
541 ACTTCAAGGA CCCCAAGCGG CTGTACTGCA AAAACGGGGG TTTCTTCCTG CGCATCCACC
601 CCGACGGTCG AGTTGACGGG GTCCGGGAGA AGAGCGACCC TCACATCAAA CTACAACTTC
661 AAGCAGAAGA GAGAGGAGTT GTGTCTATCA AAGGAGTGTG TGCTAACCGT TACCTTGCTA
721 TGAAGGAAGA TGGAAGATTA CTGGCTTCTA AATGTGTTAC GGATGAGTGT TTCTTTTTTG
781 AACGATTGGA ATCTAATAAC TACAATACTT ACCGGTCAAG GAAATACACC AGTTGGTATG
841 TGGCACTGAA ACGAACTGGG CAGTATAAAC TTGGATCCAA AACAGGACCT GGGCAGAAAG
901 CTATACTTTT TCTTCCAATG TCTGCTAAGA GCTGA
```

Horse FGF2 gene coding sequence (aa 1-155) (SEQ ID NO: 179)
(GenBank accession no. NM_001195221, which is
hereby incorporated by reference in its entirety):

```
 54                                                             ATGGCAG
 61 CCGGGAGCAT CACCACGCTG CCCGCCCTGC CGAGGACGG CGGCAGCGGC GCCTTCCCGC
121 CCGGCCACTT CAAGGACCCC AAGCGGCTCT ACTGCAAAAA CGGGGGCTTC TTCCTGCGCA
181 TCCACCCCGA CGGCCGAGTG GACGGGGTCC GGGAGAAGAG CGACCCTCAC ATCAAACTAC
241 AACTTCAAGC AGAAGAGAGA GGGGTTGTGT CTATCAAAGG AGTGTGTGCG AACCGTTATC
301 TTGCTATGAA GGAAGATGGA AGGTTACTGG CTTCTAAATG TGTTACGGAC GAGTGTTTCT
361 TTTTTGAACG ATTGGAATCT AATAACTACA ATACTTACCG GTCAAGGAAA TACTCCAGTT
421 GGTATGTGGC CCTGAAACGA ACGGGGCAGT ATAAACTTGG ACCCAAAACA GGACCTGGAC
481 AGAAAGCTAT ACTTTTTCTT CCAATGTCTG CTAAGAGCTG A
```

Cattle FGF2 gene coding sequence (aa 1-155) (SEQ ID NO: 180)
(GenBank accession no. NM_174056, which is hereby
incorporated by reference in its entirety):

```
104                                         ATGGCCG CCGGGAGCAT
121 CACCACGCTG CCAGCCCTGC CGGAGGACGG CGGCAGCGGC GCTTTCCCGC CGGCCACTT
181 CAAGGACCCC AAGCGGCTGT ACTGCAAGAA CGGGGGCTTC TTCCTGCGCA TCCACCCCGA
241 CGGCCGAGTG GACGGGGTCC GCGAGAAGAG CGACCCACAC ATCAAACTAC AACTTCAAGC
301 AGAAGAGAGA GGGGTTGTGT CTATCAAAGG AGTGTGTGCA AACCGTTACC TTGCTATGAA
361 AGAAGATGGA AGATTACTAG CTTCTAAATG TGTTACAGAC GAGTGTTTCT TTTTTGAACG
421 ATTGGAGTCT AATAACTACA ATACTTACCG GTCAAGGAAA TACTCCAGTT GGTATGTGGC
481 ACTGAAACGA CTGGGCAGT ATAAACTTGG ACCCAAAACA GGACCTGGGC AGAAAGCTAT
541 ACTTTTTCTT CCAATGTCTG CTAAGAGCTG A
```

Olive baboon FGF2 gene coding sequence (1-155)
(SEQ ID NO: 181) (GenBank accession no.
XM_003899161, which is hereby incorporated
by reference in its entirety):

```
467                                            ATGG CAGCCGGGAG
481 CATCACCACG CTGCCCGCCT TGCCCGAGGA TGGCGGCAGC GGCGCCTTCC CGCCCGGCCA
541 CTTCAAGGAC CCCAAGCGGC TGTACTGCAA AAACGGGGGC TTCTTCCTGC GCATTCACCC
601 CGACGGCCGA GTTGACGGGG TCCGGGAGAA GAGCGACCCT CACATCAAAT TACAACTTCA
661 AGCAGAAGAG AGAGGAGTTG TGTCTATCAA AGGAGTGTGT GCTAACCGTT ACCTTGCTAT
721 GAAGGAAGAT GGAAGATTAC TGGCTTCTAA ATGTGTTACG GATGAGTGTT TCTTTTTTGA
781 ACGATTGGAA TCTAATAACT ACAATACTTA CCGGTCAAGG AAATACACCA GTTGGTATGT
841 GGCACTGAAA CGAACTGGGC AGTATAAACT TGGATCCAAA ACAGGACCTG GCAGAAAGC
901 TATACTTTTT CTTCCAATGT CTGCTAAGAG CTGA
```

Alpaca FGF2 gene coding sequence (aa 111-265)
(SEQ ID NO: 182) (Ensembl accession no.
ENSVPAT00000010536, which is hereby incorporated by
reference in its entirety):

```
341                                ATGGCAGCTG GGAGCATCAC CACGCTGCCC
361 GCCCTGCCGG AGGACGGCGG CAGCGGCGCC TTCCCGCCCG GCCACTTCAA GGACCCCAAG
```

TABLE 4-continued

```
421  CGGTTGTACT GCAAAAACGG GGGCTTCTTC CTGCGCATCC ACCCCGACGG CCGAGTGGAC
481  GGGGTCCGGG AGAAGAGCGA CCCTCACATC AAACTACAAC TTCAAGCAGA AGAGAGAGGG
541  GTCGTGTCTA TCAAAGGAGT GTGTGCAAAC CGTTACCTTG CTATGAAGGA AGATGGAAGA
601  TTACTGGCTT CTAAATGTGT CACAGACGAG TGTTTCTTTT TTGAACGATT GGAATCTAAT
661  AACTACAATA CTTACCGGTC AAGGAAATAC TCCAGTTGGT ATGTGGCACT GAAACGAACT
721  GGGCAGTACA AACTTGGACC CAAAACAGGA CCTGGGCAGA AAGCTATACT TTTCCTTCCA
781  ATGTCTGCTA AGAGCTGA
```

Sheep FGF2 gene coding sequence (aa 1-155)
(SEQ ID NO: 183) (GenBank accession no.
NM_001009769, which is hereby incorporated
by reference in its entirety):

```
  1  ATGGCCGCCG GGAGCATCAC CACGCTGCCA GCCCTGCCGG AGGACGGCGG CAGCAGCGCT
 61  TTCCCGCCCG GCCACTTTAA GGACCCCAAG CGGCTGTACT GCAAGAACGG GGGCTTCTTC
121  CTGCGCATCC ACCCCGACGG CCGAGTGGAC GGGGTCCGCG AGAAGAGCGA CCCTCACATC
181  AAACTACAAC TTCAAGCAGA AGAGAGAGGG GTTGTGTCTA TCAAAGGAGT GTGTGCAAAC
241  CGTTACCTTG CTATGAAAGA AGATGGAAGA TTACTAGCTT CTAAATGTGT TACAGACGAG
301  TGTTTCTTTT TTGAACGATT GGAGTCTAAT AACTACAATA CTTACCGGTC AAGGAAATAC
361  TCCAGTTGGT ATGTGGCACT GAAACGAACT GGGCAGTATA AACTTGGACC CAAAACAGGA
421  CCTGGGCAGA AAGCTATACT TTTTCTTCCA ATGTCTGCTA AGAGCTGA
```

Western roe deer FGF2 gene coding sequence (1-108;
partial amino acid sequence corresponding to human FGF2
residues 42 to 149) (SEQ ID NO: 184) (GenBank accession
no. AF152587, which is hereby incorporated by reference in
its entirety):

```
  1  GCGCATCCAC CCCGACGGCC GAGTGGACGG GGTCCGCGAG AAGAGTGACC CTCACATCAA
 61  ACTACAACTT CAAGCAGAAG AGAGAGGGGT TGTGTCTATC AAAGGAGTGT GTGCGAACCG
121  TTATCTTGCT ATGAAAGAAG ACGGAAGATT ATTGGCTTCA AAATGTGTTA CAGACGAATG
181  TTTCTTTTTT GAACGATTGG AGTCTAATAA CTACAATACT TACCGGTCAA GGAAATACTC
241  CAGTTGGTAT GTGGCACTGA AACGAACTGG GCAGTATAAA CTTGGACCCA AAACAGGACC
301  TGGGCAGAAA GCTATACTTT TCTT
```

Elephant FGF2 gene coding sequence (1-96; partial amino
acid sequence corresponding to human FGF2 residues 60
to 155) (SEQ ID NO: 185) (Ensembl accession no.
ENSLAFT00000008249, which is hereby incorporated by
reference in its entirety):

```
  1  GTTAAACTAC AGCTTCAAGC AGAAGAGAGA GGTGTTGTGT CTATCAAAGG AGTGTGTGCC
 61  AACCGTTATC TGGCTATGAA GGAAGATGGA AGATTGCTGG CTTCTAGATG TGTGACAGAT
121  GAATGTTTCT TCTTTGAACG ACTGGAATCT AATAACTACA ATACTTACCG GTCAAGGAAA
181  TACACCAGTT GGTATGTGGC ACTGAAACGA ACGGGGCAGT ATAAACTTGG ATCCAAAACA
241  GGACCTGGAC AGAAAGCTAT ACTTTTTCTT CCCATGTCTG CTAAGAGC
```

Pig FGF2 gene coding sequence (1-120; partial amino
acid sequence corresponding to human FGF2 residues 36
to 155) (SEQ ID NO: 186) (GenBank accession no. AJ577089
and Ensembl accession no. ENSSSCT00000009952,
which is hereby incorporated by reference in its entirety):

```
  1  GAACGGGGGC TTCTTCCTGC GCATCCACCC CGACGGCCGA GTGGATGGGG TCCGGGAGAA
 61  GAGCGACCCT CACATCAAAC TACAACTTCA AGCAGAAGAG AGAGGGGTTG TGTCTATCAA
121  AGGAGTGTGT GCAAACCGTT ATCTTGCTAT GAAGGAAGAT GGAAGGATTAC TGGCTTCTAA
181  ATGTGTTACA GACGAGTGTT TCTTTTTTGA ACGACTGGAA TCTAATAACT ACAATACTTA
241  CCGGTCGAGG AAATACTCCA GTTGGTATGT GGCACTGAAA CGAACTGGGC AGTATAAACT
301  TGGACCCAAA ACAGGACCTG GGCAGAAAGC TATACTTTTT CTTCCAATGT CTGCTAAGAG
361  C
```

Panda FGF2 gene coding sequence (1-96; partial amino
acid sequence corresponding to human FGF2 residues 60
to 155) (SEQ ID NO: 187) (Ensembl accession no.
ENSAMET00000019232, which is hereby incorporated by
reference in its entirety):

```
  1  GTCAAACTGC AACTTCAAGC GGAAGAGAGA GGGGTTGTAT CCATCAAAGG AGTATGTGCA
 61  AATCGCTATC TTGCCATGAA GGAAGATGGA AGATTACTGG CTTCTAAATG TGTTACCGAT
121  GAGTGTTTCT TTTTGAGCG ACTGGAATCT AATAACTACA ATACTTACCG GTCAAGGAAA
181  TACTCCAGTT GGTATGTGGC ACTGAAACGA ACTGGGCAGT ATAAACTTGG ACCCAAAACA
241  GGACCTGGGC AGAAAGCTAT ACTTTTTCTT CCAATGTCTG CTAAGAGC
```

Sloth FGF2 gene coding sequence (aa 14-168)
(SEQ ID NO: 188) (Ensembl accession no.
ENSCHOT00000011394, which is hereby
incorporated by reference in its entirety):

```
 40                                                      A TGGCAGCCGG GAGCATCACC
 61  ACGCTGCCCG CCCTGCCCGA GGACGGAGGC AGCGGCGCCT TACCGCCCGG CCACTTCAAA
```

TABLE 4-continued

```
121 GATCCCAAGC GGCTCTACTG CAAAAACGGG GGCTTCTTCC TGCGTATCCA TCCCGACGGC
181 AGAGTGGACG GGGTCCGGGA GAAGAGCGAC CCCCACATCA AACTACAACT TCAAGCAGAA
241 GAGAGAGGGG TTGTGTCTAT CAAAGGTGTG TGTGCAAACC GATATCTTGC TATGAAGGAA
301 GATGGAAGAT TACAGGCTTC TAAATGTGTA ACGGACGAGT GTTTCTTTTT TGAACGATTG
361 GAATCTAATA ACTACAATAC GTACCGATCA AGGAAATACT CCAGTTGGTA TGTGGCACTG
421 AAACGAACTG GCAATATAAC ACTTGGACCC AAAACAGGAC CTGGGCAGAA AGCCATACTT
481 TTTCTTCCAA TGTCTGCTAA GAGCTGA
```

Water buffalo FGF2 gene coding sequence
(aa 1-155) (SEQ ID NO: 189) (GenBank
accession no. JQ326277, which is hereby
incorporated by reference in its entirety):

```
  1 ATGGCCGCCG GGAGCATCAC CACGCTGCCA CCCCTGCCGG AGGACGGCGG CAGCGGCGCT
 61 TTCCCGCCCG GCCACTTCAA GGACCCCAAG CGGCTGTACT GCAAGAACGG GGGCTTCTTC
121 CTGCGCATCC ACCCCGACGG CCGAGTGGAC GGGGTCCGCG AGAAGAGCGA CCCACACATC
181 AAACTACAAC TTCAAGCAGA AGAGAGAGGG GTTGTGTCTA TCAAAGGAGT GTGTGCAAAC
241 CGTTACCTTG CTATGAAAGA AGATGGAAGA TTACTAGCTT CCAAATGTGT TACAGACGAG
301 TGTTTCTTTT TTGAACGATT GGAGTCTAGT AACTACAATA CTTACCGGTC AAGGAAATAC
361 TCCAGTTGGT ATGTGGCACT GAAACGAACT GGGCAGTATA AACTTGGACC CAAAACAGGA
421 CCTGGGCAGA AAGCTATACT TTTTCTTCCA ATGTCTGCTA AGAGCTGA
```

Dog FGF2 gene coding sequence (aa 40-194)
(SEQ ID NO: 190) (GenBank accession no.
XM_003432481, which is hereby
incorporated by reference in its entirety):

```
118                                                                ATG
121 GCAGCCGGGA GCATCACCAC GCTGCCCGCC CTGCCGGAGG ACGGCGGCAG CGGCGCCTTC
181 CCGCCCGGCC ACTTCAAGGA CCCCAAGAGG CTGTACTGCA AAAAGGGGG  CTTCTTCCTG
241 CGGATCCACC CCGACGGCCG GGTGGACGGG GTCCGGGAGA GAGCGATCC  CCACGTCAAA
301 TTGCAACTTC AAGCAGAAGA GAGAGGCGTT GTGTCCATCA AAGGAGTATG TGCAAATCGC
361 TATCTTGCTA TGAAGGAAGA TGGAAGATTA CTGGCTTCA AATGTGTTAC TGACGAGTGC
421 TTCTTTTTTG AACGATTGGA ATCTAATAAC TACAATACTT ACCGGTCAAG GAAATACTCC
481 AGTTGGTATG TGGCACTGAA ACGAACTGGG CAGTATAAAC TTGGACCAAA AACAGGACCT
541 GGGCAGAAAG CTATACTTTT TCTTCCAATG TCTGCTAAGA GCTGA
```

Norway rat FGF2 gene coding sequence
(aa 1-154) (SEQ ID NO: 191) (GenBank
accession no. NM_019305, which
is hereby incorporated by reference in its
entirety):

```
533                                                              ATGGCTGC
541 CGGCAGCATC ACTTCGCTTC CCGCACTGCC GGAGGACGGC GGCGGCGCCT TCCCACCCGG
601 CCACTTCAAG GATCCCAAGC GGCTCTACTG CAAGAACGGC GGCTTCTTCC TGCGCATCCA
661 TCCAGACGGC CGCGTGGACG GCGTCCGGGA GAAGAGCGAC CCACACGTCA AACTACAGCT
721 CCAAGCAGAA GAGAGAGGAG TTGTGTCCAT CAAGGGAGTG TGTGCGAACC GGTACCTGGC
781 TATGAAGGAA GATGGACGGC TGCTGGCTTC TAAGTGTGTT ACAGAAGAGT GTTTCTTCTT
841 TGAACGCCTG GAGTCCAATA ACTACAACAC TTACCGGTCA CGGAAATACT CCAGTTGGTA
901 TGTGGCACTG AAACGAACTG GCAGTATAA  ACTCGGATCC AAAACGGGGC CTGGACAGAA
961 GGCCATACTG TTTCTTCCAA TGTCTGCTAA GAGCTGA
```

Naked mole-rat FGF2 gene coding sequence
(1-134; partial amino acid sequence corresponding
to human FGF2 residues 22 to 155) (SEQ ID NO: 192)
(GenBank accession no. JH173674, which is hereby
incorporated by reference in its entirety):

```
378500          C CACCCGGCCA CTTCAAGGAC CCAAAGCGGC
378531 TGTACTGCAA AAACGGGGGC TTCTTCCTGC GCATCCACCC CGACGGCCGC
378581 GTGGACGGGG TCCGGGAGAA GAGCGACCCT CACG
418784    TCAAACT ACAACTTCAA GCAGAAGAGA GAGGAGTTGT GTCTATTAAG
418831 GGAGTGTGTG CGAACCGTTA CCTTGCTATG AAGGAAGATG GAAGATTACT
418881 GGCTTCT
433983   AAATGTGT TACAGATGAG TGTTTCTTTT TTGAACGATT GGAATCTAAT
434031 AACTACAATA CTTATCGGTC AAGGAAATAC TCCAGTTGGT ATGTGGCACT
434081 GAAACGAACT GGACAATATA AACTTGGATC CAAAACAGGA CCGGGGCAGA
434131 AAGCTATACT TTTTCTTCCA ATGTCTGCTA AGAGCTGA
```

Bushbaby FGF2 gene coding sequence (aa 52-206)
(SEQ ID NO: 193) (Ensembl accession no.
ENSOGAT00000025228, which is hereby incorporated
by reference in its entirety):

```
154                                        ATGGCAG CCGGGAGCAT CACCACGCTG
181 CCCTCCCTGC CCGAGGACGG CGGCAGCGAC GCCTTTCCGC CCGGCCACTT CAAGGACCCC
241 AAGCGACTGT ACTGCAAAAA CGGGGGCTTC TTCCTGCGCA TCCACCCCGA CGGCCGAGTG
301 GACGGGGTCC GGGAGAAGAG CGACCCTTAC ATCAAACTAC AACTTCAAGC AGAAGAGAGA
361 GGAGTTGTGT CTATCAAAGG AGTGTGTGCG AACCGTTACC TTGCTATGAA GGAAGACGGA
```

TABLE 4-continued

```
421 AGATTGCTGG CTTCTAAATT GATTACAGAC GAGTGCTTCT TTTTTGAACG ACTGGAATCT
481 AATAACTACA ATACTTACCG GTCAAGAAAA TACTCCAGTT GGTATGTGGC ACTGAAACGA
541 ACTGGACAGT ATAAACTTGG ATCCAAAACA GGACCTGGGC AGAAAGCTAT ACTTTTTCTT
601 CCAATGTCTG CTAAGAGCTG A
```

House mouse FGF2 gene coding sequence (aa 1-154)
(SEQ ID NO: 194) (GenBank accession no.
NM_008006, which is hereby incorporated
by reference in its entirety):

```
198                        ATG GCTGCCAGCG GCATCACCTC GCTTCCCGCA CTGCCGGAGG
241 ACGGCGGCGC CGCCTTCCCA CCAGGCCACT TCAAGGACCC CAAGCGGCTC TACTGCAAGA
301 ACGGCGGCTT CTTCCTGCGC ATCCATCCCG ACGGCCGCGT GGATGGCGTC CGCGAGAAGA
361 GCGACCCACA CGTCAAACTA CAACTCCAAG CAGAAGAGAG AGGAGTTGTG TCTATCAAGG
421 GAGTGTGTGC CAACCGGTAC CTTGCTATGA AGGAAGATGG ACGGCTGCTG GCTTCTAAGT
481 GTGTTACAGA AGAGTGTTTC TTCTTTGAAC GACTGGAATC TAATAACTAC AATACTTACC
541 GGTCACGGAA ATACTCCAGT TGGTATGTGG CACTGAAACG AACTGGGCAG TATAAACTCG
601 GATCCAAAAC GGGACCTGGA CAGAAGGCCA TACTGTTTCT TCCAATGTCT GCTAAGAGCT
661 GA
```

Squirrel FGF2 gene coding sequence (1-144;
partial amino acid sequence corresponding to
human FGF2 residues 12 to 155) (SEQ ID NO: 195)
(Ensembl accession no. ENSSTOT00000022105,
which is hereby incorporated by reference in its
entirety):

```
  1 CTGCCCGAGG ACGGCGGCGG CGGCGCCTTC CCGCCCGGCC ACTTTAAGGA CCCCAAGCGG
 61 CTCTACTGCA AAAACGGAGG CTTCTTCCTG CGCATCCACC CCGACGGCCG AGTGGACGGG
121 GTCCGGGAGA AGAGCGACCC CCACATCAAG CTCCAGCTTC AAGCCGAAGA CCGAGGGGTT
181 GTGTCCATCA AGGGAGTGTG TGCAAACCGA TACCTGGCCA TGAAGGAGGA CGGGAGGCTC
241 CTGGCTTCTA AATGTGTTAC GGACGAGTGT TTCTTTTTTG AACGACTGGA ATCAAATAAC
301 TACAATACTT ACCGGTCAAG GAAATACTCC AGTTGGTATG TGGCCCTGAA ACGAACAGGG
361 CAGTATAAAC TTGGATCCAA AACAGGACCT GGGCAGAAAG CTATACTTTT TCTTCCAATG
421 TCTGCTAAGA GC
```

Domestic cat FGF2 gene coding sequence (1-106;
partial amino acid sequence corresponding to
human FGF2 residues 25 to 130) (SEQ ID NO: 196)
(GenBank accession no. EU314952, which is hereby
incorporated by reference in its entirety):

```
  1 CCACTTCAAG GACCCCAAGC GTCTGTACTG CAAAAACGGG GGCTTCTTCC TGCGCATCCA
 61 CCCCGACGGC CGAGTGGATG GGGTCCGGGA GAAGAGCGAC CCTCACATCA AACTGCAACT
121 TCAGGCAGAA GAGAGAGGGG TTGTGTCCAT CAAAGGAGTC TGTGCAAACC GCTATCTTGC
181 CATGAAGGAA GATGGAAGAT TACTGGCTTC TAAATGTGTT ACGGACGAGT GTTTCTTTTT
241 TGAACGATTG GAATCTAATA ACTACAATAC TTATCGGTCA AGGAAATACT CCAGCTGGTA
301 TGTGGCACTG AAACGAAC
```

Guinea pig FGF2 gene coding sequence (1-96;
partial amino acid sequence corresponding to
human FGF2 residues 60 to 155) (SEQ ID NO: 197)
(Ensembl accession no. ENSCPOT00000005443,
which is hereby incorporated by reference in
its entirety):

```
  1 GTTAAACTAC AACTTCAAGC CGAAGACAGA GGAGTTGTGT CTATCAAGGG AGTCTGTGCG
 61 AACCGTTACC TTGCTATGAA GGAAGACGGA AGATTATTGG CTTCCAAATG TGTTACAGAT
121 GAATGTTTCT TTTTTGAACG ACTGGAATCT AATAACTACA ACACTTACCG GTCAAGGAAA
181 TACTCCAGTT GGTATGTGGC ACTGAAACGA ACTGGACAAT ATAAACTTGG GTCCAAAACA
241 GGACCAGGGC AGAAAGCCAT ACTTTTTCTT CCAATGTCTG CGAAGAGC
```

Tasmanian devil FGF2 gene coding sequence
(aa 48-203) (SEQ ID NO: 198) (Ensembl accession
no. ENSSHAP00000012215, which is hereby
incorporated by reference in its entirety):

```
142                       ATGGCCGCG GCAGCATCA CCACGTTGCC GGCCCTGGCC
181 GGGGATGGAG CCAGCGGGGG CGCCTTTCCC CCGGGCCACT TCCAGGACCC CAAGCGGCTG
241 TACTGCAAGA ACGGAGGCTT CTTCTTGCGC ATCCATCCCG ACGGTCACGT GGACGGCATC
301 CGCGAGAAGA GCGATCCGCA CATTAAACTT CAGCTTCAGG CAGAAGAGAG AGGAGTAGTG
361 TCTATTAAAG GAGTTTGTGC CAACCGCTAT CTTGCCATGA AGAGGATGG CAGATTACTG
421 GCTCTGAAAT GTGTGACTGA AGAGTGTTTC TTCTTTGAAC GTCTAGAGTC CAACAATTAC
481 AACACTTATC GCTCAAGGAA ATACTCCAAT TGGTATGTGG CATTGAAACG CACAGGCCAG
541 TATAAGCTTG GATCCAAAGAC TGGACCAGGG CAGAAAGCCA TCCTTTTCCT TCCCATGTCT
601 GCTAAGAGCT GA
```

TABLE 4-continued

Gray short-tailed opossum FGF2 gene coding
sequence (aa 1-155) (SEQ ID NO: 199)
(GenBank accession no. NM_001033976,
which is hereby incorporated by reference in
its entirety):

```
 29                        AT GGCCGCAGGC AGCATCACCA CGCTGCCAGC
 61 CCTGTCCGGG GACGGAGGCG GCGGGGCGC CTTTCCCCCG GGCCACTTCA AGGACCCCAA
121 GCGGCTGTAC TGCAAGAACG GAGGCTTCTT CCTGCGCATC CACCCCGACG GCCGTGTGGA
181 CGGCATCCGC GAGAAGAGCG ACCCGAACAT TAAACTACAA CTTCAGGCAG AAGAGAGAGG
241 AGTGGTGTCT ATTAAAGGAG TATGTGCCAA TCGCTATCTT GCCATGAAGG AAGATGGAAG
301 ATTATTGGCT TTGAAATATG TGACCGAAGA GTGTTTCTTT TTCGAACGCT TGGAGTCCAA
361 CAACTACAAC ACTTATCGCT CGAGGAAATA TTCCAATTGG TACGTGGCAC TGAAACGAAC
421 GGGGCAGTAC AAGCTTGGAT CCAAGACTGG CCCGGGGCAG AAAGCCATCC TTTTCCTCCC
481 CATGTCTGCT AAGAGCTGA
```

Rabbit FGF2 gene coding sequence (aa 1-155)
(SEQ ID NO: 200) (GenBank accession no.
XM_002717238, which is hereby
incorporated by reference in its entirety):

```
  1 ATGGCAGCCG AGAGCATCAC CACGCTGCCC GCCCTGCCGG AGGATGGAGG CAGCGGCGCC
 61 TTCCCGCCCG GCCACTTCAA GGACCCCAAG CGGCTGTACT GCAAAAACGG GGGTTTCTTC
121 CTGCGTATCC ACCCCGACGG CCGCGTGGAC GGGGTCCGGG AGAAGAGCGA CCCACACATC
181 AAATTACAAC TTCAAGCAGA AGAGAGAGGA GTTGTATCCA TCAAAGGTGT GTGTGCAAAC
241 CGTTACCTTG CTATGAAGGA AGATGGAAGA CTGCTGGCTT CTAAATGTGT TACAGACGAG
301 TGCTTCTTTT TTGAACGACT GGAGTCTAAT AACTACAATA CTTACCGGTC AAGGAAATAT
361 TCCAGCTGGT ATGTGGCACT GAAACGAACT GGGCAGTATA AACTTGGATC CAAAACAGGA
421 CCTGGGCAGA AGGCTATACT TTTTCTTCCA ATGTCTGCTA AGAGCTGA
```

Turkey FGF2 gene coding sequence (1-125;
partial amino acid sequence corresponding to
human FGF2 residues 31 to 155) (SEQ ID NO: 201)
(Ensembl accession no. ENSMGAT00000011845,
which is hereby incorporated by reference in
its entirety):

```
  1 CGGCTCTACT GTAAGAACGG CGGCTTCTTC CTGCGCATCA ATCCCGACGG CAGAGTGGAC
 61 GGCGTCCGCG AGAAGAGCGA TCCGCACATC AAACTGCAGC TTCAGGCAGA AGAAAGAGGA
121 GTGGTATCAA TCAAAGGTGT AAGTGCAAAC CGCTTTCTGG CTATGAAGGA GGATGGCAGA
181 TTGCTGGCAC TGAAATGTGC AACAGAAGAA TGTTTCTTTT TTGAGCGTTT GGAATCTAAT
241 AATTATAACA CTTACCGGTC ACGGAAGTAC TCTGATTGGT ATGTGGCACT GAAAAGAACT
301 GGACAGTACA AGCCCGGACC AAAAACTGGA CCTGGACAGA AAGCTATCCT TTTTCTTCCA
361 ATGTCTGCTA AAAGC
```

Gallus gallus FGF2 gene coding sequence (aa 1-158)
(SEQ ID NO: 202) (GenBank accession no.
NM_205433, which is hereby incorporated by
reference in its entirety):

```
 98                        ATG GCGGCGGGGG CGGCGGGGAG
121 CATCACCACG CTGCCGGCGC TGCCCGACGA CGGGGGGCGG GGCGCTTTTC CCCCCGGGCA
181 CTTCAAGGAC CCCAAGCGGC TCTACTGCAA GAACGGCGGC TTCTTCCTGC GCATCAACCC
241 CGACGGCAGG GTGGACGGCG TCCGCGAGAA GAGCGATCCG CACATCAAAC TGCAGCTTCA
301 AGCAGAAGAA AGAGGAGTAG TATCAATCAA AGGCGTAAGT GCAAACCGCT TTCTGGCTAT
361 GAAGGAGGAT GGCAGATTGC TGGCACTGAA ATGTGCAACA GAGGAATGTT TCTTTTTCGA
421 GCGCTTGGAA TCTAATAACT ATAACACTTA CCGGTCACGG AAGTACTCTG ATTGGTATGT
481 GGCACTGAAA AGGACTGGAC AGTACAAGCC CGGACCAAAA ACTGGACCTG GACAGAAAGC
541 TATCCTTTTT CTTCCAATGT CTGCTAAAAG CTGA
```

Zebra finch FGF gene coding sequence (aa 1-153)
(SEQ ID NO: 203) (GenBank accession no.
XM_002188361, which is hereby incorporated
by reference in its entirety):

```
  1 ATGGCGGCGG CGGGGGGCAT CGCTACGCTG CCCGACGACG GCGGCAGCGG CGCCTTTCCC
 61 CCGGGGCACT TCAAGGACCC CAAGCGCCTG TACTGCAAGA ACGGCGGCTT CTTCCTGCGC
121 ATCAACCCCG ACGGGAAGGT GGACGGCGTC CGCGAGAAGA GCGACCCGCA CATCAAGCTG
181 CAGCTTCAGG CGGAGGAACG AGGAGTGGTG TCCATCAAAG GTGTCAGTGC AATCGCTTC
241 CTGGCCATGA AAGAGGATGG CAGATTGCTG GCCTTGAAAT ATGCAACAGA AGAATGTTTC
301 TTTTTTGAAC GTTTGGAATC CAATAACTAT AACACTTACC GGTCACGGAA ATACTCGGAT
361 TGGTATGTGG CACTGAAAAG AACTGGACAG TACAAACCTG GACCAAAAC TGGACCTGGA
421 CAGAAAGCTA TCCTTTTCCT TCCTATGTCT GCTAAAAGCT GA
```

TABLE 4-continued

Japanese firebelly newt FGF2 gene coding sequence
(aa 1-155) (SEQ ID NO: 204) (GenBank accession no.
AB064664, which is hereby incorporated by reference
in its entirety):

```
384                         ATGGCTG CTGGGAGCAT CACCAGTCTC CCTGCCCTAC
421 CCGAGGACGG GAATGGCGGC ACCTTCACAC CCGGCGGATT CAAAGAGCCG AAGAGGCTGT
481 ACTGCAAGAA CGGGGGCTTC TTTCTCCGGA TCAACTCCGA CGGCAAGGTG GACGGAGCCC
541 GGGAGAAGAG CGACTCCTAC ATTAAACTGC AGCTTCAAGC AGAAGAGCGC GGTGTGGTGT
601 CCATCAAGGG AGTATGTGCA AACCGCTATC TCGCTATGAA GGATGATGGC AGGCTGATGG
661 CGCTGAAATG GATAACCGAT GAATGCTTCT TTTTCGAGCG ACTGGAGTCC AACAACTATA
721 ACACGTATCG ATCACGGAAA TATTCCGATT GGTATGTGGC GCTGAAAAGA ACTGGGCAAT
781 ACAAAAATGG ATCAAAAACC GGAGCAGGAC AGAAAGCAAT CCTTTTTCTA CCCATGTCGG
841 CCAAGAGTTG A
```

African clawed frog FGF2 gene coding sequence
(aa 1-155) (SEQ ID NO: 205) (GenBank accession
no. NM_001099871, which is hereby
incorporated by reference in its entirety):

```
335                         ATGGCG GCAGGGAGCA TCACAACTCT
361 GCCAACTGAA TCCGAGGATG GGGGAAACAC TCCTTTTTCA CCAGGGAGTT TTAAAGACCC
421 CAAGAGGCTC TACTGCAAGA ACGGGGGCTT CTTCCTCAGG ATAAACTCAG ACGGGAGAGT
481 GGACGGGTCA AGGGACAAAA GTGACTGCA CATAAAATTA CAGCTACAAG CTGTAGAGCG
541 GGGAGTGGTA TCAATAAAGG GAATCACTGC AAATCGCTAC CTTGCCATGA AGGAAGATGG
601 GAGATTAACA TCGCTGAGGT GTATAACAGA TGAATGCTTC TTTTTTGAAC GACTGGAAGC
661 TAATAACTAC AACACTTACC GGTCTCGGAA ATACAGCAGC TGGTATGTGG CACTAAAGCG
721 AACCGGGCAG TACAAAAATG GATCGAGCAC TGGACCGGGA CAAAAGCTA TTTTATTTCT
781 CCCAATGTCC GCAAAGAGCT GA
```

White-eared opossum FGF2 gene coding sequence
(aa 1-156) (SEQ ID NO: 206) (GenBank accession no.
EF057322, which is hereby incorporated by reference
in its entirety):

```
  1 ATGGCAGCAG GCAGCATCAC CACATTGCCG GCCCTGTCCG GGGACGGAGG CGGCGGGGGA
 61 GCCTTTCCTC CAGGCCACTT CAAGGACCCC AAGCGGCTGT ACTGCAAGAA CGGAGGCTTC
121 TTCCTGCGCA TCCACCCCGA CGGCCGCGTG GACGGCATCC GCGAGAAGAG CGACCCCGAAC
181 ATTAAACTAC AACTTCAGGC AGAAGAGAGA GGAGTAGTGT CTATTAAAGG AGTATGTGCC
241 AACCGATATC TTGCCATGAA GGAGGATGGC AGATTATTGG CTTTGAAATA TGTGACCGAA
301 GAGTGTTTCT TTTTTGAACG TTTGGAGTCC AACAACTACA ACACTTATCG CTCAAGAAAA
361 TATTCCAATT GGTATGTGGC ACTGAAACGA ACGGGGCAGT ATAAGCTTGG ATCCAAGACT
421 GGCCCGGGGC AGAAAGCCAT CCTTTTCTCC CCATGTCTGC TAAGATGCTG A
```

Microbat FGF2 gene coding sequence (1-96; partial
amino acid sequence corresponding to human FGF2
residues 60 to 155) (SEQ ID NO: 207) (Ensembl
accession no. ENSMLUT00000027717, which is
hereby incorporated by reference in its entirety):

```
  1 GTCAAACTCC AACTTCAAGC AGAAGAGAGA GGGGTCGTGT CTATCAAAGG AGTGTGTGCC
 61 AACCGCTATC TCGCTATGAA GGAGGACGGC CGGTTACAGG CTTCTAAATG TGTTACGGAT
121 GAGTGTTTCT TTTTTGAACG GTTGGAATCC AATAACTACA ACACTTACCG GTCAAGAAAG
181 TACTCCAGTT GGTATGTGGC ATTGAAGCGG AATGGGCAGT ATAAACTTGG ACCCAAAACA
241 GGACCTGGCC AGAAAGCCAT ACTTTTTCTT CCCATGTCTG CTAAGAGC
```

Anole lizard FGF2 gene coding sequence (1-140;
partial amino acid sequence corresponding to human
FGF2 residues 16 to 155) (SEQ ID NO: 208)
(Ensembl accession no. ENSACAT00000011897,
which is hereby incorporated by reference in
its entirety):

```
  1 GCGGCGGCGG CCTCTTTCCC CCCGGGCCCC TTCAAGGACC CCAAGCGCCT CTACTGCAAG
 61 AACGGGGGCT TCTTCCTGCG GATCAACCCC GACGGCGGCG TGGACGGCGT CCGAGAGAAG
121 AGCGACCCCA ACATCAAATT GCTGCTCCAG GCAGAGGAGA GAGGTGTAGT GTCCATCAAA
181 GGTGTATGCG CAAACCGTTT CCTGGCTATG AATGAAGACG GTCGATTGTT AGCACTGAAA
241 TACGTAACAG ATGAATGCTT CTTTTTTGAA CGCTTGGAAT CTAATAATTA CAATACTTAT
301 CGGTCTCGTA AATACCGTGA TTGGTACATT GCACTGAAAC GAACTGGTCA GTACAAACTT
361 GGACCAAAAA CTGGACGAGG CCAGAAAGCT ATCCTTTTCC TTCCAATGTC TGCCAAAAGT
```

Armadillo FGF2 gene coding sequence (124-217;
partial amino acid sequence corresponding to human
FGF2 residues 1 to 94) (SEQ ID NO: 209) (Ensembl
accession no. ENSDNOT00000014647, which is
hereby incorporated by reference in its entirety):

```
361         A TGGCAGCCGG GAGCATCACC ACGCTGCCCG CTCTGCCCGA GGACGGCGGC
421 AGCGGCGCCT TCCCGCCGGG CCACTTCAAG GACCCCAAGC GGCTGTACTG CAAAAACGGG
```

TABLE 4-continued

```
481 GGCTTCTTCC TGCGCATCCA TCCCGACGGC CGAGTGGACG GGGTCCGGGA GAAGAGCGAC
541 CCTAACATCA AACTACAACT TCAAGCAGAA GAGAGAGGGG TCGTGTCTAT CAAAGGCGTG
601 TGTGCGAACC GTTACCTTGC TATGCGGGAA GACGGAAGAC TCCAGGCGTC T
```

Tree shrew FGF2 gene coding sequence (1-189)
(SEQ ID NO: 210) (Ensembl accession no.
ENSTBET00000001143, which is hereby
incorporated by reference in its entirety):

```
  1 GCGGGGGTTA GAGCTGAGAG GGAGGAGGCA CCGGGGAGCG GTGACAGCCG GGGGACCGAT
 61 CCCGCCGCGC GTTCGCTCAT CAGGAGGCCG GATGCTGCAG CGCGAGAGGC GCTTCTTGGA
121 GCCAGGAGCC GGGTTCAGGG CAGCTCCACC TCCTGGCCAG CCTCGTCACG AACCGGGATC
181 AAGTTGCCGG ACGACTCAGG TCAAGGAATG GGCGGCTATC CTCTGGACCG CCCGAGCCGG
241 AGCACAGGGC GAGGGCTGGG CGGTGCCCCG GACCCTGCCG TAAAACTACA GCTTCAAGCG
301 GAAGAGAGAG GGGTCGTGTC TATCAAAGGA GTGTGTGCAA ACCGTTACCT GGCCATGAAG
361 GAGGATGGGC GACTGCTGGC TTCTAAATGT GTTACAGATG AGTGTTTCTT TTTTGAACGA
421 CTGGAATCTA ATAACTACAA TACTTACCGG TCCCGAAAGT ACTCCAGCTG GTATGTGGCA
481 CTGAAACGAA CTGGGCAGTA TAAACTTGGA TCCAAAACAG GACCTGGGCA GAAAGCTATA
541 CTTTTTCTTC CAATGTCTGC TAAAAGC
```

Western clawed frog FGF2 gene coding sequence
(aa 1-154) (SEQ ID NO: 211) (GenBank accession
no. NM_001017333, which is hereby
incorporated by reference in its entirety):

```
171                                                    ATGGCAGCAG
181 GAAGCATCAC AACCCTACCA ACCGAATCTG AGGATGGAAA CACTCCTTTC CCACCGGGGA
241 ACTTTAAGGA CCCCAAGAGG CTCTACTGCA AGAATGGGGG CTACTTCCTC AGGATTAACT
301 CAGACGGGGA AGTGGACGGA TCAAGGGATA AAAGTGACTT ACACATAAAA TTACAGCTAC
361 AAGCAGTAGA GCGGGGAGTG GTATCAATAA AGGGAATCAC TGCAAATCGC TACCTTGCCA
421 TGAAGGAAGA TGGGAGATTA ACATCGCTGA AGTGTATAAC AGATGAATGC TTCTTTTATG
481 AACGATTGGA AGCTAATAAC TACAACACTT ACCGGTCTCG GAAAACAAC AGCTGGTATG
541 TGGCACTAAA GCGAACTGGG CAGTATAAAA ATGGATCGAC CACTGGACCA GGACAAAAAG
601 CTATTTTGTT TCTCCCAATG TCAGCAAAAA GCTGA
```

Coelacanth FGF2 gene coding sequence (aa 1-155)
(SEQ ID NO: 212) (Ensembl accession no.
ENSLACT00000019333, which is hereby
incorporated by reference in its entirety):

```
  1                                  ATGGCTGCGG GAGGAATCAC TACCCTGCCG GCGGTACCTG
 41 AGGATGGAGG CAGCAGCACC TTCCCCTCAG GAAACTTCAA GGAGCCCAAG AGACTTTACT
101 GTAAGAATGG AGGCTATTTC TTAAGGATAA ACCCCGATGG AAGAGTGGAT GGAACAAGGG
161 AGAAAAATGA TCCTTATATA AAATTACAAC TGCAAGCTGA ATCTATAGGA GTGGTGTCGA
221 TAAAGGGAGT TTGTTCAAAC CGTTACCTAG CGATGAATGA AGACTGTAGA CTTTTTGGAT
281 TGAAATATCC AACGGATGAA TGTTTCTTCC ATGAGAGGCT GGAGTCCAAC AACTACAATA
341 CTTATCGTTC AAAGAAGTAT TCGGATTGGT ATGTGGCGCT GAAACGGACT GGTCAGTACA
401 AACCTGGGCC AAAAACTGGA CTGGGACAAA AAGCAATCCT TTTCCTTCCG ATGTCTGCCA
461 AGAGTTGA
```

Spotted green pufferfish FGF2 gene coding sequence
(aa 34-188) (SEQ ID NO: 213) (Ensembl accession no.
ENSTNIT00000016254, which is hereby
incorporated by reference in its entirety):

```
  1 ATGGCCACGG GAGGGATCAC GACGCTTCCA TCCACACCTG AAGACGGCGG CAGCAGCGGC
 61 TTTCCTCCCG GCAGCTTCAA GGATCCCAAA AGGCTCTACT GTAAAAACGG AGGTTTCTTC
121 CTGAGGATCA AGTCCGACGG GGTCGTGGAC GGAATCCGGG AGAAGAGTGA CCCCCACATA
181 AAGCTTCAGC TCCAGGCGAC CTCTGTGGGG GAGGTGGTCA TCAAGGGGGT GTGCGCTAAC
241 CGCTATCTGG CCATGAACAG AGATGGACGG CTGTTCGGAA CGAAACGAGC CACGGACGAA
301 TGCCATTTCT TAGAGCGGCT TGAGAGCAAC AACTACAACA CTTACCGCTC CAGGAAGTAC
361 CCAACCATGT TTGTGGGACT GACGCGGACG GGCCAGTACA AGTCTGGGAG CAAAACTGGA
421 CCGGGCCAAA AGGCCATCCT TTTTCTTCCG ATGTCCGCCA ATGCTAA
```

Stickleback FGF2 gene coding sequence (aa 1-155)
(SEQ ID NO: 214) (Ensembl accession no.
ENSGACT00000022120, which is hereby
incorporated by reference in its entirety):

```
  1                                     AT GGCCACGGCA GGCTTCGCGA CGCTTCCCTC CACGCCCGAA
 43 GACGGCGGCA GCGGCGGCTT CACCCCCGGG GGATTCAAGG ATCCCAAGAG GCTGTACTGC
103 AAAAACGGGG GCTTCTTCTT GAGGATCAGG TCCGACGGGA GTGTAGATGG AATCAGGGAG
163 AAGAGCGACG CCCACATAAA GCTCCAAATC CAGGCGACGT CGGTCGGGGA GGTGGTCATC
223 AAAGGAGTCT GTGCCAACCG CTATCTGGCC ATGAACAGAG ACGGCCGGCT GTTCGGAGTG
283 AGACGGGCGA CGGACGAATG CTACTTCCTG GAGCGGCTGG AGAGTAACAA CTACAACACC
343 TACCGCTCCA GGAAGTACCC CGGCATGTAC GTGGCTCTGA AGCGGACCGG CCAGTACAAG
403 TCCGGGAGCA AAACCGGACC CGGTCAAAAG GCCATTCTGT TCCTCCCCAT GTCGGCTAAG
463 TGCTAA
```

TABLE 4-continued

*Fugu rubripes* FGF2 gene coding sequence (aa 1-155)
(SEQ ID NO: 215) (Ensembl accession no.
ENSTRUT00000022363, which is hereby incorporated
by reference in its entirety):

```
127      ATGG CCACGGGAGG GATCACAACA CTTCCATCCA CACCTGAAGA CGGCGGCAGC
181 GGCGGTTTTC CTCCCGGGAG CTTCAAGGAT CCCAAAAGGC TGTACTGTAA AAACGGCGGC
241 TTCTTCCTGA GGATCAGGTC CGACGGGGCC GTGGACGGAA CCCGGGAGAA GACTGACCCC
301 CACATAAAGC TTCAGCTCCA GGCGACCTCT GTGGGGGAGG TGGTCATCAA GGGGGTTTGT
361 GCTAATCGTT ATCTGGCCAT GAACAGAGAT GGACGACTGT TTGGAATGAA ACGAGCGACG
421 GATGAATGCC ACTTCTTAGA GCGGCTCGAG AGCAACAACT ACAACACCTA CCGCTCCAGG
481 AAGTACCCCA ACATGTTTGT GGGACTGACG CGAACTGGCA ACTACAAGTC TGGGACTAAA
541 ACTGGACCGG GCCAAAAGGC CATCCTCTTT CTTCCGATGT CGGCCAAATA CTAA
```

Rainbow trout FGF2 gene coding sequence (aa 1-155)
(SEQ ID NO: 216) (GenBank accession no.
NM_001124536, which is hereby incorporated
by reference in its entirety):

```
390                        A TGGCCACAGG AGAAATCACC ACTCTACCCG
421 CCACACCTGA AGATGGAGGC AGTGGCGGCT TCCTTCCAGG AAACTTTAAG GAGCCCAAGA
481 GGTTGTACTG TAAAAATGGA GGCTACTTCT TGAGGATAAA CTCTAACGGA AGCGTGGACG
541 GGATCAGAGA TAAGAACGAC CCCCACAATA AGCTTCAACT CCAGGCGACC TCAGTGGGGG
601 AAGTAGTAAT CAAAGGGGTC TCAGCCAACC GCTATCTGGC CATGAATGCA GATGGAAGAC
661 TGTTTGGACC GAGACGGACA ACAGATGAAT GCTACTTCAT GGAGAGGCTG GAGAGTAACA
721 ACTACAACAC CTACCGCTCT CGAAAGTACC CTGAAATGTA TGTGGCACTG AAAAGGACTG
781 GCCAGTACAA GTCAGGATCC AAAACTGGAC CCGGCCAAAA AGCCATCCTC TTCCTCCCCA
841 TGTCAGCCAG ACGCTGA
```

Salmon FGF2 gene coding sequence (1-150)
(SEQ ID NO: 217) (GenBank accession no.
EU816603, which is hereby incorporated by
reference in its entirety):

```
99402                                      ATGGCCACA GGAGAAATCA
99421 CCACTCTACC CGCCACACCT GAAGATGGAG GCAGTGGCGG CTTCCCTCCA GGAAACTTTA
99481 AGGATCCCAA GAGGCTGTAC TGTAAAAACG GGGCTACTT CTTGAGAATA AACTCTAATG
99541 GAAGCGTGGA CGGGATCCGA GAGAAGAACG ACCCCCACA
100968                                              AAC AGCCTCAATT
100981 TGTCAGGGCA TGGACTCTTC AAGGTGTCAA ACGTTCCACA GGGATGCTGG CCCATGTTGA
101041 CTCCAACGCT TCCCACAATT GTGTCAAGGT GGCTGGATGT TCTTTGGGAG
101845                  AATTTG GCAGTATGTC CAACCGGCCT CATAACCGCA
101881 GACCACGTGT AGCTACACCA GCCCAGGACC TCCACATCCG GCTTCTTCAT CTACGGGATC
101941 GTCTGAAACC AGCCACCCGA ACAGCTGATA AAACTGAGGA GTATTTCTGT CTGTAA
```

Zebrafish FGF2 gene coding sequence (aa 1-154)
(SEQ ID NO: 218) (GenBank accession no.
AY269790, which is hereby incorporated by
reference in its entirety):

```
 43                                         ATGGCCAC CGGAGGGATC
 61 ACCACACTCC CGGCCGCTCC GGACGCCGAA ACAGCAGCT TTCCCGCGGG CAGCTTCAGG
121 GATCCCAAGC GCCTGTACTG CAAAAACGGA GGATTCTTCC TGCGGATCAA CGCGGACGGC
181 CGAGTGGACG GAGCCCGAGA CAAGAGCGAC CCGCACATTG TCTGCAGCT GCAGGCGACG
241 GCAGTGGGTG AAGTACTCAT TAAAGGCATC TGTACCAACC GTTTCCTTGC CATGAACGCA
301 GACGGACGAC TGTTCGGGAC GAAAAGGACC ACAGATGAAT GTTATTTCCT GGAGCGCCTG
361 GAGTCCAACA ACTACACAC ATACAGATCC CGCAAGTATC CCGACTGGTA CGTGGCTCTG
421 AAGAGAACCG GCCAGTATAA AAGCGGCTCT AAAACCAGCC CGGGACAGAA GGCCATCCTG
481 TTTCTGCCCA TGTCGGCCAA ATGCTGA
```

Nile tilapia FGF2 gene coding sequence (aa 1-155)
(SEQ ID NO: 219) (GenBank accession no.
XM_003443364, which is hereby
incorporated by reference in its entirety):

```
  1 ATGGCCACGG GAGGAATCAC AACACTTCCC GCTACACCTG AAGACGGCGG CAGCAGCGGC
 61 TTTCCTCCTG GGAACTTCAA GGACCCTAAA AGGCTGTACT GTAAAAATGG TGGCTTCTTC
121 TTGAGGATAA AATCTGATGG AGGAGTGGAT GGAATACGAG AGAAAAACGA CCCCCACATA
181 AAGCTTCAAC TCCAGGCGAC CTCAGTGGGA GAAGTGGTCA TCAAAGGGAT TTGTGCAAAC
241 CGATATCTGG CAATGAACAG AGATGGACGA CTGTTTGGAG CGAGAAGAGC AACAGATGAG
301 TGCTACTTCT TAGAGCGGCT CGAGAGCAAC AACTACAACA CCTACCGCTC CAGGAAGTAC
361 CCAAACATGT ACGTGGCGCT GAAGCGGACT GGCCAGTACA AGTCTGAAGC CAAACTGGAC
421 CCGGGTCAAA AGGCAATTCT CTTTCTCCCA ATGTCTGCTA ATGCTAA
```

TABLE 4-continued

Medaka FGF2 gene coding sequence (aa 1-155)
(SEQ ID NO: 220) (Ensembl accession no.
ENSORLT00000025835, which is hereby
incorporated by reference in its entirety):

```
  1 ATGGCTACGG GAGAAATCAC AACACTTCCC TCCCCAGCTG AAAACAGCAG AAGCGATGGC
 61 TTTCCTCCAG GGAACTACAA GGATCCTAAG AGGCTCTACT GTAAAAATGG AGGTTTGTTT
121 TTGAGGATTA AACCTGATGG AGGAGTGGAT GGAATCCGGG AAAAAAAAGA TCCCCACGTT
181 AAGCTTCGCC TTCAGGCTAC CTCAGCGGGA GAGGTGGTGA TCAAGGAGT TTGTTCAAAC
241 AGATATCTGG CGATGCATGG AGATGGACGT CTATTTGGAG TGAGACAAGC AACAGAGGAA
301 TGCTACTTCT TGGAGCGACT AGAGAGCAAC AACTATAACA CCTATCGCTC TAAAAAGTAC
361 CCAAACATGT ACGTGGCACT GAAGCGGACA GGCCAGTACA AACCTGGAAA CAAAACTGGA
421 CCAGGTCAAA AGGCCATTCT CTTTCTGCCT ATGTCTGCCA AGTACTAA
```

As noted above, also encompassed within the present invention are portions of paracrine FGFs other than FGF1 and/or FGF2 (e.g., FGF4, FGF5, FGF6, FGF9, FGF16, and FGF20). The portion of the paracrine FGF may be from human FGF4, FGF5, FGF6, FGF9, FGF16, and/or FGF20 having the amino acid sequences shown in Table 5, or orthologs thereof.

TABLE 5

Amino acid sequence of human FGF4 (SEQ ID NO: 221) (GenBank accession no. NP_001998, which is hereby incorporated by reference in its entirety):

```
  1 MSGPGTAAVA LLPAVLLALL APWAGRGGAA APTAPNGTLE AELERRWESL VALSLARLPV
 61 AAQPKEAAVQ SGAGDYLLGI KRLRRLYCNV GIGFHLQALP DGRIGGAHAD TRDSLLELSP
121 VERGVVSIFG VASRFFVAMS SKGKLYGSPF FTDECTFKEI LLPNNYNAYE SYKYPGMFIA
181 LSKNGKTKKG NRVSPTMKVT HFLPRL
```

Amino acid sequence of human FGF5 (SEQ ID NO: 222) (GenBank Accession No. NP_004455, which is hereby incorporated by reference in its entirety):

```
  1 MSLSFLLLLF FSHLILSAWA HGEKRLAPKG QPGPAATDRN PRGSSSRQSS SSAMSSSSAS
 61 SSPAASLGSQ GSGLEQSSFQ WSPSGRRTGS LYCRVGIGFH LQIYPDGKVN GSHEANMLSV
121 LEIFAVSQGI VGIRGVFSNK FLAMSKKGKL HASAKFTDDC KFRERFQENS YNTYASAIHR
181 TEKTGREWYV ALNKRGKAKR GCSPRVKPQH ISTHFLPRFK QSEQPELSFT VTVPEKKKPP
241 SPIKPKIPLS APRKNTNSVK YRLKFRFG
```

Amino acid sequence of human FGF6 (SEQ ID NO: 223) (NP_066276, which is hereby incorporated by reference in its entirety):

```
  1 MALGQKLFIT MSRGAGRLQG TLWALVFLGI LVGMVVPSPA GTRANNTLLD SRGWGTLLSR
 61 SRAGLAGEIA GVNWESGYLV GIKRQRRLYC NVGIGFHLQV LPDGRISGTH EENPYSLLEI
121 STVERGVVSL FGVRSALFVA MNSKGRLYAT PSFQEECKFR ETLLPNNYNA YESDLYQGTY
181 IALSKYGRVK RGSKVSPIMT VTHFLPRI
```

Amino acid sequence of human FGF9 (SEQ ID NO: 224) (GenBank accession no. NP_002001, which is hereby incorporated by reference in its entirety):

```
  1 MAPLGEVGNY FGVQDAVPFG NVPVLPVDSP VLLSDHLGQS EAGGLPRGPA VTDLDHLKGI
 61 LRRRQLYCRT GPHLEIFPNG TIQGTRKDHS RFGILEFISI AVGLVSIRGV DSGLYLGMNE
121 KGELYGSEKL TQECVFREQF EENWYNTYSS NLYKHVDTGR RYYVALNKDG TPREGTRTKR
181 HQKFTHFLPR PVDPDKVPEL YKDILSQS
```

Amino acid sequence of human FGF16 (SEQ ID NO: 225) (GenBank accession no. NP_003859, which is hereby incorporated by reference in its entirety):

```
  1 MAEVGGVFAS LDWDLHGFSS SLGNVPLADS PGFLNERLGQ IEGKLQRGSP TDFAHLKGIL
 61 RRRQLYCRTG FHLEIFPNGT VHGTRHDHSR FGILEFISLA VGLISIRGVD SGLYLGMNER
121 GELYGSKKLT RECVFREQFE ENWYNTYAST LYKHSDSERQ YYVALNKDGS PREGYRTKRH
181 QKFTHFLPRP VDPSKLPSMS RDLFHYR
```

Amino acid sequence of human FGF20 (SEQ ID NO: 226) (GenBank accession no. NP_062825, which is hereby incorporated by reference in its entirety):

```
  1 MAPLAEVGGF LGGLEGLGQQ VGSHFLLPPA GERPPLLGER RSAAERSARG GPGAAQLAHL
 61 HGILRRRQLY CRTGFHLQIL PDGSVQGTRQ DHSLFGILEF ISVAVGLVSI RGVDSGLYLG
121 MNDKGELYGS EKLTSECIFR EQFEENWYNT YSSNIYKHGD TGRRYFVALN KDGTPRDGAR
181 SKRHQKFTHF LPRPVDPERV PELYKDLLMY T
```

It will be understood that the portion of the paracrine FGF according to the present invention may be derived from a nucleotide sequence that encodes human FGF4, FGF5, FGF6, FGF9, FGF16, and/or FGF20 having the nucleotide sequences shown in Table 6, or orthologs thereof.

TABLE 6

Human FGF4 gene coding sequence (1-206) (SEQ ID NO: 227) (GenBank accession no. NM_002007, which is hereby incorporated by reference in its entirety):

```
320                              A TGTCGGGGCC CGGGACGGCC GCGGTAGCGC TGCTCCCGGC
361 GGTCCTGCTG GCCTTGCTGG CGCCCTGGGC GGGCCGAGGG GGCGCCGCCG CACCCACTGC
421 ACCCAACGGC ACGCTGGAGG CCGAGCTGGA GCGCCGCTGG GAGAGCCTGG TGGCGCTCTC
481 GTTGGCGCGC CTGCCGGTGG CAGCGCAGCC CAAGGAGGCG GCCGTCCAGA GCGGCGCCGG
541 CGACTACCTG CTGGGCATCA AGCGGCTGCG GCGGCTCTAC TGCAACGTGG GCATCGGCTT
601 CCACCTCCAG GCGCTCCCCG ACGGCCGCAT CGGCGGCGCG CACGCGGACA CCCGCGACAG
661 CCTGCTGGAG CTCTCGCCCG TGGAGCGGGG CGTGGTGAGC ATCTTCGGCG TGGCCAGCCG
721 GTTCTTCGTG GCCATGAGCA GCAAGGGCAA GCTCTATGGC TCGCCCTTCT TCACCGATGA
781 GTGCACGTTC AAGGAGATTC TCCTTCCCAA CAACTACAAC GCCTACGAGT CCTACAAGTA
841 CCCCGGCATG TTCATCGCCC TGAGCAAGAA TGGGAAGACC AAGAAGGGGA ACCGAGTGTC
901 GCCCACCATG AAGGTCACCC ACTTCCTCCC CAGGCTGTGA
```

Human FGF5 gene coding sequence (1-268) (SEQ ID NO: 228) (GenBank Accession No. NM_004464, which is hereby incorporated by reference in its entirety):

```
238                                                                    ATG
241 AGCTTGTCCT TCCTCCTCCT CCTCTTCTTC AGCCACCTGA TCCTCAGCGC CTGGGCTCAC
301 GGGGAGAAGC GTCTCGCCCC CAAAGGGCAA CCCGGACCCG CTGCCACTGA TAGGAACCCT
361 AGAGGCTCCA GCAGCAGACA GAGCAGCAGT AGCGCTATGT CTTCCTCTTC TGCCTCCTCC
421 TCCCCCGCAG CTTCTCTGGG CAGCCAAGGA AGTGGCTTGG AGCAGAGCAG TTTCCAGTGG
481 AGCCCCTCGG GGCGCCGGAC CGGCAGCCTC TACTGCAGAG TGGGCATCGG TTTCCATCTG
541 CAGATCTACC CGGATGGCAA AGTCAATGGA TCCCACGAAG CCAATATGTT AAGTGTTTTG
601 GAAATATTTG CTGTGTCTCA GGGGATTGTA GGAATACGAG GAGTTTTCAG CAACAAATTT
661 TTAGCGATGT CAAAAAAAGG AAAACTCCAT GCAAGTGCCA AGTTCACAGA TGACTGCAAG
721 TTCAGGGAGC GTTTTCAAGA AAATAGCTAT AATACCTATG CCTCAGCAAT ACATAGAACT
781 GAAAAAACAG GGCGGGAGTG GTATGTGGCC CTGAATAAAA GAGGAAAAGC CAAACGAGGG
841 TGCAGCCCCC GGGTTAAACC CCAGCATATC TCTACCCATT TTCTGCCAAG ATTCAAGCAG
901 TCGGAGCAGC CAGAACTTTC TTTCACGGTT ACTGTTCCTG AAAAGAAAAA GCCACCTAGC
961 CCTATCAAGC CAAAGATTCC CCTTTCTGCA CCTCGGAAAA ATACCAACTC AGTGAAATAC
1021 AGACTCAAGT TCGCTTTGG ATAA
```

Human FGF6 gene coding sequence (1-208) (SEQ ID NO: 229) (NM_020996, which is hereby incorporated by reference in its entirety):

```
45                                                        ATGGCC CTGGGACAGA
61 AACTGTTCAT CACTATGTCC CGGGGAGCAG GACGTCTGCA GGGCACGCTG TGGGCTCTCG
121 TCTTCCTAGG CATCCTAGTG GGCATGGTGG TGCCCTCGCC TGCAGGCACC CGTGCCAACA
181 ACACGCTGCT GGACTCGAGG GGCTGGGGCA CCCTGCTGTC CAGGTCTCGC GCGGGGCTAG
241 CTGGAGAGAT TGCCGGGGTG AACTGGGAAA GTGGCTATTT GGTGGGGATC AAGCGGCAGC
301 GGAGGCTCTA CTGCAACGTG GGCATCGGCT TTCACCTCCA GGTGCTCCCC GACGGCCGGA
361 TCAGCGGGAC CCACGAGGAG AACCCCTACA GCCTGCTGGA AATTTCCACT GTGGAGCGAG
421 GCGTGGTGAG TCTCTTTGGA GTGAGAAGTG CCCTCTTCGT TGCCATGAAC AGTAAAGGAA
481 GATTGTACGC AACGCCCAGC TTCCAAGAAG AATGCAAGTT CAGAGAAACC CTCCTGCCCA
541 ACAATTACAA TGCCTACGAG TCAGACTTGT ACCAAGGGAC CTACATTGCC CTGAGCAAAT
601 ACGGACGGGT AAAGCGGGGC AGCAAGGTGT CCCCGATCAT GACTGTCACT CATTTCCTTC
661 CCAGGATCTA A
```

Human FGF9 gene coding sequence (1-208) (SEQ ID NO: 230) (GenBank accession no. NM_002010, which is hereby incorporated by reference in its entirety):

```
838                                                                    ATG
841 GCTCCCTTAG GTGAAGTTGG GAACTATTTC GGTGTGCAGG ATGCGGTACC GTTTGGGAAT
901 GTGCCCGTGT TGCCGGTGGA CAGCCCGGTT TTGTTAAGTG ACCACCTGGG TCAGTCCGAA
961 GCAGGGGGGC TCCCCAGGGG ACCCGCAGTC ACGGACTTGG ATCATTTAAA GGGGATTCTC
1021 AGGCGGAGGC AGCTATACTG CAGGACTGGA TTTCACTTAG AAATCTTCCC CAATGGTACT
1081 ATCCAGGGAA CCAGGAAAGA CCACAGCCGA TTTGGCATTC TGGAATTTAT CAGTATAGCA
1141 GTGGGCCTGG TCAGCATTCG AGGCGTGGAC AGTGGACTCT ACCTCGGGAT GAATGAGAAG
1201 GGGGAGCTGT ATGGATCAGA AAAACTAACC CAAGAGTGTG TATTCAGAGA ACAGTTCGAA
1261 GAAAACTGGT ATAATACGTA CTCATCAAAC CTATATAAGC ACGTGGACAC TGGAAGGCGA
1321 TACTATGTTG CATTAAATAA AGATGGGACC CCGAGAGAAG GGACTAGGAC TAAACGGCAC
1381 CAGAAATTCA CACATTTTT ACCTAGACCA GTGGACCCCG ACAAAGTACC TGAACTGTAT
1441 AAGGATATTC TAAGCCAAAG TTGA
```

Human FGF16 gene coding sequence (1-207) (SEQ ID NO: 231) (GenBank accession no. NM_003868, which is hereby incorporated by reference in its entirety):

```
1 ATGGCAGAGG TGGGGGGCGT CTTCGCCTCC TTGGACTGGG ATCTACACGG CTTCTCCTCG
61 TCTCTGGGGA ACGTGCCCTT AGCTGACTCC CCAGGTTTCC TGAACGAGCG CCTGGGCCAA
```

TABLE 6-continued

```
121 ATCGAGGGGA AGCTGCAGCG TGGCTCACCC ACAGACTTCG CCCACCTGAA GGGGATCCTG
181 CGGCGCCGCC AGCTCTACTG CCGCACCGGC TTCCACCTGG AGATCTTCCC CAACGGCACG
241 GTGCACGGGA CCCGCCACGA CCACAGCCGC TTCGGAATCC TGGAGTTTAT CAGCCTGGCT
301 GTGGGGCTGA TCAGCATCCG GGGAGTGGAC TCTGGCCTGT ACCTAGGAAT GAATGAGCGA
361 GGAGAACTCT ATGGGTCGAA GAAACTCACA CGTGAATGTG TTTTCCGGGA ACAGTTTGAA
421 GAAAACTGGT ACAACACCTA TGCCTCAACC TTGTACAAAC ATTCGGACTC AGAGAGACAG
481 TATTACGTGG CCCTGAACAA AGATGGCTCA CCCCGGGAGG GATACAGGAC TAAACGACAC
541 CAGAAATTCA CTCACTTTTT ACCCAGGCCT GTAGATCCTT CTAAGTTGCC CTCCATGTCC
601 AGAGACCTCT TTCACTATAG GTAA
```

Human FGF20 gene coding sequence (1-211) (SEQ ID NO: 232) (GenBank accession no. NM_019851, which is hereby incorporated by reference in its entirety):

```
134                ATGGCTC CCTTAGCCGA AGTCGGGGGC TTTCTGGGCG GCCTGGAGGG
181 CTTGGGCCAG CAGGTGGGTT CGCATTTCCT GTTGCCTCCT GCCGGGGAGC GGCCGCCGCT
241 GCTGGGCGAG CGCAGGAGCG CGGCGGAGCG GGCGCGCGC GGCGGGCCGG GGGCTGCGCA
301 GCTGGCGCAC CTGCACGGCA TCCTGCGCCG CCGGCAGCTC TATTGCCGCA CCGGCTTCCA
361 CCTGCAGATC CTGCCCGACG GCAGCGTGCA GGGCACCCGG CAGGACCACA GCCTCTTCGG
421 TATCTTGGAA TTCATCAGTG TGGCAGTGGG ACTGGTCAGT ATTAGAGGTG TGGACAGTGG
481 TCTCTATCTT GGAATGAATG ACAAAGGAGA ACTCTATGGA TCAGAGAAAC TTACTTCCGA
541 ATGCATCTTT AGGGAGCAGT TTGAAGAGAA CTGGTATAAC ACCTATTCAT CTAACATATA
601 TAAACATGGA GACACTGGCC GCAGGTATTT TGTGGCACTT AACAAAGACG GAACTCCAAG
661 AGATGGCGCC AGGTCCAAGA GGCATCAGAA ATTTACACAT TTCTTACCTA GACCAGTGGA
721 TCCAGAAAGA GTTCCAGAAT TGTACAAGGA CCTACTGATG TACACTTGA
```

As noted above, the chimeric protein includes a portion of a paracrine FGF coupled to a C-terminal region derived from an FGF19. FGF19 has been shown to target and have effects on both adipocytes and hepatocytes. For example, mice harboring a FGF19 transgene, despite being on a high-fat diet, show increased metabolic rates, increased lipid oxidation, a lower respiratory quotient and weight loss. Moreover, such mice showed lower serum levels of leptin, insulin, cholesterol and triglycerides, and normal levels of blood glucose despite the high-fat diet and without appetite diminishment (Tomlinson et al., "Transgenic Mice Expressing Human Fibroblast Growth Factor-19 Display Increased Metabolic Rate and Decreased Adiposity," *Endocrinology* 143(5), 1741-1747 (2002), which is hereby incorporated by reference in its entirety). Obese mice that lacked leptin but harbored a FGF19 transgene showed weight loss, lowered cholesterol and triglycerides, and did not develop diabetes. Obese, diabetic mice that lacked leptin, when injected with recombinant human FGF19, showed reversal of their metabolic characteristics in the form of weight loss and lowered blood glucose (Fu et al., "Fibroblast Growth Factor 19 Increases Metabolic Rate and Reverses Dietary and Leptin-deficient Diabetes," *Endocrinology* 145(6), 2594-2603 (2004), which is hereby incorporated by reference in its entirety).

In one embodiment of the present invention, FGF19 is human FGF19 and has an amino acid sequence of SEQ ID NO: 233 (GenBank Accession No. NP_005108, which is hereby incorporated by reference in its entirety), or a portion thereof, as follows:

```
  1 MRSGCVVVHV WILAGLWLAV AGRPLAFSDA GPHVHYGWGD
    PIRLRHLYTS GPHGLSSCFL

61 RIRADGVVDC ARGQSAHSLL EIKAVALRTV AIKGVHSVRY
    LCMGADGKMQ GLLQYSEEDC

121 AFEEEIRPDG YNVYRSEKHR LPVSLSSAKQ RQLYKNRGFL
    PLSHFLPMLP MVPEEPEDLR

181 GHLESDMFSS PLETDSMDPF GLVTGLEAVR SPSFEK
```

In one embodiment, the C-terminal portion of FGF19 of the chimeric protein of the present invention does not include any of residues 1 to 168 of SEQ ID NO: 1. In certain embodiments of the present invention, the chimeric protein of the present invention does not include residues corresponding to residues spanning residues 1 to 168 of SEQ ID NO:1. In one embodiment, the C-terminal portion of FGF19 begins at a residue corresponding to any one of residues 169, 197, or 204 of SEQ ID NO: 1.

In another embodiment, the C-terminal portion of FGF19 of the chimeric protein of the present invention comprises an amino acid sequence spanning residues corresponding to residues selected from the group consisting of from position 204 to 216 of SEQ ID NO: 1, from position 197 to 216 of SEQ ID NO: 1, and from position 169 to 216 of SEQ ID NO: 1. In yet another embodiment, the C-terminal portion of FGF19 of the chimeric protein of the present invention comprises an amino acid sequence spanning residues of SEQ ID NO:1, which correspond to residues 191 to 206 or 191 to 209 of SEQ ID NO: 1.

In one embodiment of the present invention, FGF19 or a portion thereof is from a mammalian FGF19. In one embodiment of the present invention, FGF19 or a portion thereof is from a vertebrate FGF19. In one embodiment, FGF19 or a portion thereof is from a non-human vertebrate FGF19. It will be understood that this includes orthologs of human FGF19, or a polypeptide or protein obtained from one species that is the functional counterpart of a polypeptide or protein from a different species. In one embodiment, the C-terminal portion of FGF19 of the chimeric protein of the present invention is from human FGF19. In one embodiment of the present invention, the C-terminal portion of FGF19 is from an ortholog of human FGF19 from *gorilla gorilla, pan troglodytes, macaca mulatta, pongo abelii, nomascus leucogenys, callithrix jacchus, microcebus murinus, choloepus hoffmanni, ailuropoda melanoleuca, sus scrofa, bos taurus, canis lupus familiaris, oryctolagus, pteropus vampyrus, tursiops truncates, myotis lucifugus, ornithorhynchus anatinus, monodelphis domestica, anolis carolinensis, ochotona princeps, cavia porcellus, tupaia belangeri, rattus norvegicus, mus musculus, gallus gallus, taeniopygia guttata, danio rerio, xenopus (siluran) tropicalis, otolemur garnettii, felis catus, pelodiscus sinensis, latimeria chalumnae, mustela putorius furo, takifugu rubripes, equus caballus, oryzias latipes, xiphophorus maculatus, ictidomys tridecemlineatus, gasterosteus aculeatus, oreochromis niloticus, meleagris gallopavo, papio anubis,* saimiri boliviensis boliviensis, pteropus alecto, myotis davidii, tupaia chinensis*, or *heterocephalus glaber*.

In other embodiments of the present invention, the portion of FGF19 of the chimeric protein of the present invention is from an ortholog of human FGF19 having an amino acid sequence as shown in Table 7. The portions of an ortholog of human FGF19 of a chimeric protein according to the present invention include portions corresponding to the above-identified amino acid sequences of human FGF19. Corresponding portions may be determined by, for example, sequence analysis and structural analysis. The high degree of FGF19 sequence conservation among orthologs is shown in FIG. 12.

TABLE 7

*Gorilla gorilla* (*gorilla*) FGF19 (Ensembl Accession No. ENSGGOP00000021055, which is hereby incorporated by reference in its entirety) (SEQ ID NO: 234)

```
  1 MRSGCVVVHV WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

*Pan troglodytes* (chimpanzee) FGF19 (Ensembl Accession No. ENSPTRP00000006877, which is hereby incorporated by reference in its entirety) (SEQ ID NO: 235)

```
  1 MRNGCVVVHV WILAGLWLAV AGRPLAFSDA GRHVHYCWGD PIPLRHLYTS GPHGLSSCFL
 61 RIPANCVMNC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

*Macaca mulatta* (Rhesus monkey) FGF19 (GenBank Accession No. XP_001100825, which is hereby incorporated by reference in its entirety) (SEQ ID NO: 236)

```
  1 MRSGCVVVHA WILASLWLAV AGRPLAFSDA GPHVHYGWGD PIRLRHLYTS GPHGLSSCFL
 61 RIRTDGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MAPEEPEDLR
181 GHLESDMFSS PLETDSMDPF GLVTGLEAVR SPSFEK
```

*Pongo abelii* (Sumatran orangutan) FGF19 (GenBank Accession No. XP_002821459, which is hereby incorporated by reference in its entirety) (SEQ ID NO: 237)

```
  1 MRSGCVVVHA WILAGLWLAV AGRPLAFSDS GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 RHLESDMFSS PLETDSMDPF GLVTGLEAVR SPSFEK
```

*Nomascus leucogenys* (Northern white-cheeked gibbon) FGF19 (Genbank Accession No. XP_003278071, which is hereby incorporated by reference in its entirety) (SEQ ID NO: 238)

```
  1 MRSECVVVHA WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

*Callithrix jacchus* (white-tufted-ear marmoset) FGF19 (GenBank Accession No. XP_002763730, which is hereby incorporated by reference in its entirety) (SEQ ID NO: 239)

```
  1 MWKATAGGQQ GQSEAQMSTC PHVPRPLWIA QSCLFSLQLQ YSEEDCAFEE EIRPDGYNVY
 61 WSEKHRLPVS LSSAKQRQLY KKRGFLPLSH FLPMLPIAPE EPEDLRGHLE SDVFSSPLET
121 DSMDPFGLVT GLEAVNSPSF EK
```

*Microcebus murinus* (mouse lemur) FGF19 (Ensembl Accession No. ENSMICP00000002788, which is hereby incorporated by reference in its entirety) (SEQ ID NO: 240)

```
  1 MPSGQSGCVA ARALILAGLW LTAAGRPLAF SDAGPHVHYG WGEPIRLRHL YTAGPHGLSS
 61 CFLRIRADGS VDCARGQSAH SLLEIRAVAL RTVAIKGVHS VRYLCMGADG RMQGLLRYSE
121 EDCAFEEEIR PDGYNVYRSE KHRLPVSLSS ARQRQLYKGR GFLPLSHFLP MLPVTPAETG
181 DLRDHLESDM FASPLETDSM DPFGIATRLG VVKSPSFQK
```

*Choloepus hoffmanni* (sloth) FGF19 (Ensembl Accession No. ENSCHOP00000002044, which is hereby incorporated by reference in its entirety) (SEQ ID NO: 241) (partial amino acid sequence corresponding to human FGF19 residues 79 to 216)

```
  1 LLEMKAVALR AVAIKGVHSA LYLCMNADGS LHGLPRYSAE DCAFEEEIRP DGYNVYWSRK
 61 HGLPVSLSSA KQRQLYKGRG FLPLSHFLPM LPMTPAEPAD PGDDVESDMF SSPLETDSMD
121 PFGIASRLEL VNSPSFQT
```

TABLE 7-continued

*Ailuropoda melanoleuca* (giant panda) FGF19 (GenBank Accession No. XP_002927952, which is hereby incorporated by reference in its entirety) (SEQ ID NO: 242) (partial amino acid sequence corresponding to human FGF19 residues 12 to 216)

```
124     VLAGLCL AVAGRPLAFS DAGPHVHYGW GEPIRLRHLY TAGPHGLSSC FLRIRADGGV
181 DCARGQSAHS LVEIRAVALR TVAIKGVHSV RYLCMGADGR MQGLPQYSAG DCAFEEEIRP
241 DGYNVYRSKK HRLPVSLSGA KQRQLYKDRG FLPLSHFLPM LPGSPAEPRD LQDHAESDGF
301 SAPLETDSMD PFGIATKMGL VKSPSFQK
```

*Sus scrofa* (pig) FGF19 (Ensembl Accession No. ENSSSCP00000013682, which is hereby incorporated by reference in its entirety) (SEQ ID NO: 243)

```
  1 MRSAPSRCAV VRALVLAGLW LAAAGRPLAF SDAGPHVHYG WGESVRLRHL YTASPHGVSS
 61 CFLRIHSDGP VDCAPGQSAH SLMEIRAVAL STVAIKGERS RYLCMGADGK MQGQTQYSDE
121 DCAFEEEIRP DGYNVYWSKK HHLPVSLSSA RQRQLYKGRG FLPLSHFLPM LSTLPAEPED
181 LQDPFKSDLF SLPLETDSMD PFRIAAKLGA VKSPSFYK
```

*Bos taurus* (bovine) FGF19 (GenBank Accession No. XP_599739, which is hereby incorporated by reference in its entirety) (SEQ ID NO: 244)

```
136              MRSAP SRCAVARALV LAGLWLAAAG RPLAFSDAGP HVHYGWGESV
181 RLRHLYTAGP QGLYSCFLRI HSDGAVDCAQ VQSAHSLMEI RAVALSTVAI KGERSVLYLC
241 MDADGKMQGL TQYSAEDCAF EEEIRPDGYN VYWSRKHHLP VSLSSSRQRQ LFKSRGFLPL
301 SHFLPMLSTI PAEPEDLQEP LKPDFFLPLK TDSMDPFGLA TKLGSVKSPS FYN
```

*Canis lupus familiaris* (dog) FGF19 (GenBank Accession No. XP_540802, which is hereby incorporated by reference in its entirety) (SEQ ID NO: 245) (partial amino acid sequence corresponding to human FGF19 residues 25 to 216)

```
  1 LAFSDAGPHV HSFWGEPIRL RHLYTAGPHG LSSCFLRIRA DGGVDCARGQ SAHSLMEMRA
 61 VALRTVAIKG VHSGRYLCMG ADGRMQGLPQ YSAGDCTFEE EIRPDGYNVY WSKKHHLPIS
121 LSSAKQRQLY KGRGFLPLSH FLPILPGSPT EPRDLEDHVE SDGFSASLET DSMDPFGIAT
181 KIGLVKSPSF QK
```

*Oryctolagus cuniculus* (rabbit) FGF19 (GenBank Accession No. XP_002724495, which is hereby incorporated by reference in its entirety) (SEQ ID NO: 246)

```
  1 MRRAPSGGAA ARALVLAGLW LAAAARPLAL SDAGPHLHYG WGEPVRLRHL YATSAHGVSH
 61 CFLRIRADGA VDCERSQSAH SLLEIRAVAL RTVAFKGVHS SRYLCMGADG RMRGQLQYSE
121 EDCAFQEEIS SGYNVYRSTT HHLPVSLSSA KQRHLYKTRG FLPLSHFLPV LPLASEETAA
181 LGDHPEADLF SPPLETDSMD PFGMATKLGP VKSPSFQK
```

*Pteropus vampyrus* (megabat) FGF19 (Ensembl Accession No. ENSPVAP00000009339, which is hereby incorporated by reference in its entirety) (SEQ ID NO: 247)

```
  1 MRSPCAVARA LVLAGLWLAS AAGPLALSDA GPHVHYGWGE AIRLRHLYTA GPHGPSSCFL
 61 RIRADGAVDC ARGQSAHSLV EIRAVALRNV AIKGVHSVRY LCMGADGRML GLLQYSADDC
121 AFEEEIRPDG YNVYHSKKHH LPVSLSSAKQ RQLYKDRGFL PLSHFLPMLP RSPTEPENFE
181 DHLEADTFSS LETDDMDPFG IASKLGLEES PSFQK
```

*Tursiops truncatus* (dolphin) FGF19 (Ensembl Accession No. ENSTTRP00000000061, which is hereby incorporated by reference in its entirety) (SEQ ID NO: 248)

```
  1 MRSAPSRCAV ARALVLAGLW LAAAGRPLAF SDAGPHVHYG WGESVRLRHL YTAGPQGLSS
 61 CFLRIHSDGA VDCAPVQSAH SLMEIRAVAL STVAIKGERS VLYLCMGADG KMQGLSQYSA
121 EDCAFEEEIR PDGYNVYWSK KHHLPVSLSS ARQRQLFKGR GFLPLSHFLP MLSTIPTEPD
181 EIQDHLKPDL FALPLKTDSM DPFGLATKLG VVKSPSFYK
```

*Myotis lucifugus* (microbat) FGF19 (Ensembl Accession No. ENSMLUP00000002279, which is hereby incorporated by reference in its entirety) (SEQ ID NO: 249)

```
  1 MQSAWSRRVV ARALVLASLG LASAGGPLGL SDAGPHVHYG WGESIRLRHL YTSGPHGPSS
 61 CFLRIRADGA VDCARGQSAH SLVEIRAVAL RKVAIKGVHS ALYLCMGGDG RMLGLPQFSP
121 EDCAFEEEIR PDGYNVYRSQ KHQLPVSLSS ARQRQLFKAR GFLPLSHFLP MLPSSPAGPV
181 PRERPSEPDE FSSPLETDSM DPFGIANNLR LVRSPSFQE
```

TABLE 7-continued

*Ornithorhynchus anatinus* (platypus) FGF19 (GenBank Accession No. XP_001506714, which is hereby incorporated by reference in its entirety)(SEQ ID NO: 250) (partial amino acid sequence corresponding to human FGF19 residues 79 to 216)

```
  1 MLSCVVLPSL LEIKAVAVRT VAIKGVHISR YLCMEEDGKT PWARLLEIKA VAVRTVAIKG
 61 VHSSRYLCME EDGKLHGQIW YSAEDCAFEE EIRPDGYNVY KSKKYGVPVS LSSAKQRQQF
121 KGRDFLPLSR FLPMINTVPV EPAEFGDYAD YFESDIFSSP LETDSMDPFR IAPKLSPVKS
181 PSFQK
```

*Monodelphis domestica* (opossum) FGF19 (GenBank Accession No. XP_001506714, which is hereby incorporated by reference in its entirety) (SEQ ID NO: 251)

```
  1 MAQLLAPLLT LAALWLAPTA RARPLVDAGP HVYYGWGEPI RLRHLYTANR HGLASFSFLR
 61 IHRDGRVDGS RSQSALSLLE IKAVALRMVA IKGVHSSRYL CMGDAGKLQG SVRFSAEDCT
121 FEEQIRPDGY NVYQSPKYNL PVSLCTDKQR QQAHGKEHLP LSHFLPMINA IPLEAEEPEG
181 PRMLAAPLET DSMDPFGLTS KLLPVKSPSF QK
```

*Anolis carolinensis* (anole lizard) FGF19 (GenBank Accession No. XP_003214715, which is hereby incorporated by reference in its entirety) (SEQ ID NO: 252)

```
  1 MCRRALPLLG ALLGLAAVAS RALPLTDAGP HVSYGWGEPV RLRHLYTAGR QGLFSQFLRI
 61 HADGRVDGAG SQNRQSLLEI RAVSLRAVAL KGVHSSRYLC MEEDGRLRGM LRYSAEDCSF
121 EEEMRPDGYN IYKSKKYGVL VSLSNARQRQ QFKGKDFLPL SHFLPMINTV PVESADFGEY
181 GDTRQHYESD IFSSRLETDS MDPFGLTSEV SSVQSPSFGK
```

*Ochotona princeps* (pika) FGF19 (Ensembl Accession No. ENSOPRP00000009838, which is hereby incorporated by reference in its entirety) (SEQ ID NO: 253) (partial amino acid sequence corresponding to human FGF19 residues 12 to 77 and 113 to 216)

```
  1 VRSRGAMARA LVLATLWLAA TGRPLALSDA GPHLHYGWGE PIRLRHLYAT SAHGLSHCFL
 61 RIRTDGTVDC ERSQSAH--- ---------- ---------- ---------- --LQYSEEDC
121 AFEEEISSGY NVYRSRRYQL PVSLGSARQR QLQRSRGFLP LSHFLPVLPA ASEEVAAPAD
181 HPQADPFSPL ETDSMDPFGM ATKRGLVKSP SFQK
```

*Cavia porcellus* (guinea pig) FGF19 (Ensembl Accession No. ENSCPOP00000007325, which is hereby incorporated by reference in its entirety) (SEQ ID NO: 254)

```
  1 MWSAPSGCVV IRALVLAGLW LAVAGRPLAR RSLALSDQGP HLYYGWDQPI RLRHLYAAGP
 61 YGRSRCFLRI HTDGAVDCVE EQSEHCLLEI RAVALETVAI KDINSVRYLC MGPDGRMRGL
121 PWYSEEDCAF KEEISYPGYS VYRSQKHHLP IVLSSVKQRQ QYQSKGVVPL SYFLPMLPKA
181 SVEPSDEEES SVFSLPLKTD SMDPFGMASE IGLVKSPSFQ K
```

*Tupaia belangeri* (tree shrew) FGF19 (Ensembl Accession No. ENSTBEP00000000264, which is hereby incorporated by reference in its entirety) (SEQ ID NO: 255) (partial amino acid sequence corresponding to human FGF19 (residues 1 to 112 and 136 to 216)

```
  1 MRRTPSGFAV ARVLFLGSLW LAAAGSPLAL SDAGPHVNYG WDESIRLRHL YTASPHGSTS
 61 CFLRIRDDGS VDCARGQSLH SLLEIKAVAL QTVAIKGVYS VRYLCMDADG RMQGL-----
121 ---------- --------ST KHGLPVSLSS AKQRQLLTVR GFPSLPHFLL MMAKTSAGPG
181 NPRDHPGSNT FSLPLETDSM DPFGMTTRHG LVKSPSFQN
```

*Rattus norvegicus* (Norway rat) FGF15 (GenBank Accession No. NP_570109, which is hereby incorporated by reference in its entirety) (SEQ ID NO: 256)

```
  1 MARKWSGRIV ARALVLATLW LAVSGRPLVQ QSQSVSDEGP LFLYGWGKIT RLQYLYSAGP
 61 YVSNCFLRIR SDGSVDCEED QNERNLLEFR AVALKTIAIK DVSSVRYLCM SADGKIYGLI
121 RYSEEDCTFR EEMDCLGYNQ YRSMKHHLHI IFIKAKPREQ LQGQKPSNFI PIFHRSFFES
181 TDQLRSKMFS LPLESDSMDP FRMVEDVDHL VKSPSFQK
```

*Mus musculus* (house mouse) FGF15 (GenBank Accession No. NP_032029, which is hereby incorporated by reference in its entirety) (SEQ ID NO: 257)

```
  1 MARKWNGRAV ARALVLATLW LAVSGRPLAQ QSQSVSDEDP LFLYGWGKIT
    RLQYLYSAGP
 61 YVSNCFLRIR SDGSVDCEED QNERNLLEFR AVALKTIAIK DVSSVRYLCM SADGKIYGLI
121 RYSEEDCTFR EEMDCLGYNQ YRSMKHHLHI IFIQAKPREQ LQDQKPSNFI PVFHRSFFET
181 GDQLRSKMFS LPLESDSMDP FRMVEDVDHL VKSPSFQK
```

TABLE 7-continued

*Gallus gallus* (chicken) FGF19 (GenBank Accession No. NP_990005, which is hereby incorporated by reference in its entirety) (SEQ ID NO: 258)

```
  1 MGPARPAAPG AALALLGIAA AAAAARSLPL PDVGGPHVNY GWGEPIRLRH LLHRPGKHGL
 61 FSCFLRIGGD GRVDAVGSQS PQSLLEIRAV AVRTVAIKGV QSSRYLCMDE AGRLHGQLSY
121 SIEDCSFEEE IRPDGYNVYK SKKYGISVSL SSAKQRQQFK GKDFLPLSHF LPMINTVPVE
181 VTDFGEYGDY SQAFEPEVYS SPLETDSMDP FGITSKLSPV KSPSFQK
```

*Taeniopygia guttata* (zebra finch) FGF19 (GenBank Accession No. XP_002194493, which is hereby incorporated by reference in its entirety) (SEQ ID NO: 259)

```
  1 MVIISNLYLM QNDVMMNMRR APLRVHAARS SATPASALPL PPPDAGPHLK YGWGEPIRLR
 61 HLYTASKHGL FSCFLRIGAD GRVDAAGSQS PQSLLEIRAV AVRTVAIKGV QSSRYLCMDE
121 AGRLHGQLRN STEDCSFEEE IRPDGYNVYR SKKHGISVSL SSAKQRQQFK GKDFLPLSHF
181 LPMINTVPME SADFGEYGDY SQAFEAEAFS SPLETDSMDP FGIASKLSLV KSPSFQN
```

*Danio rerio* (zebrafish) FGF19 (GenBank Accession No. NP_001012246, which is hereby incorporated by reference in its entirety) (SEQ ID NO: 260)

```
  1 MLLLLFVTVC GSIGVESLPL PDSGPHLAND WSEAVRLRHL YAARHGLHLQ INTDGEIIGS
 61 TCKARTVSLM EIWPVDTGCV AIKGVASSRF LCMERLGNLY GSHIYTKEDC SFLERILPDG
121 YNVYFSSKHG ALVTLSGAKN KLHSNDGTSA SQFLPMINTL SEEHTKQHSG EQHSSVNHGQ
181 DHQLGLEIDS MDPFGKISQI VIQSPSFNKR
```

*Xenopus* (*Silurana*) *tropicalis* (western clawed frog) FGF19 (GenBank Accession No. NP_001136297, which is hereby incorporated by reference in its entirety) (SEQ ID NO: 261)

```
  1 MWKTLPWILV PMMVAVLYFL GGAESLPLFD AGPHMQNGWG ESIRIRHLYT ARRFGHDSYY
 61 LRIHEDGRVD GDRQQSMHSL LEIRAIAVGI VAIKGYRSSL YLCMGSEGKL YGMHSYSQDD
121 CSFEEELLPD GYNMYKSRKH GVAVSLSKEK QKQQYKGKGY LPLSHFLPVI SWVPMEPTGD
181 VEDDIYRFPF NTDTKSVIDS LDTLGLMDFS SYHKK
```

*Otolemur garnettii* (bushbaby) FGF19 (Ensembl Accession No. ENSOGAP00000017975, which is hereby incorporated by reference in its entirety) (SEQ ID NO: 262)

```
  1 MPSGLRGRVV AGALALASFW LAVAGRPLAF SDAGPHVHYG WGEPIRLRHL YTAGPHGLSS
 61 CFLRVRTDGA VDCARGQSAH SLLEIRAVAL RTVAIKGVHS ARYLCMGADG RMQGLPQYSE
121 EDCAFEEEIR PDGYNVYWSE KHRLPVSLSS ARQRQLYKGR GFLPLSHFLP MLPVTPAEPG
181 DLRDHLESDM FSLPLETDSM DPFGIATRLG VVKSPSFQK
```

*Felis catus* (cat) FGF19 (Ensembl Accession No. ENSFCAP00000022548, which is hereby incorporated by reference in its entirety) (SEQ ID NO: 263)

```
  1 MRSAPSQCAV TRALVLAGLW LAAAGRPLAF SDAGPHVHYG WGEPIRLRHL YTAGPHGLSS
 61 CFLRIRADGG VDCARSQSAH SLVEIRAVAL RTVAIKGVHS VRYLCMGADG RMQGLLQYSA
121 GDCAFQEEIR PDGYNVYRSE KHRLPVSLSS AIQRQLYKGR GFLPLSHFLP MLPGSPAEPR
181 DLQDHVESER FSSPLETDSM DPFGIATKMG LVKSPSFQK
```

*Pelodiscus sinensis* (Chinese softshell turtle) FGF19 (Ensembl Accession No. ENSPSIP00000010374, which is hereby incorporated by reference in its entirety) (SEQ ID NO: 264)

```
  1 MWRSLCKSHT SLALLGLCFA VVVRSLPFSD AGPHVNYGWG EPIRLRHLYT ASRHGLFNYF
 61 LRISSDGKVD GTSIQSPHSL LEIRAVAVRT VAIKGVHSSR YLCMEEDGKL HGLLRYSTED
121 CSFEEEIRPD GYNVYKSKKY GISVSLSSAK QRQQFKGKDF LPLSHFLPMI NTVPVESMDF
181 GEYGDYSHTF ESDLFSSPLE TDSMDPFGIT SKISPVKSPS FQK
```

*Latimeria chalumnae* (coelacanth) FGF19 (Ensembl Accession No. ENSLACP00000014596, which is hereby incorporated by reference in its entirety) (SEQ ID NO: 265)

```
  1 MLQALYNLCT ALVLFKLPFA MVGYTLPSAN EGPHLNYDWG ESVRLKHLYT SSKHGLISYF
 61 LQINDDGKVD GTTTRSCYSL LEIKSVGPGV LAIKGIQSSR YLCVEKDGKL HGSRTYSADD
121 CSFKEDILPD GYTIYVSKKH GSVVNLSNHK QKRQRNRRTL PPFSQFLPLM DTIRVECMNC
181 GEHCDDNLHD ELETGLSMDP FESTSKKSFQ SPSFHNR
```

*Mustela putorius furo* (ferret) FGF19 (Ensembl Accession No. ENSMPUP00000004571, which is hereby incorporated by reference in its entirety) (SEQ ID NO: 266)

```
  1 MRSAASRCAV ARALVLAGLW LAAAGRPLAF SDAGPHVHYG WGEPIRLRHL YTAGPHGLSS
 61 CFLRIRADGG VDCARGQSAH SLVEIRAVAL RTVAIKGVYS DRYLCMGADG RMQGLPQYSA
121 GDCAFEEEIR PDGYNVYRSK KHRLPVSLSS AKQRQLYKDR GFLPLSHFLP MLPGSLAEPR
181 DLQDHVEADG FSAPLETDSM DPFGIATKMG LVKSPSFQK
```

TABLE 7-continued

*Takifugu rubripes* (fugu) FGF19 (Ensembl Accession No. ENSTRUP00000007110, which is hereby incorporated by reference in its entirety) (SEQ ID NO: 267)

```
  1 SSTRISGNMV LLMLPITVAN LFLCAGVLSL PLLDQGSHFP QGWEQVVRFR HLYAASAGLH
 61 LLITEEGSIQ GSADPTLYSL MEIRPVDPGC VVIRGAATTR FLCIEGAGRL YSSQTYSKDD
121 CTFREQILAD GYSVYRSVGH GALVSLGNYR QQLRGEDWSV PTLAQFLPRI SSLDQDFKAA
181 LDETEKPEQT APQRSEPVDM VDSFGKLSQI IHSPSFHK
```

*Equus caballus* (horse) FGF19 (Ensembl Accession No. ENSECAP00000017705, which is hereby incorporated by reference in its entirety) (SEQ ID NO: 268); partial sequence corresponding to human FGF19 residues 20 to 113

```
  1 AAGRPLALSD AGPHVHYGWG EPIRLRHLYT AGPHGLSSCF LRIRADGAVD CARGQSAHSL
 61 VEIRAVALRT VAIKGVHSVR YLCMGADGRM QGLV
```

*Oryzias latipes* (medaka) FGF19 (Ensembl Accession No. ENSORLP00000000352, which is hereby incorporated by reference in its entirety) (SEQ ID NO: 269)

```
  1 TMLLIVVTIS TMVFSDSGVS SMPLSDHGPH ITHSWSQVVR LRHLYAVKPG QHVQIREDGH
 61 IHGSAEQTLN SLLEIRPVAP GRVVFRGVAT SRFLCMESDG RLFSSHTFDK DNCVFREQIL
121 ADGYNIYISD QHGTLLSLGN HRQRQQGLDR DVPALAQFLP RISTLQQGVY PVPDPPHQMR
181 TMQTEKTLDA TDTFGQLSKI IHSPSFNKR
```

*Xiphophorus maculatus* (platyfish) FGF19 (Ensembl Accession No. ENSXMAP00000001516, which is hereby incorporated by reference in its entirety) (SEQ ID NO: 270)

```
  1 MFVFILCIAG ELFTLGVFCM PMMDQGPLVT HGWGQVVRHR HLYAAKPGLH LLISEDGQIH
 61 GSADQTLYSL LEIQPVGPGR VVIKGVATTR FLCMESDGRL YSTETYSRAD CTFREQIQAD
121 GYNVYTSDSH GALLSLGNNQ QRHSGSDRGV PALARFLPRL NTLQQAVPTE PDVPDQLSPE
181 KVQQTVDMVA SFGKLSHIIH SPSFHKR
```

*Ictidomys tridecemlineatus* (squirrel) FGF19 (Ensembl Accession No. ENSSTOP00000021639, which is hereby incorporated by reference in its entirety) (SEQ ID NO: 271)

```
  1 MRSAPSGRAL ARALVLASLW LAVAGRPLAR RSLALSDQGP HLYYGWDQPI RLRHLYAAGP
 61 YGFSNCFLRI RTDGAVDCEE KQSERSLMEI RAVALETVAI KDINSVRYLC MGADGRIQGL
121 PRYSEEECTF KEEISYDGYN VYRSQKYHLP VVLSSAKQRQ LYQSKGVVPL SYFLPMLPLA
181 SAETRDRLES DVFSLPLETD SMDPFGMASE VGLKSPSFQK
```

*Gasterosteus aculeatus* (stickleback) FGF19 (Ensembl Accession No. ENSGACP00000018732, which is hereby incorporated by reference in its entirety) (SEQ ID NO: 272)

```
  1 MLLLLVPAYV ASVFLALGVV CLPLTDQGLH MADDWGQSVR LKHLYAASPG LHLLIGEDGR
 61 IQGSAQQSPY SLLEISAVDP GCVVIRGVAT ARFLCIEGDG RLYSSDTYSR DDCTFREQIL
121 PDGYSVYVSH GHGALLSLGN HRQRLQGRDH GVPALAQFLP RVSTMDQASA PDAPGQTATE
181 TEEPVDSFGK LSQIIHSPSF HER
```

*Oreochromis niloticus* (tilapia) FGF19 (Ensembl Accession No. ENSONIP00000022796, which is hereby incorporated by reference in its entirety) (SEQ ID NO: 273)

```
  1 MLLLLIVSIV NMLFGVGMVC MPLSDNGPHI AHGWAQVVRL RHLYATRPGM HLLISEGGQI
 61 RGSAVQTLHS LMEIRPVGPG RVVIRGVATA RFLCIEDDGT LYSSHAYSRE DCIFREQILP
121 DGYNIYISDR HGVLLSLGNH RQRLQGLDRG DPALAQFLPR ISTLNQIPSP GANIGDHMKV
181 AKTEEPVDTI DSFGKFSQII DSPSFHKR
```

*Meleagris gallopavo* (turkey) FGF19 (Ensembl Accession No. ENSMGAP00000010265, which is hereby incorporated by reference in its entirety) (SEQ ID NO: 274); partial sequence corresponding to human FGF19 residues 71 to 216

```
  1 VGNQSPQSIL EITAVDVGIV AIKGLFSGRY LAMNKRGRLY ASLSYSIEDC SFEEEIRPDG
 61 YNVYKSKKYG ISVSLSSAKQ RQQFKGKDFL PLSHFLPMIN TVPVEVTDFG EYGDYSQAFE
121 PEVYSSPLET DSMDPFGITS KLSPVKSPSF QK
```

*Papio anubis* (olive baboon) FGF19 (GenBank Accession No. XP_003909471, which is hereby incorporated by reference in its entirety) (SEQ ID NO: 275)

```
  1 MRSGCVVVHA WILASLWLAV AGRPLAFSDA GPHVHYGWGD PIRLRHLYTS GPHGLSSCFL
 61 RIRTDGVVDC ARGQSAHSLL EIKAVALRTV AIKGVHSVRY LCMGADGKMQ GLLQYSEEDC
121 AFEEEIRPDG YNVYRSQKHR LPVSLSSAKQ RQLYKNRGFL PLSHFLPMLP MAPEEPEDLR
181 GPLESDMFSS PLETDSMDPF GLVTGLEAVR SPSFEK
```

TABLE 7-continued

*Saimiri boliviensis boliviensis* (Bolivian squirrel monkey) FGF19 (GenBank Accession No. XP_003941214, which is hereby incorporated by reference in its entirety) (SEQ ID NO: 276)

```
  1 MRSGCVVVHA WILAGLWLAV VGRPLAFSDA GPHVHYGWGD PIRLRHLYTS SPHGLSSCFL
 61 RIRSDGVVDC ARGQSAHSLL EIKAVALRTV AIKGVHSSRY LCMGADGRLQ GLFQYSEEDC
121 AFEEEIRPDG YNVYLSEKHR LPVSLSSAKQ RQLYKKRGFL PLSHFLPMLP RAPEEPDDLR
181 GHLESDVFSS PLETDSMDPF GLVTGLEAVN SPSFEK
```

*Pteropus alecto* (black flying fox) FGF19 (GenBank Accession No. ELK13233, which is hereby incorporated by reference in its entirety) (SEQ ID NO: 277)

```
  1 MRSPCAVARA LVLAGLWLAS AAGPLALSDA GPHVHYGWGE AIRLRHLYTA GPHGPSSCFL
 61 RIRADGAVDC ARGQSAHSLV EIRAVALRNV AIKGVHSVRY LCMGADGRML GLLQYSADDC
121 AFEEEIRPDG YNVYHSKKHH LPVSLSSAKQ RQLYKDRGFL PLSHFLPMLP RSPTEPENFE
181 DHLEADTFSS PLETDDMDPF GIASKLGLEE SPSFQK
```

*Myotis davidii* (David's myotis) FGF19 (GenBank Accession No. ELK24234, which is hereby incorporated by reference in its entirety) (SEQ ID NO: 278)

```
  1 MSGQNSGRHG SRPGLDEEPE PGPLELRALG STRADPQLCD FLENHFLGYT CLELDICLAT
 61 YLGVSHWGES IRLRHLYTSG PHGPSSCFLR IRVDGAVDCA RGQSAHSLVE IRAVALRKVA
121 IKGVHSALYL CMEGDGRMRG LPQFSPEDCA FEEEIRPDGY NVYRSQKHQL PVSLSSARQR
181 QLFKARGFLP LSHFLPMLPS SPAEPVHRER PLEPDAFSSP LETDSMDPFG IANNLRLVKS
241 PSFQK
```

*Tupaia chinensis* (Chinese tree shrew) FGF19 (GenBank Accession No. ELW64990, which is hereby incorporated by reference in its entirety) (SEQ ID NO: 279); residues 1-257, excluding 13-19

```
  1 MRRTWSGFAV AT-------R AGSPLALADA GPHVNYGWDE SIRLRHLYTA SLHGSTSCFL
 61 RIRDDGSVGC ARGQSMHSLL EIKAVALQTV AIKGVYSVRY LCMDTDGRMQ GLPQYSEEDC
121 TFEEEIRSDG HNVYRSKKHG LPVSLSSAKQ RQLYKGRGFL SLSHFLLMMP KTSAGPGNPR
181 DQRNPRDQRD PNTFSLPLET DSMDPFGMTT RHGLLLDSCC ASLVLLNIST DGEFSPYGNI
241 LRPSFRFKLF KMKKVTN
```

*Heterocephalus glaber* (naked mole-rat) FGF19 (GenBank Accession No. EHB12332, which is hereby incorporated by reference in its entirety) (SEQ ID NO: 280)

```
  1 MRFSKSTCGF FNHQRLQALW LSLSSVKWVL DAAVEGRPIR LRHLYAAGPY GRSRCFLRIH
 61 TDGAVDCVEE QSEHCLLEIR AVALETVAIK DINSVRYLCM GPDGRMQGLP WYSEEDCAFK
121 EEISYPGYSV YRSQKHHLPI VLSSVKQRQQ YQSKGVVPLS YFLPMLPKAS VEPGDEEESA
181 FSLPLKTDSM DPFGMASEIG LAKSPSFQK
```

In one embodiment, a C-terminal portion of FGF19 of the chimeric protein of the present invention comprises the conserved amino acid sequence TGLEAV(R/N)SPSFEK (SEQ ID NO: 281). In one embodiment, a C-terminal portion of FGF19 comprises the conserved amino acid sequence MDPFGLVTGLEAV(R/N)SPSFEK (SEQ ID NO: 282). In one embodiment, the C-terminal portion of FGF19 of the chimeric protein of the present invention comprises the conserved amino acid sequence LP(M/I)(V/A)PEEPEDLR(G/R) HLESD(M/V)FSSPLETDSMDPFGLVTGLEAV(R/N) SPSFEK (SEQ ID NO: 283).

In one embodiment, the C-terminal portion of FGF19 of the chimeric protein of the present invention consists of an amino acid sequence selected from the group consisting of TGLEAV(R/N)SPSFEK (SEQ ID NO: 281); MDPF-GLVTGLEAV(R/N)SPSFEK (SEQ ID NO: 282); and LP(M/I)(V/A)PEEPEDLR(G/R)HLESD(M/V)FSSPLETDSMD-PFGLVTGLEAV(R/N)SPSFEK (SEQ ID NO: 283).

In certain embodiments according to the present invention, the C-terminal portion of FGF19 of the chimeric protein of the present invention includes a polypeptide sequence that has at least 80%, at least 85%, at least 90%, at least 95%, at least 97%, or at least 99% amino acid sequence identity to the amino acid sequences of any of TGLEAV(R/N)SPSFEK (SEQ ID NO: 281); MDPFGLVTGLEAV(R/N)SPSFEK (SEQ ID NO: 282); or LP(M/I)(V/A)PEEPEDLR(G/R) HLESD(M/V)FSSPLETDSMDPFGLVTGLEAV(R/N)SPS-FEK (SEQ ID NO: 283). In certain embodiments according to the present invention, the C-terminal portion of FGF19 of the chimeric protein of the present invention includes a polypeptide sequence that has at least 80%, at least 85%, at least 90%, at least 95%, at least 97%, or at least 99% amino acid sequence homology to the amino acid sequences of any of TGLEAV(R/N)SPSFEK (SEQ ID NO: 281); MDPF-GLVTGLEAV(R/N)SPSFEK (SEQ ID NO: 282); or LP(M/I)(V/A)PEEPEDLR (G/R)HLESD(M/V)FSSPLETDSMD-PFGLVTGLEAV(R/N)SPSFEK (SEQ ID NO: 283).

It will be understood that the portion from FGF19 of the chimeric protein of the present invention may be from a nucleotide sequence that encodes an FGF19 protein (e.g., those encoding orthologs) from a mammal or even a non-mammalian species. For example, a nucleotide sequence encoding a mammalian or non-mammalian FGF19 protein according to the present invention may include, but is not limited to, those FGF-encoding nucleotide sequences shown in Table 8.

TABLE 8

Human FGF19 gene coding sequence (1-216)(SEQ ID NO: 284) (GenBank Accession No. NM_005117, which is hereby incorporated by reference in its entirety)

```
 464    ATGCGGA GCGGGTGTGT GGTGGTCCAC GTATGGATCC TGGCCGGCCT CTGGCTGGCC
 521 GTGGCCGGGC GCCCCCTCGC CTTCTCGGAC GCGGGGCCCC ACGTGCACTA CGGCTGGGGC
 581 GACCCCATCC GCCTGCGGCA CCTGTACACC TCCGGCCCCC ACGGGCTCTC CAGCTGCTTC
 641 CTGCGCATCC GTGCCGACGG CGTCGTGGAC TGCGCGGGG GCCAGAGCGC GCACAGTTTG
 701 CTGGAGATCA AGGCAGTCGC TCTGCGGACC GTGGCCATCA AGGGCGTGCA CAGCGTGCGG
 761 TACCTCTGCA TGGGCGCCGA CGGCAAGATG CAGGGGCTGC TTCAGTACTC GGAGGAAGAC
 821 TGTGCTTTCG AGGAGGAGAT CCGCCCAGAT GGCTACAATG TGTACCGATC CGAGAAGCAC
 881 CGCCTCCCGG TCTCCCTGAG CAGTGCCAAA CAGCGGCAGC TGTACAAGAA CAGAGGCTTT
 941 CTTCCACTCT CTCATTTCCT GCCCATGCTG CCCATGGTCC CAGAGGAGCC TGAGGACCTC
1001 AGGGGCCACT TGGAATCTGA CATGTTCTCT TCGCCCCTGG AGACCGACAG CATGGACCCA
1061 TTTGGGCTTG TCACCGGACT GGAGGCCGTG AGGAGTCCCA GCTTTGAGAA GTAA
```

Gorilla FGF19 gene coding sequence (1-216) (SEQ ID NO: 285) (Ensembl Accession No. ENSGGOT00000028361, which is hereby incorporated by reference in its entirety)

```
 463    ATGCGGAG CGGGTGTGTG GTGGTCCACG TCTGGATCCT GGCCGGCCTC TGGCTGGCCG
 521 TGGCCGGGCG CCCCCTCGCC TTCTCGGACG CGGGGCCCCA CGTGCACTAC GGCTGGGGCG
 581 ACCCCATCCG CCTGCGGCAC CTGTACACCT CCGGCCCCCA CGGGCTCTCC AGCTGCTTCC
 641 TGCGCATCCG TGCCGACGGC GTCGTGGACT GCGCGCGGGG CCAGAGCGCG CACAGTTTGC
 701 TGGAGATCAA GGCAGTCGCT CTGCGGACCG TGGCCATCAA GGGCGTGCAC AGCGTGCGGT
 761 ACCTCTGCAT GGGCGCCGAC GGCAAGATGC AGGGGCTGCT TCAGTACTCG GAGGAAGACT
 821 GTGCTTTCGA GGAGGAGATC CGCCCAGATG GCTACAATGT GTACCGATCT GAGAAGCACC
 881 GCCTCCCGGT CTCCCTGAGC AGTGCCAAAC AGCGGCAGCT GTACAAGAAC AGAGGCTTTC
 941 TTCCGCTCTC TCATTTCCTG CCCATGCTGC CCATGGTCCC AGAGGAGCCT GAGGACCTCA
1001 GGGGCCACTT GGAATCTGAC ATGTTCTCTT CACCCCTGGA GACCGACAGC ATGGACCCAT
1061 TTGGGCTTGT CACCGGACTG GAGGCCGTGA GGAGTCCTAG CTTTGAGAAG TAA
```

Pan troglodytes gene coding sequence (1-216) (chimpanzee) FGF19(SEQ ID NO: 286) (Ensembl Accession No. ENSPTRT00000007454, which is hereby incorporated by reference in its entirety)

```
   1 ATGCGGAACG GGTGTGTGGT GGTCCACGTC TGGATCCTGG CCGGCCTCTG GCTGGCCGTG
  61 GCCGGGCGCC CCCTCGCCTT CTCGGACGCG GGGCGCCACG TGCACTACTG CTGGGGCGAC
 121 CCCATCCCCC TGCGGCACCT GTACACCTCC GGCCCCCATG GCTCTCCAG CTGCTTCCTG
 181 CGCATCCCTG CGAACTGCGT CATGAACTGC GCGCGGGGCC AGAGCGCGCA CAGTTTGCTG
 241 GAGATCAAGG CAGTCGCTCT GCGGACCGTG GCCATCAAGG GCGTGCACAG CGTGCGGTAC
 301 CTCTGCATGG GCGCCGACGG CAAGATGCAG GGGCTGCTTC AGTACTCGGA GGAAGACTGT
 361 GCTTTCGAGG AGGAGATCCG CCCAGATGGC TACAATGTGT ACCGATCCGA GAAGCACCGC
 421 CTCCCGGTCT CCCTGAGCAG TGCCAAACAG CGGCAGCTGT ACAAGAACAG AGGCTTTCTT
 481 CCACTCTCTC ATTTCCTGCC CATGCTGCCC ATGGTCCCAG AGGAGCCTGA GGACCTCAGG
 541 GGCCACTTGG AATCTGACAT GTTCTCTTCG CCCCTGGAGA CCGACAGCAT GGACCCATTT
 601 GGGCTTGTCA CCGGACTGGA GGCCGTGAGG AGTCCCAGCT TTGAGAAGTA A
```

Macaca mulatta gene coding sequence (1-216) (Rhesus monkey) FGF19 (SEQ ID NO: 287) (GenBank Accession No. XM_001100825, which is hereby incorporated by reference in its entirety)

```
 758        ATG AGGAGCGGGT GTGTGGTGGT CCACGCCTGG ATCCTGGCCA GCCTCTGGCT
 811 GGCCGTGGCC GGGCGTCCCC TCGCCTTCTC GGACGCGGGG CCCCACGTGC ACTACGGCTG
 871 GGGCGACCCC ATCCGCCTGC GGCACCTGTA CACCTCCGGC CCCCATGGGC TCTCCAGCTG
 931 CTTCCTGCGC ATCCGCACCG ACGGCGTCGT GGACTGCGCG CGGGGCCAAA GCGCGCACAG
 991 TTTGCTGGAG ATCAAGGCAG TAGCTCTGCG GACCGTGGCC ATCAAGGGCG TGCACAGCGT
1051 GCGGTACCTC TGCATGGGCG CCGACGGCAA GATGCAGGGG CTGCTTCAGT ACTCAGAGGA
1111 AGACTGTGCT TTCGAGGAGG AGATCCGCCC TGATGGCTAC AATGTATACC GATCCGAGAA
1171 GCACCGCCTC CCGGTCTCTC TGAGCAGTGC CAAACAGAGG CAGCTGTACA AGAACAGAGG
1231 CTTTCTTCCG CTCTCTCATT TCCTACCCAT GCTGCCCATG GCCCCAGAGG AGCCTGAGGA
1291 CCTCAGGGGC CACTTGGAAT CTGACATGTT CTCTTCGCCC CTGGAGACTG ACAGCATGGA
1351 CCCATTTGGG CTTGTCACCG GACTGGAGGC GGTGAGGAGT CCCAGCTTTG AGAAATAA
```

Pongo abelii gene coding sequence (1-216) (Sumatran orangutan) FGF19 (SEQ ID NO: 288) (GenBank Accession No. XM_002821413, which is hereby incorporated by reference in its entirety)

```
 763   ATGCGGAG CGGGTGTGTG GTGGTCCACG CCTGGATCCT GGCCGGCCTC TGGCTGGCCG
 821 TGGCCGGGCG CCCCCTCGCC TTCTCGGACT CGGGGCCCCA CGTGCACTAC GGCTGGGGCG
 881 ACCCCATCCG CCTGCGGCAC CTGTACACCT CCGGCCCCCA CGGGCTCTCC AGCTGCTTCC
 941 TGCGCATCCG TGCCGACGGC GTCGTGGACT GCGCGCGGGG CCAGAGCGCG CACAGTTTGC
1001 TGGAGATCAA GGCAGTCGCT CTGCGGACCG TGGCCATCAA GGGCGTGCAC AGCGTGCGGT
1061 ACCTCTGCAT GGGCGCCGAC GGCAAGATGC AGGGGCTGCT TCAGTACTCG GAGGAAGACT
1121 GTGCTTTCGA GGAGGAGATC CGCCCAGATG GCTACAATGT GTACCGATCC GAGAAGCACC
1181 GCCTCCCGGT CTCCCTGAGC AGTGCCAAAC AGCGGCAGCT GTACAAGAAC AGGGGCTTTC
1241 TTCCGCTCTC TCATTTCCTG CCCATGCTGC CCATGGTCCC AGAGGAGCCT GAGGACCTCA
1301 GGCGCCACTT GGAATCCGAC ATGTTCTCTT CGCCCCTGGA GACCGACAGC ATGGACCCAT
1361 TTGGGCTTGT CACCGGACTG GAGGCCGTGA GGAGTCCCAG CTTTGAGAAA TAA
```

TABLE 8-continued

*Nomascus leucogenys* gene coding sequence (1-216) (Northern white-cheeked gibbon) FGF19 (SEQ ID NO: 289) (Genbank Accession No. XM_003278023, which is hereby incorporated by reference in its entirety)

```
 456      ATGCG GAGCGAGTGT GTGGTGGTCC ACGCCTGGAT CCTGGCCGGC CTCTGGCTGG
 511 CAGTGGCCGG GCGCCCCCTC GCCTTTTCGG ACGCGGGGCC CCACGTGCAC TACGGCTGGG
 571 GCGACCCCAT CCGTCTGCGG CACCTGTACA CCTCCGGCCC CCACGGGCTC TCCAGCTGCT
 631 TCCTGCGCAT CCGTGCCGAC GGCGTCGTGG ACTGCGCGCG GGGCCAGAGC GCGCACAGTT
 691 TGCTGGAGAT CAAGGCAGTC GCTCTGCGGA CCGTGGCCAT AAAGGGCGTG CACAGCGTGC
 751 GGTACCTCTG CATGGGCGCC GACGGCAAGA TGCAGGGGCT GCTTCAGTAT TCGGAGGAAG
 811 ACTGTGCTTT CGAGGAGGAG ATCCGCCCAG ATGGCTACAA TGTGTACCGA TCCGAGAAGC
 871 ACCGCCTCCC CGTCTCCCTG AGCAGTGCCA AACAGCGGCA GCTGTATAAG AACAGAGGCT
 931 TTCTTCCACT CTCTCATTTC CTGCCCATGC TGCCCATGGT CCCAGAGGAG CCTGAGGACC
 991 TCAGGGGCCA CTTGGAATCT GACATGTTCT CTTCGCCCCT GGAGACCGAC AGCATGGACC
1051 CATTTGGGCT TGTCACCGGA CTGGAGGCCG TGAGGAGTCC CAGCTTTGAG AAATAA
```

*Callithrix jacchus* gene coding sequence (1-142) (white-tufted-ear marmoset) FGF19 (SEQ ID NO: 290) (GenBank Accession No. XM_002763684, which is hereby incorporated by reference in its entirety)

```
  1 ATGTGGAAGG CCACCGCTGG TGGCCAGCAG GGACAGTCCG AAGCACAAAT GTCCACATGT
 61 CCCCATGTTC CTCGTCCTCT GTGGATTGCT CAGAGCTGCC TGTTTTCTCT GCAGCTCCAG
121 TACTCGGAGG AAGACTGTGC TTTCGAGGAG GAGATCCGCC CTGATGGCTA CAATGTGTAC
181 TGGTCCGAGA AGCACCGCCT CCCCGTCTCC CTGAGCAGCG CCAAACAGCG GCAGCTGTAC
241 AAGAAACGAG GCTTTCTTCC ACTGTCCCAT TTCCTGCCCA TGCTGCCCAT AGCCCCAGAA
301 GAGCCTGAGG ACCTCAGGGG ACACCTGGAA TCTGACGTGT TCTCTTCACC CCTGGAGACT
361 GACAGCATGG ACCCATTTGG GCTTGTCACG GGACTGGAGG CGGTGAACAG TCCCAGCTTT
421 GAGAAGTAA
```

*Microcebus murinus* gene coding sequence (1-219)(mouse lemur) FGF19 (SEQ ID NO: 291) (Ensembl Accession No. ENSMICT00000003065, which is hereby incorporated by reference in its entirety)

```
  1 ATGCCGAGCG GGCAAAGCGG TTGTGTGGCG GCCCGCGCCC TGATCCTGGC CGGCCTCTGG
 61 CTGACCGCGG CCGGGCGCCC GCTGGCCTTC TCCGACGCGG GCCCGCACGT GCACTACGGC
121 TGGGGCGAGC CCATCCGCCT GCGGCACCTG TACACCGCCG GCCCCCACGG CCTCTCCAGC
181 TGCTTCCTGC GCATCCGCGC AGACGGCTCC GTGGACTGCG CGCGGGGCCA GAGCGCACAC
241 AGTTTGCTGG AGATCAGGGC GGTCGCTCTT CGGACTGTGG CCATCAAGGG CGTGCACAGC
301 GTGCGGTACC TCTGCATGGG CGCAGACGGC AGGATGCAGG GCTGCTCCG GTACTCGGAG
361 GAAGACTGTG CCTTCGAGGA GGAGATCCGC CCCGATGGCT ACAACGTGTA CCGGTCTGAG
421 AAGCACCGCC TGCCGGTGTC TCTGAGCAGC GCCAGGCAGA GGCAGCTGTA CAAGGGCAGG
481 GGCTTCCTGC CGCTCTCTCA CTTCCTGCCC ATGCTGCCCG TGACCCCGGC AGAGACCGGG
541 GACCTCAGGG ACCACTTGGA GTCCGACATG TTCGCTTCGC CCCTGGAGAC CGACAGCATG
601 GACCCGTTTG GGATCGCCAC CAGACTTGGG GTGGTGAAGA GTCCCAGCTT TCAGAAATGA
```

*Choloepus hoffmanni* gene coding sequence (1-138) (sloth) FGF19 (SEQ ID NO: 292) (Ensembl Accession No. ENSCHOT00000002324, which is hereby incorporated by reference in its entirety)

```
  1 TTGCTCGAAA TGAAGGCAGT GGCGCTGCGG GCCGTGGCCA TCAAGGGCGT GCACAGTGCT
 61 CTGTACCTCT GCATGAACGC CGACGGCAGT CTGCACGGGC TGCCTCGGTA CTCTGCAGAA
121 GACTGTGCTT TGAGGAGGA AATCCGCCCC GACGGCTACA ATGTGTACTG GTCTAGGAAG
181 CACGGCCTCC CTGTCTCTTT GAGCAGTGCA AAACAGAGGC AGCTGTACAA AGGCAGAGGC
241 TTTCTGCCCC TGTCCCACTT CCTGCCCATG CTGCCCATGA CGCCGGCCGA GCCCGCAGAC
301 CCCGGGGATG ACGTGGAGTC GGACATGTTC TCTTCACCTC TGGAAACCGA CAGCATGGAT
361 CCTTTTGGAA TTGCCTCCAG ACTTGAGCTT GTGAACAGTC CAGCTTTCAG CATAA
```

*Ailuropoda melanoleuca* gene coding sequence (124-328) (giant panda) FGF19 (SEQ ID NO: 293) (GenBank Accession No. XM_002927906, which is hereby incorporated by reference in its entirety)

```
 69         GG TCCTAGCCGG CCTCTGCCTG GCGGTAGCCG GGCGCCCCT AGCCTTCTCG
421 GACGCGGGGC CGCACGTGCA CTACGGCTGG GGTGAGCCCA TCCGCCTACG GCACCTGTAC
481 ACCGCCGGCC CCACGGCCT CTCCAGCTGC TTCCTGCGCA TCCGTGCCGA CGGCGGGGTT
541 GACTGCGCGC GGGGCCAGAG CGCGCACAGT TTGGTGGAGA TCAGGGCAGT CGCTCTGCGG
601 ACCGTGGCCA TCAAGGGTGT GCACAGCGTC CGGTACCTCT GCATGGGCGC GACGGCAGG
661 ATGCAAGGGC TGCCTCAGTA CTCTGCAGGG GACTGTGCTT TCGAGGAGGA GATCCGCCCC
721 GACGGCTACA ATGTGTACCG GTCCAAGAAG CACCGTCTCC CCGTCTCTCT GAGCGGTGCC
781 AAACAGAGGC AGCTTTACAA AGACAGAGGC TTTCTGCCCC TGTCCCACTT CTTGCCCATG
841 CTGCCCGGGA GCCCAGCAGA GCCCAGGGAC CTCCAGGACC ATGCGGAGTC GGACGGGTTT
901 TCTGCACCCC TAGAAACAGA CAGCATGGAC CCTTTTGGGA TCGCCACCAA AATGGGACTA
961 GTGAAGAGTC CCAGCTTCCA GAAATAA
```

*Sus scrofa* gene coding sequence (1-218) (pig) FGF19 (SEQ ID NO: 294) (Ensembl Accession No. ENSSSCT00000014068, which is hereby incorporated by reference in its entirety)

```
  1 ATGCGGAGCG CTCCGAGCCG GTGCGCGGTG GTCCGCGCCC TGGTCCTGGC CGGCCTCTGG
 61 CTGGCCGCAG CCGGGCGCCC CCTAGCCTTC TCGGATGCTG GGCCGCACGT GCACTACGGC
```

TABLE 8-continued

```
121 TGGGGCGAGT CGGTCCGCCT GCGGCACCTG TACACTGCGA GTCCCCACGG CGTCTCCAGC
181 TGCTTCCTGC GCATCCACTC AGACGGCCCC GTGGACTGCG CGCCGGGACA GAGCGCGCAC
241 AGTTTGATGG AGATCAGGGC AGTCGCGCTG AGTACCGTGG CGATCAAGGG CGAGCGCAGC
301 GGCCGTTACC TCTGCATGGG CGCCGACGGC AAGATGCAAG GGCAGACTCA GTACTCGGAT
361 GAGGACTGTG CTTTCGAGGA GGAGATCCGC CCTGATGGCT ACAACGTGTA CTGGTCCAAG
421 AAACACCATC TGCCCGTCTC TCTGAGCAGC GCCAGGCAGA GGCAGCTGTA CAAAGGCAGG
481 GGCTTCCTGC CGCTGTCCCA CTTTCTGCCC ATGCTGTCCA CTCTCCCAGC CGAGCCGGAG
541 GACCTCCAGG ACCCCTTCAA GTCCGACCTG TTTTCTTTGC CCCTGGAAAC GGACAGCATG
601 GACCCTTTCC GGATCGCCGC CAAACTGGGA GCGGTGAAGA GTCCCAGCTT CTATAAATAA
```

Bos taurus gene coding sequence (136-353)(bovine) FGF19 (SEQ ID NO: 295) (GenBank Accession No. XM_599739, which is hereby incorporated by reference in its entirety)

```
 406                                                ATGCG GAGCGCTCCG
 421 AGCCGGTGCG CCGTGGCCCG CGCCCTGGTC CTGGCTGGCC TCTGGCTGGC CGCAGCCGGG
 481 CGCCCCCTGG CCTTCTCGGA TGCGGGGCCG CACGTGCACT ACGGCTGGGG CGAGTCGGTT
 541 CGCTTGCGGC ACCTGTATAC CGCGGGCCCG CAGGGCCTCT ACAGCTGCTT TCTGCGCATC
 601 CACTCCGACG GCGCCGTGGA CTGCGCGCAG GTCCAGAGCG CGCACAGTTT GATGGAGATC
 661 AGGGCGGTCG CTCTGAGCAC CGTAGCCATC AAGGGCGAGC GCAGCGTGCT GTACCTCTGC
 721 ATGGACGCCG ACGGCAAGAT GCAAGGACTG ACCCAGTACT CTGACGAGGA CTGTGCTTTC
 781 GAGGAGGAGA TCCGTCCTGA CGGCTACAAC GTGTACTGGT CCAGGAAGCA CCATCTCCCG
 841 GTCTCCCTGA GCAGCTCCAG GCAGAGGCAG CTGTTCAAAA GCAGGGGCTT CCTGCCGCTG
 901 TCTCACTTCC TGCCCATGCT GTCCACCATC CCAGCCGAAC CTGAAGACCT CCAGGAACCC
 961 CTGAAGCCTG ATTTCTTTCT GCCCCTGAAA ACAGATAGCA TGGACCCTTT CGGGCTCGCC
1021 ACCAAACTGG GATCGGTGAA GAGTCCCAGC TTCTATAATT AA
```

Canis lupus familiaris gene coding sequence (1-192)(dog) FGF19 (SEQ ID NO: 296) (GenBank Accession No. XM_540802, which is hereby incorporated by reference in its entirety)

```
  1 CTAGCCTTCT CCGACGCGGG GCCGCACGTG CACTCCTTCT GGGGGGAGCC CATCCGCCTG
 61 CGGCACCTGT ACACCGCCGG CCCCCACGGC CTCTCCAGCT GCTTCCTGCG CATCCGCCGG
121 GACGGCGGGG TGGACTGCGC GCGGGGCCAG AGCGCGCACA GTCTGATGGA GATGAGGGCG
181 GTCGCTCTGC GGACCGTGGC CATCAAGGGC GTGCACAGCG GCCGGTACCT CTGCATGGGC
241 GCCGACGGCA GGATGCAAGG GCTGCCTCAG TACTCCGCCG GAGACTGTAC TTTCGAGGAG
301 GAGATCCGTC CCGATGGCTA CAATGTGTAC TGGTCCAAGA AGCACCATCT CCCCATCTCT
361 CTGAGTAGTG CCAAACAGAG GCAGCTCTAC AAGGGCAGGG GCTTTTTGCC CCTGTCCCAC
421 TTCTTACCTA TCTTGCCCGG GAGCCCAACA GAGCCCAGGG ACCTGGAAGA CCATGTGGAG
481 TCTGACGGGT TTTCTGCATC CCTGGAAACA GACAGCATGG ACCCTTTTGG GATCGCCACC
541 AAAATTGGAC TAGTGAAGAG TCCCAGTTTC CAAAAATAA
```

Oryctolagus cuniculus gene coding sequence (1-218) (rabbit) FGF19 (SEQ ID NO: 297) (GenBank Accession No. XM_002724449, which is hereby incorporated by reference in its entirety)

```
  1 ATGCGCCGCG CGCCGAGCGG AGGTGCCGCG GCCCGCGCCT TGGTCCTGGC CGGCCTCTGG
 61 CTGGCCGCGG CCGCGCGCCC CTTGGCCTTG TCCGACGCGG GCCCGCATCT GCACTACGGC
121 TGGGGCGAGC CCGTCCGCCT GCGGCACCTG TACGCCACCA GCGCCCACGG CGTCTCGCAC
181 TGCTTCCTGC GTATACGCGC CGACGGCGCC GTGGACTGCG AGGGAGCCA GAGCGCACAC
241 AGCTTGCTGG AGATCCGAGC GGTCGCCCTG CGCACCGTGG CCTTCAAGGG CGTGCACAGC
301 TCCCGCTACC TCTGCATGGG CGCCGACGGC AGGATGCGGG GGCAGCTGCA GTACTCGGAG
361 GAGGACTGTG CCTTCCAGGA GGAGATCAGC TCCGGCTACA ACGTGTACCG CTCCACGACG
421 CACCACCTGC CCGTGTCTCT GAGCAGTGCC AAGCAGAGAC ACCTGTACAA GACCAGAGGC
481 TTCCTGCCCC TCTCCCACTT CCTGCCCGTG CTGCCCCTGG CCTCCAGGA GACCGCGGCC
541 CTCGGCGACC ACCCTGAAGC CGACCTGTTC TCCCCGCCCC TGGAAACCGA CAGCATGGAC
601 CCCTTCGGCA TGGCCACCAA GCTCGGGCCG GTGAAGAGCC CCAGCTTTCA GAAGTAG
```

Pteropus vampyrus gene coding sequence (1-216) (megabat) FGF19 (SEQ ID NO: 298) (Ensembl Accession No. ENSPVAT00000009907, which is hereby incorporated by reference in its entirety)

```
  1 ATGCGGAGCC CGTGCGCTGT GGCCCGCGCC TTGGTCCTGG CCGGCCTCTG GCTGGCCTCA
 61 GCTGCGGGCC CCCTCGCCCT CTCGGACGCG GGGCCGCACG TGCACTACGG CTGGGGCGAG
121 GCCATCCGCC TGCGGCACCT GTACACCGCC GGCCCCCACG GCCCTCCAG CTGCTTCCTG
181 CGCATCCGCG CGGATGGGGC GGTGGACTGC GCGCGGGGCC AGAGCGCGCA CAGTTTGGTG
241 GAAATCCGGG CTGTCGCCCT GCGGAACGTG GCTATCAAGG GCGTGCACAG CGTCCGATAC
301 CTCTGCATGG GAGCCGACGG CAGGATGCTA GGGCTGCTTC AGTACTCCGC TGACGACTGC
361 GCCTTCGAGG AGGAGATCCG CCCGGACGGC TACAACGTGT ACCACTCCAA GAAGCACCAC
421 CTCCCGGTCT CTCTGAGCAG TGCCAAGCAG AGGCAACTGT ACAAGGACAG GGGCTTCCTG
481 CCCCTGTCCC ATTTCCTGCC CATGCTGCCC AGGAGCCCGA CAGAGCCCGA GAACTTCGAA
541 GACCACTTGG AGGCCGACAC GTTTTCCTCG CCCCTGGAGA CAGACGACAT GGACCCTTTT
601 GGGATTGCCA GTAAATTGGG GCTGGAGGAA AGTCCCAGCT TCCAGAAGTA A
```

Tursiops truncatus gene coding sequence (1-219) (dolphin) FGF19 (SEQ ID NO: 299) (Ensembl Accession No. ENSTTRT00000000066, which is hereby incorporated by reference in its entirety)

```
  1 ATGCGGAGCG CTCCGAGCCG GTGCGCCGTG GCCCGCGCCC TGGTCCTGGC CGGCCTCTGG
 61 CTGGCTGCAG CCGGGCGCCC CCTAGCCTTC TCGGATGCCG GGCCGCACGT GCACTACGGC
```

TABLE 8-continued

```
121 TGGGGCGAGT CCGTCCGCCT GCGGCACCTG TACACCGCGG GTCCCCAGGG CCTCTCCAGC
181 TGCTTCCTGC GCATCCACTC AGACGGCGCC GTGGACTGCG CGCCGGTTCA GAGCGCGCAC
241 AGTTTGATGG AGATCAGGGC AGTCGCTCTG AGTACCGTGG CCATCAAGGG CGAACGCAGC
301 GTCCTGTACC TCTGCATGGG CGCCGACGGC AAAATGCAAG GGCTGAGTCA GTACTCAGCT
361 GAGGACTGTG CCTTTGAGGA GGAAATCCGT CCGGACGGCT ACAACGTGTA CTGGTCCAAG
421 AAACACCACC TCCCGGTGTC CCTGAGCAGC GCCAGGCAGC GGCAGCTGTT CAAAGGCAGG
481 GGTTTCCTGC CGCTGTCTCA CTTCCTTCCC ATGCTGTCCA CCATCCCCAC AGAGCCCGAT
541 GAAATCCAGG ACCACTTGAA GCCCGATTTG TTTGCTTTGC CCCTGAAAAC AGATAGCATG
601 GACCCATTTG GGCTCGCCAC CAAACTGGGA GTGGTGAAGA GTCCCAGCTT CTATAAGTAA
```

*Myotis lucifugus* gene coding sequence (1-219) (microbat) FGF19 (SEQ ID
NO: 300) (Ensembl Accession No. ENSMLUT00000002508, which is hereby
incorporated by reference in its entirety)

```
  1 ATGCAAAGCG CGTGGAGCCG ACGCGTTGTG GCCCGAGCCC TGGTCTTGGC CAGCCTCGGG
 61 CTGGCCTCAG CCGGGGGGCC CCTCGGTCTT TCGGACGCTG GGCCGCACGT GCACTACGGC
121 TGGGGGGAGT CCATCCGCCT GCGCCACCTG TACACCTCCG GCCCCCACGG CCCATCCAGC
181 TGCTTCCTGC GCATCCGCGC TGACGGCGCA GTGGACTGCG CGCGGGGCCA GAGCGCGCAC
241 AGTTTGGTGG AGATCAGGGC CGTCGCCTTG CGGAAAGTGG CCATCAAGGG CGTGCACAGC
301 GCCCTGTACC TCTGCATGGG AGGCGACGGC AGGATGCTGG GGCTGCCTCA GTTCTCGCCC
361 GAGGACTGTG CTTTCGAGGA GGAGATCCGC CCGGACGGCT ACAACGTGTA CCGGTCCCAG
421 AAGCACCAGC TGCCCGTCTC GCTGAGCAGT GCCCGGCAGA GGCAGCTGTT CAAGGCCCGG
481 GGCTTCCTGC CGCTGTCCCA CTTCCTGCCC ATGCTGCCCA GCAGCCCCGC GGGACCCGTG
541 CCCCGAGAGC GCCCCTCGGA GCCGGACGAG TTCTCTTCGC CCCTGGAAAC AGACAGCATG
601 GACCCTTTTG GGATTGCCAA CAACCTGAGG CTGGTGAGAA GTCCCAGCTT TCAGGAATAA
```

*Ornithorhynchus anatinus* gene coding sequence (1-185) (platypus) FGF19
(SEQ ID NO: 301) (GenBank Accession No. XM_001506664, which is hereby
incorporated by reference in its entirety)

```
  1 ATGCTTTCCT GTGTGGTTTT GCCTAGTCTG CTGGAGATCA AGGCGGTGGC CGTGCGCACG
 61 GTGGCCATCA AAGGGGTCCA CATCTCTCGG TACCTCTGCA TGGAAGAGGA TGGGAAAACT
121 CCATGGGCAC GTCGCTGGA GATCAAGGCG GTGGCCGTGC GCACGGTGGC CATCAAAGGG
181 GTCCACAGCT CTCGGTACCT CTGCATGGAA GAGGATGGAA AACTCCATGG GCAGATTTGG
241 TATTCTGCAG AAGACTGTGC TTTTGAAGAG GAAATACGTC CAGATGGCTA CAATGTGTAT
301 AAATCTAAGA AATATGGTGT TCCTGTTTCT TTAAGCAGCG CCAAACAAAG GCAGCAATTC
361 AAAGGAAGAG ACTTTCTGCC TCTTTCTCGT TTCTTGCCAA TGATCAACAC AGTGCCTGTG
421 GAGCCAGCAG AGTTTGGGGA CTATGCCGAT TACTTTGAAT CAGATATATT TTCCTCACCT
481 CTGGAAACTG ACAGCATGGA CCCATTTAGA ATTGCCCCTA AACTGTCCCC TGTAAAGAGC
541 CCCAGCTTTC AGAAATAA
```

*Monodelphis domestica* gene coding sequence (1-212) (opossum) FGF19
(SEQ ID NO: 302) (GenBank Accession No. XM_001373653, which is hereby
incorporated by reference in its entirety)

```
  1 ATGGCCCAGC TCCTGGCCCC GCTCCTCACC CTGGCTGCTC TCTGGCTGGC CCCGACGGCG
 61 CGTGCCCGAC CGCTGGTGGA CGCCGGGCCT CACGTCTACT ACGGCTGGGG GGAGCCCATT
121 CGTCTGCGGC ATCTCTACAC GGCCAATCGG CACGGGCTCG CCAGCTTCTC CTTCCTCCGG
181 ATCCACCGCG ACGGCCGCGT GGACGGCAGC CGGAGTCAGA GCGCGCTCAG TTTGCTGGAG
241 ATCAAGGCGG TAGCTCTTCG GATGGTGGCG ATCAAAGGTG TCCATAGCTC TCGGTACCTG
301 TGTATGGGAG ACGCCGGGAA ACTCCAGGGA TCGGTGAGGT TCTCGGCCGA GGACTGCACC
361 TTCGAGGAGC AGATTCGCCC CGACGGCTAC AACGTGTACC AGTCCCCCAA GTACAACCTC
421 CCCGTCTCGC TCTGCACTGA CAAGCAGAGG CAGCAGGCCC ACGGCAAGGA GCACCTGCCC
481 CTGTCCCACT TCCTGCCCAT GATCAATGCT ATTCCTTTGG AGGCGGAGGA GCCCGAGGGC
541 CCCAGGATGT TGGCGGCGCC TCTGGAGACG GACAGCATGG ACCCCTTCGG CCTCACCTCC
601 AAGCTGTTGC CGGTCAAGAG CCCCAGCTTT CAGAAATAA
```

*Anolis carolinensis* gene coding sequence (1-220) (anole lizard) FGF19
(SEQ ID NO: 303) (GenBank Accession No. XM_003214667, which is hereby
incorporated by reference in its entirety)

```
  1 ATGTGTCGGC GGGCGTTGCC TCTGCTGGGG GCCCTTCTGG GCTTGGCGGC CGTGGCCTCC
 61 CGCGCCCTCC CGCTCACCGA CGCCGGGCCC CACGTCAGCT ACGGCTGGGG GGAGCCCGTC
121 CGGCTCAGGC ACCTCTACAC CGCGGGGCGG CAGGGCCTCT TCAGCCAGTT CCTCCGCATC
181 CACGCCGACG GGAGAGTCGA CGGCGCCGGC AGCCAGAACC GGCAGAGTTT GCTGGAGATC
241 CGCGCGGTCT CGTTGCGCGC CGTGGCCCTC AAAGGCGTGC ACAGCTCCCG CTACCTCTGC
301 ATGGAGGAGG ACGGCCGGCT CCGCGGGATG CTCAGATATT CTGCAGAAGA CTGTTCCTTT
361 GAAGAGGAGA TGCGTCCAGA TGGCTACAAT ATCTACAAGT CAAAGAAATA CGGAGTTTTG
421 GTCTCCCTAA GTAATGCCAG ACAAGACACA CAATTCAAAG GGAAAGATTT CTTCCTTTTG
481 TCTCATTTCT TGCCGATGAT CAACACTGTG CCAGTGGAGT CTGCAGACTT GGAGAGTAT
541 GGTGACACCA GGCAGCATTA TGAATCGGAT ATTTTCAGTT CACGTCTTGA AACTGACAGC
601 ATGGACCCTT TTGGCCTCAC TTCAGAAGTG TCATCAGTAC AAAGTCCTAG CTTTGGGAAA
661 TAA
```

*Ochotona princeps* gene coding sequence (1-214, excluding 78-112)(pika)
FGF19 (SEQ ID NO: 304) (Ensembl Accession No. ENSOPRT00000010769,
which is hereby incorporated by reference in its entirety)

```
  1 GTGCGGAGCA GGGGAGCCAT GGCCCGCGCT CTGGTTCTAG CCACTCTCTG GCTGGCCGCG
 61 ACGGGGCGGC CGCTGGCCTT GTCCGACGCG GGGCCGCACC TGCACTACGG CTGGGGCGAG
```

TABLE 8-continued

```
121 CCCATCCGCC TGCGGCACCT GTACGCCACC AGCGCCCACG GCCTCTCGCA CTGCTTTTTG
181 CGCATCCGTA CCGACGGCAC CGTGGACTGC GAGCGCAGCC AGAGCGCGCA CA--------
    ---------- ---------- ---------- ---------- ---------- ----------
242 ---------- ---------- ---------- ------CTAC AGTACTCGGA GGAGGACTGC
266 GCCTTCGAAG AGGAGATCAG CTCTGGCTAT AACGTGTACC GCTCCAGGAG GTACCAGCTG
326 CCCGTGTCCC TGGGCAGCGC CAGGCAGAGG CAGCTGCAGC GGAGCCGTGG CTTCCTGCCC
386 CTGTCCCACT TCCTGCCGGT GCTGCCCGCG GCCTCGGAGG AGGTGGCGGC CCCCGCTGAC
446 CACCCGCAAG CAGACCCTTT CTCGCCCCTG GAGACCGACA GCATGGACCC ATTTGGAATG
506 GCCACCAAGC GGGGGCTGGT GAAGAGCCCC AGCTTCCAGA AGTGA
```

*Cavia porcellus* gene coding sequence (1-221)(guinea pig) FGF19 (SEQ ID NO: 305) (Ensembl Accession No. ENSCPOT00000008222, which is hereby incorporated by reference in its entirety)

```
  1 ATGTGGAGTG CGCCGAGCGG ATGTGTGGTG ATCCGCGCCC TGGTCCTGGC TGGCCTGTGG
 61 CTGGCGGTGG CGGGGCGCCC CCTGGCCCGG CGGTCTCTCG CGCTATCTGA CCAGGGGCCG
121 CACTTGTACT ACGGCTGGGA CCAGCCGATC CGCCTTCGGC ACCTGTACGC CGCGGGCCCC
181 TACGGCCGCT CGCGCTGCTT CCTGCGCATT CACACGGACG GCGCGGTGGA CTGCGTCGAG
241 GAACAGAGCG AGCACTGTTT GCTGGAGATC AGAGCAGTCG CTCTGGAGAC CGTGGCCATC
301 AAGGACATAA ACAGCGTCCG GTACCTGTGC ATGGGCCCCG ACGGCAGGAT GCGGGGCCTG
361 CCCTGGTATT CGGAGGAGGA CTGTGCCTTC AAGGAAGAGA TCACTACCC GGGCTACAGC
421 GTGTACCGCT CCCAGAAGCA CCACCTCCCC ATCGTGCTGA GCAGTGTCAA GCAGAGGCAG
481 CAGTACCAGA GCAAGGGGGT GGTGCCCCTG TCCTACTTCC TGCCCATGCT GCCCAAGGCC
541 TCTGTGGAGC CAGCGACGA GGAGGAATCC AGCGTGTTCT CGTTGCCCCT GAAGACGGAC
601 AGCATGGACC CCTTTGGGAT GGCCAGTGAG ATCGGGCTGG TGAAGAGTCC CAGCTTTCAG
661 AAGTAA
```

*Tupaia belangeri* gene coding sequence (1-219, excluding 116-138)(tree shrew) FGF19 (SEQ ID NO: 306) (from Ensembl Accession No. ENSTBET00000000307, which is hereby incorporated by reference in its entirety)

```
  1 ATGAGGAGAA CACCGAGCGG GTTTGCAGTG GCCCGTGTCC TCTTCCTGGG
    CAGCCTTTGG
 61 CTGGCCGCAG CCGGGAGCCC CTTGGCCCTG TCCGACGCCG GGCCGCATGT GAACTACGGC
121 TGGGATGAGT CCATACGCCT GCGACACTTG TACACCGCCA GCCCGCACGG CTCCACCAGC
181 TGCTTCTTGC GCATCCGTGA CGACGGCTCA GTGGACTGCG CGCGGGGCCA GAGTTTGCAC
241 AGTTTGCTGG AGATCAAGGC AGTCGCTTTG CAGACCGTGG CCATCAAAGG CGTGTACAGT
301 GTCCGCTACC TCTGCATGGA CGCCGACGGC AGGATGCAGG GGCTG----- ----------
361 ---------- ---------- ---------- ---------- ---------- NNGGTCCACG
369 AAGCACGGCC TCCCAGTCTC CCTGAGCAGT GCCAAGCAGA GGCAGCTGTT AACGGTTAGG
429 GGCTTTCCTT CCCTTCCCCA CTTCCTGCTC ATGATGGCCA AGACTTCAGC AGGGCCTGGA
489 AACCCCAGGG ACCACCCAGG GTCTAACACT TTCTCGTTGC CCCTGGAAAC TGATAGCATG
549 GACCCATTTG GGATGACCAC CAGACATGGG CTGGTGAAGA GTCCCAGCTT TCAAAACTAA
```

*Rattus norvegicus* gene coding sequence (1-218)(Norway rat) FGF15(GenBank Accession No. NM_130753, which is hereby incorporated by reference in its entirety) (SEQ ID NO: 307)

```
  1 ATGGCGAGAA AGTGGAGTGG GCGTATTGTG GCCCGAGCTC TGGTCCTGGC CACTCTGTGG
 61 CTGGCCGTGT CTGGGCGTCC CCTGGTCCAG CAATCCCAGT CTGTGTCGGA TGAAGGTCCA
121 CTCTTTCTCT ATGGCTGGGG CAAGATTACC CGCCTGCAGT ACCTGTACTC TGCTGGTCCC
181 TACGTCTCCA ACTGCTTCCT GCGTATCCGG AGTGACGGCT CTGTGGACTG CGAGGAGGAC
241 CAGAACGAAC GAAATCTGTT GGAGTTCCGC GCGGTTGCTC TGAAGACAAT TGCCATCAAG
301 GACGTCAGCA GCGTGCGGTA CCTCTGCATG AGCGCCGACG GCAAGATATA CGGGCTGATT
361 CGCTACTCGG AGGAAGACTG TACCTTCAGG GAGGAAATGG ACTGTTTGGG CTACAACCAG
421 TACAGGTCCA TGAAGCACCA CCTCCACATC ATCTTCATCA AGGCCAAGCC CAGAGAGCAG
481 CTCCAGGGCC AGAAACCTTC AAACTTTATC CCCATATTTC ACCGGTCTTT CTTTGAATCC
541 ACGGACCAGC TGAGGTCTAA AATGTTCTCT CTGCCCCTGG AGAGCGACAG CATGGATCCG
601 TTCAGAATGG TGGAGGATGT GGACCACCTA GTGAAGAGTC CAGCTTCCA GAAATGA
```

*Mus musculus* gene coding sequence (1-218)(house mouse) FGF15 (SEQ ID NO: 308) (GenBank Accession No. NM_008003, which is hereby incorporated by reference in its entirety)

```
148                    ATG GCGAGAAAGT GGAACGGGCG TGCGGTGGCC
181 CGAGCCCTGG TCCTGGCCAC TCTGTGGCTG GCTGTGTCTG GCGTCCCCT GGCTCAGCAA
241 TCCCAGTCTG TGTCAGATGA AGATCCACTC TTTCTCTACG GCTGGGGCAA GATTACCCGC
301 CTGCAGTACC TGTACTCCGC TGGTCCCTAT GTCTCCAACT GCTTCCTCCG AATCCGGAGC
361 GACGGCTCTG TGGACTGCGA GGAGGACCAA AACGAACGAA ATTTGTTGGA ATTCCGCGCG
421 GTCGCTCTGA AGACGATTGC CATCAAGGAC GTCAGCAGCG TGCGGTACCT CTGCATGAGC
481 GCGGACGGCA AGATATACGG GCTGATTCGC TACTCCGAGG AAGACTGTAC CTTCAGGGAG
541 GAAATGGACT GTTTAGGCTA CAACCAGTAC AGATCCATGA AGCACCATCT CCATATCATC
601 TTCATCCAGG CCAAGCCCAG AGAACAGCTC CAGGACCAGA AACCCTCAAA CTTTATCCCC
661 GTGTTTCACC GCTCCTTCTT TGAAACCGGG GACCAGCTGA GGTCTAAAAT GTTCTCCCTG
721 CCCCTGGAGA GTGACAGCAT GGATCCGTTC AGGATGGTGG AGGATGTAGA CCACCTAGTG
781 AAGAGTCCCA GCTTCCAGAA ATGA
```

TABLE 8-continued

*Gallus gallus* gene coding sequence (1-227)(chicken) FGF19 (SEQ ID NO: 309) (GenBank Accession No. NM_204674, which is hereby incorporated by reference in its entirety)

```
127         ATGG GGCCGGCCCG CCCCGCCGCA CCCGGCGCTG CCCTGGCGCT GCTGGGGATC
181 GCCGCCGCCG CCGCCGCCGC CAGGTCCCTG CCGCTGCCCG ACGTCGGGGG TCCGCACGTC
241 AACTACGGCT GGGGGGAACC CATCCGGCTG CGGCACCTAC TACACCGCCC AGGCAAGCAC
301 GGGCTCTTCA GCTGCTTCCT GCGCATCGGC GGCGACGGCC GGGTGGACGC TGTCGGTAGC
361 CAGAGCCCGC AGAGTCTGTT GGAGATCCGC GCCGTGGCGG TGCGCACCGT GGCCATCAAG
421 GGCGTGCAGA GCTCCCGCTA CCTCTGCATG GACGAGGCGG GGCGGCTGCA CGGGCAGCTC
481 AGCTATTCCA TTGAGGACTG TTCCTTTGAA GAGGAGATTC GTCCAGACGG CTACAACGTG
541 TATAAATCAA AGAAATACGG GATATCGGTG TCTTTGAGCA GTGCCAAACA AAGACAGCAA
601 TTCAAAGGAA AAGATTTTCT CCCGCTGTCT CACTTCTTAC CCATGATCAA CACTGTGCCA
661 GTGGAGGTGA CAGACTTTGG TGAATATGGT GATTACAGCC AGGCTTTTGA GCCAGAGGTC
721 TACTCATCGC CTCTCGAAAC GGACAGCATG GATCCCTTTG GGATCACTTC CAAACTGTCT
781 CCAGTGAAGA GCCCCAGCTT TCAGAAATGA
```

*Taeniopygia guttata* gene coding sequence (1-237)(zebra finch) FGF19 (SEQ ID NO: 310) (GenBank Accession No. XM_002194457, which is hereby incorporated by reference in its entirety)

```
  1 ATGGTTATCA TAAGCAATCT ATATCTGATG CAGAACGATG TTATGATGAA TATGAGGCGA
 61 GCACCCCTTC GCGTTCACGC TGCTCGCTCT TCGGCCACCC CTGCCTCCGC GCTGCCGCTG
121 CCGCCGCCCG ACGCCGGCCC GCACCTCAAA TACGGCTGGG GAGAGCCCAT CCGGCTGCGG
181 CACCTCTACA CCGCCAGCAA GCACGGGCTC TTCAGCTGCT TCCTGCGTAT CGGCGCTGAC
241 GGCCGGGTGG ACGCGGCCGG CAGCCAGAGC CCGCAGAGCC TGCTAGAGAT CCGCGCCGTG
301 GCCGTGCGCA CCGTGCCCAT CAAGGGCGTG CAGAGCTCCC GGTACCTGTG CATGGACGAG
361 GCGGGGCGGC TGCACGGGCA GCTCAGGAAT TCCACTGAAG ACTGCTCCTT TGAGGAGGAG
421 ATTCGCCCAG ACGGCTACAA TGTGTATAGA TCTAAAAAAC ATGGAATATC GGTGTCTTTG
481 AGCAGTGCCA AACAAAGACA GCAGTTCAAG GGGAAAGATT TCCTTCCCCT GTCTCACTTC
541 TTGCCCATGA TCAACACTGT GCCCATGGAG TCAGCAGACT TTGGTGAATA TGGTGATTAC
601 AGCCAGGCCT TGAGGCAGA GGCCTTCTCC TCACCTCTGG AGACGGACAG CATGGACCCC
661 TTTGGCATCG CCTCCAAACT GTCCCTAGTG AAGAGCCCTA GCTTCAAAA CTGA
```

*Danio rerio* gene coding sequence (1-210)(zebrafish) FGF19 (SEQ ID NO: 311) (GenBank Accession No. NM_001012246, which is hereby incorporated by reference in its entirety)

```
  1 ATGCTCCTCT TACTCTTTGT CACTGTTTGT GGAAGTATCG GCGTGGAGAG CCTCCCGTTG
 61 CCCGACTCTG GTCCACATTT GGCAAATGAC TGGAGTGAAG CCGTCCGGCT ACGACATCTG
121 TACGCAGCCA GACATGGCTT ACATCTGCAA ATAAACACAG ACGGAGAAAT CATTGGATCC
181 ACATGCAAAG CTCGGACAGT AAGTTTGATG GAGATATGGC CGGTGGACAC AGGCTGCGTA
241 GCCATTAAGG GAGTTGCAAG CTCCCGATTT CTTTGCATGG AAAGACTGGG AAACCTGTAC
301 GGATCGCACA TTTACACTAA AGAGGACTGC TCTTTTTTGG AACGCATCCT TCCAGACGGC
361 TACAACGTCT ACTTCTCGAG CAAACACGGA GCTCTTGTGA CTTTAAGTGG TGCGAAAAAC
421 AAGTTGCACA GTAACGATGG GACTTCTGCA TCCCAGTTCC TCCCCATGAT CAACACATTG
481 TCAGAGGAAC ACACTAAACA GCACTCAGGG GAACAGCACT CTTCTGTTAA CCATGGACAG
541 GACCATCAGT TGGGCCTTGA AATAGACAGT ATGGACCCTT TCGGAAAGAT CTCTCAAATA
601 GTGATCCAGA GTCCCAGCTT CAACAAAGA TGA
```

*Xenopus (Silurana) tropicalis* gene coding sequence (1-215)(Western clawed frog) FGF19 (SEQ ID NO: 312) (GenBank Accession No. NM_001142825, which is hereby incorporated by reference in its entirety)

```
  1 ATGTGGAAGA CCCTGCCTTG GATTTTGGTT CCCATGATGG TGGCCGTGCT GTATTTCCTC
 61 GGAGGGGCGG AAAGTCTGCC GCTTTTTGAT GCCGGGCCGC ACATGCAGAA CGGCTGGGGG
121 GAGTCGATCA GAATTCGGCA CCTGTATACG GCCAGGAGGT TCGGGCACGA CAGCTACTAC
181 CTCCGGATAC ACGAGGATGG CAGAGTCGAT GGTGACAGGC AACAAAGCAT GACACAGTTTA
241 TTGGAAATCA GAGCAATTGC AGTTGGAATT GTTGCCATTA AGGGTATCG CAGCTCTCTG
301 TACCTGTGCA TGGGGTCCGA GGGAAAACTC TATGGAATGC ACAGTTACTC CCAGGATGAT
361 TGCTCTTTTG AAGAGGAGCT TCTCCCGGAT GGATACAACA TGTATAAATC AAGGAAACAT
421 GGCGTTGCTG TCTCCCTAAG CAAGGAGAAG CAGAAGCAAC AATACAAAGG AAAGGGCTAC
481 CTCCCGTTGT CCCATTTCCT ACCCGTGATA AGCTGGGTGC CCATGGAGCC CACCGGGAGAT
541 GTAGAAGATG ATATCTACAG GTTTCCATTC AATACGGACA CAAAAGTGT CATTGACAGC
601 CTTGATACCC TGGGACTAAT GGATTTTTCG AGTTATCACA GAAATAG
```

*Otolemur garnettii* (bushbaby) FGF19 gene coding sequence (1-219)(SEQ ID NO: 313) (Ensembl accession no. ENSOGAT00000031686, which is hereby incorporated by reference in its entirety)

```
  1 ATGCCCAGCG GGCTGAGAGG GCGTGTGGTA GCCGGCGCCC TGGCCCTGGC CAGCTTCTGG
 61 CTGGCCGTGG CCGGGCGCCC GCTGGCCTTC TCGGATGCCG GCCCTCACGT GCACTACGGC
121 TGGGGTGAGC CCATCCGCCT GCGACACCTG TACACCGCCG GCCCCACGG CCTCTCCAGC
181 TGCTTCCTGC GCGTACGCAC CGACGGTGCG GTAGACTGGC CGCGGGGCCA GAGCGCACAC
241 AGTTTGCTGG AAATCAGGGC CGTCGCTCTC CGGACCGTGG CCATCAAAGG CGTGCACACG
301 GCGCGGTACC TCTGCATGGG CGCCGACGGC AGGATGCAGG GGCTGCCTCA GTACTCGGAG
361 GAAGACTGTG CCTTTGAGGA GGAGATCCGG CCAGACGGCT ACAACGTCTA CTGGTCTGAG
421 AAGCACCGCC TGCCGGTGTC TCTGAGCAGT GCCCGGCAGA GGCAGCTGTA CAAGGGCAGG
481 GGCTTTCTGC CGCTCTCTCA CTTCCTGCCC ATGCTGCCTG TGACCCCAGC CGAGCCCGGG
```

TABLE 8-continued

541 GACCTCAGAG ACCACCTGGA ATCCGACATG TTCTCTTTGC CCCTGGAAAC TGACAGCATG
601 GATCCATTTG GGATCGCCAC CAGACTGGGC GTGGTGAAGA GTCCCAGCTT TCAGAAATGA

*Felis catus* (cat) FGF19 gene coding sequence (1-219)(SEQ ID NO: 314)
(Ensembl accession no. ENSFCAT00000026317, which is hereby
incorporated by reference in its entirety)

1 ATGCGGAGCG CGCCGAGCCA GTGCGCGGTA ACCCGCGCCC TGGTCCTAGC CGGTCTCTGG
 61 CTGGCAGCAG CCGGGCGCCC CCTAGCCTTC TCGGACGCGG GGCCTCACGT GCACTACGGC
121 TGGGGTGAGC CCATCCGCCT GCGGCACCTG TACACCGCCG GCCCCCACGG CCTCTCCAGC
181 TGCTTCCTGC GCATCCGAGC CGACGGGGGG GTTGACTGCG CGCGGAGCCA GAGCGCGCAC
241 AGTTTGGTGG AGATCAGGGC AGTCGCTCTG CGGACCGTGG CCATCAAGGG CGTGCACAGC
301 GTCCGGTACC TCTGCATGGG CGCCGACGGC AGGATGCAAG GGCTGCTTCA GTACTCTGCT
361 GGGGACTGTG CCTTCCAAGA GGAGATCCGC CCCGACGGCT ACAATGTGTA CCGGTCCGAG
421 AAGCACCGTC TCCCCGTCTC TTTGAGTAGT GCCATACAGA GGCAGCTGTA CAAGGGCAGA
481 GGGTTTTTGC CCCTGTCCCA TTTCTTGCCC ATGCTGCCCG GCAGCCCAGC AGAGCCCAGG
541 GACCTCCAGG ACCACGTGGA GTCGGAGAGG TTTTCTTCAC CCCTGGAAAC AGACAGCATG
601 GACCCTTTTG GGATTGCCAC CAAAATGGGG TTAGTGAAGA GTCCCAGCTT CCAAAAGTAA

*Pelodiscus sinensis* (Chinese softshell turtle) FGF19 gene coding
sequence (1-223)(SEQ ID NO: 315) (Ensembl accession no.
ENSPSIT00000010427, which is hereby incorporated by reference in its
entirety)

241                                    ATGTGGAG GAGCCTGTGC AAATCTCACA
301 CGTCTCTGGC TCTGCTGGGA CTCTGCTTTG CGGTGGTCGT GAGATCTCTG CCTTTCTCGG
361 ATGCAGGGCC ACATGTGAAC TATGCTGGG GGGAGCCTAT TCGATTAAGG CACCTATACA
421 CCGCCAGCAG ACACGGGCTG TTCAATTACT TCCTGAGGAT CAGCAGTGAT GGCAAAGTGG
481 ATGGCACCAG CATTCAGAGT CCTCACAGTC TGCTGGAAAT CAGGGCTGTG GCAGTTCGCA
541 CGGTGGCGAT CAAGGGCGTC CACAGTTCCC GGTACCTCTG CATGGAAGAA GACGGGAAGC
601 TGCATGGACT TCTCAGGTAT TCTACAGAAG ATTGCTCCTT TGAAGAGGAG ATACGCCCAG
661 ATGGCTACAA TGTATATAAA TCAAAGAAAT ATGGAATCTC TGTGTCCTTA AGTAGTGCCA
721 AACAAAGACA ACAATTCAAA GGAAAAGACT TTCTTCCATT GTCTCACTTC TTGCCTATGA
781 TCAATACAGT ACCTGTGGAG TCAATGGATT TTGGAGAATA TGGTGATTAT AGTCATACTT
841 TTGAATCAGA TCTATTCTCT TCACCTCTCG AAACTGACAG CATGGATCCC TTTGGAATCA
901 CCTCTAAAAT ATCTCCAGTG AAGAGCCCCA GCTTTCAGAA ATAA

*Latimeria chalumnae* (coelacanth) FGF19 gene coding sequence (1-217)
(SEQ ID NO: 316) (Ensembl accession no. ENSLACT00000014697, which
is hereby incorporated by reference in its entirety)

1 ATGTTACAGG CACTGTACAA TCTCTGTACA GCTCTAGTTT TGTTTAAGCT TCCTTTTGCA
 61 ATGGTGGGGT ACACCCTGCC TTCTGCCAAT GAAGGGCCCC ATCTGAACTA TGACTGGGGA
121 GAATCTGTAA GACTCAAACA TCTGTACACA TCTAGCAAGC ATGGATTGAT CAGTTACTTT
181 TTACAGATCA ATGATGATGG CAAAGTAGAT GGGACCACTA CACGAAGCTG TTATAGTTTG
241 CTCGAAATAA AATCAGTGGG GCCAGGAGTT TTGGCAATTA AAGGCATACA GGGATCCAGA
301 TACCTTTGTG TCGAGAAGGA TGGAAAATTG CATGGATCGC GCACTTATTC AGCAGACGAT
361 TGCTCCTTCA AAGAGGATAT ACTCCCAGAT GGTTACACTA TCTACGTGTC AAAGAAACAT
421 GGATCTGTTG TTAATCTGAG CAACCACAAA CAGAAACGTC AGAGAAATCG CAGAACCCTG
481 CCTCCATTTT CTCAGTTCCT ACCGCTTATG GACACCATTC GTGTGGAGTG CATGAACTGC
541 GGGGAGCACT GTGACGACAA CCTGCATGAC GAGCTAGAAA CAGGACTGTC CATGGATCCC
601 TTTGAAAGTA CATCCAAAAA ATCCTTTCAG AGTCCCAGCT TCACAATAG ATAA

*Mustela putorius furo* (ferret) FGF19 gene coding sequence (1-219)(SEQ
ID NO: 317) (Ensembl accession no. ENSMPUT00000004650, which is hereby
incorporated by reference in its entirety)

421    ATGCGG AGCGCCGCGA GTCGGTGCGC GGTAGCCCGC GCGCTGGTCC TAGCCGGCCT
 481 TTGGCTGGCC GCAGCGGGC GCCCCCTAGC CTTCTCGGAC GCGGGCCGC ACGTGCACTA
 541 TGGCTGGGGT GAGCCCATCC GCCTACGGCA CCTGTACACC GCCGGCCCCC ACGGCCTCTC
 601 CAGCTGCTTC CTGCGCATCC GTGCCGACGG CGGGGTTGAC TGCGCGCGGG GCCAGAGCGC
 661 GCACAGTTTG GTGGAGATCC GGGCAGTCGC TCTGCGGACG GTGGCCATCA AGGGCGTGTA
 721 CAGCGACCGC TATCTCTGCA TGGGTGCGGA CGGCAGGATG CAAGGGCTGC CTCAGTACTC
 781 CGCCGGAGAC TGTGCCTTTCG AGGAGGAGAT CCGCCCTGAT GGCTACAACG TGTACCGGTC
 841 CAAGAAGCAC CGTCTCCCCG TCTCCCTGAG CAGTGCGAAA CAAAGGCAGC TGTACAAGGA
 901 CCGGGGCTTT TTGCCTCTGT CCCATTTCTT GCCCATGCTG CCCGGGAGCC TGGCGGAGCC
 961 CAGGGACCTC CAGGACCACG TGGAGGCTGA TGGGTTTTCT GCCCCCCTAG AAACAGACAG
1021 CATGGACCCT TTTGGGATTG CCACCAAAAT GGGACTAGTG AAGAGTCCCA GCTTCCAAAA
1081 ATGA

*Takifugu rubripes* (fugu) FGF19 gene coding sequence (1-218)(SEQ ID
NO: 318) (Ensembl accession no. ENSTRUT00000007155, which is hereby
incorporated by reference in its entirety)

1 TCATCTACAA GGATTAGTGG AAACATGGTT CTCCTCATGC TCCCCATCAC CGTTGCAAAC
 61 CTCTTCCTCT GTGCTGGAGT TCTCTCCTTG CCTTTGTTGG ATCAAGGGTC TCATTTTCCC
121 CAAGGCTGGG AACAGGTAGT CCGCTTCAGG CACCTGTATG CTGCCAGTGC AGGGCTGCAC
181 CTGCTGATCA CTGAAGAGGG CTCGATCCAA GGCTCTGCAG ATCCAACTTT ATACAGCCTG
241 ATGGAGATCC GTCCGGTGGA CCCAGGCTGT GTTGTCATTA GAGGAGCAGC AACCACACGC
301 TTCCTCTGCA TAGAAGGTGC TGGAAGACTG TACTCATCAC AGACCTACAG CAAAGACGAC

TABLE 8-continued

```
361 TGTACCTTCA GAGAGCAAAT CCTAGCAGAC GGCTACAGCG TCTACAGATC TGTCGGACAC
421 GGAGCTCTGG TCAGTCTGGG AAACTACCGG CAGCAGCTGA GGGGGGAGGA CTGGAGCGTT
481 CCGACACTGG CTCAGTTCCT CCCCAGAATA AGTTCACTGG ATCAGGACTT TAAAGCTGCT
541 CTTGACGAGA CTGAGAAGCC AGAACAAACT GCACCTCAAA GATCGGAACC TGTCGACATG
601 GTGGACTCAT TTGGAAAGCT CTCTCAGATC ATCCACAGTC CCAGTTTTCA CAAG
```

*Equus caballus* (horse) FGF19 gene coding sequence (1-216, excluding 1-19 and 114-216)(SEQ ID NO: 319) (Ensembl accession no. ENSECAT00000021494, which is hereby incorporated by reference in its entirety)

```
  1 ---------- ---------- ---------- ---------- ---------- -------GCG
  4 GCCGGGCGCC CCCTAGCCTT GTCCGACGCT GGGCCGCACG TGCACTACGG CTGGGGCGAG
 64 CCGATCCGCC TGCGGCACCT GTACACCGCC GGCCCCACG GCCTCTCCAG CTGCTTCCTG
124 CGCATCCGCG CCGATGGCGC CGTGGACTGC GCGCGGGGCC AGAGCGCGCA CAGTTTGGTG
184 GAGATCAGAG CAGTCGCTCT GCGCACCGTG GCCATCAAGG GCGTGCACAG CGTCCGGTAC
244 CTCTGCATGG GCGCCGACGG CAGGATGCAA GGGCTGGTA
```

*Oryzias latipes* (medaka) FGF19 gene coding sequence (1-209)(SEQ ID NO: 320) (Ensembl accession no. ENSORLT00000000352, which is hereby incorporated by reference in its entirety)

```
  1 ACCATGCTGC TCATTGTGGT CACCATTTCC ACAATGGTGT TTTCTGACTC TGGAGTTTCC
 61 AGCATGCCGC TCTCTGATCA TGGACCCCAC ATCACTCACA GCTGGAGCCA AGTGGTCCGC
121 CTCCGGCACC TGTACGCGGT CAAGCCTGGA CAACATGTCC AGATCAGAGA GGATGGACAC
181 ATCCACGGCT CAGCAGAACA AACTCTGAAC AGCCTGCTGG AGATCCGTCC GGTTGCTCCG
241 GGACGGGTGG TCTTCAGAGG AGTAGCCACC TCAAGGTTTC TGTGCATGGA GAGCGACGGC
301 AGACTCTTCT CCTCACACAC ATTTGACAAG GACAACTGCG TCTTCAGAGA GCAGATCTTG
361 GCAGACGGCT ACAACATCTA CATTTCAGAT CAGCATGGAA CCCTGCTTAG TTTGGGAAAC
421 CACCGGCAAA GGCAGCAGGG TTTAGACCGG GATGTTCCAG CCCTGGCTCA GTTCCTCCCC
481 AGGATCAGCA CCCTGCAGCA GGGCGTGTAC CCAGTGCCAG ACCCCCCCCA CCAGATGAGA
541 ACAATGCAAA CAGAGAAGAC TCTAGATGCC ACGGACACAT TTGGGCAACT CTCTAAAATC
601 ATTCACAGTC CCAGCTTCAA CAAAAGATGA
```

*Xiphophorus maculatus* (platyfish) FGF19 gene coding sequence (1-207) (SEQ ID NO: 321) (Ensembl accession no. ENSXMAT00000001519, which is hereby incorporated by reference in its entirety)

```
  1                                                              ATG
  4 TTTGTGTTCA TTCTATGCAT TGCTGGTGAA CTTTTTACTC TGGGAGTATT TTGCATGCCA
 64 ATGATGGACC AGGGGCCACT TGTCACCCAT GGCTGGGGCC AGGTGGTCCG GCACCGGCAT
124 CTGTATGCAG CCAAGCCAGG ACTGCACCTA CTGATCAGTG AGGATGGACA AATCCACGGT
184 TCCGCAGATC AAACTCTTTA CAGCCTGCTG GAGATCCAAC CTGTTGGCCC GGACGTGTT
244 GTGATCAAAG GAGTGGCAAC CACACGCTTC CTCTGCATGG AGAGCGACGG CAGATTGTAC
304 TCAACTGAAA CATACAGCAG AGCTGACTGC ACCTTCAGAG AACAGATCCA GGCAGACGGC
364 TACAACGTCT ACACCTCTGA TAGCCATGGA GCCCTCCTCA GTTTGGGAAA CAACCAGCAA
424 AGACACAGCG GCTCAGACCG TGGTGTTCCA GCTCTGGCCC GCTTTCTTCC CAGGTTAAAC
484 ACCCTTCAGC AGGCCGTCCC CACAGAGCCG GATGTTCCTG ATCAGCTCAG TCCAGAGAAA
544 GTACAACAGA CTGTGGACAT GGTGGCCTCC TTTGGCAAGC TCTCTCATAT AATTCACAGT
604 CCCAGCTTCC ATAAGAGATG A
```

*Ictidomys tridecemlineatus* (squirrel) FGF19 gene coding sequence (1-220) (SEQ ID NO: 322) (Ensembl accession no. ENSSTOT00000026298, which is hereby incorporated by reference in its entirety)

```
  1 ATGCGGAGCG CGCCGAGCGG ACGTGCCTTA GCCCGCGCCC TGGTGCTGGC CAGCCTCTGG
 61 TTGGCAGTGG CCGGACGACC CCTGGCCCGG CGCTCTCTGG CTCTCTCCGA CCAGGGGCCA
121 CACTTGTACT ATGGCTGGGA TCAGCCCATC CGCCTCCCGC ACCTGTACGC CGCGGGCCCC
181 TACGGCTTCT CCAACTGTTT CCTGCGCATC CGCACCGACG GCGCCGTGGA CTGCGAGGAG
241 AAGCAGAGCG AGCGTAGTTT GATGGAGATC AGGGCGGTCG CTCTGGAGAC TGTGGCCATC
301 AAGGACATAA ACAGCGTCCG GTACCTCTGC ATGGGCGCCG ACGGCAGGAT ACAGGGACTG
361 CCTCGGTACT CGGAGGAAGA GTGCACGTTC AAGGAGGAGA TCAGCTATGA CGGCTACAAC
421 GTGTACCGGT CCCAGAAGTA CCACCTTCCC GTGGTGCTCA GCAGTGCCAA GCAGCGGCAG
481 CTGTACCAGA GCAAGGGCGT GGTTCCCCTG TCCTACTTCC TGCCCATGCT GCCCCTGGCC
541 TCTGCGGAGA CCAGGGACCG CTTGGAATCC GATGTGTTCT CTTTACCTCT GGAAACTGAC
601 AGCATGGACC CGTTTGGGAT GGCCAGTGAA GTGGGCCTGA AGAGCCCAG CTTCCAGAAG
661 TAA
```

*Gasterosteus aculeatus* (stickleback) FGF19 gene coding sequence (1-203) (SEQ ID NO: 323) (Ensembl accession no. ENSGACT00000018770, which is hereby incorporated by reference in its entirety)

```
  1 ATGCTGCTGC TGCTGGTCCC CGCGTACGTT GCCAGTGTGT TTTTAGCTCT CGGGGTTGTT
 61 TGCTTGCCCC TAACAGATCA GGGTCTCCAC ATGGCCGACG ACTGGGGCCA GTCGGTCCGA
121 CTCAAGCACC TGTACGCCGC CAGCCCGGGA CTCCACCTG TGATCGGGGA GGATGGTCGG
181 ATCCAAGGCT CGGCGCAGCA AAGCCCCTAC AGCCTGCTGG AGATCAGTGC AGTGGATCCG
241 GGCTGTGTGG TCATCAGAGG AGTAGCAACC GCACGGTTTC TCTGCATCGA AGGCGATGGA
301 AGACTGTACT CATCGGACAC CTACAGCAGA GACGACTGCA CCTTCAGGGA GCAGATCCTC
361 CCGGACGGCT ACAGCGTCTA CGTCTCCCAT GGACACGGGG CCCTGCTCAG CCTGGGGAAC
421 CACAGGCAGA GGCTGCAGGG TCGAGACCAC GGCGTGCCGG CTCTGGCCCA GTTCCTCCCG
```

TABLE 8-continued

```
481 AGGGTCAGCA CCATGGATCA GGCCTCGGCC CCCGACGCGC CGGGCAGAC CGCCACCGAG
541 ACGGAAGAGC CCGTGGACTC GTTTGGAAAG CTCTCTCAGA TCATTCACAG TCCCAGCTTC
601 CACGAGAGAT GA
```

*Oreochromis niloticus* (tilapia) FGF19 gene coding sequence (1-208)(SEQ ID NO: 324) (Ensembl accession no. ENSONIT00000022816, which is hereby incorporated by reference in its entirety)

```
 55                                                              ATGCTG
 61 CTGCTCCTCA TCGTATCCAT TGTCAATATG CTTTTTGGTG TTGGAATGGT TTGCATGCCC
121 CTGTCAGACA ACGGGCCCCA CATCGCCCAC GGCTGGGCCC AGGTGGTCCG GCTCAGGCAC
181 CTTTACGCCA CCAGACCGGG AATGCACCTG CTGATCAGTG AGGGTGGACA GATCCGTGGT
241 TCTGCCGTCC AGACTCTGCA CAGCCTAATG GAGATTCGTC CAGTCGGTCC AGGCCGTGTT
301 GTCATCAGAG GGGTAGCAAC CGCAAGGTTT CTCTGCATAG AAGACGACGG CACACTGTAC
361 TCATCGCACG CCTACAGCAG AGAGGACTGC ATCTTCAGAG AGCAGATCTT GCCAGATGGG
421 TACAACATCT ACATCTCTGA CAGACATGGA GTCCTGCTCA GTCTGGGAAA CCACCGGCAA
481 AGACTGCAGG GCTTAGACCG AGGAGATCCA GCCCTGGCCC AGTTCCTCCC CAGGATCAGC
541 ACTCTGAATC AAATCCCTTC CCCTGGGGCA AACATCGGTG ACCACATGAA AGTAGCAAAA
601 ACAGAAGAAC CTGTGGACAC AATAGATTCA TTTGGAAAGT TCTCTCAGAT CATTGACAGT
607 CCCAGCTTCC ATAAGAGATG A
```

*Meleagris gallopavo* (turkey) FGF19 gene coding sequence (1-216, excluding 1-70)(SEQ ID NO: 325) (Ensembl accession no. ENSMGAT00000011114, which is hereby incorporated by reference in its entirety)

```
  1 GTAGGCAATC AATCACCACA GAGCATCCTT GAAATAACTG CTGTTGATGT CGGGATCGTC
 61 GCTATCAAGG GCTTGTTCTC TGGCAGATAC CTGGCCATGA ACAAAAGGGG CAGGCTTTAT
121 GCATCACTCA GCTATTCCAT TGAGGACTGT TCCTTTGAAG AGGAGATTCG TCCAGATGGC
181 TATAACGTGT ATAAATCAAA GAAATACGGA ATATCAGTGT CTTTGAGCAG TGCCAAACAA
241 AGACAACAAT TCAAAGGAAA AGATTTTCTC CCACTGTCTC ACTTCTTACC CATGATCAAC
301 ACTGTGCCAG TGGAGGTGAC AGACTTTGGT GAATACGGTG ATTACAGCCA GGCTTTTGAG
361 CCAGAGGTCT ACTCATCGCC TCTCGAAACG GACAGCATGG ATCCCTTTGG GATCACTTCC
421 AAACTGTCTC CAGTGAAGAG CCCCAGCTTT CAGAAA
```

*Papio anubis* (olive baboon) FGF19 gene coding sequence (1-216)(SEQ ID NO: 326) (GenBank accession no. XM_003909422, which is hereby incorporated by reference in its entirety)

```
 758                                   ATG AGGAGCGGGT GTGTGGTGGT
 781 CCACGCCTGG ATCCTGGCCA GCCTCTGGCT GGCCGTGGCC GGGCGTCCCC TCGCCTTCTC
 841 GGACGCGGGG CCCCACGTGC ACTACGGCTG GGGCGACCCC ATCCGCCTGC GGCACCTGTA
 901 CACCTCCGGC CCCACGGGC TCTCCAGCTG CTTCCTGCGC ATCCGCACCG ACGGCGTCGT
 961 GGACTGCGCG CGGGGCCAAA GCGCGCACAG TTTGCTGGAG ATCAAGGCAG TAGCTCTGCG
1021 GACCGTGGCC ATCAAGGGCG TGCACAGCGT GCGGTACCTC TGCATGGGCG CCGACGGCAA
1081 GATGCAGGGG CTGCTTCAGT ACTCAGAGGA AGACTGCT TTCGAGGAGG AGATCCGCCC
1141 TGATGGCTAC AATGTATACC GATCCCAGAA GCACCGCCTC CCGGTCTCCC TGAGCAGTGC
1201 CAAACAGCGG CAGCTGTACA AGAACAGAGG CTTTCTTCCG CTGTCTCATT TCCTGCCCAT
1261 GCTGCCCATG GCCCCAGAGG AGCCTGAGGA CCTCAGGGGC CCCTTGGAAT CTGACATGTT
1321 CTCTTCGCCC CTGGAGACTG ACAGCATGGA CCCATTTGGG CTTGTCACCG GACTGGAGGC
1381 GGTGAGGAGT CCCAGCTTTG AGAAATAA
```

*Saimiri boliviensis boliviensis* (Bolivian squirrel monkey) FGF19 gene coding sequence (1-216)(SEQ ID NO: 327) (GenBank accession no. XM_003941165, which is hereby incorporated by reference in its entirety)

```
231                                                          ATGCGGAGCG
241 GGTGTGTGGT GGTCCACGCC TGGATCCTGG CTGGCCTCTG GCTGGCTGTG GTCGGGCGCC
301 CCCTCGCCTT CTCCGATGCG GGGCCGCATG TGCATTACGG CTGGGGCGAC CCCATTCGCC
361 TGCGGCACCT GTACACCTCC AGCCCCCACG GCCTCTCCAG CTGCTTCCTG CGCATCCGCA
421 GCGACGGCGT CGTGGACTGC GCGCGGGGCC AGAGCGCGCA CAGTTTGCTG GAGATCAAGG
481 CAGTCGCTCT AAGGACCGTG GCCATCAAGG GCGTGCACAG CTCGCGGTAC CTCGCATGG
541 GCGCCGACGG CAGGCTGCAG GGCTGTTCC AGTACTCGGA GGAAGACTGT GCTTTCGAGG
601 AGGAGATCCG CCCCGACGGC TACAATGTGT ACCTATCCGA GAAGCACCGC CTCCCGGTCT
661 CCCTGAGCAG CGCCAAACAG CGGCAGCTGT ACAAGAAACG AGGCTTTCTT CCGCTGTCCC
721 ATTTCCTGCC CATGCTGCCC AGAGCCCCAG AGGAGCCTGA GGCCACTTGG
781 AATCTGACGT GTTCTCTTCA CCCCTGGAGA CTGATAGCAT GGACCCATTT GGGCTTGTCA
841 CGGGACTGGA GGCGGTGAAC AGTCCCAGCT TTGAGAAGTA A
```

*Pteropus alecto* (black flying fox) FGF19 gene coding sequence (1-216) (SEQ ID NO: 328) (generated using SMS Reverse Translate tool on the ExPASy Bioinformatics Resource website (www.expasy.org)

```
  1 ATGCGCAGCC CGTGCGCGGT GGCGCGCGCG CTGGTGCTGG CGGGCCTGTG GCTGGCGAGC
 61 GCGGCGGGCC CGCTGGCGCT GAGCGATGCG GGCCCGCATG TGCATTATGG CTGGGGCGAA
121 GCGATTCGCC TGCGCCATCT GTATACCGCG GGCCCGCATG GCCCGAGCAG CTGCTTTCTG
181 CGCATTCGCG CGGATGGCGC GGTGGATTGC GCGCGCGGCC AGAGCGCGCA TAGCCTGGTG
241 GAAATTCGCG CGGTGGCGCT GCGCAACGTG GCGATTAAAG GCGTGCATAG CGTGCGCTAT
301 CTGTGCATGG GCGCGGATGG CCGCATGCTG GGCCTGCTGC AGTATAGCGC GGATGATTGC
```

TABLE 8-continued

```
361 GCGTTTGAAG AAGAAATTCG CCCGGATGGC TATAACGTGT ATCATAGCAA AAAACATCAT
421 CTGCCGGTGA GCCTGAGCAG CGCGAAACAG CGCCAGCTGT ATAAAGATCG CGGCTTTCTG
481 CCGCTGAGCC ATTTTCTGCC GATGCTGCCG CGCAGCCCGA CCGAACCGGA AAACTTTGAA
541 GATCATCTGG AAGCGGATAC CTTTAGCAGC CCGCTGGAAA CCGATGATAT GGATCCGTTT
601 GGCATTGCGA GCAAACTGGG CCTGGAAGAA AGCCCGAGCT TTCAGAAA
```

*Myotis davidii* (David's myotis) FGF19 gene coding sequence (1-245)(SEQ ID NO: 329) (generated using SMS Reverse Translate tool on the ExPASy Bioinformatics Resource website (www.expasy.org))

```
  1 ATGAGCGGCC AGAACAGCGG CCGCCATGGC AGCCGCCCGG GCCTGGATGA AGAACCGGAA
 61 CCGGGCCCGC TGGAACTGCG CGCGCTGGGC AGCACCCGCG CGGATCCGCA GCTGTGCGAT
121 TTTCTGGAAA ACCATTTTCT GGGCTATACC TGCCTGGAAC TGGATATTTG CCTGGCGACC
181 TATCTGGGCG TGAGCCATTG GGGCGAAAGC ATTCGCCTGC GCCATCTGTA TACCAGCGGC
241 CCGCATGGCC CGAGCAGCTG CTTTCTGCGC ATTCGCTGG ATGGCGCGGT GGATTGCGCG
301 CGCGGCCAGA GCGCGCATAG CCTGGTGGAA ATTCGCGCG TGGCGCTGCG CAAAGTGGCG
361 ATTAAAGGCG TGCATAGCGC GCTGTATCTG TGCATGGAAG GCGATGGCCG CATGCGCGGC
421 CTGCCGCAGT TTAGCCCGGA AGATTGCGCG TTTGAAGAAG AAATTCGCCC GGATGGCTAT
481 AACGTGTATC GCAGCCAGAA ACATCAGCTG CCGGTGAGCC TGAGCAGCGC GCGCCAGCGC
541 CAGCTGTTTA AAGCGCGCGG CTTTCTGCCG CTGAGCCATT TTCTGCCGAT GCTGCCGAGC
601 AGCCCGGCGG AACCGGTGCA TCGCGAACGC CCGCTGGAAC CGGATGCGTT TAGCAGCCCG
661 CTGGAAACCG ATAGCATGGA TCCGTTTGGC ATTGCGAACA ACCTGCGCCT GGTGAAAAGC
721 CCGAGCTTTC AGAAA
```

*Tupaia chinensis* (Chinese tree shrew) FGF19 gene coding sequence (1-257, excluding 13-19)(SEQ ID NO: 330) (generated using SMS Reverse Translate tool on the ExPASy Bioinformatics Resource website (www.expasy.org))

```
  1 ATGCGCCGCA CCTGGAGCGG CTTTGCGGTG GCGACC---- ---------- ----CGCGCG
 61 GGCAGCCCGC TGGCGCTGGC GGATGCGGGC CCGCATGTGA ACTATGGCTG GGATGAAAGC
121 ATTCGCCTGC GCCATCTGTA TACCGCGAGC CTGCATGGCA GCACCAGCTG CTTTCTGCGC
181 ATTCGCGATG ATGGCAGCGT GGGCTGCGCG CGCGGCCAGA GCATGCATAG CCTGCTGGAA
241 ATTAAAGCGG TGGCGCTGCA GACCGTGGCG ATTAAAGGCG TGTATAGCGT GCGCTATCTG
301 TGCATGGATA CCGATGGCCG CATGCAGGGC CTGCCGCAGT ATAGCGAAGA AGATTGCACC
361 TTTGAAGAAG AAATTCGCAG CGATGGCCAT AACGTGTATC GCAGCAAAAA ACATGGCCTG
421 CCGGTGAGCC TGAGCAGCGC GAAACAGCGC CAGCTGTATA AAGCGCGCGG CTTTCTGAGC
481 CTGAGCCATT TTCTGCTGAT GATGCCGAAA ACCAGCGCGG GCCCGGGCAA CCCGCGCGAT
541 CAGCGCAACC CGCGCGATCA GCGCGATCCG AACACCTTTA GCCTGCCGCT GGAAACCGAT
601 AGCATGGATC CGTTTGGCAT GACCACCCGC CATGGCCTGC TGCTGGATAG CTGCTGCGCG
661 AGCCTGGTGC TGCTGAACAT TAGCACCGAT GGCGAATTTA GCCCGTATGG CAACATTCTG
721 CGCCCGAGCT TCGCTTTAA ACTGTTTAAA ATGAAAAAAG TGACCAAC
```

*Heterocephalus glaber* (naked mole-rat) FGF19 gene coding sequence (1-209) (SEQ ID NO: 331) (generated using SMS Reverse Translate tool on the ExPASy Bioinformatics Resource website (www.expasy.org))

```
  1 ATGCGCTTTA GCAAAAGCAC CTGCGGCTTT TTTAACCATC AGCGCCTGCA GGCGCTGTGG
 61 CTGAGCCTGA GCAGCGTGAA ATGGGTGCTG GATGCGCGG TGGAAGGCCG CCCGATTCGC
121 CTGCGCCATC TGTATGCGGC GGGCCCGTAT GGCCGCAGCC GCTGCTTTCT GCGCATTCAT
181 ACCGATGGCG CGGTGGATTG CGTGGAAGAA CAGAGCGAAC ATTGCCTGCT GGAAATTCGC
241 GCGGTGGCGC TGGAAACCGT GGCGATTAAA GATATTAACA GCGTGCGCTA TCTGTGCATG
301 GGCCCGGATG GCCGCATGCA GGGCCTGCCG TGGTATAGCG AAGAAGATTG CGCGTTTAAA
361 GAAGAAATTA GCTATCCGGG CTATAGCGTG TATCGCAGCC AGAAACATCA TCTGCCGATT
421 GTGCTGAGCA GCGTGAAACA GCGCCAGCAG TATCAGAGCA AAGCGTGGT GCCGCTGAGC
481 TATTTTCTGC CGATGCTGCC GAAAGCGAGC GTGGAACCGG GCGATGAAGA AGAAAGCGCG
541 TTTAGCCTGC CGCTGAAAAC CGATAGCATG GATCCGTTTG GCATGGCGAG CGAAATTGGC
601 CTGGCGAAAA GCCCGAGCTT TCAGAAA
```

In one embodiment of the present invention, the chimeric protein may include one or more substitutions for or additions of amino acids from another FGF. In one embodiment, the C-terminal portion from FGF19 includes a modification that includes a substitution for or addition of amino acid residues from an FGF21 (including a human FGF21 and orthologs of human FGF21). In one embodiment the FGF21 is a human FGF21 protein having an amino acid sequence of SEQ ID NO: 332 (GenBank Accession No. NP_061986, which is hereby incorporated by reference in its entirety) or a portion thereof, as follows:

```
  1 MDSDETGFEH SGLWVSVLAG LLLGACQAHP IPDSSPLLQF
    GGQVRQRYLY TDDAQQTEAH
 61 LEIREDGTVG GAADQSPESL LQLKALKPGV IQILGVKTSR
    FLCQRPDGAL YGSLHFDPEA
121 CSFRELLLED GYNVYQSEAH GLPLHLPGNK SPHRDPAPRG
    PARFLPLPGL PPALPEPPGI
181 LAPQPPDVGS SDPLSMVGPS QGRSPSYAS
```

Exemplary substitutions and additions of such residues are shown in FIG. 13.

In one embodiment, the C-terminal portion from FGF19 comprises a modification that includes a substitution of amino acid residues from an FGF21. In one embodiment, the modification comprises a substitution for or addition of amino acid residues 168 to 209 of SEQ ID NO: 332 (FGF21).

In one embodiment, the modification is a substitution of amino acid residues from SEQ ID NO: 332 (FGF21) for corresponding amino acid residues of SEQ ID NO: 233. The corresponding residues of FGFs may be identified by sequence analysis and/or structural analysis. See FIGS. 2, 11, and 13. In one embodiment, the modification includes a substitution of a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid residues 168 to 209 of SEQ ID NO: 332 (FGF21) for the corresponding contiguous stretch of amino acid residues of SEQ ID NO: 233. In one embodiment, amino acid residues 169 to 173, 169 to 196, or 169 to 203 of SEQ ID NO: 233 are substituted with the corresponding amino acid residues selected from the sequence comprising amino acid residues 168 to 209 of SEQ ID NO: 332 (FGF21).

In one embodiment, the modification includes a substitution of one or more individual amino acid residues from residues 168 to 209 of SEQ ID NO: 332 (FGF21) for the corresponding amino acid residues of SEQ ID NO: 233. In one embodiment, the C-terminal portion includes substitutions of one or more of amino acid residues 169, 170, 171, 172, 174, 175, 183, 184, 185, 186, 187, 188, 189, 190, 192, 193, 194, 195, 197, 200, 201, 202, 206, 207, 208, 209, 214, 215, or 216 of SEQ ID NO: 1 for the corresponding amino acid residues of SEQ ID NO: 332 (FGF21).

In one embodiment of the present invention, the C-terminal portion from FGF19 includes a modification that includes a deletion of amino acid residues that are absent in the corresponding C-terminal portion from FGF21. As shown in FIG. 13, FGF19 residues that are absent in the corresponding C-terminal portion of FGF21 may be identified by sequence analysis and/or structural analysis. In one embodiment, the modification comprises a deletion of amino acid residues selected from residues 204 to 216, 197 to 216, 174 to 216, or 169 to 216 of SEQ ID NO: 233. In one embodiment, the modification comprises a deletion corresponding to amino acid residue 204 of SEQ ID NO: 233. In one embodiment, the modification includes a deletion of amino acid residues 178, 179, 180, 181, and/or 182 of SEQ ID NO: 233 individually or in combination.

Chimeric proteins according to the present invention may be isolated proteins or polypeptides. The isolated chimeric proteins of the present invention may be prepared for use in the above described methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

Chimeric proteins according to the present invention may be isolated proteins or polypeptides. The isolated chimeric proteins of the present invention may be prepared for use in the above described methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

In one embodiment, the chimeric protein of the present invention includes the amino acid sequence of SEQ ID NO: 333, SEQ ID NO: 334, SEQ ID NO: 335, or SEQ ID NO: 336, as shown in Table 9.

TABLE 9

| Description of Chimeric Protein | Sequence |
|---|---|
| Amino acid sequence of a FGF1/FGF19 chimera composed of residues M1 to L150 of human FGF1 harboring K127D/K128Q/K133V triple mutation (bold) and residues L169 to K216 of human FGF19 (bold) | SEQ ID NO: 333<br>MAEGEITTFT ALTEKFNLPP GNYKKPKLLY CSNGGHFLRI LPDGTVDGTR DRSDQHIQLQ LSAESVGEVY IKSTETGQYL AMDTDGLLYG SQTPNEECLF LERLEENHYN TYISKKHAEK NWFVGLDQNG SCVRGPRTHY GQKAILFLPL LPMVPEEPED LRGHLESDMF SSPLETDSMD PFGLVTGLEA VRSPSFEK |
| Amino acid sequence of a FGF1/FGF19 chimera composed of residues K25 to L150 of human FGF1 harboring K127D/K128Q/K133V triple mutation (bold) and residues L169 to K216 of human FGF19 (bold) | SEQ ID NO: 334<br>KPKLLY CSNGGHFLRI LPDGTVDGTR DRSDQHIQLQ LSAESVGEVY IKSTETGQYL AMDTDGLLYG SQTPNEECLF LERLEENHYN TYISKKHAEK NWFVGLDQNG SCVRGPRTHY GQKAILFLPL LPMVPEEPED LRGHLESDMF SSPLETDSMD PFGLVTGLEA VRSPSFEK |
| Amino acid sequence of a FGF2/FGF19 chimera composed of residues M1 to M151 of human FGF2 harboring K128D/R129Q/K134V triple mutation (bold) and residues L169 to K216 of human FGF19 (bold) | SEQ ID NO: 335<br>MAAGSITTLP ALPEDGGSGA FPPGHFKDPK RLYCKNGGFF LRIHPDGRVD GVREKSDPHI KLQLQAEERG VVSIKGVCAN RYLAMKEDGR LLASKCVTDE CFFFERLESN NYNTYRSRKY TSWYVALDQT GQYVLGSKTG PGQKAILFLP MLPMVPEEPE DLRGHLESDM FSSPLETDSM DPFGLVTGLE AVRSPSFEK |
| Amino acid sequence of a FGF2/FGF19 chimera composed of residues H25 to M151 of human FGF2 harboring K128D/R129Q/K134V triple mutation (bold) and residues L169 to K216 of human FGF19 (bold) | SEQ ID NO: 336<br>HFKDPK RLYCKNGGFF LRIHPDGRVD GVREKSDPHI KLQLQAEERG VVSIKGVCAN RYLAMKEDGR LLASKCVTDE CFFFERLESN NYNTYRSRKY TSWYVALDQT GQYVLGSKTG PGQKAILFLP MLPMVPEEPE DLRGHLESDM FSSPLETDSM DPFGLVTGLE AVRSPSFEK |

Chimeric proteins according to the present invention may be isolated proteins or polypeptides. The isolated chimeric proteins of the present invention may be prepared for use in accordance with the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule comprises the nucleotide sequence of SEQ ID NO: 337, SEQ ID NO: 338, SEQ ID NO: 339, or SEQ ID NO: 340, as shown in Table 10.

TABLE 10

| Description of Chimeric Protein | Sequence |
| --- | --- |
| Nucleotide sequence of a FGF1/FGF19 chimera composed of residues M1 to L150 of human FGF1 harboring K127D/K128Q/K133V triple mutation (bold) and residues L169 to K216 of human FGF19 (bold) | SEQ ID NO: 337<br>ATGGCTGAAG GGGAAATCAC CACCTTCACA<br>GCCCTGACCG AGAAGTTTAA TCTGCCTCCA<br>GGGAATTACA AGAAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>CTGCCCATGG TCCCAGAGGA GCCTGAGGAC<br>CTCAGGGGCC ACTTGGAATC TGACATGTTC<br>TCTTCGCCCC TGGAGACCGA CAGCATGGAC<br>CCATTTGGGC TTGTCACCGG ACTGGAGGCC<br>GTGAGGAGTC CCAGCTTTGA GAAG |
| Nucleotide sequence of a FGF1/FGF19 chimera composed of residues K25 to L150 of human FGF1 harboring K127D/K128Q/K133V triple mutation (bold) and residues L169 to K216 of human FGF19 (bold) | SEQ ID NO: 338<br>AAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>CTGCCCATGG TCCCAGAGGA GCCTGAGGAC<br>CTCAGGGGCC ACTTGGAATC TGACATGTTC<br>TCTTCGCCCC TGGAGACCGA CAGCATGGAC<br>CCATTTGGGC TTGTCACCGG ACTGGAGGCC<br>GTGAGGAGTC CCAGCTTTGA GAAG |
| Nucleotide sequence of a FGF2/FGF19 chimera composed of residues M1 to M151 of human FGF2 harboring K128D/R129Q/K134V triple mutation (bold) and residues L169 to K216 of human FGF19 (bold) | SEQ ID NO: 339<br>ATG GCAGCCGGGA<br>GCATCACCAC GCTGCCCGCC TTGCCCGAGG<br>ATGGCGGCAG CGGCGCCTTC CCGCCCGGCC<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTGGA TCAGACTGGG CAGTATGTTC<br>TTGGATCCAA AACAGGACCT GGGCAGAAAG<br>CTATACTTTT TCTTCCAATG CTGCCCATGG<br>TCCCAGAGGA GCCTGAGGAC CTCAGGGGCC<br>ACTTGGAATC TGACATGTTC TCTTCGCCCC<br>TGGAGACCGA CAGCATGGAC CCATTTGGGC<br>TTGTCACCGG ACTGGAGGCC GTGAGGAGTC<br>CCAGCTTTGA GAAG |

TABLE 10-continued

| Description of Chimeric Protein | Sequence |
|---|---|
| Nucleotide sequence of a FGF2/FGF19 chimera composed of residues H25 to M151 of human FGF2 harboring K128D/R129Q/K134V triple mutation (bold) and residues L169 to K216 of human FGF19 (bold) | SEQ ID NO: 340<br>                                                           C<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTGGA TCAGACTGGG CAGTATGTTC<br>TTGGATCCAA AACAGGACCT GGGCAGAAAG<br>CTATACTTTT TCTTCCAATG CTGCCCATGG<br>TCCCAGAGGA GCCTGAGGAC CTCAGGGGCC<br>ACTTGGAATC TGACATGTTC TCTTCGCCCC<br>TGGAGACCGA CAGCATGGAC CCATTTGGGC<br>TTGTCACCGG ACTGGAGGCC GTGAGGAGTC<br>CCAGCTTTGA GAAG |

Another aspect of the present invention relates to a nucleic acid construct comprising a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

Also encompassed are vectors or expression vectors comprising such nucleic acid molecules and host cells comprising such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the protein has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Another aspect of the present invention relates to a pharmaceutical composition that includes a chimeric protein according to the present invention and a pharmaceutically acceptable carrier.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the pharmaceutical composition includes an organotropic targeting agent. In one embodiment, the targeting agent is covalently linked to the chimeric protein via a linker that is cleaved under physiological conditions.

Chimeric and/or modified proteins according to the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the chimeric and/or modified proteins may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The chimeric and/or modified proteins may also be fused to a macromolecule other than protein that confers a longer half-life to the protein upon in vivo administration. Suitable macromolecules include, without limitation, polyethylene glycols (PEGs). Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., which are hereby incorporated by reference in their entirety.

The pharmaceutical composition according to the present invention can be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The formulations may conveniently be presented in unit dosage form and may be prepared by any of the methods well known in the art of pharmacy.

Another aspect of the present invention relates to a method for treating a subject suffering from a disorder. This method involves selecting a subject suffering from the disorder and administering the pharmaceutical composition according to the present invention to the selected subject under conditions effective to treat the disorder. In one embodiment the disorder is diabetes, obesity, or metabolic syndrome.

Accordingly, another aspect of the present invention relates to a method for treating a subject suffering from a disorder. This method involves selecting a subject suffering from the disorder. The method also involves providing a chimeric FGF protein, where the chimeric FGF protein includes an N-terminus coupled to a C-terminus. The N-terminus includes a portion of a paracrine FGF and the C-terminus includes a C-terminal portion of FGF19. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

The portion of the paracrine FGF may also be modified to alter receptor-binding specificity and/or receptor-binding affinity compared to the portion without the modification. Suitable chimeric proteins for use in accordance with this aspect of the present invention are described above and throughout the present application.

In one embodiment, the selected subject is a mammal. In one embodiment, the selected subject is a human. In another embodiment, the selected subject is a rodent.

In one embodiment, the selected subject is in need of increased FGF19-βKlotho-FGF receptor ("FGFR") complex formation.

In one embodiment, the disorder is a selected from diabetes, obesity, and metabolic syndrome. As used herein, diabetes includes type I diabetes, type II diabetes, gestational diabetes, and drug-induced diabetes. In yet another embodiment, the subject has obesity. In yet another embodiment, the subject has metabolic syndrome.

The chimeric protein of the present invention or pharmaceutical composition thereof can be used to treat a number of conditions. In one embodiment, the condition is one which the therapeutic outcome includes a decrease in blood glucose, a decrease in blood fructosamine, an increase in energy expenditure, an increase in fat utilization, a decrease in body weight, a decrease in body fat, a decrease in triglycerides, a decrease in free fatty acids, an increase in fat excretion, an improvement, or even a preservation, of pancreatic β-cell function and mass, a decrease in total blood cholesterol, a decrease in blood low-density lipoprotein cholesterol, an increase in blood high-density lipoprotein cholesterol, an increase in blood adiponectin, an increase in insulin sensitivity, an increase in leptin sensitivity, a decrease in blood insulin, a decrease in blood leptin, a decrease in blood glucagon, an increase in glucose uptake by adipocytes, a decrease in fat accumulation in hepatocytes, and/or an increase in fat oxidation in hepatocytes. Each of these parameters can be measured by standard methods, for example, by measuring oxygen consumption to determine metabolic rate, using scales to determine weight, and measuring lean body mass composition or mass to determine fat. Moreover, the presence and amount of triglycerides, free fatty acids, glucose and leptin can be determined by standard methods (e.g., blood test).

Additional conditions that are treatable in accordance with the present invention include one or more of type 1 diabetes, type 2 diabetes, gestational diabetes, drug-induced diabetes, high blood glucose, metabolic syndrome, lipodystrophy syndrome, dyslipidemia, insulin resistance, leptin resistance, atherosclerosis, vascular disease, inflammatory disease, fibrotic disease, hypercholesterolemia, hypertriglyceridemia, non-alcoholic fatty liver disease, overweight, and obesity.

In one embodiment, the chimeric protein of the present invention or pharmaceutical composition thereof is administered with a pharmaceutically-acceptable carrier.

The chimeric protein according to the present invention or pharmaceutical composition thereof can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. Formulations including chimeric proteins according to the present invention may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions comprising the chimeric protein according to the present invention, as determined by good medical practice and the clinical condition of the individual patient.

When in vivo administration of a chimeric protein of the present invention or is employed, normal dosage amounts may vary from, for example, about 10 ng/kg to up to 100 mg/kg of mammal body weight or more per day. In one embodiment, the dosage may be from about 1 μg/kg/day to 10 mg/kg/day, depending upon the route of administration. In one embodiment, the chimeric protein according to the present invention is administered at a dose of about 0.1 to 10 mg/kg once or twice daily. In one embodiment, the chimeric protein according to the present invention is administered at a dose of about 1 to 9, 1 to 8, 1 to 7, 1 to 6, 1 to 5, 1 to 4, 1 to 3, or 1 to 2 mg/kg. In one embodiment, the dosage is the same as that of a native FGF21 therapeutic. In one embodiment, the dosage is less than that of a native FGF21 therapeutic, but has the same effect as a higher dosage of a native FGF21 therapeutic. Guidance as to particular dosages and methods of delivery of proteins is provided in the literature; see, for example, U.S. Pat. Nos. 4,657,760; 5,206,344; or U.S. Pat. No. 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated. Microencapsulation of recombinant proteins for sustained release has been successfully performed with human growth hormone (rhGH), interferon-(rhIFN-), interleukin-2, and MN rgp120. Johnson et al., "Preparation and Characterization of Poly(D,L-lactide-co-glycolide) Microspheres for Controlled Release of Human Growth Hormone," *Nat. Med.* 2:795-799 (1996); Yasuda, "Sustained Release Formulation of Interferon," *Biomed. Ther.* 27:1221-1223 (1993); Hora et al., "Controlled Release of Interleukin-2 from Biodegradable Microspheres," *Nat. Biotechnol.* 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The chimeric protein of the present invention or pharmaceutical composition thereof may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

In some embodiments, the chimeric protein of the present invention or a pharmaceutical composition thereof is administered in a therapeutically effective amount in combination with a therapeutically effective amount of a second agent. In one embodiment, the chimeric protein of the present invention or pharmaceutical composition thereof is administered in conjunction with the second agent, i.e., the respective periods of administration are part of a single administrative regimen. In one embodiment, the chimeric protein of the present invention or pharmaceutical composition thereof and the second agent are administered concurrently, i.e., the respective periods of administration overlap each other. In one embodiment, the chimeric protein of the present invention or pharmaceutical composition thereof and the second agent are administered non-concurrently, i.e., the respective periods of administration do not overlap each other. In one embodiment, the chimeric protein of the present invention or pharmaceutical composition thereof and the second agent are administered sequentially, i.e., the chimeric protein of the present invention or pharmaceutical composition thereof is administered prior to and/or after the administration of the second agent. In one embodiment, the chimeric protein of the present invention or pharmaceutical composition thereof and the second agent are administered simultaneously as separate compositions. In one embodiment, the chimeric protein of the present invention or pharmaceutical composition thereof and the second agent are administered simultaneously as part of the same compositions.

In one embodiment, the second agent is an anti-inflammatory agent, an anti-fibrotic agent, an antihypertensive agent, an anti-diabetic agent, a triglyceride-lowering agent, and/or cholesterol-lowering drug such as a drug of the "statin" class. In one embodiment, the second agent is insulin. In one embodiment, the insulin is rapid acting, short acting, regular acting, intermediate acting, or long acting insulin. In one embodiment, the insulin is and/or comprises Humalog®, Lispro, Novolog®, Apidra®, Humulin®, Aspart, regular insulin, NPH, Lente, Ultralente, Lantus®, Glargine, Levemir®, or Detemir. In one embodiment, the second agent is a statin. In one embodiment, the statin is and/or comprises Atorvastatin (e.g., Lipitor® or Torvast®), Cerivastatin (e.g., Lipobay® or Baycol®), Fluvastatin (e.g., Lescol® or LescolXL®), Lovastatin (e.g., Mevacor®, Altocor®, or Altoprev®) Mevastatin, Pitavastatin (e.g., Livalo® or Pitava®), Pravastatin (e.g., Pravachol®, Selektine, or Lipostat®) Rosuvastatin (e.g., Crestor®), Simvastatin (e.g., Zocor® or Lipex®), Vytorin®, Advicor®, Besylate Caduet® or Simcor®.

In one embodiment of the present invention, the chimeric protein according to the present invention or the pharmaceutical composition thereof is administered with an anti-inflammatory agent, an antifibrotic agent, an antihypertensive agent, an antidiabetic agent, a triglyceride-lowering agent, and/or a cholesterol-lowering agent.

Another aspect of the present invention relates to a method of making a chimeric FGF protein possessing enhanced endocrine activity. This method involves introducing one or more modifications to a FGF protein, where the modification decreases the affinity of the FGF protein for heparin and/or heparan sulfate and coupling a C-terminal portion of FGF19 that includes a βKlotho co-receptor binding domain to the modified FGF protein's C-terminus, whereby a chimeric FGF protein possessing enhanced endocrine activity is made.

Suitable C-terminal portions of FGF19 are described above. In one embodiment, the C-terminal region from FGF19 is derived from a mammalian FGF19. In one embodiment, the C-terminal region derived from FGF19 is from a vertebrate FGF19.

In one embodiment, the chimeric FGF protein has greater binding affinity for FGFR than native FGF19. In one embodiment the chimeric FGF protein possesses enhanced endocrine activity compared to the chimeric FGF protein in the absence of the modification or the βKlotho co-receptor binding domain. In one embodiment, the native endocrine FGF ligand having the βKlotho co-receptor binding domain is native FGF21. In one embodiment, the FGFR is FGFR1c, FGFR2c, or FGFR4.

In one embodiment the chimeric FGF protein has greater stability than a native endocrine FGF ligand possessing the βKlotho co-receptor binding domain. In one embodiment, increasing the stability includes an increase in thermal stability of the protein as compared to either wild type protein or native endocrine FGF ligand. In one embodiment, increasing the stability includes increasing the half-life of the protein in the blood circulation as compared to wild type protein or native endocrine FGF ligand.

In one embodiment, the method involves introducing one or more modifications to the FGF protein, where the modification alters the receptor-binding specificity of the FGF protein. In one embodiment, the method involves introducing one or more modifications to the FGF protein, where the modification alters the receptor-binding affinity of the FGF protein.

In one embodiment, the FGF is derived from a mammalian FGF. In one embodiment, the FGF is derived from a vertebrate FGF. In one embodiment, the FGF protein is a paracrine FGF molecule. In one embodiment the FGF molecule is FGF1 or FGF2. In one embodiment, the FGF protein is an FGF protein that possesses intrinsically greater binding affinity for FGF receptor than a native endocrine FGF ligand. In one embodiment, the FGF protein is an FGF protein that possesses intrinsically greater thermal stability than a native endocrine FGF ligand. In one embodiment, the method involves introducing one or more modifications to the FGF protein, where the modification alters receptor-binding specificity and/or receptor-binding affinity of the FGF protein. In one embodiment, the method involves introducing one or more modifications to the FGF protein, where the modification alters the stability of the FGF protein. For example, receptor-binding specificity of FGF1, which by nature binds to all the seven principal FGFRs, may be altered to, for example, reduce any risk for adverse effects (e.g., mitogenicity). Paracrine FGFs, portions of paracrine FGFs, and modifications thereto are described above.

In one embodiment, the chimeric FGF protein is effective to treat diabetes, obesity, and/or metabolic syndrome.

Suitable methods of generating chimeric proteins according to the present invention include standard methods of synthesis known in the art, as described above.

Yet another aspect of the present invention relates to a method of facilitating fibroblast growth factor receptor ("FGFR")-βKlotho co-receptor complex formation. This method involves providing a cell that includes a βKlotho co-receptor and an FGFR and providing a chimeric FGF protein. The chimeric FGF protein includes a C-terminal portion of FGF19 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-βKlotho co-receptor complex formation.

Suitable portions of the paracrine FGFs for use in accordance with the present invention are described above. Suitable modifications to the paracrine FGFs for use in accordance with the present invention are also described above. Suitable C-terminal portions from FGF19 are described above and throughout the present application.

In one embodiment according to the present invention, βKlotho is mammalian β3Klotho. In one embodiment, βKlotho is human or mouse βKlotho. In one particular embodiment of the present invention, βKlotho is human or mouse βKlotho including the amino acid sequence of SEQ ID NO: 341 (i.e., GenBank Accession No. NP_783864, which is hereby incorporated by reference in its entirety) or SEQ ID NO: 342 (i.e., GenBank Accession No. NP_112457, which is hereby incorporated by reference in its entirety), respectively, as follows:

```
SEQ ID NO: 341:
   1 MKPGCAAGSP GNEWIFFSTD EITTRYRNTM SNGGLQRSVI LSALILLRAV TGFSGDGRAI
  61 WSKNPNFTPV NESQLFLYDT FPKNFFWGIG TGALQVEGSW KKDGKGPSIW DHFIHTHLKN
 121 VSSTNGSSDS YIFLEKDLSA LDFIGVSFYQ FSISWPRLFP DGIVTVANAK GLQYYSTLLD
 181 ALVLRNIEPI VTLYHWDLPL ALQEKYGGWK NDTIIDIFND YATYCFQMFG DRVKYWITIH
 241 NPYLVAWHGY GTGMHAPGEK GNLAAVYTVG HNLIKAHSKV WHNYNTHFRP HQKGWLSITL
 301 GSHWIEPNRS ENTMDIFKCQ QSMVSVLGWF ANPIHGDGDY PEGMRKKLFS VLPIFSEAEK
 361 HEMRGTADFF AFSFGPNNFK PLNTMAKMGQ NVSLNLREAL NWIKLEYNNP RILIAENGWF
 421 TDSRVKTEDT TAIYMMKNFL SQVLQAIRLD EIRVFGYTAW SLLDGFEWQD AYTIRRGLFY
 481 VDFNSKQKER KPKSSAHYYK QIIRENGFSL KESTPDVQGQ FPCDFSWGVT ESVLKPESVA
 541 SSPQFSDPHL YVWNATGNRL LHRVEGVRLK TRPAQCTDFV NIKKQLEMLA RMKVTHYRFA
 601 LDWASVLPTG NLSAVNRQAL RYYRCVVSEG LKLGISAMVT LYYPTHAHLG LPEPLLHADG
 661 WLNPSTAEAF QAYAGLCFQE LGDLVKLWIT INEPNRLSDI YNRSGNDTYG AAHNLLVAHA
 721 LAWRLYDRQF RPSQRGAVSL SLHADWAEPA NPYADSHWRA AERFLQFEIA WFAEPLFKTG
 781 DYPAAMREYI ASKHRRGLSS SALPRLTEAE RRLLKGTVDF CALNHFTTRF VMHEQLAGSR
 841 YDSDRDIQFL QDITRLSSPT RLAVIPWGVR KLLRWVRRNY GDMDIYITAS GIDDQALEDD
 901 RLRKYYLGKY LQEVLKAYLI DKVRIKGYYA FKLAEEKSKP RFGFFTSDFK AKSSIQFYNK
 961 VISSRGFPFE NSSSRCSQTQ ENTECTVCLF LVQKKPLIFL GCCFFSTLVL LLSIAIFQRQ
1021 KRRKFWKAKN LQHIPLKKGK RVVS

SEQ ID NO: 342:
   1 MKTGCAAGSP GNEWIFFSSD ERNTRSRKTM SNRALQRSAV LSAFVLLRAV TGFSGDGKAI
  61 WDKKQYVSPV NPSQLFLYDT FPKNFSWGVG TGAFQVEGSW KTDGRGPSIW DRYVYSHLRG
 121 VNGTDRSTDS YIFLEKDLLA LDFLGVSFYQ FSISWPRLFP NGTVAAVNAQ GLRYYRALLD
 181 SLVLRNIEPI VTLYHWDLPL TLQEEYGGWK NATMIDLFND YATYCFQTFG DRVKYWITIH
 241 NPYLVAWHGF GTGMHAPGEK GNLTAVYTVG HNLIKAHSKV WHNYDKNFRP HQKGWLSITL
 301 GSHWIEPNRT DNMEDVINCQ HSMSSVLGWF ANPIHGDGDY PEFMKTGAMI PEFSEAEKEE
 361 VRGTADFFAF SFGPNNFRPS NTVVKMGQNV SLNLRQVLNW IKLEYDDPQI LISENGWFTD
 421 SYIKTEDTTA IYMMKNFLNQ VLQAIKFDEI RVFGYTAWTL LDGFEWQDAY TTRRGLFYVD
 481 FNSEQKERKP KSSAHYYKQI IQDNGFPLKE STPDMKGRFP CDFSWGVTES VLKPEFTVSS
 541 PQFTDPHLYV WNVTGNRLLY RVEGVRLKTR PSQCTDYVSI KKRVEMLAKM KVTHYQFALD
 601 WTSILPTGNL SKVNRQVLRY YRCVVSEGLK LGVFPMVTLY HPTHSHLGLP LPLLSSGGWL
 661 NMNTAKAFQD YAELCFRELG DLVKLWITIN EPNRLSDMYN RTSNDTYRAA HNLMIAHAQV
 721 WHLYDRQYRP VQHGAVSLSL HCDWAEPANP FVDSHWKAAE RFLQFEIAWF ADPLFKTGDY
 781 PSVMKEYIAS KNQRGLSSSV LPRFTAKESR LVKGTVDFYA LNHFTTRFVI HKQLNTNRSV
 841 ADRDVQFLQD ITRLSSPSRL AVTPWGVRKL LAWIRRNYRD RDIYITANGI DDLALEDDQI
 901 RKYYLEKYVQ EALKAYLIDK VKIKGYYAFK LTEEKSKPRF GFFTSDFRAK SSVQFYSKLI
 961 SSSGLPAENR SPACGQPAED TDCTICSFLV EKKPLIFFGC CFISTLAVLL SITVFHHQKR
1021 RKFQKARNLQ NIPLKKGHSR VFS
```

In one particular embodiment of the present invention, βKlotho is human or mouse βKlotho encoded by a nucleotide sequence including the nucleotide sequences of SEQ ID NO: 343 (GenBank Accession No. NM_175737, which is hereby incorporated by reference in its entirety) and SEQ ID NO: 344 (GenBank Accession No. NM_031180, which is hereby incorporated by reference in its entirety), as follows:

```
SEQ ID NO: 343 (Human βKlotho gene coding sequence):
  98      ATG AAGCCAGGCT GTGCGGCAGG ATCTCCAGGG AATGAATGGA TTTTCTTCAG
 151 CACTGATGAA ATAACCACAC GCTATAGGAA TACAATGTCC AACGGGGGAT TGCAAAGATC
 211 TGTCATCCTG TCAGCACTTA TTCTGCTACG AGCTGTTACT GGATTCTCTG GAGATGGAAG
 271 AGCTATATGG TCTAAAAATC CTAATTTTAC TCCGGTAAAT GAAAGTCAGC TGTTTCTCTA
 331 TGACACTTTC CCTAAAAACT TTTTCTGGGG TATTGGGACT GGAGCATTGC AAGTGGAAGG
 391 GAGTTGGAAG AAGGATGAA AAGGACCTTC TATATGGGAT CATTTCATCC ACACACACCT
 451 TAAAAATGTC AGCAGCACGA ATGGTTCCAG TGACAGTTAT ATTTTTCTGG AAAAAGACTT
 511 ATCAGCCCTG GATTTTATAG GAGTTTCTTT TTATCAATTT TCAATTTCCT GGCCAAGGCT
 571 TTTCCCCGAT GGAATAGTAA CAGTTGCCAA CGCAAAAGGT CTGCAGTACT ACAGTACTCT
 631 TCTGGACGCT CTAGTGCTTA GAAACATTGA ACCTATAGTT ACTTTATACC ACTGGGATTT
 691 GCCTTTGGCA CTACAAGAAA AATATGGGGG GTGGAAAAAT GATACCATAA TAGATATCTT
 751 CAATGACTAT GCCACATACT GTTTCCAGAT GTTTGGGGAC CGTGTCAAAT ATTGGATTAC
 811 AATTCACAAC CCATATCTAG TGGCTTGGCA TGGGTATGGG ACAGGTATGC ATGCCCCTGG
 871 AGAGAAGGGA AATTTAGCAG CTGTCTACAC TGTGGGACAC AACTTGATCA AGGCTCACTC
 931 GAAAGTTTGG CATAACTACA ACACACATTT CCGCCCACAT CAGAAGGGTT GGTTATCGAT
 991 CACGTTGGGA TCTCATTGGA TCGAGCCAAA CCGGTCGGAA AACACGATGG ATATATTCAA
1051 ATGTCAACAA TCCATGGTTT CTGTGCTTGG ATGGTTTGCC AACCCTATCC ATGGGGATGG
1111 CGACTATCCA GAGGGGATGA GAAAGAAGTT GTTCTCCGTT CTACCCATTT TCTCTGAAGC
1171 AGAGAAGCAT GAGATGAGAG GCACAGCTGA TTTCTTTGCC TTTTCTTTTG GACCCAACAA
1231 CTTCAAGCCC CTAAACACCA TGGCTAAAAT GGGACAAAAT GTTTCACTTA ATTTAAGAGA
1291 AGCGCTGAAC TGGATTAAAC TGGAATACAA CAACCCTCGA ATCTTGATTG CTGAGAATGG
1351 CTGGTTCACA GACAGTCGTG TGAAAACAGA AGACACCACG GCCATCTACA TGATGAAGAA
```

-continued

```
1411 TTTCCTCAGC CAGGTGCTTC AAGCAATAAG GTTAGATGAA ATACGAGTGT TTGGTTATAC
1471 TGCCTGGTCT CTCCTGGATG GCTTTGAATG GCAGGATGCT TACACCATCC GCCGAGGATT
1531 ATTTTATGTG GATTTTAACA GTAAACAGAA AGAGCGGAAA CCTAAGTCTT CAGCACACTA
1591 CTACAAACAG ATCATACGAG AAAATGGTTT TTCTTTAAAA GAGTCCACGC CAGATGTGCA
1651 GGGCCAGTTT CCCTGTGACT TCTCCTGGGG TGTCACTGAA TCTGTTCTTA AGCCCGAGTC
1711 TGTGGCTTCG TCCCCACAGT TCAGCGATCC TCATCTGTAC GTGTGGAACG CCACTGGCAA
1771 CAGACTGTTG CACCGAGTGG AAGGGGTGAG GCTGAAAACA CGACCCGCTC AATGCACAGA
1831 TTTTGTAAAC ATCAAAAAAC AACTTGAGAT GTTGGCAAGA ATGAAAGTCA CCCACTACCG
1891 GTTTGCTCTG GATTGGGCCT CGGTCCTTCC CACTGGCAAC CTGTCCGCGG TGAACCGACA
1951 GGCCCTGAGG TACTACAGGT GCGTGGTCAG TGAGGGGCTG AAGCTTGGCA TCTCCGCGAT
2011 GGTCACCCTG TATTATCCGA CCCACGCCCA CCTAGGCCTC CCCGAGCCTC TGTTGCATGC
2071 CGACGGGTGG CTGAACCCAT CGACGGCCGA GGCCTTCCAG GCCTACGCTG GCTGTGCTT
2131 CCAGGAGCTG GGGGACCTGG TGAAGCTCTG GATCACCATC AACGAGCCTA ACCGGCTAAG
2191 TGACATCTAC AACCGCTCTG GCAACGACAC CTACGGGGCG GCGCACAACC TGCTGGTGGC
2251 CCACGCCCTG GCCTGGCGCC TCTACGACCG GCAGTTCAGG CCCTCACAGC GCGGGGCCGT
2311 GTCGCTGTCG CTGCACGCGG ACTGGGCGGA ACCCGCCAAC CCCTATGCTG ACTCGCACTG
2371 GAGGGCGGCC GAGCGCTTCC TGCAGTTCGA GATCGCCTGG TTCGCCGAGC CGTCTTCAA
2431 GACCGGGGAC TACCCCGCGG CCATGAGGGA ATACATTGCC TCCAAGCACC GACGGGGGCT
2491 TTCCAGCTCG GCCCTGCCGC GCCTCACCGA GGCCGAAAGG AGGCTGCTCA AGGGCACGGT
2551 CGACTTCTGC GCGCTCAACC ACTTCACCAC TAGGTTCGTG ATGCACGAGC AGCTGGCCGG
2611 CAGCCGCTAC GACTCGGACA GGGACATCCA GTTTCTGCAG GACATCACCC GCCTGAGCTC
2671 CCCCAGCGCG CTGGCTGTGA TTCCCTGGGG GGTGCGCAAG CTGCTGCGGT GGGTCCGGAG
2731 GAACTACGGC GACATGGACA TTTACATCAC CGCCAGTGGC ATCGACGACC AGGCTCTGGA
2791 GGATGACCGG CTCCGGAAGT ACTACCTAGG GAAGTACCTT CAGGAGGTGC TGAAAGCATA
2851 CCTGATTGAT AAAGTCAGAA TCAAAGGCTA TTATGCATTC AAACTGGCTG AAGAGAAATC
2911 TAAACCCAGA TTTGGATTCT TCACATCTGA TTTTAAAGCT AAATCCTCAA TACAATTTTA
2971 CAACAAAGTG ATCAGCAGCA GGGGCTTCCC TTTTGAGAAC AGTAGTTCTA GATGCAGTCA
3031 GACCCAAGAA AATACAGAGT GCACTGTCTG CTTATTCCTT GTGCAGAAGA AACCACTGAT
3091 ATTCCTGGGT TGTTGCTTCT TCTCCACCCT GGTTCTACTC TTATCAATTG CCATTTTTCA
3151 AAGGCAGAAG AGAAGAAAGT TTTGGAAAGC AAAAAACTTA CAACACATAC CATTAAAGAA
3211 AGGCAAGAGA GTTGTTAGCT AA

SEQ ID NO: 344 (House mouse βKlotho gene coding sequence):
   2 ATGAAGACA GGCTGTGCAG CAGGGTCTCC GGGGAATGAA TGGATTTTCT TCAGCTCTGA
  61 TGAAAGAAAC ACACGCTCTA GGAAAACAAT GTCCAACAGG GCACTGCAAA GATCTGCCGT
 121 GCTGTCTGCG TTTGTTCTGC TGCGAGCTGT TACCGGCTTC TCCGGAGACG GGAAAGCAAT
 181 ATGGGATAAA AAACAGTACG TGAGTCCGGT AAACCCAAGT CAGCTGTTCC TCTATGACAC
 241 TTTCCCTAAA AACTTTTCCT GGGGCGTTGG GACCGGACAA TTTCAAGTGG AAGGGAGTTG
 301 GAAGACAGAT GGAAGAGGAC CCTCGATCTG GGATCGGTAC GTCTACTCAC ACTTGTTGGC
 361 TGTCAACGGC ACAGACAGAT CCACTGACAG TTACATCTTT CTGGAAAAAG ACTTGTTGGC
 421 TCTGGATTTT TTAGGAGTTT CTTTTTATCA GTTCTCAATC TCCTGGCCAC GGTTGTTTCC
 481 CAATGGAACA GTAGCAGCAG TGAATGCGCA AGGTCTCCGG TACTACCGTG CACTTCTGGA
 541 CTCGCTGGTA CTTAGGAATA CTGAGCCCAT TGTTACCTTG TACCATTGGG ATTTGCCTCT
 601 GACGCTCCAG GAAGAATATG GGGGCTGAAA AATGCAACT ATGATAGATC TCTTCAACGA
 661 CTATGCCACA TACTGCTTCC AGACCTTTGG AGACCGTGTC AAATATTGGA TTACAATTCA
 721 CAACCCTTAC CTTGTTGCTT GGCATGGGTT TGGCACAGGT ATGCATGCAC CAGGAGAGAA
 781 GGGAAATTTA ACAGCTGTCT ACACTGTGGG ACACAACCTG ATCAAGGCAC ATTCAAAGT
 841 GTGGCATAAC TACGACAAAA ACTTCCGCCC TCATCAGAAG GGTTGGCTCT CCATCACCTT
 901 GGGGTCCCAT TGGATAGAGC CAAACAGAAC AGACAACATG GAGGACGTGA TCAACTGCCA
 961 GCACTCCATG TCCTCTGTGC TTGGATGGTT CGCCAACCCC ATCCACGGGG ACGGCGACTA
1021 CCCTGAGTTC ATGAAGACGG GCGCCATGAT CCCCGAGTTC TCTGAGGCAG GAAAGGAGGA
1081 GGTGAGGGGC ACGGCTGATT TCTTTGCCTT TTCCTTCGGG CCCAACAACT TCAGGCCCTC
1141 AAACACCGTG TGAAAATGG ACAAAATGT ATCACTCAAC TTAAGGCAGG TGCTGAACTG
1201 GATTAAACTG GAATACGATG ACCCTCAAAT CTTGATTTCG GAGAACGGCT GGTTCACAGA
1261 TAGCTATATA AAGACAGAGG ACACCACGGC CATCTACATG ATGAAGAATT TCCTAAACCA
1321 GGTTCTTCAA GCAATAAAAT TTGATGAAAT CCGCGTGTTT GGTTATACGG CCTGGACTCT
1381 CCTGGATGGC TTTGAGTGGC AGGATGCCTA TACGACCCGA CGAGGGCTGT TTATGTGGA
1441 CTTTAACAGT GAGCAGAAAG AGAGGAAACC CAAGTCCTCG GCTCATTACT ACAAGCAGAT
1501 CATACAAGAC AACGGCTTCC CTTTGAAAGA GTCCACGCCA GACATGAAGG GTCGGTTCCC
1561 CTGTGATTTC TCTTGGGGAG TCACTGAGTC TGTTCTTAAG CCCGAGTTTA CGGTCTCCTC
1621 CCCGCAGTTT ACCGATCCTC ACCTGTATGT GTGGAATGTC ACTGGCAACA GATTGCTCTA
1681 CCGAGTGGAA GGGGTAAGGC TGAAAACAAG ACCATCCCAG TGCACAGATT ATGTGAGCAT
1741 CAAAAAACGA GTTGAAATGT TGGCAAAAAT GAAAGTCACC CACTACCAGT TTGCTCTGGA
1801 CTGGACCTCT ATCCTTCCCA CTGGCAATCT GTCCAAAGTT AACAGACAAG TGTTAAGGTA
1861 CTATAGGTGT GTGGTGAGCG AAGGACTGAA GCTGGGCGTC TTCCCCATGG TGACGTTGTA
1921 CCACCCAACC CACTCCCATC TCGGCCTCCC CCTGCCACTT CTGAGCAGTG GGGGTGGCT
1981 AAACATGAAC ACAGCCAAGG CCTTCCAGGA CTACGCTGAG CTGTGCTTCC GGGAGTTGGG
2041 GGACTTGGTG AAGCTCTGGA TCACCATCAA TGAGCCTAAC AGGCTGAGTG ACATGTACAA
2101 CCGCACGAGT AATGACACCT ACCGTGCAGC CCACAACCTG ATGATCGCCC ATGCCCAGGT
2161 CTGGCACCTC TATGATAGGC AGTATAGGCC GGTCCAGCAT GGGGCTGTGT CGCTGTCCTT
2221 ACATTGCGAC TGGGCAGAAC CTGCCAACCC CTTTGTGGAT TCACACTGGA AGGCAGCCGA
2281 GCGCTTCCTC CAGTTTGAGA TCGCTGGTT TGCAGATCCG GTCTTCAAGA CTGGCGACTA
2341 TCCATCGGTT ATGAAGGAAT ACATCGCCTC CAAGAACCAG CGAGGGCTGT CTAGCTCAGT
2401 CCTGCCGCGC TTCACCGCGA AGGAGAGCAG GCTGGTGAAG GGTACCGTCG ACTTCTACGC
2461 ACTGAACCAC TTCACTACGA GGTTCGTGAT ACACAAGCAG CTGAACACCA ACCGCTCAGT
2521 TGCAGACAGG GACGTCCAGT TCCTGCAGGA CATCACCCGC CTAAGCTGCC CCAGCCGCCT
2581 GGCTGTAACA CCCTGGGGAG TGCGCAAGCT CCTTGCGTGG ATCCGGAGGA ACTACAGAGA
2641 CAGGGATATC TACATCACAG CCAATGGCAT CGATGACCTG GCTCTAGAGG ATGATCAGAT
2701 CCGAAAGTAC TACTTGGAGA AGTATGTCCA GGAGGCTCTG AAAGCATATC TCATTGACAA
2761 GGTCAAAATC AAAGGCTACT ATGCATTCAA ACTGACTGAA GAGAAATCTA AGCCTAGATT
2821 TGGATTTTTC ACCTCTGACT TCAGAGCTAA GTCCTCTGTC CAGTTTTACA GCAAGCTGAT
```

```
-continued
2881 CAGCAGCAGT GGCCTCCCCG CTGAGAACAG AAGTCCTGCG TGTGGTCAGC CTGCGGAAGA
2941 CACAGACTGC ACCATTTGCT CATTTCTCGT GGAGAAGAAA CCACTCATCT TCTTCGGTTG
3001 CTGCTTCATC TCCACTCTGG CTGTACTGCT ATCCATCACC GTTTTTCATC ATCAAAAGAG
3061 AAGAAAATTC CAGAAAGCAA GGAACTTACA AAATATACCA TTGAAGAAAG GCCACAGCAG
3121 AGTTTTCAGC TAA
```

In one embodiment, the FGFR is FGFR1c, FGFR2c, or FGFR4. In one embodiment of the present invention, the FGF receptor is FGFR1c receptor. In one particular embodiment, the FGFR1c receptor is the human FGFR1c receptor (GenBank Accession No. NP_075598, which is hereby incorporated by reference in its entirety). In another embodiment, the FGF receptor is FGFR2c receptor. In one particular embodiment, the FGFR2c receptor is the human FGFR2c receptor (GenBank Accession No. NP_000132, which is hereby incorporated by reference in its entirety). In another embodiment, the FGF receptor is FGFR4 receptor. In one particular embodiment, the FGFR4 receptor is the human FGFR4 receptor (GenBank Accession No. NP002002, which is hereby incorporated by reference in its entirety).

In one embodiment, the method of facilitating FGFR-βKlotho co-receptor complex formation is carried out in vitro. In one embodiment, the method is carried out in an adipocyte. In another embodiment, the method is carried out in a skeletal muscle cell, a pancreatic β cell, or a hepatocyte.

In one embodiment, the method of facilitating FGFR-βKlotho co-receptor complex formation is carried out in vivo. In one embodiment, the method is carried out in a mammal. In one particular embodiment, the mammal is a mouse. In one embodiment, the mouse is an ob/ob or db/db mouse.

Yet a further aspect of the present invention relates to a method of screening for agents capable of facilitating FGFR-βKlotho complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF19. The portion of the paracrine FGF is modified to decrease binding affinity for heparin and/or heparan sulfate compared to the portion without the modification. The portion of the paracrine FGF may also be modified to alter receptor-binding specificity and/or receptor-binding affinity compared to the portion without the modification. This method also involves providing a binary βKlotho-FGFR complex and providing one or more candidate agents. This method further involves combining the chimeric FGF, the binary βKlotho-FGFR complex, and the one or more candidate agents under conditions permitting the formation of a ternary complex between the chimeric FGF and the binary βKlotho-FGFR complex in the absence of the one or more candidate agents. This method also involves identifying the one or more candidate agents that decrease ternary complex formation between the chimeric FGF and the binary βKlotho-FGFR complex compared to the ternary complex formation in the absence of the one or more candidate agents as suitable for treating the disorder.

The portion of the paracrine FGF may also be modified to alter receptor-binding specificity and/or reduce receptor-binding affinity compared to the portion without the modification.

Suitable chimeric proteins for use in accordance with this aspect of the present invention are described above and throughout the present application. Suitable paracrine FGFs, as well as suitable modifications to decrease binding affinity for heparin and/or heparan sulfate, to alter receptor-binding specificity and/or receptor-binding affinity compared to the portion without the modification, are also described above.

In one embodiment, the modulation is a competitive interaction between the chimeric FGF molecule and the one or more candidate agents for binding to the binary βKlotho-FGFR complex.

In one embodiment, the FGFR is FGFR1c, FGFR2c, or FGFR4.

In one embodiment, the disorder is a selected from diabetes, obesity, and metabolic syndrome. In one embodiment, the disorder is diabetes selected from type II diabetes, gestational diabetes, or drug-induced diabetes. In one embodiment, the disorder is type I diabetes. In one embodiment, the disorder is obesity. In one embodiment, the disorder is metabolic syndrome.

In one embodiment of the screening aspects of the present invention, a plurality of compounds or agents is tested. Candidate agents may include small molecule compounds or larger molecules (e.g., proteins or fragments thereof). In one embodiment, the candidate compounds are biomolecules. In one embodiment, the biomolecules are proteins. In one embodiment, the biomolecules are peptides. In one embodiment, the candidates are peptides or peptide mimetics having similar structural features to native FGF ligand. In one embodiment, the candidate agent is a second chimeric FGF molecule. In one particular embodiment, the peptides are synthetic peptides. In one embodiment, the compounds are small organic molecules.

In one embodiment of the screening aspects of the present invention, the method is carried out using a cell-based assay. In one embodiment, the identifying is carried out using a cell-based assay.

In one embodiment of the screening aspects of the present invention, the method is carried out using a binding assay. In one embodiment, the binding assay is a direct binding assay. In one embodiment, the binding assay is a competition-binding assay. In one embodiment, the modulation stabilizes the ternary complex between the chimeric FGF molecule and the binary βKlotho-FGFR complex. In one embodiment, the stabilization is compared to the native ternary complex.

In one embodiment, the modulation is an allosteric or kinetic modulation. In one embodiment, the allosteric or kinetic modulation is compared to the native ternary complex. Such stabilization or allosteric or kinetic modulation can be measured using methods known in the art (e.g., by use of surface plasmon resonance (SPR) spectroscopy experiments as described in the Examples infra).

In one embodiment, the binding assay is carried out using surface plasmon resonance spectroscopy. In one embodiment, the identifying is carried out using a binding assay. In one embodiment, the identifying is carried out using surface plasmon resonance spectroscopy.

In one embodiment of the screening aspects of the present invention, the cell-based assay is carried out with adipocytes. In one embodiment, the cell-based assay is carried out with skeletal muscle cells. In one embodiment, the cell-based assay is carried out with pancreatic β cells. In one embodiment, the cell-based assay is carried out with hepatocytes. In one embodiment, stimulation of glucose uptake is the assay readout. In one embodiment, induction of glucose transporter 1 gene expression is the assay readout. In one embodiment, a dose-response curve is generated for the stimulation of glucose uptake by a candidate compound to determine potency and efficacy of the candidate compound. In one embodiment, a dose-response curve is generated for the induction of glucose transporter 1 gene expression by a candidate compound to determine potency and efficacy of the candidate compound. For example, if the dose-response curve is shifted to the left compared to that obtained for the chimeric FGF protein, the candidate compound has greater potency than the chimeric FGF protein and/or native FGF19. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF19.

In one embodiment of the screening aspects of the present invention, the cell-based assay is carried out with mammalian cells ectopically expressing βKlotho. In one particular embodiment, the cells are HEK293 cells. In one embodiment, activation of FGF receptor is the assay readout. In one embodiment, tyrosine phosphorylation of an FGF receptor substrate is used as readout for FGF receptor activation. In one particular embodiment, the FGF receptor substrate is FGF receptor substrate 2α. In one embodiment, activation of downstream mediators of FGF signaling is used as readout for (or an indicator of) FGF receptor activation. In one particular embodiment, the downstream mediator of FGF signaling is 44/42 mitogen-activated protein kinase. In one embodiment, the downstream mediator of FGF signaling is a transcription factor. In one particular embodiment, the transcription factor is early growth response 1. In one embodiment, a dose-response curve is generated for βKlotho-dependent activation of FGF receptor by a candidate compound to determine potency and efficacy of the candidate compound. For example, if the dose-response curve is shifted to the left compared to that obtained for the chimeric FGF protein, the candidate compound is more potent than the chimeric FGF protein and/or native FGF19. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF19.

In one embodiment of the screening aspects of the present invention, the surface plasmon resonance spectroscopy-based assay is carried out using the chimeric FGF protein as ligand coupled to a biosensor chip. In one embodiment, mixtures of βKlotho ectodomain with increasing concentrations of a candidate compound are passed over a biosensor chip containing chimeric FGF protein. In one embodiment, mixtures of the binary complex of FGFR ligand-binding domain and βKlotho ectodomain with increasing concentrations of a candidate compound are passed over a biosensor chip containing chimeric FGF protein. In one particular embodiment, the FGFR ligand-binding domain is the FGFR1c ligand-binding domain. In one embodiment, an inhibition-binding curve is plotted for a candidate compound to determine potency of the candidate compound. For example, if the inhibition-binding curve is shifted to the left compared to that obtained for the chimeric FGF protein, the candidate compound has greater potency than the chimeric FGF protein and/or native FGF19. In one embodiment, an $IC_{50}$ value is derived from the inhibition-binding curve of a candidate compound to determine potency of the candidate compound. An $IC_{50}$ value smaller than that obtained for containing chimeric FGF protein identifies a candidate compound as more potent than the chimeric FGF protein and/or native FGF19. In one embodiment, the inhibition constant $K_i$ is determined for a candidate compound to determine potency of the candidate compound. A $K_i$ value smaller than that obtained for native FGF19 identifies a candidate compound as more potent than the chimeric FGF protein and/or native FGF19.

In one embodiment of the screening aspects of the present invention, the method is carried out in vivo. In one embodiment, the method is carried out in a mammal. In one particular embodiment, the mammal is a mouse. In one embodiment, the mammal has obesity, diabetes, or a related metabolic disorder. In one embodiment, the ability of a candidate compound to potentiate the hypoglycemic effect of insulin is used as readout for FGF19-like metabolic activity. This involves fasting the mammal for a period of time prior to insulin injection and measuring fasting blood glucose levels. The mammal is then injected with insulin alone or co-injected with insulin plus a candidate compound. Blood glucose levels are measured at several time points after the injection. If a candidate compound potentiates the hypoglycemic effect of insulin to a greater degree than the chimeric FGF protein and/or native FGF19 does, the candidate compound exhibits enhanced efficacy. Likewise, if a candidate compound potentiates the hypoglycemic effect of insulin to a similar degree than the chimeric FGF protein and/or native FGF19 does but at a lower dose compared to that of the chimeric FGF protein and/or native FGF19 and/or for a longer period of time compared to the chimeric FGF protein and/or native FGF19, the candidate compound has enhanced agonistic properties. In one embodiment, the ability of a candidate compound to elicit a hypoglycemic effect in a mammal with diabetes, obesity, or a related metabolic disorder is used as readout for FGF21-like metabolic activity. This involves injecting a mammal suffering from diabetes, obesity, or a related metabolic disorder with the candidate compound. Blood glucose levels are measured before the injection and at several time points thereafter. If a candidate compound has a greater hypoglycemic effect than the chimeric FGF protein and/or native FGF21 does, the candidate compound exhibits enhanced efficacy. Likewise, if a candidate compound shows a similar hypoglycemic effect than the chimeric FGF protein and/or native FGF21 does but at a lower dose compared to that of the chimeric FGF protein and/or native FGF21 and/or for a longer period of time compared to the chimeric FGF protein and/or native FGF21, the candidate compound has enhanced agonistic properties.

EXAMPLES

Example 1

Purification of FGF, FGFR, and Klotho Proteins

Figures 5A, 5B, 5C, 5D, 5E, 5F, 5G:
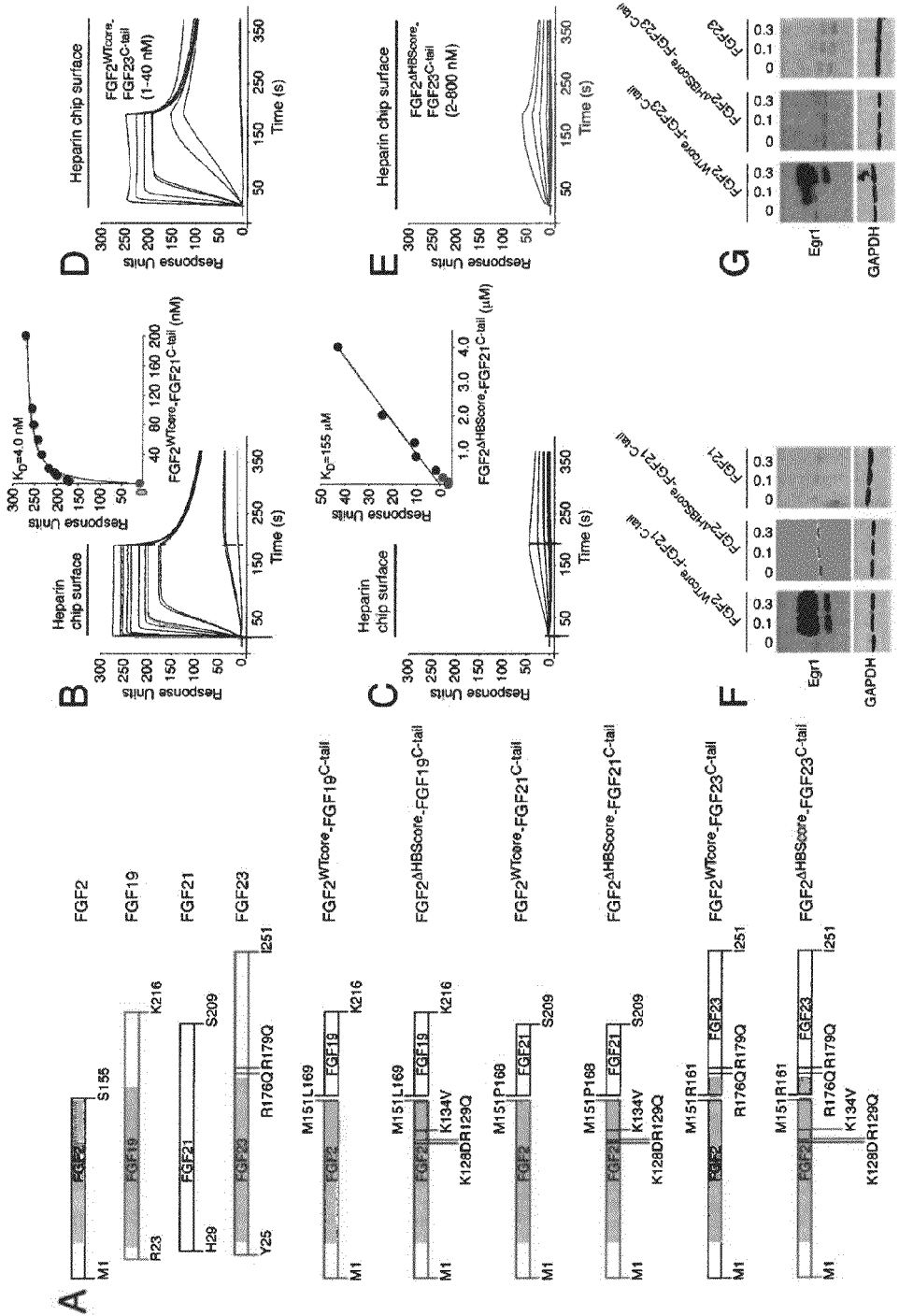
FIGS. 5A-5G show design and results relating to the conversion of FGF2 into an endocrine ligand.

The N-terminally hexahistidine-tagged, mature form of human FGF19 (SEQ ID NO: 233) (R23 to K216), human FGF21 (SEQ ID NO: 332) (H29 to S209; FIG. 5A), and human FGF23 (Y25 to I251; FIG. 5A) was refolded in vitro from bacterial inclusion bodies, and purified by published protocols (Ibrahimi et al., Hum. Mol. Genet. 13:2313-2324 (2004); Plotnikov et al., Cell 101:413-424 (2000), which is hereby incorporated by reference in its entirety). The amino acid sequence of human FGF23 (SEQ ID NO:345) (GenBank accession no. AAG09917, which is hereby incorporated by reference in its entirety) is as follows:

```
1   MLGARLRLWV  CALCSVCSMS  VLRAYPNASP  LLGSSWGGLI
    HLYTATARNS  YHLQIHKNGH
```

```
 61 VDGAPHQTIY SALMIRSEDA GFVVITGVMS RRYLCMDFRG
    NIFGSHYFDP ENCRFQHQTL

121 ENGYDVYHSP QYHFLVSLGR AKRAFLPGMN PPPYSQFLSR
    RNEIPLIHFN TPIPRRHTRS

181 AEDDSERDPL NVLKPRARMT PAPASCSQEL PSAEDNSPMA
    SDPLGVVRGG RVNTHAGGTG

241 PEGCRPFAKF I
```

Figure 6:
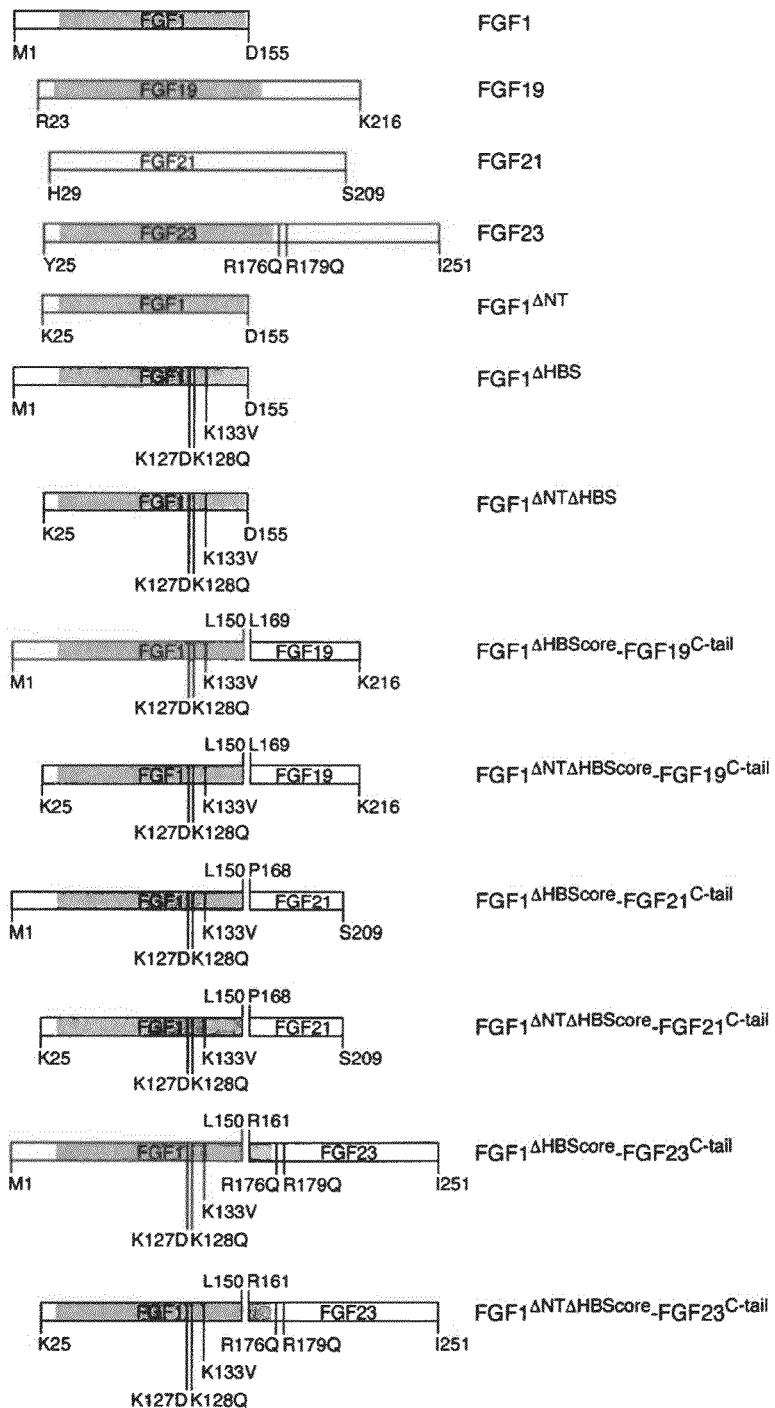
FIG. 6 is a schematic illustrating the conversion of FGF1 into an endocrine ligand. Shown are schematic drawings of human FGF1, FGF19, FGF21, FGF23, and exemplary FGF1-FGF19, FGF1-FGF21, and FGF1-FGF23 chimeras according to the present invention. Amino acid boundaries of each ligand and of each component of the chimeras are labeled with residue letter and number. The β-trefoil core domain for the known ligand crystal structures is shaded gray. HS-binding residues mutated in the FGF1 portion of chimeras are labeled with residue letter and number. Also labeled are the arginine residues of the proteolytic cleavage site in the C-terminal region of FGF23 that were mutated to glutamine in both FGF23 and the FGF1-FGF23 chimeras.

HS-binding site mutants of FGF19 (K149A) and FGF23 (R140A/R143A) were purified from bacterial inclusion bodies by similar protocols as the wild-type proteins. In order to minimize proteolysis of FGF23 wild-type and mutant proteins, arginine residues 176 and 179 of the proteolytic cleavage site $^{176}$RXXR$^{179}$ were replaced with glutamine as it occurs in the phosphate wasting disorder "autosomal dominant hypophosphatemic rickets" (ADHR) (White et al., *Nat. Genet.* 26:345-348 (2000); White et al., *Kidney Int.* 60:2079-2086 (2001), which are hereby incorporated by reference in their entirety). Human FGF1 (M1 to D155; FIG. 6), N-terminally truncated human FGF1 (K25 to D155, termed FGF1$^{\Delta NT}$; FIG. 6), human FGF2 (M1 to S155; FIG. 5A), and human FGF homologous factor 1B (FHF1B; M1 to T181) were purified by published protocols (Plotnikov et al., *Cell* 101:413-424 (2000); Olsen et al., *J. Biol. Chem.* 278:34226-34236 (2003), which are hereby incorporated by reference in their entirety).

Chimeras composed of the core domain of FGF2 (M1 to M151) and the C-terminal region of either FGF21 (P168 to S209) or FGF23 (R161 to I251) (termed FGF2$^{WTcore}$-FGF21$^{C-tail}$ and FGF2$^{WTcore}$-FGF23$^{C-tail}$, respectively; FIG. 5A) were purified by the same protocol as that for native FGF2 (Plotnikov et al., *Cell* 101:413-424 (2000), which is hereby incorporated by reference in its entirety). Analogous chimeras containing three mutations in the HS-binding site of the FGF2 core (K128D/R129Q/K134V) (termed FGF2$^{\Delta HBScore}$-FGF21$^{C-tail}$ and FGF2$^{\Delta HBScore}$-FGF23$^{C-tail}$, respectively, FIG. 5A) were purified from the soluble bacterial cell lysate fraction by ion-exchange and size-exclusion chromatographies. In order to minimize proteolysis of the chimeras containing the C-terminal sequence from R161 to I251 of FGF23, arginine residues 176 and 179 of the proteolytic cleavage site $^{176}$RXXR$^{179}$ located within this sequence were replaced with glutamine as it occurs in ADHR (White et al., *Nat. Genet.* 26:345-348 (2000); White et al., *Kidney Int.* 60:2079-2086 (2001), which are hereby incorporated by reference in their entirety). In addition, in order to prevent disulfide-mediated dimerization of FGF2 and chimeric FGF2 proteins, cysteine residues 78 and 96 were mutated to serine. An HS-binding site mutant of FGF1 (K127D/K128Q/K133V) (termed FGF1$^{\Delta HBScore}$; FIG. 6) and chimeras composed of the core domain of the HS-binding site mutant of FGF1 (M1 to L150, K127D/K128Q/K133V) and the C-terminal region of either FGF19 (L169 to K216) or FGF21 (P168 to S209) (termed FGF1$^{\Delta HBScore}$-FGF19$^{C-tail}$ and FGF1$^{\Delta HBScore}$-FGF21$^{C-tail}$, respectively; FIG. 6) were purified from the soluble bacterial cell lysate fraction by ion-exchange and size-exclusion chromatographies. The N-terminally hexahistidine-tagged C-terminal tail peptide of FGF23 (S180 to I251, termed FGF23$^{C-tail}$) was purified by a published protocol (Goetz et al., *Proc. Nat'l. Acad. Sci. U.S.A.* 107:407-412 (2010), which is hereby incorporated by reference in its entirety). The ligand-binding domain of human FGFR1c (D142 to R365) was refolded in vitro from bacterial inclusion bodies, and purified by published protocols (Ibrahimi et al., *Hum. Mol. Genet.* 13:2313-2324 (2004); Plotnikov et al., *Cell* 101:413-424 (2000), which are hereby incorporated by reference in their entirety). The ectodomain of murine αKlotho (A35 to K982) and the ectodomain of murine βKlotho (F53 to L995) were expressed in HEK293 cells as fusion proteins with a C-terminal FLAG tag (Kurosu et al., *J. Biol. Chem.* 281:6120-6123 (2006); Kurosu et al., *Science* 309:1829-1833 (2005), which are hereby incorporated by reference in their entirety). The binary complex of FGFR1c ligand-binding domain with αKlotho ectodomain (referred to as αKlotho-FGFR1c complex) was prepared by a published protocol (Goetz et al., *Proc. Nat'l. Acad. Sci. U.S.A.* 107:407-412 (2010), which is hereby incorporated by reference in its entirety). The binary complex of FGFR1c ligand-binding domain with βKlotho ectodomain (referred to as βKlotho-FGFR1c complex) was prepared in the same fashion as the αKlotho-FGFR1c complex.

Example 2

Analysis of FGF-Heparin and FGF-FGFR-α/βKlotho Interactions by Surface Plasmon Resonance Spectroscopy Surface plasmon resonance (SPR) experiments were performed on a Biacore 2000 instrument (Biacore AB), and the interactions were studied at 25° C. in HBS-EP buffer (10 mM HEPES-NaOH, pH 7.4, 150 mM NaCl, 3 mM EDTA, 0.005% (v/v) polysorbate 20). To study endocrine FGF-heparin interactions, a heparin chip was prepared by immobilizing biotinylated heparin (Sigma-Aldrich) on flow channels of a research-grade streptavidin chip (Biacore AB). The coupling density was ~5 fmol mm$^{-2}$ of flow channel. To measure binding of chimeric FGF2 proteins to heparin, biotinylated heparin was coupled to a streptavidin chip at an approximately 4-fold lower density as judged based on the binding responses obtained for FGF1. To study FGF-FGFR-α/βKlotho interactions, FGF chips were prepared by covalent coupling of FGF proteins through their free amino groups on flow channels of research grade CM5 chips (Biacore AB). Proteins were injected over a chip at a flow rate of 50 μl min$^{-1}$, and at the end of each protein injection (180 and 300 s, respectively), HBS-EP buffer (50 μl min$^{-1}$) was flowed over the chip to monitor dissociation for 180 or 240 s. The heparin chip surface was regenerated by injecting 50 μl of 2.0 M NaCl in 10 mM sodium acetate, pH 4.5. For FGF chips, regeneration was achieved by injecting 2.0 M NaCl in 10 mM sodium/potassium phosphate, pH 6.5. To control for nonspecific binding in experiments where an FGF ligand was immobilized on the chip, FHF1B, which shares structural similarity with FGFs but does not exhibit any FGFR binding (Olsen et al., *J. Biol. Chem.* 278:34226-34236 (2003), which is hereby incorporated by reference in its entirety), was coupled to the control flow channel of the chip (~15-30 fmol mm$^{-2}$). In experiments where heparin was immobilized on the chip, the control flow channel was left blank. The data were processed with BiaEvaluation software (Biacore AB). For each protein injection over the heparin chip, the nonspecific responses from the control flow channel were subtracted from the responses recorded for the heparin flow channel. Similarly, for each protein injection over a FGF chip, the nonspecific responses from the FHF1B control flow channel were subtracted from the responses recorded for the FGF flow channel. Where possible, equilibrium dissociation constants ($K_D$s) were calculated from fitted saturation binding curves. Fitted binding curves were judged to be accurate based on the distribution of the residuals (even and near zero) and $\chi^2$ (<10% of $R_{max}$).

To examine whether the K149A mutation abrogates residual heparin binding of FGF19, increasing concentrations of wild-type FGF19 were passed over a heparin chip. Thereafter, the FGF19$^{K149A}$ mutant was injected over the heparin chip at the highest concentration tested for the wild-type ligand. The effect of the R140A/R143A double mutation in the HS-binding site of FGF23 on residual heparin binding of FGF23 was examined in the same fashion as was the effect of the HS-binding site mutation in FGF19.

To verify that the K128D/R129Q/K134V triple mutation in the HS-binding site of the FGF2 core domain diminishes heparin-binding affinity of the FGF2 core, increasing concentrations of FGF2$^{\Delta HBScore}$-FGF21$^{C\text{-}tail}$ and FGF2$^{\Delta HBScore}$-FGF23$^{C\text{-}tail}$ were passed over a heparin chip. As a control, binding of FGF2$^{WTcore}$-FGF21$^{C\text{-}tail}$ and FGF2$^{WTcore}$-FGF23$^{C\text{-}tail}$ to heparin was studied.

To examine whether the FGF2$^{\Delta HBScore}$-FGF23$^{C\text{-}tail}$ chimera can compete with FGF23 for binding to the αKlotho-FGFR1c complex, FGF23 was immobilized on a chip (~16 fmol mm$^{-2}$ of flow channel). Increasing concentrations of FGF2$^{\Delta HBScore}$-FGF23$^{C\text{-}tail}$ were mixed with a fixed concentration of αKlotho-FGFR1c complex in HBS-EP buffer, and the mixtures were injected over the FGF23 chip. As controls, the binding competition was carried out with FGF23 or FGF2 as the competitor in solution. As an additional specificity control, competition of the FGF2$^{\Delta HBScore}$-FGF23$^{C\text{-}tail}$ chimera with FGF21 for binding to the αKlotho-FGFR1c complex was studied. αKlotho-FGFR1c complex was mixed with FGF2$^{\Delta HBScore}$-FGF23$^{C\text{-}tail}$ or FGF23 at a molar ratio of 1:10, and the mixture was injected over a chip containing immobilized FGF21 (~12 fmol mm$^{-2}$ of flow channel).

To test whether the FGF2$^{\Delta HBScore}$-FGF21$^{C\text{-}tail}$ chimera can compete with FGF21 for binding to the βKlotho-FGFR1c complex, increasing concentrations of FGF2$^{\Delta HBScore}$-FGF21$^{C\text{-}tail}$ were mixed with a fixed concentration of βKlotho-FGFR1c complex in HBS-EP buffer, and the mixtures were passed over a chip containing immobilized FGF21 (~19 fmol mm$^{-2}$ of flow channel). As controls, the binding competition was carried out with FGF21 or FGF2 as the competitor in solution. As an additional specificity control, competition of the FGF2$^{\Delta HBScore}$-FGF21$^{C\text{-}tail}$ chimera with FGF23 for binding to the αKlotho-FGFR1c complex was studied. αKlotho-FGFR1c complex was mixed with FGF2$^{\Delta HBScore}$-FGF21$^{C\text{-}tail}$ or FGF21 at a molar ratio of 1:10, and the mixture was injected over a chip containing immobilized FGF23 (~12 fmol mm$^{-2}$ of flow channel).

To measure binding of FGFR1c to each of the three endocrine FGFs, increasing concentrations of FGFR1c ligand-binding domain were injected over a chip containing immobilized FGF19, FGF21, and FGF23 (~30 fmol mm$^{-2}$ of flow channel). As a control, binding of FGFR1c to FGF2 immobilized on a chip was studied. As additional controls, binding of the αKlotho-FGFR1c complex to FGF23 and binding of FGFR1c to the C-terminal tail peptide of FGF23 was measured.

Example 3

Analysis of Phosphorylation of FRS2α and 44/42 MAP Kinase in Hepatoma and Epithelial Cell Lines To examine whether the FGF19$^{K149A}$ and FGF23$^{R140A/R143A}$ mutants can activate FGFR in a α/βKlotho-dependent fashion, induction of tyrosine phosphorylation of FGFR substrate 2α (FRS2α) and downstream activation of MAP kinase cascade was used as readout for FGFR activation. Subconfluent cells of the H4IIE rat hepatoma cell line, which endogenously expresses βKlotho (Kurosu et al., *J. Biol. Chem.* 282:26687-26695 (2007), which is hereby incorporated by reference in its entirety), were serum starved for 16 h and then stimulated for 10 min with the FGF19$^{K149A}$ mutant or wild-type FGF19 (0.2 ng ml$^{-1}$ to 2.0 μg ml$^{-1}$). Similarly, subconfluent cells of a HEK293 cell line ectopically expressing the transmembrane isoform of murine αKlotho (Kurosu et al., *J. Biol. Chem.* 281:6120-6123 (2006), which is hereby incorporated by reference in its entirety) were treated with the FGF23$^{R140A/R143A}$ mutant or wild-type FGF23 (0.1 to 100 ng ml$^{-1}$). After stimulation, the cells were lysed (Kurosu et al., *Science* 309:1829-1833 (2005), which is hereby incorporated by reference in its entirety), and cellular proteins were resolved on SDS-polyacrylamide gels and transferred to nitrocellulose membranes. The protein blots were probed with antibodies to phosphorylated FRS2α, phosphorylated 44/42 MAP kinase, total (phosphorylated and nonphosphorylated) 44/42 MAP kinase, and αKlotho. Except for the anti-αKlotho antibody (KM2119) (Kato et al., *Biochem. Biophys. Res. Commun.* 267:597-602 (2000), which is hereby incorporated by reference in its entirety), all antibodies were from Cell Signaling Technology.

Example 4

Analysis of Egr1 Protein Expression in an Epithelial Cell Line

To examine whether the FGF2$^{\Delta HBScore}$-FGF21$^{C\text{-}tail}$ and FGF2$^{\Delta HBScore}$-FGF23$^{C\text{-}tail}$ chimeras can activate FGFR in a HS-dependent fashion, induction of protein expression of the transcription factor early growth response 1 (Egr1), a known downstream mediator of FGF signaling, was used as readout for FGFR activation. HEK293 cells were serum starved overnight and then stimulated for 90 min with FGF2$^{\Delta HBScore}$-FGF21$^{C\text{-}tail}$ or FGF2$^{\Delta HBScore}$-FGF23$^{C\text{-}tail}$ (0.1 and 0.3 nM). Cell stimulation with FGF2$^{WTcore}$-FGF21$^{C\text{-}tail}$, FGF2$^{WTcore}$-FGF23$^{C\text{-}tail}$, FGF21, and FGF23 served as controls. To test whether the FGF2$^{\Delta HBScore}$-FGF21$^{C\text{-}tail}$ chimera can activate FGFR in a βKlotho-dependent fashion, HEK293 cells transfected with murine βKlotho were serum starved overnight and then stimulated for 90 min with FGF2$^{\Delta HBScore}$-FGF21$^{C\text{-}tail}$ or FGF21 (3 to 300 ng ml$^{-1}$). After stimulation, the cells were lysed (Kurosu et al., *Science* 309:1829-1833 (2005), which is hereby incorporated by reference in its entirety), and cellular proteins were resolved on SDS-polyacrylamide gels and transferred to nitrocellulose membranes. The protein blots were probed with antibodies to Egr1 and glyceraldehyde 3-phosphate dehydrogenase (GAPDH). The anti-Egr1 antibody was from Cell Signaling Technology and the anti-GAPDH antibody was from Abcam.

Example 5

Analysis of CYP7A1 and CYP8B1 mRNA Expression in Murine Liver Tissue

To examine the metabolic activity of the FGF19$^{K149A}$ mutant in vivo, 6- to 8-week old C57BL/6 mice were fasted overnight and then given intraperitoneally a single dose (1 mg kg body weight$^{-1}$) of FGF19$^{K149A}$ or FGF19 as a control. 6 h after the injection, the mice were sacrificed, and liver tissue was excised and frozen. Total RNA was isolated from liver tissue, and mRNA levels of cholesterol 7α-hydroxylase (CYP7A1) and sterol 12α-hydroxylase (CYP8B1) were measured using quantitative real time RT-PCR as described previously (Inagaki et al., *Cell Metab.* 2:217-225 (2005); Kim et al., *J. Lipid Res.* 48:2664-2672 (2007), which are hereby incorporated by reference in their entirety). The Institutional Animal Care and Use Committee at the University of Texas Southwestern Medical Center at Dallas had approved the experiments.

Example 6

Measurement of Serum Phosphate in Mice

The metabolic activity of the FGF23$^{R140A/R143A}$ mutant was examined both in normal mice and in Fgf23 knockout mice. 4- to 5-week old C57BL/6 mice were given intraperitoneally a single dose (0.29 mg kg body weight$^{-1}$) of FGF23$^{R140A/R143A}$ or FGF23 as a control. Before the injection and 8 h after the injection, blood was drawn from the cheek pouch and spun at 3,000×g for 10 min to obtain serum. Phosphate concentration in serum was measured using the Phosphorus Liqui-UV Test (Stanbio Laboratory). 6- to 8-week old Fgf23 knockout mice (Sitara et al., *Matrix Biol.* 23:421-432 (2004), which is hereby incorporated by reference in its entirety) (56) were given two injections of FGF23$^{R140A/R143A}$ or FGF23 at 8 h intervals (0.71 mg kg body weight$^{-1}$ each), and blood samples were collected for phosphate analysis before the first injection and 8 h after the second injection.

To test whether the FGF2$^{\Delta HBScore}$-FGF23$^{C-tail}$ chimera exhibits FGF23-like metabolic activity, 5- to 6-week old C57BL/6 mice were given a single injection of FGF2$^{\Delta HBScore}$-FGF23$^{C-tail}$ (0.21 mg kg body weight$^{-1}$). As controls, mice were injected with FGF2$^{WTcore-FGF}$23$^{C-tail}$ or FGF23. Before the injection and 8 h after the injection, blood samples were collected for measurement of serum phosphate. To confirm that αKlotho is required for the metabolic activity of the FGF2$^{\Delta HBScore}$-FGF23$^{C-tail}$ chimera, 7- to 8-week old αKlotho knockout mice (Lexicon Genetics) were injected once with FGF2$^{\Delta HBScore}$-FGF23$^{C-tail}$ or FGF23 as a control (0.51 mg kg body weight$^{-1}$). Before the injection and 8 h after the injection, blood samples were collected for phosphate analysis. The Harvard University Animal Care and Research committee board had approved all the experiments.

Example 7

Analysis of CYP27B1 mRNA Expression in Murine Renal Tissue

The ability of the FGF2$^{\Delta HBScore}$-FGF23$^{C-tail}$ chimera to reduce renal expression of 25-hydroxyvitamin D$_3$ 1α-hydroxylase (CYP27B1) was used as another readout for FGF23-like metabolic activity. C57BL/6 mice injected with FGF2$^{\Delta HBScore}$-FGF23$^{C-tail}$, FGF2$^{WTcore}$-FGF23$^{C-tail}$, or FGF23 were sacrificed 8 h after the protein injection, and renal tissue was excised and frozen. CYP27B1 mRNA levels in total renal tissue RNA were measured using real time quantitative PCR as described previously (Nakatani et al., *FASEB J.* 23:3702-3711 (2009); Ohnishi et al., *Kidney Int.* 75:1166-1172 (2009), which are hereby incorporated by reference in their entirety). The Harvard University Animal Care and Research committee board had approved the experiments.

Example 8

Insulin Tolerance Test in Mice

The ability of the FGF2$^{\Delta HBScore}$-FGF21$^{C-tail}$ chimera to potentiate the hypoglycemic effect of insulin was used as readout for FGF21-like metabolic activity (Ohnishi et al., *FASEB J.* 25:2031-2039 (2011), which is hereby incorporated by reference in its entirety). 8- to 12-week old C57BL/6 mice were kept on normal chow. On the day of the insulin tolerance test, mice were fasted for 4 h and then bled from the cheek pouch for measuring fasting blood glucose levels. Thereafter, mice were administered intraperitoneally insulin (0.5 units kg body weight$^{-1}$) alone or insulin (0.5 units·kg body weight$^{-1}$) plus FGF2$^{\Delta HBScore}$-FGF21$^{C-tail}$ chimera (0.3 mg kg body weight$^{-1}$). As a control, mice were co-injected with insulin plus FGF21. At the indicated time points after the injection (FIG. 7G), blood was drawn from the tail vein. Glucose concentrations in the blood samples were determined using Bayer Contour® blood glucose test strips (Bayer Corp.). The Harvard University Animal Care and Research committee board had approved the experiments.

Example 9

Analysis of Blood Glucose in ob/ob Mice ob/ob mice were injected subcutaneously with FGF1$^{\Delta NT}$, FGF1$^{\Delta HBS}$, or FGF1$^{\Delta HBScore}$-FGF21$^{C-tail}$ chimera. Injection of native FGF1 or native FGF21 served as controls. A single bolus of 0.5 mg of protein per kg of body weight was injected. This dose was chosen on the basis that maximal efficacy of the hypoglycemic effect of native FGF1 is seen at this dose. Before the protein injection and at the indicated time points after the injection (FIGS. 9A-9C), blood glucose concentrations were measured using an OneTouch Ultra glucometer (Lifescan). The Institutional Animal Care and Use Committee at the Salk Institute for Biological Sciences at La Jolla had approved the experiments.

Example 10

Statistical Analysis

Data are expressed as mean±SEM. A Student's t test or analysis of variance (ANOVA) was used as appropriate to make statistical comparisons. A value of P<0.05 was considered significant.

Example 11

HS is Dispensable for the Metabolic Activity of FGF19 and FGF23

In order to engineer endocrine FGFs devoid of HS binding, the FGF19 crystal structure (PDB ID: 2P23; (Goetz et al., *Mol. Cell Biol.* 27:3417-3428 (2007), which is hereby incorporated by reference in its entirety) was compared with that of FGF2 bound to a heparin hexasaccharide (PDB ID: 1FQ9; (Schlessinger et al., *Mol. Cell* 6:743-750 (2000), which is hereby incorporated by reference in its entirety)). This analysis shows that solvent-exposed residues K149, Q150, Q152, and R157 of FGF19 lie at the corresponding HS-binding site of this ligand, and hence could account for the residual HS binding of FGF19 (FIGS. 1A, 1B, and 2). Likewise, comparative analysis of the FGF23 crystal structure (PDB ID: 2P39; (Goetz et al., *Mol. Cell Biol.* 27:3417-3428 (2007), which is hereby incorporated by reference in its entirety)) with that of heparin-bound FGF2 (PDB ID: 1FQ9; (Schlessinger et al., *Mol. Cell* 6:743-750 (2000), which is hereby incorporated by reference in its entirety)) points to R48, N49, R140, and R143 as candidates mediating the residual HS binding of this ligand (FIGS. 1A, 1C, and 2). In agreement with the structural predictions, replacement of K149 alone in FGF19 with alanine and combined substitution of R140 and R143 in FGF23 for alanine were sufficient to abolish residual HS binding of these ligands (FIGS. 3B-3E).

Figures 4A, 4B, 4C, 4D:
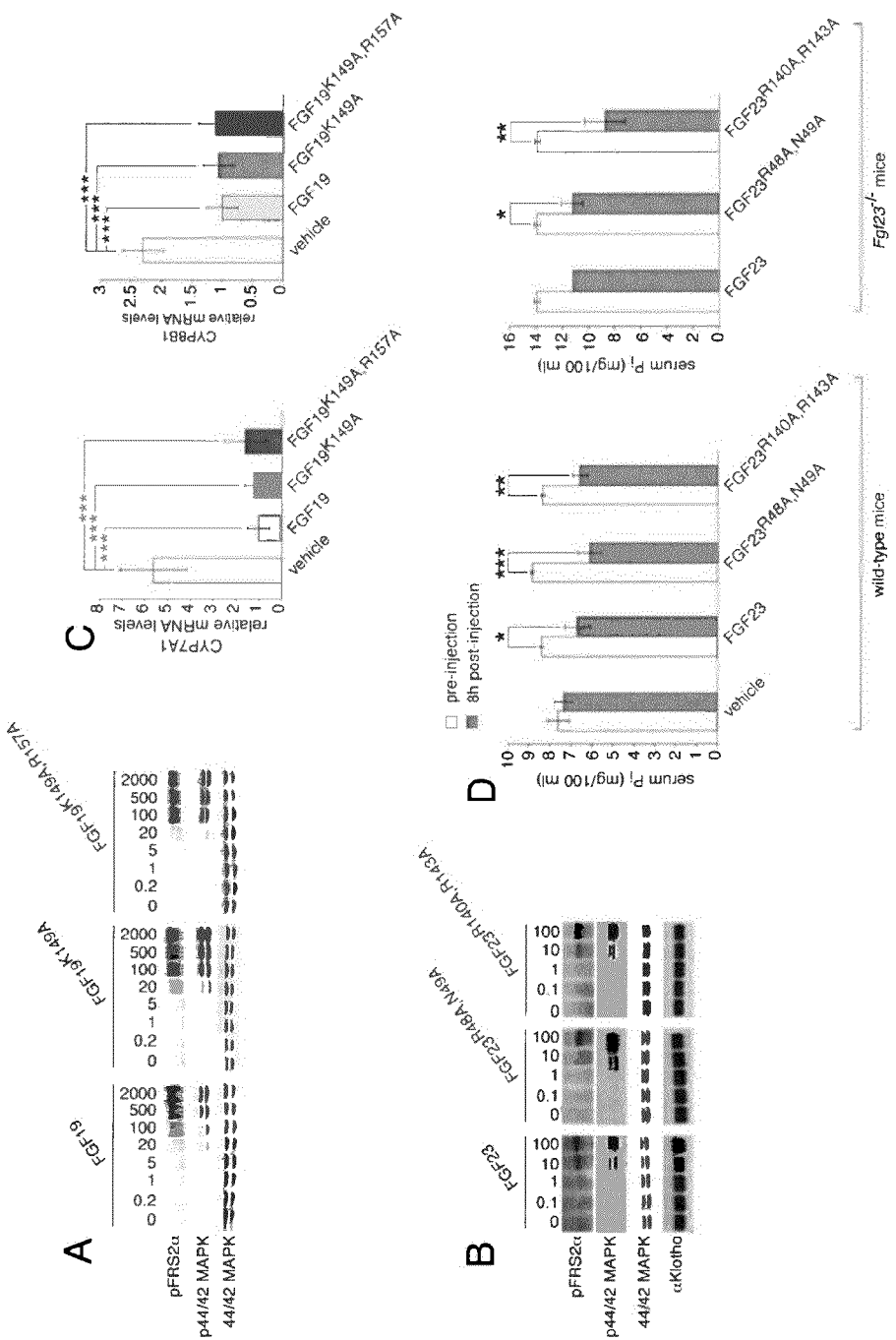
FIGS. 4A-4D show results demonstrating that HS is dispensable for the metabolic activity of FGF19 and FGF23.

To test the impact of knocking out residual HS binding of FGF19 on the signaling by this ligand, H4IIE hepatoma cells were stimulated with the FGF19$^{K149A}$ mutant or wild-type FGF19. H4IIE cells endogenously express FGFR4 and βKlotho (Kurosu et al., *J. Biol. Chem.* 282:26687-26695 (2007), which is hereby incorporated by reference in its entirety), the cognate receptor and co-receptor, respectively, for FGF19. The FGF19$^{K149A}$ mutant was as effective as wild-type FGF19 in inducing tyrosine phosphorylation of FRS2α and downstream activation of MAP kinase cascade (FIG. 4A). These data show that elimination of residual HS binding has no impact on the ability of FGF19 to signal in cultured cells. To test whether the same holds true for FGF23 signaling, HEK293 cells, which naturally express two of the three cognate receptors of FGF23, namely FGFR1c and FGFR3c (Kurosu et al., *J. Biol. Chem.* 281:6120-6123 (2006), which is hereby incorporated by reference in its entirety) were transfected with the transmembrane isoform of αKlotho, the co-receptor of FGF23. These cells were treated with the FGF23$^{R140A/R143A}$ double mutant or wild-type FGF23. The FGF23$^{R140A/R143A}$ mutant had the same capacity as wild-type FGF23 in inducing phosphorylation of FRS2α and downstream activation of MAP kinase cascade (FIG. 4B). These data show that similar to FGF19, FGF23 does not need to bind HS in order to activate FGFR in cultured cells.

To substantiate the findings in cells, the metabolic activity of wild-type and mutated ligands in vivo were compared. Mice were injected with the FGF19$^{K149A}$ mutant or wild-type FGF19 and liver gene expression of CYP7A1 and CYP8B1, which are key enzymes in the major bile acid biosynthetic pathway (Russell, D. W., *Annu. Rev. Biochem.* 72:137-174 (2003), which is hereby incorporated by reference in its entirety), was analyzed. Like wild-type FGF19, the FGF19$^{K149A}$ mutant markedly decreased CYP7A1 and CYP8B1 mRNA levels (FIG. 4C), demonstrating that knockout of residual HS binding does not affect the metabolic activity of FGF19. To examine whether residual HS binding is also dispensable for the metabolic activity of FGF23, mice were injected with the FGF23$^{R140A/R143A}$ mutant or wild-type FGF23 and serum phosphate concentrations were measured. The FGF23$^{R140A/R143A}$ mutant reduced serum phosphate as effectively as wild-type FGF23 (FIG. 4D). Moreover, when injected into Fgf23 knockout mice, the FGF23$^{R140A/R143A}$ mutant exhibited as much of phosphate-lowering activity as wild-type FGF23 (FIG. 4D). These data show that, as in the case of FGF19, abolishment of residual HS binding does not impact the metabolic activity of FGF23 leading to the conclusion that HS is not a component of the endocrine FGF signal transduction unit (FIG. 1D).

Example 12

Conversion of a Paracrine FGF into an Endocrine Ligand Confirms that HS is Dispensable for the Metabolic Activity of Endocrine FGFs If HS is dispensable for the metabolic activity of endocrine FGFs, then it should be feasible to convert a paracrine FGF into an endocrine FGF by eliminating HS-binding affinity of the paracrine FGF and substituting its C-terminal tail for that of an endocrine FGF containing the Klotho co-receptor binding site. Reducing HS-binding affinity will allow the ligand to freely diffuse and enter the blood circulation while attaching the C-terminal tail of an endocrine FGF will home the ligand into its target tissues. FGF2, a prototypical paracrine FGF, was chosen for conversion into FGF23-like and FGF21-like ligands, respectively. FGF2 was selected as paracrine ligand for this protein engineering exercise because it preferentially binds to the "c" isoform of FGFR1, the principal receptor mediating the metabolic activity of FGF23 (Gattineni et al., *Am. J. Physiol. Renal Physiol.* 297:F282-291 (2009); Liu et al., *J. Am. Soc. Nephrol.* 19:2342-2350 (2008), which are hereby incorporated by reference in their entirety) and FGF21 (Kurosu et al., *J. Biol. Chem.* 282:26687-26695 (2007), which is hereby incorporated by reference in its entirety), respectively. In the crystal structure of heparin-bound FGF2 (PDB ID: 1FQ9; (Schlessinger et al., *Mol. Cell* 6:743-750 (2000), which is hereby incorporated by reference in its entirety)), K128, R129, and K134 mediate the majority of hydrogen bonds with heparin and hence mutation of these residues was predicted to cause a major reduction in HS-binding affinity of FGF2 (FIGS. 1A, 2, and 5A). Accordingly, these three residues were mutated and then the short C-terminal tail of the mutated FGF2 was replaced with the C-terminal tail of FGF23 (R161 to I251) or the C-terminal tail of FGF21 (P168 to S209) (FIG. 5A). The resulting chimeras were termed FGF2$^{\Delta HBScore}$-FGF23$^{C-tail}$ and FGF2$^{\Delta HBScore}$-FGF21$^{C-tail}$ (FIG. 5A). To demonstrate that reduction in HS-binding affinity is required for converting FGF2 into an endocrine ligand, two control chimeras were made in which the HS-binding site of the FGF2 core was left intact (FGF2$^{WTcore}$-FGF23$^{C-tail}$ and FGF2$^{WTcore}$-FGF21$^{C-tail}$; FIG. 5A).

Consistent with the structural prediction, FGF2$^{\Delta HBScore}$-FGF23$^{C-tail}$ and FGF2$^{\Delta HBScore}$-FGF21$^{C-tail}$ exhibited poor binding affinity for HS compared to the corresponding control chimeras with intact HS-binding site (FIGS. 5B-5E). Since HS is an obligatory cofactor in paracrine FGF signaling, the FGF2$^{\Delta HBScore}$-FGF23$^{C-tail}$ and FGF2$^{\Delta HBScore}$-FGF21$^{C-tail}$ chimeras were predicted to lose the ability to activate FGFR1c in an HS-dependent fashion. To test this, HEK293 cells, which endogenously express FGFR1c, were stimulated with FGF2$^{\Delta HBScore}$-FGF2$^{C-tail}$ or FGF2$^{WTcore}$-FGF23$^{C-tail}$. Induction of protein expression of the transcription factor Egr1, a known downstream mediator of FGF signaling, was used as readout for FGFR activation. As shown in FIG. 5G, the FGF2$^{\Delta HBScore}$-FGF23$^{C-tail}$ chimera, like native FGF23, was ineffective in inducing Egr1 expression at concentrations at which the FGF2$^{WTcore}$-FGF23$^{C-tail}$ chimera elicited a near maximal effect. The same observations were made for the FGF2$^{\Delta HBScore}$-FGF21$^{C-tail}$ chimera (FIG. 5F). These data show that, similar to native FGF23 and FGF21, the FGF2$^{\Delta HBScore}$-FGF23$^{C-tail}$ and FGF2$^{\Delta HBScore}$-FGF21$^{C-tail}$ chimeras lost the ability to activate FGFR in an HS-dependent, paracrine fashion.

Figures 7A, 7B, 7C, 7D, 7E, 7F, 7G:
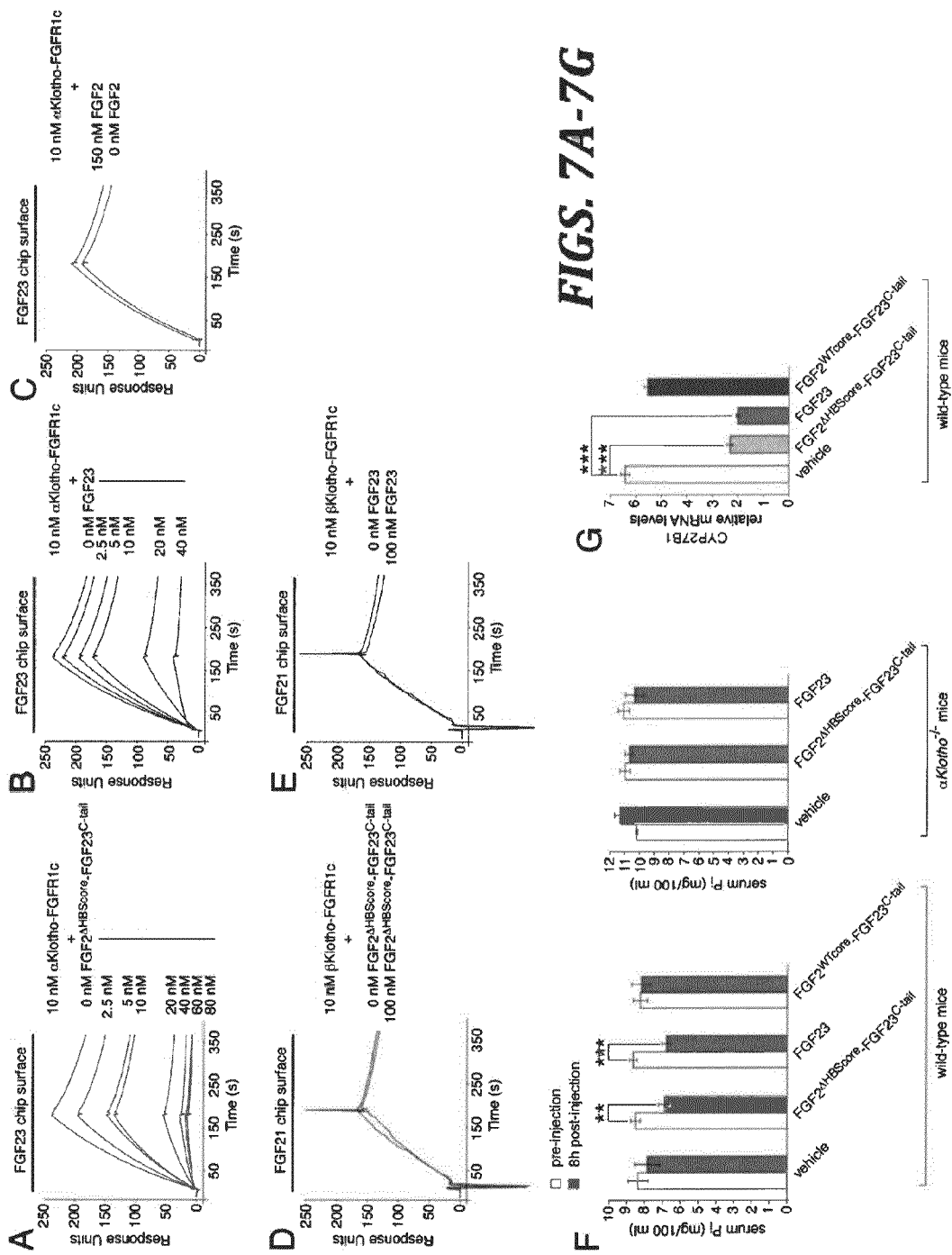
FIGS. 7A-7G show results demonstrating that the FGF2$^{\Delta HBScore}$-FGF23$^{C-tail}$ chimera exhibits FGF23-like activity.
Figures 8A, 8B, 8C, 8D, 8E, 8F, 8G:
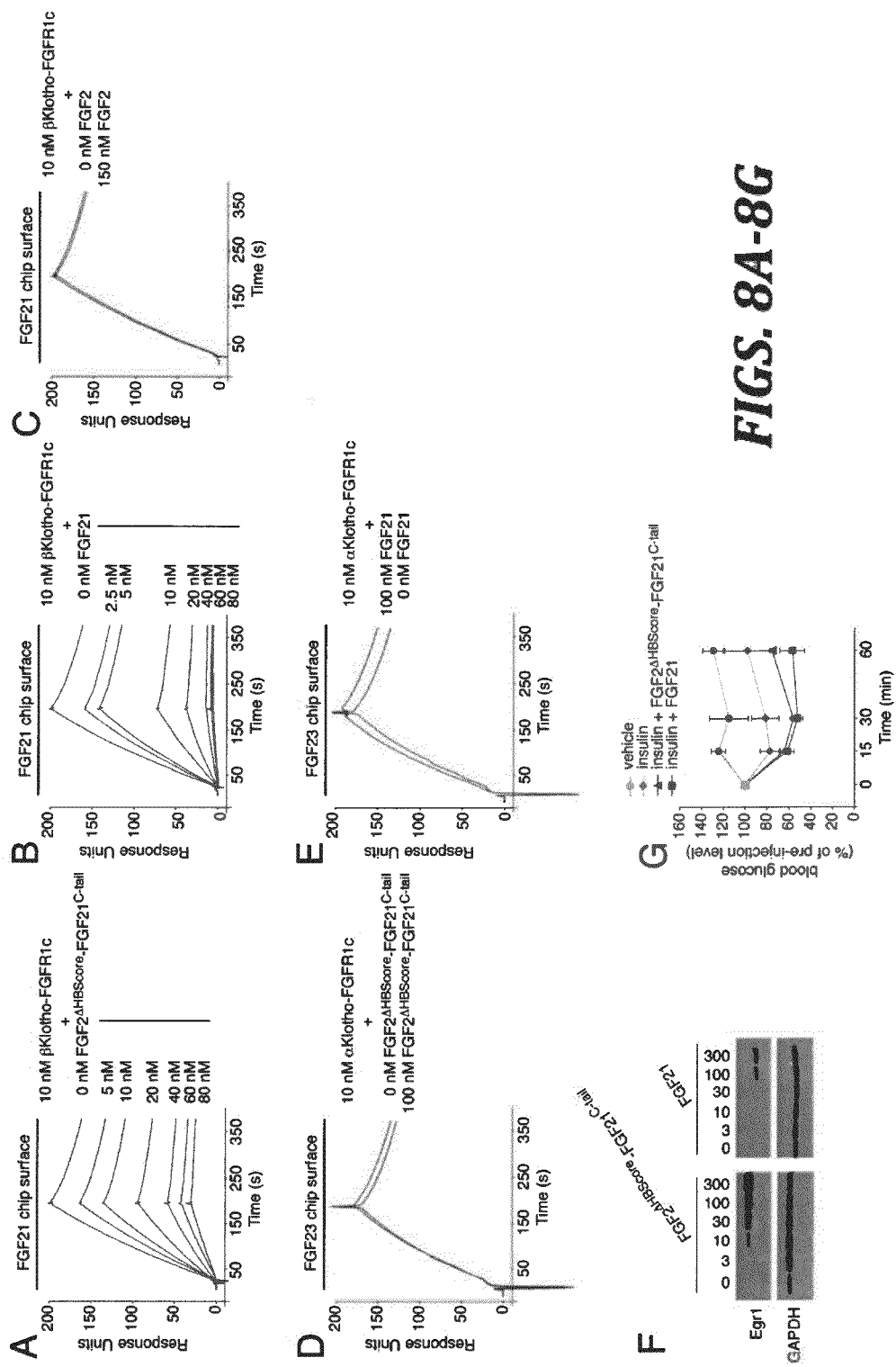
FIGS. 8A-8G show results demonstrating that the FGF2$^{\Delta HBScore}$-FGF21$^{C-tail}$ chimera exhibits FGF21-like activity.

To determine whether the FGF2$^{\Delta HBScore}$-FGF2$^{C-tail}$ and FGF2$^{\Delta HBScore}$-FGF21$^{C-tail}$ chimeras gained the ability to signal in a Klotho co-receptor-dependent, endocrine fashion, it was first analyzed whether these chimeras can form ternary complexes with FGFR1c and Klotho co-receptor. To this end, a SPR-based binding competition assay was employed. FGF23 was immobilized onto a SPR biosensor chip, and mixtures of a fixed concentration of binary αKlotho-FGFR1c complex with increasing concentrations of FGF2$^{\Delta HBScore}$-FGF23$^{C-tail}$ chimera were passed over the chip. FGF2$^{\Delta HBScore}$-FGF23$^{C-tail}$ competed, in a dose-dependent fashion, with immobilized FGF23 for binding to the αKlotho-FGFR1c complex (FIG. 7A), demonstrating that the chimera, like native FGF23 (FIG. 7B), is able to form a ternary complex with FGFR1c and αKlotho. To test whether the FGF2$^{\Delta HBScore}$-FGF21$^{C\text{-}tail}$ chimera can likewise form a ternary complex with FGFR1c and βKlotho, FGF21 was coupled to a SPR biosensor chip, and mixtures of the binary βKlotho-FGFR1c complex with FGF2$^{\Delta HBScore}$-FGF21$^{C\text{-}tail}$ were passed over the chip. FGF2$^{\Delta HBScore}$-FGF21$^{C\text{-}tail}$ effectively competed with immobilized FGF21 for binding to the βKlotho-FGFR1c complex (FIG. 8A), demonstrating that the chimera, like native FGF21 (FIG. 8B), is capable of binding to the binary complex of FGFR1c and βKlotho. Notably, native FGF2 failed to compete with FGF23 for binding to the αKlotho-FGFR1c complex (FIG. 7C), and with FGF21 for binding to the βKlotho-FGFR1c complex (FIG. 8C) since it lacks the Klotho co-receptor binding domain. To further confirm the binding specificity of the FGF2$^{\Delta HBScore}$-FGF23$^{C\text{-}tail}$ chimera for the αKlotho-FGFR1c complex, FGF2$^{\Delta HBScore}$-FGF23$^{C\text{-}tail}$ and βKlotho-FGFR1c complex were mixed at a molar ratio of 10:1, and the mixture was injected over a chip containing immobilized FGF21. FGF2$^{\Delta HBScore}$-FGF23$^{C\text{-}tail}$, like native FGF23, failed to compete with FGF21 for binding to the βKlotho-FGFR1c complex (FIGS. 7D and 7E). Similarly, the FGF2$^{\Delta HBScore}$-FGF21$^{C\text{-}tail}$ chimera, like native FGF21, failed to compete with FGF23 for binding to the αKlotho-FGFR1c complex (FIGS. 8D and 8E). For the FGF2$^{\Delta HBScore}$-FGF21$^{C\text{-}tail}$ chimera, we investigated whether it is able to activate FGFR1c in a βKlotho-dependent fashion in cells. HEK293 cells were transfected with βKlotho and then stimulated with FGF2$^{\Delta HBScore}$-FGF21$^{C\text{-}tail}$ or FGF21. Similar to native FGF21, the FGF2$^{\Delta HBScore}$-FGF21$^{C\text{-}tail}$ chimera induced Egr1 protein expression in HEK293-βKlotho cells (FIG. 8F), indicating that the chimera is capable of activating FGFR1c in the presence of βKlotho.

To provide definite proof for the ligand conversion, the metabolic activity of the chimeras in vivo was tested. Specifically, the ability of the FGF2$^{\Delta HBScore}$-FGF23$^{C\text{-}tail}$ chimera to lower serum phosphate and to reduce renal gene expression of CYP27B1, which catalyzes the conversion of vitamin D into its bioactive form, was examined. Mice were injected with FGF2$^{\Delta HBScore}$-FGF23$^{C\text{-}tail}$ or as controls, FGF23 or FGF2$^{WTcore}$-FGF23$^{C\text{-}tail}$, and serum phosphate concentrations and renal CYP27B1 mRNA levels were measured. Similar to native FGF23, the FGF2$^{\Delta HBScore}$-FGF23$^{C\text{-}tail}$ chimera caused a decrease in serum phosphate in wild-type mice (FIG. 7F). The chimera also induced a marked decrease in CYP27B1 mRNA levels, just like the native FGF23 ligand (FIG. 7G). These data show that the FGF2$^{\Delta HBScore}$-FGF23$^{C\text{-}tail}$ chimera acts as an FGF23-like hormone. Importantly, the FGF2$^{WTcore}$-FGF23$^{C\text{-}tail}$ chimera failed to decrease serum phosphate or CYP27B1 mRNA levels (FIGS. 7F and 7G). This is expected because, owing to its high affinity for HS, this chimera should be trapped in the vicinity of the injection site and hence not be able to enter the blood circulation. Moreover, these data show that adding the Klotho co-receptor binding site is not sufficient to convert a paracrine FGF into an endocrine ligand. To confirm that the metabolic activity of the FGF2$^{\Delta HBScore}$-FGF23$^{C\text{-}tail}$ chimera is dependent on αKlotho, αKlotho knockout mice were injected with FGF$^{\Delta HBScore}$-FGF23$^{C\text{-}tail}$ or FGF23 as control and serum concentrations of phosphate were measured. As shown in FIG. 7F, FGF2$^{\Delta HBScore}$-FGF23$^{C\text{-}tail}$ failed to lower serum phosphate, demonstrating that the chimera, like native FGF23 (FIG. 7F), requires αKlotho for metabolic activity.

To determine whether the FGF2$^{\Delta HBScore}$-FGF21$^{C\text{-}tail}$ chimera exhibits FGF21-like metabolic activity, its ability to potentiate the hypoglycemic effect of insulin was examined (Ohnishi et al., *FASEB J.* 25:2031-2039 (2011), which is hereby incorporated by reference in its entirety). Mice were injected with insulin plus FGF2$^{\Delta HBScore}$-FGF21$^{C\text{-}tail}$, insulin plus FGF21, or insulin alone, and blood glucose concentrations were monitored for up to one hour after the injection. Similar to FGF21, the FGF2$^{\Delta HBScore}$-FGF21$^{C\text{-}tail}$ chimera enhanced the hypoglycemic effect of insulin (FIG. 8G), demonstrating that the chimera acts as an FGF21-like hormone.

Figures 9A, 9B, 9C:
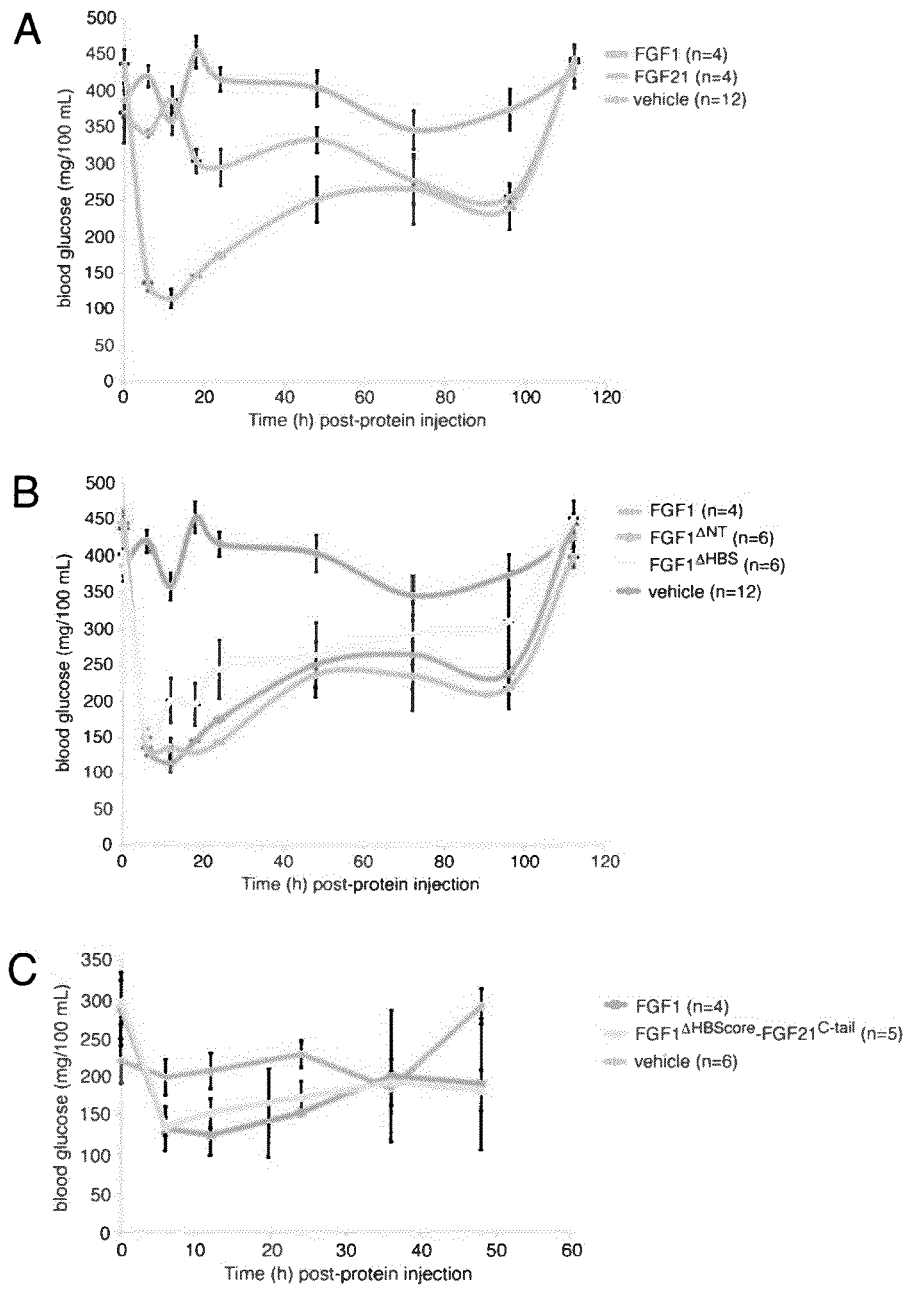
FIGS. 9A-9C show the glucose-lowering effects in ob/ob mice of FGF1 variants according to the present invention.

To substantiate further the concept of FGF ligand conversion, another FGF21-like ligand was engineered using FGF1 as paracrine FGF, and the metabolic activity of the engineered protein was tested in vivo in a mouse model of diabetes and obesity. Besides serving as an additional proof-of-concept, the use of FGF1 for this particular ligand conversion was appealing because FGF1 on its own plays an essential role in glucose metabolism (Jonker et al., "A PPARγ-FGF1 Axis is Required for Adaptive Adipose Remodeling and Metabolic Homeostasis," *Nature* 485:391-394 (2012), which is hereby incorporated by reference in its entirety). Notably, similar to FGF21, FGF1 is induced postprandially in gonadal white adipose tissue by the nuclear hormone receptor PPARγ (peroxisome proliferator activated receptor-γ) (Jonker et al., "A PPARγ-FGF1 Axis is Required for Adaptive Adipose Remodeling and Metabolic Homeostasis," *Nature* 485:391-394 (2012); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). FGF1 is required for the remodeling of adipose tissue to adjust to fluctuations in nutrient availability (Jonker et al., "A PPARγ-FGF1 Axis is Required for Adaptive Adipose Remodeling and Metabolic Homeostasis," *Nature* 485:391-394 (2012), which is hereby incorporated by reference in its entirety), and this process is influenced by FGF21 (Hotta et al., "Fibroblast Growth Factor 21 Regulates Lipolysis in White Adipose Tissue But is Not Required for Ketogenesis and Triglyceride Clearance in Liver," *Endocrinology* 150:4625-4633 (2009); Dutchak et al., "Fibroblast Growth Factor-21 Regulates PPARγ Activity and the Antidiabetic Actions of Thiazolidinediones," *Cell* 148: 556-567 (2012), which are hereby incorporated by reference in their entirety). As part of a positive feedback loop, FGF21 stimulates PPARγ activity in adipocytes (Dutchak et al., "Fibroblast Growth Factor-21 Regulates PPARγ Activity and the Antidiabetic Actions of Thiazolidinediones," *Cell* 148: 556-567 (2012), which is hereby incorporated by reference in its entirety), raising the intriguing possibility that FGF21 regulates FGF1 signaling in adipose tissue through PPARγ. An FGF1$^{\Delta HBScore}$-FGF21$^{C\text{-}tail}$ chimera was generated in the same manner as the FGF2$^{\Delta HBScore}$-FGF21$^{C\text{-}tail}$ chimera (FIGS. 5 and 6). Specifically, K127, K128, and K133 of FGF1, which correspond to the key HS-binding residues identified in the crystal structure of heparin-bound FGF2 (PDB ID: 1FQ9; (Schlessinger et al., *Mol. Cell* 6:743-750 (2000), which is hereby incorporated by reference in its entirety)), were mutated and then the short C-terminal tail of the mutated FGF1 was replaced with the C-terminal tail of FGF21 (P168 to S209) (FIG. 6). A full-length FGF1 protein harboring the HS-binding site mutations was used as a control (FIG. 6). Consistent with the structural prediction, this protein exhibited poor binding affinity for HS compared to wild-type FGF1 as evidenced by the fact that, unlike the wild-type ligand, the mutant protein did not bind to a Heparin sepharose column. A subcutaneous bolus injection of the FGF1$^{\Delta HBScore}$-FGF21$^{C\text{-}tail}$ chimera elicited a hypoglycemic effect in ob/ob mice (FIG. 9C), demonstrating that the chimera has metabolic activity. The effect was of similar magnitude as that observed for native FGF1 (FIG. 9C), which itself has a much greater hypoglycemic effect in ob/ob mice than native FGF21 (FIG. 9A). The HS-binding site mutant of FGF1, which was included as a control in these experiments, showed a similar hypoglycemic effect as the wild-type ligand (FIG. 9B), indicating that the loss in HS-binding affinity had no impact on the metabolic activity of FGF1. To alter the receptor-binding specificity of FGF1 such that FGF1 selectively binds to the "c" splice isoform of FGFR1, the principal receptor mediating the metabolic activity of FGF21, an N-terminally truncated FGF1 protein was made (FIG. 6). The truncated FGF1 ligand lacked twenty four residues from the N-terminus including the nine residues that are critical for the promiscuous binding of FGF1 to both splice isoforms of FGFR1-3 (Beenken et al., "Plasticity in Interactions of Fibroblast Growth Factor 1 (FGF1) N Terminus with FGF Receptors Underlies Promiscuity of FGF1," *J Biol Chem* 287(5):3067-3078 (2012), which is hereby incorporated by reference in its entirety). Based on the crystal structures of FGF1-FGFR complexes, the truncation was also predicted to reduce the receptor-binding affinity of FGF1, and hence the ligand's mitogenicity. The truncated FGF1 protein induced a similar hypoglycemic effect in ob/ob mice as native FGF1 did (FIG. 9B), indicating that the metabolic activity of FGF1 is mediated through the "c" splice isoform of FGFR. Together, these findings provide a starting point for engineering FGF1 ligands that have no mitogenicity but the same or enhanced metabolic activity compared to native FGF1.

The demonstrated ability to convert a paracrine FGF into an endocrine ligand by means of reducing HS-binding affinity of the paracrine FGF and adding the Klotho co-receptor binding site substantiates that HS does not participate in the formation of the endocrine FGF signal transduction unit. The dispensability of HS for the metabolic activity of endocrine FGFs has an intriguing implication as to how these FGFs have evolved to become hormones. It appears that these ligands have lost the requirement to bind HS in order to signal, while acquiring the ability to bind Klotho co-receptors, which is necessary to direct these ligands to their target organs.

Figures 10A, 10B, 10C, 10D, 10E, 10F:
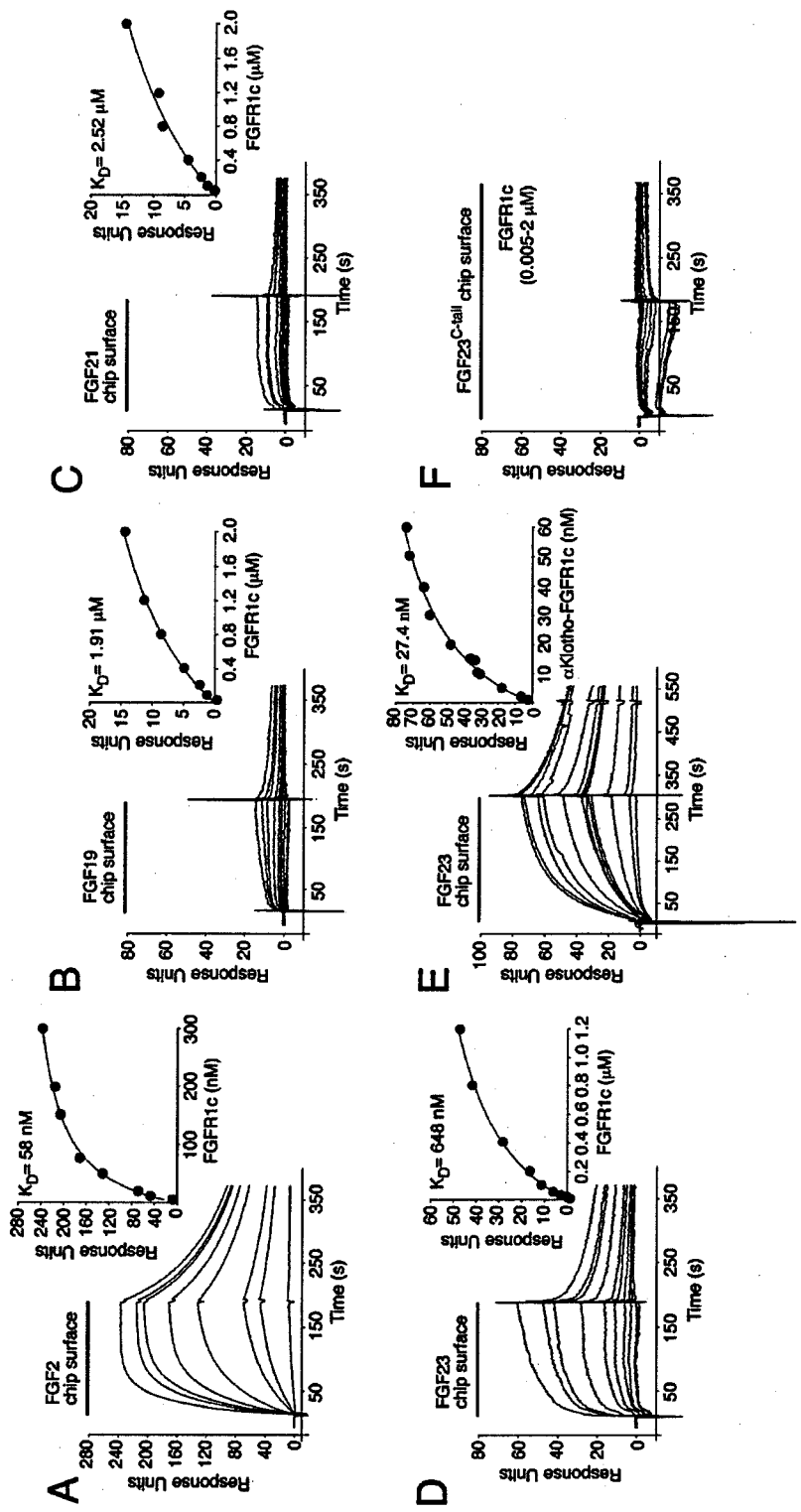
FIGS. 10A-10F show results demonstrating that endocrine FGFs have low binding affinity for FGFR1c compared to FGF2.

In the target tissue, Klotho co-receptors constitutively associate with cognate receptors of endocrine FGFs to offset the inherently low receptor-binding affinity of endocrine FGFs (FIGS. 10B-10D; Kurosu et al., *J. Biol. Chem.* 282: 26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). This low binding affinity is due to the fact that key receptor-binding residues in the β-trefoil core of endocrine FGFs are replaced by residues that are suboptimal for receptor binding (Goetz et al., *Mol. Cell Biol.* 27:3417-3428 (2007), which is hereby incorporated by reference in its entirety). To measure the degree to which Klotho co-receptors enhance the receptor-binding affinity of endocrine FGFs, SPR experiments were conducted using FGF23 and FGFR1c and αKlotho co-receptor as an example (see FIGS. 10A-10F). The SPR data show that αKlotho enhances the affinity of FGF23 for FGFR1c by over 20-fold (FIGS. 10D and 10E). The affinity of FGF23 for FGFR1c in the presence of αKlotho is comparable to that of FGF2 for FGFR1c in the absence of its HS cofactor (FIGS. 10A and 10E). It should be noted, however, that HS further increases the binding affinity of FGF2 for FGFR1c by at least an order of magnitude (Pantoliano et al., *Biochemistry* 33:10229-10248 (1994); Roghani et al., *J. Biol. Chem.* 269:3976-3984 (1994), which are hereby incorporated by reference in their entirety). Hence, the receptor-binding affinity of FGF23 in the presence of αKlotho co-receptor still is lower than that of FGF2 in the presence of HS cofactor. These observations imply that the signaling capacity of the endocrine FGF signal transduction unit should be weaker than that of the paracrine FGF signaling unit. Indeed, cell-based studies show that even in the presence of their Klotho co-receptor, endocrine FGFs are inferior to paracrine FGFs at activating FGFR-induced intracellular signaling pathways (Kurosu et al., *J. Biol. Chem.* 282:26687-26695 (2007); Urakawa et al., *Nature* 444:770-774 (2006), which are hereby incorporated by reference in their entirety).

The finding that endocrine FGFs do not need to rely on HS for signaling has another important implication in regard to the role of Klotho co-receptors. Since FGFR dimerization is a prerequisite for FGF signaling in general, it is proposed that Klotho co-receptors not only enhance the binding affinity of endocrine ligand for receptor but also promote receptor dimerization upon ligand binding. In other words, Klotho co-receptors must fulfill the same dual role that HS plays in signaling by paracrine FGFs (FIG. 1D). The ligand conversion also provides the framework for the rational design of endocrine FGF-like molecules for the treatment of metabolic disorders. An FGF23-like molecule, for example, will be useful for the treatment of inherited or acquired hyperphosphatemia, and an FGF21-like molecule, for example, for the treatment of type 2 diabetes, obesity, and related metabolic disorders.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a mammal having diabetes, comprising:
   administering an FGF1 peptide comprising amino acids 1-155 of SEQ ID NO: 1 with a K127D, K128Q and K133V substitution (FGF1$^{\Delta HBS}$) in an amount effective to lower blood glucose levels in the mammal, thereby treating the mammal.

2. The method of claim 1, wherein the mammal has one or more of type 1 diabetes, type 2 diabetes, gestational diabetes, and drug-induced diabetes.

3. The method of claim 1, wherein the FGF1 peptide is administered at a dose of 0.1 to 10 mg/kg once or twice a day.

4. The method of claim 1, wherein the FGF1 peptide is administered at a dose of 0.5 mg/kg.

5. The method of claim 1, wherein administering comprises oral, parenteral, subcutaneous, intravenous, intramuscular, or intraperitoneal administration.

6. The method of claim 1, wherein the FGF1 peptide is administered with a pharmaceutically-acceptable carrier.

7. The method of claim 1, wherein the FGF1 peptide is co-administered with one or more agents selected from the group consisting of an anti-inflammatory agent, an antifibrotic agent, an antihypertensive agent, an antidiabetic agent, a triglyceride-lowering agent, and a cholesterol-lowering agent.

8. The method of claim 1, wherein the mammal is a human.

9. The method of claim 1, wherein the FGF1 peptide consists of the amino acid sequence shown in:
   amino acids 1-155 of SEQ ID NO: 1 with a K127D, K128Q and K133V substitution (FGF1$^{\Delta HBS}$).

10. A method of treating a mammal having diabetes, comprising:
    administering an FGF1 peptide fragment comprising amino acids 25-155 of SEQ ID NO: 1 with a K127D, K128Q and K133V substitution (FGF1$^{\Delta NT\ \Delta HBS}$) in an amount effective to lower blood glucose levels in the mammal, thereby treating the mammal.

11. The method of claim 10, wherein the mammal has one or more of type 1 diabetes, type 2 diabetes, gestational diabetes, and drug-induced diabetes.

12. The method of claim 10, wherein the FGF1 peptide fragment is administered at a dose of 0.1 to 10 mg/kg once or twice a day.

13. The method of claim 10, wherein the FGF1 peptide fragment is administered at a dose of 0.5 mg/kg.

14. The method of claim 10, wherein administering comprises oral, parenteral, subcutaneous, intravenous, intramuscular, or intraperitoneal administration.

15. The method of claim 10, wherein the FGF1 peptide fragment is administered with a pharmaceutically-acceptable carrier.

16. The method of claim 10, wherein the FGF1 peptide fragment is co-administered with one or more agents selected from the group consisting of an anti-inflammatory agent, an antifibrotic agent, an antihypertensive agent, an antidiabetic agent, a triglyceride-lowering agent, and a cholesterol-lowering agent.

17. The method of claim 10, wherein the mammal is a human.

18. The method of claim 10, wherein the FGF1 peptide fragment consists of the amino acid sequence shown in amino acids 25-155 of SEQ ID NO: 1 with a K127D, K128Q and K133V substitution (FGF1$^{\Delta NT\ \Delta HBS}$).

19. A method of treating a mammal having diabetes, comprising:
    administering an FGF1 peptide fragment consisting of amino acids 25-155 of SEQ ID NO: 1 (FGF1$^{\Delta NT}$) in an amount effective to lower blood glucose levels in the mammal, thereby treating the mammal.

20. The method of claim 19, wherein the mammal has one or more of type 1 diabetes, type 2 diabetes, gestational diabetes, drug-induced diabetes, and high blood glucose.

21. The method of claim 19, wherein the FGF1 peptide fragment is administered at a dose of 0.1 to 10 mg/kg once or twice a day.

22. The method of claim 19, wherein the FGF1 peptide fragment is administered at a dose of 0.5 mg/kg.

23. The method of claim 19, wherein administering comprises oral, parenteral, subcutaneous, intravenous, intramuscular, or intraperitoneal administration.

24. The method of claim 19, wherein the FGF1 peptide fragment is administered with a pharmaceutically-acceptable carrier.

25. The method of claim 19, wherein the FGF1 peptide fragment is co-administered with one or more agents selected from the group consisting of an anti-inflammatory agent, an antifibrotic agent, an antihypertensive agent, an antidiabetic agent, a triglyceride-lowering agent, and a cholesterol-lowering agent.

26. The method of claim 19, wherein the mammal is a human.

* * * * *